United States Patent
Smith, II et al.

(10) Patent No.: US 10,611,776 B2
(45) Date of Patent: Apr. 7, 2020

(54) SPIROHEPTANE SALICYLAMIDES AND RELATED COMPOUNDS AS INHIBITORS OF ROCK

(71) Applicant: BRISTOL-MYERS SQUIBB COMPANY, Princeton, NJ (US)

(72) Inventors: Leon M. Smith, II, Somerset, NJ (US); Vladimir Ladziata, Ewing, NJ (US); Indawati De Lucca, Pennington, NJ (US); Donald J. P. Pinto, Churchville, PA (US); Michael J. Orwat, New Hope, PA (US); Andrew K. Dilger, Ewing, NJ (US); Kumar Balashanmuga Pabbisetty, Piscataway, NJ (US); Wu Yang, Princeton Junction, NJ (US); Scott A. Shaw, Lawrence Township, NJ (US); Peter W. Glunz, Yardley, PA (US); Manoranjan Panda, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/067,619

(22) PCT Filed: Jan. 13, 2017

(86) PCT No.: PCT/US2017/013323
§ 371 (c)(1),
(2) Date: Jul. 2, 2018

(87) PCT Pub. No.: WO2017/123860
PCT Pub. Date: Jul. 20, 2017

(65) Prior Publication Data
US 2019/0016735 A1  Jan. 17, 2019

Related U.S. Application Data

(60) Provisional application No. 62/278,122, filed on Jan. 13, 2016.

(51) Int. Cl.
| | |
|---|---|
| C07D 513/04 | (2006.01) |
| C07D 213/64 | (2006.01) |
| A61P 15/10 | (2006.01) |
| A61P 9/10 | (2006.01) |
| C07D 239/06 | (2006.01) |

(52) U.S. Cl.
CPC ............. C07D 513/04 (2013.01); A61P 9/10 (2018.01); A61P 15/10 (2018.01); C07D 213/64 (2013.01); C07D 239/06 (2013.01)

(58) Field of Classification Search
CPC .. C07D 213/64; C07D 239/06; C07D 513/04; A61P 9/10; A61P 15/10
See application file for complete search history.

(56) References Cited

U.S. PATENT DOCUMENTS

2010/0056518 A1  3/2010  Plettenburg et al.

FOREIGN PATENT DOCUMENTS

| EP | 2025676 A1 | 2/2009 |
|---|---|---|
| WO | 2014/113620 A2 | 7/2014 |
| WO | 2014/134388 A1 | 9/2014 |
| WO | 2014/134391 A1 | 9/2014 |
| WO | 2015/002915 A1 | 1/2015 |
| WO | 2015/002926 A1 | 1/2015 |
| WO | 2016/010950 A1 | 1/2016 |
| WO | 2016/028971 A1 | 2/2016 |
| WO | 2016/112236 A1 | 7/2016 |
| WO | 2016/144936 A1 | 9/2016 |
| WO | 2017/205709 A1 | 11/2017 |
| WO | 2018/009622 A1 | 1/2018 |
| WO | 2018/009625 A1 | 1/2018 |
| WO | 2018/009627 A1 | 1/2018 |
| WO | 2018/102325 A1 | 6/2018 |

*Primary Examiner* — Joseph R Kosack
(74) *Attorney, Agent, or Firm* — Hong Liu

(57) ABSTRACT

The present invention provides compounds of Formula (I): or stereoisomers, tautomers, or pharmaceutically-acceptable salts thereof wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

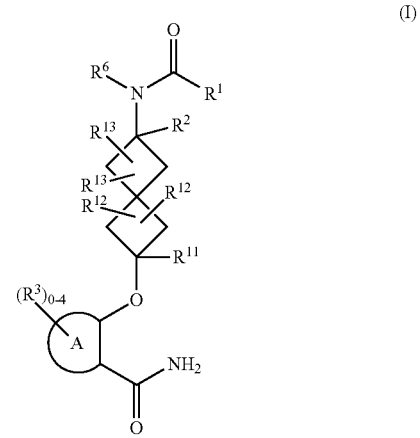

17 Claims, No Drawings
Specification includes a Sequence Listing.

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: FITC-AHA at N Terminus attached at A1 - A11
<220> FEATURE:
<221> NAME/KEY: MISC_FEATURE
<223> OTHER INFORMATION: OH at C Terminus attached at A1 - A11

<400> SEQUENCE: 1

Ala Lys Arg Arg Arg Leu Ser Ser Leu Arg Ala
1               5                   10
```

SPIROHEPTANE SALICYLAMIDES AND RELATED COMPOUNDS AS INHIBITORS OF ROCK

CROSS REFERENCE TO RELATED APPLICATIONS

This application is a 371 application of PCT/US2017/013323, filed Jan. 13, 2017, which is entitled to priority pursuant to 35 U.S.C. § 119(e) to U.S. provisional patent application No. 62/278,122, filed Jan. 13, 2016, which is incorporated herein in its entirety.

FIELD OF THE INVENTION

The present invention relates generally to novel spiroheptane salicylamides and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (19%)). ROCK has been identified as an effector molecule of RhoA, a small GTP-binding protein (G protein) that play s a key role in multiple cellular signaling pathway s. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T et al., *J. Pharmacol. Exp Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh. S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol Ther.*, 18:67-74 (2005)), cancer (Rattan. R. et al., *J. Neurosci. Res.*, 83:243-255 (2006); Lepley. D. et al., *Cancer Res.*, 65:3788-3795 (2005)), fibrotic diseases (Jiang. C et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer's disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S., Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2012/0122842 A1, US 2010/0041645 A1, US 2008/0161297 A1, and Hu, E. et al., *Exp. Opin. Ther. Targets*, 9:715-736 (2005), and WO2014/113620, WO 2014/134388, WO 2014/134391, WO2015/002915, WO2015/002926, WO2016/010950, WO2016/028971, WO2016/112236, and WO2016/144936, of which the later nine references are assigned to the present applicant), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel spiroheptane salicylamides, their analogues, including stereoisomers, enantiomers, diastereoisomers, tautomers, pharmaceutically-acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, enantiomers, diastereoisomers, tautomers, pharmaceutically-acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above.

Examples of such diseases that may be treated include, for example, hypertension, atherosclerosis, restenosis, stroke, heart failure, renal failure, coronary artery disease, peripheral artery disease, coronary vasospasm, cerebral vasospasm ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

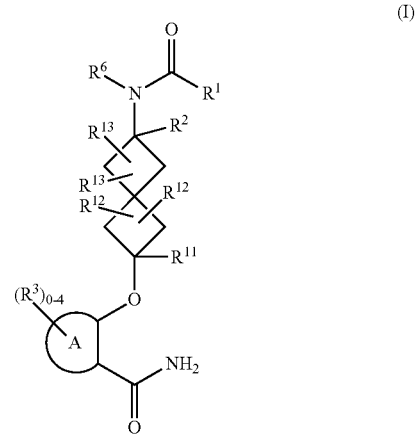

or stereoisomers, enantiomers, diastereoisomers, tautomers, pharmaceutically-acceptable salts, sovates, or prodrugs thereof, wherein:

Ring A is selected from phenyl or 6-membered heteroaryl comprising carbon atoms and 1-2 nitrogen atoms;

$R^1$ is selected from $C_{1-4}$ alkyl, $NR^5R^5$, $OR^5$, —$(CR^4R^4)_n$ $C_{3-10}$ carbocycle and —$(CR^4R^4)_n$-4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$ is independently selected from H and $C_{1-5}$ alkyl optionally substituted with halogen, $C_{1-4}$ alkoxy, —OH, CN, —$CO_2H$, z-$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$; wherein said alkyl and alkoxy are substituted with 0-4 $R^9$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl)$_2$, —$OCH_2CO_2H$, —$NHCO(C_{1-4}$ alkyl), —$NHCO_2$ ($C_{1-4}$ alkyl), —$NHSO_2(C_{1-4}$ alkyl), —$SO_2NH_2$, —C(=NH) $NH_2$, a carbocycle, and a heterocycle, wherein said alkyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —$NHCO(C_{1-4}$ alkyl), —$NHCOCF_3$, —$NHCO_2$ ($C_{1-4}$ alkyl), —$NHCO_2(CH_2)_2O(C_{1-4}$ alkyl), —$NHCO_2$ $(CH_2)_3O(C_{1-4}$ alkyl), —$NHCO_2(CH_2)_2OH$, —$NHCO_2$ $(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC $(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, —$(CH_2)_n$—$C(O)C_{1-4}$ alkyl, —$(CH_2)_n$—$C(O)$carbocycle, —$(CH_2)_n$—$C(O)$heterocycle, —$(CH_2)_n$—$C(O)NR^aR^a$, —$(CH_2)_n$—$NR^aC(O)$ $C_{1-4}$alkyl, —$(CH_2)_n$—$C(O)OC_{1-4}$alkyl, —$(CH_2)_n$—$C(O)$ $C_{1-4}$alkyl, —$(CH_2)_n$—$C(O)O$-carbocycle, —$(CH_2)_n$—$C(O)$ O-heterocycle, —$(CH_2)_n$—$SO_2$alkyl, —$(CH_2)_n$ $SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_n NR^aR^a$, —$(CHR^{10})_n CONR^aR^a$, —$(CHR^{10})_n NR^aCO(C_{1-4}$ alkyl), —$O(CHR^{10})_n$carbocycle, —$O(CHR^{10})_n$ heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^{11}$ is independently selected from H and $C_{1-3}$ alkyl optionally substituted with halogen, $C_{1-4}$ alkoxy, —OH, CN, —$CO_2H$, —$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$;

$R^{12}$ and $R^{13}$ are independently selected from H, OH, —$OC_{1-3}$ alkyl substituted with 0-4 $R^d$, $C_{1-4}$ alkyl with substituted with 0-4 $R^d$;

$R^a$, at each occurrence, is independently selected from H, $C_{1-4}$ alkyl, —$(CH_2)_n OH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)$ $C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —CONH $(C_{1-4}$ alkyl), —$CON(C_{1-4}$ alkyl)$_2$, —CONH—$C_{1-4}$ alkylene-$O(C_{1-4}$ alkyl), —CONH—$C_{1-4}$ alkylene-$N(C_{1-4}$ alkyl)$_2$, —CONH—$C_{1-4}$ alkylene-$N(C_{1-4}$ alkyl)$_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$, wherein said alkyl and alkoxy are substituted with $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl);

n, at each occurrence, is independently selected from 0, 1, 2, 3, and 4; and p, at each occurrence, is independently selected from 0, 1, and 2.

In another aspect, the present invention provides compounds of Formula (Ia):

(Ia)

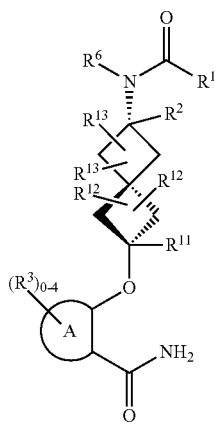

or stereoisomers, enantiomers, diastereoisomers, tautomers, pharmaceutically-acceptable salts, sovates, or prodrugs thereof, wherein:

Ring A is selected from phenyl or 6-membered heteroaryl comprising carbon atoms and 1-2 nitrogen atoms;

$R^1$ is selected from $C_{1-4}$ alkyl, $NR^5R^5$, $OR^5$, —$(CR^4R^4)_n$ $C_{3-10}$ carbocycle and —$(CR^4R^4)_n$-4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$ is independently selected from H and $C_{1-4}$ alkyl optionally substituted with halogen, $C_{1-4}$ alkoxy, —OH, CN, —$CO_2H$, —$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$; wherein said alkyl and alkoxy are substituted with 0-4 $R^9$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl)$_2$, —$OCH_2CO_2H$, —$NHCO(C_{1-4}$ alkyl), —$NHCO_2$ $(C_{1-4}$ alkyl), —$NHSO_2(C_{1-4}$ alkyl), —$SO_2NH_2$, —C(=NH)$NH_2$, a carbocycle, and a heterocycle, wherein said alkyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

$R^7$, at each occurrence, is independently selected from H, =O, $NO_2$, halogen, $C_{1-4}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —NHCO($C_{1-4}$ alkyl), —$NHCOCF_3$, —$NHCO_2$ ($C_{1-4}$ alkyl), —$NHCO_2(CH_2)_2O(C_{1-4}$ alkyl), —$NHCO_2$ $(CH_2)_3O(C_{1-4}$ alkyl), —$NHCO_2(CH_2)_2OH$, —$NHCO_2$ $(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, —$(CH_2)_n$—$C(O)C_{1-4}$ alkyl, —$(CH_2)_n$—C(O)carbocycle, —$(CH_2)_n$—C(O)heterocycle, —$(CH_2)_n$—$C(O)NR^aR^a$, —$(CH_2)_n$—$NR^aC(O)$ $C_{1-4}$alkyl, —$(CH_2)_n$—$C(O)OC_{1-4}$alkyl, —$(CH_2)_n$—C(O) $C_{1-4}$alkyl, —$(CH_2)_n$—C(O)O-carbocycle, —$(CH_2)_n$—C(O) O-heterocycle, —$(CH_2)_n$—$SO_2$alkyl, —$(CH_2)_n$ $SO_2$carbocycle, —$(CH_2)_n$—$SO_2$heterocycle, —$(CH_2)_n$— $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_n$$NR^aR^a$, —$(CHR^{10})_n$$CONR^aR^a$, —$(CHR^{10})_n$ $NR^aCO(C_{1-4}$ alkyl), —$O(CHR^{10})_n$carbocycle, —$O(CHR^{10})_n$ heterocycle, —$O(CHR^{10})_n$$NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^{11}$ is independently selected from H and $C_{1-3}$ alkyl optionally substituted with halogen, $C_{1-4}$ alkoxy, —OH, CN, —$CO_2H$, —$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$;

$R^{12}$ and $R^{13}$ are independently selected from H, OH, —$OC_{1-4}$ alkyl substituted with 0-4 $R^d$, $C_{1-3}$ alkyl with substituted with 0-4 $R^d$;

$R^a$, at each occurrence, is independently selected from H, $C_{1-4}$ alkyl, —$(CH_2)_n$OH, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, OC(O) $C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —CONH $(C_{1-4}$ alkyl), —$CON(C_{1-4}$ alkyl)$_2$, —CONH—$C_{1-4}$ alkylene-$O(C_{1-4}$ alkyl), —CONH—$C_{1-4}$ alkylene-$N(C_{1-4}$ alkyl)$_2$, —CONH—$C_{1-4}$ alkylene-$N(C_{1-4}$ alkyl)$_2$, —$C_{1-4}$ alkylene- O—P(O)(OH)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl);

n, at each occurrence, is independently selected from 0, 1, 2, 3, and 4; and p, at each occurrence, is independently selected from 0, 1, and 2.

In another aspect, the present invention provides compounds of Formula (II):

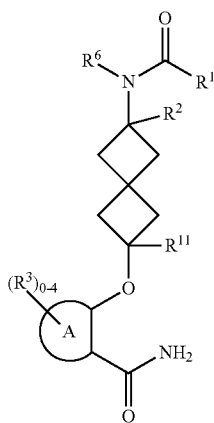

(II)

or stereoisomers, enantiomers, diastereoisomers, tautomers, pharmaceutically-acceptable salts, sovates, or prodrugs thereof, wherein:

Ring A is selected from phenyl or 6-membered heteroaryl comprising carbon atoms and 1-2 nitrogen atoms;

R$^1$ is selected from C$_{1-4}$ alkyl, NR$^5$R$^5$, OR$^5$, —(CR$^4$R$^4$)$_n$ C$_{3-10}$ carbocycle and —(CR$^4$R$^4$)$_n$-4- to 15-membered heterocycle comprising carbon atoms and 1-4 heteroatoms selected from N, NR$^8$, O, and S(O)$_p$; wherein said alkyl, carbocycle, and heterocycle are substituted with 1-4 R$^7$;

R$^2$ is independently selected from H and C$_{1-5}$ alkyl optionally substituted with halogen, C$_{1-4}$ alkoxy, —OH, CN, —CO$_2$H, —CO$_2$(C$_{1-4}$ alkyl), —CO(C$_{1-4}$ alkyl), —CONH$_2$, —CONH(C$_{1-4}$ alkyl), and —CON(C$_{1-4}$ alkyl)$_2$; wherein said alkyl and alkoxy are substituted with 0-4 R$^9$;

R$^3$, at each occurrence, is independently selected from halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, a carbocycle, and a heterocycle, wherein said alkyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, a carbocycle, and a heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$-4- to 10-membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form a 4- to 15-membered substituted with 1-4 R$^7$;

R$^6$, at each occurrence, is independently selected from H, C$_{1-4}$ alkyl, CH$_2$NH$_2$, C$_{1-4}$ haloalkyl, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), a carbocycle, and a heterocycle, wherein said alkyl, alkoxy, haloalkyl, carbocycle, and heterocycle are substituted with 0-4 R$^9$;

R$^7$, at each occurrence, is independently selected from H, =O, NO$_2$, halogen, C$_{1-7}$ alkyl, C$_{2-4}$ alkenyl, C$_{2-4}$ alkynyl, C$_{1-4}$ alkoxy, CN, OH, CHF$_2$, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCOH, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —S(O)$_p$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-6}$ alkyl, C$_{2-4}$ alkenyl, C$_{2-4}$ alkynyl, —(CH$_2$)$_n$—C(O)C$_{1-4}$alkyl, —(CH$_2$)$_n$—C(O)carbocycle, —(CH$_2$)$_n$—C(O)heterocycle, —(CH$_2$)$_n$—C(O)NR$^a$R$^a$, —(CH$_2$)$_n$—NR$^a$C(O)C$_{1-4}$ alkyl, —(CH$_2$)$_n$—C(O)OC$_{1-4}$alkyl, —(CH$_2$)$_n$—C(O)C$_{1-4}$ alkyl, —(CH$_2$)$_n$—C(O)O-carbocycle, —(CH$_2$)$_n$—C(O)O-heterocycle, —(CH$_2$)$_n$—SO$_2$alkyl, —(CH$_2$)$_n$SO$_2$carbocycle, —(CH$_2$)$_n$—SO$_2$heterocycle, —(CH$_2$)$_n$—SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, =O, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$ heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^{11}$ is independently selected from H and C$_{1-4}$ alkyl optionally substituted with halogen, C$_{1-4}$ alkoxy, —OH, CN, —CO$_2$H, —CO$_2$(C$_{1-4}$ alkyl), —CO(C$_{1-4}$ alkyl), —CONH$_2$, —CONH(C$_{1-4}$ alkyl), and —CON(C$_{1-4}$ alkyl)$_2$;

$R^a$, at each occurrence, is independently selected from H, $C_{1-4}$ alkyl, —$(CH_2)_n$OH, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)$ $C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —CONH$(C_{1-4}$ alkyl), —$CON(C_{1-4}$ alkyl)$_2$, —CONH—$C_{1-4}$ alkylene-$O(C_{1-4}$ alkyl), —CONH—$C_{1-4}$ alkylene-$N(C_{1-4}$ alkyl)$_2$, —CONH—$C_{1-4}$ alkylene-$N(C_{1-4}$ alkyl)$_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$, wherein said alkyl and alkoxy are substituted with $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4; and p, at each occurrence, is independently selected from 0, 1, and 2.

In another aspect, the present invention provides compounds of Formula (IIa):

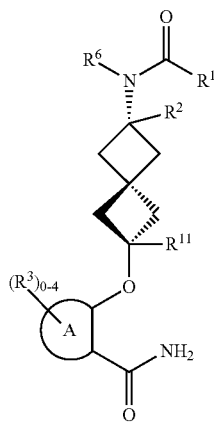

(IIa)

or stereoisomers, enantiomers, diastereoisomers, tautomers, pharmaceutically-acceptable salts, sovates, or prodrugs thereof, wherein:

Ring A is selected from phenyl or 6-membered heteroaryl comprising carbon atoms and 1-2 nitrogen atoms;

$R^1$ is selected from $C_{1-4}$ alkyl, $NR^5R^5$, $OR^5$, —$(CR^4R^4)_n$ $C_{3-10}$ carbocycle and —$(CR^4R^4)_n$-4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$ is independently selected from H and $C_{1-4}$ alkyl optionally substituted with halogen, $C_{1-4}$ alkoxy, —OH, CN, —$CO_2H$, —$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$; wherein said alkyl and alkoxy are substituted with 0-4 $R^9$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl)$_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —$C(=NH)NH_2$, a carbocycle, and a heterocycle, wherein said alkyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

$R^7$, at each occurrence, is independently selected from H, =O, $NO_2$, halogen, $C_{1-7}$ alkyl, $C_{1-4}$ alkenyl, $C_{1-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, —$(CH_2)_n$—$C(O)C_{1-4}$ alkyl, —$(CH_2)_n$—$C(O)$carbocycle, —$(CH_2)_n$—$C(O)$heterocycle, —$(CH_2)_n$—$C(O)NR^aR^a$, —$(CH_2)_n$—$NR^aC(O)C_{1-4}$ alkyl, —$(CH_2)_n$—$C(O)OC_{1-4}$alkyl, —$(CH_2)_n$—$C(O)C_{1-4}$ alkyl, —$(CH_2)_n$—$C(O)O$-carbocycle, —$(CH_2)_n$—$C(O)O$-heterocycle, —$(CH_2)_n$—$SO_2$alkyl, —$(CH_2)_n$ $SO_2$carbocycle, —$(CH_2)_n$—$SO_2$heterocycle, —$(CH_2)_n$—

SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, =O, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$ heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^{11}$ is independently selected from H and C$_{1-4}$ alkyl optionally substituted with halogen, C$_{1-4}$ alkoxy, —OH, CN, —CO$_2$H, —CO$_2$(C$_{1-4}$ alkyl), —CO(C$_{1-4}$ alkyl), —CONH$_2$, —CONH(C$_{1-4}$ alkyl), and —CON(C$_{1-4}$ alkyl)$_2$;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, OC(O)C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (III):

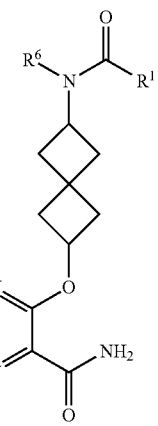

(III)

or stereoisomers, enantiomers, diastereoisomers, tautomers, pharmaceutically-acceptable salts, sovates, or prodrugs, wherein:

U and V are independently selected from CH, CR$^3$, and N;

R$^1$ is selected from C$_{1-4}$ alkyl, NR$^5$R$^5$, OR$^5$, —(CR$^4$R$^4$)$_n$C$_{3-10}$ carbocycle and —(CR$^4$R$^4$)$_n$-4- to 15-membered heterocycle comprising carbon atoms and 1-4 heteroatoms selected from N, NR$^8$, O, and S(O)$_p$; wherein said alkyl, carbocycle, and heterocycle are substituted with 1-4 R$^7$;

R$^3$, at each occurrence, is independently selected from halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ allyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, a carbocycle, and a heterocycle, wherein said alkyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, a carbocycle, and a heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$- 4- to 10-membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form a 4- to 15-membered heterocycle substituted with 1-4 R$^7$;

R$^6$, at each occurrence, is independently selected from H, C$_{1-4}$ alkyl, CH$_2$NH$_2$, C$_{1-4}$ haloalkyl, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), a carbocycle, and a heterocycle, wherein said alkyl, alkoxy, haloalkyl, carbocycle, and heterocycle are substituted with 0-4 R$^9$;

R$^7$, at each occurrence, is independently selected from H, =O, NO$_2$, halogen, C$_{1-6}$ alkyl, C$_{2-4}$ alkenyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCOH, —NHCO(C$_{1-4}$ alkyl), —NHCOCF$_3$, —NHCO$_2$(C$_{1-4}$ alkyl), —NHCO$_2$ —(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —S(O)$_p$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkoxyl, a carbocycle, and a heterocycle are substituted with 0-4 R$^9$;

R$^8$, at each occurrence, is independently selected from H, C$_{1-4}$ alkyl, C$_{2-4}$ alkenyl, C$_{2-4}$ alkynyl, —(CH$_2$)$_n$—C(O)C$_{1-4}$ alkyl, —(CH$_2$)$_n$—C(O)carbocycle, —(CH$_2$)$_n$—C(O)heterocycle, —(CH$_2$)$_n$—C(O)NR$^a$R$^a$, —(CH$_2$)$_n$—NR$^a$C(O)C$_{1-4}$ alkyl, —(CH$_2$)$_n$—C(O)OC$_{1-4}$alkyl, —(CH$_2$)$_n$—C(O)C$_{1-4}$ alkyl, —(CH$_2$)$_n$—C(O)O-carbocycle, —(CH$_2$)$_n$—C(O)O-heterocycle, —(CH$_2$)$_n$—SO$_2$alkyl, —(CH$_2$)$_n$SO$_2$carbocycle, —(CH$_2$)$_n$—SO$_2$heterocycle, —(CH$_2$)$_n$—SO$_2$NR$^a$R$^a$, —(CH$_2$)$_n$-carbocycle, and —(CH$_2$)$_n$-heterocycle, wherein said alkyl, alkenyl, alkynyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, =O, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$ heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, OC(O)C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (IIIa):

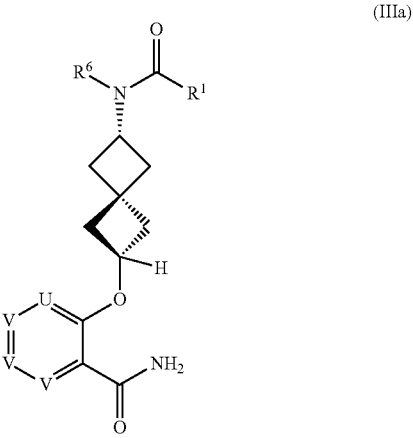

(IIIa)

or stereoisomers, enantiomers, diastereoisomers, tautomers, pharmaceutically-acceptable salts, sovates, or prodrugs, wherein:

U and V are independently selected from CH, CR$^3$, and N;

R$^1$ is selected from C$_{1-4}$ alkyl, NR$^5$R$^5$, OR$^5$, —(CR$^4$R$^4$)$_n$C$_{3-10}$ carbocycle and —(CR$^4$R$^4$)$_n$-4- to 15-membered heterocycle comprising carbon atoms and 1-4 heteroatoms selected from N, NR$^8$, O, and S(O)$_p$; wherein said alkyl, carbocycle, and heterocycle are substituted with 1-4 R$^7$;

R$^3$, at each occurrence, is independently selected from halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, a carbocycle, and a heterocycle, wherein said alkyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, a carbocycle, and a heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$-4- to 10-membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form a 4- to 15-membered heterocycle substituted with 1-4 R$^7$;

R$^6$, at each occurrence, is independently selected from H, C$_{1-4}$ alkyl, CH$_2$NH$_2$, C$_{1-4}$ haloalkyl, C$_{1-4}$ alkoxy, CH$_2$OH, CH₂O(C₁₋₄ alkyl), CH₂CO₂H, CH₂CO₂(C₁₋₄ alkyl), a carbocycle, and a heterocycle, wherein said alkyl, alkoxy, haloalkyl, carbocycle, and heterocycle are substituted with 0-4 $R^9$;

$R^7$, at each occurrence, is independently selected from H, =O, NO₂, halogen, C₁₋₆ alkyl, C₂₋₄ alkenyl, C₁₋₄ alkoxy, CN, OH, CF₃, —(CH₂)$_n$—CO₂H, —(CH₂)$_n$—CO₂(C₁₋₄ alkyl), —(CH₂)$_n$—NR⁸R⁸, —NHCOH, —NHCO(C₁₋₄ alkyl), —NHCOCF₃, —NHCO₂(C₁₋₄ alkyl), —NHCO₂(CH₂)₂O(C₁₋₄ alkyl), —NHCO₂(CH₂)₃O(C₁₋₄ alkyl), —NHCO₂(CH₂)₂OH, —NHCO₂(CH₂)₂NH₂, —NHCO₂(CH₂)₂N(C₁₋₄ alkyl)₂, —NHCO₂CH₂CO₂H, —CH₂NHCO₂(C₁₋₄ alkyl), —NHC(O)NR⁸R⁸, —NHSO₂(C₁₋₄ alkyl), —S(O)$_p$(C₁₋₄ alkyl), —SO₂NH₂, —SO₂NH(C₁₋₄ alkyl), —SO₂N(C₁₋₄ alkyl)₂, —SO₂NH(CH₂)₂OH, —SO₂NH(CH₂)₂O(C₁₋₄ alkyl), —(CH₂)$_n$—CONR⁸R⁸, —O(CH₂)$_n$-carbocycle, —O(CH₂)$_n$-heterocycle, —NHCO-carbocycle, —NH CO-heterocycle, —(CH₂)$_n$-carbocycle, and —(CH₂)$_n$-heterocycle comprising carbon atoms and 1-4 heteroatoms selected from N, NR⁸, O, and S(O)$_p$, wherein said alkyl, alkenyl, alkoxyl, a carbocycle, and a heterocycle are substituted with 0-4 $R^9$;

$R^8$, at each occurrence, is independently selected from H, C₁₋₄ alkyl, C₂₋₄ alkenyl, C₂₋₄ alkynyl, —(CH₂)$_n$—C(O)C₁₋₄ alkyl, —(CH₂)$_n$—C(O)carbocycle, —(CH₂)$_n$—C(O)heterocycle, —(CH₂)$_n$—C(O)NR$^a$R$^a$, —(CH₂)$_n$—NR$^a$C(O)C₁₋₄ alkyl, —(CH₂)$_n$—C(O)OC₁₋₄alkyl, —(CH₂)$_n$—C(O)C₁₋₄ alkyl, —(CH₂)$_n$—C(O)O-carbocycle, —(CH₂)$_n$—C(O)O-heterocycle, —(CH₂)$_n$—SO₂alkyl, —(CH₂)$_n$SO₂carbocycle, —(CH₂)$_n$—SO₂heterocycle, —(CH₂)$_n$—SO₂NR$^a$R$^a$, —(CH₂)$_n$-carbocycle, and —(CH₂)$_n$-heterocycle, wherein said alkyl, alkenyl, alkynyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, NO₂, CHF₂, CF₃, C₁₋₄ alkyl, C₁₋₄ alkoxy, CH₂OH, CO(C₁₋₄ alkyl), CO₂H, CO₂(C₁₋₄ alkyl), —(CHR¹⁰)$_n$NR$^a$R$^a$, —(CHR¹⁰)$_n$CONR$^a$R$^a$, —(CHR¹⁰)$_n$NR$^a$CO(C₁₋₄ alkyl), —O(CHR¹⁰)$_n$carbocycle, —O(CHR¹⁰)$_n$ heterocycle, —O(CHR¹⁰)$_n$NR$^a$R$^a$, and —(CR¹⁰R¹⁰)$_n$-4- to 10-membered heterocycle, wherein said alkyl, alkoxy, carbocycle, and heterocycle are substituted with 0-4 $R^b$;

$R^{10}$, at each occurrence, is independently selected from H and C₁₋₄ alkyl;

$R^a$, at each occurrence, is independently selected from H, C₁₋₄ alkyl, —(CH₂)$_n$OH, CO(C₁₋₄ alkyl), COCF₃, CO₂(C₁₋₄ alkyl), —CONH₂, —CONH—C₁₋₄ alkylene-CO₂(C₁₋₄ alkyl), C₁₋₄ alkylene-CO₂(C₁₋₄ alkyl), $R^c$, CO₂$R^c$, and CONH$R^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, C₁₋₄ alkyl, C₁₋₄ alkoxy, OCF₃, OC(O)C₁₋₄ alkyl, NH₂, NO₂, N(C₁₋₄ alkyl)₂, CO(C₁₋₄ alkyl), CO(C₁₋₄ haloalkyl), CO₂(C₁₋₄ alkyl), CONH₂, —CONH(C₁₋₄ alkyl), —CON(C₁₋₄ alkyl)₂, —CONH—C₁₋₄ alkylene-O(C₁₋₄ alkyl), —CONH—C₁₋₄ alkylene-N(C₁₋₄ alkyl)₂, —CONH—C₁₋₄ alkylene-N(C₁₋₄ alkyl)₂, —C₁₋₄ alkylene-O—P(O)(OH)₂, —NHCO₂(C₁₋₄ alkyl), —$R^c$, CO$R^c$, CO₂$R^c$, and CONH$R^c$, wherein said alkyl and alkoxy are substituted with $R^d$;

$R^c$, at each occurrence, is independently selected from —(CH₂)$_n$—C₃₋₆ cycloalkyl, —(CH₂)$_n$-phenyl, and —(CH₂)$_n$-5- to 6-membered heterocycle containing carbon atoms and 1-4 heteroatoms selected from the group consisting of: N, NH, N(C₁₋₄ alkyl), O, and S(O)$_p$; wherein each ring moiety is substituted with 0-2 $R^d$;

$R^d$, at each occurrence, is independently selected from =O, halogen, —OH, C₁₋₄ alkyl, NH₂, NH(C₁₋₄ alkyl), N(C₁₋₄ alkyl)₂, C₁₋₄ alkoxy, and —NHCO(C₁₋₄ alkyl), and a heterocycle containing carbon atoms and 1-4 heteroatoms selected from the group consisting of: N, NH, N(C₁₋₄ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (IV):

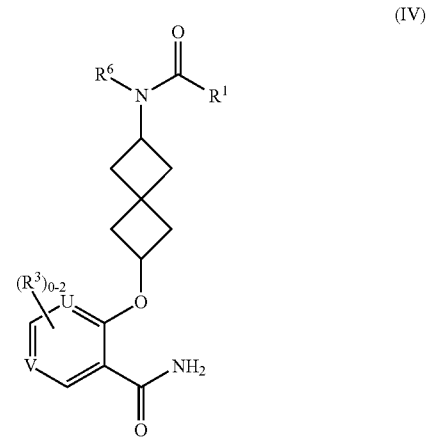

(IV)

or stereoisomers, enantiomers, diastereoisomers, tautomers, pharmaceutically-acceptable salts, sovates, or prodrugs, wherein:

U and V are independently selected from CH, CR³, and N;

$R^1$ is selected from —(CH₂)$_n$—C₃₋₁₀ carbocycle, and —(CH₂)$_n$-5- to 10-membered heterocycle, wherein said carbocycle and heterocycle are substituted with 1-4 $R^7$;

$R^3$, at each occurrence, is independently selected from halogen, C₁₋₆ alkyl, C₁₋₄ alkoxy, C₁₋₄ alkylthio, C₁₋₄ haloalkyl, —CH₂OH, —OCH₂F, —OCHF₂, —OCF₃, CN, and —NH₂;

$R^5$, at each occurrence, is independently selected from H, C₁₋₄ alkyl, —(CR⁶R⁶)$_n$—C₃₋₁₀ carbocycle, and —(CR⁶R⁶)$_n$-4- to 10-membered heterocycle comprising carbon atoms and 1-4 heteroatoms selected from N, NR⁸, O, and S(O)$_p$, wherein said alkyl, carbocycle, and heterocycle are substituted with 1-4 $R^7$;

alternatively, $R^5$ and $R^5$ are taken together with the nitrogen atom to which they are attached to form a 4- to 10-membered heterocycle substituted with 1-4 $R^7$;

$R^6$, at each occurrence, is independently selected from H and C₁₋₄ alkyl;

$R^7$, at each occurrence, is independently selected from H, =O, NO₂, halogen, C₁₋₄ alkyl, C₁₋₄ alkoxy, CN, OH, CF₃, —(CH₂)$_n$—CO₂H, —(CH₂)$_n$—CO₂(C₁₋₄ alkyl), —(CH₂)$_n$—NR⁸R⁸, —NHCOH, —NHCO(C₁₋₄ alkyl), —NHCOCF₃, —NHCO₂(C₁₋₄ alkyl), —NHCO₂(CH₂)₂O(C₁₋₄ alkyl), —NHCO₂(CH₂)₃O(C₁₋₄ alkyl), —NHCO₂(CH₂)₂OH, —NHCO₂(CH₂)₂NH₂, —NHCO₂(CH₂)₂N(C₁₋₄ alkyl)₂, —NHCO₂CH₂CO₂H, —CH₂NHCO₂(C₁₋₄ alkyl), —NHC(O)NR⁸R⁸, —NHSO₂(C₁₋₄ alkyl), —S(O)$_p$(C₁₋₄ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NH CO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, C$_{2-4}$ alkenyl, C(O)C$_{1-4}$alkyl, C(O)carbocycle, C(O)heterocycle, —(CH$_2$)$_n$—C(O)NR$^a$R$^a$, —(CH$_2$)$_n$—NR$^a$C(O)C$_{1-4}$alkyl, C(O)OC$_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, alkenyl, carbocycle, and heterocycle are substituted with 0-4 R$^9$;

R$^9$, at each occurrence, is independently selected from halogen, OH, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$ heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, OC(O)C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N (C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (IVa):

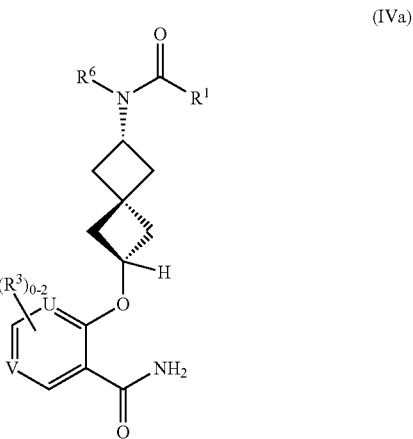

(IVa)

or a stereoisomer, an enantiomer, a diastereoisomer, a tautomer, a pharmaceutically-acceptable salt thereof, wherein:

U and V are independently selected from CH, CR$^3$, and N;

R$^1$ is selected from —(CH$_2$)$_n$—C$_{3-10}$ carbocycle, and —(CH$_2$)$_n$-5- to 10-membered heterocycle, wherein said carbocycle and heterocycle are substituted with 1-4 R$^7$;

R$^3$, at each occurrence, is independently selected from halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, and —NH$_2$;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4- to 10-membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form a 4- to 10-membered heterocycle substituted with 1-4 R$^7$;

R$^6$, at each occurrence, is independently selected from H and C$_{1-4}$ alkyl;

R$^7$, at each occurrence, is independently selected from H, =O, NO$_2$, halogen, C$_{1-6}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCOH, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO(C$_{1-4}$ alkyl), —NHC(O)NR$^8$R$^8$, —NHSO$_2$(C$_{1-4}$ alkyl), —S(O)$_p$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkoxyl, carbocycle, and heterocycle are substituted with 0-4 R$^9$;

R$^8$, at each occurrence, is independently selected from H, C$_{1-4}$ allyl, C$_{1-4}$ alkenyl, C(O)C$_{1-4}$alkyl, C(O)carbocycle, C(O)heterocycle, —(CH$_2$)$_n$—C(O)NR$^a$R$^a$, —(CH$_2$)$_n$NR$^a$C(O)C$_{1-4}$alkyl, C(O)OC$_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, alkenyl, carbocycle, and heterocycle are substituted with 0-4 R$^9$;

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), $—(CHR^{10})_nNR^aR^a$, $—(CHR^{10})_nCONR^aR^a$, $—(CHR^{10})_n NR^aCO(C_{1-4}$ alkyl), $—O(CHR^{10})_n$carbocycle, $—O(CHR^{10})_n$ heterocycle, $—O(CHR^{10})_nNR^aR^a$, and $—(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^a$, at each occurrence, is independently selected from H, $C_{1-4}$ alkyl, $—(CH_2)_nOH$, $CO(C_{1-4}$ alkyl), $COCF_3$, $CO_2(C_{1-4}$ alkyl), $—CONH_2$, $—CONH—C_{1-4}$ alkylene-$CO_2(C_{1-4}$ alkyl), $C_{1-4}$ alkylene-$CO_2(C_{1-4}$ alkyl), $R^c$, $CO_2R^6$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $OC(O)C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, $—CONH(C_{1-4}$ alkyl), $—CON(C_{1-4}$ alkyl)$_2$, $—CONH—C_{1-4}$ alkylene-$O(C_{1-4}$ alkyl), $—CONH—C_{1-4}$ alkylene-$N(C_{1-4}$ alkyl)$_2$, $—CONH—C_{1-4}$ alkylene-N $(C_{1-4}$ alkyl)$_2$, $—C_{1-4}$ alkylene-$O—P(O)(OH)_2$, $—NHCO_2(C_{1-4}$ alkyl), $—R^c$, $COR^c$, $CO_2R^c$, and $CONHR^c$, wherein said alkyl and alkoxy are substituted with $R^d$;

$R^c$, at each occurrence, is independently selected from $—(CH_2)_n—C_{3-6}$ cycloalkyl, $—(CH_2)_n$-phenyl, and $—(CH_2)_n$-5- to 6-membered heterocycle containing carbon atoms and 1-4 heteroatoms selected from the group consisting of: N, NH, N($C_{1-4}$ alkyl), O, and S(O)$_p$; wherein each ring moiety is substituted with 0-2 $R^d$;

$R^d$, at each occurrence, is independently selected from =O, halogen, —OH, $C_{1-4}$ alkyl, $NH_2$, NH($C_{1-4}$ alkyl), N($C_{1-4}$ alkyl)$_2$, $C_{1-4}$ alkoxy, and —NHCO($C_{1-4}$ alkyl), and a heterocycle containing carbon atoms and 1-4 heteroatoms selected from the group consisting of: N, NH, N($C_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (IV) or (IVa) or stereoisomers, enantiomers, diastereoisomers, tautomers, pharmaceutically-acceptable salts, sovates, or prodrugs, wherein:

$R^1$ is selected from

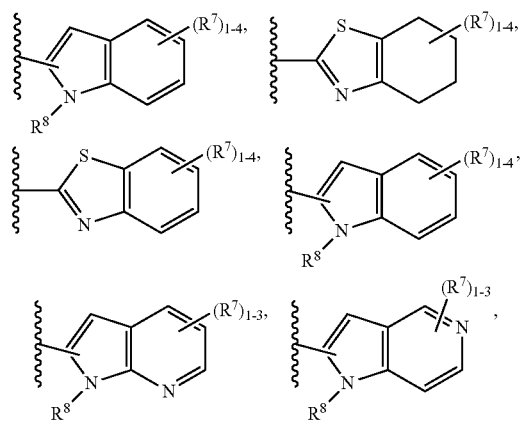

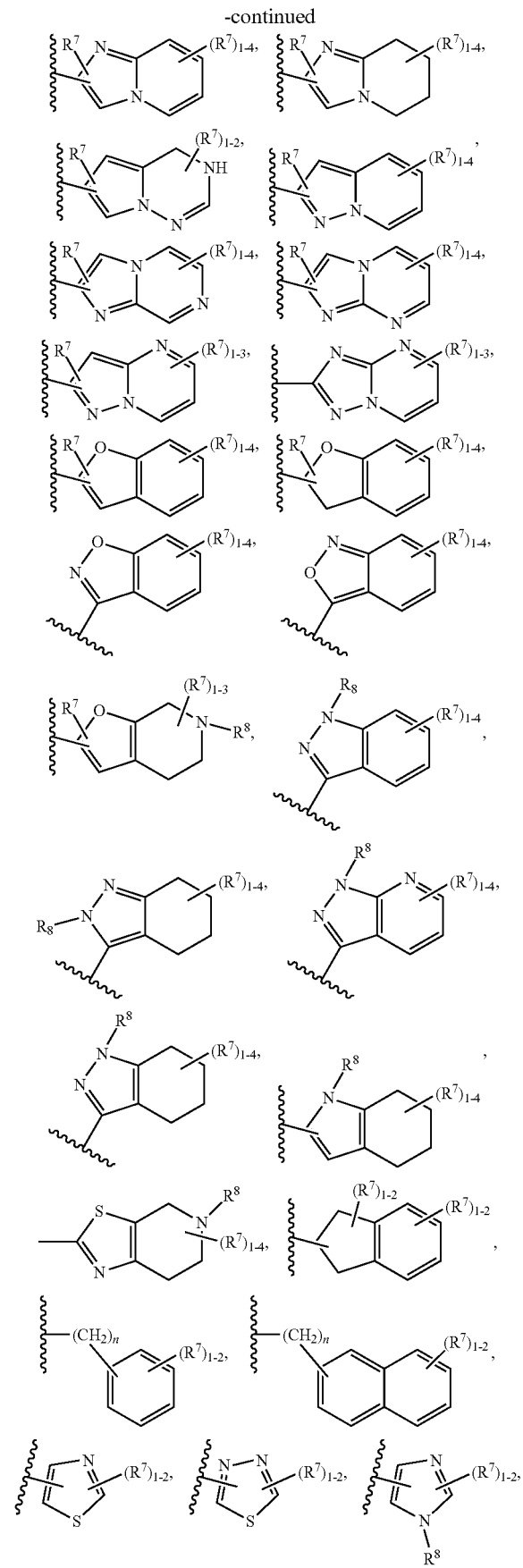

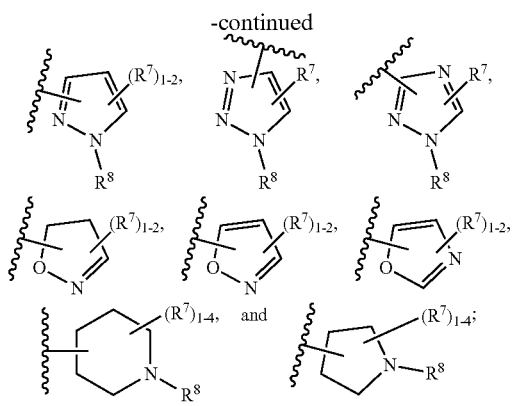

R[7], at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, —(CH$_2$)$_n$—C(O)NR$^a$R$^a$, C(O)OC$_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, CN, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —(CH$_2$)$_n$NHCO(C$_{1-4}$ alkyl), —O(CH$_2$)$_n$heterocycle, —O(CH$_2$)$_{2-4}$NR$^a$R$^a$, and —(CR$^{10}$R$^{10}$)$_n$-4- to 10-membered heterocycle, wherein said alkyl, alkoxyl, carbocycle, and heterocycle are substituted with 0-4 R$^b$;

R$^{10}$, at each occurrence, is independently selected from H and C$_{1-4}$ alkyl;

R$^a$, at each occurrence, is independently selected from H and C$_{1-4}$ alkyl; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$; and R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N (C$_{1-4}$ alkyl)$_2$, and —NHCO$_2$(C$_{1-4}$ alkyl);

other variables are as defined in Formula (IV) or (IVa) above.

In another aspect, the present invention provides compounds of Formula (IV) or (IVa) or stereoisomers, enantiomers, diastereoisomers, tautomers, pharmaceutically-acceptable salts, sovates, or prodrugs, wherein:

R$^1$ is selected from

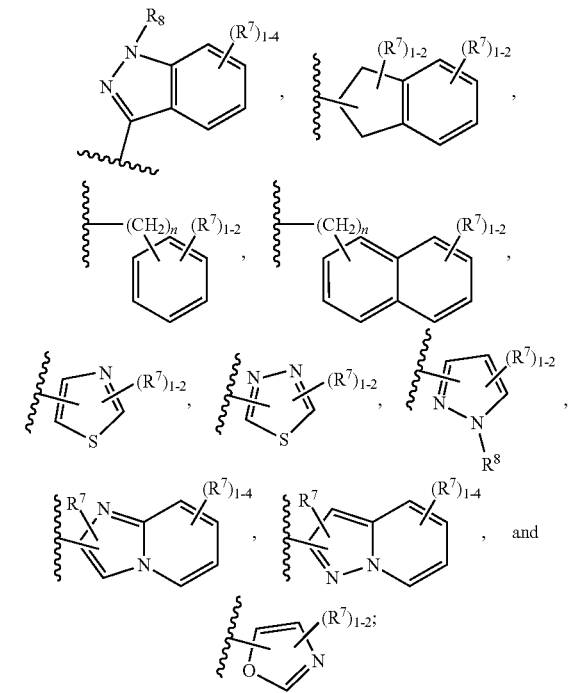

R$^7$, at each occurrence, is independently selected from H, halogen, C$_{1-4}$ alkyl, C$_{1-4}$ alkoxy, —NR$^8$R$^8$, C$_{3-6}$ cycloalkyl, phenyl, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, —(CH$_2$)$_n$—C$_{3-6}$ cycloalkyl, —(CH$_2$)$_n$-phenyl, and —(CH$_2$)$_n$-heterocycle, wherein said alkyl, cycloalkyl, phenyl, and heterocycle are substituted with 0-4 R$^9$;

alternatively, R$^8$ and R$^8$ are taken together with the nitrogen atom to which they are attached to form a heterocycle selected from

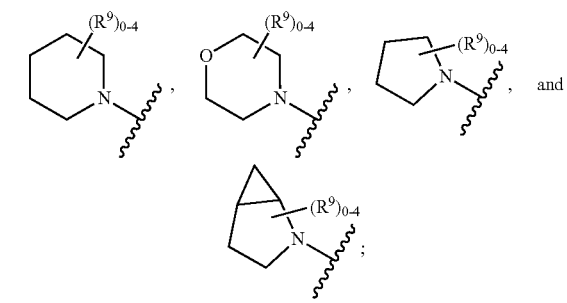

R$^9$, at each occurrence, is independently selected from F, Cl, OH, CN, C$_{1-4}$ alkyl, C$_{1-4}$ alkoxy, —(CH$_2$)$_n$NR$^a$R$^a$, and a 4- to 10-membered heterocycle, wherein said alkyl, alkoxyl, and heterocycle are substituted with 0-4 R$^b$;

$R^a$, at each occurrence, is independently selected from H, $C_{1-4}$ alkyl, —$(CH_2)_n$OH, CO($C_{1-4}$ alkyl), COCF$_3$, CO$_2$($C_{1-4}$ alkyl), —CONH$_2$, —CONH—$C_{1-4}$ alkylene-CO$_2$($C_{1-4}$ alkyl), and $C_{1-4}$ alkylene-CO$_2$($C_{1-4}$ alkyl); and $R^b$, at each occurrence, is independently selected from halogen, $C_{1-4}$ alkyl, $C_{1-4}$ alkoxy, OCF$_3$, NH$_2$, NO$_2$, N($C_{1-4}$ alkyl)$_2$, CO($C_{1-4}$ alkyl), CO($C_{1-4}$ haloalkyl), CO$_2$($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —CONH—$C_{1-4}$ alkylene-N($C_{1-4}$ alkyl)$_2$, —$C_{1-4}$ alkylene-O—P(O)(OH)$_2$, and —NHCO$_2$ ($C_{1-4}$ alkyl);

other variables are as defined in Formula (IV) or (IV) above.

In another aspect, the present invention provides compounds of Formula (V):

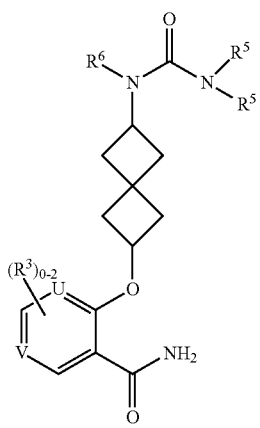

(V)

or stereoisomers, enantiomers, diastereoisomers, tautomers, pharmaceutically-acceptable salts, sovates, or prodrugs thereof, wherein:

U and V are independently selected from CH, CR$^3$, and N;

$R^5$, at each occurrence, is independently selected from H, $C_{1-4}$ alkyl, —$(CR^6R^6)_n$—$C_{3-10}$ carbocycle, and —$(CR^6R^6)_n$-4 to 10-membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

alternatively, R$^5$ and R$^5$ are taken together with the nitrogen atom to which they are attached to form a 4- to 10-membered heterocycle substituted with 1-4 R$^7$;

$R^7$, at each occurrence, is independently selected from H, =O, NO$_2$, halogen, $C_{1-4}$ alkyl, $C_{1-4}$ alkoxy, CN, OH, CF$_3$, —$(CH_2)_n$—CO$_2$H, —$(CH_2)_n$—CO$_2$($C_{1-4}$ alkyl), —$(CH_2)_n$—NR$^8$R$^8$, —NHCO($C_{1-4}$ alkyl), —NHCOCF$_3$, —NHCO$_2$($C_{1-4}$ alkyl), —NHCO$_2$(CH$_2$)$_2$O($C_{1-4}$ alkyl), —NHCO$_2$(CH$_2$)$_3$O($C_{1-4}$ alkyl), —NHCO$_2$(CH$_2$)$_2$OH, —NHCO$_2$(CH$_2$)$_2$NH$_2$, —NHCO$_2$(CH$_2$)$_2$N($C_{1-4}$ alkyl)$_2$, —NHCO$_2$CH$_2$CO$_2$H, —CH$_2$NHCO($C_{1-4}$ alkyl), —NHC(O)NR$^8$R$^8$, —NHSO$_2$($C_{1-4}$ alkyl), —SO$_2$NH$_2$, —SO$_2$NH ($C_{1-4}$ alkyl), —SO$_2$N($C_{1-4}$ alkyl)$_2$, —SO$_2$NH(CH$_2$)$_2$OH, —SO$_2$NH(CH$_2$)$_2$O($C_{1-4}$ alkyl), —$(CH_2)_n$—CONR$^8$R$^8$, —O(CH$_2$)$_n$-carbocycle, —O(CH$_2$)$_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

$R^8$, at each occurrence, is independently selected from H, $C_{1-4}$ alkyl, C(O)$C_{1-4}$alkyl, C(O)carbocycle, C(O)heterocycle, —$(CH_2)_n$C(O)NR$^a$R$^a$, C(O)O$C_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —$(CH_2)_n$-carbocycle, and —$(CH_2)_n$-heterocycle, wherein said alkyl, carbocycle, and heterocycle are substituted with 0-4 R$^9$;

$R^9$, at each occurrence, is independently selected from halogen, OH, CN, NO$_2$, CHF$_2$, CF$_3$, $C_{1-4}$ alkyl, $C_{1-4}$ alkoxy, CH$_2$OH, CO($C_{1-4}$ alkyl), CO$_2$H, CO$_2$($C_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO($C_{1-4}$ alkyl), —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

$R^{10}$, at each occurrence, is independently selected from H and $C_{1-4}$ alkyl;

$R^a$, at each occurrence, is independently selected from H, $C_{1-4}$ alkyl, —$(CH_2)_n$OH, CO($C_{1-4}$ alkyl), COCF$_3$, CO$_2$($C_{1-4}$ alkyl), —CONH$_2$, —CONH—$C_{1-4}$ alkylene-CO$_2$($C_{1-4}$ alkyl), $C_{1-4}$ alkylene-CO$_2$($C_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

$R^b$, at each occurrence, is independently selected from =O, halogen, $C_{1-4}$ alkyl, $C_{1-4}$ alkoxy, OCF$_3$, NH$_2$, NO$_2$, N($C_{1-4}$ alkyl)$_2$, CO($C_{1-4}$ alkyl), CO($C_{1-4}$ haloalkyl), CO$_2$ ($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —CONH—$C_{1-4}$ alkylene-N ($C_{1-4}$ alkyl)$_2$, —$C_{1-4}$ alkylene-O—P(O)(OH)$_2$, —NHCO$_2$($C_{1-4}$ alkyl), —R$^c$, COR$^c$, CO$_2$R$^c$, and CONHR$^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and S(O)$_p$; wherein each ring moiety is substituted with 0-2 R$^d$;

$R^d$, at each occurrence, is independently selected from =O, halogen, —OH, $C_{1-4}$ alkyl, NH$_2$, NH($C_{1-4}$ alkyl), N($C_{1-4}$ alkyl)$_2$, $C_{1-4}$ alkoxy, and —NHCO($C_{1-4}$ alkyl), and a heterocycle containing carbon atoms and 1-4 heteroatoms selected from the group consisting of: N, NH, N($C_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (Va):

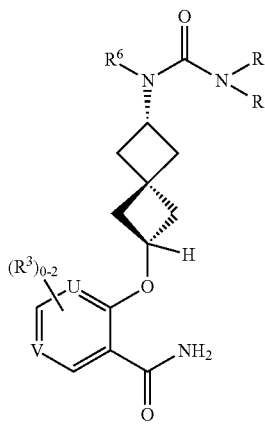

(Va)

or stereoisomers, enantiomers, diastereoisomers, tautomers, pharmaceutically-acceptable salts, sovates, or prodrugs thereof, wherein:

U and V are independently selected from CH, $CR^3$, and N;

$R^5$, at each occurrence, is independently selected from H, $C_{1-4}$ alkyl, —$(CR^6R^6)_n$—$C_{3-10}$ carbocycle, and —$(CR^6R^6)_n$-4 to 10-membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form a 4- to 10-membered heterocycle substituted with 1-4 $R^7$;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, —$(CH_2)_nC(O)NR^aR^a$, $C(O)OC_{1-4}$alkyl, $C(O)O$-carbocycle, $C(O)O$-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_nNR^aR^a$, —$(CHR^{10})_nCONR^aR^a$, —$(CHR^{10})_nNR^aCO(C_{1-4}$ alkyl), —$O(CHR^{10})_n$carbocycle, —$O(CHR^{10})_n$heterocycle, —$O(CHR^{10})_nNR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, —$CONH$—$C_{1-4}$ alkylene-N $(C_{1-4}$ alkyl)$_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4; and p, at each occurrence, is independently selected from 0, 1, and 2.

In another aspect, the present invention provides compounds of Formula (V) or (Va) or stereoisomers, enantiomers, diastereoisomers, tautomers, pharmaceutically-acceptable salts, sovates, or prodrugs thereof, wherein:

$R^5$ is selected from H, $C_{1-4}$ alkyl, —$(CH_2)_n$—$C_{3-10}$ carbocycle, —$(CH_2)_n$-aryl, —$(CH_2)_n$-4- to 10-membered heterocycle selected from

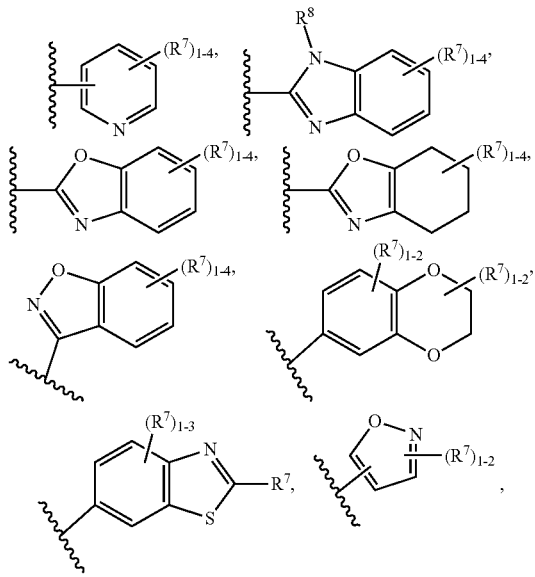

-continued

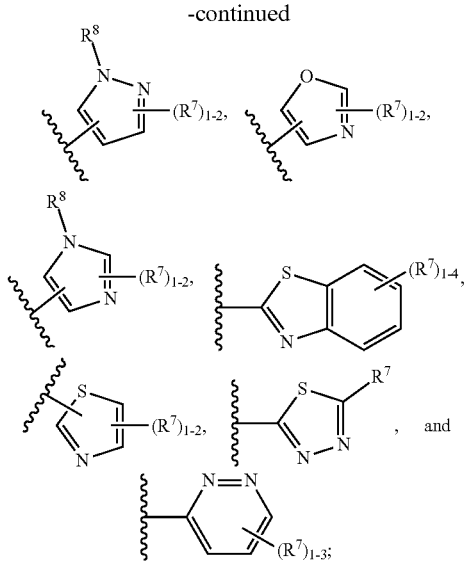

wherein said alkyl, cycloalkyl, aryl are substituted with 1-4 R$^7$;

alternatively, R$^5$ and R$^5$ are taken together with the nitrogen atom to which they are attached to form a heterocycle selected from

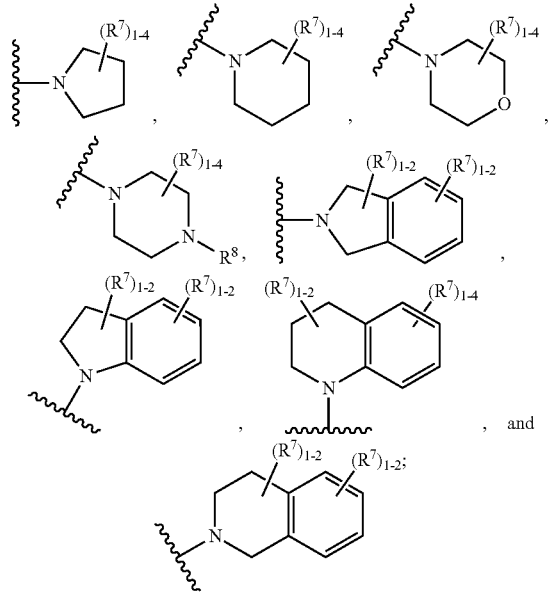

R$^7$, at each occurrence, is independently selected from H, halogen, C$_{1-4}$ alkyl, C$_{1-4}$ alkoxy, CN, OH, CF$_3$, —NR$^8$R$^8$, —(CH$_2$)$_n$-carbocycle, and —(CH$_2$)$_n$-heterocycle, wherein said alkyl, alkoxyl, carbocycle, and heterocycle are substituted with 0-4 R$^9$.

R$^8$, at each occurrence, is independently selected from H and C$_{1-4}$ alkyl; and R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —NH$_2$, and a 4- to 10-membered heterocycle; and other variables are as defined in Formula (V) or (Va) above.

In another aspect, the present invention provides compounds of Formula (VI):

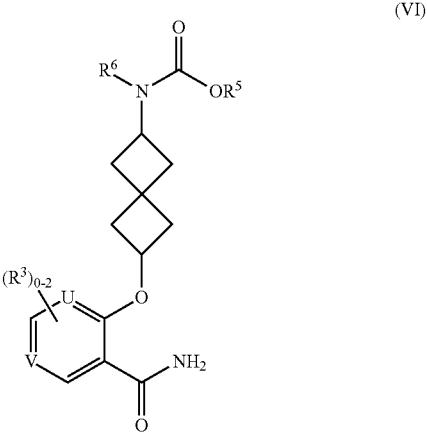

(VI)

or stereoisomers, enantiomers, diastereoisomers, tautomers, pharmaceutically-acceptable salts, sovates, or prodrugs thereof, wherein:

U and V are independently selected from CH, CR$^3$, and N;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4 to 10-membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, —(CH$_2$)$_n$C(O)NR$^a$R$^a$, C(O)OC$_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N (C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (VIa):

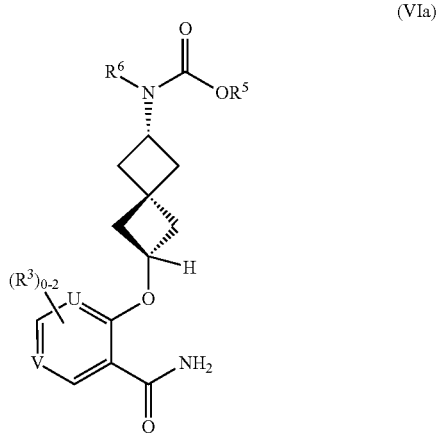

(VIa)

or stereoisomers, enantiomers, diastereoisomers, tautomers, pharmaceutically-acceptable salts, sovates, or prodrugs thereof, wherein:

U and V are independently selected from CH, CR$^3$, and N;

R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4 to 10-membered heterocycle comprising carbon atoms and 1-4 heteroatoms selected from N, NR$^8$, O, and S(O)$_p$, wherein said alkyl, carbocycle, and heterocycle are substituted with 1-4 R$^7$;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, C(O)C$_{1-4}$alkyl, C(O)carbocycle, C(O)heterocycle, —(CH$_2$)$_n$C(O)NR$^a$R$^a$, C(O)OC$_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N (C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (VII):

(VII)

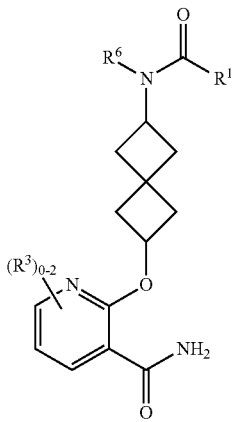

or stereoisomers, enantiomers, diastereoisomers, tautomers, pharmaceutically-acceptable salts, sovates, or prodrugs thereof, wherein:

$R^1$ is selected from

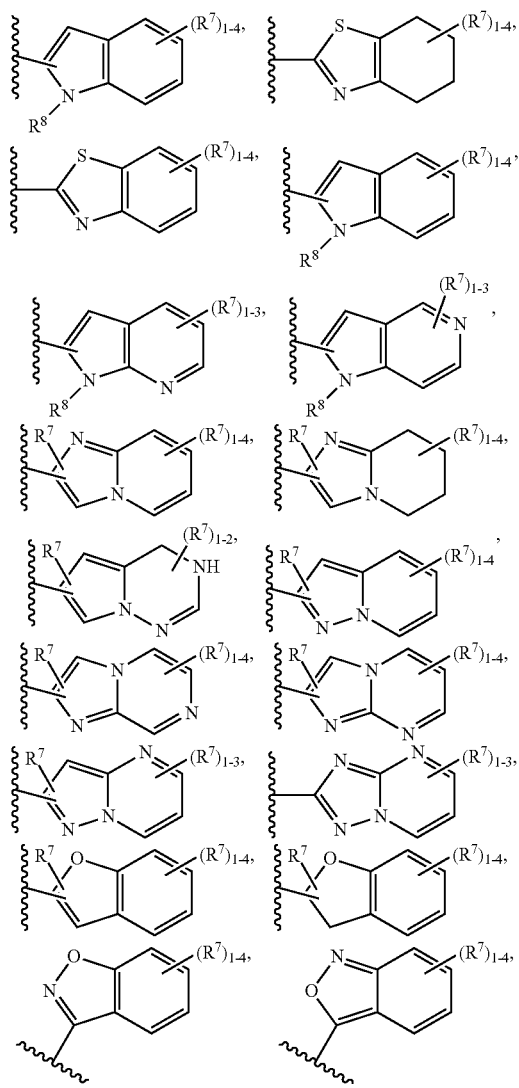

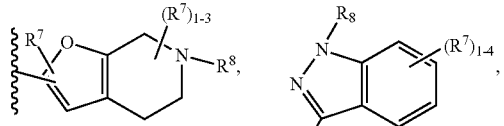

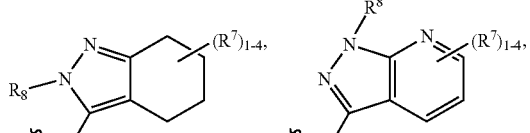

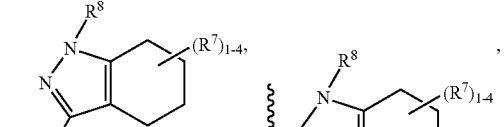

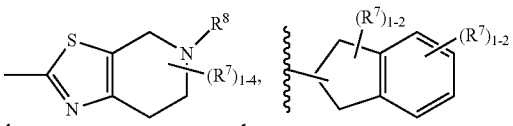

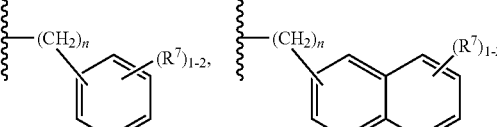

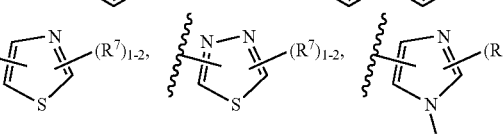

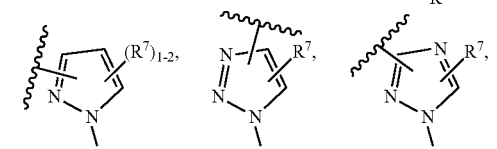

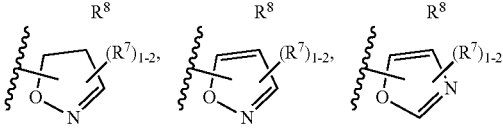

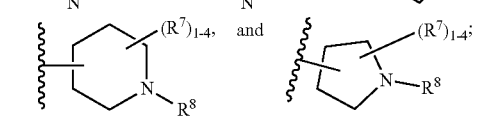

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, —$(CH_2)_n$—$C(O)NR^aR^a$, $C(O)OC_{1-4}$alkyl, $C(O)O$-carbocycle, $C(O)O$-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$(CH_2)_nNHCO(C_{1-4}$ alkyl), —$O(CH_2)_n$heterocycle, —$O(CH_2)_{2-4}NR^aR^a$, and —$(CR^{10}R^{10})_n$-4- to 10-membered heterocycle, wherein said alkyl, alkoxyl, carbocycle, and heterocycle are substituted with 0-4 $R^b$;

$R^{10}$, at each occurrence, is independently selected from H and $C_{1-4}$ alkyl;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2$ ($C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, —$CONH$—$C_{1-4}$ alkylene-N $(C_{1-4}$ alkyl)$_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and a heterocycle containing carbon atoms and 1-4 heteroatoms selected from the group consisting of: N, NH, N(Cu alkyl), O, and $S(O)_p$;

n, at each occurrence, is independently selected from 0, 1, 2, 3, and 4; and p, at each occurrence, is independently selected from 0, 1, and 2.

In another aspect, the present invention provides compounds of Formula (VIIa):

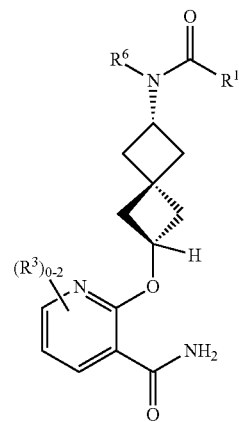

(VIIa)

or stereoisomers, enantiomers, diastereoisomers, tautomers, pharmaceutically-acceptable salts, sovates, or prodrugs thereof, wherein:

$R^1$ is selected from

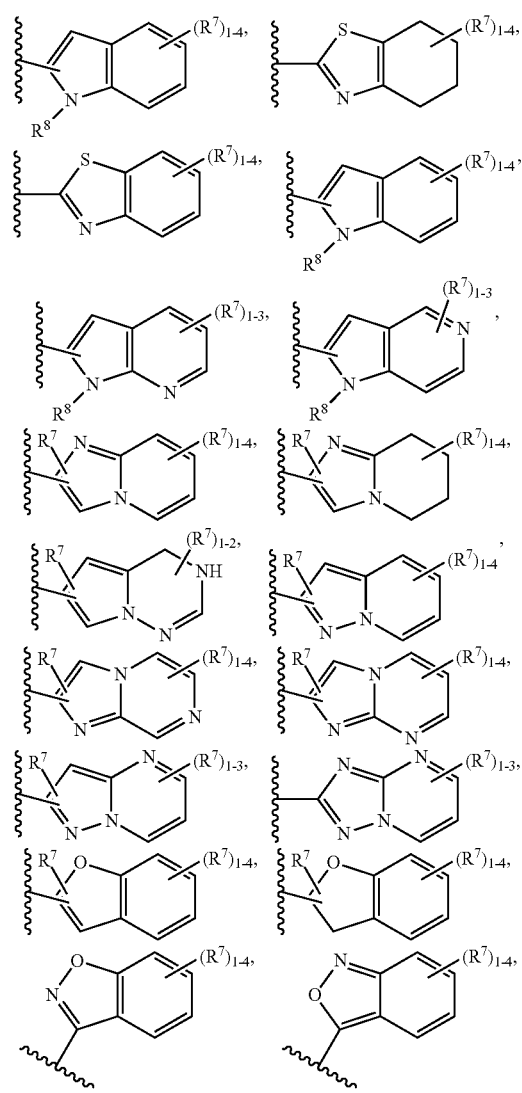

-continued

[chemical structures]

R⁷, at each occurrence, is independently selected from H, =O, NO₂, halogen, C₁₋₄ alkyl, C₁₋₄ alkoxy, CN, OH, CF₃, —(CH₂)$_n$—CO₂H, —(CH₂)$_n$—CO₂(C₁₋₄ alkyl), —(CH₂)$_n$—NR⁸R⁸, —NHCO(C₁₋₄ alkyl), —NHCOCF₃, —NHCO₂(C₁₋₄ alkyl), —NHCO₂(CH₂)₂O(C₁₋₄ alkyl), —NHCO₂(CH₂)₃O(C₁₋₄ alkyl), —NHCO₂(CH₂)₂OH, —NHCO₂(CH₂)₂NH₂, —NHCO₂(CH₂)₂N(C₁₋₄ alkyl)₂, —NHCO₂CH₂CO₂H, —CH₂NHCO₂(C₁₋₄ alkyl), —NHC(O)NR⁸R⁸, —NHSO₂(C₁₋₄ alkyl), —SO₂NH₂, —SO₂NH(C₁₋₄ alkyl), —SO₂N(C₁₋₄ alkyl)₂, —SO₂NH(CH₂)₂OH, —SO₂NH(CH₂)₂O(C₁₋₄ alkyl), —(CH₂)$_n$—CONR⁸R⁸, —O(CH₂)$_n$-carbocycle, —O(CH₂)$_n$-heterocycle, —NHCO-carbocycle, —NHCO-heterocycle, —(CH₂)$_n$-carbocycle, and —(CH₂)$_n$-heterocycle comprising carbon atoms and 1-4 heteroatoms selected from N, NR⁸, O, and S(O)$_p$, wherein said alkyl, alkenyl, alkynyl, alkoxyl, carbocycle, and heterocycle are substituted with 0-4 R⁹;

R⁸, at each occurrence, is independently selected from H, C₁₋₄ alkyl, C(O)C₁₋₄alkyl, C(O)carbocycle, C(O)heterocycle, —(CH₂)$_n$—C(O)NR$^a$R$^a$, C(O)OC₁₋₄alkyl, C(O)O-carbocycle, C(O)O-heterocycle, SO₂alkyl, SO₂carbocycle, SO₂heterocycle, SO₂NR$^a$R$^a$, —(CH₂)$_n$-carbocycle, and —(CH₂)$_n$-heterocycle, wherein said alkyl, carbocycle, and heterocycle are substituted with 0-4 R⁹;

alternatively, R⁸ and R⁸ are taken together with the nitrogen atom to which they are attached to form a 4- to 10-membered heterocycle substituted with 0-4 R⁹;

R⁹, at each occurrence, is independently selected from halogen, OH, CN, NO₂, CHF₂, CF₃, C₁₋₄ alkyl, C₁₋₄ alkoxy, CH₂OH, CO₂H, CO₂(C₁₋₄ alkyl), CONH₂, —(CH₂)$_n$NR$^a$R$^a$, —(CH₂)$_n$CONR$^a$R$^a$, —(CH₂)$_n$NHCO(C₁₋₄ alkyl), —O(CH₂)$_n$heterocycle, —O(CH₂)₂₋₄NR$^a$R$^a$, and —(CR¹⁰R¹⁰)$_n$-4- to 10-membered heterocycle, wherein said alkyl, alkoxyl, carbocycle, and heterocycle are substituted with 0-4 R$^b$;

R¹⁰, at each occurrence, is independently selected from H and C₁₋₄ alkyl;

R$^a$, at each occurrence, is independently selected from H, C₁₋₄ alkyl, —(CH₂)$_n$OH, CO(C₁₋₄ alkyl), COCF₃, CO₂(C₁₋₄ alkyl), —CONH₂, —CONH—C₁₋₄ alkylene-CO₂(C₁₋₄ alkyl), C₁₋₄ alkylene-CO₂(C₁₋₄ alkyl), R$^c$, CO₂R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, halogen, C₁₋₄ alkyl, C₁₋₄ alkoxy, OCF₃, NH₂, NO₂, N(C₁₋₄ alkyl)₂, CO(C₁₋₄ alkyl), CO(C₁₋₄ haloalkyl), CO₂(C₁₋₄ alkyl), CONH₂, —CONH(C₁₋₄ alkyl), —CON(C₁₋₄ alkyl)₂, —CONH—C₁₋₄ alkylene-O(C₁₋₄ alkyl), —CONH—C₁₋₄ alkylene-N(C₁₋₄ alkyl)₂, —CONH—C₁₋₄ alkylene-N(C₁₋₄ alkyl)₂, —C₁₋₄ alkylene-O—P(O)(OH)₂, —NHCO₂(C₁₋₄ alkyl), —R$^c$, COR$^c$, CO₂R$^c$, and CONHR$^c$;

R$^c$, at each occurrence, is independently selected from —(CH₂)$_n$—C₃₋₆ cycloalkyl, —(CH₂)$_n$-phenyl, and —(CH₂)$_n$-5- to 6-membered heterocycle containing carbon atoms and 1-4 heteroatoms selected from the group consisting of: N, NH, N(C₁₋₄ alkyl), O, and S(O)$_p$; wherein each ring moiety is substituted with 0-2 R$^d$;

R$^d$, at each occurrence, is independently selected from =O, halogen, —OH, C₁₋₄ alkyl, NH₂, NH(C₁₋₄ alkyl), N(C₁₋₄ alkyl)₂, C₁₋₄ alkoxy, and —NHCO(C₁₋₄ alkyl), and a heterocycle containing carbon atoms and 1-4 heteroatoms selected from the group consisting of: N, NH, N(C₁₋₄ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (I):

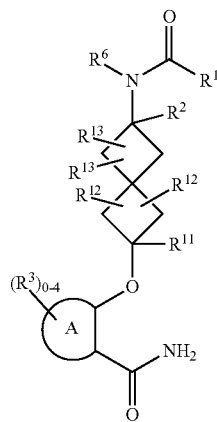

(I)

or stereoisomers, enantiomers, diastereoisomers, tautomers, pharmaceutically-acceptable salts, sovates, or prodrugs thereof, wherein:

Ring A is selected from phenyl or 6-membered heteroaryl comprising carbon atoms and 1-3 nitrogen atoms;

$R^1$ is selected from $C_{1-4}$ alkyl, $NR^5R^5$, $OR^5$, $-(CR^4R^4)_nC_{3-10}$ carbocycle and $-(CR^4R^4)_n$-4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$ is independently selected from H and $C_{1-4}$ alkyl optionally substituted with halogen, $C_{1-4}$ alkoxy, —OH, CN, —$CO_2$H, —$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$;

$R^3$, at each occurrence, is independently selected from halogen, $C_{1-6}$ alkyl, $C_{2-6}$ alkenyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl)$_2$, —$OCH_2CO_2H$, —$NHCO(C_{1-4}$ alkyl), —$NHCO_2$ ($C_{1-4}$ alkyl), —$NHSO_2(C_{1-4}$ alkyl), —$SO_2NH_2$, —$C(=NH)$ $NH_2$, a carbocycle, and a heterocycle, wherein said alkyl, $C_{2-6}$ alkenyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered heterocycle substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

$R^7$, at each occurrence, is independently selected from H, =O, $NO_2$, halogen, $C_{1-7}$ alkyl, $C_{1-4}$ alkenyl, $C_{1-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —$NHCO(C_{1-4}$ alkyl), —$NHCOCF_3$, —$NHCO_2$ ($C_{1-4}$ alkyl), —$NHCO_2(CH_2)_2O(C_{1-4}$ alkyl), —$NHCO_2$ ($CH_2)_3O(C_{1-4}$ alkyl), —$NHCO_2(CH_2)_2OH$, —$NHCO_2$ $(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC $(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, —$(CH_2)_n$ —$C(O)C_{1-4}$alkyl, —$(CH_2)_n$—$C(O)$carbocycle, —$(CH_2)_n$—$C(O)$heterocycle, —$(CH_2)_n$—$C(O)NR^aR^a$, —$(CH_2)_n$—$NR^aC(O)C_{1-4}$alkyl, —$(CH_2)_n$—$C(O)OC_{1-4}$alkyl, —$(CH_2)_n$—$C(O)C_{1-4}$alkyl, —$(CH_2)_n$—$C(O)O$-carbocycle, —$(CH_2)_n$—$C(O)O$-heterocycle, —$(CH_2)_n$—$SO_2$alkyl, —$(CH_2)_n$$SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, alkenyl, alkynyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, $CO_2(C_{1-4}$ alkyl), —$(CHR^{10})_n$ $NR^aR^a$, $S(O)_p(C_{1-4}$ alkyl), —$(CHR^{10})_n$$CONR^aR^a$, —$(CHR^{10})_n$$NR^dCO(C_{1-4}$ alkyl), —$(CHR^{10})_n$$OCONR^a$ $(CH_2)_nCO_2R^a$, $S(O)_pC_{1-4}$alkyl, $S(O)_pNR^aR^a$, —$O$ $(CHR^{10})_n$carbocycle, —$O(CHR^{10})_n$heterocycle, —$O(CHR^{10})_n$$NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^{11}$ is independently selected from H and $C_{1-3}$ alkyl optionally substituted with halogen, $C_{1-4}$ alkoxy, —OH, CN, —$CO_2H$, —$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$;

$R^{12}$ and $R^{13}$ are independently selected from H, OH, —$OC_{1-3}$ alkyl substituted with 0-4 $R^d$, $C_{1-3}$ alkyl with substituted with 0-4 $R^d$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)$ $C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2H$, $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$NHC_{1-4}$ alkyl, —$CONH$—$C_{1-4}$ alkylene-$N(C_{1-4}$ alkyl)$_2$, —$C_{1-4}$ alkylene-O—P(O)(OH)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl);

n, at each occurrence, is independently selected from 0, 1, 2, 3, and 4; and p, at each occurrence, is independently selected from 0, 1, and 2.

In another aspect, the present invention provides compounds of Formula (II):

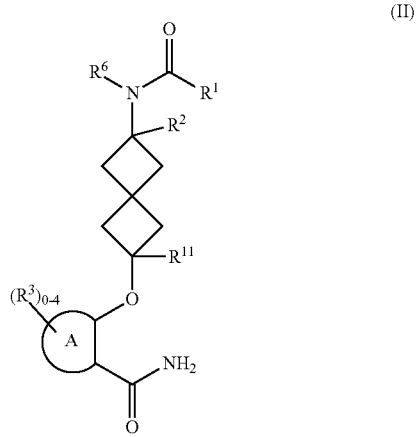

(II)

or stereoisomers, enantiomers, diastereoisomers, tautomers, pharmaceutically-acceptable salts, sovates, or prodrugs thereof, wherein:

Ring A is selected from phenyl or 6-membered heteroaryl comprising carbon atoms and 1-2 nitrogen atoms:

R$^1$ is selected from NR$^5$R$^5$, OR$^5$, —(CR$^4$R$^4$)$_n$C$_{3-10}$ carbocycle and —(CR$^4$R$^4$)$_n$-4- to 12-membered heterocycle comprising carbon atoms and 1-4 heteroatoms selected from N, NR$^8$, O, and S(O)$_p$; wherein said carbocycle, and heterocycle are substituted with 1-4 R$^7$;

R$^2$ is independently selected from H and C$_{1-5}$ alkyl optionally substituted with halogen, C$_{1-4}$ alkoxy, —OH, and CN, R$^3$, at each occurrence, is independently selected from halogen, C$_{1-6}$ alkyl, C$_{2-6}$ alkenyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$ (C$_{1-4}$ alkyl), —NHSO$_2$(C$_{1-4}$ alkyl), —SO$_2$NH$_2$, —C(=NH) NH$_2$, a carbocycle, and a heterocycle, wherein said alkyl, C$_{2-6}$ alkenyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, a carbocycle, and a heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$- 4- to 10-membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form a 4- to 15-membered heterocycle substituted with 1-4 R$^7$;

R$^6$, at each occurrence, is independently selected from H, C$_{1-4}$ alkyl, CH$_2$NH$_2$, C$_{1-4}$ haloalkyl, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), a carbocycle, and a heterocycle, wherein said alkyl, alkoxy, haloalkyl, carbocycle, and heterocycle are substituted with 0-4 R$^9$;

R$^7$, at each occurrence, is independently selected from H, =O, NO$_2$, halogen, C$_{1-4}$ alkyl, C$_{2-4}$ alkenyl, C$_{1-4}$ alkynyl, C$_{1-4}$ alkoxy, CN, OH, CHF$_2$, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCOH, —NHCO(C$_{1-4}$ alkyl), —NHCOCF$_3$, —NHCO$_2$ (C$_{1-4}$ alkyl), —NHCO$_2$(CH$_2$)$_2$O(C$_{1-4}$ alkyl), —NHCO$_2$ (CH$_2$)$_3$O(C$_{1-4}$ alkyl), —NHCO$_2$(CH$_2$)$_2$OH, —NHCO$_2$ (CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC (O)NR$^8$R$^8$, —NHSO$_2$(C$_{1-4}$ alkyl), —S(O)$_p$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-6}$ alkyl, C$_{2-4}$ alkenyl, C$_{2-4}$ alkynyl, —(CH$_2$)$_n$—C (O)C$_{1-4}$alkyl, —(CH$_2$)$_n$—C(O)carbocycle, —(CH$_2$)$_n$—C (O)heterocycle, —(CH$_2$)$_n$—C(O)NR$^a$R$^a$, —(CH$_2$)$_n$—NR$^a$C (O)C$_{1-4}$alkyl, —(CH$_2$)$_n$—C(O)OC$_{1-4}$alkyl, —(CH$_2$)$_n$—C (O)C$_{1-4}$alkyl, —(CH$_2$)$_n$—C(O)O-carbocycle, —(CH$_2$)$_n$—C (O)O-heterocycle, —(CH$_2$)$_n$—SO$_2$alkyl, —(CH$_2$)$_n$ SO$_2$carbocycle, —(CH$_2$)$_n$—SO$_2$heterocycle, —(CH$_2$)$_n$ SO$_2$NR$^a$R$^a$, —(CH$_2$)$_n$-carbocycle, and —(CH$_2$)$_n$-heterocycle, wherein said alkyl, alkenyl, alkynyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, =O, CN, NO$_2$, C$_{1-4}$ alkyl, C$_{1-4}$ alkoxy, CO(C$_{1-4}$ alkyl), CO$_2$H, CO$_2$(C$_{1-4}$ alkyl), —(CHR$^{10}$)$_n$ NR$^a$R$^a$, S(O)$_p$(C$_{1-4}$ alkyl), —(CHR$^{10}$)$_n$CONR$^a$R$^a$, —(CHR$^{10}$)$_n$NR$^a$CO(C$_{1-4}$ alkyl), —(CHR$^{10}$)$_n$OCONR$^a$ (CH$_2$)$_n$CO$_2$R$^a$, S(O)$_p$C$_{1-4}$alkyl, S(O)$_p$NR$^a$R$^a$, —O (CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^{11}$ is independently selected from H and C$_{1-3}$ alkyl optionally substituted with halogen, C$_{1-4}$ alkoxy, —OH, and CN;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, OC(O) C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$H, CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl);

n, at each occurrence, is independently selected from 0, 1, 2, 3, and 4; and p, at each occurrence, is independently selected from 0, 1, and 2.

In another aspect, the present invention provides compounds of Formula (III):

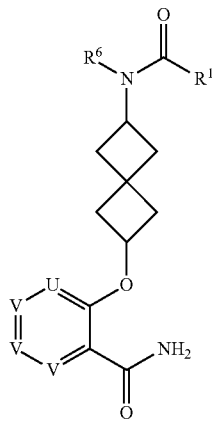

(III)

or stereoisomers, enantiomers, diastereoisomers, tautomers, pharmaceutically-acceptable salts, sovates, or prodrugs thereof, wherein:

U and V are independently selected from CH, CR$^3$, and N;

R$^1$ is selected from NR$^5$R$^5$, OR$^5$, —(CR$^4$R$^4$)$_n$C$_{3-10}$ carbocycle and —(CR$^4$R$^4$)$_n$-4- to 15-membered heterocycle comprising carbon atoms and 1-4 heteroatoms selected from N, NR$^8$, O, and S(O)$_p$; wherein said carbocycle, and heterocycle are substituted with 1-4 R$^7$;

R$^3$, at each occurrence, is independently selected from halogen, C$_{1-6}$ alkyl, C$_{2-6}$ alkenyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$ (C$_{1-4}$ alkyl), —NHSO$_2$(C$_{1-4}$ alkyl), —SO$_2$NH$_2$, —C(=NH) NH$_2$, a carbocycle, and a heterocycle, wherein said alkyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, a carbocycle, and a heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$-4- to 10-membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form a 4- to 15-membered heterocycle substituted with 1-4 R$^7$;

R$^6$, at each occurrence, is independently selected from H, C$_{1-4}$ alkyl, CH$_2$NH$_2$, C$_{1-4}$ haloalkyl, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), a carbocycle, and a heterocycle, wherein said alkyl, alkoxy, haloalkyl, carbocycle, and heterocycle are substituted with 0-4 R$^9$;

R$^7$, at each occurrence, is independently selected from H, =O, NO$_2$, halogen, C$_{1-4}$ alkyl, C$_{2-4}$ alkenyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCOH, —NHCO(C$_{1-4}$ alkyl), —NHCOCF$_3$, —NHCO$_2$(C$_{1-4}$ alkyl), —NHCO$_2$ (CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$ (CH$_2$)$_2$N(C$_{1-4}$ alkyl)$_2$, —NHCO$_2$CH$_2$CO$_2$H, —CH$_2$NHCO$_2$ (C$_{1-4}$ alkyl), —NHC(O)NR$^8$R$^8$, —NHSO$_2$(C$_{1-4}$ alkyl), —S(O)$_p$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH (CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkoxyl, a carbocycle, and a heterocycle are substituted with 0-4 R$^9$;

R$^8$, at each occurrence, is independently selected from H, C$_{1-4}$ alkyl, C$_{2-4}$ alkenyl, C$_{2-4}$ alkynyl, —(CH$_2$)$_n$ —C(O)C$_{1-4}$alkyl, —(CH$_2$)$_n$—C(O)carbocycle, —(CH$_2$)$_n$—C(O)heterocycle, —(CH$_2$)$_n$—C(O)NR$^a$R$^a$, —(CH$_2$)$_n$—NR$^a$C(O)C$_{1-4}$alkyl, —(CH$_2$)$_n$—C(O)OC$_{1-4}$alkyl, —(CH$_2$)$_n$—C(O)C$_{1-4}$alkyl, —(CH$_2$)$_n$—C(O)O-carbocycle, —(CH$_2$)$_n$—C(O)O-heterocycle, —(CH$_2$)$_n$—SO$_2$alkyl, —(CH$_2$)$_n$ SO$_2$carbocycle, —(CH$_2$)$_n$—SO$_2$heterocycle, —(CH$_2$)$_n$—SO$_2$NR$^a$R$^a$, —(CH$_2$)$_n$-carbocycle, and —(CH$_2$)$_n$-heterocycle, wherein said alkyl, alkenyl, alkynyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, =O, CN, NO$_2$, C$_{1-4}$ alkyl, C$_{1-4}$ alkoxy, CO(C$_{1-4}$ alkyl), CO$_2$H, CO$_2$(C$_{1-4}$ alkyl), —(CHR$^{10}$)$_n$ NR$^a$R$^a$, S(O)$_p$(C$_{1-4}$ alkyl), —(CHR$^{10}$)$_n$CONR$^a$R$^a$, —(CHR$^{10}$)$_n$NR$^a$CO(C$_{1-4}$ alkyl), —(CHR$^{10}$)$_n$OCONR$^a$ (CH$_2$)$_n$CO$_2$R$^a$, S(O)$_p$C$_{1-4}$alkyl, S(O)$_p$NR$^a$R$^a$, —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, OC(O)C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$H, CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (IV):

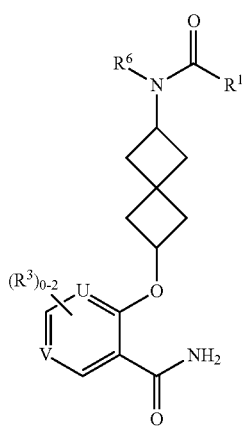

(IV)

or stereoisomers, enantiomers, diastereoisomers, tautomers, pharmaceutically-acceptable salts, sovates, or prodrugs thereof, wherein:

U and V are independently selected from CH, CR$^3$, and N; provided at least one of U and V is N;

R$^1$ is selected from —(CH$_2$)$_n$—C$_{3-10}$ carbocycle, and —(CH$_2$)$_n$-5- to 14-membered heterocycle, wherein said carbocycle and heterocycle are substituted with 1-4 R$^7$;

R$^3$, at each occurrence, is independently selected from halogen, C$_{1-6}$ alkyl, and C$_{1-4}$ alkoxy;

R$^6$, at each occurrence, is independently selected from H and C$_{1-4}$ alkyl;

R$^7$, at each occurrence, is independently selected from H, =O, NO$_2$, halogen, C$_{1-6}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCOH, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —S(O)$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NH CO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, C$_{2-4}$ alkenyl, C(O)C$_{1-4}$alkyl, C(O)carbocycle, C(O)heterocycle, —(CH$_2$)$_n$—C(O)NR$^a$R$^a$, —(CH$_2$)$_n$—NR$^a$C(O)C$_{1-4}$alkyl, C(O)OC$_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, alkenyl, carbocycle, and heterocycle are substituted with 0-4 R$^9$;

R$^9$, at each occurrence, is independently selected from halogen, OH, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$ heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, OC(O)C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —NHCO$_2$(C$_{1-4}$ alkyl), —R$^c$, COR$^c$, CO$_2$R$^c$, and CONHR$^c$, w herein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(Cu alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (IVb):

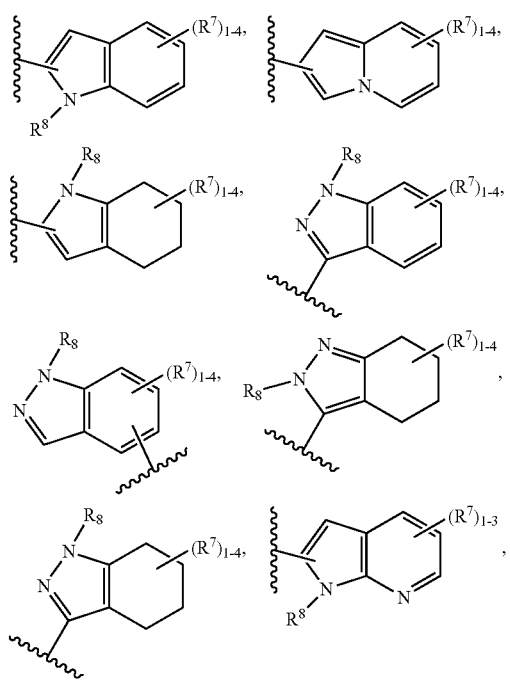

(IVb)

or stereoisomers, enantiomers, diastereoisomers, tautomers, pharmaceutically-acceptable salts, sovates, or prodrugs thereof, wherein:

R$^1$ is selected from

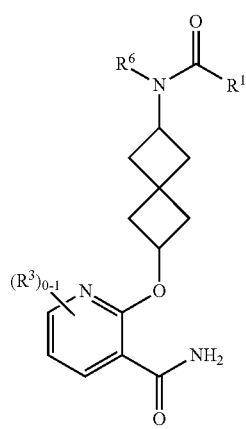

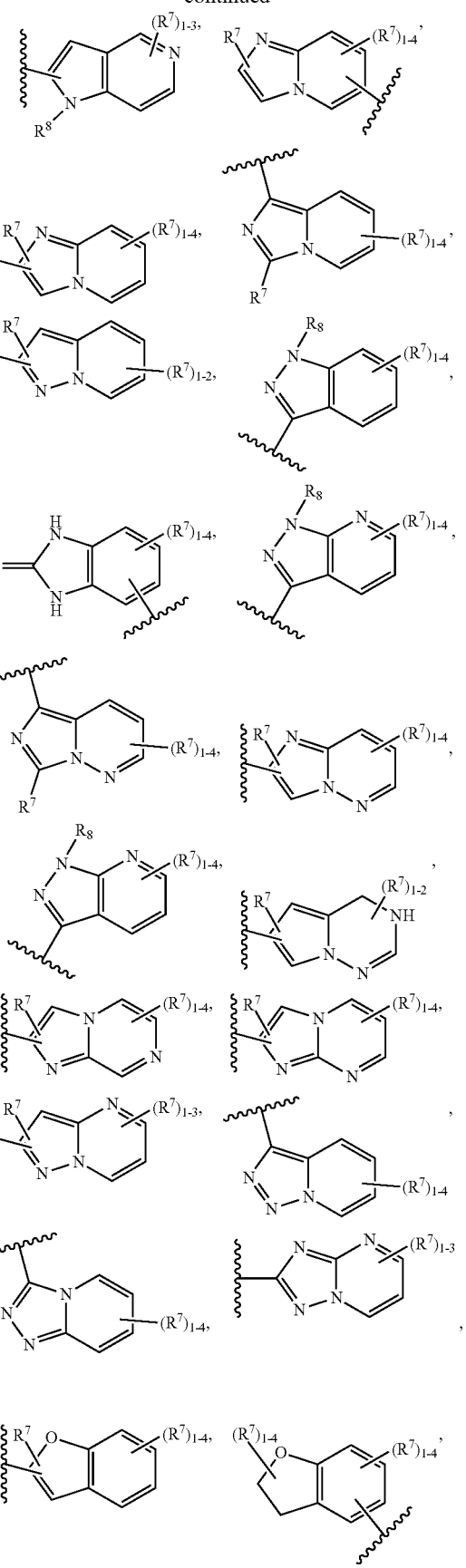

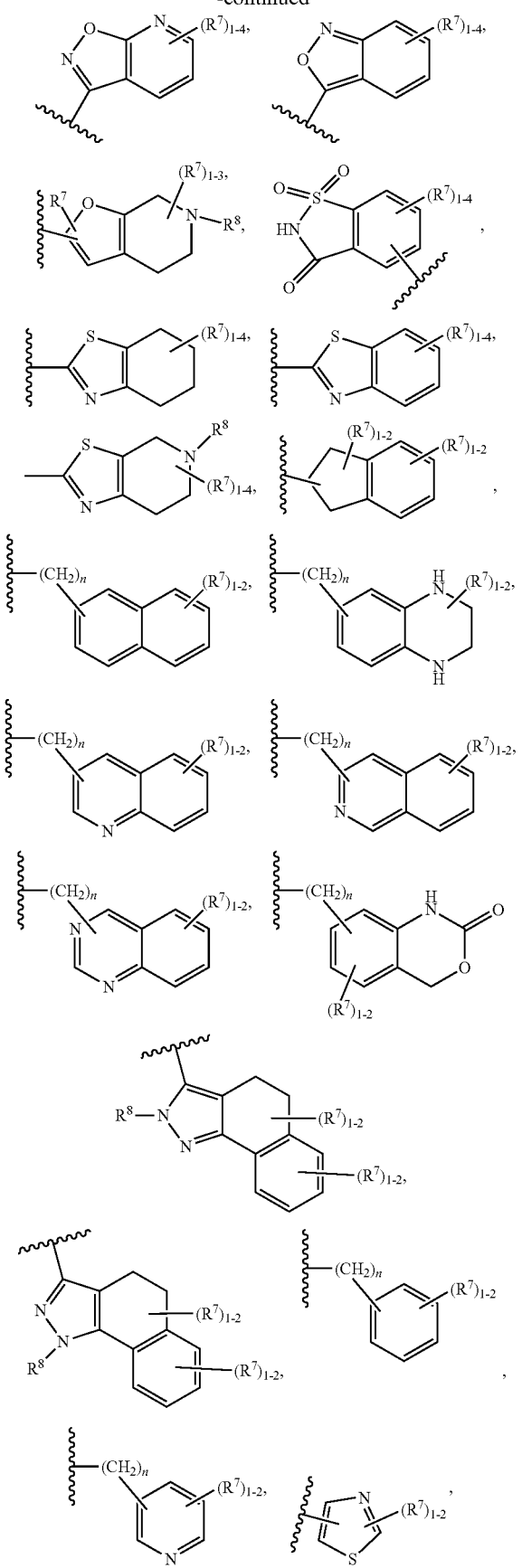
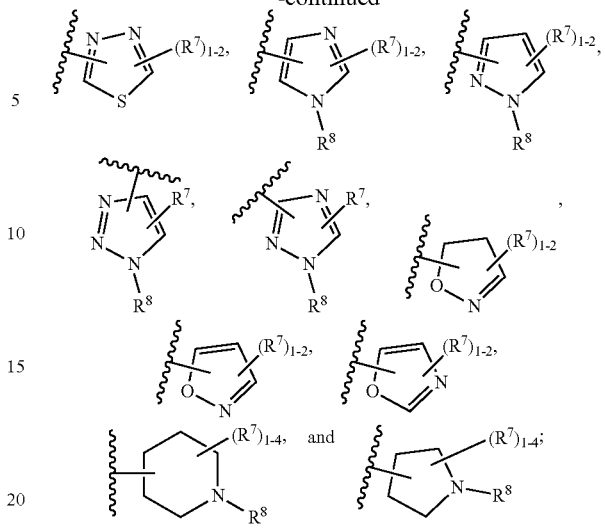

$R^3$ is $C_{1-4}$ alkoxy;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NH CO-heterocycle, —$SO_2N(C_{1-4}$ alkyl$)_2$-carbocycle, —$SO_2N(C_{1-4}$ alkyl)-heterocycle comprising carbon atoms and 1-4 heteroatoms selected from N, $NR^8$, O, and $S(O)_p$, $(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, —$(CH_2)_n$—$C(O)NR^aR^a$, $C(O)OC_{1-4}$alkyl, C(O)O-carbocycle, C(O)O-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$(CH_2)_nNHCO(C_{1-4}$ alkyl), —$S(O)_2(C_{1-4}$ alkyl), —$S(O)_2(C_{1-4}$ alkyl), —$O(CH_2)_n$heterocycle, —$O(CH_2)_{2-4}NR^aR^a$, and —$(CR^{10}R^{10})_n$-4- to 10-membered heterocycle, wherein said alkyl, alkoxyl, carbocycle, and heterocycle are substituted with 0-4 $R^b$;

$R^{10}$, at each occurrence, is independently selected from H and $C_{1-4}$ alkyl;

$R^a$, at each occurrence, is independently selected from H and $C_{1-4}$ alkyl; alternatively. $R^a$ and $R^a$ are taken together with the nitrogen atom to which they are attached to form a 4- to 10-membered heterocycle, wherein said alkyl, alkylene, and heterocycle are substituted with 0-4 $R^b$; and $R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl$)$, $CO(C_{1-4}$ haloalkyl$)$, $CO_2$ $(C_{1-4}$ alkyl$)$, $CONH_2$, —$CONH(C_{1-4}$ alkyl$)$, —$CON(C_{1-4}$ alkyl$)_2$, —CONH—$C_{1-4}$ alkylene-$O(C_{1-4}$ alkyl$)$, —CONH—$C_{1-4}$ alkylene-$N(C_{1-4}$ alkyl$)_2$, and —$NHCO_2$ $(C_{1-4}$ alkyl$)$.

In another aspect, the present invention provides compounds of Formula (IVb) or stereoisomers, enantiomers, diastereoisomers, tautomers, pharmaceutically-acceptable salts, sovates, or prodrugs thereof, wherein:

$R^1$ is selected from,

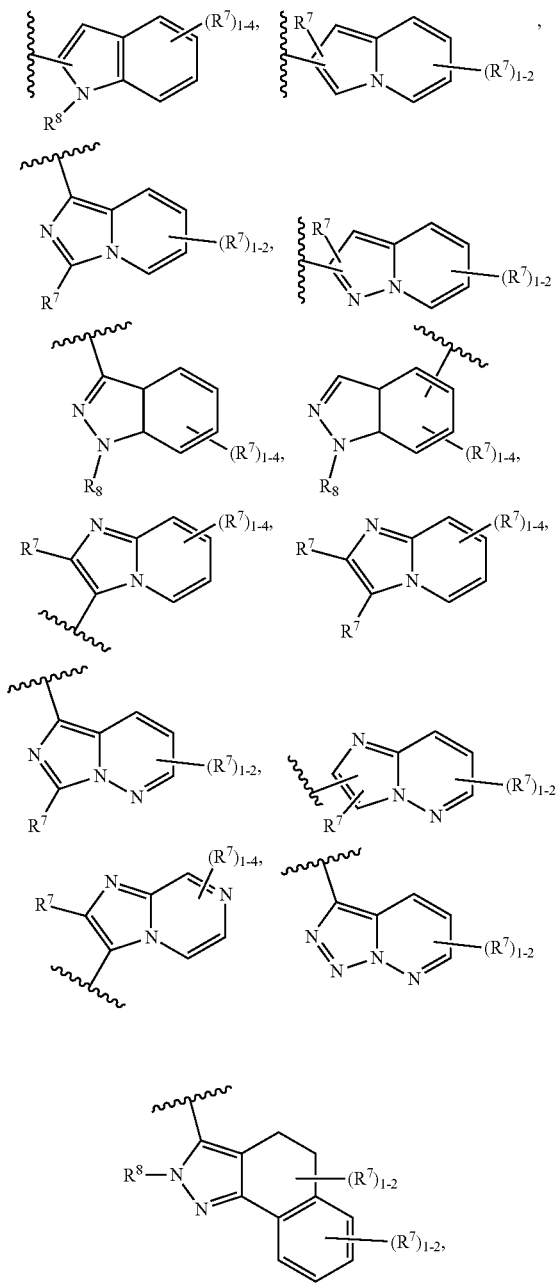

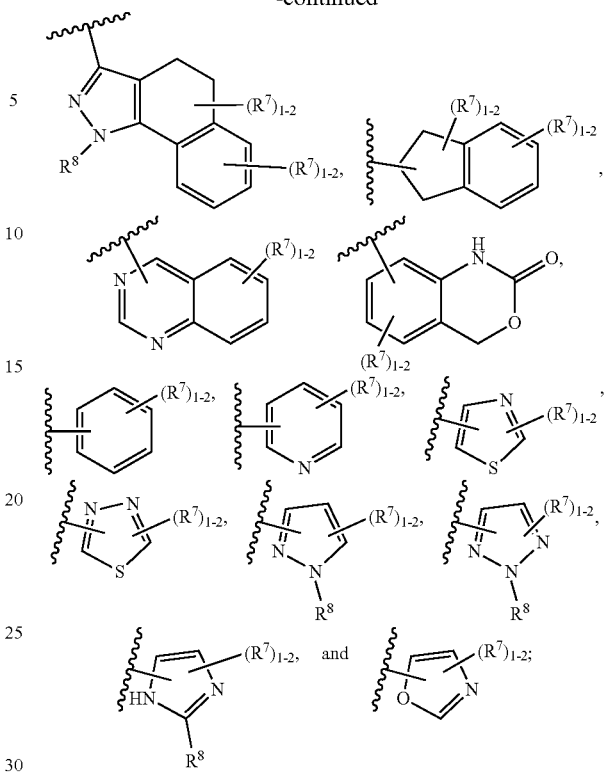

$R^7$, at each occurrence, is independently selected from H, halogen, $C_{1-4}$ alkyl, $C_{1-4}$ alkoxy, —$NR^8R^8$, $C_{3-6}$ cycloalkyl, phenyl, and —$(CH_2)_n$-heterocycle comprising carbon atoms and 1-4 heteroatoms selected from N, $NR^8$, O, and $S(O)_p$, wherein said alkyl, alkoxyl, cycloalkyl phenyl, and heterocycle are substituted with 0-4 $R^9$;

$R^8$, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

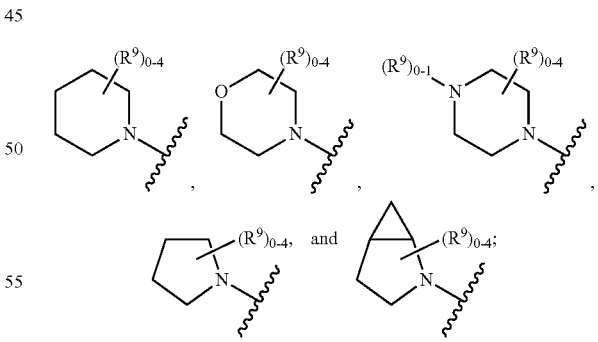

$R^9$, at each occurrence, is independently selected from F, Cl, OH, =O, CN, $C_{1-4}$ alkyl, $C_{1-4}$ alkoxy, —$(CH_2)_nNR^aR^a$, —$(CH_2)_nCONR^aR^a$, $C_{3-6}$ cycloalkyl, and a 4- to 10-membered heterocycle, wherein said alkyl, alkoxyl, cycloalkyl, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl$)$, $COCF_3$, $CO_2(C_{1-4}$ alkyl$)$, —$CONH_2$, —CONH—$C_{1-4}$ alkylene-$CO_2(C_{1-4}$ alkyl$)$, and $C_{1-4}$ alkylene-$CO_2(C_{1-4}$ alkyl$)$; and $R^b$, at each occurrence, is independently selected from halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, —$CONH$—$C_{1-4}$ alkylene-$O(C_{1-4}$ alkyl), —$CONH$—$C_{1-4}$ alkylene-$N(C_{1-4}$ alkyl$)_2$, and —$NHCO_2(C_{1-4}$ alkyl); and other variables are as defined in Formula (IVb).

In another aspect, the present invention provides compounds of Formula (IVb) or stereoisomers, enantiomers, diastereoisomers, tautomers, pharmaceutically-acceptable salts, sovates, or prodrugs thereof, wherein:

$R^1$ is selected from

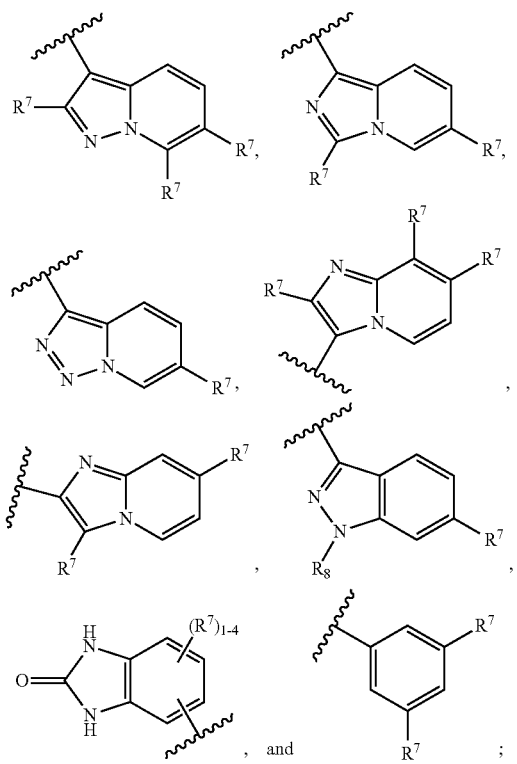

$R^7$, at each occurrence, is independently selected from H, halogen, CN, $C_{1-4}$ alkyl, $C_{1-4}$ alkoxy, —$NR^8R^8$, $C_{3-6}$ cycloalkyl, phenyl, and heterocycle comprising carbon atoms and 1-4 heteroatoms selected from N, $NR^8$, O, and $S(O)_p$, wherein said alkyl, alkoxyl, cycloalkyl, phenyl, and heterocycle are substituted with 0-4 $R^9$;

$R^8$, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

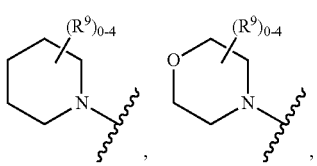

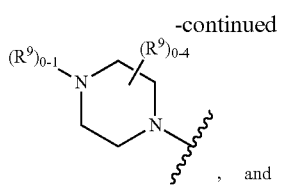

$R^9$, at each occurrence, is independently selected from F, Cl, OH, CN, $C_{1-4}$ alkyl, $C_{1-4}$ alkoxy, —$(CH_2)_nNR^aR^a$, $C_{3-6}$ cycloalkyl, and a 4- to 10-membered heterocycle, wherein said alkyl, alkoxyl, cycloalkyl, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), and $C_{1-4}$ alkylene-$CO_2(C_{1-4}$ alkyl);

$R^b$, at each occurrence, is independently selected from halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, —$CONH$—$C_{1-4}$ alkylene-$O(C_{1-4}$ alkyl), —$CONH$—$C_{1-4}$ alkylene-$N(C_{1-4}$ alkyl$)_2$, and —$NHCO_2(C_{1-4}$ alkyl); and other variables are as defined in Formula (IVb).

In another aspect, the present invention provides compounds of Formula (IVc):

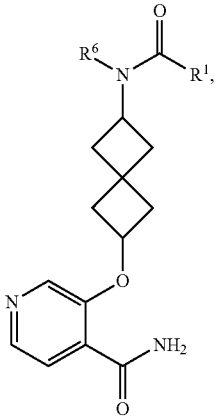

(IVc)

or stereoisomers, enantiomers, diastereoisomers, tautomers, pharmaceutically-acceptable salts, sovates, or prodrugs thereof, wherein:

$R^1$ is selected from

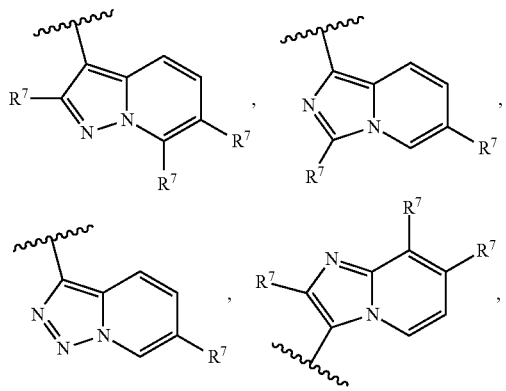

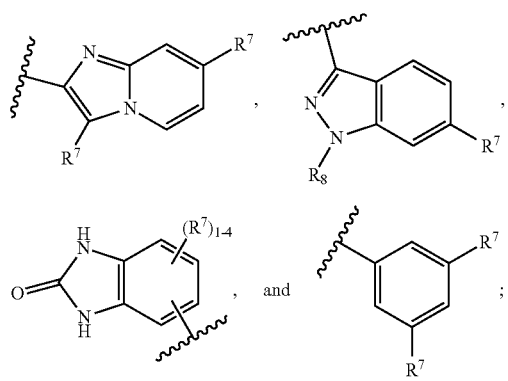

R⁷, at each occurrence, is independently selected from H, halogen, CN, $C_{1-4}$ alkyl, $C_{1-4}$ alkoxy, —NR⁸R⁸, $C_{3-6}$ cycloalkyl, phenyl, and heterocycle comprising carbon atoms and 1-4 heteroatoms selected from N, NR⁸, O, and $S(O)_p$, wherein said alkyl, alkoxyl, cycloalkyl, phenyl, and heterocycle are substituted with 0-4 R⁹;

R⁸, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 R⁹;

alternatively, R⁸ and R⁸ are taken together with the nitrogen atom to which they are attached to form a heterocycle selected from

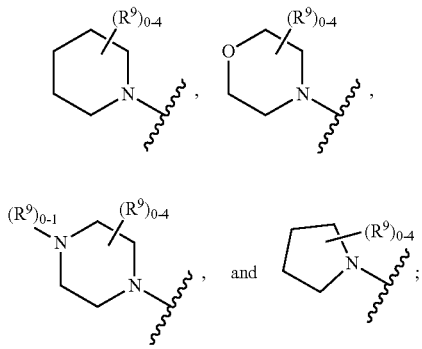

R⁹, at each occurrence, is independently selected from F, Cl, OH, CN, $C_{1-4}$ alkyl, $C_{1-4}$ alkoxy, —$(CH_2)_n NR^a R^a$, $C_{1-4}$ cycloalkyl, and a 4- to 10-membered heterocycle, wherein said alkyl, alkoxyl, cycloalkyl, and heterocycle are substituted with 0-4 $R^b$;

$R^a$, at each occurrence, is independently selected from H, $C_{1-4}$ alkyl, —$(CH_2)_n OH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), and $C_{1-4}$ alkylene-$CO_2(C_{1-4}$ alkyl); and $R^b$, at each occurrence, is independently selected from halogen, $C_{1-4}$ alkyl, $C_{1-4}$ alkoxy, $OCF_3$, $NH_2$, $NO_2$, $N(C_{1-4}$ alkyl)₂, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)₂, —CONH—$C_{1-4}$ alkylene-$O(C_{1-4}$ alkyl), —CONH—$C_{1-4}$ alkylene-$N(C_{1-4}$ alkyl)₂, and —$NHCO_2(C_{1-4}$ alkyl).

In another aspect, the present invention provides compounds of Formula (IVd):

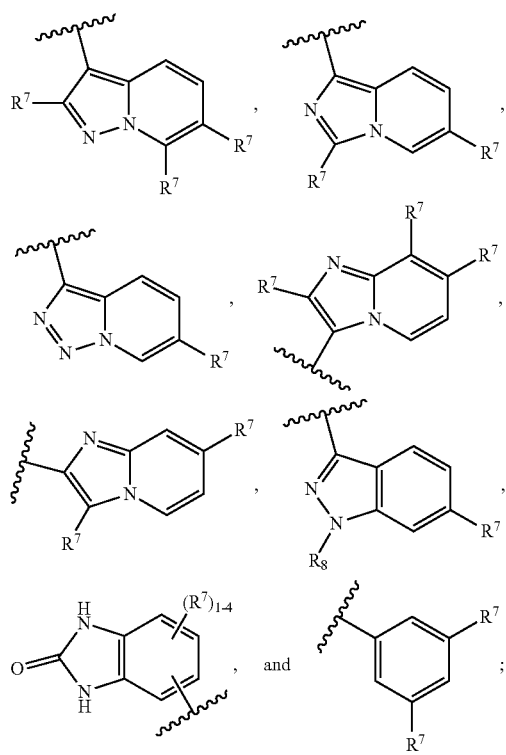

or stereoisomers, enantiomers, diastereoisomers, tautomers, pharmaceutically-acceptable salts, sovates, or prodrugs thereof, wherein:

R¹ is selected from

R⁷, at each occurrence, is independently selected from H, halogen, CN, $C_{1-4}$ alkyl, $C_{1-4}$ alkoxy, —NR⁸R⁸, $C_{3-6}$ cycloalkyl, phenyl, and heterocycle comprising carbon atoms and 1-4 heteroatoms selected from N, NR⁸, O, and $S(O)_p$, wherein said alkyl, alkoxyl, cycloalkyl, phenyl, and heterocycle are substituted with 0-4 R⁹;

R⁸, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 R⁹;

alternatively, R⁸ and R⁸ are taken together with the nitrogen atom to which they are attached to form a heterocycle selected from

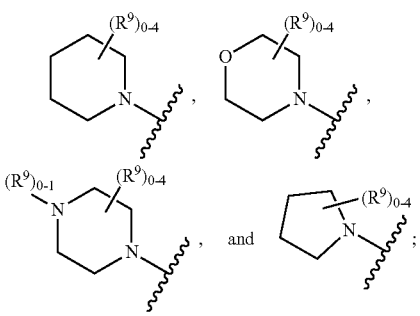

R⁹, at each occurrence, is independently selected from F, Cl, OH, CN, $C_{1-4}$ alkyl, $C_{1-4}$ alkoxy, —$(CH_2)_nNR^aR^a$, $C_{3-6}$ cycloalkyl, and a 4- to 10-membered heterocycle, wherein said alkyl, alkoxyl, cycloalkyl, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), and $C_{1-4}$ alkylene-$CO_2(C_{1-4}$ alkyl); and $R^b$, at each occurrence, is independently selected from halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, and —$NHCO_2(C_{1-4}$ alkyl).

In another aspect, the present invention provides compounds of Formula (IVe):

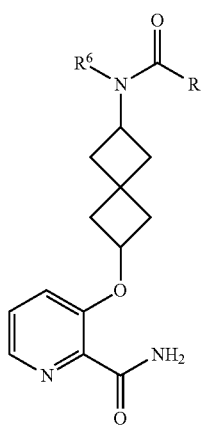

(IVe)

or stereoisomers, enantiomers, diastereoisomers, tautomers, pharmaceutically-acceptable salts, sovates, or prodrugs thereof, wherein:

$R^1$ is selected from

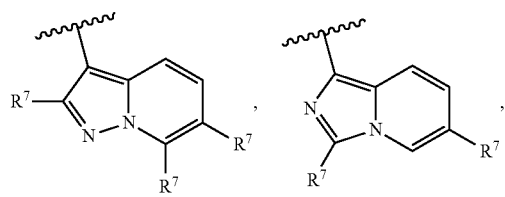

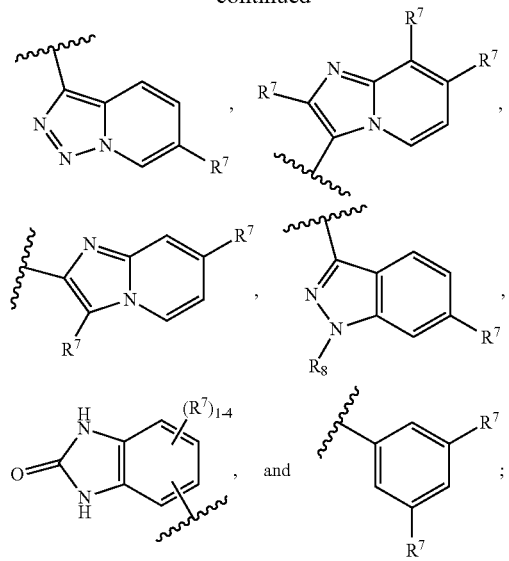

$R^7$, at each occurrence, is independently selected from H, halogen, CN, $C_{1-4}$ alkyl, $C_{1-4}$ alkoxy, —$NR^8R^8$, $C_{3-6}$ cycloalkyl, phenyl, and heterocycle comprising carbon atoms and 1-4 heteroatoms selected from N, $NR^8$, O, and $S(O)_p$, wherein said alkyl, alkoxyl, cycloalkyl, phenyl, and heterocycle are substituted with 0-4 $R^9$;

$R^8$, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

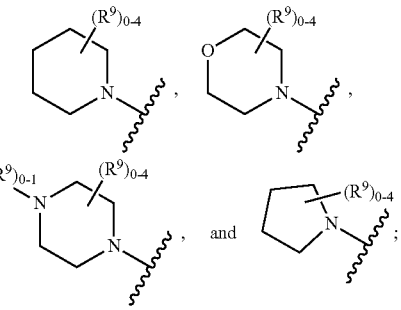

$R^9$, at each occurrence, is independently selected from F, Cl, OH, CN, $C_{1-4}$ alkyl, $C_{1-4}$ alkoxy, —$(CH_2)_nNR^aR^a$, $C_{1-4}$ cycloalkyl, and a 4- to 10-membered heterocycle, wherein said alkyl, alkoxyl, cycloalkyl, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), and $C_{1-4}$ alkylene-$CO_2(C_{1-4}$ alkyl); and $R^b$, at each occurrence, is independently selected from halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, and —$NHCO_2(C_{1-4}$ alkyl).

In another aspect, the present invention provides compounds of Formula (IVf):

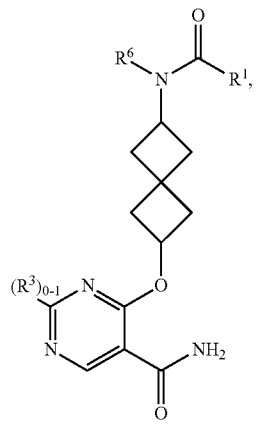

(IVf)

or stereoisomers, enantiomers, diastereoisomers, tautomers, pharmaceutically-acceptable salts, sovates, or prodrugs thereof, wherein:

$R^1$ is selected from

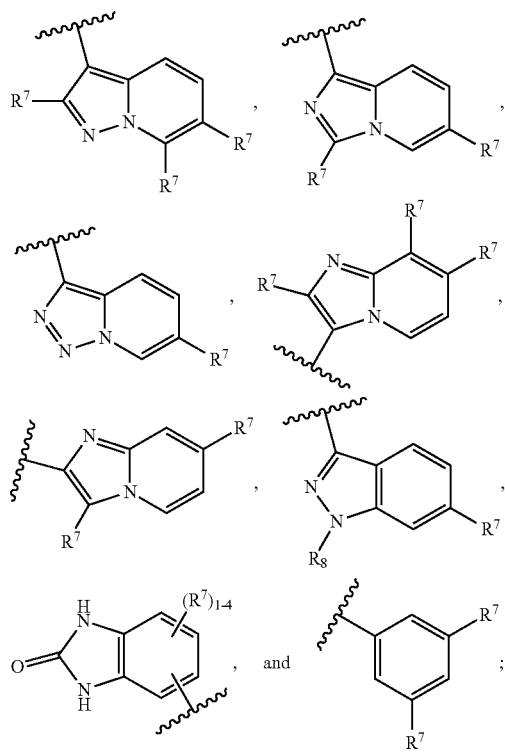

$R^3$ is $C_{1-4}$ alkoxy;

$R^7$, at each occurrence, is independently selected from H, halogen, CN, $C_{1-4}$ alkyl, $C_{1-4}$ alkoxy, —$NR^8R^8$, $C_{3-6}$ cycloalkyl, phenyl, and heterocycle comprising carbon atoms and 1-4 heteroatoms selected from N, $NR^8$, O, and $S(O)_p$, wherein said alkyl, alkoxyl, cycloalkyl, phenyl, and heterocycle are substituted with 0-4 $R^9$;

$R^8$, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

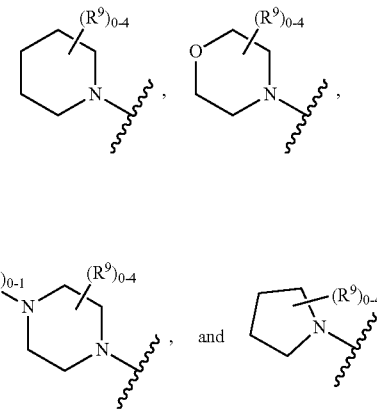

$R^9$, at each occurrence, is independently selected from F, Cl, OH, CN, $C_{1-4}$ alkyl, $C_{1-4}$ alkoxy, —$(CH_2)_nNR^aR^a$, $C_{3-6}$ cycloalkyl, and a 4- to 10-membered heterocycle, wherein said alkyl, alkoxyl, cycloalkyl, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), and $C_{1-4}$ alkylene-$CO_2(C_{1-4}$ alkyl); and $R^b$, at each occurrence, is independently selected from halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, and —$NHCO_2(C_{1-4}$ alkyl).

In another aspect, the present invention provides compounds of Formula (IVg):

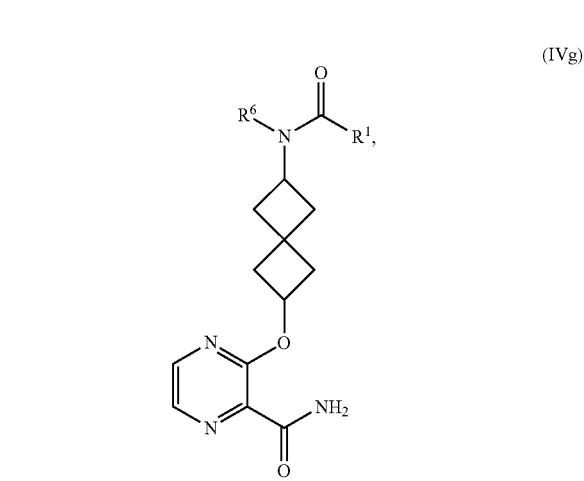

(IVg)

or stereoisomers, enantiomers, diastereoisomers, tautomers, pharmaceutically-acceptable salts, sovates, or prodrugs thereof, wherein:

$R^1$ is selected from

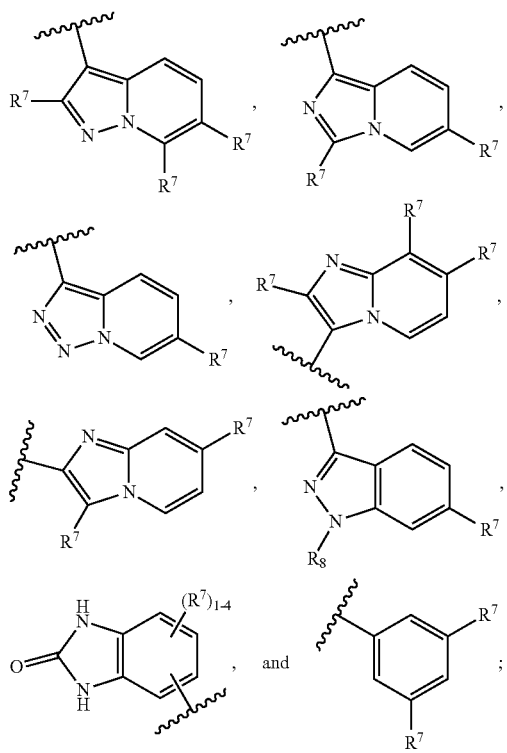

, and

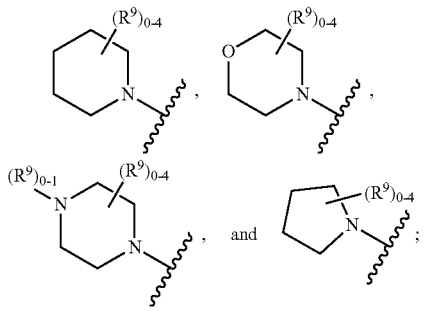

;

$R^7$, at each occurrence, is independently selected from H, halogen, CN, $C_{1-4}$ alkyl, $C_{1-4}$ alkoxy, —$NR^8R^8$, $C_{3-6}$ cycloalkyl, phenyl, and heterocycle comprising carbon atoms and 1-4 heteroatoms selected from N, $NR^8$, O, and $S(O)_p$, wherein said alkyl, alkoxyl, cycloalkyl, phenyl, and heterocycle are substituted with 0-4 $R^9$;

$R^8$, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

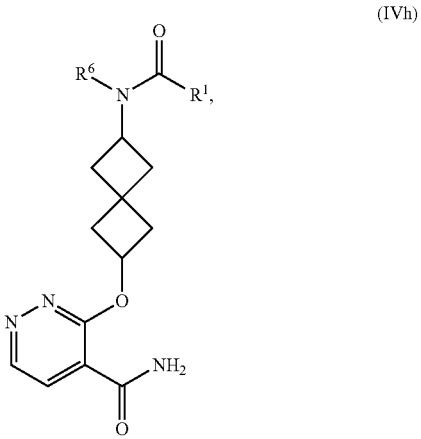

$R^9$, at each occurrence, is independently selected from F, Cl, OH, CN, $C_{1-4}$ alkyl, $C_{1-4}$ alkoxy, —$(CH_2)_nNR^aR^a$, $C_{1-4}$ cycloalkyl, and a 4- to 10-membered heterocycle, wherein said alkyl, alkoxyl, cycloalkyl, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), and $C_{1-4}$ alkylene-$CO_2(C_{1-4}$ alkyl); and $R^b$, at each occurrence, is independently selected from halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, and —$NHCO_2(C_{1-4}$ alkyl).

In another aspect, the present invention provides compounds of Formula (IVh):

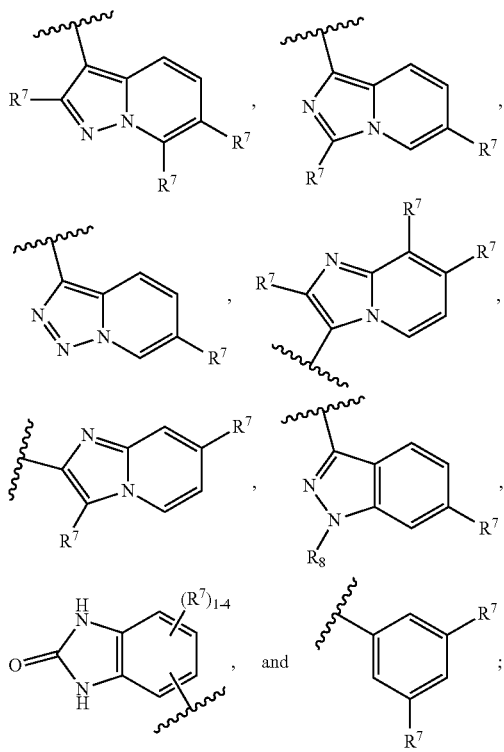

(IVh)

or stereoisomers, enantiomers, diastereoisomers, tautomers, pharmaceutically-acceptable salts, sovates, or prodrugs thereof, wherein:

$R^1$ is selected from

, and

;

$R^7$, at each occurrence, is independently selected from H, halogen, CN, $C_{1-4}$ alkyl, $C_{1-4}$ alkoxy, —$NR^8R^8$, $C_{3-6}$ cycloalkyl, phenyl, and heterocycle comprising carbon atoms and 1-4 heteroatoms selected from N, $NR^8$, O, and $S(O)_p$, wherein said alkyl, alkoxyl, cycloalkyl, phenyl, and heterocycle are substituted with 0-4 $R^9$;

$R^8$, at each occurrence, is independently selected from H, $C_{1-4}$ alkyl, $—(CH_2)_n—C_{3-6}$ cycloalkyl, $—(CH_2)_n$-phenyl, and $—(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

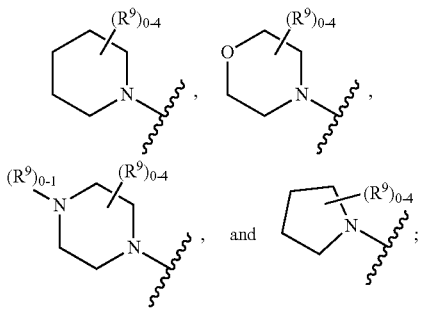

$R^9$, at each occurrence, is independently selected from F, Cl, OH, CN, $C_{1-4}$ alkyl, $C_{1-4}$ alkoxy, $—(CH_2)_nNR^aR^a$, $C_{3-6}$ cycloalkyl, and a 4- to 10-membered heterocycle, wherein said alkyl, alkoxyl, cycloalkyl, and heterocycle are substituted with 0-4 $R^b$;

$R^a$, at each occurrence, is independently selected from H, $C_{1-4}$ alkyl, $—(CH_2)_nOH$, $CO(C_{1-4}$ alkyl), $COCF_3$, $CO_2(C_{1-4}$ alkyl), $—CONH_2$, $—CONH—C_{1-4}$ alkylene-$CO_2(C_{1-4}$ alkyl), and $C_{1-4}$ alkylene-$CO_2(C_{1-4}$ alkyl); and $R^b$, at each occurrence, is independently selected from halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, $—CONH(C_{1-4}$ alkyl), $—CON(C_{1-4}$ alkyl)$_2$, $—CONH—C_{1-4}$ alkylene-$O(C_{1-4}$ alkyl), $—CONH—C_{1-4}$ alkylene-$N(C_{1-4}$ alkyl)$_2$, and $—NHCO_2(C_{1-4}$ alkyl).

In another aspect, the present invention provides compounds of Formula (IVi):

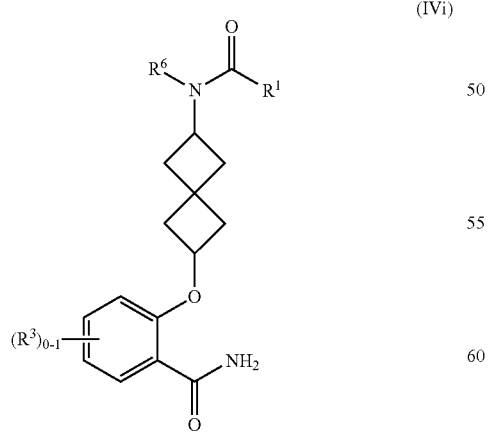

(IVi)

or stereoisomers, enantiomers, diastereoisomers, tautomers, pharmaceutically-acceptable salts, sovates, or prodrugs thereof, wherein:

$R^1$ is independently selected from

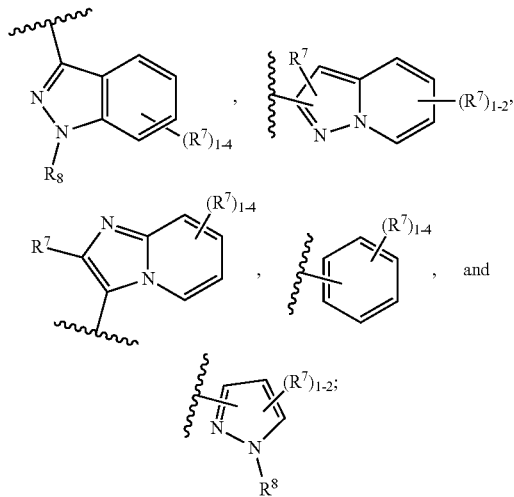

$R^3$, at each occurrence, is independently selected from halogen, $C_{1-6}$ alkyl, $C_{2-6}$ alkenyl, $C_{1-4}$ alkoxy,

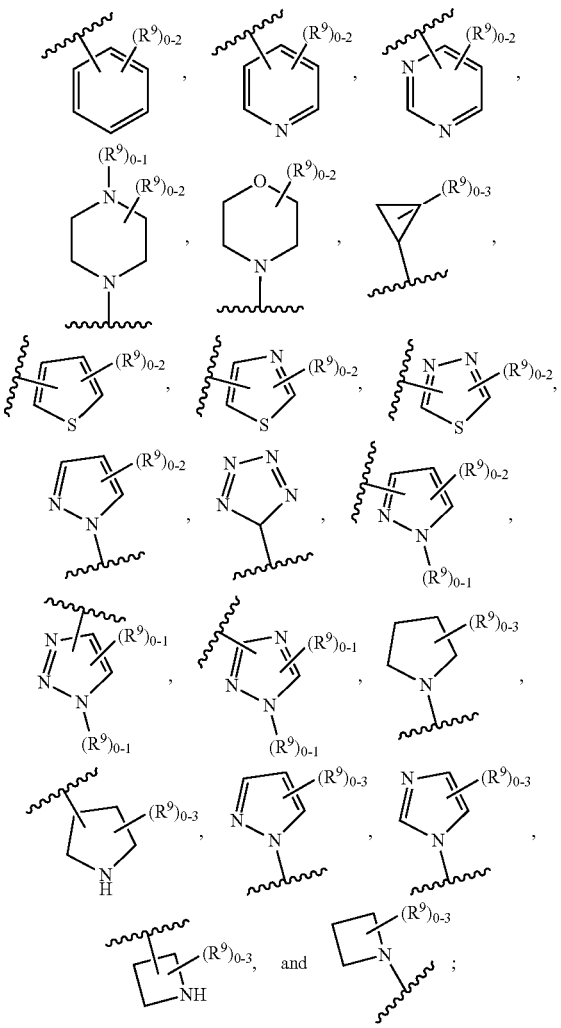

wherein said alkyl, alkenyl, and alkoxy are substituted with 0-4 $R^9$;

$R^7$, at each occurrence, is independently selected from H, $C_{1-4}$ alkyl, $C_{1-4}$ alkoxy, $-NR^8R^8$, $-S(O)_2(C_{1-4}$ alkyl), $-O$-heterocycle, $C_{3-6}$ cycloalkyl, phenyl, and heterocycle comprising carbon atoms and 1-4 heteroatoms selected from N, $NR^8$, O, and $S(O)_p$, wherein said alkyl, alkoxyl, cycloalkyl phenyl, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, $-(CH_2)_n-C(O)NR^aR^a$, $C(O)OC_{1-4}$alkyl, C(O)O-carbocycle, C(O)O-heterocycle, $SO_2$alkyl, $SO_2$carbocycle, $SO_2$heterocycle, $SO_2NR^aR^a$, $-(CH_2)_n$-carbocycle, and $-(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, $CO_2(C_{1-4}$ alkyl), $-(CHR^{10})_n NR^aR^a$, $S(O)_p(C_{1-4}$ alkyl), $-(CHR^{10})_n CONR^aR^a$, $-(CHR^{10})_n NR^aCO(C_{1-4}$ alkyl), $-(CHR^{10})_n OCONR^a(CH_2)_nCO_2R^a$, $S(O)_pC_{1-4}$alkyl, $S(O)_pNR^aR^a$, $-O(CHR^{10})_n$carbocycle, $-O(CHR^{10})_n$heterocycle, $-O(CHR^{10})_n NR^aR^a$, and $-(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^a$, at each occurrence, is independently selected from H and $C_{1-4}$ alkyl;

alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$; and $R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2H$, $CO_2(C_{1-4}$ alkyl), $CONH_2$, $-CONH(C_{1-4}$ alkyl), $-CON(C_{1-4}$ alkyl$)_2$, $-CONH-C_{1-4}$ alkylene-O($C_{1-4}$ alkyl), $-CONH-C_{1-4}$ alkylene-N($C_{1-4}$ alkyl$)_2$, and $-NHCO_2(C_{1-4}$ alkyl).

In another aspect, the present invention provides compounds of Formula (IVj):

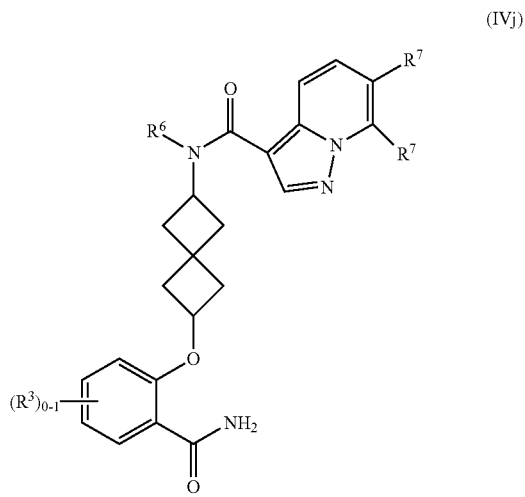

(IVj)

or stereoisomers, enantiomers, diastereoisomers, tautomers, pharmaceutically-acceptable salts, sovates, or prodrugs thereof, wherein:

$R^3$, at each occurrence, is independently selected from F, Cl, Br, $C_{1-6}$ alkyl, $C_{2-6}$ alkenyl, $C_{1-4}$ alkoxy,

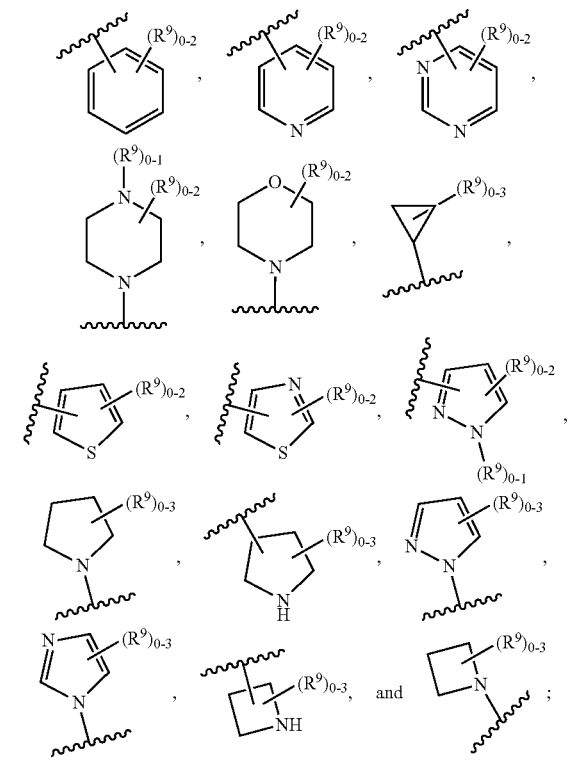

wherein said alkyl, alkenyl, and alkoxy are substituted with 0-4 $R^9$;

$R^7$, at each occurrence, is independently selected from H, $C_{1-4}$ alkyl substituted with 0-4 $R^9$, $C_{1-4}$ alkoxy substituted with 0-4 $R^9$, $NR^8R^8$, $C_{3-6}$ cycloalkyl, $-O$-heterocycle, and wherein said alkyl, alkoxy, $C_{3-6}$ cycloalkyl, heterocycle are substituted with 0-4 $R^9$ and wherein the heterocycle comprising carbon atoms and 1-4 heteroatoms selected from N, $NR^8$, O, and $S(O)_p$;

$R^8$, at each occurrence, is independently selected from H, $C_{1-4}$ alkyl, $C(O)OC_{1-4}$alkyl and phenyl;

alternatively, $R^8$ and $R^8$ are taken together with the nitrogen atom to which they are attached to form a 4- to 10-membered heterocycle selected from

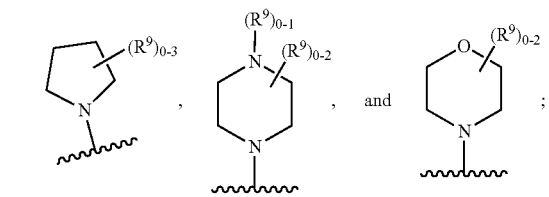

$R^9$, at each occurrence, is independently selected from halogen, OH, =O, CN, $NO_2$, $CHF_2$, $CF_3$, $C_{1-4}$ alkyl, $C_{1-4}$ alkenyl, $C_{1-4}$ alkoxy, $CH_2OH$, $CO_2H$, $CO_2(C_{1-4}$ alkyl), $CH_2OC(O)NH(CH_2)_{1-2}C(O)OH$, $CH_2OC(O)NH(CH_2)_{1-2}C(O)OC_{1-4}$ alkyl; $CONH_2$, $-(CH_2)_nNR^aR^a$, $-(CH_2)_nCON-$ $R^aR^a$, —(CH$_2$)$_n$NHCO(C$_{1-4}$ alkyl), —S(O)$_2$(C$_{1-4}$ alkyl), —S(O)$_2$NR$^a$R$^a$, —O(CH$_2$)$_n$heterocycle, —O(CH$_2$)$_{2-4}$ NR$^a$R$^a$, and —(CR$^{10}$R$^{10}$)$_n$-4- to 10-membered heterocycle, wherein said alkyl, alkenyl, alkoxyl, carbocycle, and heterocycle are substituted with 0-4 R$^b$;

R$^{10}$, at each occurrence, is independently selected from H and C$_{1-4}$ alkyl;

R$^a$, at each occurrence, is independently selected from H and C$_{1-4}$ alkyl;

alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$; and R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$H, CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, and —NHCO$_2$(C$_{1-4}$ alkyl).

In another aspect, the present invention provides compounds of Formula (IVk):

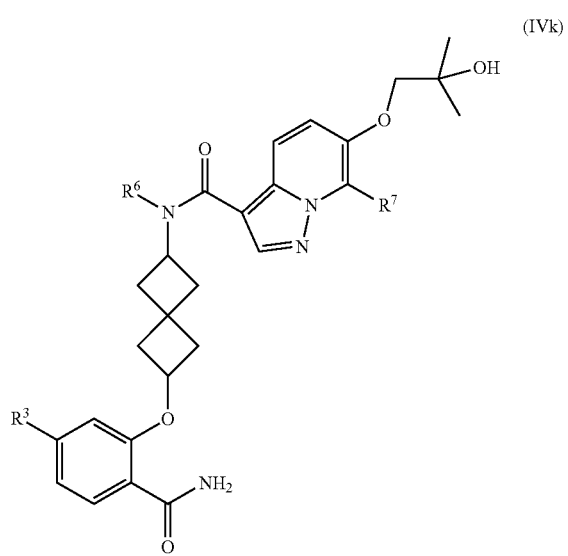

(IVk)

or stereoisomers, enantiomers, diastereoisomers, tautomers, pharmaceutically-acceptable salts, sovates, or prodrugs thereof, wherein;

R$^3$, at each occurrence, is independently selected from F, Cl, Br, C$_{1-6}$ alkyl, C$_{2-6}$ alkenyl, C$_{1-4}$ alkoxy,

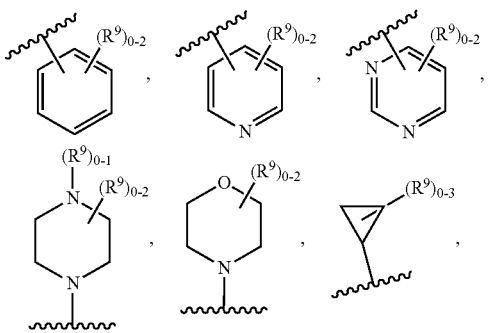

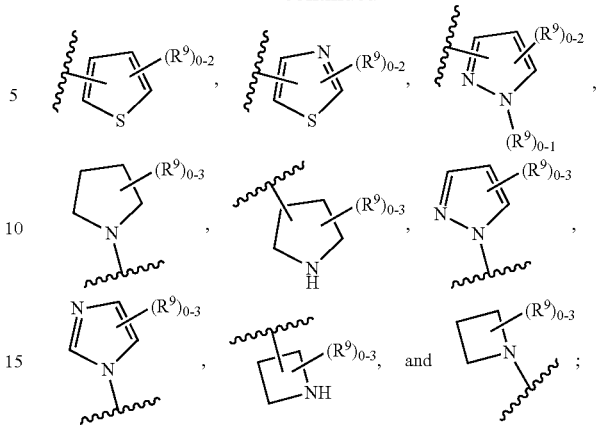

wherein said alkyl, alkenyl, and alkoxy are substituted with 0-4 R$^9$;

R$^9$, at each occurrence, is independently selected from halogen, OH, =O, CN, NO$_2$, CHF$_2$, CF$_3$, C$_{1-4}$ alkyl, C$_{2-4}$ alkenyl, C$_{1-4}$ alkoxy, CH$_2$OH, CO$_2$H, CO$_2$(C$_{1-4}$ alkyl), CH$_2$OC(O)NH(CH$_2$)$_{1-2}$C(O)OH, CH$_2$OC(O)NH(CH$_2$)$_{1-2}$C(O)OC$_{1-4}$ alkyl; CONH$_2$, —(CH$_2$)$_n$NR$^a$R$^a$, —(CH$_2$)$_n$CONR$^a$R$^a$, —(CH$_2$)$_n$NHCO(C$_{1-4}$ alkyl), —S(O)$_2$(C$_{1-4}$ alkyl), —S(O)$_2$NR$^a$R$^a$, —O(CH$_2$)$_n$heterocycle, —O(CH$_2$)$_{2-4}$NR$^a$R$^a$, and —(CH$_2$)$_n$-4- to 10-membered heterocycle, wherein said alkyl, alkenyl, alkoxyl, carbocycle, and heterocycle are substituted with 0-4 R$^b$;

R$^a$, at each occurrence, is independently selected from H and C$_{1-4}$ alkyl; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$; and R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$H, CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, and —NHCO$_2$(C$_{1-4}$ alkyl).

In another aspect, the present invention provides a compound selected from any subset list of compounds exemplified in the present application.

In another aspect, the present invention provides a compound selected from the group consisting of N-[6-(2-carbamoylphenoxy)spiro[3.3]heptan-2-yl]-5-methyl-1-phenyl-1H-pyrazole-4-carboxamide, N-[6-(2-carbamoylphenoxy)spiro[3.3]heptan-2-yl]-1-methyl-1H-indazole-3-carboxamide, N-[6-(2-carbamoylphenoxy)spiro[3.3]heptan-2-yl]-6-(2-hydroxy-2-methylpropoxy)pyrazolo[1,5-a]pyridine-3-carboxamide, N-[6-(2-carbamoylphenoxy)spiro[3.3]heptan-2-yl]-6-(oxolan-3-yloxy)pyrazolo[1,5-a]pyridine-3-carboxamide, N-[6-(2-carbamoylphenoxy)spiro[3.3]heptan-2-yl]-3-methoxy-4-(1H-pyrazol-4-yl)benzamide, 2-({6-[6-(2-hydroxy-2-methylpropoxy)pyrazolo[1,5-a]pyridine-3-amido]spiro[3.3]heptan-2-yl}oxy)pyridine-3-carboxamide, 3-({6-[6-(2-hydroxy-2-methylpropoxy)pyrazolo[1,5-a]pyridine-3-amido]spiro[3.3]heptan-2-yl}oxy)pyrazine-2-carboxamide, 4-({6-[6-(2-hydroxy-2-methylpropoxy)pyrazolo[1,5-a]pyridine-3-amido]spiro[3.3]heptan-2-yl}oxy)pyrimidine-5-carboxamide, 2-[(6-{6-[(1,3-difluoropropan-2-yl)oxy]pyrazolo[1,5-a]pyridine-3-amido}spiro[3.3]heptan-2-yl)oxy]pyridine-3-carboxamide, 2-({6-[6-(3,3,3-trifluoropropoxy)pyrazolo[1,5-a]pyridine-3-amido]spiro[3.3]heptan-2-yl}oxy)pyridine-3-carboxamide, 2-({6-[6-(oxan-4-yloxy)pyrazolo[1,5-a]pyridine-3-amido]spiro[3.3]heptan-2-yl}oxy)pyridine-3-carboxamide, N-{6-[(3-carbamoylpyridin-2-yl)oxy]spiro[3.3]heptan-2-yl}-2,3-dihydro-1H-indole-1-carboxamide, N-{6-[(3-carbamoylpyridin-2-yl)oxy]spiro[3.3]heptan-2-yl}-5-cyano-2,3-dihydro-1H-isoindole-2-carboxamide, Benzyl N-[6-(2-carbamoylphenoxy)spiro[3.3]heptan-2-yl]carbamate, N-[(aR)-6-(2-carbamoylphenoxy)spiro[3.3]heptan-2-yl]-7-cyclopropyl-6-(2-hydroxy-2-methylpropoxy)pyrazolo[1,5-a]pyridine-3-carboxamide, N-[(aR)-6-(2-carbamoylphenoxy)spiro[3.3]heptan-2-yl]-6-(2-hydroxy-2-methylpropoxy)pyrazolo[1,5-a]pyridine-3-carboxamide, N-{6-[(3-carbamoylpyridin-2-yl)oxy]spiro[3.3]heptan-2-yl}-5-methoxy-2,3-dihydro-1H-indole-1-carboxamide, N-[(aR)-6-(2-carbamoylphenoxy)spiro[3.3]heptan-2-yl]-7-(3,3,3-trifluoropropoxy)imidazo[1,2-a]pyridine-3-carboxamide, N-[(aR)-6-(2-carbamoylphenoxy)spiro[3.3]heptan-2-yl]-6-(2-hydroxy-2-methylpropoxy)-7-(3,3,3-trifluoropropyl)pyrazolo[1,5-a]pyridine-3-carboxamide, N-[(aR)-6-(2-carbamoylphenoxy)spiro[3.3]heptan-2-yl]-5-[2-(morpholin-4-yl)ethoxy]pyrazolo[1,5-a]pyridine-3-carboxamide, N-[(aR)-6-(2-carbamoylphenoxy)spiro[3.3]heptan-2-yl]-6-[2-(pyrrolidin-1-yl)ethoxy]pyrazolo[1,5-a]pyridine-3-carboxamide, N-[(aR)-6-(2-carbamoylphenoxy)spiro[3.3]heptan-2-yl]-6-(2,2-difluoroethoxy)pyrazolo[1,5-a]pyridine-3-carboxamide, N-[(aR)-6-(2-carbamoylphenoxy)spiro[3.3]heptan-2-yl]-6-(3,3-difluoropyrrolidin-1-yl)pyrazolo[1,5-a]pyridine-3-carboxamide, N-[(aR)-6-(2-carbamoylphenoxy)spiro[3.3]heptan-2-yl]-6-(difluoromethoxy)pyrazolo[1,5-a]pyridine-3-carboxamide, N-[(aR)-6-(2-carbamoylphenoxy)spiro[3.3]heptan-2-yl]-7-(3,3-difluoropyrrolidin-1-yl)imidazo[1,2-a]pyridine-3-carboxamide, N-[(aR)-6-(2-carbamoylphenoxy)spiro[3.3]heptan-2-yl]-7-[2-(pyrrolidin-1-yl)ethoxy]imidazo[1,2-a]pyridine-3-carboxamide, methyl 3-[(3-{[(aR)-6-(2-carbamoylphenoxy)spiro[3.3]heptan-2-yl]carbamoyl}pyrazolo[1,5-a]pyridin-6-yl)oxy]azetidine-1-carboxylate, N-[(aR)-6-(2-carbamoylphenoxy)spiro[3.3]heptan-2-yl]-6-[(1,1-dioxo-1$\lambda^6$-thian-4-yl)oxy]pyrazolo[1,5-a]pyridine-3-carboxamide, N-[(aR)-6-(2-carbamoylphenoxy)spiro[3.3]heptan-2-yl]-7-(morpholin-4-yl)imidazo[1,2-a]pyridine-3-carboxamide, N-[(aR)-6-(2-carbamoylphenoxy)spiro[3.3]heptan-2-yl]-7-cyclopropyl-6-(3-methanesulfonylpropoxy)pyrazolo[1,5-a]pyridine-3-carboxamide, N-[(aR)-6-(2-carbamoylphenoxy)spiro[3.3]heptan-2-yl]-7-cyclopropyl-6-(2-hydroxyethoxy)pyrazolo[1,5-a]pyridine-3-carboxamide, N-[(aR)-6-(2-carbamoylphenoxy)spiro[3.3]heptan-2-yl]-7-cyclopropyl-6-(3,3,3-trifluoropropoxy)pyrazolo[1,5-a]pyridine-3-carboxamide, N-[(aR)-6-(2-carbamoylphenoxy)spiro[3.3]heptan-2-yl]-6-(3,3,3-trifluoropropoxy)pyrazolo[1,5-a]pyridine-3-carboxamide, N-[(aR)-6-(2-carbamoylphenoxy)spiro[3.3]heptan-2-yl]-7-(1-methyl-1H-pyrazol-4-yl)imidazo[1,2-a]pyridine-3-carboxamide, N-[(aR)-6-(2-carbamoylphenoxy)spiro[3.3]heptan-2-yl]-7-cyclopropyl-6-[(1,1-dioxo-1$\lambda^6$-thian-4-yl)oxy]pyrazolo[1,5-a]pyridine-3-carboxamide, N-[(aR)-6-(2-carbamoylphenoxy)spiro[3.3]heptan-2-yl]-7-(4-methylpiperazin-1-yl)imidazo[1,2-a]pyridine-3-carboxamide, N-[(aR)-6-(2-carbamoylphenoxy)spiro[3.3]heptan-2-yl]-2,3-dihydro-1H-indole-1-carboxamide, N-[(aR)-6-(2-carbamoylphenoxy)spiro[3.3]heptan-2-yl]-5-methoxy-2,3-dihydro-1H-indole-1-carboxamide, N-[(aR)-6-(2-carbamoylphenoxy)spiro[3.3]heptan-2-yl]-5-methanesulfonyl-2,3-dihydro-1H-indole-1-carboxamide, 2-[((aR)-6-{[(4-methoxyphenyl)carbamoyl]amino}spiro[3.3]heptan-2-yl)oxy]benzamide, N-[(aR)-6-(2-carbamoylphenoxy)spiro[3.3]heptan-2-yl]-2,3-dihydro-1H-isoindole-2-carboxamide, N-((aR)-6-((3-carbamoylpyridin-2-yl)oxy)spiro[3.3]heptan-2-yl)-7-cyclopropyl-6-(2-hydroxy-2-methylpropoxy)pyrazolo[1,5-o]pyridine-3-carboxamide, 2-({(aR)-6-[6-(2-hydroxy-2-methylpropoxy)-7-(3,3,3-trifluoropropyl)pyrazolo[1,5-a]pyridine-3-amido]spiro[3.3]heptan-2-yl}oxy)pyridine-3-carboxamide, 4-({(aR)-6-[6-(2-hydroxy-2-methylpropoxy)pyrazolo[1,5-a]pyridine-3-amido]spiro[3.3]heptan-2-yl}oxy)pyridine-3-carboxamide, 3-({(aR)-6-[6-(2-hydroxy-2-methylpropoxy)pyrazolo[1,5-a]pyridine-3-amido]spiro[3.3]heptan-2-yl}oxy)pyridine-4-carboxamide, N-{(aR)-6-[(3-carbamoylpyridin-2-yl)oxy]spiro[3.3]heptan-2-yl}-1-(2-hydroxy-2-methylpropyl)-6-(1-methyl-1H-pyrazol-4-yl)-1H-indazole-3-carboxamide, 2-({(aR)-6-[8-cyclopropyl-7-(2-fluoro-2-methylpropoxy)imidazo[1,2-a]pyridine-3-amido]spiro[3.3]heptan-2-yl}oxy)pyridine-3-carboxamide, 3-({(aR)-6-[6-(2-hydroxy-2-methylpropoxy)pyrazolo[1,5-a]pyridine-3-amido]spiro[3.3]heptan-2-yl}oxy)pyridazine-4-carboxamide, 2-({(aR)-6-[7-cyclopropyl-6-(2-fluoro-2-methylpropoxy)pyrazolo[1,5-a]pyridine-3-amido]spiro[3.3]heptan-2-yl}oxy)pyridine-3-carboxamide, N-{(aR)-6-(3-carbamoylpyridin-2-yl)oxy)spiro[3.3]heptan-2-yl}-1-(2-hydroxy-2-methylpropyl)-5-(1-methyl-1H-pyrazol-4-yl)-1H-indazole-3-carboxamide, 2-[((aR)-6-{3-[1-(difluoromethyl)-1H-pyrazol-4-yl]-5-methanesulfonylbenzamido}spiro[3.3]heptan-2-yl)oxy]pyridine-3-carboxamide, 2-({(aR)-6-[3-methanesulfonyl-5-(1-methyl-1H-pyrazol-4-yl)benzamido]spiro[3.3]heptan-2-yl}oxy)pyridine-3-carboxamide, 2-[((aR)-6-{3-methanesulfonyl-5-[1-(Â²Hâ,f)methyl-1H-pyrazol-4-yl]benzamido}spiro[3.3]heptan-2-yl)oxy]pyridine-3-carboxamide, 2-({(aR)-6-[3-(1-methyl-1H-pyrazol-4-yl)benzamido]spiro[3.3]heptan-2-yl}oxy)pyridine-3-carboxamide, 2-[((aR)-6-{3'-methanesulfonyl-[1,1'-biphenyl]-3-amido}spiro[3.3]heptan-2-yl)oxy]pyridine-3-carboxamide, 2-({(aR)-6-[3-bromo-5-(3,3,3-trifluoropropoxy)benzamido]spiro[3.3]heptan-2-yl}oxy)pyridine-3-carboxamide, 2-({(aR)-6-[3-(1-methyl-1H-pyrazol-4-yl)-5-(3,3,3-trifluoropropoxy)benzamido]spiro[3.3]heptan-2-yl}oxy)pyridine-3-carboxamide, 2-({(aR)-6-[3'-methanesulfonyl-5-(3,3,3-trifluoropropoxy)-[1,1'-biphenyl]-3-amido]spiro[3.3]heptan-2-yl}oxy)pyridine-3-carboxamide, 2-[((aR)-6-{6-methoxyimidazo[1,2-b]pyridazine-2-amido}spiro[3.3]heptan-2-yl)oxy]pyridine-3-carboxamide, 2-[((aR)-6-{6-chloro-8-methoxyimidazo[1,2-b]pyridazine-3-amido}spiro[3.3]heptan-2-yl)oxy]pyridine-3-carboxamide, 2-({(aR)-6-[6-(2,2,2-trifluoroethoxy)imidazo[1,2-b]pyridazine-2-amido]spiro[3.3]heptan-2-yl}oxy)pyridine-3-carboxamide, 2-[((aR)-6-{6-chloroimidazo[1,2-b]pyridazine-2-amido}spiro[3.3]heptan-2-yl)oxy]pyridine-3-carboxamide, N2-{(aR)-6-[(3-carbamoylpyridin-2-yl)oxy]spiro[3.3]heptan-2-yl}imidazo[1,2-a]pyridine-2,6-dicarboxamide, 2-({(aR)-6-[6-(2-hydroxy-2-methylpropoxy)pyrazolo[1,5-a]pyridine-3-amido]spiro[3.3]heptan-2-yl}oxy)pyridine-3-carboxamide, 2-({(aR)-6-[8-cyclopropyl-7-(2-hydroxy-2-methylpropoxy)imidazo[1,2-a]pyridine-3-amido]spiro[3.3]heptan-2-yl}oxy)pyridine-3-carboxamide, N-{(aR)-6-[(3-carbamoylpyridin-2-yl)oxy]spiro[3.3]heptan-2-yl}-1-methyl-1H-indazole-3-carboxamide, N-((aR)-6-((3-carbamoylpyridin-2-yl)oxy)spiro[3.3]heptan-2-yl)-5-fluoro-1-(2-hydroxy-2-methylpropyl)-3a,7a-dihydro-1H-indazole-3-carboxamide, N-{(aR)-6-[(3-carbamoylpyridin-2-yl)oxy]spiro[3.3]heptan-2-yl}-1-methyl-1H-indazole-5-carboxamide, 2-({(aR)-6-[6-(2-hydroxy-2-methylpropoxy)-7-(2-oxopiperidin-1-yl)pyrazolo[1,5-a]pyridine-3-amido]spiro[3.3]heptan-2-yl}oxy)pyridine-3-carboxamide, N-{(aR)-6-[(3-carbamoylpyridin-2-yl)oxy]spiro[3.3]heptan-2-yl}-1-methyl-1H-indole-2-carboxamide, 2-[((aR)-6-{imidazo[1,2-a]pyridine-7-amido}spiro[3.3]heptan-2-yl)oxy]pyridine-3-carboxamide, N-{(aR)-6-[(3-carbamoylpyridin-2-yl)oxy]spiro[3.3]heptan-2-yl}quinoline-3-carboxamide, 2-{[(aR)-6-(1-phenyl-1H-pyrazole-4-amido)spiro[3.3]heptan-2-yl]oxy}pyridine-3-carboxamide, 2-({(aR)-6-[4-(1H-pyrazol-1-yl)benzamido]spiro[3.3]heptan-2-yl}oxy)pyridine-3-carboxamide, 2-[((aR)-6-{imidazo[1,2-a]pyridine-2-amido}spiro[3.3]heptan-2-yl)oxy]pyridine-3-carboxamide, 2-[((aR)-6-{6-cyanoimidazo[1,2-a]pyridine-2-amido}spiro[3.3]heptan-2-yl)oxy]pyridine-3-carboxamide, 2-{[(aR)-6-(3-tert-butyl-1-methyl-1H-pyrazole-5-amido)spiro[3.3]heptan-2-yl]oxy}pyridine-3-carboxamide, N-{(aR)-6-[(3-carbamoylpyridin-2-yl)oxy]spiro[3.3]heptan-2-yl}-1-[2-(2-methoxyethoxy)ethyl]-1H-indazole-3-carboxamide, 2-({(aR)-6-[3-methoxy-4-(4-methyl-1H-imidazol-1-yl)benzamido]spiro[3.3]heptan-2-yl}oxy)pyridine-3-carboxamide, 2-[((aR)-6-{6-[2-(dimethylamino)ethoxy]pyrazolo[1,5-a]pyridine-3-amido}spiro[3.3]heptan-2-yl)oxy]pyridine-3-carboxamide, 6-bromo-N-{(aR)-6-[(3-carbamoylpyridin-2-yl)oxy]spiro[3.3]heptan-2-yl}-1-(2-hydroxy-2-methylpropyl)-1H-indazole-3-carboxamide, 2-({(aR)-6-[6-(3,3,3-trifluoropropoxy)pyrazolo[1,5-a]pyridine-3-amido]spiro[3.3]heptan-2-yl}oxy)pyridine-3-carboxamide, 2-{[(aR)-6-(1,3-dimethyl-1H-pyrazole-5-amido)spiro[3.3]heptan-2-yl]oxy}pyridine-3-carboxamide, 2-({(aR)-6-[5-(cyclopropylmethoxy)-1-methyl-1H-pyrazole-3-amido]spiro[3.3]heptan-2-yl}oxy)pyridine-3-carboxamide, 2-{(aR)-6-(3-cyclopropyl-1-methyl-1H-pyrazole-5-amido)spiro[3.3]heptan-2-yloxy}pyridine-3-carboxamide, 2-({(aR)-6-[1-methyl-3-(trifluoromethyl)-1H-pyrazole-5-amido]spiro[3.3]heptan-2-yl}oxy)pyridine-3-carboxamide, 2-({(aR)-6-[1-methyl-5-(2,2,3,3-tetrafluoropropoxy)-1H-pyrazole-3-amido]spiro[3.3]heptan-2-yl}oxy)pyridine-3-carboxamide, 2-({(aR)-6-[4-methyl-2-(pyridin-2-yl)-1,3-thiazole-5-amido]spiro[3.3]heptan-2-yl}oxy)pyridine-3-carboxamide, 2-{[(aR)-6-(1-methyl-3-phenyl-1H-pyrazole-5-amido)spiro[3.3]heptan-2-yl]oxy}pyridine-3-carboxamide, 2-({(aR)-6-[2-(3,3-difluoroazetidin-1-yl)-4-methyl-1,3-thiazole-5-amido]spiro[3.3]heptan-2-yl}oxy)pyridine-3-carboxamide, 2-({(aR)-6-[1-methyl-5-(3,3,3-trifluoropropoxy)-1H-pyrazole-3-amido]spiro[3.3]heptan-2-yl}oxy)pyridine-3-carboxamide, 2-({(aR)-6-[2-(3,3-difluoropyrrolidin-1-yl)-4-methyl-1,3-thiazole-5-amido]spiro[3.3]heptan-2-yl}oxy)pyridine-3-carboxamide, 5-bromo-N-{(aR)-6-[(3-carbamoylpyridin-2-yl)oxy]spiro[3.3]heptan-2-yl}-1-(2-hydroxy-2-methylpropyl)-1H-indazole-3-carboxamide, 2-({(aR)-6-[1-(2-hydroxy-2-methylpropyl)-1H-pyrrolo[2,3-b]pyridine-3-amido]spiro[3.3]heptan-2-yl}oxy)pyridine-3-carboxamide, 2-({(aR)-6-[5-(2,2-difluoroethoxy)-1-methyl-1H-pyrazole-3-amido]spiro[3.3]heptan-2-yl}oxy)pyridine-3-carboxamide, 2-{[(aR)-6-(4-methyl-2-phenyl-1,3-thiazole-5-amido)spiro[3.3]heptan-2-yl]oxy}pyridine-3-carboxamide, N-{(aR)-6-[(3-carbamoylpyridin-2-yl)oxy]spiro[3.3]heptan-2-yl}-6-fluoro-1-(2-hydroxy-2-methylpropyl)-1H-indazole-3-carboxamide, N-{(aR)-6-[(3-carbamoylpyridin-2-yl)oxy]spiro[3.3]heptan-2-yl}-1-(2-hydroxy-2-methylpropyl)-6-(trifluoromethoxy)-1H-indazole-3-carboxamide, 2-({(aR)-6-[6-methoxy-7-(3,3,3-trifluoropropyl)pyrazolo[1,5-a]pyridine-3-amido]spiro[3.3]heptan-2-yl}oxy)pyridine-3-carboxamide, 2-[((aR)-6-{6-methoxypyrazolo[1,5-a]pyridine-3-amido}spiro[3.3]heptan-2-yl)oxy]pyridine-3-carboxamide, 2-({(aR)-6-[6-(2-hydroxy-2-methylpropoxy)-7-(1-methyl-1H-pyrazol-4-yl)pyrazolo[1,5-a]pyridine-3-amido]spiro[3.3]heptan-2-yl}oxy)pyridine-3-carboxamide, N-{(aR)-6-[(3-carbamoylpyridin-2-yl)oxy]spiro[3.3]heptan-2-yl}-1-(2-hydroxy-2-methylpropyl)-1H-indazole-3-carboxamide, N-{(aR)-6-[(3-carbamoylpyridin-2-yl)oxy]spiro[3.3]heptan-2-yl}-1-(difluoromethyl)-6-fluoro-1H-indazole-3-carboxamide, N-{(aR)-6-[(3-carbamoylpyridin-2-yl)oxy]spiro[3.3]heptan-2-yl}-2-oxo-6-(trifluoromethyl)-2,3-dihydro-1H-1,3-benzodiazole-4-carboxamide, N-{(aR)-6-[(3-carbamoylpyridin-2-yl)oxy]spiro[3.3]heptan-2-yl}-6-fluoro-1-(3,3,3-trifluoropropyl)-1H-indazole-3-carboxamide, N-{(aR)-6-[(3-carbamoylpyridin-2-yl)oxy]spiro[3.3]heptan-2-yl}-1-(difluoromethyl)-6-(1-methyl-1H-pyrazol-4-yl)-1H-indazole-3-carboxamide, 2-({(aR)-6-[7-cyclopropyl-6-(3,3,3-trifluoropropoxy)pyrazolo[1,5-a]pyridine-3-amido]spiro[3.3]heptan-2-yl}oxy)pyridine-3-carboxamide, N-{(aR)-6-[(3-carbamoylpyridin-2-yl)oxy]spiro[3.3]heptan-2-yl}-1-(difluoromethyl)-6-(2-hydroxy-2-methylpropoxy)-1H-indazole-3-carboxamide, 2-{[(aR)-6-(3-methanesulfonylbenzamido)spiro[3.3]heptan-2-yl]oxy}pyridine-3-carboxamide, 2-{[(aR)-6-(4-tert-butylpyridine-2-amido)spiro[3.3]heptan-2-yl]oxy}pyridine-3-carboxamide, N-{(aR)-6-[(3-carbamoylpyridin-2-yl)oxy]spiro[3.3]heptan-2-yl}-1-(Â²Hâ‚‚f)methyl-1H-pyrazol-4-yl]-1H-indazole-3-carboxamide, N-{(aR)-6-[(3-carbamoylpyridin-2-yl)oxy]spiro[3.3]heptan-2-yl}-1-(difluoromethyl)-6-[1-(difluoromethyl)-1H-pyrazol-4-yl]-1H-indazole-3-carboxamide, 2-({(aR)-6-[3-tert-butyl-1-(2,2-difluoroethyl)-1H-pyrazole-5-amido]spiro[3.3]heptan-2-yl}oxy)pyridine-3-carboxamide, 2-({(aR)-6-[3-tert-butyl-1-(3,3,3-trifluoropropyl)-1H-pyrazole-5-amido]spiro[3.3]heptan-2-yl}oxy)pyridine-3-carboxamide, 2-({(aR)-6-[6-(3,3,3-trifluoropropoxy)-7-(3,3,3-trifluoropropyl)pyrazolo[1,5-a]pyridine-3-amido]spiro[3.3]heptan-2-yl}oxy)pyridine-3-carboxamide, 2-[((aR)-6-{6-[(1E)-3,3,3-trifluoroprop-1-en-1-yl]pyrazolo[1,5-a]pyridine-3-amido}spiro[3.3]heptan-2-yl)oxy]pyridine-3-carboxamide, N-{(aR)-6-[(3-carbamoylpyridin-2-yl)oxy]spiro[3.3]heptan-2-yl}-6-(3,3,3-trifluoropropoxy)-1-(3,3,3-trifluoropropyl)-1H-indazole-3-carboxamide, 2-({(aR)-6-[6-(3,3,3-trifluoropropyl)pyrazolo[1,5-a]pyridine-3-amido]spiro[3.3]heptan-2-yl}oxy)pyridine-3-carboxamide, 2-{[(aR)-6-(3-bromo-5-methanesulfonylbenzamido)spiro[3.3]heptan-2-yl]oxy}pyridine-3-carboxamide, 2-[((aR)-6-{6-[2-(1H-imidazol-1-yl)ethoxy]pyrazolo[1,5-a]pyridine-3-amido}spiro[3.3]heptan-2-yl)oxy]pyridine-3-carboxamide, 2-[((aR)-6-{6-[2-(2-methoxyethoxy)ethoxy]pyrazolo[1,5-a]pyridine-3-amido}spiro[3.3]heptan-2-yl)oxy]pyridine-3-carboxamide, 2-({(aR)-6-[6-(4,4,4-trifluorobutoxy)pyrazolo[1,5-a]pyridine-3-amido]spiro[3.3]heptan-2-yl}oxy)pyridine-3-carboxamide, 2-({(aR)-6-[6-(3-methoxy-3-methylbutoxy)pyrazolo[1,5-a]pyridine-3-amido]spiro[3.3]heptan-2-yl}oxy)pyridine-3-carboxamide, 2-[((aR)-6-{6-[3-(2-oxopyrrolidin-1-yl)propoxy]pyrazolo[1,5-a]pyridine-3-amido}spiro[3.3]heptan-2-yl)oxy]pyridine-3-carboxamide, 2-[((aR)-6-{6-[2-(trifluoromethoxy)ethoxy]pyrazolo[1,5-a]pyridine-3-amido}spiro[3.3]heptan-2-yl)oxy]pyridine-3-carboxamide, 2-{[(aR)-6-(6-{2-[(4S)-2-oxo-1,3-oxazolidin-4-yl]ethoxy}pyrazolo[1,5-a]pyridine-3-amido)spiro[3.3]heptan-2-yl]oxy}pyridine-3-carboxamide, N-{(aR)-6-[(3-carbamoylpyridin-2-yl)oxy]spiro[3.3]heptan-2-yl}-6-(2-hydroxy-2-methylpropoxy)-1-(2-hydroxy-2-methylpropyl)-1H-indazole-3-carboxamide, 2-[((aR)-6-{6-[2-(4-methyl-1,3-thiazol-5-yl)ethoxy]pyrazolo[1,5-a]pyridine-3-amido}spiro[3.3]heptan-2-yl)oxy]pyridine-3-carboxamide, 2-({(aR)-6-[1-(pyridin-2-yl)-5-(trifluoromethyl)-1H-pyrazole-4-amido]spiro[3.3]heptan-2-yl}oxy)pyridine-3-carboxamide, 2-({(aR)-6-[2-(pyridin-2-yl)-1,3-thiazole-4-amido]spiro[3.3]heptan-2-yl}oxy)pyridine-3-carboxamide, 2-[((aR)-6-{3-[methyl(phenyl)sulfamoyl]benzamido}spiro[3.3]heptan-2-yl)oxy]pyridine-3-carboxamide, 1-benzyl-N-{(aR)-6-[(3-carbamoylpyridin-2-yl)oxy]spiro[3.3]heptan-2-yl}-1H-indazole-3-carboxamide, 2-({(aR)-6-[3-(2-methyl-1,3-thiazol-4-yl)benzamido]spiro[3.3]heptan-2-yl}oxy)pyridine-3-carboxamide, 2-({(aR)-6-[3-(1H-pyrazol-1-yl)benzamido]spiro[3.3]heptan-2-yl}oxy)pyridine-3-carboxamide, 2-({(aR)-6-[4-methyl-2-(pyridin-3-yl)-1,3-thiazole-5-amido]spiro[3.3]heptan-2-yl}oxy)pyridine-3-carboxamide, 2-({(aR)-6-[2-(4-methoxyphenyl)-1,3-thiazole-4-amido]spiro[3.3]heptan-2-yl}oxy)pyridine-3-carboxamide, 2-[((aR)-6-{2-[(propan-2-yl)sulfamoyl]benzamido}spiro[3.3]heptan-2-yl)oxy]pyridine-3-carboxamide, 2-({(aR)-6-[6-chloro-2-(trifluoromethyl)imidazo[1,2-a]pyridine-3-amido]spiro[3.3]heptan-2-yl}oxy)pyridine-3-carboxamide, 2-({(aR)-6-[2-(1H-1,3-benzodiazol-2-yl)benzamido]spiro[3.3]heptan-2-yl}oxy)pyridine-3-carboxamide, 2-[((aR)-6-{3-[(1H-imidazol-1-yl)methyl]benzamido}spiro[3.3]heptan-2-yl)oxy]pyridine-3-carboxamide, 2-({(aR)-6-[3-(5-methyl-1H-1,2,3,4-tetrazol-1-yl)benzamido]spiro[3.3]heptan-2-yl}oxy)pyridine-3-carboxamide, 2-[((aR)-6-{3-[2-(4-methoxyphenyl)ethyl]benzamido}spiro[3.3]heptan-2-yl)oxy]pyridine-3-carboxamide, 2-({(aR)-6-[4-(1,3-benzothiazol-2-yl)-1,3-thiazole-2-amido]spiro[3.3]heptan-2-yl}oxy)pyridine-3-carboxamide, 2-({(aR)-6-[4-(pyridin-2-yl)-1,3-thiazole-2-amido]spiro[3.3]heptan-2-yl}oxy)pyridine-3-carboxamide, 2-({(aR)-6-[2-(1-methyl-1H-1,3-benzodiazol-2-yl)-1,3-thiazole-4-amido]spiro[3.3]heptan-2-yl}oxy)pyridine-3-carboxamide, 2-({(aR)-6-[3-(3-methyl-1,2,4-oxadiazol-5-yl)benzamido]spiro[3.3]heptan-2-yl}oxy)pyridine-3-carboxamide, 2-{(aR)-6-(2-chloro-4-fluoro-5-sulfamoylbenzamido)spiro[3.3]heptan-2-yl]oxy}pyridine-3-carboxamide, N-((aR)-6-{(3-carbamoylpyridin-2-yl)oxy)spiro[3.3]heptan-2-yl)-3-oxo-2,3-dihydrobenzo[d]isothiazole-6-carboxamide 1,1-dioxide.

2-{[(aR)-6-(4-fluoro-3-sulfamoylbenzamido)spiro[3.3]heptan-2-yl]oxy}pyridine-3-carboxamide, N-{(aR)-6-[(3-carbamoylpyridin-2-yl)oxy]spiro[3.3]heptan-2-yl}-2,3-dioxo-1,2,3,4-tetrahydroquinoxaline-6-carboxamide, 2-{[(aR)-6-(4-chloro-3-sulfamoylbenzamido)spiro[3.3]heptan-2-yl]oxy}pyridine-3-carboxamide, 2-[((aR)-6-{6-chloroimidazo[1,2-a]pyridine-2-amido}spiro[3.3]heptan-2-yl)oxy]pyridine-3-carboxamide, N-{(aR)-6-[(3-carbamoylpyridin-2-yl)oxy]spiro[3.3]heptan-2-yl}-6-chloro-1-methyl-1H-indole-2-carboxamide, 2-{[(aR)-6-(5-cyano-2-fluorobenzamido)spiro[3.3]heptan-2-yl]oxy}pyridine-3-carboxamide, 2-{[(aR)-6-(3-cyano-4-fluorobenzamido)spiro[3.3]heptan-2-yl]oxy}pyridine-3-carboxamide, 2-{[(aR)-6-(3-cyano-5-fluorobenzamido)spiro[3.3]heptan-2-yl]oxy}pyridine-3-carboxamide, 2-{[(aR)-6-(3-cyanobenzamido)spiro[3.3]heptan-2-yl]oxy}pyridine-3-carboxamide, N-{(aR)-6-[(3-carbamoylpyridin-2-yl)oxy]spiro[3.3]heptan-2-yl}isoquinoline-3-carboxamide,
2-[((aR)-6-{3'-cyano-[1,1'-biphenyl]-4-amido}spiro[3.3]heptan-2-yl)oxy]pyridine-3-carboxamide,
N-{(aR)-6-[(3-carbamoylpyridin-2-yl)oxy]spiro[3.3]heptan-2-yl}-6-(4-cyanophenyl)pyridine-3-carboxamide,
2-[((aR)-6-{3'-fluoro-[1,1'-biphenyl]-4-amido}spiro[3.3]heptan-2-yl)oxy]pyridine-3-carboxamide,
2-{[(aR)-6-(2,2-dimethyl-2,3-dihydro-1-benzofuran-7-amido)spiro[3.3]heptan-2-yl]oxy}pyridine-3-carboxamide,
2-{[(aR)-6-(4-methyl-2-phenyl-1,3-oxazole-5-amido)spiro[3.3]heptan-2-yl]oxy}pyridine-3-carboxamide,
2-{[(aR)-6-(5-phenyl-1,3-oxazole-4-amido)spiro[3.3]heptan-2-yl]oxy}pyridine-3-carboxamide,
2-({(aR)-6-[7-(2-hydroxy-2-methylpropoxy)imidazo[1,2-a]pyridine-3-amido]spiro[3.3]heptan-2-yl}oxy)pyridine-3-carboxamide,
2-({(aR)-6-[7-cyclopropyl-6-(2-hydroxy-2-methylpropoxy)pyrazolo[1,5-a]pyridine-3-amido]spiro[3.3]heptan-2-yl}oxy)-6-methoxypyridine-3-carboxamide,
2-({(aR)-6-[6-(2-hydroxy-2-methylpropoxy)-7-(3,3,3-trifluoropropyl)pyrazolo[1,5-a]pyridine-3-amido]spiro[3.3]heptan-2-yl}oxy)-6-methoxypyridine-3-carboxamide,
N-{(aR)-6-[(3-carbamoyl-6-methoxypyridin-2-yl)oxy]spiro[3.3]heptan-2-yl}-5-fluoro-1-(2-hydroxy-2-methylpropyl)-1H-indazole-3-carboxamide,
2-[((aR)-6-{8-cyclopropylimidazo[1,2-a]pyridine-3-amido}spiro[3.3]heptan-2-yl)oxy]pyridine-3-carboxamide,
6-(benzyloxy)-N-{(aR)-6-[(3-carbamoylpyridin-2-yl)oxy]spiro[3.3]heptan-2-yl}-1-(difluoromethyl)-1H-indazole-3-carboxamide,
6-bromo-N-{(aR)-6-[(3-carbamoylpyridin-2-yl)oxy]spiro[3.3]heptan-2-yl}-1-(difluoromethyl)-1H-indazole-3-carboxamide,
N-{(aR)-6-[(3-carbamoylpyridin-2-yl)oxy]spiro[3.3]heptan-2-yl}-6-fluoro-1-methyl-1H-indazole-3-carboxamide,
N-{(aR)-6-[(3-carbamoylpyridin-2-yl)oxy]spiro[3.3]heptan-2-yl}-6-fluoro-1-($^2$H$_3$)methyl-1H-indazole-3-carboxamide,
N-{(aR)-6-[(3-carbamoylpyridin-2-yl)oxy]spiro[3.3]heptan-2-yl}-1-(2,2-difluoroethyl)-6-fluoro-1H-indazole-3-carboxamide,
N-{(aR)-6-[(3-carbamoylpyridin-2-yl)oxy]spiro[3.3]heptan-2-yl}-6-fluoro-2-($^2$H$_3$)methyl-2H-indazole-3-carboxamide,
N-{(aR)-6-[(3-carbamoylpyridin-2-yl)oxy]spiro[3.3]heptan-2-yl}-1-(difluoromethyl)-6-(3-methoxyphenyl)-1H-indazole-3-carboxamide,
2-({(aR)-6-[7-(pyrrolidin-1-yl)-[1,2,4]triazolo[4,3-a]pyridine-3-amido]spiro[3.3]heptan-2-yl}oxy)pyridine-3-carboxamide,
2-({(aR)-6-[7-(morpholin-4-yl)-[1,2,4]triazolo[4,3-a]pyridine-3-amido]spiro[3.3]heptan-2-yl}oxy)pyridine-3-carboxamide,
2-({(aR)-6-[3-cyano-5-(2-methyl-1,3-thiazol-5-yl)benzamido]spiro[3.3]heptan-2-yl}oxy)pyridine-3-carboxamide,
2-[((aR)-6-{3-cyano-5-[1-($^2$H$_3$)methyl-1H-pyrazol-4-yl]benzamido}spiro[3.3]heptan-2-yl)oxy]pyridine-3-carboxamide,
2-({(aR)-6-[3-cyano-5-(1,3-dimethyl-1H-pyrazol-4-yl)benzamido]spiro[3.3]heptan-2-yl}oxy)pyridine-3-carboxamide,
2-{[(aR)-6-(3-cyano-5-cyclopropylbenzamido)spiro[3.3]heptan-2-yl]oxy}pyridine-3-carboxamide,
2-[((aR)-6-{3-cyano-5-[1-methyl-3-(trifluoromethyl)-1H-pyrazol-4-yl]benzamido}spiro[3.3]heptan-2-yl)oxy]pyridine-3-carboxamide,
2-({(aR)-6-[3-cyano-5-(1,5-dimethyl-1H-pyrazol-4-yl)benzamido]spiro[3.3]heptan-2-yl}oxy)pyridine-3-carboxamide,
2-({(aR)-6-[3-cyano-5-(2-methyl-1,3-benzothiazol-5-yl)benzamido]spiro[3.3]heptan-2-yl}oxy)pyridine-3-carboxamide,
2-[((aR)-6-{3-cyano-5-[1-(2-methylpropyl)-1H-pyrazol-4-yl]benzamido}spiro[3.3]heptan-2-yl)oxy]pyridine-3-carboxamide,
2-{[(aR)-6-(3-cyano-5-{4-methyl-2-[4-(trifluoromethyl)phenyl]-1,3-thiazol-5-yl}benzamido)spiro[3.3]heptan-2-yl]oxy}pyridine-3-carboxamide,
2-({(aR)-6-[3-cyano-5-(2-oxo-1,2,3,4-tetrahydroquinolin-6-yl)benzamido]spiro[3.3]heptan-2-yl}oxy)pyridine-3-carboxamide,
2-({(aR)-6-[3-cyano-5-(3,5-dimethyl-1,2-oxazol-4-yl)benzamido]spiro[3.3]heptan-2-yl}oxy)pyridine-3-carboxamide,
2-({(aR)-6-[3-cyano-5-(6-cyanopyridin-3-yl)benzamido]spiro[3.3]heptan-2-yl}oxy)pyridine-3-carboxamide,
2-({(aR)-6-[3-cyano-5-(1-methyl-2-oxo-1,2-dihydropyridin-4-yl)benzamido]spiro[3.3]heptan-2-yl}oxy)pyridine-3-carboxamide,
2-[((aR)-6-{3-cyano-5-[3-(trifluoromethyl)-1H-pyrazol-4-yl]benzamido}spiro[3.3]heptan-2-yl)oxy]pyridine-3-carboxamide,
2-({(aR)-6-[3-cyano-5-(1-methyl-2-oxo-1,2-dihydropyridin-3-yl)benzamido]spiro[3.3]heptan-2-yl}oxy)pyridine-3-carboxamide,
2-({(aR)-6-[3-cyano-5-(1-methyl-1H-pyrazol-4-yl)benzamido]spiro[3.3]heptan-2-yl}oxy)pyridine-3-carboxamide,
2-[((aR)-6-{5-cyano-3'-methanesulfonyl-[1,1'-biphenyl]-3-amido}spiro[3.3]heptan-2-yl)oxy]pyridine-3-carboxamide,
2-({(aR)-6-[3-cyano-5-(1-methyl-1H-pyrazol-5-yl)benzamido]spiro[3.3]heptan-2-yl}oxy)pyridine-3-carboxamide,
2-[((aR)-6-{3-cyano-5-[1-(difluoromethyl)-1H-pyrazol-4-yl]benzamido}spiro[3.3]heptan-2-yl)oxy]pyridine-3-carboxamide,
2-{[(aR)-6-(3-cyano-5-{4H,5H,6H,7H-[1,3]thiazolo[5,4-c]pyridin-2-yl}benzamido)spiro[3.3]heptan-2-yl]oxy}pyridine-3-carboxamide,
2-{[(aR)-6-(3-cyano-5-{5-methyl-4H,5H,6H,7H-[1,3]thiazolo[5,4-c]pyridin-2-yl}benzamido)spiro[3.3]heptan-2-yl]oxy}pyridine-3-carboxamide,
2-({(aR)-6-[3-cyano-5-(2-methyl-1,3-thiazol-4-yl)benzamido]spiro[3.3]heptan-2-yl}oxy)pyridine-3-carboxamide,
N-[6-(2-carbamoyl-6-methoxyphenoxy)spiro[3.3]heptan-2-yl]-7-cyclopropyl-6-(2-hydroxy-2-methylpropoxy)pyrazolo[1,5-a]pyridine-3-carboxamide,
N-[6-(2-carbamoyl-6-methoxyphenoxy)spiro[3.3]heptan-2-yl]-6-(2-hydroxy-2-methylpropoxy)pyrazolo[1,5-a]pyridine-3-carboxamide,
N-[6-(2-carbamoyl-5-methoxyphenoxy)spiro[3.3]heptan-2-yl]-6-(2-hydroxy-2-methylpropoxy)pyrazolo[1,5-a]pyridine-3-carboxamide,
N-[6-(2-carbamoyl-5-methoxyphenoxy)spiro[3.3]heptan-2-yl]-7-cyclopropyl-6-(2-hydroxy-2-methylpropoxy)pyrazolo[1,5-a]pyridine-3-carboxamide, N-[6-(2-carbamoyl-4-methoxyphenoxy)spiro[3.3]heptan-2-yl]-6-(2-hydroxy-2-methylpropoxy)pyrazolo[1,5-a]pyridine-3-carboxamide, N-[6-(2-carbamoyl-4-methoxy phenoxy)spiro[3.3]heptan-2-yl]-7-cyclopropyl-6-(2-hydroxy-2-methylpropoxy)pyrazolo[1,5-a]pyridine-3-carboxamide, N-[6-(2-carbamoyl-6-methylphenoxy)spiro[3.3]heptan-2-yl]-7-cyclopropyl-6-(2-hydroxy-2-methylpropoxy)pyrazolo[1,5-a]pyridine-3-carboxamide, N-[6-(2-carbamoyl-5-methylphenoxy)spiro[3.3]heptan-2-yl]-6-(2-hydroxy-2-methylpropoxy)pyrazolo[1,5-a]pyridine-3-carboxamide, N-[6-(2-carbamoyl-4-methylphenoxy)spiro[3.3]heptan-2-yl]-7-cyclopropyl-6-(2-hydroxy-2-methylpropoxy)pyrazolo[1,5-a]pyridine-3-carboxamide, N-[6-(2-carbamoyl-5-methylphenoxy)spiro[3.3]heptan-2-yl]-7-cyclopropyl-6-(2-hydroxy-2-methylpropoxy)pyrazolo[1,5-a]pyridine-3-carboxamide, N-[6-(2-carbamoyl-4-methylphenoxy)spiro[3.3]heptan-2-yl]-6-(2-hydroxy-2-methylpropoxy)pyrazolo[1,5-a]pyridine-3-carboxamide, N-{6-(2-carbamoyl-5-(difluoromethoxy)phenoxy)spiro[3.3]heptan-2-yl}-6-(2-hydroxy-2-methylpropoxy)pyrazolo[1,5-a]pyridine-3-carboxamide, N-[6-(2-carbamoyl-5-chlorophenoxy)spiro[3.3]heptan-2-yl]-6-(2-hydroxy-2-methylpropoxy)pyrazolo[1,5-a]pyridine-3-carboxamide, N-{6-[2-carbamoyl-5-(1H-imidazol-1-yl)phenoxy]spiro[3.3]heptan-2-yl}-6-(2-hydroxy-2-methylpropoxy)pyrazolo[1,5-a]pyridine-3-carboxamide, N-{6-[2-carbamoyl-5-(pyrimidin-2-yl)phenoxy]spiro[3.3]heptan-2-yl}-6-(2-hydroxy-2-methylpropoxy)pyrazolo[1,5-a]pyridine-3-carboxamide, N-{6-[2-carbamoyl-5-(1H-pyrazol-1-yl)phenoxy]spiro[3.3]heptan-2-yl}-6-(2-hydroxy-2-methylpropoxy)pyrazolo[1,5-a]pyridine-3-carboxamide, N-{6-(2-carbamoyl-5-(4-methylpiperazin-1-yl)phenoxy)spiro[3.3]heptan-2-yl}-6-(2-hydroxy-2-methylpropoxy)pyrazolo[1,5-a]pyridine-3-carboxamide, N-{6-[2-carbamoyl-5-(pyridin-4-yl)phenoxy]spiro[3.3]heptan-2-yl}-6-(2-hydroxy-2-methylpropoxy)pyrazolo[1,5-a]pyridine-3-carboxamide, N-[6-[5-(azetidin-3-yl)-2-carbamoylphenoxy]spiro[3.3]heptan-2-yl]-6-(2-hydroxy-2-methylpropoxy)pyrazolo[1,5-a]pyridine-3-carboxamide, N-{6-[2-carbamoyl-5-(pyrrolidin-1-yl)phenoxy]spiro[3.3]heptan-2-yl}-6-(2-hydroxy-2-methylpropoxy)pyrazolo[1,5-a]pyridine-3-carboxamide, 6-(2-hydroxy-2-methylpropoxy)-N-(6-{[2'-(trifluoromethyl)-[1,1'-biphenyl]-4-yl]oxy}spiro[3.3]heptan-2-yl)pyrazolo[1,5-a]pyridine-3-carboxamide, N-[6-({2'-fluoro-[1,1'-biphenyl]-4-yl}oxy)spiro[3.3]heptan-2-yl]-6-(2-hydroxy-2-methylpropoxy)pyrazolo[1,5-a]pyridine-3-carboxamide, N-{6-[2-carbamoyl-5-(morpholin-4-yl)phenoxy]spiro[3.3]heptan-2-yl}-6-(2-hydroxy-2-methylpropoxy)pyrazolo[1,5-a]pyridine-3-carboxamide, N-{6-[2-carbamoyl-5-(6-fluoropyridin-2-yl)phenoxy]spiro[3.3]heptan-2-yl}-6-(2-hydroxy-2-methylpropoxy)pyrazolo[1,5-a]pyridine-3-carboxamide, methyl 5-[4-carbamoyl-3-({6-[6-(2-hydroxy-2-methylpropoxy)pyrazolo[1,5-a]pyridine-3-amido]spiro[3.3]heptan-2-yl}oxy)phenyl]pyridine-3-carboxylate, 2-methoxyethyl N-{5-[4-carbamoyl-3-({6-[6-(2-hydroxy-2-methylpropoxy)pyrazolo[1,5-a]pyridine-3-amido]spiro[3.3]heptan-2-yl}oxy)phenyl]pyridin-2-yl}carbamate, N-(6-{2-carbamoyl-5-[6-(2-hydroxypropan-2-yl)pyridin-3-yl]phenoxy}spiro[3.3]heptan-2-yl)-6-(2-hydroxy-2-methylpropoxy)pyrazolo[1,5-a]pyridine-3-carboxamide, N-{6-[2-carbamoyl-5-(6-methoxypyridin-2-yl)phenoxy]spiro[3.3]heptan-2-yl}-6-(2-hydroxy-2-methylpropoxy)pyrazolo[1,5-a]pyridine-3-carboxamide, N-{6-[5-(6-aminopyridin-2-yl)-2-carbamoylphenoxy]spiro[3.3]heptan-2-yl}-6-(2-hydroxy-2-methylpropoxy)pyrazolo[1,5-a]pyridine-3-carboxamide, N-{6-[2-carbamoyl-5-(pyridin-2-yl)phenoxy]spiro[3.3]heptan-2-yl}-6-(2-hydroxy-2-methylpropoxy)pyrazolo[1,5-a]pyridine-3-carboxamide, 6-(2-hydroxy-2-methylpropoxy)-N-(6-{[3'-(2,2,2-trifluoroethoxy)-[1,1'-biphenyl]-4-yl]oxy}spiro[3.3]heptan-2-yl)pyrazolo[1,5-a]pyridine-3-carboxamide, 6-(2-hydroxy-2-methylpropoxy)-N-[6-({3'-methoxy-1,1'-biphenyl-4-yl}oxy)spiro[3.3]heptan-2-yl]pyrazolo[1,5-a]pyridine-3-carboxamide, 6-(2-hydroxy-2-methylpropoxy)-N-[6-({3'-hydroxy-[1,1'-biphenyl]-4-yl}oxy)spiro[3.3]heptan-2-yl]pyrazolo[1,5-a]pyridine-3-carboxamide, N-(6-{3'-(difluoromethyl)-1,1'-biphenyl]-4-yl)oxy}spiro[3.3]heptan-2-yl)-6-(2-hydroxy-2-methylpropoxy)pyrazolo[1,5-a]pyridine-3-carboxamide, N-[6-({3'-fluoro-[1,1'-biphenyl]-4-yl}oxy)spiro[3.3]heptan-2-yl]-6-(2-hydroxy-2-methylpropoxy)pyrazolo[1,5-a]pyridine-3-carboxamide, 6-(2-hydroxy-2-methylpropoxy)-N-(6-{[3'-(trifluoromethyl)-[1,1'-biphenyl]-4-yl]oxy}spiro[3.3]heptan-2-yl)pyrazolo[1,5-a]pyridine-3-carboxamide, N-[6-({3'-cyano-[1,1'-biphenyl]-4-yl}oxy)spiro[3.3]heptan-2-yl]-6-(2-hydroxy-2-methylpropoxy)pyrazolo[1,5-a]pyridine-3-carboxamide, 6-(2-hydroxy-2-methylpropoxy)-N-(6-{[3'-(methoxymethyl)-[1,1'-biphenyl]-4-yl]oxy}spiro[3.3]heptan-2-yl)pyrazolo[1,5-a]pyridine-3-carboxamide, N-(6-{[3'-(5-amino-4-cyano-3-methyl-1H-pyrazol-1-yl)-[1,1'-biphenyl]-4-yl]oxy}spiro[3.3]heptan-2-yl)-6-(2-hydroxy-2-methylpropoxy)pyrazolo[1,5-a]pyridine-3-carboxamide, 6-(2-hydroxy-2-methylpropoxy)-N-(6-{[3'-(hydroxymethyl)-[1,1'-biphenyl]-4-yl]oxy}spiro[3.3]heptan-2-yl)pyrazolo[1,5-a]pyridine-3-carboxamide, N-{6-[2-carbamoyl-5-(6-chloropyridin-2-yl)phenoxy]spiro[3.3]heptan-2-yl}-6-(2-hydroxy-2-methylpropoxy)pyrazolo[1,5-a]pyridine-3-carboxamide, 3-[({[4'-carbamoyl-3'-({6-[6-(2-hydroxy-2-methylpropoxy)pyrazolo[1,5-a]pyridine-3-amido]spiro[3.3]heptan-2-yl}oxy)-[1,1'-biphenyl]-3-yl]methoxy}carbonyl)amino]propanoic acid, tert-butyl 3-[({[4'-carbamoyl-3'-({6-[6-(2-hydroxy-2-methylpropoxy)pyrazolo[1,5-a]pyridine-3-amido]spiro[3.3]heptan-2-yl}oxy)-[1,1'-biphenyl]-3-yl]methoxy}carbonyl)amino]propanoate, 5-fluoro-3'-({6-[6-(2-hydroxy-2-methylpropoxy)pyrazolo[1,5-a]pyridine-3-amido]spiro[3.3]heptan-2-yl}oxy)-N3-propyl-[1,1'-biphenyl]-3,4-dicarboxamide, N-(6-{[3'-(aminomethyl)-[1,1'-biphenyl]-4-yl]oxy}spiro[3.3]heptan-2-yl)-6-(2-hydroxy-2-methylpropoxy)pyrazolo[1,5-a]pyridine-3-carboxamide, N-[6-({3'-cyano-5'-fluoro-[1,1'-biphenyl]-4-yl}oxy)spiro[3.3]heptan-2-yl]-6-(2-hydroxy-2-methylpropoxy)pyrazolo[1,5-a]pyridine-3-carboxamide, N-[6-({3'-cyano-5'-nitro-[1,1'-biphenyl]-4-yl}oxy)spiro[3.3]heptan-2-yl]-6-(2-hydroxy-2-methylpropoxy)pyrazolo[1,5-a]pyridine-3-carboxamide, 4'-carbamoyl-3'-({6-[6-(2-hydroxy-2-methylpropoxy)pyrazolo[1,5-a]pyridine-3-amido]spiro[3.3]heptan-2-yl}oxy)-[1,1'-biphenyl]-3,5-dicarboxylic acid, N-{6-[2-carbamoyl-5-(pyridin-3-yl)phenoxy]spiro[3.3]heptan-2-yl}-6-(2-hydroxy-2-methylpropoxy)pyrazolo[1,5-a]pyridine-3-carboxamide, 2-amino-2-[4'-carbamoyl-3'-({(aR)-6-[6-(2-hydroxy-2-methylpropoxy)pyrazolo[1,5-a]pyridine-3-amido]spiro[3.3]heptan-2-yl}oxy)-[1,1'-biphenyl]-3-yl]acetic acid, N-(6-{[3',5'-bis(hydroxymethyl)-[1,1'-biphenyl]-4-yl]oxy}spiro[3.3]heptan-2-yl)-6-(2-hydroxy-2-methylpropoxy)pyrazolo[1,5-a]pyridine-3-carboxamide, N-[6-(2-carbamoyl-5-hydroxyphenoxy)spiro[3.3]heptan-2-yl]-6-(2-hydroxy-2-methylpropoxy)pyrazolo[1,5-a]pyridine-3-carboxamide, N-{(aR)-6-[5-(3-aminoazetidin-1-yl)-2-carbamoylphenoxy]spiro[3.3]heptan-2-yl}-6-(2-hydroxy-2-methylpropoxy)pyrazolo[1,5-a]pyridine-3-carboxamide, N-(6-{3'-(2-aminoethyl)-1,1'-biphenyl-4-yl}oxy)spiro[3.3]heptan-2-yl)-6-(2-hydroxy-2-methylpropoxy)pyrazolo[1,5-a]pyridine-3-carboxamide, N-(6-{2-carbamoyl-5-[3-(dimethylamino)propyl]phenoxy}spiro[3.3]heptan-2-yl)-6-(2-hydroxy-2-methylpropoxy)pyrazolo[1,5-a]pyridine-3-carboxamide, N-(6-{2-carbamoyl-5-[3-(dimethylamino)propyl]phenoxy}spiro[3.3]heptan-2-yl)-7-cyclopropyl-6-(2-hydroxy-2-methylpropoxy)pyrazolo[1,5-a]pyridine-3-carboxamide, N-(6-{2-carbamoyl-5-[3-(morpholin-4-yl)propyl]phenoxy}spiro[3.3]heptan-2-yl)-6-(2-hydroxy-2-methylpropoxy)pyrazolo[1,5-a]pyridine-3-carboxamide, N-(6-{2-carbamoyl-5-[3-(morpholin-4-yl)propyl]phenoxy}spiro[3.3]heptan-2-yl)-7-cyclopropyl-6-(2-hydroxy-2-methylpropoxy)pyrazolo[1,5-a]pyridine-3-carboxamide, N-(6-{2-carbamoyl-5-[3-(4-methylpiperazin-1-yl)propyl]phenoxy}spiro[3.3]heptan-2-yl)-6-(2-hydroxy-2-methylpropoxy)pyrazolo[1,5-a]pyridine-3-carboxamide, N-(6-{2-carbamoyl-5-[3-(4-methylpiperazin-1-yl)propyl]phenoxy}spiro[3.3]heptan-2-yl)-7-cyclopropyl-6-(2-hydroxy-2-methylpropoxy)pyrazolo[1,5-a]pyridine-3-carboxamide, N-[6-(2-carbamoyl-4,6-difluorophenoxy)spiro[3.3]heptan-2-yl]-6-(2-hydroxy-2-methylpropoxy)pyrazolo[1,5-a]pyridine-3-carboxamide, N-[6-(2-carbamoyl-4,6-difluorophenoxy)spiro[3.3]heptan-2-yl]-7-cyclopropyl-6-(2-hydroxy-2-methylpropoxy)pyrazolo[1,5-a]pyridine-3-carboxamide, N-[6-(2-carbamoyl-4-fluorophenoxy)spiro[3.3]heptan-2-yl]-6-(2-hydroxy-2-methylpropoxy)pyrazolo[1,5-a]pyridine-3-carboxamide, N-[6-(2-carbamoyl-4-fluorophenoxy)spiro[3.3]heptan-2-yl]-7-cyclopropyl-6-(2-hydroxy-2-methylpropoxy)pyrazolo[1,5-a]pyridine-3-carboxamide, N-[6-(5-bromo-2-carbamoylphenoxy)spiro[3.3]heptan-2-yl]-6-(2-hydroxy-2-methylpropoxy)pyrazolo[1,5-a]pyridine-3-carboxamide, N-[6-(2-carbamoyl-5-cyclopropylphenoxy)spiro[3.3]heptan-2-yl]-6-(2-hydroxy-2-methylpropoxy)pyrazolo[1,5-a]pyridine-3-carboxamide, N-[6-(2-carbamoyl-5-cyclopropylphenoxy)spiro[3.3]heptan-2-yl]-7-cyclopropyl-6-(2-hydroxy-2-methylpropoxy)pyrazolo[1,5-a]pyridine-3-carboxamide, N-{6-[2-carbamoyl-5-(1-methyl-1H-pyrazol-4-yl)phenoxy]spiro[3.3]heptan-2-yl}-6-(2-hydroxy-2-methylpropoxy)pyrazolo[1,5-a]pyridine-3-carboxamide, N-{(aR)-6-[2-carbamoyl-5-(1-methyl-1H-pyrazol-4-yl)phenoxy]spiro[3.3]heptan-2-yl}-6-(2-hydroxy-2-methylpropoxy)pyrazolo[1,5-a]pyridine-3-carboxamide, N-{6-[2-carbamoyl-5-(1-cyclopropyl-1H-pyrazol-4-yl)phenoxy]spiro[3.3]heptan-2-yl}-6-(2-hydroxy-2-methylpropoxy)pyrazolo[1,5-a]pyridine-3-carboxamide, N-(6-{2-carbamoyl-5-[1-(oxan-4-yl)-1H-pyrazol-4-yl]phenoxy}spiro[3.3]heptan-2-yl)-6-(2-hydroxy-2-methylpropoxy)pyrazolo[1,5-a]pyridine-3-carboxamide, N-(6-{2-carbamoyl-5-[1-(2-hydroxy-2-methylpropyl)-1H-pyrazol-4-yl]phenoxy}spiro[3.3]heptan-2-yl)-6-(2-hydroxy-2-methylpropoxy)pyrazolo[1,5-a]pyridine-3-carboxamide, 3-fluoro-3'-({6-[6-(2-hydroxy-2-methylpropoxy)pyrazolo[1,5-a]pyridine-3-amido]spiro[3.3]heptan-2-yl}oxy)-(1,1'-biphenyl]-4,4'-dicarboxamide, N-[6-(2-carbamoyl-5-{5-((morpholin-4-yl)methylthiophen-2-yl}phenoxy)spiro[3.3]heptan-2-yl]-6-(2-hydroxy-2-methylpropoxy)pyrazolo[1,5-a]pyridine-3-carboxamide, ethyl 2-[4'-carbamoyl-3'-({6-[6-(2-hydroxy-2-methylpropoxy)pyrazolo[1,5-a]pyridine-3-amido]spiro[3.3]heptan-2-yl}oxy)-[1,1'-biphenyl]-3-yl]acetate, 6-(2-hydroxy-2-methylpropoxy)-N-[6-({3',4',5'-trifluoro-[1,1'-biphenyl]-4-yl}oxy)spiro[3.3]heptan-2-yl]pyrazolo[1,5-a]pyridine-3-carboxamide, 6-(2-hydroxy-2-methylpropoxy)-N-[6-({3'-methanesulfonyl-[1,1'-biphenyl]-4-yl}oxy)spiro[3.3]heptan-2-yl]pyrazolo[1,5-a]pyridine-3-carboxamide, N3-[2-(dimethylamino)ethyl]-3'-({6-[6-(2-hydroxy-2-methylpropoxy)pyrazolo[1,5-a]pyridine-3-amido]spiro[3.3]heptan-2-yl}oxy)-[1,1'-biphenyl]-3,4'-dicarboxamide, 6-(2-hydroxy-2-methylpropoxy)-N-[6-({4'-methanesulfonyl-[1,1'-biphenyl]-4-yl}oxy)spiro[3.3]heptan-2-yl]pyrazolo[1,5-a]pyridine-3-carboxamide, 3'-({6-[6-(2-hydroxy-2-methylpropoxy)pyrazolo[1,5-a]pyridine-3-amido]spiro[3.3]heptan-2-yl}oxy)-N3-methyl-[1,1'-biphenyl]-3,4'-dicarboxamide, N-(6-{[3'-(3-aminopropoxy)-[1,1'-biphenyl]-4-yl]oxy}spiro[3.3]heptan-2-yl)-6-(2-hydroxy-2-methylpropoxy)pyrazolo[1,5-a]pyridine-3-carboxamide, 3'-({6-[6-(2-hydroxy-2-methylpropoxy)pyrazolo[1,5-a]pyridine-3-amido]spiro[3.3]heptan-2-yl}oxy)-[1,1'-biphenyl]-3,4'-dicarboxamide, N-(6-{2-carbamoyl-5-[(1E)-4-hydroxybut-1-en-1-yl]phenoxy}spiro[3.3]heptan-2-yl)-6-(2-hydroxy-2-methylpropoxy)pyrazolo[1,5-a]pyridine-3-carboxamide, (2E)-3-[4'-carbamoyl-3'-({6-[6-(2-hydroxy-2-methylpropoxy)pyrazolo[1,5-a]pyridine-3-amido]spiro[3.3]heptan-2-yl}oxy)-[1,1'-biphenyl]-3-yl]prop-2-enoic acid, 4-fluoro-3'-({6-[6-(2-hydroxy-2-methylpropoxy)pyrazolo[1,5-a]pyridine-3-amido]spiro[3.3]heptan-2-yl}oxy)-[1,1'-biphenyl]-3,4'-dicarboxamide, 3'-({6-[6-(2-hydroxy-2-methylpropoxy)pyrazolo[1,5-a]pyridine-3-amido]spiro[3.3]heptan-2-yl}oxy)-N3-(2-methoxyethyl)-[1,1'-biphenyl]-3,4'-dicarboxamide, 6-(2-hydroxy-2-methylpropoxy)-N-(6-{[3'-(morpholine-4-carbonyl)-[1,1'-biphenyl]-4-yl]oxy}spiro[3.3]heptan-2-yl)pyrazolo[1,5-a]pyridine-3-carboxamide, 4-fluoro-3'-({6-[6-(2-hydroxy-2-methylpropoxy)pyrazolo[1,5-a]pyridine-3-amido]spiro[3.3]heptan-2-yl}oxy)-N3-methyl-[1,1'-biphenyl]-3,4'-dicarboxamide, 4'-carbamoyl-3'-({6-[6-(2-hydroxy-2-methylpropoxy)pyrazolo[1,5-a]pyridine-3-amido]spiro[3.3]heptan-2-yl}oxy)-[1,1'-biphenyl]-3-carboxylic acid, 6-(2-hydroxy-2-methylpropoxy)-N-[6-({3'-((2-hydroxyethyl)sulfamoyl)-[1,1'-biphenyl]-4-yl}oxy)spiro[3.3]heptan-2-yl]pyrazolo[1,5-a]pyridine-3-carboxamide, 6-(2-hydroxy-2-methylpropoxy)-N-[6-({3'-sulfamoyl-[1,1'-biphenyl]-4-yl}oxy)spiro[3.3]heptan-2-yl]pyrazolo[1,5-a]pyridine-3-carboxamide, N-(6-{[4'-fluoro-3'-(1H-1,2,3,4-tetrazol-5-yl)-[1,1'-biphenyl]-4-yl]oxy}spiro[3.3]heptan-2-yl)-6-(2-hydroxy-2-methylpropoxy)pyrazolo[1,5-a]pyridine-3-carboxamide, N-{6-[5-(3-aminopropyl)-2-carbamoylphenoxy]spiro[3.3]heptan-2-yl}-6-(2-hydroxy-2-methylpropoxy)pyrazolo[1,5-a]pyridine-3-carboxamide, N-{(aR)-6-[2-carbamoyl-5-(pyrrolidin-3-yl)phenoxy]spiro[3.3]heptan-2-yl}-6-(2-hydroxy-2-methylpropoxy)pyrazolo[1,5-a]pyridine-3-carboxamide, N-[(aR)-6-(5-bromo-2-carbamoylphenoxy)spiro[3.3]heptan-2-yl]-6-(2-hydroxy-2-methylpropoxy)pyrazolo[1,5-a]pyridine-3-carboxamide, N-[(aR)-6-(2-carbamoylphenoxy)spiro[3.3]heptan-2-yl]pyrazolo[1,5-a]pyridine-3-carboxamide, N-((aR)-6-{2-carbamoyl-5-[(pyrrolidin-3-yl)methyl]phenoxy}spiro[3.3]heptan-2-yl)-6-(2-hydroxy-2-methylpropoxy)pyrazolo[1,5-a]pyridine-3-carboxamide, N-{6-[5-(4-aminobutyl)-2-carbamoylphenoxy]spiro[3.3]heptan-2-yl}-6-(2-hydroxy-2-methylpropoxy)pyrazolo[1,5-a]pyridine-3-carboxamide, 2-(2-aminoethoxy)-4-({6-[7-cyclopropyl-6-(2-hydroxy-2-methylpropoxy)pyrazolo[1,5-a]pyridine-3-amido]spiro[3.3]heptan-2-yl}oxy)pyrimidine-5-carboxamide, 2-({(aR)-6-[7-bromo-6-(2,2-difluoropropoxy)pyrazolo[1,5-a]pyridine-3-amido]spiro[3.3]heptan-2-yl}oxy)pyridine-3-carboxamide, 2-({(aR)-6-[6-(2,2-difluoropropoxy)pyrazolo[1,5-a]pyridine-3-amido]spiro[3.3]heptan-2-yl}oxy)pyridine-3-carboxamide, 2-({(aR)-6-[7-cyclopropyl-6-(2,2-difluoropropoxy)pyrazolo[1,5-a]pyridine-3-amido]spiro[3.3]heptan-2-yl}oxy)pyridine-3-carboxamide, 2-({(aR)-6-[6-(2,2-difluoropropoxy)-7-(1H-pyrazol-4-yl)pyrazolo[1,5-a]pyridine-3-amido]spiro[3.3]heptan-2-yl}oxy)pyridine-3-carboxamide, 2-[((aR)-6-{pyrazolo[1,5-a]pyridine-3-amido}spiro[3.3]heptan-2-yl)oxy]pyridine-3-carboxamide, 2-({(aR)-6-[6-(difluoromethoxy)pyrazolo[1,5-a]pyridine-3-amido]spiro[3.3]heptan-2-yl}oxy)pyridine-3-carboxamide, 2-({(aR)-6-[6-(2,2-difluoroethoxy)pyrazolo[1,5-a]pyridine-3-amido]spiro[3.3]heptan-2-yl}oxy)pyridine-3-carboxamide, 2-({6-[6-(3,3,3-trifluoro-2-hydroxypropoxy)pyrazolo[1,5-a]pyridine-3-amido]spiro[3.3]heptan-2-yl}oxy)pyridine-3-carboxamide, 2-[((aR)-6-{6-[3,3,3-trifluoro-2-hydroxy-2-(trifluoromethyl)propoxy]pyrazolo[1,5-a]pyridine-3-amido}spiro[3.3]heptan-2-yl)oxy]pyridine-3-carboxamide, 2-({(aR)-6-[6-(4,4-difluoropiperidin-1-yl)pyrazolo[1,5-a]pyridine-3-amido]spiro[3.3]heptan-2-yl}oxy)pyridine-3-carboxamide, 2-({(aR)-6-[6-(morpholin-4-yl)pyrazolo[1,5-a]pyridine-3-amido]spiro[3.3]heptan-2-yl}oxy)pyridine-3-carboxamide, 2-[((aR)-6-{6-[(3R)-3-fluoropyrrolidin-1-yl]pyrazolo[1,5-a]pyridine-3-amido}spiro[3.3]heptan-2-yl)oxy]pyridine-3-carboxamide, 2-({(aR)-6-[6-(4-methylpiperazin-1-yl)pyrazolo[1,5-a]pyridine-3-amido]spiro[3.3]heptan-2-yl}oxy)pyridine-3-carboxamide, 2-({(aR)-6-[6-(2-hydroxy-2-methylpropoxy)-7-(propan-2-yl)pyrazolo[1,5-a]pyridine-3-amido]spiro[3.3]heptan-2-yl}oxy)pyridine-3-carboxamide, 2-({(aR)-6-[6-(2-hydroxy-2-methylpropoxy)-7-methylpyrazolo[1,5-a]pyridine-3-amido]spiro[3.3]heptan-2-yl}oxy)pyridine-3-carboxamide, 2-[((aR)-6-{7-[(3S)-3-fluoropyrrolidin-1-yl]imidazo[1,2-a]pyridine-3-amido}spiro[3.3]heptan-2-yl)oxy]pyridine-3-carboxamide, 2-({(aR)-6-[7-(3,3-difluoropyrrolidin-1-yl)imidazo[1,2-a]pyridine-3-amido]spiro[3.3]heptan-2-yl}oxy)pyridine-3-carboxamide, 2-({(aR)-6-[7-(4,4-difluoropiperidin-1-yl)imidazo[1,2-a]pyridine-3-amido]spiro[3.3]heptan-2-yl}oxy)pyridine-3-carboxamide, 2-[((aR)-6-{7-[2-(pyrrolidin-1-yl)ethoxy]imidazo[1,2-a]pyridine-3-amido}spiro[3.3]heptan-2-yl)oxy]pyridine-3-carboxamide, 2-[((aR)-6-{7-[(3R)-3-hydroxypyrrolidin-1-yl]imidazo[1,2-a]pyridine-3-amido}spiro[3.3]heptan-2-yl)oxy]pyridine-3-carboxamide, 2-[((aR)-6-{6-fluoroimidazo[1,2-a]pyridine-3-amido}spiro[3.3]heptan-2-yl)oxy]pyridine-3-carboxamide, 2-({(aR)-6-[7-(1-hydroxyethyl)imidazo[1,2-a]pyridine-3-amido]spiro[3.3]heptan-2-yl}oxy)pyridine-3-carboxamide, 2-[((aR)-6-{7-[(3R)-3-fluoropyrrolidin-1-yl]imidazo[1,2-a]pyridine-3-amido}spiro[3.3]heptan-2-yl)oxy]pyridine-3-carboxamide, 2-[((aR)-6-[6-[(2R)-2-hydroxypropoxy]pyrazolo[1,5-a]pyridine-3-amido]spiro[3.3]heptan-2-yl}oxy)pyridine-3-carboxamide, 2-({(aR)-6-[7-(2,2-difluoroethoxy)imidazo[1,2-a]pyridine-3-amido]spiro[3.3]heptan-2-yl}oxy)pyridine-3-carboxamide, 2-[((aR)-6-{7-[(1,3-difluoropropan-2-yl)oxy]imidazo[1,2-a]pyridine-3-amido}spiro[3.3]heptan-2-yl)oxy]pyridine-3-carboxamide, 2-[((aR)-6-{6-[(2S)-2-hydroxypropoxy]pyrazolo[1,5-a]pyridine-3-amido}spiro[3.3]heptan-2-yl)oxy]pyridine-3-carboxamide, 2-({(aR)-6-[7-(trifluoromethyl)imidazo[1,2-a]pyridine-3-amido]spiro[3.3]heptan-2-yl}oxy)pyridine-3-carboxamide, 2-[((aR)-6-{7-methylimidazo[1,2-a]pyridine-3-amido}spiro[3.3]heptan-2-yl)oxy]pyridine-3-carboxamide, N-((aR)-6-((3-carbamoylpyridin-2-yl)oxy)spiro[3.3]heptan-2-yl)-7-(4-methylpiperazin-1-yl)imidazo[1,2-a]pyridine-3-carboxamide, 2-({(aR)-6-[7-(1-methyl-1H-pyrazol-4-yl)imidazo[1,2-a]pyridine-3-amido]spiro[3.3]heptan-2-yl}oxy)pyridine-3-carboxamide, 2-[((aR)-6-{6-cyclobutoxypyrazolo[1,5-a]pyridine-3-amido}spiro[3.3]heptan-2-yl)oxy]pyridine-3-carboxamide, N-((aR)-6-((3-carbamoylpyridin-2-yl)oxy)spiro[3.3]heptan-2-yl)-6-((1,1-dioxidotetrahydro-2H-thiopyran-4-yl)oxy)pyrazolo[1,5-a]pyridine-3-carboxamide, 2-[((aR)-6-{7-cyclopropyl-6-[2-(2,2,2-trifluoroethoxy)ethoxy]pyrazolo[1,5-a]pyridine-3-amido}spiro[3.3]heptan-2-yl)oxy]pyridine-3-carboxamide, 2-[((aR)-6-{7-cyclopropyl-6-[(1,3-difluoropropan-2-yl)oxy]pyrazolo[1,5-a]pyridine-3-amido}spiro[3.3]heptan-2-yl)oxy]pyridine-3-carboxamide, 2-[((aR)-6-{7-cyclopropyl-6-[(oxolan-2-yl)methoxy]pyrazolo[1,5-a]pyridine-3-amido}spiro[3.3]heptan-2-yl)oxy]pyridine-3-carboxamide, 2-({(aR)-6-[7-cyclopropyl-6-(oxetan-3-yloxy)pyrazolo[1,5-a]pyridine-3-amido]spiro[3.3]heptan-2-yl}oxy)pyridine-3-carboxamide, 2-[((aR)-6-{7-cyclopropyl-6-[(oxetan-2-yl)methoxy]pyrazolo[1,5-a]pyridine-3-amido}spiro[3.3]heptan-2-yl)oxy]pyridine-3-carboxamide, 2-[((aR)-6-{imidazo[1,2-a]pyrazine-3-amido}spiro[3.3]heptan-2-yl)oxy]pyridine-3-carboxamide, 2-({(aR)-6-[8-(trifluoromethyl)imidazo[1,2-a]pyridine-3-amido]spiro[3.3]heptan-2-yl}oxy)pyridine-3-carboxamide, methyl 3-{[3-({(aR)-6-[(3-carbamoylpyridin-2-yl)oxy]spiro[3.3]heptan-2-yl}carbamoyl)pyrazolo[1,5-a]pyridin-6-yl]oxy}azetidine-1-carboxylate, 2-[((aR)-6-{7-methoxyimidazo[1,2-a]pyridine-3-amido}spiro[3.3]heptan-2-yl)oxy]pyridine-3-carboxamide, 2-{[(aR)-6-(6-{2-oxa-6-azaspiro[3.3]heptan-6-yl}pyrazolo[1,5-a]pyridine-3-amido)spiro[3.3]heptan-2-yl]oxy}pyridine-3-carboxamide, 2-({(aR)-6-[6-(3,3-difluorocyclobutoxy)pyrazolo[1,5-a]pyridine-3-amido]spiro[3.3]heptan-2-yl}oxy)pyridine-3-carboxamide, N-((aR)-6-((3-carbamoylpyridin-2-yl)oxy)spiro[3.3]heptan-2-yl)-7-cyclopropyl-6-((1,1-dioxidotetrahydro-2H-thiopyran-4-yl)oxy)pyrazolo[1,5-a]pyridine-3-carboxamide, 2-({(aR)-6-[7-cyclopropyl-6-(3-methanesulfonylpropoxy)pyrazolo[1,5-a]pyridine-3-amido]spiro[3.3]heptan-2-yl}oxy)pyridine-3-carboxamide, 2-[((aR)-6-{7-cyanoimidazo[1,2-a]pyridine-3-amido}spiro[3.3]heptan-2-yl)oxy]pyridine-3-carboxamide, 2-[((aR)-6-{8-cyanoimidazo[1,2-a]pyridine-3-amido}spiro[3.3]heptan-2-yl)oxy]pyridine-3-carboxamide, 2-{[(aR)-6-(6-{2-oxa-6-azaspiro[3.3]heptan-6-yl}pyrazolo[1,5-a]pyridine-3-amido)spiro[3.3]heptan-2-yl]oxy}pyridine-3-carboxamide, 2-({(aR)-6-[7-(morpholin-4-yl)imidazo[1,2-a]pyridine-3-amido]spiro[3.3]heptan-2-yl}oxy)pyridine-3-carboxamide, 2-({(aR)-6-[7-cyclopropyl-6-(1-methyl-1H-pyrazol-4-yl)pyrazolo[1,5-a]pyridine-3-amido]spiro[3.3]heptan-2-yl}oxy)pyridine-3-carboxamide, 2-[((aR)-6-{7-[(2,2-difluoroethyl)amino]imidazo[1,2-a]pyridine-3-amido}spiro[3.3]heptan-2-yl)oxy]pyridine-3-carboxamide, 2-({(aR)-6-[7-(3-aminoazetidin-1-yl)imidazo[1,2-a]pyridine-3-amido]spiro[3.3]heptan-2-yl}oxy)pyridine-3-carboxamide, 2-({(aR)-6-[7-(3,3-difluorocyclobutoxy)imidazo[1,2-a]pyridine-3-amido]spiro[3.3]heptan-2-yl}oxy)pyridine-3-carboxamide, 2-[((aR)-6-{7-chloroimidazo[1,2-a]pyridine-3-amido}spiro[3.3]heptan-2-yl)oxy]pyridine-3-carboxamide, N-((aR)-6-((3-carbamoylpyridin-2-yl)oxy)spiro[3.3]heptan-2-yl)-7-(1,1-dioxidothiomorpholino)imidazo[1,2-a]pyridine-3-carboxamide, 2-[((aR)-6-{6-[1-($^2$H$_3$)methyl-1H-pyrazol-4-yl]-[1,2,3]triazolo[1,5-a]pyridine-3-amido}spiro[3.3]heptan-2-yl)oxy]pyridine-3-carboxamide, 2-({(aR)-6-[6-(1-cyclopropyl-1H-pyrazol-4-yl)-[1,2,3]triazolo[1,5-a]pyridine-3-amido]spiro[3.3]heptan-2-yl}oxy)pyridine-3-carboxamide, 2-[((aR)-6-{6-[1-(2-hydroxy-2-methylpropyl)-1H-pyrazol-4-yl]-[1,2,3]triazolo[1,5-a]pyridine-3-amido}spiro[3.3]heptan-2-yl)oxy]pyridine-3-carboxamide, 2-[((aR)-6-{6-[1-(propan-2-yl)-3-(trifluoromethyl)-1H-pyrazol-4-yl]-[1,2,3]triazolo[1,5-a]pyridine-3-amido}spiro[3.3]heptan-2-yl)oxy]pyridine-3-carboxamide, 2-({(aR)-6-[6-(1-methyl-1H-pyrazol-4-yl)-[1,2,3]triazolo[1,5-a]pyridine-3-amido]spiro[3.3]heptan-2-yl}oxy)pyridine-3-carboxamide, 2-[((aR)-6-{6-bromo-[1,2,3]triazolo[1,5-a]pyridine-3-amido}spiro[3.3]heptan-2-yl)oxy]pyridine-3-carboxamide, 2-({(aR)-6-[6-(morpholin-4-yl)-[1,2,3]triazolo[1,5-a]pyridine-3-amido]spiro[3.3]heptan-2-yl}oxy)pyridine-3-carboxamide, 2-({(aR)-6-[7-(1-methyl-6-oxo-1,6-dihydropyridin-3-yl)imidazo[1,2-a]pyridine-3-amido]spiro[3.3]heptan-2-yl}oxy)pyridine-3-carboxamide, 2-({(aR)-6-[6-(1-methyl-6-oxo-1,6-dihydropyridin-3-yl)pyrazolo[1,5-a]pyridine-3-amido]spiro[3.3]heptan-2-yl}oxy)pyridine-3-carboxamide, N-{(aR)-6-[(3-carbamoylpyridin-2-yl)oxy]spiro[3.3]heptan-2-yl}-1-(difluoromethyl)-6-(morpholin-4-yl)-1H-indazole-3-carboxamide, 2-({(aR)-6-[6-(benzyloxy)-7-chloro-[1,2,3]triazolo[1,5-a]pyridine-3-amido]spiro[3.3]heptan-2-yl}oxy)pyridine-3-carboxamide, 2-({(aR)-6-[6-(benzyloxy)-7-cyclopropyl-[1,2,3]triazolo[1,5-a]pyridine-3-amido]spiro[3.3]heptan-2-yl}oxy)pyridine-3-carboxamide, 2-({(aR)-6-[6-(2-hydroxy-2-methylpropoxy)-[1,2,3]triazolo[1,5-a]pyridine-3-amido]spiro[3.3]heptan-2-yl}oxy)pyridine-3-carboxamide, 6-(benzyloxy)-N-((aR)-6-((3-carbamoylpyridin-2-yl)oxy)spiro[3.3]heptan-2-yl)-5-chloro-3-cyclopropylindolizine-1-carboxamide, 2-({(aR)-6-[1-(4-bromophenyl)-5-methyl-1H-pyrazole-4-amido]spiro[3.3]heptan-2-yl}oxy)pyridine-3-carboxamide, 2-[((aR)-6-{5-methyl-1-[4-(morpholin-4-yl)phenyl]-1H-pyrazole-4-amido}spiro[3.3]heptan-2-yl)oxy]pyridine-3-carboxamide, 2-{[(aR)-6-(5-methyl-1-phenyl-1H-pyrazole-4-amido)spiro[3.3]heptan-2-yl]oxy}pyridine-3-carboxamide, 2-[((aR)-6-{7-methoxy-1-methyl-1H,4H,5H-benzo[g]indazole-3-amido}spiro[3.3]heptan-2-yl)oxy]pyridine-3-carboxamide, 2-[((aR)-6-{7-methoxy-2-methyl-2H,4H,5H-benzo[g]indazole-3-amido}spiro[3.3]heptan-2-yl)oxy]pyridine-3-carboxamide, 2-[((aR)-6-{1-[(4-fluorophenyl)methyl]-3-methyl-1H-pyrazole-4-amido}spiro[3.3]heptan-2-yl)oxy]pyridine-3-carboxamide, 2-((aR)-6-{1-[(4-fluorophenyl)methyl)-5-methyl-1H-pyrazole-4-amido}spiro[3.3]heptan-2-yl)oxy)pyridine-3-carboxamide, 2-({(aR)-6-[1-(4-chlorophenyl)-5-methyl-1H-pyrazole-4-amido]spiro[3.3]heptan-2-yl}oxy)pyridine-3-carboxamide, 2-({(aR)-6-[1-(4-cyanophenyl)-5-methyl-1H-pyrazole-4-amido]spiro[3.3]heptan-2-yl}oxy)pyridine-3-carboxamide, 2-[((aR)-6-{5-methyl-1-[4-(trifluoromethoxy)phenyl]-1H-pyrazole-4-amido}spiro[3.3]heptan-2-yl)oxy]pyridine-3-carboxamide, 2-({(aR)-6-[1-(4-methanesulfonylphenyl)-5-methyl-1H-pyrazole-4-amido]spiro[3.3]heptan-2-yl}oxy)pyridine-3-carboxamide, 2-({(aR)-6-[1-(4-cyano-2-fluorophenyl)-5-methyl-1H-pyrazole-4-amido]spiro[3.3]heptan-2-yl}oxy)pyridine-3-carboxamide, 2-{[(aR)-6-(1-phenyl-1H-1,2,3-triazole-4-amido)spiro[3.3]heptan-2-yl]oxy}pyridine-3-carboxamide, 2-{[(aR)-6-(2-phenyl-1H-imidazole-4-amido)spiro[3.3]heptan-2-yl]oxy}pyridine-3-carboxamide,
2-({(aR)-6-[1-(4-cyano-3-fluorophenyl)-5-methyl-1H-pyrazole-4-amido]spiro[3.3]heptan-2-yl}oxy)pyridine-3-carboxamide,
2-{[(aR)-6-(2,5-dimethyl-1-phenyl-1H-imidazole-4-amido)spiro[3.3]heptan-2-yl]oxy}pyridine-3-carboxamide,
2-({(aR)-6-[1-(3-chloro-2-fluorophenyl)-1H-pyrazole-4-amido]spiro[3.3]heptan-2-yl}oxy)pyridine-3-carboxamide,
2-({(aR)-6-[1-(3-chlorophenyl)-1H-pyrazole-4-amido]spiro[3.3]heptan-2-yl}oxy)pyridine-3-carboxamide,
2-({(aR)-6-[1-(3-methoxyphenyl)-1H-pyrazole-4-amido]spiro[3.3]heptan-2-yl}oxy)pyridine-3-carboxamide,
2-{[(aR)-6-(1-methyl-5-phenyl-1H-pyrazole-3-amido)spiro[3.3]heptan-2-yl]oxy}pyridine-3-carboxamide,
2-({(aR)-6-[1-(2-chlorophenyl)-1H-pyrazole-4-amido]spiro[3.3]heptan-2-yl}oxy)pyridine-3-carboxamide,
2-({(aR)-6-[1-(2-methoxyphenyl)-1H-pyrazole-4-amido]spiro[3.3]heptan-2-yl}oxy)pyridine-3-carboxamide,
2-({(aR)-6-[1-(3-cyanophenyl)-5-methyl-1H-pyrazole-4-amido]spiro[3.3]heptan-2-yl}oxy)pyridine-3-carboxamide,
2-({(aR)-6-[1-(6-methoxypyridin-3-yl)-5-methyl-1H-pyrazole-4-amido]spiro[3.3]heptan-2-yl}oxy)pyridine-3-carboxamide,
N-{(aR)-6-[(3-carbamoylpyridin-2-yl)oxy]spiro[3.3]heptan-2-yl}-1-(1-cyano-1-methylethyl)-6-fluoro-1H-indazole-3-carboxamide,
1-(1-carbamoyl-1-methylethyl)-N-{(aR)-6-[(3-carbamoylpyridin-2-yl)oxy]spiro[3.3]heptan-2-yl}-6-fluoro-1H-indazole-3-carboxamide,
6-bromo-N-{(aR)-6-[(3-carbamoylpyridin-2-yl)oxy]spiro[3.3]heptan-2-yl}-1-(1-cyano-1-methylethyl)-1H-indazole-3-carboxamide,
N-{(aR)-6-[(3-carbamoylpyridin-2-yl)oxy]spiro[3.3]heptan-2-yl}-1-[(3,3-difluoro-1-hydroxycyclobutyl)methyl]-6-(1-methyl-1H-pyrazol-4-yl)-1H-indazole-3-carboxamide,
N-{(aR)-6-[(3-carbamoylpyridin-2-yl)oxy]spiro[3.3]heptan-2-yl}-1-[(1-hydroxycyclobutyl)methyl]-6-(1-methyl-1H-pyrazol-4-yl)-1H-indazole-3-carboxamide,
N-{(aR)-6-[(3-carbamoylpyridin-2-yl)oxy]spiro[3.3]heptan-2-yl}-1-(1-cyano-1-methylethyl)-6-(1-methyl-1H-pyrazol-4-yl)-1H-indazole-3-carboxamide,
N-{(aR)-6-[(3-carbamoylpyridin-2-yl)oxy]spiro[3.3]heptan-2-yl}-1-(1-cyano-1-methylethyl)-6-[1-(difluoromethyl)-1H-pyrazol-4-yl]-1H-indazole-3-carboxamide,
1-(1-carbamoyl-1-methylethyl)-N-{(aR)-6-[(3-carbamoylpyridin-2-yl)oxy]spiro[3.3]heptan-2-yl}-6-(1-methyl-1H-pyrazol-4-yl)-1H-indazole-3-carboxamide,
1-(1-carbamoyl-1-methylethyl)-N-{(aR)-6-[(3-carbamoylpyridin-2-yl)oxy]spiro[3.3]heptan-2-yl}-6-[1-(difluoromethyl)-1H-pyrazol-4-yl]-1H-indazole-3-carboxamide,
1-(1-carbamoyl-1-methylethyl)-N-{(aR)-6-[(3-carbamoylpyridin-2-yl)oxy]spiro[3.3]heptan-2-yl}-6-(3,3,3-trifluoropropoxy)-1H-indazole-3-carboxamide,
N-{(aR)-6-[(3-carbamoylpyridin-2-yl)oxy]spiro[3.3]heptan-2-yl}-1-(1-cyano-1-methylethyl)-6-(3,3,3-trifluoropropoxy)-1H-indazole-3-carboxamide,
1-(1-carbamoyl-1-methylethyl)-N-{(aR)-6-[(3-carbamoylpyridin-2-yl)oxy]spiro[3.3]heptan-2-yl}-6-(2-hydroxy-2-methylpropoxy)-1H-indazole-3-carboxamide,
2-[((aR)-6-{6-[(3,3-difluoro-1-hydroxycyclobutyl)methoxy]pyrazolo[1,5-a]pyridine-3-amido}spiro[3.3]heptan-2-yl)oxy)pyridine-3-carboxamide,
2-[((aR)-6-{7-cyclopropyl-6-[(3,3-difluoro-1-hydroxycyclobutyl)methoxy]pyrazolo[1,5-a]pyridine-3-amido}spiro[3.3]heptan-2-yl)oxy)pyridine-3-carboxamide,
2-({(aR)-6-{6-(benzyloxy)-3-[(dimethylamino)methyl]imidazo[1,5-a]pyridine-1-amido}spiro[3.3]heptan-2-yl}oxy)pyridine-3-carboxamide,
2-[((aR)-6-{2-[4-(cyclopropanesulfonyl)phenyl]-1,3-thiazole-5-amido}spiro[3.3]heptan-2-yl)oxy]pyridine-3-carboxamide,
2-({(aR)-6-[2-(4-cyanophenyl)-1,3-thiazole-5-amido]spiro[3.3]heptan-2-yl}oxy)pyridine-3-carboxamide,
2-[((aR)-6-{2-[3-fluoro-4-(methylcarbamoyl)phenyl]-1,3-thiazole-5-amido}spiro[3.3]heptan-2-yl)oxy]pyridine-3-carboxamide,
2-({(aR)-6-[2-(3-cyanophenyl)-1,3-thiazole-5-amido]spiro[3.3]heptan-2-yl}oxy)pyridine-3-carboxamide,
2-[((aR)-6-{3-bromoimidazo[1,5-a]pyridine-1-amido}spiro[3.3]heptan-2-yl)oxy]pyridine-3-carboxamide,
2-({(aR)-6-[3-(4-methylpiperazin-1-yl)-5-(trifluoromethyl)benzamido]spiro[3.3]heptan-2-yl}oxy)pyridine-3-carboxamide,
2-{[(aR)-6-(3-tert-butylbenzamido)spiro[3.3]heptan-2-yl]oxy}pyridine-3-carboxamide,
6-bromo-N-{(aR)-6-[(3-carbamoylpyridin-2-yl)oxy]spiro[3.3]heptan-2-yl}-2-methyl-2H-indazole-4-carboxamide,
6-bromo-N-{(aR)-6-[(3-carbamoylpyridin-2-yl)oxy]spiro[3.3]heptan-2-yl}-1-methyl-1H-indazole-4-carboxamide,
N-{(aR)-6-[(3-carbamoylpyridin-2-yl)oxy]spiro[3.3]heptan-2-yl}-2-OXO-6-(trifluoromethyl)-2,4-dihydro-1H-3,1-benzoxazine-8-carboxamide,
2-({(aR)-6-[3-bromo-5-(trifluoromethyl)benzamido]spiro[3.3]heptan-2-yl}oxy)pyridine-3-carboxamide,
2-({(aR)-6-[3-(1-methyl-1H-pyrazol-4-yl)-5-(trifluoromethyl)benzamido]spiro[3.3]heptan-2-yl}oxy)pyridine-3-carboxamide,
2-({(aR)-6-[6-bromo-3-(trifluoromethyl)imidazo[1,5-a]pyridine-1-amido]spiro[3.3]heptan-2-yl}oxy)pyridine-3-carboxamide,
2-({(aR)-6-[3-(trifluoromethyl)imidazo[1,5-a]pyridine-1-amido]spiro[3.3]heptan-2-yl}oxy)pyridine-3-carboxamide,
2-({(aR)-6-[6-(benzyloxy)-3-(trifluoromethyl)imidazo[1,5-a]pyridine-1-amido]spiro[3.3]heptan-2-yl}oxy)pyridine-3-carboxamide,
1-({(aR)-6-[(3-carbamoylpyridin-2-yl)oxy]spiro[3.3]heptan-2-yl}carbamoyl)-3-(trifluoromethyl)imidazo[1,5-a]pyridin-6-yl trifluoromethanesulfonate,
2-({(aR)-6-[6-(1-methyl-1H-pyrazol-4-yl)-3-(trifluoromethyl)imidazo[1,5-a]pyridine-1-amido]spiro[3.3]heptan-2-yl}oxy)pyridine-3-carboxamide,
2-({(aR)-6-[6-(2-hydroxy-2-methylpropoxy)-3-(trifluoromethyl)imidazo[1,5-a]pyridine-1-amido]spiro[3.3]heptan-2-yl}oxy)pyridine-3-carboxamide,
2-({(aR)-6-[6-(benzyloxy)-3-(difluoromethyl)imidazo[1,5-a]pyridine-1-amido]spiro[3.3]heptan-2-yl}oxy)pyridine-3-carboxamide,
2-({(aR)-6-[3-(difluoromethyl)-6-(2-methyl-1,3-thiazol-5-yl)imidazo[1,5-a]pyridine-1-amido]spiro[3.3]heptan-2-yl}oxy)pyridine-3-carboxamide,
2-({(aR)-6-[3-(difluoromethyl)-6-(1-methyl-1H-imidazol-5-yl)imidazo[1,5-a]pyridine-1-amido]spiro[3.3]heptan-2-yl}oxy)pyridine-3-carboxamide,
2-({(aR)-6-[3-(difluoromethyl)-6-[1-methyl-3-(trifluoromethyl)-1H-pyrazol-4-yl]imidazo[1,5-a]pyridine-1-amido]spiro[3.3]heptan-2-yl}oxy)pyridine-3-carboxamide, 2-({(aR)-6-[3-(difluoromethyl)-6-(1-methyl-1H-pyrazol-4-yl)imidazo[1,5-a]pyridine-1-amido]spiro[3.3]heptan-2-yl}oxy)pyridine-3-carboxamide,
2-({(aR)-6-[3-(difluoromethyl)-6-(morpholin-4-yl)imidazo[1,5-a]pyridine-1-amido]spiro[3.3]heptan-2-yl}oxy)pyridine-3-carboxamide,
2-({(aR)-6-[3-(difluoromethyl)-6-(3-hydroxy-3-methylbutoxy)imidazo[1,5-a]pyridine-1-amido]spiro[3.3]heptan-2-yl}oxy)pyridine-3-carboxamide,
2-({(aR)-6-[3-(difluoromethyl)-6-[(2-hydroxy-2-methylpropyl)amino]imidazo[1,5-a]pyridine-1-amido]spiro[3.3]heptan-2-yl}oxy)pyridine-3-carboxamide,
2-({(aR)-6-[3-(difluoromethyl)-6-[(2-hydroxy-2-methylpropyl)amino]imidazo[1,5-a]pyridine-1-amido]spiro[3.3]heptan-2-yl}oxy)pyridine-3-carboxamide,
2-({(aR)-6-[3-(difluoromethyl)-6-[(2R,6S)-2,6-dimethylmorpholin-4-yl]imidazo[1,5-a]pyridine-1-amido]spiro[3.3]heptan-2-yl}oxy)pyridine-3-carboxamide,
2-({(aR)-6-[3-(difluoromethyl)-6-(1,3-dimethyl-1H-pyrazol-4-yl)imidazo[1,5-a]pyridine-1-amido]spiro[3.3]heptan-2-yl}oxy)pyridine-3-carboxamide,
2-({(aR)-6-[3-(2-methyl-1,3-thiazol-5-yl)-5-(trifluoromethyl)benzamido]spiro[3.3]heptan-2-yl}oxy)pyridine-3-carboxamide,
2-[((aR)-6-{3-[1-methyl-3-(trifluoromethyl)-1H-pyrazol-4-yl]-5-(trifluoromethyl)benzamido}spiro[3.3]heptan-2-yl)oxy]pyridine-3-carboxamide,
2-({(aR)-6-[3-(1,3-dimethyl-1H-pyrazol-4-yl)-5-(trifluoromethyl)benzamido]spiro[3.3]heptan-2-yl}oxy)pyridine-3-carboxamide,
2-({(aR)-6-[3-(1-methyl-1H-imidazol-5-yl)-5-(trifluoromethyl)benzamido]spiro[3.3]heptan-2-yl}oxy)pyridine-3-carboxamide,
2-({(aR)-6-[3-(4-hydroxy-4-methylpiperidin-1-yl)-5-(trifluoromethyl)benzamido]spiro[3.3]heptan-2-yl}oxy)pyridine-3-carboxamide,
2-({(aR)-6-[3-(difluoromethyl)-6-[2-(2-hydroxyethyl)morpholin-4-yl]imidazo[1,5-a]pyridine-1-amido]spiro[3.3]heptan-2-yl}oxy)pyridine-3-carboxamide,
2-{[(aR)-6-(3-{2-oxa-5-azabicyclo[2.2.1]heptan-5-yl}-5-(trifluoromethyl)benzamido)spiro[3.3]heptan-2-yl]oxy}pyridine-3-carboxamide,
2-({(aR)-6-[3-(difluoromethyl)-6-[(N-methylacetamido)methyl]imidazo[1,5-a]pyridine-1-amido]spiro[3.3]heptan-2-yl}oxy)pyridine-3-carboxamide,
2-({(aR)-6-[3-(1,5-dimethyl-1H-pyrazol-4-yl)-5-(trifluoromethyl)benzamido]spiro[3.3]heptan-2-yl}oxy)pyridine-3-carboxamide,
2-({(aR)-6-[3-(difluoromethyl)-6-[(3S)-3-(hydroxymethyl)piperazin-1-yl]imidazo[1,5-a]pyridine-1-amido]spiro[3.3]heptan-2-yl}oxy)pyridine-3-carboxamide,
2-{[(aR)-6-(3-{8-oxa-3-azabicyclo[3.2.1]octan-3-yl}-5-(trifluoromethyl)benzamido)spiro[3.3]heptan-2-yl]oxy}pyridine-3-carboxamide,
2-[((aR)-6-{6-bromo-3-methylimidazo[1,5-a]pyridine-1-amido}spiro[3.3]heptan-2-yl)oxy]pyridine-3-carboxamide,
2-({(aR)-6-[6-(1,5-dimethyl-1H-pyrazol-4-yl)-3-methylimidazo[1,5-a]pyridine-1-amido]spiro[3.3]heptan-2-yl}oxy)pyridine-3-carboxamide,
2-({(aR)-6-[6-(1,3-dimethyl-1H-pyrazol-4-yl)-3-methylimidazo[1,5-a]pyridine-1-amido]spiro[3.3]heptan-2-yl}oxy)pyridine-3-carboxamide,
2-({(aR)-6-[3-methyl-6-(1-methyl-1H-pyrazol-4-yl)imidazo[1,5-a]pyridine-1-amido]spiro[3.3]heptan-2-yl}oxy)pyridine-3-carboxamide,
2-amino-N-{(aR)-6-[(3-carbamoylpyridin-2-yl)oxy]spiro[3.3]heptan-2-yl}quinazoline-4-carboxamide,
2-[((aR)-6-{7-cyclopropyl-6-[(1-hydroxycyclobutyl)methoxy]pyrazolo[1,5-a]pyridine-3-amido}spiro[3.3]heptan-2-yl)oxy]pyridine-3-carboxamide,
2-({(aR)-6-[7-(benzyloxy)imidazo[1,2-a]pyridine-2-amido]spiro[3.3]heptan-2-yl}oxy)pyridine-3-carboxamide, and
2-[((aR)-6-{6-methoxyimidazo[1,2-a]pyridine-2-amido}spiro[3.3]heptan-2-yl)oxy]pyridine-3-carboxamide.

In another embodiment the compounds of the present invention have ROCK $IC_{50}$ values≤10 μM.

In another embodiment the compounds of the present invention have ROCK $IC_{50}$ values≤1 μM.

In another embodiment the compounds of the present invention have ROCK $IC_{50}$ values≤0.1 μM.

In another embodiment the compounds of the present invention have ROCK $IC_{50}$ values≤0.05 μM.

In another embodiment the compounds of the present invention have ROCK $IC_{50}$ values≤0.01 μM.

II. Other Embodiments of the Invention

In another embodiment, the present invention provides a composition comprising at least one of the compounds of the present invention or a stereoisomer, a tautomer, a pharmaceutically-acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically-acceptable salt, or a solvate, thereof.

In another embodiment, the present invention provides a pharmaceutical composition, comprising: a pharmaceutically acceptable carrier and a therapeutically effective amount of al least one of die compounds of the present invention or a stereoisomer, a tautomer, a pharmaceutically-acceptable salt, or a solvate thereof.

In another embodiment the present invention provides a process for making a compound of the present invention.

In another embodiment the present invention provides an intermediate for making a compound of the present invention.

In another embodiment the present invention provides a pharmaceutical composition further comprising additional therapeutic agent(s).

In another embodiment the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically-acceptable salt, or a solvate thereof. As used herein, the term "patient" encompasses all mammalian species.

In another embodiment, the present invention provides compounds according to the present invention for use as a medicament.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically-acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers.

Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The symbols "aR" and "aS" represent the configuration of substituents around a molecule that contains an axis of chirality. The isomeric descriptors "R", "S", "aR" and "aS" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentol, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and iso-propoxy), and t-butoxy. Similarly, "alkylthio" or "thioalkoxy" represents an alkyl group as defined above with the indicated number of carbon atoms attached through a sulphur bridge: for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge: for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane. [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring: and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "bicyclic spiro carbocycle" refers to 5- to 20-membered polycyclic hydrocarbon group with rings connected through one common carbon atom (called as spiro atom), wherein one or more rings may contain one or more double bonds, but none of the rings has a completely conjugated pi-electron system. Preferably a bicyclic spiro carbocycle is 6 to 14 membered, more preferably is 7 to 10 membered.

Bicyclic spiro carbocycle may be 4-membered/4-membered, 4-membered-/5-membered, 4-membered/6-membered, 5-membered/5-membered, or 5-membered/6-membered spiro ring.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinvl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring.

When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically-acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be convened in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard. H., Chapter 5, "Design and Application of Prodrugs", *A Textbook of Drug Design and Development*, pp. 113-191, Krosgaard-Larsen, P. et al., eds., Harwood Academic Publishers (1991):

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry. Biochemistry and Enzymology*. VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain an N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours. "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry. "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
CH$_2$Cl$_2$ Dichloromethane
CH$_3$CN or ACN Acetonitrile
CDCl$_3$ deutero-chloroform
CHCl$_3$ Chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1.2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCl N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH Ethanol
GMF glass microfiber filter
Grubbs (II) (1,3-bis(2,4,6-trimethylphenyl)-2-imidazolidinlidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH Methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ Ammonia
NH$_4$Cl ammonium chloride
NH$_4$OH ammonium hydroxide OTf triflate or trifluoromethanesulfonate
Pd$_2$(dba)$_3$ tris(di benzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
i-PrOH or IPA isopropanol
PS polystyrene
SEM-Cl 2-(trimethysilyl)ethoxymethyl chloride
SiO$_2$ silica oxide
SnCl$_2$ tin(III) chloride
TBAI tetra-n-butylammonium iodide
TEA triethylamine
TFA trifluoroacetic acid
THF tetrahydrofuran
TMSCHN$_2$ trimethylsilyldiazomethane
T3P® propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM MgCl$_2$, 0.015% Brij-35, 4 mM DTT, 5 μM ATP and 1.5 μM peptide substrate (FITC-AHA-AKRRRLSSLRA-OH) (SEQ ID NO. 1). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LAB-CHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity.

Representative Examples were tested in the ROCK2 assay described above and found having ROCK2 inhibitory activity. Their ROCK2 inhibitory activity (IC$_{50}$ values) of ≤3 μM (3000 nM) was observed and shown in Table A below. The ranges of the ROCK2 IC$_{50}$ values are as follows: ROCK2 IC$_{50}$: ++++(<5 nM)+++(5-50 nM)++(50-250 nM)+(250 to 2500 nM)

TABLE A

| Example No. | ROCK2 Activity |
| --- | --- |
| 1 | ++ |
| 2 | ++ |
| 3 | +++ |
| 4 | +++ |
| 5 | ++ |
| 6 | ++++ |
| 7 | + |
| 8 | ++ |
| 9 | +++ |
| 10 | +++ |
| 11 | +++ |
| 12 | ++ |
| 13 | ++ |
| 14 | + |
| 15 | ++++ |
| 16 | ++++ |
| 17 | ++ |
| 18 | ++++ |
| 19 | ++++ |
| 20 | +++ |
| 21 | +++ |
| 22 | +++ |
| 23 | ++++ |
| 24 | +++ |
| 25 | ++++ |
| 26 | +++ |
| 27 | +++ |
| 28 | ++++ |
| 29 | +++ |
| 30 | ++++ |
| 31 | +++ |
| 32 | ++++ |
| 33 | ++++ |
| 34 | +++ |
| 35 | ++++ |
| 36 | +++ |
| 37 | ++ |
| 38 | +++ |
| 39 | ++ |
| 40 | ++ |
| 41 | ++ |
| 42 | ++++ |
| 43 | ++++ |
| 44 | + |
| 45 | ++ |
| 46 | ++++ |
| 47 | +++ |
| 48 | ++ |
| 49 | ++++ |
| 50 | +++ |
| 51 | +++ |
| 52 | +++ |
| 53 | +++ |
| 54 | ++ |
| 55 | ++ |
| 56 | +++ |
| 57 | ++ |
| 58 | ++ |
| 59 | + |
| 60 | + |
| 61 | ++ |
| 62 | + |
| 63 | + |
| 64 | +++ |
| 65 | ++++ |
| 66 | +++ |
| 67 | +++ |
| 68 | ++ |
| 69 | ++ |
| 70 | ++ |
| 71 | + |
| 72 | +++ |
| 73 | +++ |
| 74 | + |
| 75 | + |
| 76 | + |
| 77 | +++ |
| 78 | ++ |
| 79 | ++ |
| 80 | +++ |
| 81 | +++ |
| 82 | ++++ |
| 83 | + |
| 84 | ++ |
| 85 | ++ |
| 86 | ++ |
| 87 | ++ |
| 88 | + |

TABLE A-continued

| Example No. | ROCK2 Activity |
|---|---|
| 89 | + |
| 90 | ++ |
| 91 | ++ |
| 92 | ++ |
| 93 | +++ |
| 94 | +++ |
| 95 | ++ |
| 96 | ++ |
| 97 | +++ |
| 98 | +++ |
| 99 | +++ |
| 100 | +++ |
| 101 | +++ |
| 102 | +++ |
| 103 | ++++ |
| 104 | ++++ |
| 105 | ++++ |
| 106 | ++++ |
| 107 | +++ |
| 108 | ++++ |
| 109 | ++ |
| 110 | +++ |
| 111 | ++++ |
| 112 | ++++ |
| 113 | + |
| 114 | + |
| 115 | +++ |
| 116 | +++ |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | ++++ |
| 127 | +++ |
| 128 | +++ |
| 129 | + |
| 130 | + |
| 131 | +++ |
| 132 | +++ |
| 133 | +++ |
| 134 | ++ |
| 135 | + |
| 136 | + |
| 138 | + |
| 139 | + |
| 140 | + |
| 141 | + |
| 142 | ++ |
| 143 | + |
| 144 | + |
| 145 | + |
| 146 | ++ |
| 147 | + |
| 148 | ++ |
| 149 | ++ |
| 150 | +++ |
| 151 | + |
| 152 | +++ |
| 153 | + |
| 154 | ++ |
| 155 | + |
| 156 | ++ |
| 157 | ++ |
| 158 | ++ |
| 159 | ++ |
| 160 | ++ |
| 161 | +++ |
| 162 | +++ |
| 163 | + |
| 164 | + |
| 165 | ++ |
| 166 | +++ |
| 167 | ++++ |

TABLE A-continued

| Example No. | ROCK2 Activity |
|---|---|
| 168 | ++++ |
| 169 | +++ |
| 170 | ++ |
| 171 | +++ |
| 172 | +++ |
| 173 | +++ |
| 174 | +++ |
| 175 | ++++ |
| 176 | + |
| 177 | +++ |
| 178 | |
| 179 | +++ |
| 180 | ++++ |
| 181 | ++++ |
| 182 | ++++ |
| 183 | +++ |
| 184 | +++ |
| 185 | ++++ |
| 186 | ++++ |
| 187 | ++++ |
| 188 | + |
| 189 | ++++ |
| 190 | +++ |
| 191 | +++ |
| 192 | +++ |
| 193 | +++ |
| 194 | +++ |
| 195 | ++++ |
| 196 | ++++ |
| 197 | +++ |
| 198 | ++++ |
| 199 | +++ |
| 200 | +++ |
| 203 | +++ |
| 208 | + |
| 209 | + |
| 210 | +++ |
| 211 | ++++ |
| 212 | + |
| 213 | +++ |
| 214 | + |
| 215 | +++ |
| 216 | +++ |
| 217 | ++++ |
| 218 | + |
| 219 | +++ |
| 220 | +++ |
| 221 | ++ |
| 222 | +++ |
| 223 | +++ |
| 224 | +++ |
| 225 | +++ |
| 226 | ++ |
| 227 | +++ |
| 228 | ++ |
| 229 | +++ |
| 230 | ++ |
| 231 | ++++ |
| 232 | +++ |
| 233 | +++ |
| 234 | ++ |
| 235 | +++ |
| 236 | +++ |
| 237 | +++ |
| 238 | ++ |
| 239 | +++ |
| 240 | +++ |
| 241 | +++ |
| 242 | +++ |
| 243 | ++ |
| 244 | ++++ |
| 245 | +++ |
| 246 | +++ |
| 247 | ++++ |
| 248 | +++ |
| 249 | ++++ |
| 250 | ++ |
| 251 | +++ |

TABLE A-continued

| Example No. | ROCK2 Activity |
| --- | --- |
| 252 | +++ |
| 253 | +++ |
| 254 | +++ |
| 255 | +++ |
| 256 | +++ |
| 257 | +++ |
| 258 | ++++ |
| 259 | +++ |
| 260 | +++ |
| 261 | ++++ |
| 262 | +++ |
| 263 | +++ |
| 264 | ++ |
| 265 | +++ |
| 266 | ++ |
| 267 | +++ |
| 268 | + |
| 269 | ++ |
| 270 | ++ |
| 271 | +++ |
| 272 | ++++ |
| 273 | +++ |
| 274 | ++++ |
| 275 | +++ |
| 276 | +++ |
| 277 | +++ |
| 278 | +++ |
| 279 | +++ |
| 280 | +++ |
| 281 | +++ |
| 282 | +++ |
| 283 | ++ |
| 284 | ++++ |
| 285 | +++ |
| 286 | +++ |
| 287 | +++ |
| 288 | +++ |
| 289 | ++++ |
| 290 | +++ |
| 291 | +++ |
| 292 | ++++ |
| 293 | +++ |
| 294 | +++ |
| 295 | +++ |
| 296 | +++ |
| 297 | ++++ |
| 298 | ++++ |
| 299 | +++ |
| 300 | ++++ |
| 301 | +++ |
| 302 | ++++ |
| 303 | ++ |
| 304 | +++ |
| 305 | ++++ |
| 306 | ++ |
| 307 | +++ |
| 308 | ++++ |
| 309 | ++++ |
| 310 | ++++ |
| 311 | ++ |
| 312 | +++ |
| 313 | +++ |
| 314 | ++++ |
| 315 | +++ |
| 316 | ++++ |
| 317 | +++ |
| 318 | ++++ |
| 319 | +++ |
| 320 | +++ |
| 321 | +++ |
| 322 | ++++ |
| 323 | ++++ |
| 324 | ++++ |
| 325 | +++ |
| 326 | +++ |
| 327 | ++ |
| 328 | ++ |
| 329 | ++++ |
| 330 | +++ |
| 331 | +++ |
| 332 | +++ |
| 333 | +++ |
| 334 | ++ |
| 335 | +++ |
| 336 | +++ |
| 337 | +++ |
| 338 | +++ |
| 339 | +++ |
| 340 | +++ |
| 341 | ++++ |
| 342 | ++++ |
| 343 | +++ |
| 344 | +++ |
| 345 | + |
| 346 | ++ |
| 347 | +++ |
| 348 | ++ |
| 349 | +++ |
| 350 | +++ |
| 351 | ++++ |
| 352 | +++ |
| 353 | ++ |
| 354 | ++ |
| 355 | ++ |
| 356 | +++ |
| 357 | ++++ |
| 358 | +++ |
| 359 | ++ |
| 360 | +++ |
| 361 | ++ |
| 362 | ++ |
| 363 | ++++ |
| 364 | ++++ |
| 365 | +++ |
| 366 | +++ |
| 367 | ++++ |
| 368 | +++ |
| 369 | + |
| 370 | ++++ |
| 371 | +++ |
| 372 | ++++ |
| 373 | + |
| 374 | ++ |
| 375 | ++ |
| 376 | +++ |
| 377 | +++ |
| 378 | ++ |
| 379 | ++ |
| 380 | +++ |
| 381 | + |
| 382 | +++ |
| 383 | +++ |
| 384 | +++ |
| 385 | +++ |
| 386 | +++ |
| 387 | +++ |
| 388 | ++ |
| 389 | ++ |
| 390 | + |
| 391 | ++ |
| 392 | ++ |
| 393 | +++ |
| 394 | +++ |
| 395 | +++ |
| 396 | +++ |
| 397 | +++ |
| 398 | +++ |
| 399 | ++ |
| 400 | +++ |
| 401 | ++++ |
| 402 | +++ |
| 403 | +++ |
| 404 | +++ |
| 405 | ++++ |
| 406 | ++++ |
| 407 | ++++ |

TABLE A-continued

| Example No. | ROCK2 Activity |
| --- | --- |
| 408 | +++ |
| 409 | ++++ |
| 410 | +++ |
| 411 | +++ |
| 412 | +++ |
| 413 | +++ |
| 415 | ++++ |
| 416 | +++ |
| 417 | +++ |
| 418 | +++ |
| 419 | ++ |
| 420 | +++ |
| 421 | +++ |
| 422 | +++ |
| 423 | +++ |
| 424 | +++ |
| 425 | +++ |
| 426 | +++ |
| 427 | +++ |
| 428 | ++++ |
| 429 | +++ |
| 430 | +++ |
| 431 | +++ |
| 432 | +++ |
| 433 | ++++ |
| 434 | +++ |
| 435 | ++++ |
| 436 | ++++ |
| 437 | +++ |
| 438 | +++ |
| 439 | ++++ |
| 440 | ++++ |
| 441 | ++++ |
| 442 | + |
| 443 | + |
| 444 | ++++ |
| 445 | ++++ |
| 446 | ++++ |
| 447 | +++ |
| 448 | ++++ |
| 449 | +++ |
| 450 | +++ |
| 451 | +++ |
| 452 | +++ |
| 453 | +++ |
| 454 | ++++ |
| 455 | +++ |
| 456 | ++++ |
| 457 | ++ |
| 458 | +++ |
| 459 | +++ |
| 460 | +++ |
| 461 | ++ |
| 462 | ++++ |
| 463 | ++ |
| 464 | + |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as w ell as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, die most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically-acceptable salt form thereof: and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, 4th Edition, Wiley-Interscience (2006)).

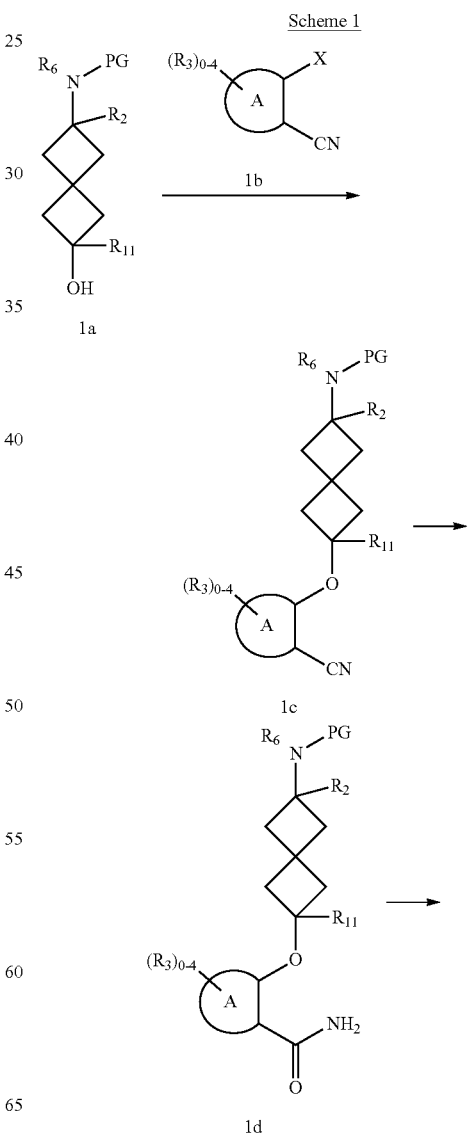

Scheme 1

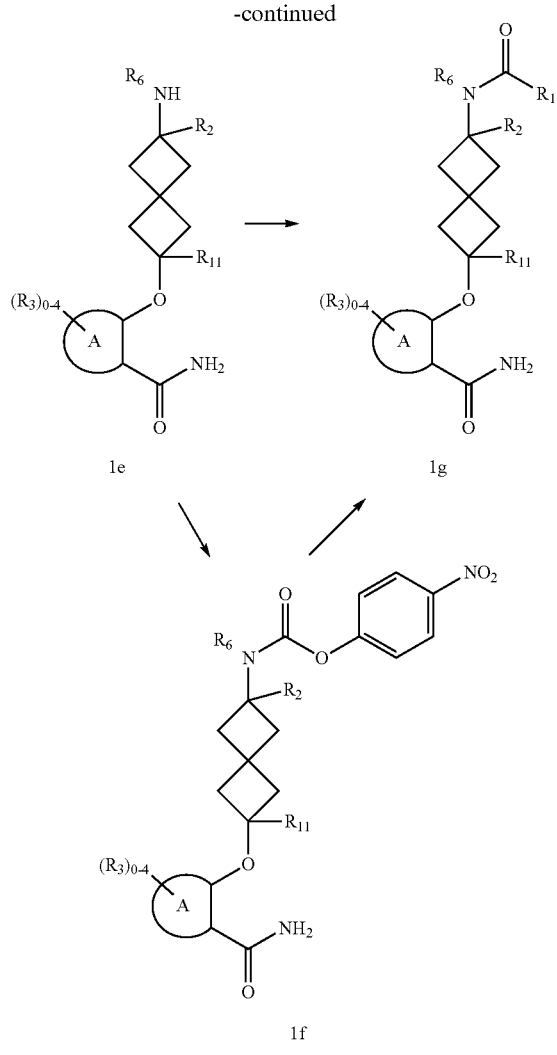

1e

1f

1g via reaction with a chloroformate reagent and a base such as TEA or DIEA. Ureas may be formed via treatment with an isocyanate. Alternatively, reaction of amine 1e with 4-nitrophenyl chloroformate affords carbamate 1f. Treatment of 1f with an alcohol in the presence of base affords the carbamate product 1g. Treatment of 1f with an amine in the presence of base affords the urea product 1g.

Scheme 2

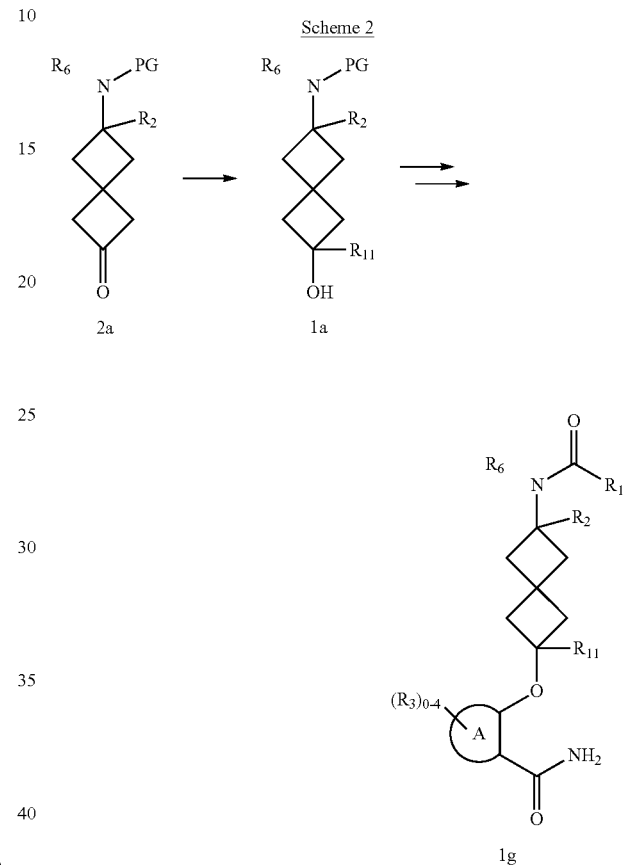

2a    1a

1g

Scheme 1 shows the synthesis of compound 1g from spiroheptane alcohol 1a and aryl/heteroaryl nitrile 1b. Spiroheptane alcohol 1a and aryl/heteroaryl nitrile 1b are either commercially available or can be prepared by known methods. Treatment of alcohol 1a with a base such as NaH, followed by addition to aryl/heteroaryl nitrile 1b, where X is a leaving group such as F, Cl, Br or mesylate. Alternatively, coupling between 1a and 1b (when X=OH) can be accomplished via a Mitsunobu reaction. When $R_6$=H, reaction with an electrophilic reagent in the presence of base affords product 1c, where $R_6$ is an alkyl or substituted alkyl group. $R_6$ may be further derivatized after installation into 1c or in subsequent compounds. Nitrile intermediate 1c can be converted to the primary amide 1d via treatment with $K_2CO_3$/MgO and $H_2O_2$. Removal of a protecting group (PG) on 1d, via appropriate means based upon the particular protecting group, affords amine 1e. When $R_6$=H, reductive amination with an appropriate ketone or aldehyde using a reagent such as $NaBH_3CN$ or $Na(OAc)_3BH$ affords product 1e, where $R_6$ is an alkyl or substituted alkyl group. $R_6$ may be further derivatized after installation into 1e or in subsequent compounds. Amine 1e is converted directly to 1g (amide, carbamate, or urea) by treatment with appropriate reagents. Amides can be formed via coupling of carboxylic acids, using a coupling reagent such as BOP, T3P or HATU, or via reaction with an acid chloride. Carbamates can be prepared Scheme 2 shows the installation of $R_{11}$ in alcohol 1a, ketone 2a is either commercially available or can be prepared by known methods. Reaction of 2a with an organometallic reagent bearing an $R_{11}$ group, such as a Grignard reagent ($R_{11}$—MgBr) or an organolithium species ($R_{11}$—Li), affords alcohol 1a. $R_{11}$ may be further derivatized after installation into 1a or subsequent compounds. Compound 1a can be converted to 1g as described above.

Scheme 3.

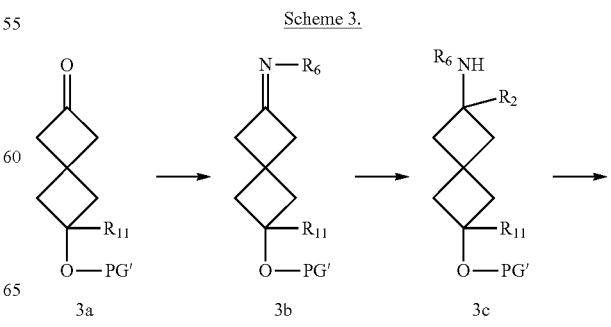

3a    3b    3c

-continued

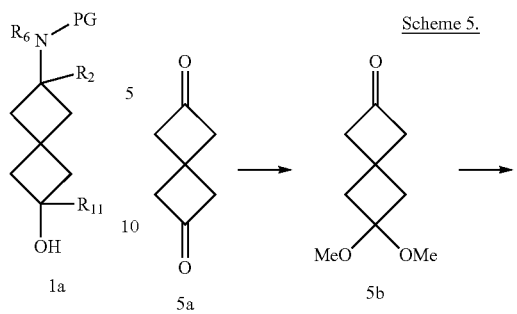

1a

Scheme 3 shows the synthesis of spiroheptane alcohol 1a from ketone 3a, which is either commercially available or can be prepared by known methods. Reaction with $R_6$—$NH_2$ under dehydrating conditions, i.e., Dean-Stark trap, molecular sieves, or trimethylorthoformate, affords imine 3b. Reduction of 3b with a reagent such as $NaBH_4$ affords 3c, where $R_2$=H. alternatively, reaction of 3b with an organometallic reagent bearing an $R_2$ group, such as a Grignard reagent ($R_2$—MgBr) or an organolithium species ($R_2$—Li), affords amine 3c. Protection of the amine functionality and removal of protecting group PG' under appropriate conditions (i.e., TBAF when PG'=TBS) affords compound 1a, which can be processed to target molecules (1g).

Scheme 4.

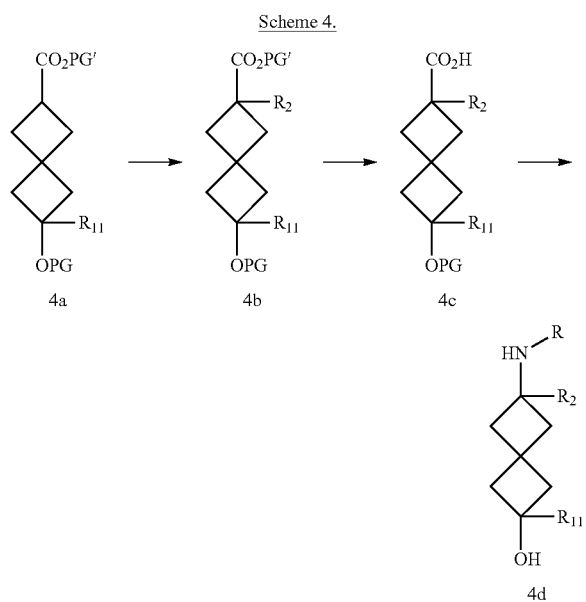

Scheme 4 shows the synthesis of alcohol 4d from ester 4a, which is either commercially available or can be prepared by known methods. Deprotonation of ester 4a with a base such as NaHMDS or LDA, followed addition of an electrophile $R_2$—X, where X is a leaving group such as a halogen or a mesylate, affords 4b. $R_2$ may be further derivatized after installation into 4b or subsequent compounds. Saponification of 4b affords acid 4c. Curtius rearrangement of 4c (possible reagents include DPPA and an alcohol such as t-BuOH or BnOH) affords after removal of PG amine derivative 4d. Compound 4d can be process to 1g, as outlined above.

Scheme 5.

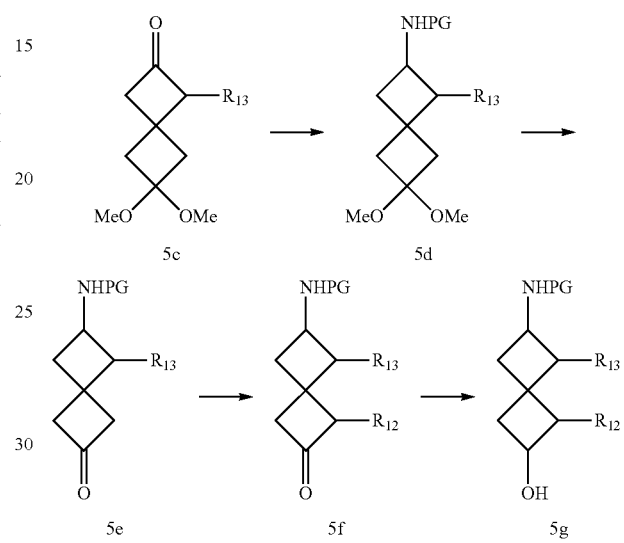

Scheme 5 shows a route to substituted spiroheptane 5g. Commercially available (or prepared via known procedures) diketone 5a is converted to the monoketal 5b, and subsequently is functionalized via deprotonation with a base such as LiHMDS, LDA, etc., and an electrophile such as $R_{13}X$ to provide 5c. This procedure may be repeated to allow for multiple $R_{13}$ groups on the same ring. Reductive amination under appropriate conditions (such as amine/$NaBH_4$/methanol) affords analog 5d. Ensuing cleavage of the ketal group under acidic conditions, such as TsOH or HCl, unmasks ketone 5e. Optionally, 5e may be functionalized via deprotonation with a base such as LiHMDS, LDA, etc., and treatment with an electrophile such as $R_{12}X$ to provide 5f. This procedure may be repeated to allow for multiple $R_{12}$ groups on the same ring of 5f. Reduction of the ketone functionality in 5f affords 5g. Compound 5g can be converted to compounds related to 1g as described above.

Scheme 6.

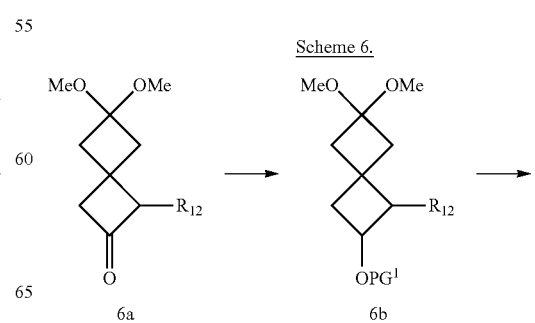

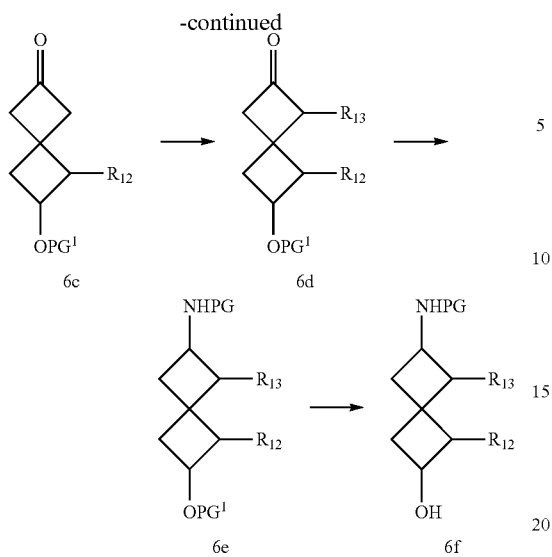

Scheme 6 shows the synthesis of substituted spiroheptane 6f. Intermediate 6a can be prepared similarly to 5c in scheme 5, but using electrophile $R_{12}$—X. This alkylation procedure may be repeated to allow for multiple $R_{12}$ groups on the same ring. Compound 6a may be reduced with a reagent such as $NaBH_4$, and the resultant alcohol protected to give compound 6b. Ketal cleavage and reductive amination affords compound 6c. Optionally, 6c may be functionalized via deprotonation with a base such as LiHMDS, LDA, etc., and treatment with an electrophile such as $R_{13}X$ to provide 6d. This procedure may be repeated to allow for multiple $R_{13}$ groups on the same ring of 6d. Reductive amination under appropriate conditions (such as amine/$NaBH_4$/methanol) affords analog 6e. Selective deprotection affords alcohol 6f. Compound 6f can be converted to compounds related to 1g as described above.

Purification of intermediates and final products was carried out via either normal or reverse phase chromatography. Normal phase chromatography was carried out using pre-packed $SiO_2$ cartridges eluting with either gradients of hexanes and EtOAc, DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% $CH_3CN$, 0.1% TFA) and Solvent B (10% water, 90% $CH_3CN$, 0.1% TFA, UV 220 nm) or with gradients of Solvent A (98% water, 2% $CH_3CN$, 0.05% TFA) and Solvent B (98% $CH_3CN$, 2% water, 0.05% TFA, UV 220 nm) (or) Sunfire Prep C18 OBD 5u 30×100 mm, 25 min gradient from 0-100% B. A=$H_2O$/$CH_3CN$/TFA 90:10:0.1. B=$CH_3CN$/$H_2O$/TFA 90:10:0.1

Unless otherwise stated, analysis of final products was carried out by reverse phase analytical HPLC.

Method A: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate: Temperature: 50 OC: Gradient: 0-100% B over 3 minutes, then a 0.75-minute hold at 100% B; Flow: 1.11 mL/min.

Method B: Waters Acquity UPLC BEH C18, 2.1×50 mm, 1.7-μm particles; Mobile Phase A: 5:95 acetonitrile: water with 0.1% TFA; Mobile Phase B: 95:5 acetonitrile: water with 0.1% TFA; Temperature: 50 OC; Gradient: 0-100% B over 3 minutes, then a 0.75-minute hold at 100% B: Flow: 1.11 mL/min.

INTERMEDIATE 1

Preparation of Benzyl (6-hydroxyspiro[3.3]heptan-2-yl)carbamate

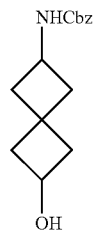

INTERMEDIATE 1A

Preparation of Benzyl (6-oxospiro[3.3]heptan-2-yl)carbamate

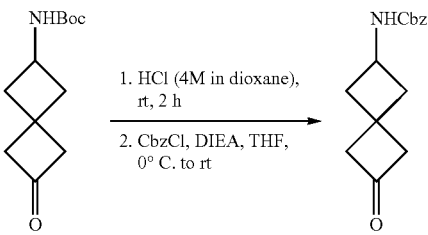 [SMILES: CC(C)(C)OC(=O)NC1CC2(CC(=O)C2)C1 ; O=C1CC2(C1)CC(NC(=O)OCc1ccccc1)C2]

Commercially available tert-butyl (6-oxospiro[3.3]heptan-2-yl)carbamate (0.150 g, 0.666 mmol) was dissolved in HCl (4 M in dioxane) (5.0 mL, 20 mmol). After stirring for 2 h, the reaction mixture was concentrated, and co-evaporated with $Et_2O$ (4×10 mL), and further dried under high vacuum. The deprotected aminospiroketone. HCl salt was suspended in anhydrous THF (5 mL) and cooled to 0° C. Afterwards. Cbz-Cl (0.105 mL, 0.732 mmol) was added dropwise, followed by immediate addition of DIEA (0.291 mL, 1.66 mmol). The reaction mixture was stirred at 0° C. for 30 min, then ice bath was removed, and the reaction mixture was stirred at rt. After 1 h, the reaction mixture was quenched with MeOH (0.5 mL), concentrated and the residue was purified normal phase chromatography to give benzyl (6-oxospiro[3.3]heptan-2-yl)carbamate (0.153 g, 89% yield) as a colorless syrup. MS (ESI) m/z: 260.1 $(M+H)^+$. $^1H$ NMR (500 MHz, $CDCl_3$) δ ppm 7.36 (s, 5H), 5.10 (s, 2H), 4.95 (br s, 1H), 4.31-4.15 (m, 1H), 3.14 (br d, J=2.9 Hz, 2H), 3.09-3.04 (m, 2H), 2.71-2.50 (m, 2H), 2.27-2.13 (m, 2H).

117

INTERMEDIATE 1

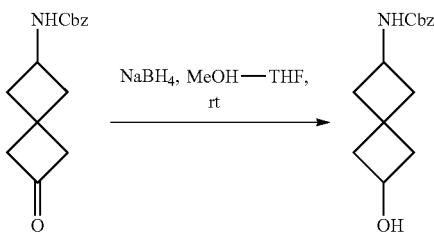

Benzyl (6-oxospiro[3.3]heptan-2-yl)carbamate (0.153 g, 0.590 mmol) was dissolved in anhydrous THF (3 mL)/MeOH (3 mL) and cooled to 0° C. NaBH$_4$ (0.033 g, 0.885 mmol) was added in one portion and stirred at 0° C. for 30 min before allowing the reaction mixture to come to rt. After an additional 30 min, the reaction was quenched with saturated NH$_4$Cl (1 mL). The organics were removed by concentrating under reduced pressure. The resulting residue was dissolved in EtOAc (50 mL) and treated with saturated NH$_4$Cl (25 mL). After 5 min, the organic phase was separated, washed with brine (25 mL), dried over Na$_2$SO$_4$, filtered, and concentrated to afford benzyl (6-hydroxyspiro [3.3]heptan-2-yl)carbamate (0.154 g, 0.589 mmol, 100%6 yield) as a white solid. The material was used as is in the next step. MS (ESI) m/z: 262.1 (M+H)$^+$. $^1$H NMR (500 MHz, CDCl$_3$) δ ppm 7.27 (s, 5H), 5.10-4.95 (m, 2H), 4.08-3.95 (m, 1H), 3.74 (br s, 3H), 2.47-2.13 (m, 4H), 1.94-1.70 (m, 4H).

INTERMEDIATE 2

Preparation of 6-(2-Hydroxy-2-methylpropoxy) pyrazolo-[1,5-a]pyridine-3-carboxylic acid

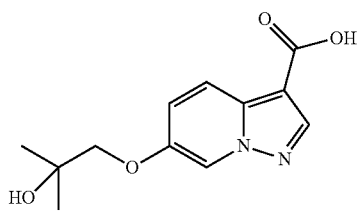 [SMILES: CC(C)(O)COc1ccc2c(C(=O)O)cnn2c1]

Ethyl 6-hydroxypyrazolo[1,5-a]pyridine-3-carboxylate (0.250 g, 1.21 mmol) was suspended in MeCN (10 mL), then 2,2-dimethyloxirane (1.62 mL, 18.2 mmol), K$_2$CO$_3$ (0.67 g, 4.85 mmol) and water (0.667 mL) were added. The reaction mixture was stirred under microwave irradiation at 120° C. for 30 min. The reaction mixture was concentrated under reduced pressure, the residue was dissolved in MeOH (4.5 mL)/THF (4.5 mL), and LiOH (1 M aq.) (3.64 mL, 3.64 mmol) was added. The reaction mixture was stirred under microwave irradiation at 120° C. for 15 min. Solvent was removed under reduced pressure, and the residue was purified by reverse phase HPLC to afford Intermediate 2 (0.185 g, 61% yield) as a white solid. MS (ESI) m/z: 251.0. (M+H)$^+$. $^1$H NMR (500 MHz. DMSO-d$_6$) δ ppm 8.55 (d, J=1.7 Hz, 1H), 8.28 (s, 1H), 7.96 (d, J=9.4 Hz, 1H), 7.38 (dd, J=9.6, 2.2 Hz, 1H), 3.82 (s, 2H), 1.22 (s, 6H).

118

INTERMEDIATE 3

Preparation of Methyl 6-(benzyloxy)-7-bromopyrazolo[1,5-a]pyridine-3-carboxylate

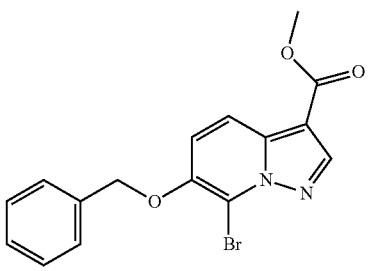 [SMILES: COC(=O)c1cnn2c(Br)c(OCc3ccccc3)ccc12]

TFA (30 mL) was placed in the round-bottom flask equipped with a magnetic stirred, and the reaction mixture was cooled to 0° C. under Ar. Then, tert-butyl (mesitylsulfonyl)oxycarbamate (6.34 g, 20.0 mmol) was added portionwise over 5 min, and the reaction mixture was stirred at 0° C. for 1 h under Ar. Afterwards, the reaction mixture was quenched with ice water (100 mL), producing white solid. The reaction mixture was diluted with cold water (150 mL), the solid was filtered off, and was washed with cold water until pH~7.0. The obtained solid was dissolved in DCM (75 mL), and was stirred with Na$_2$SO$_4$ at 0° C. for 15 min to remove water. Afterwards, Na$_2$SO$_4$ was removed by filtration, and the DCM solution was added to a cooled (ice bath) solution of 3-(benzyloxy)-2-bromopyridine (4.41 g, 16.1 mmol) in DCM (25 mL). The reaction mixture was stirred at 0° C. for 2 h. Then, ice bath was removed, and the reaction mixture was allowed to reach rt and was stirred at this temperature for 1 h. Solvent was removed under reduced pressure, the residue was dissolved in DMF (100 mL), then methyl propiolate (2.86 mL, 32.1 mmol) and K$_2$CO$_3$ (6.66 g, 48.2 mmol) were added sequentially. The obtained suspension was stirred at rt for 16 h. The reaction mixture was diluted with EtOAc (500 mL), washed with water (3×250 mL), brine (250 mL), dried (Na$_2$SO$_4$) and filtered. The residue was purified by normal phase chromatography to give Intermediate 3 (0.88 g, 15% yield) as an off-white solid. MS (ESI) m/z: 360.8 (M+H)$^+$. $^1$H NMR (300 MHz, CDCl$_3$) δ ppm 8.45 (s, 1H), 8.15 (d, J=9.6 Hz, 1H), 7.48-7.16 (m, 6H), 5.24 (s, 2H), 3.91 (s, 3H).

INTERMEDIATE 4

Preparation of 7-Cyclopropyl-6-(2-hydroxy-2-methylpropoxy)pyrazolo[1,5-a]pyridine-3-carboxylic acid

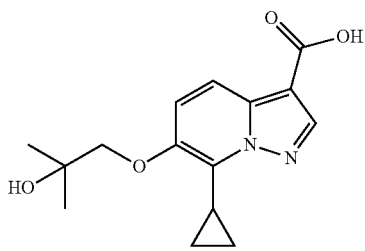 [SMILES: CC(C)(O)COc1ccc2c(C(=O)O)cnn2c1C1CC1]

INTERMEDIATE 4A

Preparation of Methyl 6-(benzyloxy)-7-cyclopropyl-pyrazolo[1,5-a]pyridine-3-carboxylate

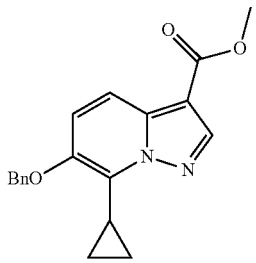 [SMILES: COC(=O)c1cnn2c(C3CC3)c(OCc3ccccc3)ccc12]

Intermediate 3 (350 mg, 0.969 mmol), cyclopropylboronic acid (333 mg, 3.88 mmol), palladium(II) acetate (10.98 mg, 0.048 mmol), tricyclohexylphosphonium tetrafluoroborate (35.7 mg, 0.097 mmol) and phosphoric acid, potassium salt (617 mg, 2.91 mmol) were placed in a pressure vial, and the mixture was degassed (3× Ar/vacuum). Then, PhMe (10 mL) and water (0.2 mL) were added, and the reaction mixture was degassed again. Afterwards, the vial was capped, the reaction mixture was heated to 100° C. for 16 h. Solvent was removed under reduced pressure, and the residue was purified by normal phase chromatography to give Intermediate 4A (279 mg, 89% yield) as a white solid. MS (ESI) m/z: 323.0 (M+H)+. 1H NMR (500 MHz, DMSO-d6) δ ppm 8.38 (s, 1H), 7.98 (d, J=9.4 Hz, 1H), 7.46-7.38 (m, 4H), 7.37-7.33 (m, 1H), 7.30 (d, J=9.6 Hz, 1H), 5.11 (s, 2H), 3.89 (s, 3H), 2.49 (tt, J=8.7, 5.6 Hz, 1H), 1.46-1.41 (m, 2H), 1.17-1.11 (m, 2H).

INTERMEDIATE 4B

Preparation of Methyl 7-cyclopropyl-6-hydroxy-pyrazolo-[1,5-a]pyridine-3-carboxylate

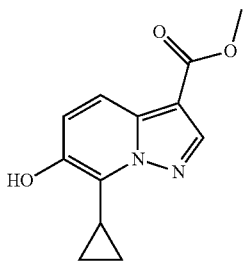 [SMILES: COC(=O)c1cnn2c(C3CC3)c(O)ccc12]

Intermediate 4A (150 mg, 0.465 mmol) was dissolved in THF (4 mL)/MeOH (4 mL), and TEA (0.324 mL, 2.33 mmol) was added. The reaction mixture was degassed (3× vacuum/Ar), then palladium on carbon (10 wt %) (49.5 mg, 0.047 mmol) was added. The reaction mixture was degassed again, and it was stirred under dihydrogen atmosphere (1 atm: balloon) for 1 h. Pd—C was filtered off using membrane filter, and the filtrate was concentrated to afford Intermediate 4B (103 mg, 95% yield) as a white solid. MS (ESI) m/z: 233.1 (M+H)+. 1H NMR (500 MHz, DMSO-d6) δ ppm 9.74 (br s, 1H), 8.32 (s, 1H), 7.81 (d, J=9.4 Hz, 1H), 7.30 (d, J=9.4 Hz, 1H), 3.79 (s, 3H), 2.48-2.44 (m, 1H), 1.44-1.37 (m, 2H), 1.06-0.98 (m, 2H).

INTERMEDIATE 4

Intermediate 4B (0.050 g, 0.215 mmol) was suspended in MeCN (2.0 mL), then 2,2-dimethyloxirane (0.288 mL, 3.23 mmol), K2CO3 (0.119 g, 0.861 mmol) and water (0.133 mL) were added. The reaction mixture was stirred under microwave irradiation at 120° C. for 30 min. The reaction mixture was concentrated under reduced pressure, the residue was dissolved in MeOH (1 mL)/THF (1 mL), and LiOH (1 M aq.) (0.646 mL, 0.646 mmol) was added. The reaction mixture was stirred under microwave irradiation at 120° C. for 15 min. Solvent was removed under reduced pressure, the residue was purified by reverse phase HPLC to afford Intermediate 4 (0.037 g, 59% yield) as a white solid. MS (ESI) m/z: 291.0 (M+H)+; 1H NMR (500 MHz, DMSO-d6) δ ppm 8.34 (s, 1H), 7.90 (d, J=9.6 Hz, 1H), 7.57 (d, J=9.6 Hz, 1H), 3.81 (s, 2H), 2.63 (tt, J=8.8, 5.6 Hz, 1H), 1.55-1.49 (m, 2H), 1.25 (s, 6H), 1.11-1.02 (m, 2H).

INTERMEDIATE 5

Preparation of Methyl 6-((1,3-difluoropropan-2-yl)oxy)pyrazolo[1,5-a]pyridine-3-carboxylate

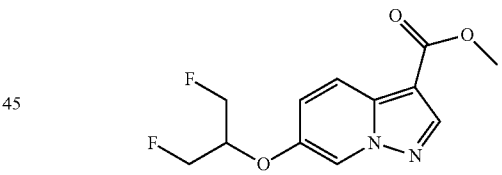

Methyl 6-hyydroxypyrazolo[1,5-a]pyridine-3-carboxylate (0.100 g, 0.520 mmol), 1,3-difluoropropan-2-ol (0.090 mL, 1.04 mmol), and 1,1'-(azodicarbonyl)dipiperidine (0.394 g, 1.56 mmol) were placed in a pressure vial. Then, anhydrous PhMe (5 mL) and tri-N-butylphosphine (0.390 mL, 1.56 mmol) were added, and the reaction mixture was stirred at 140° C. under microwave irradiation for 15 min. The reaction mixture was quenched with MeOH (1 mL), diluted with EtOAc (50 mL), Celite® was added, and solvent was removed under reduced pressure. The residue was purified by flash chromatography to give Intermediate 5 (0.124 g, 88% yield) as a white solid. MS (ESI) m/z: 271.0 (M+H)+. 1H NMR (500 MHz, DMSO-d6) δ ppm 8.83 (d, J=1.7 Hz, 1H), 8.39 (s, 1H), 8.01 (d, J=9.6 Hz, 1H), 7.49 (dd, J=9.5, 2.3 Hz, 1H), 5.11-4.96 (m, 1H), 4.90-4.84 (m, 1H), 4.80-4.72 (m, 2H), 4.67 (dd, J=10.6, 5.1 Hz, 1H), 3.82 (s, 3H); 19F-NMR: (471 MHz, DMSO-d6) δ ppm −231.76 (s, 2F).

INTERMEDIATE 6

Preparation of Methyl 6-(3,3,3-trifluoropropoxy)-pyrazolo[1,5-a]pyridine-3-carboxylate

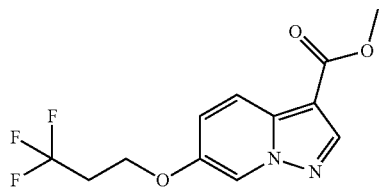 [SMILES: COC(=O)c1cnn2cc(OCCC(F)(F)F)ccc12]

Intermediate 6 was prepared by following a similar procedure to that described for Intermediate 5 employing the appropriate alcohol. MS (ESI) m/z: 289.0 (M+H)$^+$. $^1$H NMR (500 MHz, DMSO-$d_6$) δ ppm 8.70 (d, J=1.9 Hz, 1H), 8.38 (s, 1H), 7.98 (d, J=9.6 Hz, 1H), 7.40 (dd, J=9.6, 2.2 Hz, 1H), 4.33 (t, J=5.9 Hz, 2H), 3.82 (s, 3H), 2.85 (qt, J=11.3, 5.8 Hz, 2H); $^{19}$F-NMR: (471 MHz, DMSO-$d_6$) δ ppm −63.03 (s, 3F).

INTERMEDIATE 7

Preparation of Methyl 6-((tetrahydro-2H-pyran-4-yl)oxy)pyrazolo[1,5-a]pyridine-3-carboxylate

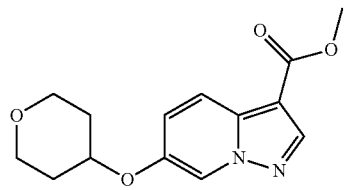 [SMILES: COC(=O)c1cnn2cc(OC3CCOCC3)ccc12]

Intermediate 7 was prepared by following a similar procedure to that described for Intermediate 5 employing the appropriate alcohol. MS (ESI) m/z: 277.0 (M+H)$^+$. $^1$H NMR (500 MHz, DMSO-$d_6$) δ ppm 8.75 (s, 1H), 8.37 (s, 1H), 7.98 (d, J=9.6 Hz, 1H), 7.44 (dd, J=9.6, 2.2 Hz, 1H), 4.67 (tt, J=8.7, 4.1 Hz, 1H), 3.87 (dt, J=11.7, 4.3 Hz, 2H), 3.82 (s, 3H), 3.49 (ddd, J=11.8, 9.4, 2.8 Hz, 2H), 2.07-1.99 (m, 2H), 1.68-1.56 (m, 2H).

INTERMEDIATE 8

Preparation of 6-((Tetrahydrofuran-3-yl)oxy)pyrazolo[1,5-a]pyridine-3-carboxylic acid

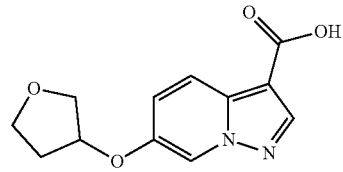 [SMILES: O=C(O)c1cnn2cc(OC3CCOC3)ccc12]

Methyl 6-hydroxypyrazolo[1,5-a]pyridine-3-carboxylate (0.200 g, 1.04 mmol) was suspended in MeCN (10 mL), then 3-bromotetrahydrofuran (0.131 mL, 1.35 mmol), K$_2$CO$_3$ (0.575 g, 4.16 mmol) and H$_2$O (0.667 mL) were added. The reaction mixture was stirred under microwave irradiation at 120° C. for 30 min. The reaction mixture was concentrated under reduced pressure, the residue dissolved in MeOH (4 mL)/THF (4 mL), and 1M LiOH (4.16 mL, 4.16 mmol) was added. The reaction mixture was stirred under microwave irradiation at 150° C. for 15 min. The reaction mixture was acidified with TFA, filtered, and purified by reverse phase HPLC to afford 6-((tetrahydrofuran-3-yl)oxy)pyrazolo[1,5-a]pyridine-3-carboxylic acid (0.155 g, 60% yield) as an off-white solid. MS (ESI) m/z: 249.0 (M+H)$^+$. $^1$H NMR (500 MHz, DMSO-$d_6$) δ ppm 12.36 (br s, 1H), 8.58 (d, J=1.7 Hz, 1H), 8.30 (s, 1H), 7.96 (d, J=9.6 Hz, 1H), 7.34 (dd, J=9.6, 2.2 Hz, 1H), 5.12 (ddt, J=6.1, 4.0, 1.7 Hz, 1H), 3.93-3.83 (m, 3H), 3.77 (td, J=8.4, 4.4 Hz, 1H), 2.32-2.20 (m, 1H), 2.09-1.98 (m, 1H).

INTERMEDIATE 9

Preparation of 3-methoxy-4-(1H-pyrazol-4-yl)benzoic acid

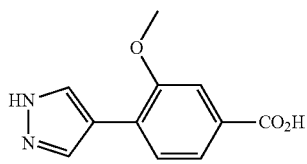 [SMILES: COc1cc(C(=O)O)ccc1-c1cn[nH]c1]

INTERMEDIATE 9A

Preparation of methyl 3-methoxy-4-(1H-pyrazol-4-yl)benzoate

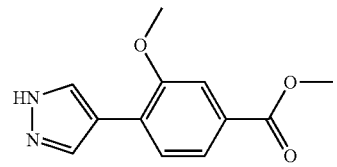 [SMILES: COC(=O)c1ccc(-c2cn[nH]c2)c(OC)c1]

To a solution of methyl 4-bromo-3-methoxybenzoate (1.32 g, 5.39 mmol) in dioxane (30 mL) and water (5 mL) were added tert-butyl 4-(4,4,5,5-tetramethyl-1,3,2-dioxaborolan-2-yl)-1H-pyrazole-1-carboxylate (1.90 g, 6.46 mmol), potassium phosphate (2.86 g, 13.47 mmol) and PdCl$_2$(dppf) (0.197 g, 0.269 mmol) at rt. The reaction was stirred under argon at 100° C. for 3 h. The reaction mixture was diluted with EtOAc, washed with H$_2$O. The organic phase was dried over sodium sulfate, filtered and concentrated. The residue was dissolved in DCM (10 mL) and TFA (5 mL) was added. The reaction was stirred at rt for 1.5 hrs. Solvent was removed. The residue was taken into EtOAc, which was washed with NaHCO$_3$ (3×) and brine, dried over Na$_2$SO$_4$, filtered and concentrated. The crude product was purified by normal phase chromatography. Desired product was isolated as white solid (0.86 g, 69% yield). MS (ESI) m/z: 233.0 (M+H)$^+$. $^1$H NMR (400 MHz, CDCl$_3$) δ ppm 8.13 (s, 2H), 7.73-7.66 (m, 1H), 7.66-7.56 (m, 2H), 3.98 (s, 3H), 3.94 (s, 3H).

INTERMEDIATE 9

To a solution of Intermediate 9A (860 mg, 3.70 mmol) in THF (10 mL) and water (5 mL) was added LiOH (133 mg, 5.55 mmol) at RT. The reaction was stirred under argon at rt for 5 h. The reaction was neutralized with 1 N HCl solution. Solvent was removed to give pale solid of Intermediate 143 (810 mg, 100% yield), which was used without further purification. MS (ESI) m/z: 219.0 (M+H)$^+$. $^1$H NMR (400 MHz, DMSO-d$_6$) δ ppm 7.91 (br. s, 2H), 7.54 (br. s, 1H), 7.43 (br. s, 2H), 3.84 (s, 3H).

INTERMEDIATE 10

Preparation of 2-((6-Aminospiro[3.3]heptan-2-yl)oxy)benzamide

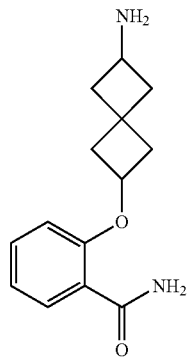 [SMILES: NC(=O)c1ccccc1OC1CC2(CC(N)C2)C1]

INTERMEDIATE 10A

Preparation of Benzyl (6-(2-cyanophenoxy)spiro[3.3]-heptan-2-yl)carbamate

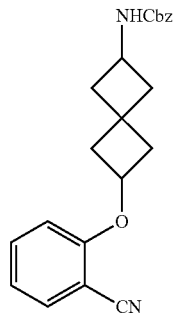 [SMILES: N#Cc1ccccc1OC1CC2(CC(NC(=O)OCc3ccccc3)C2)C1]

NaH (60% wt. in mineral oil) (33.7 mg, 0.842 mmol) was added in one portion to a solution of benzyl (6-hydroxyspiro[3.3]heptan-2-yl)carbamate (Intermediate 1) (100 mg, 0.383 mmol) dissolved in anhydrous THF (3.0 mL) at 0° C. After 30 min, 2-fluorobenzonitrile (0.104 mL, 0.957 mmol) was added in one portion and the reaction mixture gradually allowed to come to rt. After 16 h, the reaction mixture was quenched with NH$_4$Cl (2 mL), diluted with EtOAc (100 mL), washed with water (2×50 mL), brine (25 mL), dried (Na$_2$SO$_4$), filtered, and concentrated. The crude residue was purified by normal phase chromatography to give benzyl (6-(2-cyanophenoxy)spiro[3.3]heptan-2-yl)carbamate (78 mg, 56% yield) as a colorless syrup, which solidified upon standing. MS (ESI) m/z: 363.1 (M+H)$^+$. $^1$H NMR (500 MHz, CDCl$_3$) δ ppm 7.55 (dd, J=7.4, 1.7 Hz, 1H), 7.48 (ddd, J=8.7, 7.3, 1.7 Hz, 1H), 7.41-7.30 (m, 5H), 6.99 (td, J=7.6, 1.0 Hz, 1H), 6.77 (d, J=8.5 Hz, 1H), 5.09 (s, 2H), 4.84 (br d, J=6.3 Hz, 1H), 4.67 (quin, J=6.8 Hz, 1H), 4.21-4.08 (m, 1H), 2.66 (dt, J=11.3, 5.6 Hz, 1H), 2.56-2.43 (m, 3H), 2.36-2.26 (m, 2H), 2.03-1.93 (m, 2H).

INTERMEDIATE 10B

Preparation of Benzyl (6-(2-carbamoylphenoxy)spiro-[3,3]heptan-2-yl)carbamate

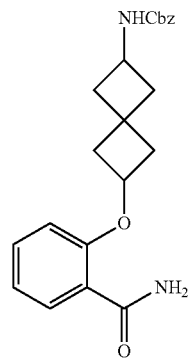 [SMILES: NC(=O)c1ccccc1OC1CC2(CC(NC(=O)OCc3ccccc3)C2)C1]

Benzyl (6-(2-cyanophenoxy)spiro[3.3]heptan-2-yl)carbamate (78 mg, 0.215 mmol) was dissolved in DMSO (2.0 mL) and treated with K$_2$CO$_3$ (89 mg, 0.646 mmol) followed by MgO (43.4 mg, 1.08 mmol). Afterwards, aq. hydrogen peroxide (30% wt.) (0.242 mL, 2.37 mmol) was added dropwise over 5 min (slightly exothermic). After 5 h. the reaction mixture was diluted with EtOAc (50 mL) and 1M HCl (25 mL). The organic phase was separated, washed with brine (25 mL), dried (Na$_2$SO$_4$), filtered, and concentrated to afford benzyl (6-(2-carbamoylphenoxy)spiro[3.3]heptan-2-yl)carbamate (80 mg, 98% yield) as a colorless film. This material was carried to next reaction without further purification. MS (ESI) m/z: 381.1 (M+H)$^+$. $^1$H NMR (500 MHz, CDCl$_3$) δ ppm 8.21 (dd, J=7.8, 1.8 Hz, 1H), 7.75 (br s, 1H), 7.45-7.41 (m, 1H), 7.36 (s, 5H), 7.10-7.04 (m, 1H), 6.77 (d, J=8.3 Hz, 1H), 5.09 (s, 2H), 4.85 (br s, 1H), 4.20-4.11 (m, 1H), 2.72 (br dd, J=11.0, 5.8 Hz, 1H), 2.59-2.51 (m, 2H), 2.50-2.41 (m, 1H), 2.34-2.22 (m, 2H), 2.04-1.95 (m, 2H).

INTERMEDIATE 10

Pd/C (10 wt %) (22.38 mg, 0.021 mmol) was added to a degassed solution of benzyl (6-(2-carbamoylphenoxy)spiro[3.3]heptan-2-yl)carbamate (80 mg, 0.210 mmol) and TEA (0.147 mL, 1.051 mmol) in THF (4 mL)/MeOH (4 mL). The reaction mixture was degassed again and subjected to a hydrogen atmosphere (1 atm; balloon) for 1 h. The suspension was filtered through a plug of Celite® and the filtrate was concentrated to afford 2-((6-aminospiro[3.3]heptan-2-yl)oxy)benzamide (50 mg, 97% yield) as a colorless film. MS (ESI) m/z: 247.0 (M+H)$^+$. $^1$H NMR (500 MHz, CD$_3$OD) δ ppm 7.96 (dd, J=7.8, 1.8 Hz, 1H), 7.46 (ddd, J=8.3, 7.4, 1.9 Hz, 1H), 7.07-7.01 (m, 1H), 6.96-6.91 (m, 1H), 4.79 (t, J=6.9 Hz, 1H), 3.42-3.33 (m, 1H), 2.73-2.66 (m, 1H), 2.55 (dt, J=11.8, 5.9 Hz, 1H), 2.49-2.42 (m, 1H), 2.33 (ddd, J=11.7, 6.7, 5.5 Hz, 1H), 2.27-2.17 (m, 2H), 1.92 (ddd, J=11.3, 8.5, 3.0 Hz, 2H).

INTERMEDIATE 11

Preparation of 2-((6-aminospiro[3.3]heptan-2-yl)oxy)nicotinamide

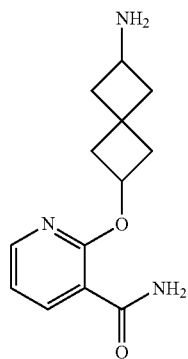 [SMILES: NC(=O)c1cccnc1OC1CC2(CC(N)C2)C1]

Intermediate 11 was prepared by following a similar procedure to that described for Intermediate 10 replacing 2-fluorobenzonitrile with 2-chloronicotinonitrile. MS (ESI) m/z: 248.1 (M+H)+.

INTERMEDIATE 12

Preparation of 3-((6-aminospiro[3.3]heptan-2-yl)oxy)pyrazine-2-carboxamide

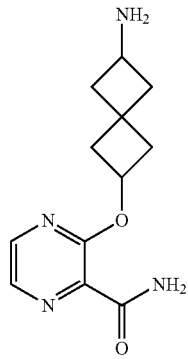 [SMILES: NC(=O)c1nccnc1OC1CC2(CC(N)C2)C1]

Intermediate 12 was prepared by following a similar procedure to that described for Intermediate 10 replacing 2-fluorobenzonitrile with 3-chloropyrazine-2-carbonitrile. MS (ESI) m/z: 249.1 (M+H)+.

INTERMEDIATE 13

Preparation of 4-nitrophenyl (6-((3-carbamoylpyridin-2-yl)oxy)spiro[3.3]heptan-2-yl)carbamate

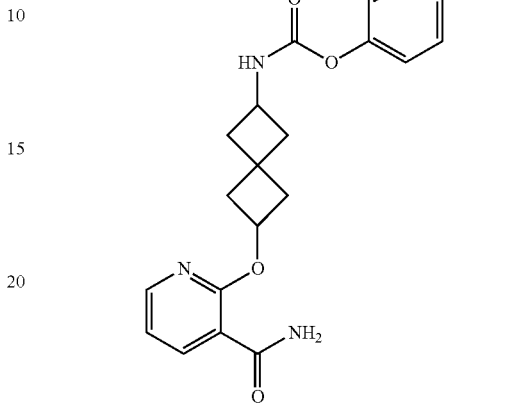

To 4-nitrophenyl chloroformate (0.065 g, 0.324 mmol) and impure Intermediate 11 (0.08 g, 0.324 mmol) in DCM at 0° C., was slowly added, pyridine (0.105 mL, 1.294 mmol). The reaction was allowed to warm to rt and stir 18 h. The reaction was concentrated and the residue partitioned with EtOAc/water. The organic layer was washed with 1.0 N HCl solution, water, dried over MgSO4, filtered, and concentrated to afford intermediate 13 (115 mg, 52%, 60% purity) as a clear oil, which was used without further purification. MS (ESI) m/z: 413.1 (M+H)+.

INTERMEDIATE 14

Preparation of 4-((6-aminospiro[3.3]heptan-2-yl)oxy)pyrimidine-5-carboxamide

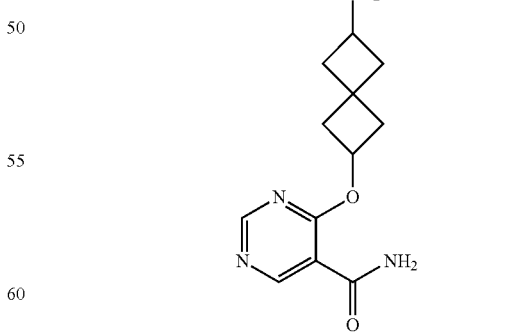

Intermediate 14 was prepared by following a similar procedure to that described for Intermediate 10 replacing 2-fluorobenzonitrile with 4-chloropyrimidine-5-carbonitrile. MS (ESI) m/z: 249.0 (M+H)+.

INTERMEDIATE 15

Preparation of 4-nitrophenyl ((aR)-6-(2-carbamoylphenoxy)spiro[3.3]heptan-2-yl)carbamate

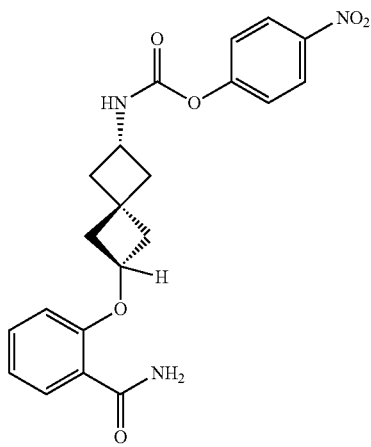

2-((6-aminospiro[3.3]heptan-2-yl)oxy)benzamide (Example 15A) (50 mg, 0.20 mmol) was dissolved in anhydrous THF (5 mL), and DIEA (0.089 mL, 0.508 mmol) was added. The reaction mixture was cooled to 0° C., and 4-nitrophenyl carbonochloridate (49 mg, 0.24 mmol) was added in one portion. The reaction mixture was stirred at 0° C. for 30 min. The reaction mixture was filtered through a membrane filter, and the product was used as a solution in THF. MS (ESI) m/z: 412.1 (M+H)$^+$.

INTERMEDIATE 16

Preparation of 7-(3,3,3-trifluoropropoxy)imidazo[1,2-a]pyridine-3-carboxylic acid

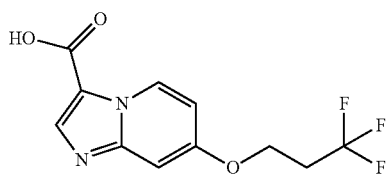 [SMILES: O=C(O)c1cnc2cc(OCCC(F)(F)F)ccn12]

INTERMEDIATE 16A

Preparation of ethyl 7-hydroxyimidazo[1,2-a]pyridine-3-carboxylate

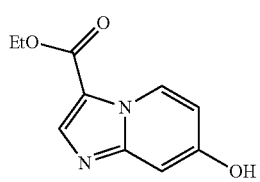 [SMILES: CCOC(=O)c1cnc2cc(O)ccn12]

To a suspension of 2-aminopyridin-4-ol (1.00 g, 9.08 mmol) in EtOH (10 mL) at rt, was added (E)-ethyl 2-chloro-3-hydroxyacrylate (2.05 g, 13.62 mmol) dropwise. The reaction was stirred under N$_2$ at 60° C. overnight. The solvent was removed. The crude product was purified by flash chromatography (0% to 15% MeOH/DCM gradient) to obtain ethyl 7-hydroxyimidazo[1,2-a]pyridine-3-carboxylate (1.18 g, 63% yield), as a light brown solid. $^1$H NMR (400 MHz, Methanol-d$_4$) δ ppm 9.37 (dd, J=7.7, 0.4 Hz, 1H), 8.50 (s, 1H). 7.23-7.13 (m, 2H), 4.50 (q, J=7.1 Hz, 2H), 1.45 (t, J=7.0 Hz, 3H). MS (ESI) m/z: 207.0 (M+H)$^+$.

INTERMEDIATE 16B

Preparation of ethyl 7-(3,3,3-trifluoropropoxy)imidazo[1,2-a]pyridine-3-carboxylate

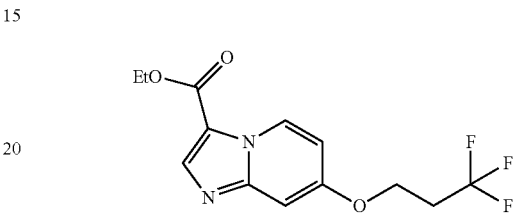

To a pressure vial containing ethyl 7-hydroxyimidazo[1,2-a]pyridine-3-carboxylate (50 mg, 0.242 mmol), 3,3,3-trifluoropropan-1-ol (55.3 mg, 0.485 mmol), 1,1'-(azodicarbonyl)dipiperidine (184 mg, 0.727 mmol), were added toluene (3 mL) and tri-n-butylphosphine (0.179 mL, 0.727 mmol). The reaction was heated in a microwave at 150° C. for 15 min. The solvent was removed. The crude product was purified by flash chromatography (0% to 100% EtOAc/hexanes gradient) to afford ethyl 7-(3,3,3-trifluoropropoxy)imidazo[1,2-a]pyridine-3-carboxylate (25 mg, 34% yield), as a white solid. MS (ESI) m/z: 303.0 (M+H)$^+$.

INTERMEDIATE 16

To a solution of ethyl 7-(3,3,3-trifluoropropoxy)imidazo[1,2-a]pyridine-3-carboxylate (10 mg, 0.033 mmol) in THF (2 mL) were added LiOH (7.92 mg, 0.331 mmol) and H$_2$O (0.5 mL) at rt. The reaction was stirred at 50° C. overnight. The solvent was removed. The crude product was purified by reverse phase chromatography to afford Intermediate 16. (7 mg, 77% yield), as a white solid. MS (ESI) m/z: 275.1 (M+H)$^+$.

INTERMEDIATE 17

Preparation of 6-(2-hydroxy-2-methylpropoxy)-7-(3,3,3-trifluoropropyl)pyrazolo[1,5-a]pyridine-3-carboxylic acid

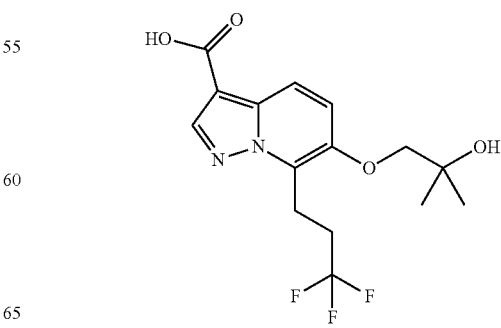

INTERMEDIATE 17A

Preparation methyl 6-(benzyloxy)-7-(3,3,3-trifluoropropyl)pyrazolo[1,5-a]pyridine-3-carboxylate

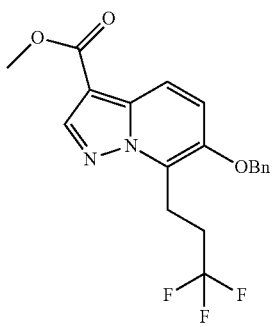 [SMILES: COC(=O)c1cnn2c(CCC(F)(F)F)c(OCc3ccccc3)ccc12]

Methyl 6-(benzyloxy)-7-bromopyrazolo[1,5-a]pyridine-3-carboxylate (0.400 g, 1.107 mmol), potassium (3,3,3-trifluoropropyl)trifluoroborate (0.248 g, 1.22 mmol), potassium carbonate (0.459 g, 3.32 mmol) and Pd-RuPhos G2 (0.043 g, 0.055 mmol) were placed in a pressure vial. Then PhMe (5.0 mL) and water (0.5 mL) were added, and the reaction mixture was degassed (3×, vacuum/Ar). The pressure vial was capped, and the reaction mixture was stirred at 80° C. for 84 h. The reaction mixture was diluted with EtOAc (50 mL), Celite was added, and the solvent was removed under reduced pressure. The residue was purified by flash chromatography (0-35% EtOAc/hexanes) to give methyl 6-(benzyloxy)-7-(3,3,3-trifluoropropyl)pyrazolo[1,5-a]pyridine-3-carboxylate (0.262 g, 63% yield) as a white solid. MS (ESI) m/z: 379.1 (M+H)$^+$. $^1$H-NMR: (500 MHz, CDCl3) δ ppm 8.37 (s, 1H), 8.07 (d, J=9.6 Hz, 1H), 7.40 (d, J=4.7 Hz 5H), 7.37-7.33 (m, 1H), 5.17 (s, 2H), 3.90 (s, 3H), 3.52-3.46 (m, 2H), 2.54-2.42 (m, 2H). $^{19}$F-NMR: (471 MHz, CDCl$_3$) δ ppm −66.64 (s, 3F).

INTERMEDIATE 17B

Preparation methyl 6-hydroxy-7-(3,3,3-trifluoropropyl)pyrazolo[1,5-a]pyridine-3-carboxylate

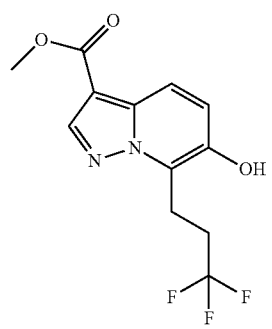 [SMILES: COC(=O)c1cnn2c(CCC(F)(F)F)c(O)ccc12]

Methyl 6-(benzyloxy)-7-(3,3,3-trifluoropropyl)pyrazolo[1,5-a]pyridine-3-carboxylate (0.240 g, 0.634 mmol) was dissolved in THF (4 mL) and MeOH (4 mL), and TEA (0.442 mL, 3.17 mmol) was added. The reaction mixture was degassed (3× vacuum/Ar), then Pd—C (10 wt %) (0.068 g, 0.063 mmol) was added. The reaction mixture was degassed again, and it was stirred under H$_2$ atmosphere (1 atm: balloon) for 1 h. The mixture was filtered, and the filtrate was concentrated to afford methyl 6-hydroxy-7-(3,3,3-trifluoropropyl)pyrazolo[1,5-a]pyridine-3-carboxylate (0.183 g, 100% yield) as an off-white solid. MS (ESI) m/z: 289.0 (M+H)$^+$. $^1$H-NMR: (500 MHz, DMSO-d$_6$) δ ppm 10.12 (br s, 1H), 8.38 (s, 1H), 7.91 (d, J=9.4 Hz, 1H), 7.39 (d, J=9.6 Hz, 1H), 3.81 (s, 3H), 3.44-3.35 (m, 2H), 2.74-2.60 (m, 2H), $^{19}$F-NMR: (471 MHz, DMSO-d$_6$) δ ppm −65.22 (s, 3F).

INTERMEDIATE 17

Methyl 6-hydroxy-7-(3,3,3-trifluoropropyl)pyrazolo[1,5-a]pyridine-3-carboxylate (0.100 g, 0.347 mmol) was suspended in MeCN (3.00 mL), then 2,2-dimethyloxirane (0.232 mL, 2.60 mmol), K$_2$CO$_3$ (0.192 g, 1.39 mmol) and water (0.200 mL) were added. The reaction mixture was stirred under microwave irradiation at 120° C. for 30 min. The reaction mixture was concentrated under reduced pressure, the residue was dissolved in MeOH (1.5 mL)/THF (1.5 mL), and LiOH (1 M aq.) (1.041 mL, 1.041 mmol) was added. The reaction mixture was stirred under microwave irradiation at 120° C. for 15 min. Solvent was removed under reduced pressure, the residue was dissolved in DMF/MeCN/H$_2$O/TFA and was purified by preparative HPLC to afford 6-(2-hydroxy-2-methylpropoxy)-7-(3,3,3-trifluoropropyl)pyrazolo[1,5-a]pyridine-3-carboxylic acid (37 mg, 31% yield) as a white solid. MS (ESI) m/z: 370.0 (M+H)$^+$. $^1$H-NMR: (500 MHz, DMSO-d$_6$) δ ppm 12.38 (br s, 1H), 8.40 (s, 1H), 8.00 (d, J=9.6 Hz, 1H), 7.67 (d, J=9.6 Hz, 1H), 4.71 (br s, 1H), 3.87 (s, 2H), 3.52-3.44 (m, 2H), 2.77-2.64 (m, 2H), 1.25 (s, 6H). $^{19}$F-NMR: (471 MHz, DMSO-d$_6$) δ ppm −65.28 (s, 3F)

INTERMEDIATE 18

Preparation of 5-(2-morpholinoethoxy)pyrazolo[1,5-a]pyridine-3-carboxylic acid

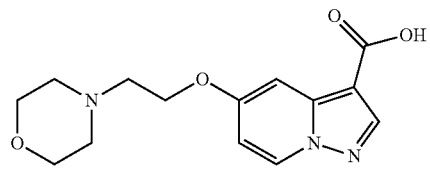 [SMILES: O=C(O)c1cnn2ccc(OCCN3CCOCC3)cc12]

INTERMEDIATE 18A

Preparation of ethyl 5-hydroxypyrazolo[1,5-a]pyridine-3-carboxylate

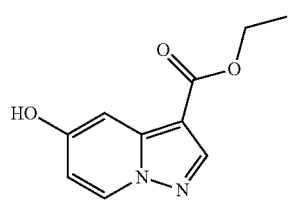

ethyl 5-methoxypyrazolo[1,5-a]pyridine-3-carboxylate (580 mg, 2.63 mmol) was mixed with aluminum tribromide (3.51 mg, 13.2 mmol) in EtSH (5 mL). The mixture was stirred at rt for 3 h. The mixture was cooled to 0° C., then was diluted with DCM. MeOH was added dropwise, followed by water. The mixture was extracted with EtOAc. The organic phase was concentrated. The residue was purified by flash chromatography (0-40% EtOAc/hexanes gradient) to afford 5-(2-morpholinoethoxy)pyrazolo[1,5-a]pyridine-3-carboxylic acid (180 mg, 33% yield). MS (ESI) m/z: 207.2 (M+H)+. 1H NMR (400 MHz, Methanol-d4) δ ppm 8.42 (dd, J=7.5, 0.4 Hz, 1H), 8.21 (s, 1H), 7.41-7.27 (m, 1H), 6.67 (dd, J=7.5, 2.6 Hz, 1H), 4.32 (q, J=7.0 Hz, 2H), 1.39 (t, J=7.2 Hz, 3H).

INTERMEDIATE 18B

Preparation of ethyl 5-(2-morpholinoethoxy)pyrazolo[1,5-a]pyridine-3-carboxylate

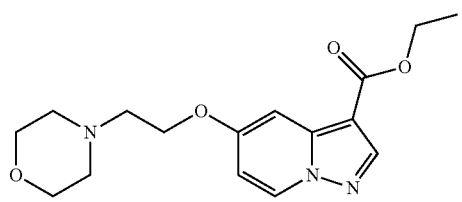 [SMILES: CCOC(=O)c1cnn2ccc(OCCN3CCOCC3)cc12]

To a vial containing ethyl 5-hydroxypyrazolo[1,5-a]pyridine-3-carboxylate (40 mg, 0.194 mmol) in DMF (2 mL), were added 4-(2-bromoethyl)morpholine, hydrobromide (80 mg, 0.291 mmol) and Cs2CO3 (190 mg, 0.582 mmol). The vial was sealed and the mixture was stirred at 70° C. for 16 h. The mixture was filtered and the filtrate was concentrated. The residue was purified by flash chromatography (0-20% MeOH/DCM gradient) to afford ethyl 5-(2-morpholinoethoxy)pyrazolo[1,5-a]pyridine-3-carboxylate (51 mg, 82% yield) as a white solid. MS (ESI) m/z: 320.3 (M+H)+. 1H NMR (400 MHz, CDCl3) δ ppm 8.30 (dd, J=7.5, 0.7 Hz, 1H), 8.25 (s, 1H), 7.40 (d, J=2.6 Hz, 1H), 6.60 (dd, J=7.5, 2.6 Hz, 1H), 4.33 (q, J=7.0 Hz, 2H), 4.19 (t, J=5.6 Hz, 2H), 3.78-3.67 (m, 4H), 2.83 (t, J=5.6 Hz, 2H), 2.61-2.53 (m, 4H), 1.37 (t, J=7.2 Hz, 3H).

INTERMEDIATE 18

To ethyl 5-(2-morpholinoethoxy)pyrazolo[1,5-a]pyridine-3-carboxylate (51 mg, 0.16 mmol) in MeOH (1 mL) and THF (1 mL), was added 1M LiOH (2 mL, 2.000 mmol). The mixture was stirred at rt overnight, then was concentrated. The mixture was acidified with TFA, then was purified by preparative HPLC to afford Intermediate 18 (60 mg, 93% yield) as a white solid. MS (ESI) m/z: 292.3 (M+H)+. 1H NMR (400 MHz. Methanol-d4) δ ppm 8.53 (dd, J=7.6, 0.5 Hz, 1H), 8.29 (s, 1H), 7.50 (d, J=2.6 Hz, 1H), 6.83 (dd, J=7.5, 2.6 Hz, 1H), 4.58-4.51 (m, 2H), 4.05 (br. s., 2H), 3.88 (br. s., 2H), 3.78-3.70 (m, 2H), 3.65-3.48 (m, 2H), 3.45-3.34 (m, 2H).

INTERMEDIATE 19

6-(2-(pyrrolidin-1-yl)ethoxy)pyrazolo[1,5-a]pyridine-3-carboxylic acid, TFA

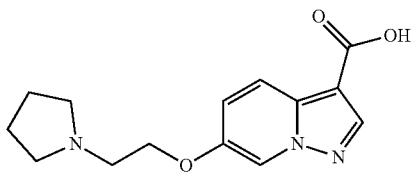 [SMILES: O=C(O)c1cnn2cc(OCCN3CCCC3)ccc12]

ethyl 6-hydroxypyrazolo[1,5-a]pyridine-3-carboxylate (0.025 g, 0.12 mmol) was dissolved in MeCN (1.0 mL)/THF (1.0 mL), then 1-(2-bromoethyl)pyrrolidine, hydrobromide (0.035 g, 0.133 mmol) and cesium carbonate (0.079 g, 0.24 mmol) were added. The reaction mixture was stirred under microwave irradiation at 120° C. for 15 min. The reaction mixture was concentrated under reduced pressure, the residue was dissolved in MeOH (1 mL)/THF (1 mL), and LiOH (1 M aq.) (0.364 mL, 0.364 mmol) was added. The reaction mixture was stirred under microwave irradiation at 120° C. for 15 min. The reaction mixture was acidified with TFA, DMF was added, and the obtained solution was purified by preparative HPLC to afford 6-(2-(pyrrolidin-1-yl)ethoxy)pyrazolo[1,5-a]pyridine-3-carboxylic acid, TFA (0.029 g, 61% yield) as a white solid. MS (ESI) m/z: 276.0 (M+H)+. 1H-NMR: (500 MHz, DMSO-d6) δ ppm 9.96 (br s, 1H), 8.78 (d, J=1.7 Hz, 1H), 8.40 (s, 1H), 8.08 (d, J=9.6 Hz, 1H), 7.48 (dd, J=9.6, 2.2 Hz, 1H), 4.50-4.45 (m, 2H), 3.71 (br d, J=4.1 Hz, 2H), 2.16-2.03 (m, 4H), 2.00-1.88 (m, 4H).

INTERMEDIATE 20

6-(2,2-difluoroethoxy)pyrazolo[1,5-a]pyridine-3-carboxylic acid

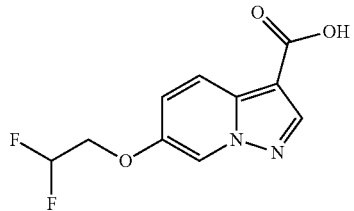 [SMILES: O=C(O)c1cnn2cc(OCC(F)F)ccc12]

Ethyl 6-hydroxypyrazolo[1,5-a]pyridine-3-carboxylate (0.080 g, 0.389 mmol) was suspended in MeCN (3.0 mL), then 2,2-difluoroethyl trifluoromethanesulfonate (0.062 mL, 0.47 mmol) and cesium carbonate (0.379 g, 1.16 mmol) were added. The reaction mixture was stirred under microwave irradiation at 120° C. for 15 min. The reaction mixture was concentrated under reduced pressure, the residue was dissolved in MeOH (1.5 mL)/THF (1.5 mL), and LiOH (1 M aq.) (1.94 mL, 1.94 mmol) was added. The reaction mixture was stirred under microwave irradiation at 120° C. for 15 min. The reaction mixture was purified by preparative HPLC to afford 6-(2,2-difluoroethoxy)pyrazolo[1,5-a]pyridine-3-carboxylic acid (0.064 g, 68% yield) as a white solid. MS (ESI) m/z: 243.0 (M+H)+. 1H-NMR: (500 MHz, DMSO-d6) δ ppm 12.41 (s, 1H), 8.72 (d, J=1.7 Hz, 1H), 8.32 (s, 1H), 7.99 (d, J=10.2 Hz, 1H), 7.43 (dd, J=9.6, 2.5 Hz, 1H), 6.45 (tt, J=54.3, 3.5 Hz, 1H), 4.44 (td, J=14.6, 3.4 Hz, 2H). $^{19}$F-NMR: (471 MHz, DMSO-d$_6$) δ ppm −125.92 (s, 2F).

INTERMEDIATE 21

6-(3,3-difluoropyrrolidin-1-yl)pyrazolo[1,5-a]pyridine-3-carboxylic acid

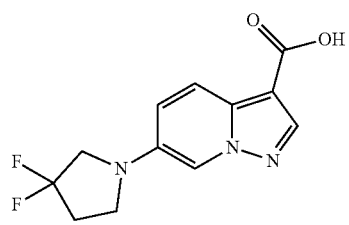 [SMILES: O=C(O)c1cnn2cc(N3CCC(F)(F)C3)ccc12]

Methyl 6-bromopyrazolo[1,5-a]pyridine-3-carboxylate (0.050 g, 0.196 mmol), 3,3-difluoropyrrolidine. HCl (0.056 g, 0.39 mmol), BINAP (11 mg, 0.018 mmol), Pd(OAc)$_2$ (2.6 mg, 0.012 mmol) and cesium carbonate (0.224 g, 0.686 mmol) were placed in a pressure vial. The reaction mixture was degassed (3× vacuum/Ar), then toluene (1 mL) was added. The reaction mixture was degassed again, and stirred at 100° C. for 1 d. Solvent was removed under reduced pressure. The obtained residue was dissolved in MeOH (1.0 mL)/THF (1.0 mL), and LiOH (1 M aq.) (0.588 mL, 0.588 mmol) was added. The reaction mixture was stirred under microwave irradiation at 120° C. for 15 min. The mixture was acidified with TFA, the solvent was removed under reduced pressure, the residue was purified by preparative HPLC to afford 6-(3,3-difluoropyrrolidin-1-yl)pyrazolo[1,5-a]pyridine-3-carboxylic acid (23 mg, 44% yield) as an off-white solid. MS (ESI) m/z: 268.0 (M+H)$^+$. $^1$H-NMR: (500 MHz, DMSO-d$_6$) δ ppm 12.24 (br s, 1H), 8.22 (s, 1H), 8.10 (d, J=1.7 Hz, 1H), 7.93 (d, J=9.6 Hz, 1H), 7.34 (dd, J=9.5, 2.1 Hz, 1H), 3.75 (t, J=13.3 Hz, 2H), 3.53 (t, J=7.2 Hz, 2H), 2.63-2.51 (m, 2H). $^{19}$F-NMR: (471 MHz, DMSO-d$_6$) δ ppm −96.75 (s, 2F).

INTERMEDIATE 22

6-(difluoromethoxy)pyrazolo[1,5-a]pyridine-3-carboxylic acid

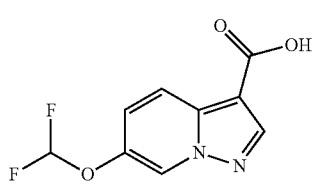 [SMILES: O=C(O)c1cnn2cc(OC(F)F)ccc12]

INTERMEDIATE 22A ethyl 6-(difluoromethoxy)pyrazolo[1,5-a]pyridine-3-carboxylate

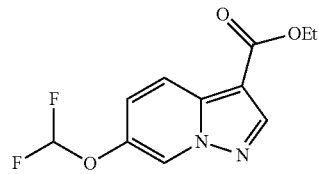 [SMILES: CCOC(=O)c1cnn2cc(OC(F)F)ccc12]

Ethyl 6-hydroxypyrazolo[1,5-a]pyridine-3-carboxylate (0.100 g, 0.485 mmol), K$_2$CO$_3$ (0.134 g, 0.970 mmol), and Sodium chlorodifluoroacetate (0.148 g, 0.970 mmol) were dissolved in DMF (2.2 mL) and Water (0.22 mL). The reaction was heated to 130° C. for 20 min. The reaction was diluted with water (50 mL) and EtOAc (100 mL). Organic phase was separated, washed with water (3×25 mL) and brine (25 mL), and dried (Na$_2$SO$_4$). EtOAc was removed under reduced pressure and the residue was purified by flash chromatography (0-40% EtOAc/hexanes gradient) to give ethyl 6-(difluoromethoxy)pyrazolo[1,5-a]pyridine-3-carboxylate (74 mg, 60% yield) as a white solid. MS (ESI) m/z: 257.0 (M+H)$^+$. $^1$H-NMR: (500 MHz, DMSO-d$_6$) δ ppm 9.03 (d, J=1.7 Hz, 1H), 8.49 (s, 1H), 8.11 (dd, J=9.6, 0.8 Hz, 1H), 7.61 (dd, J=9.6, 1.9 Hz, 1H), 7.30 (t, J=73.3 Hz, 1H), 4.31 (q, J=7.1 Hz, 2H), 1.34 (t, J=7.2 Hz, 3H). $^1$H-NMR: (471 MHz, DMSO-d$_6$) δ ppm −82.68 (s, 2F)

INTERMEDIATE 22

Ethyl 6-(difluoromethoxy)pyrazolo[1,5-a]pyridine-3-carboxylate (0.050 g, 0.195 mmol) was dissolved in MeOH (1.5 mL)/THF (1.500 mL), and LiOH (1 M aq.) (0.585 mL, 0.585 mmol) was added. The reaction mixture was stirred under microwave irradiation at 150° C. for 15 min. Solvent was removed under reduced pressure, the residue was purified by preparative HPLC to afford 6-(difluoromethoxy)pyrazolo[1,5-a]pyridine-3-carboxylic acid (0.035 g, 79% yield) as a white solid. MS (ESI) m/z: 229.3 (M+H)$^+$. $^1$H-NMR: (500 MHz, DMSO-d$_6$) δ ppm 8.99 (s, 1H), 8.43 (s, 1H), 8.11 (d, J=9.6 Hz, 1H), 7.56 (dd, J=9.5, 2.1 Hz, 1H), 7.28 (t, J=73.2 Hz, 1H). $^{19}$F-NMR: (471 MHz, DMSO-d$_6$) δ ppm −82.58 (s, 2F)

INTERMEDIATE 23

7-(3,3-difluoropyrrolidin-1-yl)imidazo[1,2-a]pyridine-3-carboxylic acid, TFA

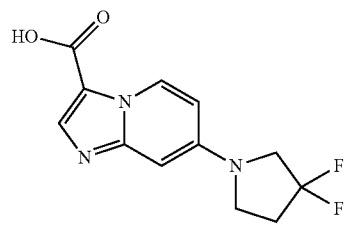 [SMILES: O=C(O)c1cnc2cc(N3CCC(F)(F)C3)ccn12]

INTERMEDIATE 23A ethyl 7-(3,3-difluoropyrrolidin-1-yl)imidazo[1,2-a]pyridine-3-carboxylate

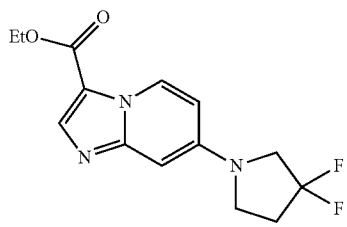 [SMILES: CCOC(=O)c1cnc2cc(N3CCC(F)(F)C3)ccn12]

Ethyl 7-bromoimidazo[1,2-a]pyridine-3-carboxylate (0.100 g, 0.372 mmol), 3,3-difluoropyrrolidine, HCl (0.069 g, 0.48 mmol), BINAP (0.021 g, 0.033 mmol) and cesium carbonate (0.303 g, 0.929 mmol) were placed in a pressure vial. The reaction mixture was degassed (3× vacuum/Ar), then toluene (2 mL) was added. The reaction mixture was degassed again, and stirred at 120° C. for 3 h. The reaction was cooled to rt. The solvent was removed. The crude product was purified by flash chromatography. (0% to 15% MeOH/DCM gradient) to afford ethyl 7-(3,3-difluoropyrrolidin-1-yl)imidazo[1,2-a]pyridine-3-carboxylate (102 mg, 93% yield), as an off-white solid. MS (ESI) m/z: 296.0 (M+H)$^+$. $^1$H NMR (400 MHz, CDCl$_3$) δ ppm 9.07 (d, J=7.7 Hz, 1H), 8.14 (s, 1H), 6.55 (d, J=2.4 Hz, 1H), 6.46 (dd, J=7.6, 2.5 Hz, 1H), 4.37 (q, J=7.0 Hz, 2H), 3.76 (t, J=12.9 Hz, 2H), 3.64 (t, J=7.3 Hz, 2H), 2.67-2.45 (m, 2H), 1.39 (t, J=7.0 Hz, 3H). $^{19}$F NMR (376 MHz, CDCl$_3$) δ −99.91 (s, 2F).

INTERMEDIATE 23

To a solution of ethyl 7-(3,3-difluoropyrrolidin-1-yl)imidazo[1,2-a]pyridine-3-carboxylate (102 mg, 0.345 mmol) in THF (4 mL) and water (1 mL) was added LiOH (41.4 mg, 1.727 mmol). The reaction was stirred at 50° C. for 16 h. The solvent was removed and the residue was purified by preparative HPLC to afford 7-(3,3-difluoropyrrolidin-1-yl)imidazo[1,2-a]pyridine-3-carboxylic acid, TFA (89 mg, 68% yield), as a white solid. MS (ESI) m/z: 268.0 (M+H)$^+$. $^1$H NMR (400 MHz, DMSO-d$_6$) δ ppm 9.09 (d, J=7.7 Hz, 1H), 8.45 (s, 1H), 7.05 (dd, J=7.8, 2.5 Hz, 1H), 6.62 (d, J=2.4 Hz, 1H), 3.97 (t, J=13.0 Hz, 2H), 3.72 (t, J=7.3 Hz, 2H), 2.63 (tt, J=14.3, 7.4 Hz, 2H). $^{19}$F NMR (376 MHz, DMSO-d$_6$) d −73.75 (s, 3F), −99.89 (s, 2F).

INTERMEDIATE 24

Methyl 6-((1-(methoxycarbonyl)azetidin-3-yl)oxy)pyrazolo[1,5-a]pyridine-3-carboxylate

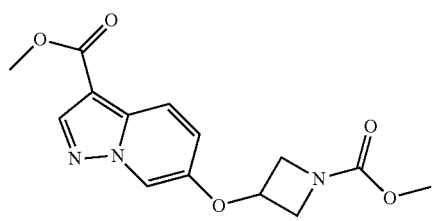

Methyl 6-hydroxypyrazolo[1,5-a]pyridine-3-carboxylate (0.100 g, 0.520 mmol), methyl 3-hydroxyazetidine-1-carboxylate (0.136 g, 1.04 mmol), and 1,1'-(azodicarbonyl)dipiperidine (0.394 g, 1.56 mmol) were placed in a pressure vial. Toluene (5 mL) and tri-n-butylphosphine (0.39 mL, 1.56 mmol) were added, and the reaction mixture was stirred at 140° C. under microwave irradiation for 15 min. The reaction mixture was quenched with MeOH (5 mL), diluted with MeOH/DCM (20 mL), and the solvent was removed under reduced pressure. The residue was purified by flash chromatography (0-100% EtOAc/DCM) to give methyl 6-((1-(methoxycarbonyl)azetidin-3-yl)oxy)pyrazolo[1,5-a]pyridine-3-carboxylate (0.109 g, 69% yield) as a white solid. MS (ESI) m/z: 306.0 (M+H)$^+$. $^1$H-NMR: (500 MHz, DMSO-d6) δ ppm 8.47 (d, J=1.7 Hz, 1H), 8.38 (s, 1H), 8.01 (d, J=9.6 Hz, 1H), 7.42 (dd, J=9.6, 2.2 Hz, 1H), 5.15-5.09 (m, 1H), 4.46-4.39 (m, 2H), 3.97-3.89 (m, 2H), 3.82 (s, 3H), 3.58 (s, 3H).

INTERMEDIATE 25

Methyl 6-((1,1-dioxidotetrahydro-2H-thiopyran-4-yl)oxy)pyrazolol[1,5-a]pyridine-3-carboxylate

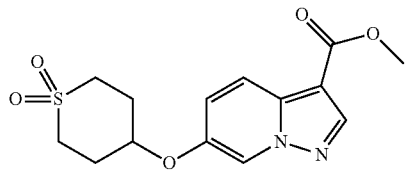 [SMILES: COC(=O)c1cnn2cc(OC3CCS(=O)(=O)CC3)ccc12]

Methyl 6-hydroxypyrazolo[1,5-a]pyridine-3-carboxylate (0.100 g, 0.520 mmol), 4-hydroxytetrahydro-2H-thiopyran 1,1-dioxide (0.094 g, 0.62 mmol), and 1,1'-(azodicarbonyl)dipiperidine (0.328 g, 1.30 mmol) were placed in a pressure vial. Then, anhydrous PhMe (4 mL) and tri-N-butylphosphine (0.325 mL, 1.30 mmol) were added, and the reaction mixture was stirred at 120° C. under microwave irradiation for 45 min. The reaction mixture was quenched with MeOH (1 mL), diluted with EtOAc (50 mL), Celite was added, and solvent was removed under reduced pressure. The residue was purified by flash chromatography (solid loading, 0-100% EtOAc/DCM gradient) to give methyl 6-((1,1-dioxidotetrahydro-2H-thiopyran-4-yl)oxy)pyrazolo[1,5-a]pyridine-3-carboxylate (0.110 g, 65% yield) as a white solid. MS (ESI) m/z: 325.0 (M+H)$^+$. $^1$H-NMR: (500 MHz, DMSO-d6) δ ppm 8.84 (d, J=2.2 Hz, 1H), 8.39 (s, 1H), 8.00 (d, J=9.4 Hz, 1H), 7.53 (dd, J=9.6, 1.9 Hz, 1H), 4.78 (quin, J=4.6 Hz, 1H), 3.82 (s, 3H), 3.30-3.23 (m, 2H), 3.19-3.12 (m, 2H), 2.26 (q, J=5.4 Hz, 4H).

INTERMEDIATE 26

Ethyl 7-morpholinoimidazo[1,2-a]pyridine-3-carboxylate

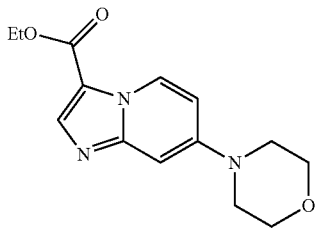 [SMILES: CCOC(=O)c1cnc2cc(N3CCOCC3)ccn12]

Ethyl 7-bromoimidazo[1,2-a]pyridine-3-carboxylate (0.100 g, 0.372 mmol). Pd(OAc)$_2$ (5.0 mg, 0.022 mmol), BINAP (0.021 g, 0.033 mmol) and cesium carbonate (0.182 g, 0.557 mmol) were placed in a pressure vial. The reaction mixture was degassed (3× vacuum/Ar), then toluene (2 mL) and morpholine (0.042 mL, 0.48 mmol) were added. The reaction mixture was degassed again, and then stirred at 120° C. for 3 h. The reaction was concentrated. The crude product was purified by flash chromatography. (0% to 15% MeOH/DCM gradient) to afford ethyl 7-morpholinoimidazo[1,2-a]pyridine-3-carboxylate (89 mg, 87%6 yield), as a light tan solid. MS (ESI) m's: 276.1 (M+H)$^+$. $^1$H NMR (400 MHz, CDCl$_3$) δ ppm 9.04 (d, J=7.7 Hz, 1H), 8.14 (s, 1H), 6.86 (d, J=2.4 Hz, 1H), 6.74 (dd, J=7.7, 2.6 Hz, 1H), 4.36 (q, J=7.0 Hz, 2H), 3.93-3.75 (m, 4H), 3.33-3.16 (m, 4H), 1.39 (t, J=7.2 Hz, 3H).

INTERMEDIATE 27

Methyl 7-cyclopropyl-6-(3-(methylsulfonyl)propoxy)pyrazolo[1,5-a]pyridine-3-carboxylate

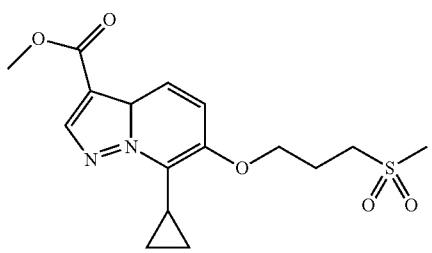

Methyl 7-cyclopropyl-6-hydroxypyrazolo[1,5-a]pyridine-3-carboxylate (0.075 g, 0.32 mmol), 3-(methylsulfonyl)propan-1-ol (0.089 g, 0.65 mmol), and 1,1'-(azodicarbonyl)dipiperidine (0.244 g, 0.969 mmol) were placed in a pressure vial. Then, PhMe (4 mL) and tri-N-butylphosphine (0.242 mL, 0.969 mmol) were added, and the reaction mixture was stirred at 140° C. under microwave irradiation for 15 min. The reaction mixture was quenched with MeOH (5 mL), diluted with MeOH/DCM (20 mL), and the solvent was removed under reduced pressure. The residue was purified by flash chromatography (0-75% EtOAc/DCM gradient) to give methyl 7-cyclopropyl-6-(3-(methylsulfonyl)propoxy)pyrazolo[1,5-a]pyridine-3-carboxylate (0.094 g, 83% yield) as a white solid. MS (ESI) m/z: 353.1 (M+H)$^+$. $^1$H-NMR: (500 MHz, CDCl$_3$) δ ppm 8.40 (s, 1H), 8.02 (d, J=9.6 Hz, 1H), 7.29-7.24 (m, 1H), 4.21 (t, J=5.9 Hz, 2H), 3.91 (s, 3H), 3.34-3.25 (m, 2H), 3.00 (s, 3H), 2.49-2.43 (m, 1H), 2.43-2.36 (m, 2H), 1.41-1.35 (m, 2H), 1.22-1.17 (m, 2H).

INTERMEDIATE 28

Methyl 7-cyclopropyl-6-(2-((tetrahydro-2H-pyran-2-yl)oxy)ethoxy)pyrazolo[1,5-a]pyridine-3-carboxylate

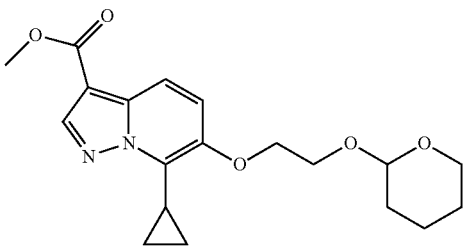 [SMILES: COC(=O)c1cnn2c(C3CC3)c(OCCOC3CCCCO3)ccc12]

Methyl 7-cyclopropyl-6-hydroxypyrazolo[1,5-a]pyridine-3-carboxylate (0.100 g, 0.431 mmol), 2-((tetrahydro-2H-pyran-2-yl)oxy)ethanol (0.117 mL, 0.861 mmol), and 1,1'-(azodicarbonyl)dipiperidine (0.326 g, 1.29 mmol) were placed in a pressure vial. Then, anhydrous PhMe (4 mL) and tri-N-butylphosphine (0.323 mL, 1.29 mmol) were added, and the reaction mixture was stirred at 140° C. under microwave irradiation for 15 min. The reaction mixture was quenched with MeOH (5 mL), diluted with MeOH/DCM (20 mL), and the solvent was removed under reduced pressure. The residue was purified by flash chromatography (0-50% EtOAc/DCM gradient) to give methyl 7-cyclopropyl-6-(2-((tetrahydro-2H-pyran-2-yl)oxy)ethoxy)pyrazolo[1,5-a]pyridine-3-carboxylate (0.145 g, 93% yield) as a white solid. MS (ESI) m/z: 361.1 (M+H)$^+$. $^1$H-NMR: (500 MHz, CDCl$_3$) δ ppm 8.39 (s, 1H), 7.99 (d, J=9.6 Hz, 1H), 7.34 (d, J=9.4 Hz, 1H), 4.72 (t, J=3.3 Hz, 1H), 4.22 (t, J=4.7 Hz, 2H), 4.07 (dt, J=11.3, 4.4 Hz, 1H), 3.91 (s, 3H), 3.79 (dt, J=11.0, 5.2 Hz, 1H), 3.59-3.48 (m, 2H), 2.62-2.52 (m, 1H), 1.92-1.81 (m, 2H), 1.80-1.68 (m, 2H), 1.67-1.62 (m, 2H), 1.52-1.47 (m, 2H), 1.20-1.12 (m, 2H).

INTERMEDIATE 29

Methyl 7-cyclopropyl-6-(3,3,3-trifluoropropoxy)pyrazolo[1,5-a]pyridine-3-carboxylate

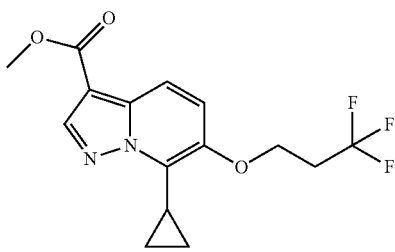 [SMILES: COC(=O)c1cnn2c(C3CC3)c(OCCC(F)(F)F)ccc12]

Methyl 7-cyclopropyl-6-hydroxypyrazolo[1,5-a]pyridine-3-carboxylate (0.050 g, 0.215 mmol), 3,3,3-trifluoropropan-1-ol (0.037 mL, 0.43 mmol), and 1,1'-(azodicarbonyl)dipiperidine (0.163 g, 0.646 mmol) were placed in a pressure vial. Then, anhydrous PhMe (4 mL) and tri-N-butylphosphine (0.161 mL, 0.646 mmol) were added, and the reaction mixture was stirred at 140° C. under microwave irradiation for 15 min. The reaction mixture was quenched with MeOH (5 mL), diluted with MeOH/DCM (20 mL), and the solvent was removed under reduced pressure. The residue was purified by flash chromatography (0-50% EtOAc/DCM gradient) to give methyl 7-cyclopropyl-6-(3,3,3-trifluoropropoxy)pyrazolo[1,5-a]pyridine-3-carboxylate (44 mg, 62% yield) as a white solid. MS (ESI) m/z: 329.0 (M+H)$^+$. $^1$H-NMR: (500 MHz, CDCl$_3$) δ ppm 8.40 (s, 1H), 8.03 (d, J=9.4 Hz, 1H), 7.26 (d, J=9.6 Hz, 1H), 4.27 (t, J=6.5 Hz, 2H), 3.91 (s, 3H), 2.67 (qt, J=10.5, 6.5 Hz, 2H), 2.46 (tt, J=8.7, 5.6 Hz, 1H), 1.43-1.38 (m, 2H), 1.22-1.16 (m, 2H). $^{19}$F-NMR: (471 MHz, CDCl$_3$) δ ppm −64.60 (s, 3F).

INTERMEDIATE 30

Methyl 6-(3,3,3-trifluoropropoxy)pyrazolo[1,5-a]pyridine-3-carboxylate

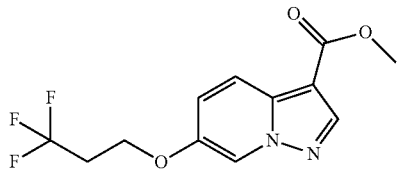 [SMILES: COC(=O)c1cnn2cc(OCCC(F)(F)F)ccc12]

Methyl 6-hydroxypyrazolo[1,5-a]pyridine-3-carboxylate (0.100 g, 0.520 mmol), 3,3,3-trifluoropropan-1-ol (0.096 mL, 1.041 mmol), and 1,1'-(azodicarbonyl)dipiperidine (0.394 g, 1.561 mmol) were placed in a pressure vial. Then, anhydrous PhMe (5 mL) and tri-N-butylphosphine (0.390 mL, 1.561 mmol) were added, and the reaction mixture was stirred at 140° C. under microwave irradiation for 15 min. The reaction mixture was quenched with MeOH (1 mL), diluted with EtOAc (50 mL), Celite was added, and solvent was removed under reduced pressure. The residue was purified by ISCO (solid loading on Celite, 0-60% EtOAc/DCM gradient) to give methyl 6-(3,3,3-trifluoropropoxy)pyrazolo[1,5-a]pyridine-3-carboxylate (0.064 g, 42% yield) as a white solid. MS (ESI) m/z: 289.0 (M+H)$^+$. $^1$H-NMR: (500 MHz, DMSO-d$_6$) δ ppm 8.70 (d, J=1.9 Hz, 1H), 8.38 (s, 1H), 7.98 (d, J=9.6 Hz, 1H), 7.40 (dd, J=9.6, 2.2 Hz, 1H), 4.33 (t, J=5.9 Hz, 2H), 3.82 (s, 3H), 2.85 (qt, J=11.3, 5.8 Hz, 2H). $^{19}$F-NMR: (471 MHz, DMSO-d6) δ ppm −63.03 (s, 3F).

INTERMEDIATE 31

Ethyl 7-(1-methyl-1H-pyrazol-4-yl)imidazo[1,2-a]pyridine-3-carboxylate

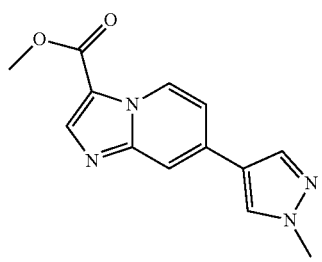

To a solution of ethyl 7-bromoimidazo[1,2-a]pyridine-3-carboxylate (100 mg, 0.372 mmol) in dioxane (3 mL) and water (0.5 mL) were added 1-methyl-4-(4,4,5,5-tetramethyl-1,3,2-dioxaborolan-2-yl)-1H-pyrazole (93 mg, 0.45 mmol), K$_3$PO$_4$ (197 mg, 0.929 mmol) and XPhos-Pd-G2 (14.6 mg, 0.019 mmol) at rt. The reaction was stirred under N$_2$ at 100° C. for 1 h. The reaction was cooled to rt. The solvent was removed and the crude product was purified by flash chromatography (0% to 15% MeOH/DCM gradient) to afford ethyl 7-(1-methyl-1H-pyrazol-4-yl)imidazo[1,2-a]pyridine-3-carboxylate (98 mg, 98% yield), as a white solid. MS (ESI) m/z: 271.0 (M+H)$^+$. $^1$H NMR (400 MHz, CDCl$_3$) δ ppm 9.21 (dd, J=7.3, 0.7 Hz, 1H), 8.25 (s, 1H), 7.85 (s, 1H), 7.74 (s, 2H), 7.13 (dd, J=7.3, 1.8 Hz, 1H), 4.40 (q, J=7.0 Hz, 2H), 3.97 (s, 3H), 1.41 (t, J=7.0 Hz, 3H).

INTERMEDIATE 32

Methyl 7-cyclopropyl-6-((1,1-dioxidotetrahydro-2H-thiopyran-4-yl)oxy)pyrazolo[1,5-a]pyridine-3-carboxylate

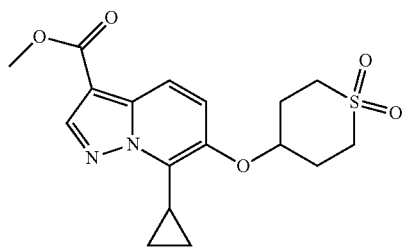 [SMILES: COC(=O)c1cnn2c(C3CC3)c(OC3CCS(=O)(=O)CC3)ccc12]

INTERMEDIATE 32A

Methyl 7-cyclopropyl-6-((tetrahydro-2H-thiopyran-4-yl)oxy)pyrazolo[1,5-a]pyridine-3-carboxylate

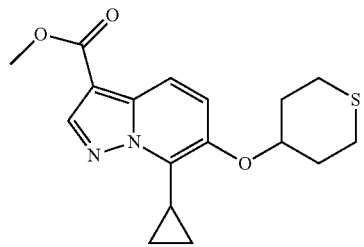 [SMILES: COC(=O)c1cnn2c(C3CC3)c(OC3CCSCC3)ccc12]

Methyl 7-cyclopropyl-6-hydroxypyrazolo[1,5-a]pyridine-3-carboxylate (0.100 g, 0.431 mmol), tetrahydro-2H-thiopyran-4-ol (0.102 g, 0.861 mmol), and 1,1'-(azodicarbonyl)dipiperidine (0.326 g, 1.29 mmol) were placed in a pressure vial. Then, anhydrous PhMe (4 mL) and tri-N-butylphosphine (0.323 mL, 1.29 mmol) were added, and the reaction mixture was stirred at 140° C. under microwave irradiation for 15 min.

The reaction mixture was quenched with MeOH (5 mL), diluted with MeOH/DCM (20 mL), and the solvent was removed under reduced pressure. The residue was purified by flash chromatography (0-50% EtOAc/DCM gradient) to give methyl 7-cyclopropyl-6-((tetrahydro-2H-thiopyran-4-yl)oxy)pyrazolo[1,5-a]pyridine-3-carboxylate (0.134 g, 94% yield) as a colorless syrup. MS (ESI) m/z: 333.1 (M+H)⁺. ¹H-NMR: (500 MHz, CDCl₃) δ ppm 8.38 (s, 1H), 7.99 (d, J=9.4 Hz, 1H), 7.22 (d, J=9.6 Hz, 1H), 4.31-4.22 (m, 1H), 3.90 (s, 3H), 2.97-2.88 (m, 2H), 2.65-2.55 (m, 2H), 2.44-2.36 (m, 1H), 2.30-2.20 (m, 2H), 2.08-1.98 (m, 2H), 1.46-1.39 (m, 2H), 1.21-1.15 (m, 2H).

INTERMEDIATE 32

Methyl 7-cyclopropyl-6-((tetrahydro-2H-thiopyran-4-yl) oxy)pyrazolo[1,5-a]pyridine-3-carboxylate (0.100 g, 0.301 mmol) was dissolved in anhydrous DCM (5 mL). The reaction mixture was cooled to 0° C. m-CPBA (77% wt.) (0.148 g, 0.662 mmol) was added, and the reaction mixture was stirred at 0° C. for 15 min, then cooling bath was removed and the reaction mixture was stirred at rt for 1 h. The solvent was removed under reduced pressure, and the residue was purified by flash chromatography (0-65% EtOAc/DCM gradient) to give methyl 7-cyclopropyl-6-((1, 1-dioxidotetrahydro-2H-thiopyran-4-yl)oxy)pyrazolo[1,5-a]pyridine-3-carboxylate (0.094 g, 86% yield) as a colorless foam. MS (ESI) m/z: 365.1 (M+H)⁺. ¹H-NMR: (500 MHz, CDCl₃) δ ppm 8.41 (s, 1H), 8.06 (d, J=9.6 Hz, 1H), 7.23 (d, J=9.4 Hz, 1H), 4.62-4.56 (m, 1H), 3.91 (s, 3H), 3.52-3.43 (m, 2H), 3.03 (br d, J=13.2 Hz, 2H), 2.52-2.45 (m, 2H), 2.45-2.36 (m, 2H), 2.32-2.23 (m, 1H), 1.37-1.32 (m, 2H), 1.29-1.23 (m, 2H).

INTERMEDIATE 33

Methyl 7-(4-methylpiperazin-1-yl)imidazo[1,2-a]pyridine-3-carboxylate

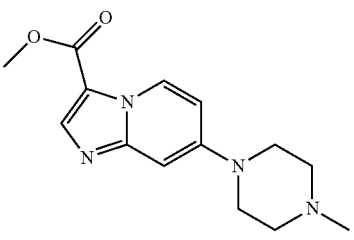

Ethyl 7-bromoimidazo[1,2-a]pyridine-3-carboxylate (0.100 g, 0.372 mmol), 1-methylpiperazine (0.048 g, 0.483 mmol), BINAP (0.021 g, 0.033 mmol) and cesium carbonate (0.182 g, 0.557 mmol) were placed in a pressure vial. The reaction mixture was degassed (3× vacuum/Ar), then toluene (2 mL) was added. The reaction mixture was degassed again, and stirred at 120° C. for 5 h. The reaction was cooled to rt and the solvent was removed. The solid was dissolved with MeOH and evaporated onto celite. The crude product was purified by flash chromatography (solid loading from celite, 0% to 15% MeOH/DCM gradient) to afford methyl 7-(4-methylpiperazin-1-yl)imidazo[1,2-a]pyridine-3-carboxylate (0.083 g, 81% yield) as a light tan solid. MS (ESI) m/z: 275.0 (M+H)⁺. ¹H NMR (400 MHz, CDCl₃) δ ppm 9.01 (d, J=7.7 Hz, 1H), 8.13 (s, 1H), 6.87 (d, J=2.4 Hz, 1H), 6.76 (dd, J=7.8, 2.3 Hz, 1H), 3.89 (s, 3H), 3.42-3.27 (m, 4H), 2.63-2.52 (m, 4H), 2.36 (s, 3H).

INTERMEDIATE 34

7-(2-(Pyrrolidin-1-ylethoxy)imidazo[1,2-a]pyridine-3-carboxylic acid

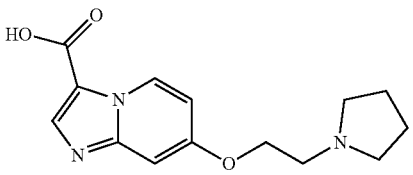 [SMILES: O=C(O)c1cnc2cc(OCCN3CCCC3)ccn12]

Ethyl 7-bromoimidazo[1,2-a]pyridine-3-carboxylate (0.100 g, 0.372 mmol), allylpalladium chloride dimer (2.0 mg, 5.6 μmol), ROCKPHOS (5.2 mg, 0.011 mmol) and cesium carbonate (0.182 g, 0.557 mmol) were placed in a pressure vial. The reaction mixture was degassed (3× vacuum/Ar), then toluene (2 mL) was added, followed by the addition of 2-(pyrrolidin-1-yl)ethanol (0.064 g, 0.56 mmol). The reaction mixture was degassed again, and stirred at 120° C. for 5 h. The reaction was cooled to rt. To the reaction was added water (1 mL) and LiOH (50 mg). The reaction was heated at 60° C. overnight. The solvents were removed. The crude product was purified by preparative HPLC to afford Intermediate 34 (55 mg, 54% yield), as a white solid. MS (ESI) m/z: 276.0 (M+H)⁺. ¹H NMR (400 MHz, DMSO-d₆) δ 9.17 (d, J=7.5 Hz, 1H), 7.33 (d, J=2.4 Hz, 1H), 7.07 (d, J=1.8 Hz, 1H), 7.02 (dd, J=7.6, 2.5 Hz, 1H), 4.54-4.36 (m, 2H), 3.86-2.93 (m, 6H), 2.06 (d, J=9.0 Hz, 2H), 1.95-1.75 (m, 2H).

INTERMEDIATE 35

Preparation of benzyl ((aR)-6-hydroxyspiro[3.3]heptan-2-yl)carbamate

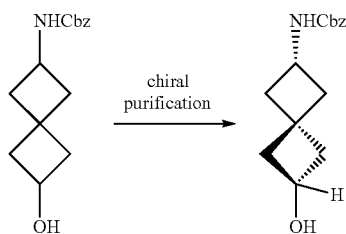

Intermediate 1 (100 mg, 0.383 mmol) was subjected to chiral prep HPLC (Instrument: PIC Solution Prep SFC (column: Chiralpak IF, 30×250 mm, 5 micron; Mobile Phase: 15% MeOH+0.1% DEA/85% CO₂; Flow Conditions: 85 mL/min, 150 Bar, 40° C.; Detector Wavelength: 220 nm; Injection Details: 0.5 mL of each fraction) and the first peak was collected to afford Example 35 (48 mg, 48% yield) as an off white solid. MS (ESI) m/z: 262.0 (M+H)⁺. ¹H NMR: (500 MHz, CDCl₃) δ ppm 7.35 (s, 5H), 5.08 (br s, 2H), 4.82 (br s, 1H), 4.20 (quin, J=7.2 Hz, 1H), 4.10 (br d, J=7.4 Hz, 1H), 2.47 (br d, J=4.4 Hz, 1H), 2.44-2.33 (m, 2H), 2.31-2.24 (m, 1H), 1.99-1.80 (m, 4H).

INTERMEDIATE 36

Preparation of 5-fluoro-1-(2-hydroxy-2-methylpropyl)-1H-indazole-3-carboxylic acid

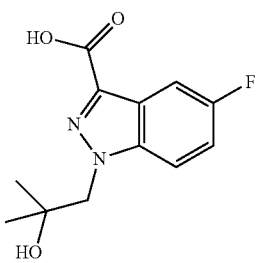 [SMILES: CC(C)(O)Cn1nc(C(=O)O)c2cc(F)ccc21]

INTERMEDIATE 36A

Preparation of methyl 5-fluoro-1-(2-hydroxy-2-methylpropyl)-1H-indazole-3-carboxylate

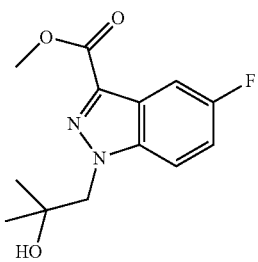 [SMILES: COC(=O)c1nn(CC(C)(C)O)c2ccc(F)cc12]

To a vial containing methyl 5-fluoro-1H-indazole-3-carboxylate (200 mg, 1.030 mmol) in CH$_3$CN (3 mL), were added 2,2-dimethyloxirane (0.458 mL, 5.15 mmol) and Cs$_2$CO$_3$ (403 mg, 1.236 mmol). The vial was sealed and the mixture was stirred at 80° C. for 3 h. Afterwards, the suspension was filtered, concentrated and the crude residue purified by normal phase chromatography to afford the desired product as a white solid (47.4%). MS (ESI) m/z: 267.1 (M+H)$^+$. $^1$H NMR: (400 MHz, CDCl$_3$) δ 7.81-7.76 (m, 1H), 7.58-7.52 (m, 1H), 7.18 (td, J=8.9, 2.4 Hz, 1H), 4.42 (s, 2H), 4.02-3.97 (m, 3H), 1.26 (s, 6H).

INTERMEDIATE 36

The ester (130 mg, 0.488 mmol) was dissolved in THF (2 mL), add lithium hydroxide (0.976 mL, 0.976 mmol), stirred rt for 16 h. Afterwards, water was added, acidified with 1N HCl, extracted with EtOAc, washed with brine, dried over Na$_2$SO$_4$, concentrated to afford 5-fluoro-1-(2-hydroxy-2-methylpropyl)-1H-indazole-3-carboxylic acid (115 mg, 93% yield) as a white solid. MS (ESI) m/z: 253.1 (M+H)$^+$. $^1$H NMR: (500 MHz, Methanol-d4) δ 7.77-7.68 (m, 2H), 7.32-7.20 (m, 1H), 4.43 (s, 2H), 1.30-1.21 (m, 6H).

INTERMEDIATE 37

Preparation of 6-(2-hydroxy-2-methylpropoxy)-7-(2-oxopiperidin-1-yl)pyrazolo[1,5-a]pyridine-3-carboxylic acid

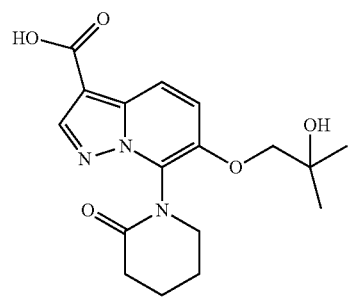 [SMILES: CC(C)(O)COc1ccc2c(C(=O)O)cnn2c1N1CCCCC1=O]

INTERMEDIATE 37A

Preparation of methyl 6-hydroxy-7-(2-oxopiperidin-1-yl)pyrazolo[1,5-a]pyridine-3-carboxylate

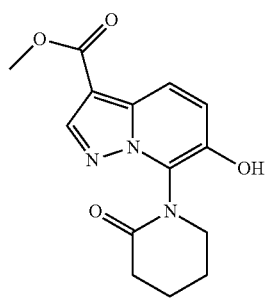 [SMILES: COC(=O)c1cnn2c(N3CCCCC3=O)c(O)ccc12]

Methyl 6-(benzyloxy)-7-bromopyrazolo[1,5-a]pyridine-3-carboxylate (0.200 g, 0.554 mmol), piperidin-2-one (0.110 g, 1.107 mmol), N,N'-dimethylethylenediamine (0.012 mL, 0.111 mmol), and potassium phosphate tribasic (0.235 g, 1.107 mmol) in Dioxane (3.34 mL) and degassed with N2. After 10 min, CuI (0.021 g, 0.111 mmol) was added, sealed and heated to 100° C. The reaction was filtered, concentrated and purified by normal phase chromatography to give a white solid. The residue was dissolved in MeOH (20 mL) was treated with 10% Pd—C(Degussa type, wet) (0.024 g, 0.111 mmol) and subjected to a hydrogen atmosphere (55 psi). After 2 h, the reaction mixture was filtered through a plug of Celite and the filtrate concentrated to give the desired product (48 mg, 30%). MS (ESI) m/z: 290.0 (M+H)$^+$.

INTERMEDIATE 37

A slurry of methyl 6-hydroxy-7-(2-oxopiperidin-1-yl)pyrazolo[1,5-a]pyridine-3-carboxylate (0.048 g, 0.166 mmol), 2,2-dimethyloxirane (0.074 mL, 0.830 mmol) and K$_2$CO$_3$ (0.092 g, 0.664 mmol) in Acetonitrile (3.67 mL)/Water (0.184 mL) was irradated at 120° C. for 60 min. Afterwards, the reaction mixture was concentrated, treated with 1.0M LiOH (0.498 mL, 0.498 mmol) in MeOH/THF (1:1; 3 mL) and irradated at 120° C. for 30 min. The mixture was concentrated to dryness and purified by reverse phase chromatography to give 6-(2-hydroxy-2-methylpropoxy)-7-(2-oxopiperidin-1-yl)pyrazolo[1,5-a]pyridine-3-carboxylic acid (0.0289 g, 50.1% yield) as a white solid. MS (ESI) m/z: 348.0 (M+H)+. 1H NMR (400 MHz, DMSO-d6) δ 12.44 (br. s., 1H), 8.36 (s, 1H), 8.05 (d, J=9.5 Hz, 1H), 7.73 (d, J=9.7 Hz, 1H), 4.66 (br. s., 1H), 3.93-3.81 (m, 2H), 3.74-3.65 (m, 1H), 3.62-3.50 (m, 1H), 2.07-1.85 (m, 4H), 1.33-1.16 (m, 6H).

INTERMEDIATE 38

Preparation of 1-(2-(2-methoxyethoxy)ethyl)-3a,7a-dihydro-1H-indazole-3-carboxylic acid

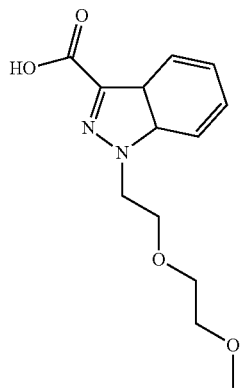 [SMILES: COCCOCCN1N=C(C(=O)O)C2C=CC=CC21]

INTERMEDIATE 38A

Preparation of ethyl 1-(2-(2-methoxyethoxy)ethyl)-3a,7a-dihydro-1H-indazole-3-carboxylate

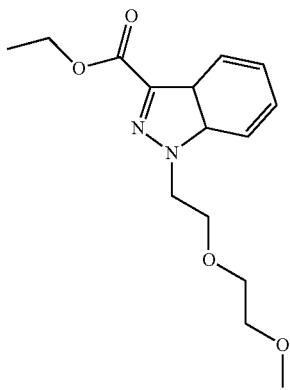 [SMILES: CCOC(=O)C1=NN(CCOCCOC)C2C=CC=CC12]

To a vial containing ethyl 1H-indazole-3-carboxylate (150 mg, 0.789 mmol) in CH3CN (3 mL), were added 1-bromo-2-(2-methoxyethoxy)ethane (217 mg, 1.183 mmol) and Cs2CO3 (385 mg, 1.183 mmol). The vial was sealed and the mixture was stirred at 80° C. overnight. Afterwards, water was added, extracted with EtOAc, washed organic layer with 10% LiCl, brine, concentrated and the residue was purified by normal phase chromatography with the second peak to elute off column being the desired product (105 mg, 40.5%). MS (ESI) m/z: 293.2 (M+H)+. 1H NMR (400 MHz, CDCl3) δ 8.20 (dt, J=8.2, 1.0 Hz, 1H), 7.63-7.57 (m, 1H), 7.42 (ddd, J=8.4, 7.0, 1.1 Hz, 1H), 7.30 (ddd, J=8.1, 7.0, 0.9 Hz, 1H), 4.67 (t, J=5.6 Hz, 2H), 4.53 (q, J=7.3 Hz, 2H), 3.97 (t, J=5.7 Hz, 2H), 3.56-3.48 (m, 2H), 3.43-3.37 (m, 2H), 3.28 (s, 3H), 1.48 (t, J=7.2 Hz, 3H).

INTERMEDIATE 38

Intermediate 38A (110 mg, 0.376 mmol) dissolved in THF (2 mL) was treated with 1.0M LiOH (0.941 mL, 0.941 mmol) at rt. After 3 h, the reaction mixture was concentrated, added water, acidified with 1N HCl, extracted with EtOAc (3×), washed with brine, dried over Na2SO4, filtered, and concentrated to give 1-(2-(2-methoxyethoxy)ethyl)-3a,7a-dihydro-1H-indazole-3-carboxylic acid (93 mg, 0.352 mmol, 94° % yield) as an colorless oil. MS (ESI) m-z: 263.3 (M+H)+. 1H NMR (500 MHz, Methanol-d4) δ 8.12 (dt, J=8.2, 0.9 Hz, 1H), 7.72-7.62 (m, 1H), 7.42 (ddd, J=8.4, 7.0, 1.1 Hz, 1H), 7.27 (ddd, J=8.1, 7.0, 0.8 Hz, 1H), 4.62 (t, J=5.4 Hz, 2H), 3.93 (t, J=5.4 Hz, 2H), 3.49-3.43 (m, 2H), 3.37-3.32 (m, 2H), 3.17 (s, 3H).

INTERMEDIATE 39

Preparation of 6-(2-(dimethylamino)ethoxy)pyrazolo[1,5-a]pyridine-3-carboxylic acid, trifluoroacetate

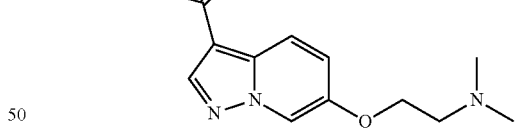

Ethyl 6-hydroxypyrazolo[1,5-a]pyridine-3-carboxylate (0.100 g, 0.485 mmol), 2-(dimethylamino)ethanol (0.086 g, 0.970 mmol), and 1,1'-(azodicarbonyl)dipiperidine (0.367 g, 1.455 mmol) were placed in a pressure vial. Then, anhydrous toluene (5 mL) and tri-N-butylphosphine (0.363 mL, 1.455 mmol) were added, and the reaction mixture irradiated at 140° C. for 20 min. The reaction mixture was quenched with MeOH (1 mL), diluted with EtOAc (50 mL), and solvent was removed under reduced pressure. The reaction mixture was concentrated under reduced pressure. The residue was dissolved in MeOH (4.0 mL)/THF (4.0 mL), treated with LiOH (1.94 mL, 1.94 mmol) irradiated at 100° C. for 15 min. The mixture was concentrated and purified by reverse phase chromatography to give the desired product (10 mg, 5.7%). MS (ESI) m/z: 250.0 (M+H)+.

147

INTERMEDIATE 40

Preparation of 6-bromo-1-(2-hydroxy-2-methylpropyl)-1H-indazole-3-carboxylic acid

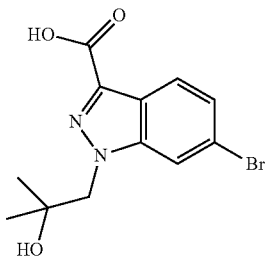 [SMILES: CC(C)(O)Cn1nc(C(=O)O)c2ccc(Br)cc21]

6-bromo-1-(2-hydroxy-2-methylpropyl)-1H-indazole-3-carboxylic acid was prepared in a similar manner as Intermediate 36, substituting methyl 6-bromo-1H-indazole-3-carboxylate for 5-fluoro-1H-indazole-3-carboxylate. MS (ESI) m/z: 312.9 (M+H)$^+$. $^1$H NMR (400 MHz. Methanol-d4) δ 8.06 (dd, J=8.7, 0.6 Hz, 1H), 8.03-8.01 (m, 1H), 7.42 (dd, J=8.6, 1.5 Hz, 1H), 4.43 (s, 2H), 1.25 (s, 6H).

INTERMEDIATE 41

Preparation of 6-(3,3,3-trifluoropropoxy)pyrazolo[1,5-a]pyridine-3-carboxylic acid

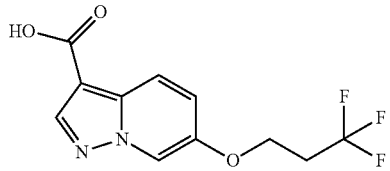 [SMILES: O=C(O)c1cnn2cc(OCCC(F)(F)F)ccc12]

Intermediate 30 (0.675 g, 2.342 mmol) was dissolved in MeOH (24.0 mL)/THF (24.0 mL), and LiOH (7.03 mL, 7.03 mmol) was added. The reaction mixture was irradiated at 100° C. for 15 min before acidifying with 1.0N HCl solution, extracted with EtOAc, washed with brine, dried over sodium sulfate, filtered, and concentrated to give the desired product (0.6087 g, 2.220 mmol, 95% yield) as a white solid. $^1$H NMR (500 MHz, CDCl$_3$) δ 8.41 (s, 1H), 8.18 (d, J=1.9 Hz, 1H), 8.14-8.10 (m, 1H), 7.26-7.19 (m, 1H), 4.25 (t, J=6.3 Hz, 2H), 2.76-2.66 (m, 2H).

INTERMEDIATE 42

Preparation of ethyl 8-cyclopropylimidazo[1,2-a]pyridine-3-carboxylate

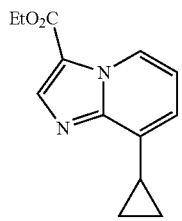 [SMILES: CCOC(=O)c1cnc2c(C3CC3)cccn12]

148

A slurry of ethyl 8-bromoimidazo[1,2-a]pyridine-3-carboxylate (0.2 g, 0.743 mmol), cyclopropylboronic acid (0.255 g, 2.97 mmol), palladium(II) acetate (8.34 mg, 0.037 mmol), potassium phosphate tribasic (0.473 g, 2.230 mmol) and tricyclohexylphosphonium tetrafluoroborate (0.027 g, 0.074 mmol) in Toluene (6)/Water (0.5 mL) was blanketed under N2 and heated to 100° C. overnight. The reaction was extracted from brine with EtOAc, the organic layer concentrated, and the residue purified by normal phase chromatography to furnish ethyl 8-cyclopropylimidazo[1,2-a]pyridine-3-carboxylate (0.064 g, 0.278 mmol, 37.4% yield). MS (ESI) m/z: 230.9 (M+H)$^+$.

INTERMEDIATE 43

Preparation of 5-(cyclopropylmethoxy)-1-methyl-1H-pyrazole-3-carboxylic acid

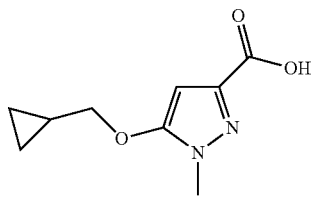

INTERMEDIATE 43A

Preparation of methyl 5-(cyclopropylmethoxy)-1-methyl-1H-pyrazole-3-carboxylate

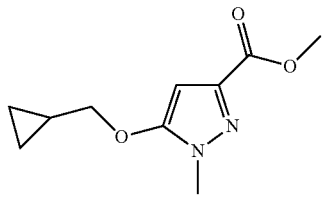

Methyl 5-hydroxy-1-methyl-1H-pyrazole-3-carboxylate (0.500 g, 3.20 mmol) was dissolved in anhydrous MeCN (15 mL), and (bromomethyl)cyclopropane (0.519 g, 3.84 mmol) and Cs$_2$CO$_3$ (1.565 g, 4.80 mmol) were added sequentially. The reaction mixture was stirred at 60° C. for 2 h. The reaction mixture was diluted with DCM, Celite was added, and the solvent was removed under reduced pressure. The residue was purified by normal phase chromatography to give methyl 5-(cyclopropylmethoxy)-1-methyl-1H-pyrazole-3-carboxylate (0.651 g, 3.10 mmol, 97% yield) as a colorless oil, which solidified upon standing. MS (ESI) m/z: 210.9 (M+H)$^+$. $^1$H NMR (400 MHz, DMSO-d$_6$) δ 6.15 (s, 1H), 3.96 (d, J=7.0 Hz, 2H), 3.76 (s, 3H), 3.64 (s, 3H), 1.30-1.17 (m, 1H), 0.61-0.54 (m, 2H), 0.38-0.32 (m, 2H).

INTERMEDIATE 43

Intermediate 43A (0.200 g, 0.951 mmol) was dissolved in THF (3.96 mL) and MeOH (0.793 mL), then 1.0M LiOH (2.85 mL, 2.85 mmol) was added. The reaction was heated to 50° C. for 1 h. The reaction mixture was quenched with TFA (0.220 mL, 2.85 mmol), concentrated, and purified by reverse phase chromatography, 5-(cyclopropylmethoxy)-1-methyl-1H-pyrazole-3-carboxylic acid (0.1133 g, 60.7% yield) as a white solid. MS (ESI) m/z: 196.9 (M+H)+. 1H NMR (400 MHz, Methanol-d4) δ 6.11 (s, 1H), 3.98 (d, J=7.3 Hz, 2H), 3.71 (s, 3H), 1.38-1.26 (m, 1H), 0.70-0.63 (m, 2H), 0.44-0.38 (m, 2H).

INTERMEDIATE 44

Preparation of 1-methyl-5-(2,2,3,3-tetrafluoropropoxy)-1H-pyrazole-3-carboxylic acid

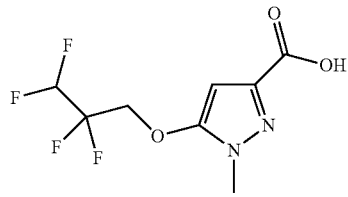 [SMILES: Cn1nc(C(=O)O)cc1OCC(F)(F)C(F)F]

1-Methyl-5-(2,2,3,3-tetrafluoropropoxy)-1H-pyrazole-3-carboxylic acid was prepared in a similar manner as Intermediate 43, substituting (bromomethyl)cyclopropane with 2,2,3,3-tetrafluoropropyl trifluoromethanesulfonate. MS (ESI) m/z: 256.8 (M+H)+. 1H NMR (400 MHz, Methanol-d4) δ 6.59-6.35 (m, 1H), 6.31 (s, 1H), 4.68 (tt, J=12.7, 1.3 Hz, 2H), 3.75 (s, 3H).

INTERMEDIATE 45

Preparation of 2-(3,3-difluoroazetidin-1-yl)-4-methylthiazole-5 carboxylic acid

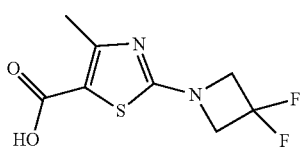

To a solution of ethyl 2-bromo-4-methylthiazole-5-carboxylate (0.200 g, 0.800 mmol) and 3,3-difluoroazetidine (0.149 g, 1.599 mmol) in THF (5 mL) at rt was added DIEA (0.419 mL, 2.399 mmol) and the mixture irradiated at 130° C. for 30 min. The reaction mixture was diluted with EtOAc (50 mL), Celite was added, and the solvent was removed under reduced pressure. The residue was purified by normal phase chromatography to give the desired intermediate as an off-white solid. The ester was dissolved in THF (5 mL) and EtOH (5 mL) and treated with LiOH (0.101 g, 2.399 mmol) in H2O (2 mL). After 4 h, the reaction was quenched with 1.0M HCl solution, concentrated, and purified by reverse phase chromatography to give the desired product (67 mg, 35.8%). MS (ESI) m/z: 234.8 (M+H)+. 1H NMR (400 MHz, Methanol-d4) δ 4.49 (t, J=11.9 Hz 4H), 2.51 (s, 3H).

INTERMEDIATE 46

Preparation of 5-bromo-1-(2-hydroxy-2-methylpropyl)-1H-indazole-3-carboxylic acid

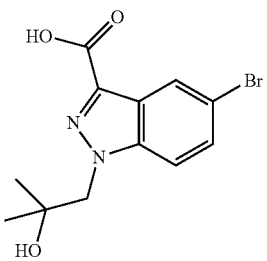 [SMILES: CC(C)(O)Cn1nc(C(=O)O)c2cc(Br)ccc21]

5-Bromo-1-(2-hydroxy-2-methylpropyl)-1H-indazole-3-carboxylic acid (855 mg, 69.6%) was prepared in a similar manner as Intermediate 36, substituting 5-fluoro-1H-indazole-3-carboxylate with 5-bromo-1H-indazole-3-carboxylate. MS (ESI) m/z: 312.9 (M+H)+. 1H NMR (400 MHz, Methanol-d4) δ 8.06 (dd, J=8.7, 0.6 Hz, 1H), 8.03-8.01 (m, 1H), 7.42 (dd, J=8.6, 1.5 Hz, 1H), 4.43 (s, 2H), 1.25 (s, 6H).

INTERMEDIATE 47

Preparation of 2-(3,3-difluoropyrrolidin-1-yl)-4-methylthiazole-5-carboxylic acid

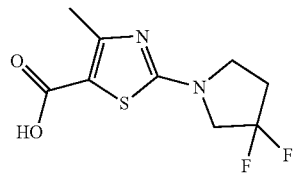 [SMILES: Cc1nc(N2CCC(F)(F)C2)sc1C(=O)O]

2-(3,3-difluoropyrrolidin-1-yl)-4-methylthiazole-5-carboxylic acid (138.6 mg, 69.8%) was prepared in a similar manner as Intermediate 45, substituting 3,3-difluoroazetidine with 3,3-difluoropyrrolidine hydrogen chloride. MS (ESI) m/z: 248.8 (M+H)+.

INTERMEDIATE 48

Preparation of 1-(2-hydroxy-2-methylpropyl)-1H-pyrazolo[3,4-b]pyridine-3-carboxylic acid

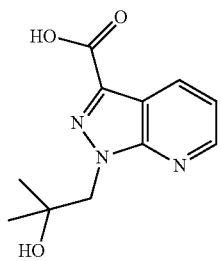

1-(2-hydroxy-2-methylpropyl)-1H-pyrazolo[3,4-b]pyridine-3-carboxylic acid (128 mg, 100%) was prepared in a similar manner as Intermediate 36, substituting 5-fluoro-1H-indazole-3-carboxylate with methyl 1H-pyrrolo[2,3-b]pyridine-3-carboxylate. MS (ESI) m/z: 235.2 (M+H)⁺. ¹H NMR (400 MHz, Methanol-d4) δ 8.47 (dd, J=7.9, 1.5 Hz, 1H), 8.29 (d, J=4.0 Hz, 1H), 8.14 (s, 1H), 7.23 (dd, J=7.9, 4.8 Hz, 1H), 4.33 (s, 2H), 1.17 (s, 6H).

INTERMEDIATE 49

Preparation of 5-(2,2-difluoroethoxy)-1-methyl-1H-pyrazole-3-carboxylic acid

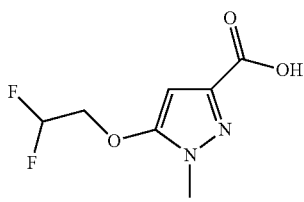

5-(2,2-difluoroethoxy)-1-methyl-1H-pyrazole-3-carboxylic acid was prepared in a similar manner as Intermediate 43, substituting (bromomethyl)cyclopropane with 2,2,3,3-tetrafluoropropyl trifluoromethanesulfonate. MS (ESI) m/z: 206.9 (M+H)⁺.

INTERMEDIATE 50

Preparation of 6-fluoro-1-(2-hydroxy-2-methylpropyl)-1H-indazole-3-carboxylic acid

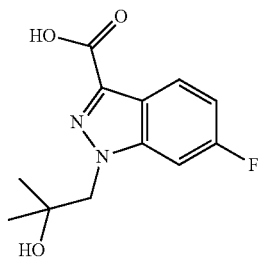 [SMILES: CC(C)(O)Cn1nc(C(=O)O)c2ccc(F)cc21]

6-fluoro-1-(2-hydroxy-2-methylpropyl)-1H-indazole-3-carboxylic acid was prepared in a similar manner as Intermediate 36, substituting methyl 5-fluoro-1H-indazole-3-carboxylate for 6-fluoro-1H-indazole-3-carboxylate. MS (ESI) m/z: 252.9 (M+H)⁺.

INTERMEDIATE 51

Preparation of 6-trifluoromethoxy-1-(2-hydroxy-2-methylpropyl)-1H-indazole-3-carboxylic acid

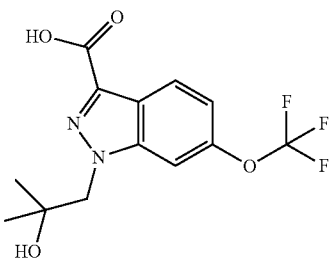 [SMILES: CC(C)(O)Cn1nc(C(=O)O)c2ccc(OC(F)(F)F)cc21]

6-trifluoromethoxy-1-(2-hydroxy-2-methylpropyl)-1H-indazole-3-carboxylic acid was prepared in a similar manner as Intermediate 36, substituting methyl 5-fluoro-1H-indazole-3-carboxylate for 6-trifluoromethoxy-1H-indazole-3-carboxylate. MS (ESI) m/z: 318.8 (M+H)⁺.

INTERMEDIATE 52

Preparation of 6-methoxy-7-(3,3,3-trifluoropropyl)pyrazolo-[1,5-a]pyridine-3-carboxylic acid

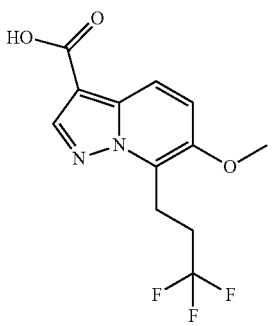

INTERMEDIATE 52A

Preparation of (E)-methyl 6-(benzyloxy)-7-(3,3,3-trifluoroprop-1-en-1-yl)pyrazolo[1,5-a]pyridine-3-carboxylate

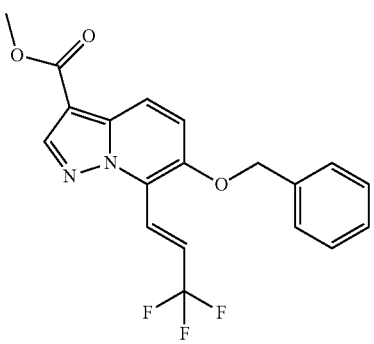 [SMILES: COC(=O)c1cnn2c(/C=C/C(F)(F)F)c(OCc3ccccc3)ccc12]

To a solution of methyl 6-(benzyloxy)-7-bromopyrazolo[1,5-a]pyridine-3-carboxylate 1 (0.500 g, 1.384 mmol) in degassed DMF (10 mL) was added tetrabutylammonium bromide (0.089 g, 0.277 mmol), and TEA (0.386 mL, 2.77 mmol). 3,3,3-trifluoroprop-1-ene (0.266 g, 2.77 mmol) was bubbled into the solution followed by the addition of dichlorobis(tri-o-tolylphosphine)-palladium(II) (0.109 g, 0.138 mmol). The mixture was purged with N₂ for 10 min and then heated at 110° C. overnight. The mixture was filtered through Celite and the filtrate partition between water and EtOAc. The combined organic layer was washed with brine, dried over MgSO₄, filtered, concentrated and purified by normal phase chromatography to give (E)-methyl 6-(benzyloxy)-7-(3,3,3-trifluoroprop-1-en-1-yl)pyrazolo[1,5-a]pyridine-3-carboxylate (0.314 g, 0.834 mmol, 60.3% yield). MS (ESI) m/z: 377.0 (M+H)⁺.

INTERMEDIATE 52B

Preparation of methyl 6-hydroxy-7-(3,3,3-trifluoropropyl)-pyrazolo[1,5-a]pyridine-3-carboxylate

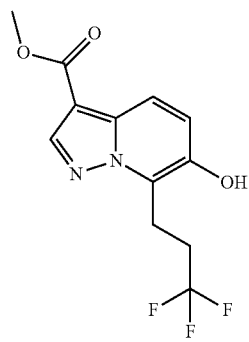 [SMILES: COC(=O)c1cnn2c(CCC(F)(F)F)c(O)ccc12]

Platinum(IV) oxide (0.019 g, 0.082 mmol) followed by 10% palladium on carbon (Degussa type) (0.018 g, 0.165 mmol) were added to a solution of (E)-methyl 6-(benzyloxy)-7-(3,3,3-trifluoroprop-1-en-1-yl)pyrazolo[1,5-a]pyridine-3-carboxylate (0.310 g, 0.824 mmol) in EtOH (20 mL) and subjected to a hydrogen atmosphere (55 psi) overnight. The suspension was filtered through a plug of Celite, and the filtrate concentrated. The residue was carried forward as is to the next reaction without further purification. MS (ESI) m/z: 388.8 (M+H)⁺.

INTERMEDIATE 52

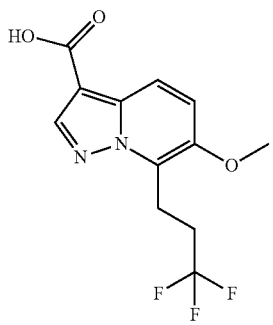 [SMILES: COc1ccc2c(C(=O)O)cnn2c1CCC(F)(F)F]

Iodomethane (0.113 g, 0.798 mmol) was added to a stirring suspension of methyl 6-hydroxy-7-(3,3,3-trifluoropropyl)pyrazolo[1,5-a]pyridine-3-carboxylate (0.115 g, 0.399 mmol) and K₂CO₃ (0.110 g, 0.798 mmol) in acetone (3.99 mL). The vessel was sealed and heated at 50° C. overnight. The reaction mixture was filtered and concentrated under reduced pressure, the residue was dissolved in MeOH (4.0 mL)/THF (4.0 mL), and LiOH (1.596 mL, 1.596 mmol) was added. The reaction mixture was stirred under microwave irradiation at 150° C. for 30 min. The reaction mixture was concentrated, acidified with TFA, and purified by reverse phase chromatography to give the desired product. MS (ESI) m/z: 288.9 (M+H)⁺. ¹H NMR (400 MHz, Methanol-d4) δ 8.40 (s, 1H), 8.12 (d, J=9.7 Hz, 1H), 7.64 (d, J=9.7 Hz, 1H), 4.01 (s, 3H), 3.58-3.51 (m, 2H), 2.73-2.60 (m, 2H).

INTERMEDIATE 53

Preparation of 6-(2-hydroxy-2-methylpropoxy)-7-(1-methyl-1H-pyrazol-4-yl)pyrazolo[1,5-a]pyridine-3-carboxylic acid

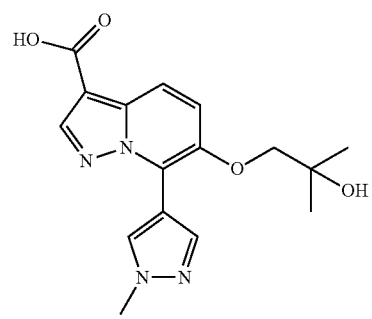 [SMILES: Cn1cc(-c2c(OCC(C)(C)O)ccc3c(C(=O)O)cnn23)cn1]

INTERMEDIATE 53A

Preparation of methyl 6-hydroxy-7-(1-methyl-1H-pyrazol-4-yl)pyrazolo[1,5-a]pyridine-3-carboxylate

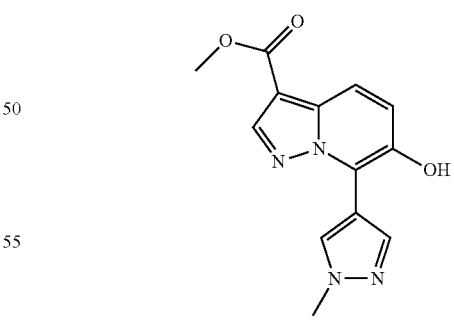

Methyl 6-(benzyloxy)-7-bromopyrazolo[1,5-a]pyridine-3-carboxylate (0.100 g, 0.277 mmol), 1-methyl-4-(4,4,5,5-tetramethyl-1,3,2-dioxaborolan-2-yl)-1H-pyrazole (0.173 g, 0.831 mmol) and Pd-XPhos G3 (0.012 g, 0.014 mmol) were placed in a pressure vial. Then, THF (8.0 mL) and phosphoric acid, potassium salt (0.5 M aq.) (1.107 mL, 0.554 mmol) were added, and the reaction mixture was degassed (3×, vacuum/Ar). The pressure vial was capped, and the reaction mixture was stirred at 120° C. for 30 min. The reaction mixture was diluted with EtOAc (50 mL), washed with brine, dried over sodium sulfate, filtered, concentrated, and purified by normal phase chromatography. This material was dissolved in EtOH (15 mL), treated with 10% Pd/C (degussa type; wet) (0.059 g, 0.055 mmol), and subjected to a hydrogen atmosphere (55 psi). After 3 h. the reaction was filtered through a plug of Celite and concentrated to give a white solid which was carried forward to the next reaction without further purification. MS (ESI) m/z: 272.8 (M+H)$^+$.

INTERMEDIATE 53

To a solution of methyl 6-hydroxy-7-(1-methyl-1H-pyrazol-4-yl)pyrazolo[1,5-a]pyridine-3-carboxylate (0.075 g, 0.275 mmol) in CH$_3$CN (3.40 mL) and H$_2$O (0.227 mL) was added K$_2$CO$_4$ (0.152 g, 1.102 mmol) and 2,2-dimethyloxirane (0.367 mL, 4.13 mmol). The reaction mixture was irradiated at 120° C. for 30 min, concentrated, and purified by normal phase chromatography. The ester was hydrolyzed by dissolving the material in MeOH (4 mL)/THF (4 mL), treatment with LiOH (2.75 mL, 2.75 mmol), and irradiated at 150° C. for 30 minutes. The organics were concentrated and the crude material purified by reverse phase chromatography to give 6-(2-hydroxy-2-methylpropoxy)-7-(1-methyl-1H-pyrazol-4-yl)pyrazolo[1,5-a]pyridine-3-carboxylic acid (0.025 g, 0.076 mmol, 27.5% yield) was isolated a white solid. MS (ESI) m/z: 330.9 (M+H)$^+$. $^1$H NMR (400 MHz, DMSO-d$_6$) δ 8.94 (s, 1H), 8.63 (s, 1H), 8.45 (s, 1H), 8.00 (d, J=9.5 Hz, 1H), 7.77 (d, J=9.7 Hz, 1H), 3.99 (s, 5H), 1.28 (s, 6H).

INTERMEDIATE 54

Preparation of 1-(2-hydroxy-2-methylpropyl)-1H-indazole-3-carboxylic acid

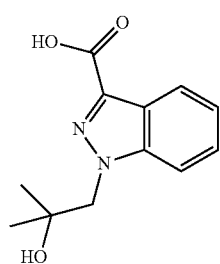 [SMILES: CC(C)(O)Cn1nc(C(=O)O)c2ccccc21]

1-(2-hydroxy-2-methylpropyl)-1H-indazole-3-carboxylic acid (314 mg, 98%) was prepared in a similar manner as Intermediate 36, substituting methyl 5-fluoro-1H-indazole-3-carboxylate with 1H-indazole-3-carboxylate. MS (ESI) m/z: 235.1 (M+H)$^+$.

INTERMEDIATE 55

Preparation of 1-(difluoromethyl)-6-fluoro-1H-indazole-3-carboxylic acid

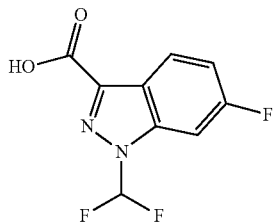 [SMILES: O=C(O)c1nn(C(F)F)c2cc(F)ccc12]

INTERMEDIATE 55A

Preparation of methyl 1-(difluoromethyl)-6-fluoro-1H-indazole-3-carboxylate

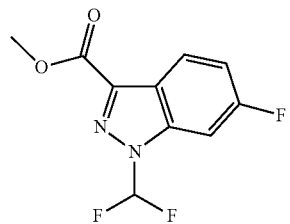 [SMILES: COC(=O)c1nn(C(F)F)c2cc(F)ccc12]

Methyl 6-fluoro-1H-indazole-3-carboxylate (0.2 g, 1.030 mmol) in THF (2 mL) was added dropwise to a suspension of NaH (0.049 g, 1.236 mmol) in THF (6 mL) and maintained at rt for 30 min. Afterwards, chlorodifluoromethane was bubbled into the reaction, the vial sealed, and the mixture heated to 70° C. overnight. Afterwards, the reaction was diluted with water, extracted with EtOAc, washed with brine, dried over sodium sulfate, filtered, and concentrated onto Celite. The crude material was purified by normal phase chromatography to give methyl 1-(difluoromethyl)-6-fluoro-1H-indazole-3-carboxylate (0.121 g, 0.496 mmol, 48.1% yield) as a white solid. MS (ESI) m/z: 244.9 (M+H)$^+$.

INTERMEDIATE 55

Methyl 1-(difluoromethyl)-6-fluoro-1H-indazole-3-carboxylate (0.115 g, 0.471 mmol) was dissolved in MeOH (4.0 mL)/THF (4.0 mL), and LiOH (1 M aq.) (2.355 mL, 2.355 mmol) was added. The reaction mixture was stirred under microwave irradition at 100° C. for 15 min, and then acidified with TFA (caution: gas evolution), purified by reverse phase chromatography to afford 1-(difluoromethyl)-6-fluoro-1H-indazole-3-carboxylic acid (0.0736 g, 0.320 mmol, 67.9% yield) as a white solid. MS (ESI) m/z: 230.8 (M+H)$^+$. $^1$H NMR (400 MHz, DMSO-d$_6$) δ 13.84 (br. s., 1H), 8.48-8.28 (m, 1H), 8.22 (dd, J=9.0, 5.1 Hz, 1H), 7.83 (dd, J=9.2, 2.2 Hz, 1H), 7.41 (td, J=9.1, 2.2 Hz, 1H).

INTERMEDIATE 56

Preparation of methyl 6-(benzyloxy)-1-(difluoromethyl)-1H-indazole-3-carboxylate

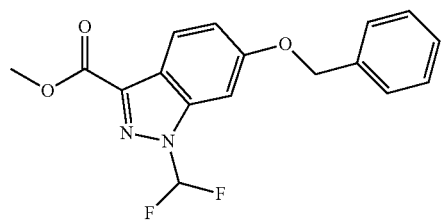 [SMILES: COC(=O)c1nn(C(F)F)c2cc(OCc3ccccc3)ccc12]

Methyl 6-(benzyloxy)-1-(difluoromethyl)-1H-indazole-3-carboxylate (176 mg, 74.8%) was prepared in a similar manner as Intermediate 55A, substituting methyl 6-fluoro-1H-indazole-3-carboxylate with methyl 6-benzyloxy-1H-indazole-3-carboxylate. MS (ESI) m/z: 333.0 (M+H)$^+$. $^1$H NMR (400 MHz, DMSO-d$_6$) δ 8.46-8.15 (m, 1H), 8.05 (d, J=9.0 Hz, 1H), 7.55-7.51 (m, 3H), 7.47-7.41 (m, 2H), 7.41-7.36 (m, 1H), 7.22 (dd, J=9.0, 2.0 Hz, 1H), 5.25 (s, 2H), 3.98 (s, 3H).

INTERMEDIATE 57

Preparation of 6methyl 6-fluoro-1-(3,3,3-trifluoropropyl)-1H-indazole-3-carboxylate

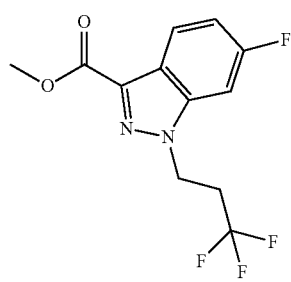 [SMILES: COC(=O)c1nn(CCC(F)(F)F)c2cc(F)ccc12]

Methyl 6-fluoro-1-(3,3,3-trifluoropropyl)-1H-indazole-3-carboxylate (176 mg, 74.8%) was prepared in a similar manner as Intermediate 55A, substituting chlorodifluoromethane with 3-bromo-1,1,1-trifluoropropane. MS (ESI) m/z: 290.9 (M+H)$^+$. $^1$H NMR (500 MHz, Methanol-d4) δ 8.19-8.14 (m 1H), 7.49 (dd, J=9.2, 2.1 Hz, 1H), 7.18 (td, J=9.1, 2.2 Hz, 1H), 4.75 (t, J=6.9 Hz, 2H), 4.04 (s, 3H), 2.94 (qt, J=10.7, 6.9 Hz, 2H).

INTERMEDIATE 58

Preparation of methyl 6-bromo-1-(difluoromethyl)-1H-indazole-3-carboxylate

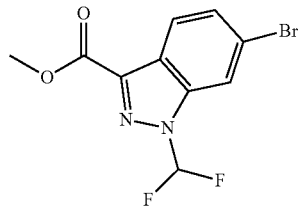 [SMILES: COC(=O)c1nn(C(F)F)c2cc(Br)ccc12]

Methyl 6-bromo-1-(difluoromethyl)-1H-indazole-3-carboxylate (255 mg, 45%) was prepared in a similar manner as Intermediate 55A, substituting methyl 6-fluoro-1H-indazole-3-carboxylate with methyl 6-bromo-1H-indazole-3-carboxylate. MS (ESI) m/z: 304.8 (M+H)$^+$. $^1$H NMR (400 MHz, DMSO-d$_6$) δ 8.53-8.21 (m, 2H), 8.12 (dd, J=8.7, 0.6 Hz, 1H), 7.70 (dd, J=8.6, 1.5 Hz, 1H), 3.99 (s, 3H).

INTERMEDIATE 59

Preparation of 1-(difluoromethyl)-6-(1-methyl-1H-pyrazol-4-yl)-1H-indazole-3-carboxylic acid

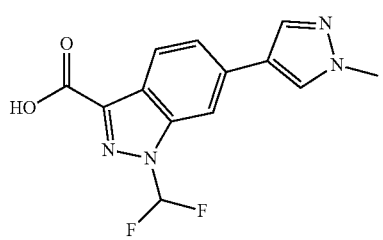 [SMILES: Cn1cc(-c2ccc3c(C(=O)O)nn(C(F)F)c3c2)cn1]

Methyl 6-bromo-1-(difluoromethyl)-1H-indazole-3-carboxylate (0.050 g, 0.164 mmol), 1-methyl-4-(4,4,5,5-tetramethyl-1,3,2-dioxaborolan-2-yl)-1H-pyrazole (0.034 g, 0.164 mmol), and Na$_2$CO$_3$ (0.052 g, 0.492 mmol) in H$_2$O (0.3 mL) were added to dioxane (3 mL) and degassed with a stream of N$_2$. After purging for 5 min, tetrakis(triphenylphosphine)palladium (0) (0.019 g, 0.016 mmol) was added and the mixture irradiated at 120° C. for 30 min. The reaction was concentrated, dissolved in MeOH/THF (4 mL, 1:1) and treated with LiOH (21 mg, 0.492 mmol), and irradiated at 100° C. for 15 min. The reaction mixture was quenched with TFA and purified by reverse phase chromatography to give the desire product (13.2 mg, 27.6%). MS (ESI) m/z: 292.9 (M+H)$^+$.

INTERMEDIATE 60

Preparation of methyl 6-fluoro-1-methyl-1H-indazole-3-carboxylate

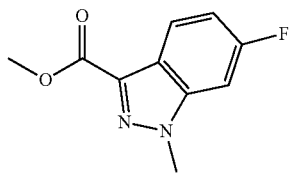

Methyl 6-fluoro-1-(3,3,3-trifluoropropyl)-1H-indazole-3-carboxylate (105.1 mg, 39.2%) was prepared in a similar manner as Intermediate 55A, substituting chlorodifluoromethane with iodomethane. The desired product peak eluted second (more polar) from normal phase chromatography. MS (ESI) m/z: 209.0 (M+H)$^+$. $^1$H NMR (500 MHz, CDCl$_3$) δ 8.19 (dd, J=9.5, 5.1 Hz, 1H), 7.14-7.08 (m, 2H), 4.13 (s, 3H), 4.04 (s, 3H).

INTERMEDIATE 61

Preparation of methyl 6-fluoro-1-($^2$H$_3$)methyl-1H-indazole-3-carboxylate

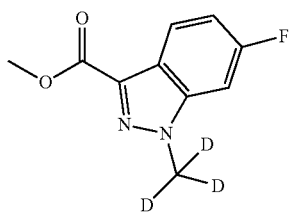 [SMILES: [2H]C([2H])([2H])n1nc(C(=O)OC)c2ccc(F)cc21]

Methyl 6-fluoro-1-(3,3,3-trifluoropropyl)-1H-indazole-3-carboxylate (106 mg, 39%) was prepared in a similar manner as Intermediate 55A, substituting chlorodifluoromethane with deuterated iodomethane. The desired product peak eluted 15 second (more polar) from normal phase chromatography. MS (ESI) m/z: 212.0 (M+H)$^+$. $^1$H NMR (500 MHz, CDCl$_3$) δ 8.00 (ddd, J=9.1, 5.3, 0.7 Hz, 1H), 7.37 (ddd, J=9.4, 2.3, 0.7 Hz, 1H), 7.09 (td, J=9.1, 2.3 Hz, 1H), 4.05 (s, 3H).

INTERMEDIATE 62

Preparation of methyl 1-(2,2-difluoroethyl)-6-fluoro-1H-indazole-3-carboxylate

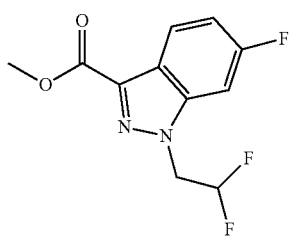 [SMILES: COC(=O)c1nn(CC(F)F)c2cc(F)ccc12]

Methyl 6-fluoro-1-(3,3,3-trifluoropropyl)-1H-indazole-3-carboxylate (105.1 mg, 39.2%) was prepared in a similar manner as Intermediate 55A, substituting chlorodifluoromethane with 1,1-difluoro-2-iodoethane. The desired product peak eluted second (more polar) from normal phase chromatography. MS (ESI) m/z: 258.9 (M+H)$^+$. $^1$H NMR (500 MHz, CDCl$_3$) δ 8.24-8.19 (m, 1H), 7.20-7.11 (m, 2H), 6.33-6.07 (m, 1H), 4.76 (td, J=13.3, 4.1 Hz, 2H), 4.06 (s, 3H).

INTERMEDIATE 63

Preparation of methyl 6-fluoro-2-($^2$H$_3$)methyl-2H-indazole-3-carboxylate

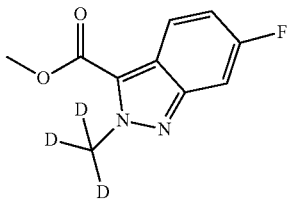 [SMILES: [2H]C([2H])([2H])n1nc2cc(F)ccc2c1C(=O)OC]

Methyl 6-fluoro-1-(3,3,3-trifluoropropyl)-1H-indazole-3-carboxylate (106 mg, 39%) was prepared in a similar manner as Intermediate 55A, substituting chlorodifluoromethane with deuterated iodomethane. The desired product peak eluted first (less polar) from normal phase chromatography. MS (ESI) m/z: 212.0 (M+H)$^+$. $^1$H NMR (500 MHz, CDCl$_3$) d 8.00 (ddd, J=9.1, 5.3, 0.7 Hz, 1H), 7.37 (ddd, J=9.4, 2.3, 0.7 Hz, 1H), 7.09 (td, J=9.1, 2.3 Hz, 1H), 4.05 (s, 3H).

INTERMEDIATE 64

Preparation of 1-(Difluoromethyl)-6-(3-methoxyphenyl)-1H-indazole-3-carboxylic acid

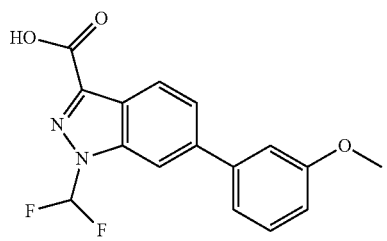 [SMILES: COc1cccc(-c2ccc3c(C(=O)O)nn(C(F)F)c3c2)c1]

Methyl 6-bromo-1-(difluoromethyl)-1H-indazole-3-carboxylate (0.050 g, 0.164 mmol), (3-methoxyphenyl)boronic acid (0.025 g, 0.164 mmol), and Na$_2$CO$_3$ (0.052 g, 0.492 mmol) in H$_2$O (0.3 mL) were added to dioxane (3 mL) and degassed with a stream of N$_2$. After purging for 5 min, tetrakis(triphenylphosphine)palladium (0) (0.019 g, 0.016 mmol) was added and the mixture irradiated at 120° C. for 30 min. The reaction was concentrated, dissolved in MeOH/THF (4 mL, 1:1) and treated with LiOH (21 mg, 0.492 mmol), and irradiated at 100° C. for 15 min. The reaction mixture was quenched with TFA and purified by reverse phase chromatography to give the desire product (13.6 mg, 26.1%) as a white solid. MS (ESI) m/z: 319.0 (M+H)$^+$.

INTERMEDIATE 65

Preparation of 7-cyclopropyl-6-(3,3,3-trifluoropropoxy)-pyrazolo[1,5-a]pyridine-3-carboxylic acid

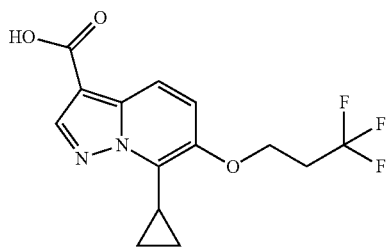 [SMILES: O=C(O)c1cnn2c(C3CC3)c(OCCC(F)(F)F)ccc12]

INTERMEDIATE 65A

Preparation of methyl 7-cyclopropyl-6-(3,3,3-trifluoropropoxy)pyrazolo[1,5-a]pyridine-3-carboxylate

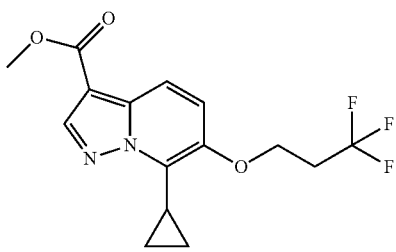 [SMILES: COC(=O)c1cnn2c(C3CC3)c(OCCC(F)(F)F)ccc12]

Methyl 7-cyclopropyl-6-hydroxypyrazolo[1,5-a]pyridine-3-carboxylate (0.05 g, 0.215 mmol), 3,3,3-trifluoropropan-1-ol (0.040 mL, 0.431 mmol), and 1,1'-(azodicarbonyl) dipiperidine (0.163 g, 0.646 mmol) were placed in a pressure vial. Then, anhydrous toluene (2.153 mL) and tri-N-butylphosphine (0.161 mL, 0.646 mmol) were added, and the reaction mixture was irradiated at 140° C. for 20 min. The reaction mixture was quenched with MeOH (1 mL), diluted with EtOAc (50 mL), washed with water, brine, dried over sodium sulfate, concentrated, and purified by normal phase chromatography to give methyl 7-cyclopropyl-6-(3,3,3-trifluoropropoxy)pyrazolo[1,5-a]pyridine-3-carboxylate (0.032 g, 45.3% yield) as a white solid. MS (ESI) m/z: 329.0 (M+H)$^+$.

INTERMEDIATE 65

Methyl 7-cyclopropyl-6-(3,3,3-trifluoropropoxy)pyrazolo[1,5-a]pyridine-3-carboxylate (0.032 g, 0.097 mmol) was dissolved in MeOH (4.0 mL)/THF (4.0 mL), 1.0M LiOH (0.292 mL, 0.292 mmol) added, the reaction mixture irradiated at 100° C. for 15 min. The reaction mixture was diluted water, acidified with 1.0N HCl solution, extracted with EtOAc, washed with brine, dried over sodium sulfate, filtered, and concentrated to give 7-cyclopropyl-6-(3,3,3-trifluoropropoxy)pyrazolo[1,5-a]pyridine-3-carboxylic acid (0.030 g, 0.095 mmol, 98% yield). MS (ESI) m/z: 315.0 (M+H)$^+$.

INTERMEDIATE 66

Preparation of methyl 1-(difluoromethyl)-6-(2-hydroxy-2-methylpropoxy)-1H-indazole-3-carboxylate

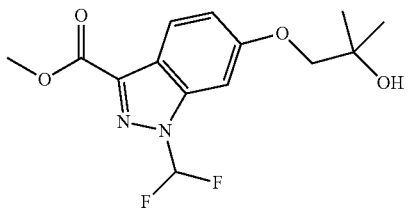 [SMILES: COC(=O)c1nn(C(F)F)c2cc(OCC(C)(C)O)ccc12]

INTERMEDIATE 66A

Preparation of methyl 1-(difluoromethyl)-6-hydroxy-1H-indazole-3-carboxylate

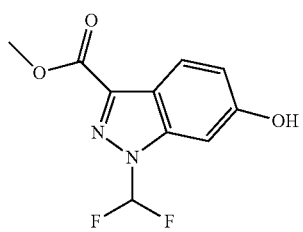 [SMILES: COC(=O)c1nn(C(F)F)c2cc(O)ccc12]

Pd—C (0.056 g, 0.053 mmol) was added to Intermediate 56 (0.176 g, 0.530 mmol) in MeOH (15 mL)/EtOAc (5 mL) and subjected to a hydrogen atmosphere (50 psi) overnight. The suspension was filtered through a plug of Celite and filtrate concentrated. This material was carried forward to the next reaction with further purification. MS (ESI) m/z: 242.9 (M+H)$^+$.

INTERMEDIATE 66

A solution of Intermediate 66A (0.128 g, 0.529 mmol) in CH$_3$CN (3 mL)/water (0.2 mL) was treated with K$_2$CO$_3$ (0.292 g, 2.114 mmol) and 2,2-dimethyloxirane (1.408 mL, 15.86 mmol) and irradiated at 120° C. for 35 min. The reaction mixture was partitioned between EtOAc and water. The organic layer was discarded. The remaining aqueous layer was acidified with 1.0N HCl solution and extracted with EtOAc. The organic layer was washed with brine, dried over sodium sulfate, filtered, and concentrated to give 1-(difluoromethyl)-6-(2-hydroxy-2-methylpropoxy)-1H-indazole-3-carboxylic acid (0.063 g, 0.210 mmol, 39.7% yield). MS (ESI) m/z: 300.9 (M+H)$^+$.

INTERMEDIATE 67

Preparation of 1-(difluoromethyl-6-[1-($^2H_3$)methyl-1H-pyrazol-3-yl]-1H-indazole-3-carboxylic acid

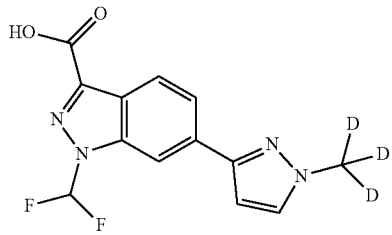 [SMILES: [2H]C([2H])([2H])n1ccc(-c2ccc3c(C(=O)O)nn(C(F)F)c3c2)n1]

1-(difluoromethyl)-6-[1-($^2H_3$)methyl-1H-pyrazol-3-yl]-1H-indazole-3-carboxylic acid carboxylate (15 mg, 31%) was prepared in a similar manner as Intermediate 59, substituting 1-methyl-4-(4,4,5,5-tetramethyl-1,3,2-dioxaborolan-2-yl)-1H-pyrazole with 1-($^2H_3$)methyl-4-(tetramethyl-1,3,2-dioxaborolan-2-yl)-1H-pyrazole. MS (ESI) m/z: 296.0 (M+H)$^+$.

INTERMEDIATE 68

Preparation of 1-(difluoromethyl)-6-(1-(difluoromethyl)-1H-pyrazol-3-yl)-1H-indazole-3-carboxylic acid

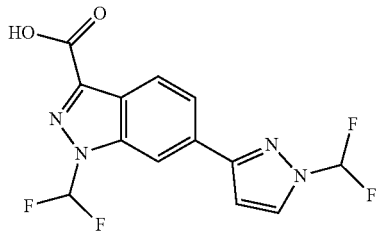 [SMILES: O=C(O)c1nn(C(F)F)c2cc(-c3ccn(C(F)F)n3)ccc12]

1-(difluoromethyl)-6-(1-(difluoromethyl)-H-pyrazol-3-yl)-H-indazole-3-carboxylic acid (17 mg, 31.6%) was prepared in a similar manner as Intermediate 59, substituting 1-methyl-4-(4,4,5,5-tetramethyl-1,3,2-dioxaborolan-2-yl)-1H-pyrazole with 1-(difluoromethyl)-4-(4,4,5,5-tetramethyl-1,3,2-dioxaborolan-2-yl)-1H-pyrazole. MS (ESI) m/z: 328.9 (M+H)$^+$. $^1$H NMR (500 MHz, Methanol-d4) δ 8.64-8.63 (m, 1H), 8.29-8.23 (m, 2H), 8.11-7.76 (m, 3H), 7.68-7.42 (m, 1H).

INTERMEDIATE 69

Preparation of 3-(tert-butyl)-1-(2,2-difluoroethyl-)-1H-pyrazole-5-carboxylic acid

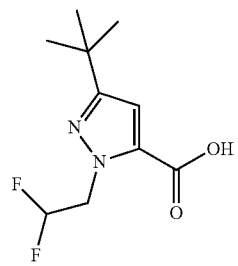 [SMILES: CC(C)(C)c1cc(C(=O)O)n(CC(F)F)n1]

INTERMEDIATE 69A

Preparation of ethyl 3-(tert-butyl)-1-(2,2-difluoroethyl)-1H-pyrazole-5-carboxylate

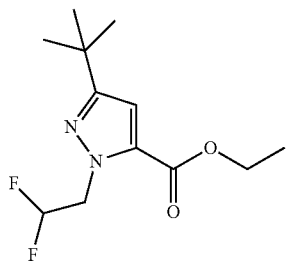 [SMILES: CCOC(=O)c1cc(C(C)(C)C)nn1CC(F)F]

Ethyl 3-(tert-butyl)-1H-pyrazole-5-carboxylate (0.500 g, 2.55 mmol) was added in small portions to a solution of potassium tert-butoxide (0.286 g, 2.55 mmol) in DMSO (5 mL) under a nitrogen atmosphere. After 15 min, 2,2-difluoroethyl trifluoromethanesulfonate (0.546 g, 2.55 mmol) was added dropwise and the mixture stirred overnight. The reaction was quenched with saturated NH$_4$Cl solution, extracted with EtOAc (2×50 mL), the organics combined and washed with brine, dried over sodium sulfate, filtered, concentrated, and normal phase chromatography to give ethyl 3-(tert-butyl)-1-(2,2-difluoroethyl)-1H-pyrazole-5-carboxylate (0.5052 g, 1.941 mmol, 76% yield) as a clear, colorless oil. MS (ESI) m/z: 261.0 (M+H)$^+$. $^1$H NMR (500 MHz, CDCl$_3$) δ 6.74 (s, 1H), 6.25-6.01 (m, 1H), 4.94-4.88 (m, 2H), 4.35 (q, J=7.2 Hz, 2H), 1.41-1.37 (m, 3H), 1.31 (s, 9H).

INTERMEDIATE 69

Ethyl 3-(tert-butyl)-1-(2,2-difluoroethyl)-1H-pyrazole-5-carboxylate (0.300 g, 1.15 mmol) was dissolved in MeOH (6.0 mL)/THF (6.0 mL), 1.0M LiOH (3.46 mL, 3.46 mmol) was added, and the reaction mixture irradiated at 100° C. for 15 min. The reaction mixture was diluted with water, acidified with 1.0N HCl solution, extracted with EtOAc, washed with brine, dried over sodium sulfate, filtered, and concentrated to give 3-(tert-butyl)-1-(2,2-difluoroethyl)-1H-pyrazole-5-carboxylic acid oil that slowly solidified over time. MS (ESI) m % z: 233.0 (M+H)$^+$. $^1$H NMR (500 MHz, CDCl₃) d 9.05 (br. s, 1H), 6.89 (s, 1H), 6.26-6.01 (m, 1H), 4.95 (td, J=13.0, 4.3 Hz, 2H), 1.33 (s, 9H).

INTERMEDIATE 70

Preparation of 3-(tert-butyl)-1-(3,3,3-trifluoropropyl)-1H-pyrazole-5-carboxylic acid

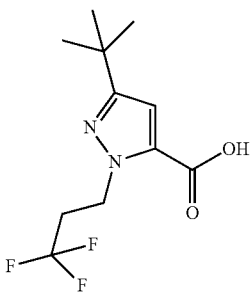 [SMILES: CC(C)(C)c1cc(C(=O)O)n(CCC(F)(F)F)n1]

3-(tert-butyl)-1-(3,3,3-trifluoropropyl)-1H-pyrazole-5-carboxylic acid (84 mg, 93%) was prepared in a similar manner as Intermediate 69, substituting 2,2-difluoroethyl trifluoromethanesulfonate with 3-bromo-1,1,1-trifluoropropane. MS (ESI) m/z: 293.0 (M+H)⁺.

INTERMEDIATE 71

Preparation of 6-(3,3,3-trifluoropropoxy)-7-(3,3,3-trifluoropropyl)pyrazolo[1,5-a]pyridine-3-carboxylic acid

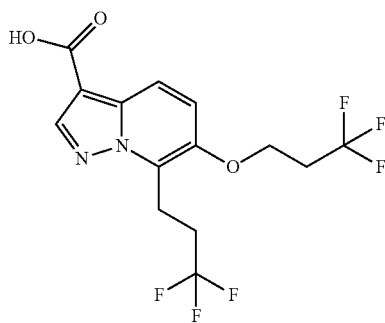 [SMILES: O=C(O)c1cnn2c(CCC(F)(F)F)c(OCCC(F)(F)F)ccc12]

INTERMEDIATE 71A

Preparation of (E)-methyl 6-(benzyloxy)-7-(3,3,3-trifluoroprop-1-en-1-yl)pyrazolo[1,5-a]pyridine-3-carboxylate

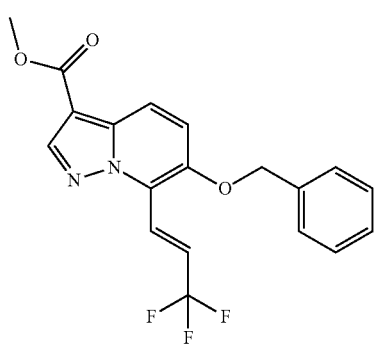 [SMILES: COC(=O)c1cnn2c(/C=C/C(F)(F)F)c(OCc3ccccc3)ccc12]

To a solution of methyl 6-(benzyloxy)-7-bromopyrazolo[1,5-a]pyridine-3-carboxylate (0.500 g, 1.384 mmol) in degassed DMF (10 mL) was added tetrabutylammonium bromide (0.089 g, 0.277 mmol), and TEA (0.386 mL, 2.77 mmol). 3,3,3-trifluoroprop-1-ene (0.266 g, 2.77 mmol) was bubbled into the solution followed by the addition of dichlorobis(tri-o-tolylphosphine)-palladium(II) (0.109 g, 0.138 mmol). The mixture was purged with N2 for 10 min. Then it was sealed and heated at 110° C. for two days. The mixture was filtered through Celite and the filtrate partitioned between water and EtOAc. Organic layer, washed with brine, dried over MgSO₄, filtered, concentrated, and purified by normal phase chromatography to give (E)-methyl 6-(benzyloxy)-7-(3,3,3-trifluoroprop-1-en-1-yl)pyrazolo[1,5-a]pyridine-3-carboxylate (0.266 g, 51.1% yield) as a light yellow solid. MS (ESI) m/z: 377.0 (M+H)⁺.

INTERMEDIATE 71B

Preparation of methyl 6-hydroxy-7-(3,3,3-trifluoropropyl)pyrazolo[1,5-a]pyridine-3-carboxylate

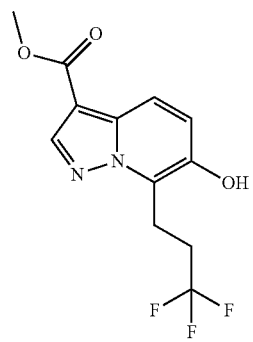 [SMILES: COC(=O)c1cnn2c(CCC(F)(F)F)c(O)ccc12]

Pd—C (10%, degussa type, wet) (0.150 g, 0.141 mmol) followed by PtO₂ (0.016 g, 0.071 mmol) were added to a solution of (E)-methyl 6-(benzyloxy)-7-(3,3,3-trifluoroprop-1-en-1-yl)pyrazolo[1,5-a]pyridine-3-carboxylate (0.266 g, 0.707 mmol) in EtOH (30 mL)/EtOAc (30 mL) and subjected to a H₂ atmosphere (55 psi). After 18 hours, the suspension was filtered through a plug of Celite and the filtrate concentrated to give the desired intermediate. MS (ESI) m/z: 289.0 (M+H)⁺.

INTERMEDIATE 71

Methyl 6-hydroxy-7-(3,3,3-trifluoropropyl)pyrazolo[1,5-a]pyridine-3-carboxylate (0.100 g, 0.347 mmol), 3,3,3-trifluoropropan-1-ol (0.059 mL, 0.694 mmol), and 1,1'-(azodicarbonyl)dipiperidine (0.263 g, 1.041 mmol) were placed in a microwave vial. Then, anhydrous toluene (8 mL) and tri-N-butylphosphine (0.260 mL, 1.041 mmol) were added, and the reaction mixture irradiated at 140° C. for 20 min. The reaction mixture was quenched with MeOH (5 mL), concentrated, and purified by normal phase chromatography to give the desired product as a white solid. MS (ESI) m/z: 384.0 (M+H)⁺.

INTERMEDIATE 72

Preparation of (E)-6-(3,3,3-trifluoroprop-1-en-1-yl)pyrazolo[1,5-a]pyridine-3-carboxylic acid

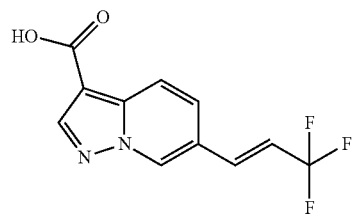 [SMILES: O=C(O)c1cnn2cc(/C=C/C(F)(F)F)ccc12]

INTERMEDIATE 72A

Preparation of (E)-methyl 6-(3,3,3-trifluoroprop-1-en-1-yl)pyrazolo[1,5-a]pyridine-3-carboxylate

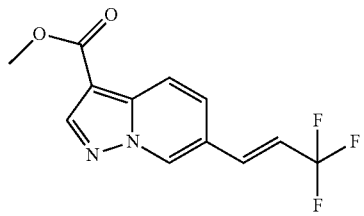 [SMILES: COC(=O)c1cnn2cc(/C=C/C(F)(F)F)ccc12]

To a solution of methyl 6-bromopyrazolo[1,5-a]pyridine-3-carboxylate in degassed DMF (10 mL) was added tetrabutylammonium bromide (0.063 g, 0.196 mmol), and TEA (0.273 mL, 1.960 mmol). 3,3,3-trifluoroprop-1-ene (0.188 g, 1.960 mmol) was bubbled into the solution followed by the addition of dichlorobis(tri-o-tolylphosphine)-palladium(II) (0.077 g, 0.098 mmol). The mixture was purged with $N_2$ for 10 min, sealed, and heated at 110° C. overnight. The mixture was filtered through Celite, partitioned between water and EtOAc, the organic washed with brine, dried over $MgSO_4$, filtered, concentrated, and purified by normal phase chromatography to give (E)-methyl 6-(3,3,3-trifluoroprop-1-en-1-yl)pyrazolo[1,5-a]pyridine-3-carboxylate (0.181 g, 68% yield). MS (ESI) m/z: 270.9 (M+H)+.

INTERMEDIATE 72

(E)-methyl 6-(3,3,3-trifluoroprop-1-en-1-yl)pyrazolo[1,5-a]pyridine-3-carboxylate (0.050 g, 0.185 mmol) was dissolved in MeOH (2.5 mL)/THF (2.5 mL), and 1.0M LiOH solution (0.555 mL, 0.555 mmol) was added. The reaction mixture was stirred under microwave irradition at 100° C. for 15 min, diluted with water, acidified with 1.0N HCl solution, extracted with EtOAc, washed with brine, dried over sodium sulfate, filtered, and concentrated to give (E)-6-(3,3,3-trifluoroprop-1-en-1-yl)pyrazolo[1,5-a]pyridine-3-carboxylic acid (0.045 g, 0.176 mmol, 95% yield) as a white solid. MS (ESI) m/z: 257.9 (M+H)+.

INTERMEDIATE 73

Preparation of 6-(3,3,3-trifluoropropoxy)-1-(3,3,3-trifluoropropyl)-1H-indazole-3-carboxylic acid

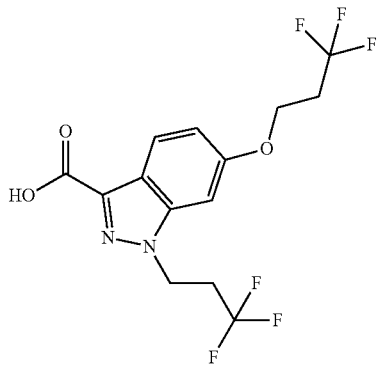 [SMILES: O=C(O)c1nn(CCC(F)(F)F)c2cc(OCCC(F)(F)F)ccc12]

INTERMEDIATE 73A

Preparation of methyl 6-(benzyloxy)-1-(3,3,3-trifluoropropyl)-1H-indazole-3-carboxylate

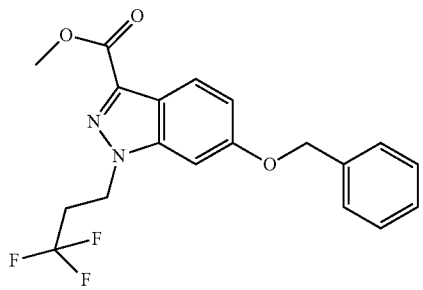 [SMILES: COC(=O)c1nn(CCC(F)(F)F)c2cc(OCc3ccccc3)ccc12]

Methyl 6-(benzyloxy)-1H-indazole-3-carboxylate (0.500 g, 1.771 mmol) in THF (5 mL) was added dropwise to a suspension of NaH (0.085 g, 2.125 mmol) in THF (10 mL) and maintained at rt for 30 min. 3-bromo-1,1,1-trifluoropropane (0.313 g, 1.771 mmol) was added and the reaction mixture stirred at rt for 30 min before heating to 70° C. overnight. The reaction was quenched with MeOH, filtered, filtrate concentrated, and purified by normal phase chromatography (97 mg, 14.5%). MS (ESI) m/z: 379.0 (M+H)+.

INTERMEDIATE 73B

Preparation of methyl 6-hydroxy-1-(3,3,3-trifluoropropyl)-1H-indazole-3-carboxylate

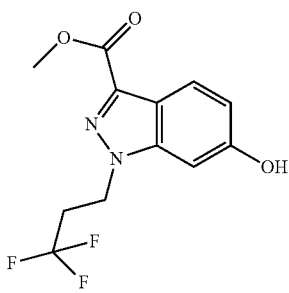 [SMILES: COC(=O)c1nn(CCC(F)(F)F)c2cc(O)ccc12]

Pd—C (10%, degussa type, wet) (0.055 g, 0.051 mmol) was added to a solution of methyl 6-(benzyloxy)-1-(3,3,3-trifluoropropyl)-1H-indazole-3-carboxylate (0.097 g, 0.256 mmol) in MeOH (20 mL) and subjected to a H2 atmosphere (55 psi). After 2 h, the suspension was filtered through a plug of Celite and filtrate concentrated to afford the desired product (47 mg, 63.6%). MS (ESI) m/z: 289.0 (M+H)$^+$.

INTERMEDIATE 73C

Preparation of methyl 6-(3,3,3-trifluoropropoxy)-1-(3,3,3-trifluoropropyl)-1H-indazole-3-carboxylate

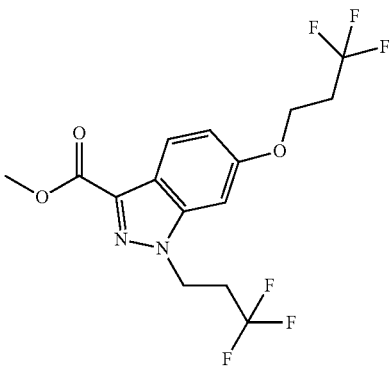 [SMILES: COC(=O)c1nn(CCC(F)(F)F)c2cc(OCCC(F)(F)F)ccc12]

Methyl 6-hydroxy-1-(3,3,3-trifluoropropyl)-1H-indazole-3-carboxylate (0.047 g, 0.163 mmol), 3,3,3-trifluoropropan-1-ol (0.028 mL, 0.326 mmol), and 1,1'-(azodicarbonyl)dipiperidine (0.123 g, 0.489 mmol) were placed in a pressure vial. Then, anhydrous toluene (4 mL) and tri-N-butylphosphine (0.122 mL, 0.489 mmol) were added, and the reaction mixture was irradiated at 140° C. for 20 min. The reaction mixture was quenched with MeOH (5 mL), concentrated, and purified by normal phase chromatography to give methyl 6-(3,3,3-trifluoropropoxy)-1-(3,3,3-trifluoropropyl)-1H-indazole-3-carboxylate (0.035 g, 0.091 mmol, 55.9% yield) as a white solid. MS (ESI) m/z: 385.0 (M+H)$^+$.

INTERMEDIATE 73

Methyl 6-(3,3,3-trifluoropropoxy)-1-(3,3,3-trifluoropropyl)-1H-indazole-3-carboxylate (0.035 g, 0.091 mmol) was dissolved in MeOH (2.0 mL)/THF (2.0 mL), treated with 1.0M LiOH (0.273 mL, 0.273 mmol), and irradiated at 100° C. for 15 min. The reaction mixture was diluted with water, acidified with 1.0N HCl solution, extracted with EtOAc, washed with brine, dried over sodium sulfate, filtered, and concentrated to give 6-(3,3,3-trifluoropropoxy)-1-(3,3,3-trifluoropropyl)-1H-indazole-3-carboxylic acid (0.0328 g, 0.089 mmol, 97% yield) as a white solid. MS (ESI) m/z: 371.0 (M+H)$^+$.

INTERMEDIATE 74

Preparation of 6-(3,3,3-trifluoropropyl)pyrazolo[1,5-a]pyridine-3-carboxylic acid

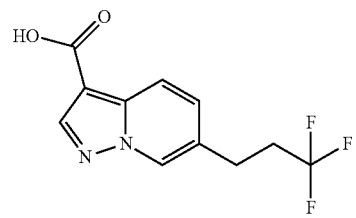 [SMILES: O=C(O)c1cnn2cc(CCC(F)(F)F)ccc12]

Platinum(IV) oxide (0.022 g, 0.096 mmol) was added to a suspension of Intermediate LS37 (0.130 g, 0.481 mmol) in EtOAc (10 mL) and subjected to a hydrogen atmosphere (55 psi). After 4 hours, the suspension was filtered through a plug of Celite and the filtrate concentrated. The residue was dissolved in THF/MeOH; 1:1, 8 mL), treated with 1.0M LiOH (1.443 mL, 1.443 mmol) in water and irradiated at 90° C. in a microwave for 15 minutes. The solution was concentrated and the resulting residue suspended in water and the pH acidified with 1.0N HCl solution, extracted with EtOAc, washed with brine, dried over sodium sulfate, filtered, and concentrated to give the desired product (103.4 mg, 83%). MS (ESI) m/z: 259.0 (M+H)$^+$.

INTERMEDIATE 75

Preparation of 6-(2-(1H-imidazol-1-yl)ethoxy)pyrazolo[1,5-a]pyridine-3-carboxylic acid

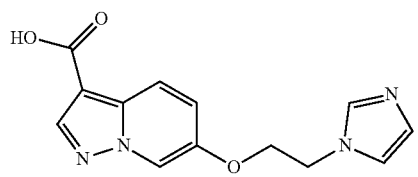 [SMILES: O=C(O)c1cnn2cc(OCCn3ccnc3)ccc12]

6-(2-(1H-imidazol-1-yl)ethoxy)pyrazolo[1,5-a]pyridine-3-carboxylic acid was prepared in a similar manner as Intermediate 39, substituting 2-(dimethylamino)ethanol with 1-(2-hydroxyethyl)imidazole. MS (ESI) m/z: 273.0 (M+H)$^+$.

INTERMEDIATE 76

Preparation of 6-(2-(2-methoxyethoxy)ethoxy)pyrazolo[1,5-a]pyridine-3-carboxylic acid

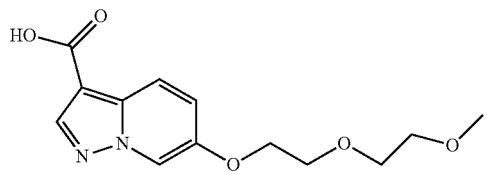 [SMILES: COCCOCCOc1ccc2c(C(=O)O)cnn2c1]

6-(2-(2-methoxyethoxy)ethoxy)pyrazolo[1,5-a]pyridine-3-carboxylic acid (92 mg, 77%) was prepared in a similar manner as Intermediate 39, substituting 2-(dimethylamino)ethanol with 2-(2-methoxyethoxy)ethanol. MS (ESI) m/z: 281.0 (M+H)$^+$.

INTERMEDIATE 77

Preparation of 6-(4,4,4-trifluorobutoxy)pyrazolo[1,5-a]pyridine-3-carboxylic acid

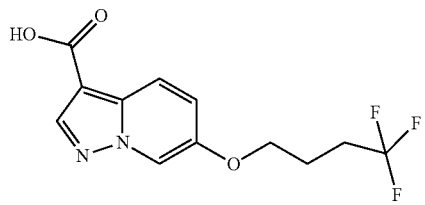 [SMILES: O=C(O)c1cnn2cc(OCCCC(F)(F)F)ccc12]

6-(4,4,4-trifluorobutoxy)pyrazolo[1,5-a]pyridine-3-carboxylic acid (117 mg, 98%) was prepared in a similar manner as Intermediate 39, substituting 2-(dimethylamino)ethanol with 4,4,4-trifluorobutan-1-ol. MS (ESI) m/z: 289.0 (M+H)$^+$.

INTERMEDIATE 78

Preparation of 6-(3-methoxy-3-methylbutoxy)pyrazolo[1,5-a]pyridine-3-carboxylic acid

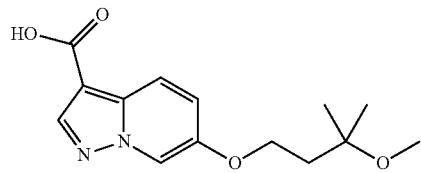 [SMILES: COC(C)(C)CCOc1ccc2c(C(=O)O)cnn2c1]

6-(3-methoxy-3-methylbutoxy)pyrazolo[1,5-a]pyridine-3-carboxylic acid (110 mg, 96%) was prepared in a similar manner as Intermediate 39, substituting 2-(dimethylamino)ethanol with 3-methoxy-3-methylbutan-1-ol. MS (ESI) m/z: 279.0 (M+H)$^+$.

INTERMEDIATE 79

Preparation of 6-(3-(2-oxopyrrolidin-1-yl)propoxy)pyrazolo-[1,5-a]pyridine-3-carboxylic acid

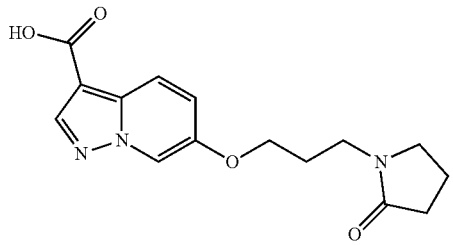 [SMILES: O=C(O)c1cnn2cc(OCCCN3CCCC3=O)ccc12]

6-(3-(2-oxopyrrolidin-1-yl)propoxy)pyrazolo[1,5-a]pyridine-3-carboxylic acid (43.5 mg, 32.5%) was prepared in a similar manner as Intermediate 39, substituting 2-(dimethylamino)ethanol with 1-(3-hydroxypropyl)pyrrolidin-2-one. MS (ESI) m/z: 304.1 (M+H)$^+$

INTERMEDIATE 80

Preparation of 6-(2-(trifluoromethoxy)ethoxy)pyrazolo[1,5-a]pyridine-3-carboxylic acid

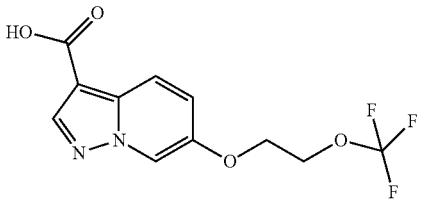 [SMILES: O=C(O)c1cnn2cc(OCCOC(F)(F)F)ccc12]

6-(2-(trifluoromethoxy)ethoxy)pyrazolo[1,5-a]pyridine-3-carboxylic acid (105 mg, 69.5%) was prepared in a similar manner as Intermediate 39, substituting 2-(dimethylamino)ethanol with 2-(trifluoromethoxy)ethanol. MS (ESI) m/z: 290.9 (M+H)$^+$. $^1$H NMR: (400 MHz, DMSO-d$_6$) δ 12.38 (br s, 1H), 8.65 (d, J=1.5 Hz, 1H), 8.31 (s, 1H), 7.98 (d, J=9.7 Hz, 1H), 7.39 (dd, J=9.5, 2.2 Hz, 1H), 4.46-4.44 (m, 2H), 4.38-4.35 (m, 2H).

INTERMEDIATE 81

Preparation of (S)-6-(2-(2-oxooxazolidin-4-yl)ethoxy)pyrazolo[1,5-a]pyridine-3-carboxylic acid

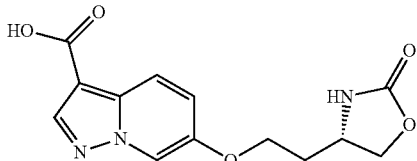

(S)-6-(2-(2-oxooxazolidin-4-yl)ethoxy)pyrazolo[1,5-a]pyridine-3-carboxylic acid (20 mg, 26.4%) was prepared in a similar manner as Intermediate 39, substituting 2-(dimethylamino)ethanol with (S)-4-(2-hydroxyethyl)oxazolidin-2-one. MS (ESI) m/z: 292.0 (M+H)$^+$.

INTERMEDIATE 82

Preparation of 6-(2-hydroxy-2-methylpropoxy)-1-(2-hydroxy-2-methylpropyl)-1H-indazole-3-carboxylic acid

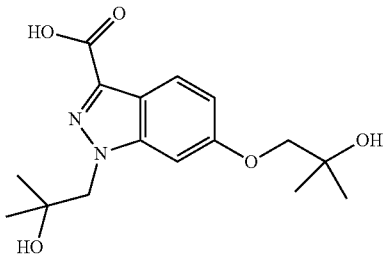 [SMILES: CC(C)(O)COc1ccc2c(C(=O)O)nn(CC(C)(C)O)c2c1]

6-(2-hydroxy-2-methylpropoxy)-1-(2-hydroxy-2-methylpropyl)-1H-indazole-3-carboxylic acid was prepared in a similar manner as Intermediate 36, substituting methyl 5-fluoro-1H-indazole-3-carboxylate with methyl 6-(benzyloxy)-1H-indazole-3-carboxylate. MS (ESI) m/z: 323.0 (M+H)$^+$.

INTERMEDIATE 83

Preparation of (6-(2-(4-methylthiazol-5-yl)ethoxy)pyrazolo[1,5-a]pyridine-3-carboxylic acid

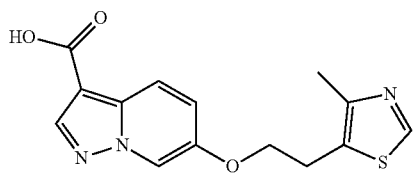 [SMILES: Cc1ncsc1CCOc1ccc2c(C(=O)O)cnn2c1]

6-(2-(4-methylthiazol-5-yl)ethoxy)pyrazolo[1,5-a]pyridine-3-carboxylic acid (10 mg, 12.7%) was prepared in a similar manner as Intermediate 39, substituting 2-(dimethylamino)ethanol with (S)-4-(2-hydroxyethyl)oxazolidin-2-one. MS (ESI) m/z: 304.0 (M+H)$^+$.

INTERMEDIATE 84

Preparation of Benzyl (6-(2-cyano-5-(3-oxopropyl)phenoxy)spiro[3.3]heptan-2-yl)carbamate

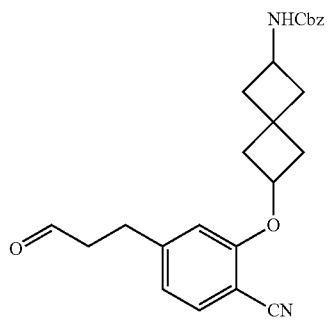 [SMILES: N#Cc1ccc(CCC=O)cc1OC1CC2(CC(NC(=O)OCc3ccccc3)C2)C1]

Intermediate 84A. Preparation of Benzyl (6-(5-bromo-2-cyanophenoxy)spiro[3.3]heptan-2-yl)carbamate.

Benzyl (6-hydroxyspiro[3.3]heptan-2-yl)carbamate Intermediate 1 (500 mg, 1.913 mmol) was dissolved to anhydrous THF (12.0 mL), and the reaction mixture was cooled 0° C. potassium tert-butoxide (225 mg, 2.009 mmol) was added in one portion, and the reaction mixture was stirred at 0° C. for 30 min. Thereafter, 4-bromo-2-fluorobenzonitrile (957 mg, 4.78 mmol) was added, cooling bath was removed, and the reaction mixture was stirred at rt for 1 h. The reaction mixture was quenched with water (1.0 mL), and concentrated. The crude product was purified by normal phase chromatography (0-75% EtOAc/hexanes gradient; eluted at ~45% EtOAc). Fractions were combined and concentrated under reduced pressure to give Intermediate 84A (614 mg, 72% yield) as a white solid. MS (ESI) m/z: 441.0 (M+H)$^+$. $^1$H-NMR (500 MHz, DMSO-$d_6$) δ ppm 7.67 (d, J=8.0 Hz, 1H), 7.52 (br d, J=7.7 Hz, 1H), 7.40-7.27 (m, 7H), 4.99 (s, 2H), 4.84 (quin, J=6.9 Hz, 1H), 3.90 (sxt, J=8.0 Hz, 1H), 2.67 (dt, J=11.1, 5.7 Hz, 1H), 2.49-2.45 (m, 1H), 2.42-2.34 (m, 1H), 2.29-2.21 (m, 1H), 2.13-2.03 (m, 2H), 2.03-1.94 (m, 2H).

175
INTERMEDIATE 84

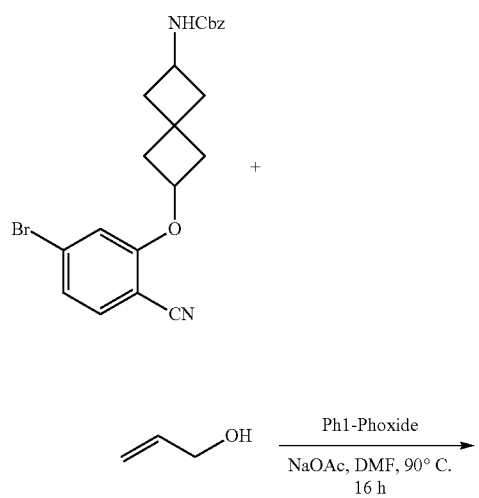

A solution of Intermediate 84A (300 mg, 0.680 mmol), prop-2-en-1-ol (0.111 mL, 1.631 mmol), dihydrogen di-mu-chlorotetrakis(diphenylphosphinato)dipalladate(2-) (37.1 mg, 0.034 mmol) and sodium acetate (145 mg, 1.767 mmol) in anhydrous DMF (6.5 mL) was degassed (3× vacuum/Ar) at rt, and then was stirred at 90° C. for 16 h under Ar atmosphere. The reaction mixture was diluted with EtOAc (100 mL), washed with water (3×50 mL), brine (1×25 mL), and dried (Na$_2$SO$_4$). EtOAc was removed under reduced pressure and the residue was by normal phase chromatography (50-100% EtOAc/hexanes gradient, eluted at ~68% EtOAc). Fractions were combined and concentrated under reduced pressure to give Intermediate 84 (153 mg, 54% yield) as a colorless film. MS (ESI) m/z: 419.1 (M+H)$^+$. $^1$H-NMR (500 MHz, DMSO-d$_6$) 9.74 (t, J=1.0 Hz, 1H), 7.38 (d, J=8.0 Hz, 1H), 7.32-7.21 (m, 5H), 6.73 (dd, J=8.0, 1.4 Hz, 1H), 6.53 (s, 1H), 5.01 (br s, 2H), 4.78 (br d, J=5.8 Hz, 1H), 4.58 (quin, J=6.8 Hz, 1H), 4.13-4.00 (m, 1H), 2.92-2.84 (m, 2H), 2.77-2.69 (m, 2H), 2.63-2.53 (m, 1H), 2.49-2.32 (m, 3H), 2.22 (td, J=12.0, 6.9 Hz, 2H), 1.95-1.86 (m, 2H).

176
INTERMEDIATE 85

Preparation of N-(6-(5-bromo-2-carbamoylphenoxy) spiro[3.3]heptan-2-yl)-6-(2-hydroxy-2-methyl-propoxy)pyrazolo[1,5-a]pyridine-3-carboxamide

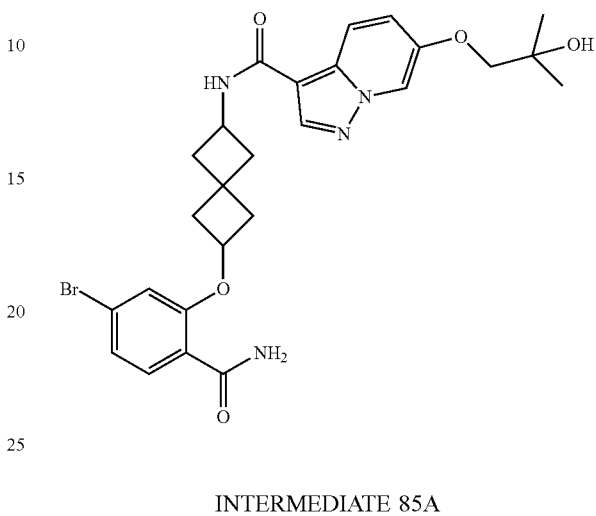

INTERMEDIATE 85A

Preparation of Benzyl (6-(5-bromo-2-cyanophenoxy)spiro[3.3]heptan-2-yl)carbamate

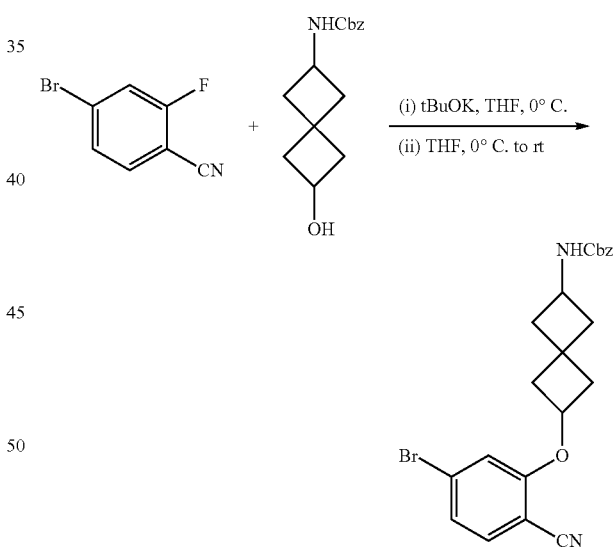

Intermediate 1 (500 mg, 1.913 mmol) was dissolved to anhydrous THF (12.0 mL), and the reaction mixture was cooled 0° C. potassium tert-butoxide (225 mg, 2.009 mmol) was added in one portion, and the reaction mixture was stirred at 0° C. for 30 min. Thereafter, 4-bromo-2-fluorobenzonitrile (957 mg, 4.78 mmol) was added, cooling bath was removed, and the reaction mixture was stirred at rt for 1 h. The reaction mixture was quenched with water (1.0 mL), and concentrated. The residue was purified by normal phase chromatography (solid loading on Celite); 0-75% EtOAc/hexanes gradient; eluted at ~45% EtOAc). Fractions were combined and concentrated under reduced pressure to give Intermediate 85A (614 mg, 73% yield) as a white solid. MS (ESI) m/z: 441.0 (M+H)$^+$. $^1$H-NMR (500 MHz, DMSO-$d_6$) δ ppm 7.67 (d, J=8.0 Hz, 1H), 7.52 (br d, J=7.7 Hz, 1H), 7.40-7.27 (m, 7H), 4.99 (s, 2H), 4.84 (quin, J=6.9 Hz, 1H), 3.90 (sxt, J=8.0 Hz, 1H), 2.67 (dt, J=11.1, 5.7 Hz, 1H), 2.49-2.45 (m, 1H), 2.42-2.34 (m, 1H), 2.29-2.21 (m, 1H), 2.13-2.03 (m, 2H), 2.03-1.94 (m, 2H).

INTERMEDIATE 85B

Preparation of Benzyl (6-(5-bromo-2-carbamoyl-phenoxy)spiro[3.3]heptan-2-yl)carbamate

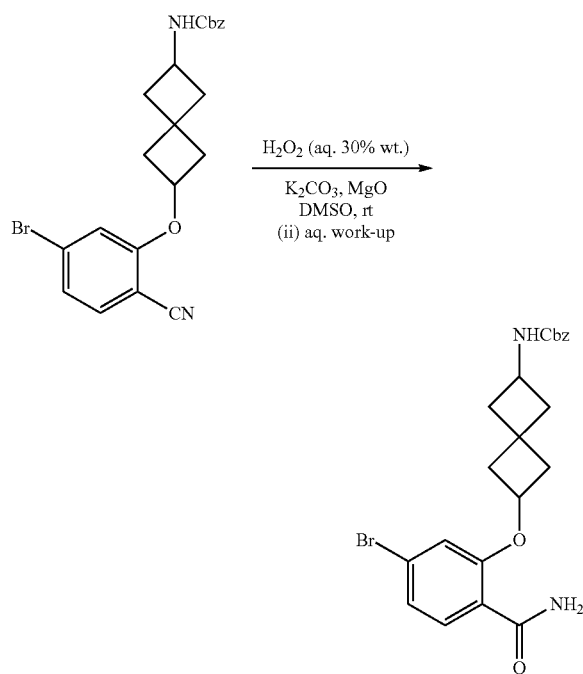

Intermediate 85A (500 mg, 1.133 mmol) was dissolved in DMSO (25.0 mL), then K$_2$CO$_3$ (470 mg, 3.40 mmol) and magnesium oxide (228 mg, 5.66 mmol) were added at rt. To the reaction was added hydrogen peroxide (30% wt. aq) (3.82 mL, 37.4 mmol) dropwise over 5 min (slight exotherm), and the reaction mixture was stirred at rt for 16 h. The reaction mixture was diluted with EtOAc (200 mL), then quenched with HCl (1 M aq.) (18.1 mL, 18.13 mmol). Organic phase was separated, washed with brine (3×100 mL), dried (Na$_2$SO$_4$) and filtered. Solvent was removed under reduced pressure to afford Intermediate 85B (453 mg, 87% yield) as a white foam. MS (ESI) m: 459.0 (M+H)$^+$. $^1$H-NMR (500 MHz, DMSO-$d_6$) δ ppm 7.68 (d, J=8.5 Hz, 1H), 7.58 (br s, 1H), 7.51 (br d, J=7.7 Hz, 1H), 7.46 (br s, 1H), 7.40-7.27 (m, 5H), 7.20 (dd, J=8.3, 1.9 Hz, 1H), 7.11 (d, J=1.7 Hz, 1H), 4.99 (s, 2H), 4.79 (quin, J=6.8 Hz, 1H), 3.95-3.85 (m, 1H), 2.65 (dt, J=11.1, 5.7 Hz, 1H), 2.46 (dt, J=11.5, 5.9 Hz, 1H), 2.42-2.33 (m, 1H), 2.28-2.20 (m, 1H), 2.19-2.12 (m, 2H), 2.03-1.97 (m, 2H).

INTERMEDIATE 85C

Preparation of tert-butyl (6-(5-bromo-2-carbamoyl-phenoxy)spiro[3.3]heptan-2-yl)carbamate

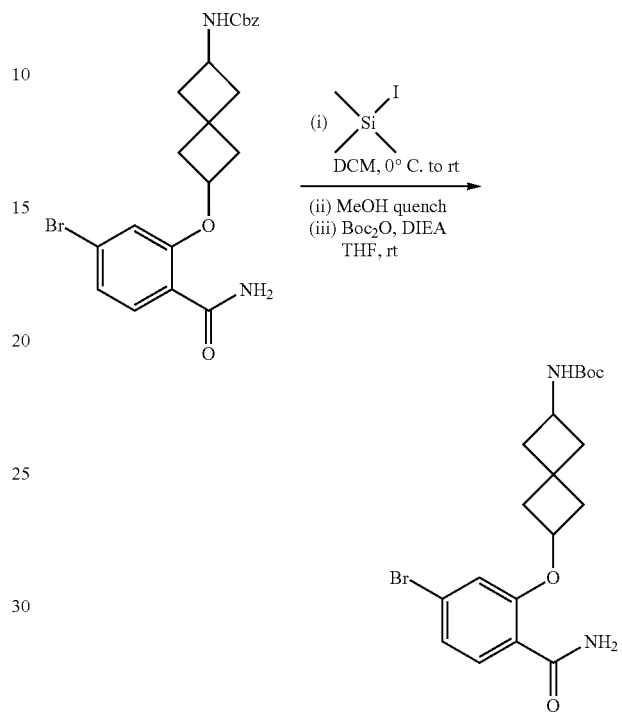

Intermediate 85B (700 mg, 1.524 mmol) was dissolved in DCM (20 mL). The reaction mixture was cooled to 0° C., and iodotrimethylsilane (0.62 mL, 4.57 mmol) was added dropwise under dinitrogen gas. The reaction mixture was stirred at 0° C. for 30 min, then the cooling bath was removed, and the reaction was further stirred at rt for 30 min. The reaction mixture was cooled to 0° C., carefully quenched with MeOH (5 mL), volatiles were removed under reduced pressure, and the residue was pumped under high vacuum for 30 min. The residue was dissolved in anhydrous THF (20 mL), then BOC$_2$O (1.42 mL, 6.10 mmol) was added, followed by DIEA (1.33 mL, 7.62 mmol). The reaction mixture was stirred at rt for 1 h. The reaction mixture was quenched with MeOH (1 mL), concentrated and purified by was purified by normal phase chromatography (20-100% EtOAc/hexanes gradient; eluted at ~88% EtOAc). Fractions were combined and concentrated under reduced pressure to give Intermediate 85C (647 mg, 1.521 mmol, 100% yield) as a white solid. MS (ESI) m/z: 424.8 (M+H)$^+$. $^1$H-NMR (500 MHz, DMSO-$d_6$) δ ppm 7.68 (d, J=8.3 Hz, 1H), 7.57 (br s, 1H), 7.46 (br s, 1H), 7.20 (dd, J=8.3, 1.7 Hz, 1H), 7.11 (d, J=1.9 Hz, 1H), 7.06 (br d, J=8.0 Hz, 1H), 4.78 (quin, J=6.9 Hz, 1H), 3.90-3.80 (m, 1H), 2.66-2.60 (m, 1H), 2.47-2.41 (m, 1H), 2.37-2.30 (m, 1H), 2.24-2.17 (m, 1H), 2.13 (ddd, J=18.0, 11.3, 7.0 Hz, 2H), 1.98-1.91 (m, 2H), 1.36 (s, 9H).

INTERMEDIATE 85D

Preparation of 2-((6-aminospiro[3.3]heptan-2-yl)oxy)-4-bromobenzamide

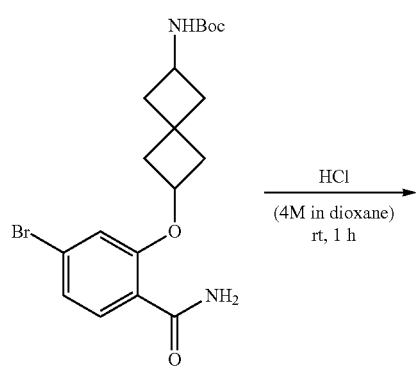

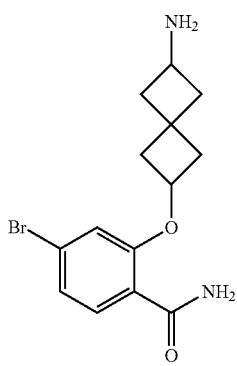

Intermediate 85C (300 mg, 0.705 mmol) was dissolved in HCl (4 M in dioxane) (6 mL, 24 mmol), and the reaction mixture was stirred at rt for 1 h. Solvent was removed under reduced pressure, and co-evaporated with Et$_2$O (2×5 mL) to give Intermediate 85D, HCl (256 mg, 0.708 mmol, 100% yield) as a white solid. MS (ESI) m/z: 324.8 (M+H)$^+$. $^1$H-NMR (500 MHz, DMSO-d$_6$) δ ppm 8.17 (br s, 3H), 7.68 (d, J=8.3 Hz, 1H), 7.58 (br s. 1H), 7.45 (br s, 1H), 7.21 (dd, J=8.4, 1.8 Hz, 1H), 7.12 (d, J=1.7 Hz, 1H), 4.80 (quin, J=6.8 Hz, 1H), 2.68 (dt, J=11.6, 5.8 Hz; 1H), 2.57-2.52 (m, 1H), 2.42 (ddd, J=11.7, 7.4, 4.8 Hz, 1H), 2.32-2.21 (m, 3H), 2.18 (dd, J=11.8, 6.9 Hz, 2H).

INTERMEDIATE 85

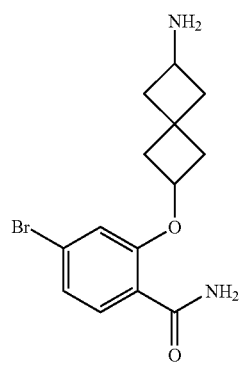

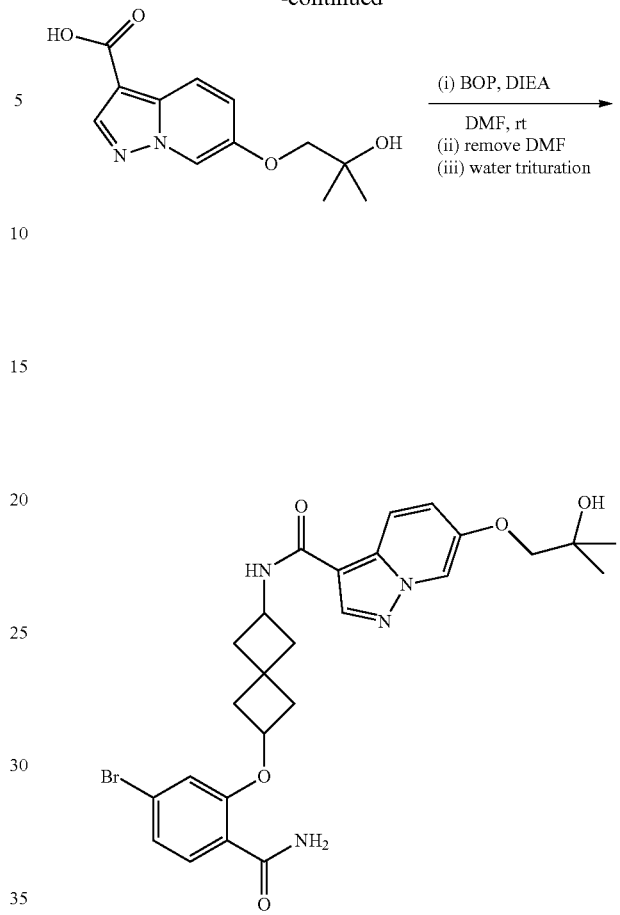

Intermediate 85D, HCl (256 mg, 0.708 mmol) and Intermediate 2 (177 mg, 0.708 mmol) were dissolved in anhydrous DMF (5.0 mL), then DIEA (0.618 mL, 3.54 mmol) was added, followed by BOP (344 mg, 0.779 mmol). The reaction mixture was stirred at rt for 1 h. The reaction mixture was quenched with MeOH (1.0 mL), and most for the solvent was removed under reduced pressure. To the obtained semi-solid residue, water was added portion-wise with sonication (total volume ~30 mL), which resulted in white solid formation. The mixture was stirred at rt for 1 h, filtered using a filter cartridge, washed with water (3×5 mL), and dried in high vacuum to afford Intermediate 85 (360 mg, 91% yield) as a white solid. MS (ESI) m/z: 556.9 (M+H)$^3$. $^1$H-NMR (500 MHz. DMSO-d$_6$) δ ppm 8.43 (s, 1H), 8.43 (d, J=2.2 Hz, 1H), 8.23 (d, J=7.4 Hz, 1H), 8.07 (d, J=9.9 Hz, 1H), 7.69 (d, J=8.3 Hz, 1H), 7.60 (br s, 1H), 7.49 (br s, 1H), 7.27 (dd, J=9.6, 2.2 Hz, 1H), 7.22 (dd, J=8.3, 1.9 Hz, 1H), 7.15 (d, J=1.7 Hz, 1H), 4.84 (quin, J=6.9 Hz, 1H), 4.37 (dq, J=16.1, 8.1 Hz, 1H), 3.79 (s, 2H), 2.72 (dt, J=11.2, 5.8 Hz, 1H), 2.57-2.52 (m, 1H), 2.47 (br dd, J=7.2, 5.0 Hz, 1H), 2.38-2.30 (m, 1H), 2.26-2.10 (m, 4H), 1.22 (s, 6H).

INTERMEDIATE 86

Preparation of tert-butyl ((aS)-6-(5-bromo-2-carbamoylphenoxy)spiro[3.3]heptan-2-yl)carbamate

INTERMEDIATE 87

Preparation of tert-butyl ((aR)-6-(5-bromo-2-carbamoylphenoxy)spiro[3.3]heptan-2-yl)carbamate

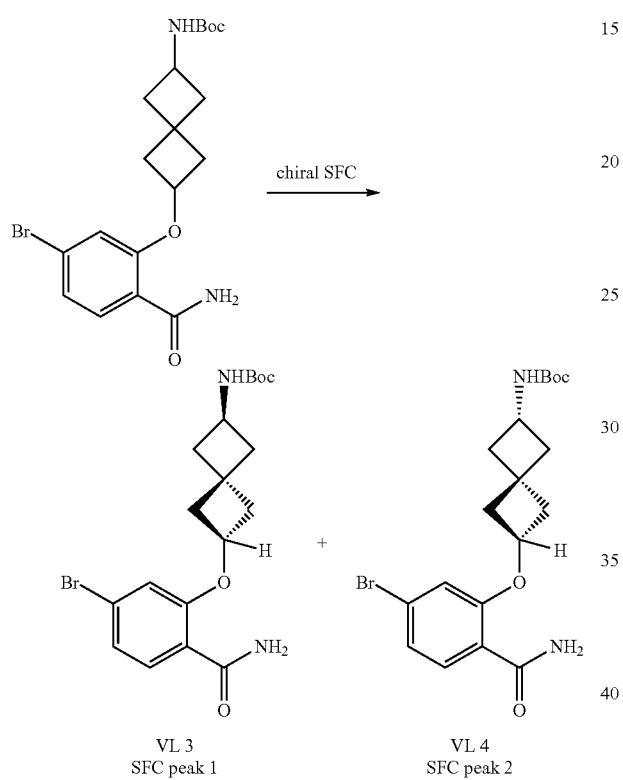

VL 3
SFC peak 1

VL 4
SFC peak 2

Intermediate 85C (347 mg, 0.816 mmol) was separated on chiral SFC (Instrument: PIC Solution SFC Prep-200; Column: CHIRALPAK® IC, 30×250 mm, 5 micron; Mobile Phase: 35% Methanol/65% $CO_2$; Flow Conditions: 85 mL/min. 150 Bar, 40° C.: Detector Wavelength: 220 nm). Collected 1st peak at 9.94 min, concentrated to afford Intermediate 86 (140 mg, 40% yield) as a white solid. MS(ESI) m/z: 425.0 (M+H)+; ee>99%; $^1$H-NMR (500 MHz, DMSO-$d_6$) δ ppm 7.68 (d, J=8.3 Hz, 1H), 7.57 (br s, 1H), 7.46 (br s, 1H), 7.20 (dd, J=8.3, 1.7 Hz, 1H), 7.11 (d, J=1.4 Hz, 1H), 7.05 (br d, J=7.4 Hz, 1H), 4.78 (quin, J=6.8 Hz, 1H), 3.90-3.78 (m, 1H), 2.62 (dt, J=11.1, 5.7 Hz, 1H), 2.45 (dt, J=11.4, 5.8 Hz, 1H), 2.39-2.29 (m, 1H), 2.24-2.17 (m, 1H), 2.13 (ddd, J=18.1, 11.3, 6.9 Hz, 2H), 2.01-1.90 (m, 2H), 1.36 (s, 9H).

Collected 2nd peak at 14.56 min, concentrated to afford Intermediate 87 (143 mg, 41% yield) as a white solid. MS(ESI) min: 425.0 (M+H)+; ee>99%; $^1$H-NMR (500 MHz, DMSO-$d_6$) δ ppm 7.68 (d, J=8.3 Hz, 1H), 7.57 (br s, 1H), 7.46 (br s, 1H), 7.20 (dd, J=8.3, 1.4 Hz, 1H), 7.11 (d, J=1.4 Hz, 1H), 7.05 (br d, J=7.4 Hz, 1H), 4.78 (quin, J=6.8 Hz, 1H), 3.90-3.78 (m, 1H), 2.62 (dt, J=11.0, 5.8 Hz, 1H), 2.45 (dt, J=11.4, 5.8 Hz, 1H), 2.38-2.30 (m, 1H), 2.24-2.17 (m, 1H), 2.13 (ddd, J=18.1, 11.3, 6.9 Hz, 2H), 2.01-1.91 (m, 2H), 1.36 (s, 9H).

INTERMEDIATE 88

Preparation of 7-bromo-N-((aR)-6-((3-carbamoylpyridin-2-yl)oxy)spiro[3.3]heptan-2-yl)-6-(2,2-difluoropropoxy)pyrazolo[1,5-a]pyridine-3-carboxamide

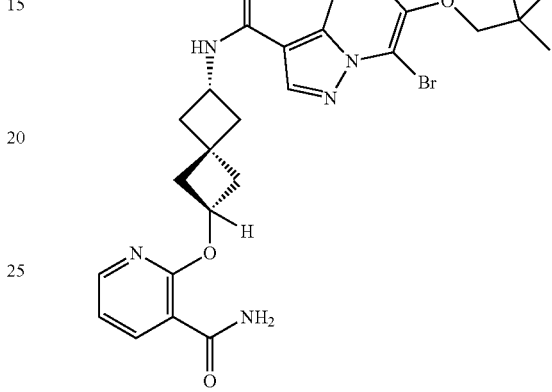

INTERMEDIATE 88A

Preparation of methyl 7-bromo-6-(2-oxopropoxy)pyrazolo[1,5-a]pyridine-3-carboxylate

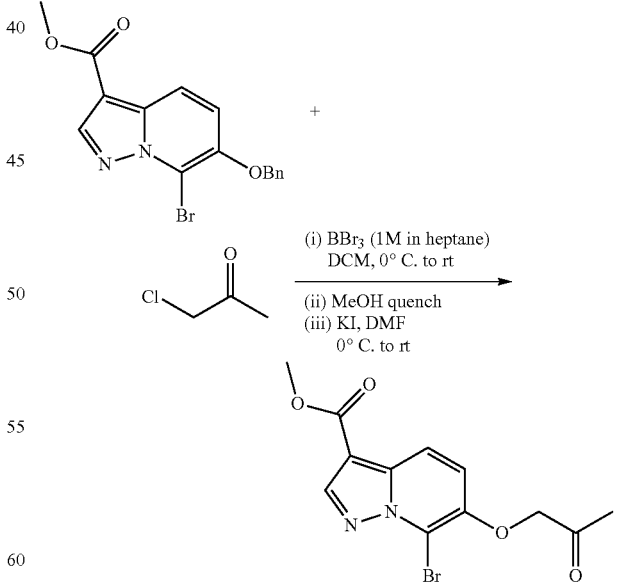

Methyl 6-(benzyloxy)-7-bromopyrazolo[1,5-a]pyridine-3-carboxylate (1.00 g, 2.77 mmol) was dissolved in DCM (55 mL), and the reaction mixture was cooled to 0° C. A solution of BBr$_3$ (1 M in heptane) (3.60 mL, 3.60 mmol) was added dropwise via syringe with stirring at 0° C. The reaction mixture was stirred at 0° C. for 15 min, and then 30 min at rt. The reaction mixture was quenched with MeOH (~5 mL), and was concentrated under reduced pressure and under vacuum to afford crude phenol as a white solid. The residue was dissolved in anhydrous DMF (25 mL), and 1-chloropropan-2-one (0.24 mL, 3.05 mmol) and KI (115 mg, 0.692 mmol) were added. The reaction mixture was cooled to 0° C., K$_2$CO$_3$ (497 mg, 3.60 mmol) was added in one portion, and the reaction mixture was allowed to react rt over 14 h (overnight). The reaction mixture was diluted with EtOAc (300 mL) and water (150 mL), organic phase was separated, washed with water (3×50 mL), brine (1×50 mL) and dried (Na$_2$SO$_4$). EtOAc was removed under reduced pressure and the residue was purified by normal phase chromatography (0-50% EtOAc/DCM gradient; eluted at ~23% EtOAc). MS (ESI) m/z: 326.8 (M+H)$^+$. $^1$H-NMR (500 MHz, DMSO-d$_6$) δ ppm 8.51 (s, 1H), 8.03 (d, J=9.6 Hz, 1H), 7.61 (d, J=9.9 Hz, 1H), 5.09 (s, 2H), 3.84 (s, 3H), 2.19 (s, 3H).

INTERMEDIATE 88B

Preparation of methyl 7-bromo-6-(2,2-difluoropropoxy)pyrazolo[1,5-a]pyridine-3-carboxylate

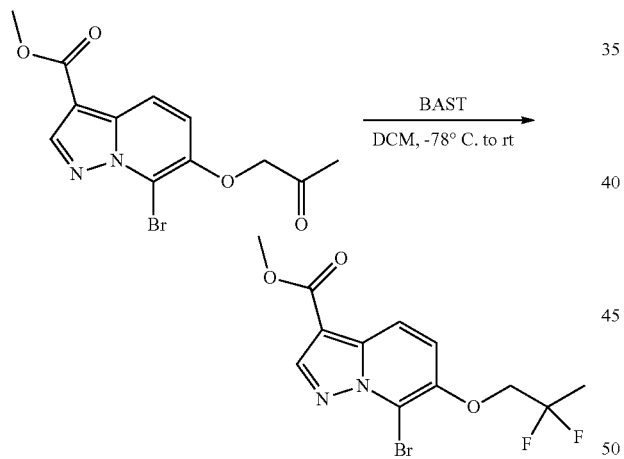

Intermediate 88A (225 mg, 0.688 mmol) was suspended in anhydrous DCM (5 mL), and the reaction mixture was cooled to −78° C. BAST (50% wt. in toluene) (1.27 mL, 3.44 mmol) was added in one portion, and the reaction mixture allowed to reach rt over 1 h, and stirred at rt for 16 h. The reaction mixture was cooled to 0° C., quenched with MeOH (5 mL), concentrated, and the residue was purified by normal phase chromatography (0-25% EtOAc/DCM gradient; eluted at ~10% EtOAc) Fractions were combined and concentrated under reduced pressure to give Intermediate 88B (230 mg, 96% yield) as a white solid. MS (ESI) m/z: 348.8 (M+H)$^+$. $^1$H-NMR (500 MHz, DMSO-d$_6$) δ ppm 8.53 (s, 1H), 8.10 (d, J=9.6 Hz, 1H), 7.78 (d, J=9.6 Hz, 1H), 4.53 (t, J=12.5 Hz, 2H), 3.85 (s, 3H), 1.80 (t, J=19.3 Hz, 3H). $^{19}$F-NMR: (471 MHz, DMSO-d$_6$) d ppm −97.27 (s, 2F).

INTERMEDIATE 88C

Preparation of 7-bromo-6-(2,2-difluoropropoxy)pyrazolo[1,5-a]pyridine-3-carboxylic acid

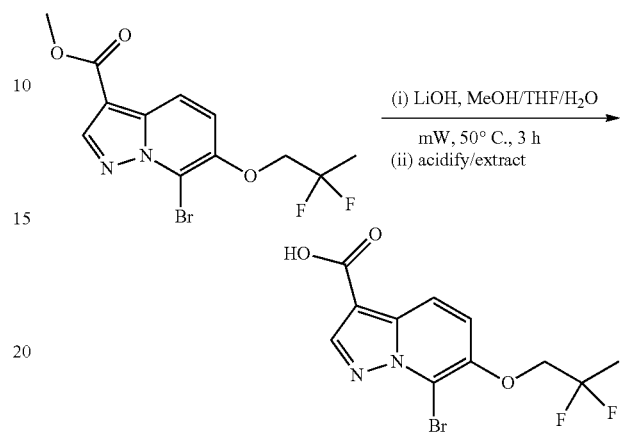

Intermediate 88B (230 mg, 0.659 mmol) was dissolved in MeOH (3.0 mL)/THF (3.0 mL), and LiOH (1 M aq.) (1.98 mL, 1.98 mmol) was added. The reaction mixture was stirred at 50° C. for 3 h. Solvent was removed under reduced pressure, the residue was dissolved in water (~10 mL), EtOAc (10 mL), and the mixture was slowly acidified with HCl (1 M aq.) (2.3 mL, 2.306 mmol) (pH~2.0). Organic phase was separated, aq. phase was extracted with EtOAc (2×15 mL). The combined organic fractions were washed with brine (1×50 mL), dried (Na$_2$SO$_4$) and filtered. EtOAc was removed under reduced pressure to afford Intermediate 88C (216 mg, 98% yield) as an off-white solid. MS (ESI) m/z: 334.8 (M+H)$^+$. $^1$H-NMR (500 MHz, DMSO-d$_6$) δ ppm 12.61 (br s, 1H), 8.46 (s, 1H), 8.09 (d, J=9.6 Hz, 1H), 7.74 (d, J=9.6 Hz, 1H), 4.52 (t, J=12.5 Hz, 2H), 1.80 (t, J=19.3 Hz, 3H). $^{19}$F-NMR: (471 MHz, DMSO-d$_6$) δ ppm −97.28 (s, 2F).

INTERMEDIATE 88

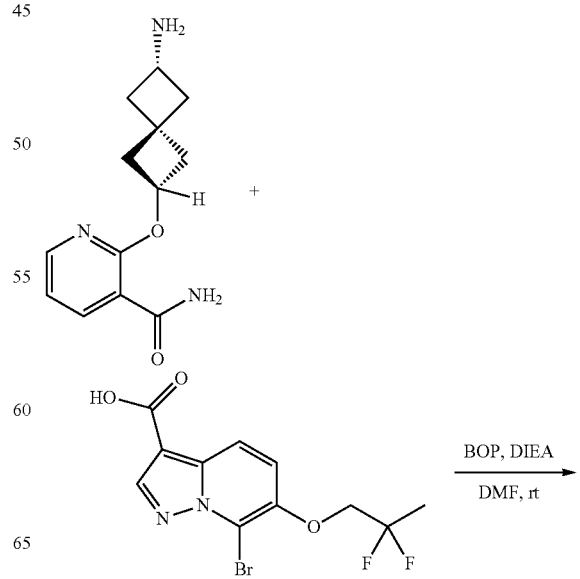

185

-continued

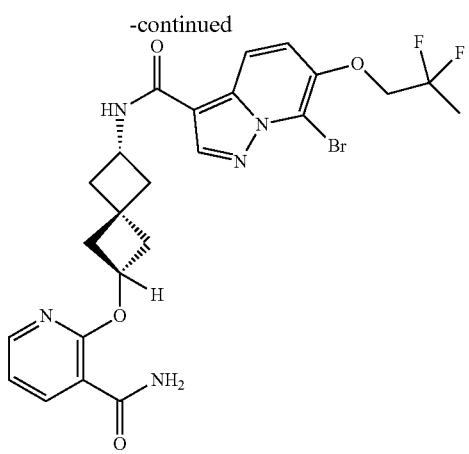

Example 42C (125 mg, 0.505 mmol) and Intermediate 88C (169 mg, 0.505 mmol) were dissolved in anhydrous DMF (3 mL), then DIEA (0.44 mL, 2.53 mmol) was added, followed by BOP (291 mg, 0.657 mmol). The reaction mixture was stirred at rt for 1 h. The reaction mixture was quenched with MeOH (1.0 mL), and most for the solvent was removed under reduced pressure. To the obtained semi-solid residue, water was added portion-wise with sonication (total volume ~25 mL), which resulted in white solid formation. The mixture was stirred at rt for 2 h, filtered using a filter cartridge, washed with water (3×5 mL), and dried in vacuum to afford Intermediate 88 (232 mg, 0.288 mmol, 56.9% yield) as an off-white solid. MS (ESI) m/z: 564.0 (M+H)$^3$. $^1$H-NMR (500 MHz, DMSO-d$_6$) δ ppm 8.61 (s, 1H), 8.47 (br d, J=7.1 Hz, 1H), 8.26 (dd, J=4.7, 1.6 Hz, 1H), 8.20 (d, J=9.7 Hz, 1H), 8.18-8.13 (m, 1H), 7.74-7.58 (m, 3H), 7.11 (dd, J=7.3, 5.0 Hz, 1H), 5.22 (quin, J=7.0 Hz, 1H), 4.48 (t, J=12.5 Hz, 2H), 4.37 (dq, J=16.0, 8.2 Hz, 1H), 2.66 (dt, J=11.0, 5.6 Hz, 1H), 2.49-2.42 (m, 2H), 2.38-2.29 (m, 1H), 2.26 (br dd. J=11.1, 7.4 Hz 1H), 2.23-2.19 (m, 1H), 2.19-2.11 (m, 2H), 1.78 (t, J=19.3 Hz, 3H).

INTERMEDIATE 89

Preparation of 6-(2-hydroxy-2-methylpropoxy)-7-isopropylpyrazolo[1,5-a]pyridine-3-carboxylic acid

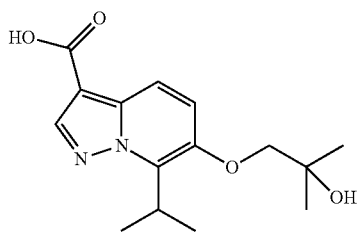

186

INTERMEDIATE 89A

Preparation of methyl methyl 6-(benzyloxy)-7-(prop-1-en-2-yl)pyrazolo[1,5-a]pyridine-3-carboxylate

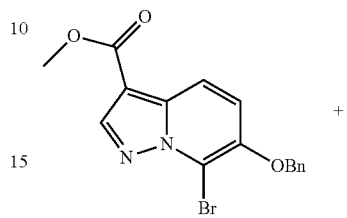

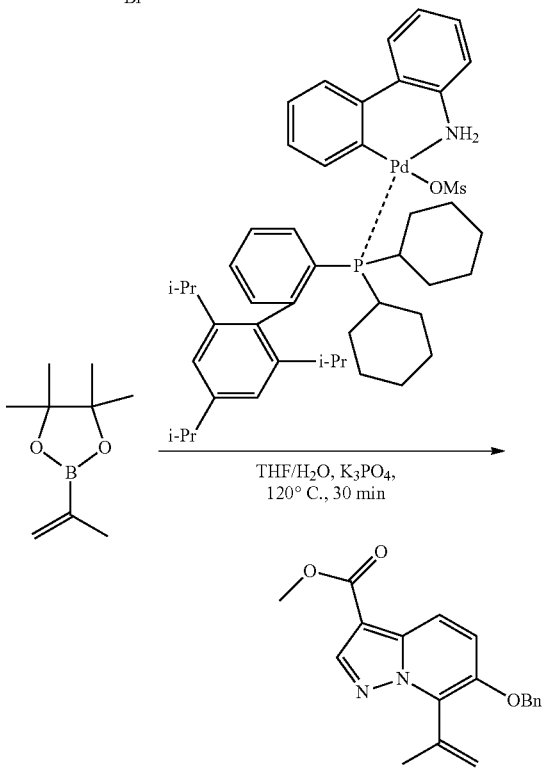

Methyl 6-(benzyloxy)-7-bromopyrazolo[1,5-a]pyridine-3-carboxylate (0.250 g, 0.692 mmol), 4,4,5,5-tetramethyl-2-(prop-1-en-2-yl)-1,3,2-dioxaborolane (0.39 mL, 2.076 mmol) and Pd-XPhos G3 (0.029 g, 0.035 mmol) were placed in a pressure vial. Then THF (8.0 mL) and phosphoric acid, potassium salt (0.5 M aq.) (2.77 mL, 1.384 mmol) were added, and the reaction mixture was degassed (3×, vacuum/Ar). The pressure vial was capped, and the reaction mixture was stirred at 120° C. for 30 min. The reaction mixture was diluted with EtOAc (50 mL), Celite was added, and the solvent was removed under reduced pressure. EtOAc was removed under reduced pressure and the residue was purified by normal phase chromatography (solid loading on Celite; 0-50% EtOAc/hexanes gradient; eluted at ~35% EtOAc). Fractions were combined and concentrated under reduced pressure to give Intermediate 89A (0.220 g, 99% yield) as an amber oil, which solidified upon standing. MS (ESI) m/z: 323.2 (M+H)$^+$. $^1$H-NMR (500 MHz, DMSO-d$_6$) δ ppm 8.37 (s, 1H), 8.05 (d, J=9.6 Hz, 1H), 7.41-7.38 (m, 3H), 7.38-7.35 (m, 2H), 7.35-7.30 (m, 1H), 5.68 (quin, J=1.4 Hz, 1H), 5.34-5.32 (m, 1H), 5.12 (s, 2H), 3.90 (s, 3H), 2.19 (t, J=1.2 Hz, 3H).

INTERMEDIATE 89B

Preparation of methyl 6-hydroxy-7-isopropylpyrazolo[1,5-a]pyridine-3-carboxylate

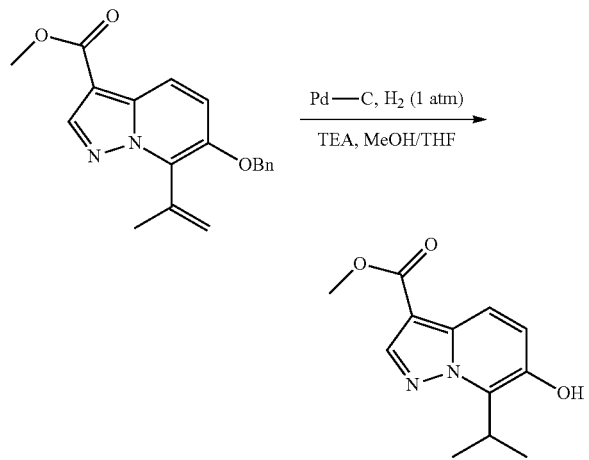

Intermediate 89A (0.220 g, 0.682 mmol) was dissolved in THF (4 mL) and MeOH (4 mL), and TEA (0.48 mL, 3.41 mmol) was added. The reaction mixture was degassed (3× vacuum/Ar), then palladium on carbon (10 wt %) (0.073 g, 0.068 mmol) was added. The reaction mixture was degassed again, and it was stirred under dihydrogen atmosphere (1 atm ballon) for 1 h. The reaction mixture was degassed again and stirred under dihydrogen atmosphere (1 atm: ballon) for 12 h. Additional amount of MeOH (4 mL). THF (4 mL), and TEA (0.476 mL, 3.41 mmol) were added. The reaction mixture was degassed (3× vacuum/Ar), then palladium on carbon (10 wt %) (0.073 g, 0.068 mmol) was added. The reaction mixture was degassed again, and it was stirred under dihydrogen atmosphere (1 atm; ballon) for 3 days. Pd—C was filtered off using membrane filter, and the filtrate was concentrated to afford Intermediate 89B (0.158 g, 0.674 mmol, 99° % yield) as an off-white solid. MS (ESI) m/z: 235.2 (M+H)$^+$. $^1$H-NMR (500 MHz, DMSO-d$_6$) δ ppm 9.79 (br s, 1H), 8.33 (s, 1H), 7.85 (d, J=9.4 Hz, 1H), 7.35 (d, J=9.4 Hz, 1H), 4.14 (spt, J=7.1 Hz, 1H), 3.80 (s, 3H), 1.44 (d, J=7.2 Hz, 6H).

INTERMEDIATE 89

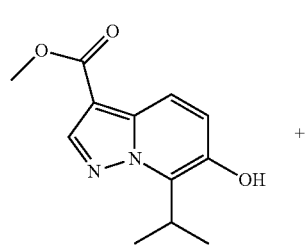

+

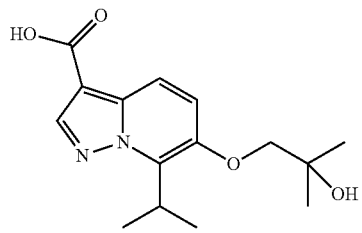 [SMILES: CC(C)c1c(OCC(C)(C)O)ccc2c(C(=O)O)cnn12]

Intermediate 89B (0.080 g, 0.342 mmol) was suspended in MeCN (3.00 mL), then 2,2-dimethyloxirane (0.23 mL, 2.56 mmol), K$_2$CO$_3$ (0.189 g, 1.366 mmol) and water (0.20 mL) were added. The reaction mixture was stirred under microwave irradiation at 120° C. for 30 min. The reaction mixture was concentrated under reduced pressure, the residue was dissolved in MeOH (1.5 mL)/THF (1.5 mL), and LiOH (1 M aq.) (1.03 mL, 1.03 mmol) was added. The reaction mixture was stirred under microwave irradiation at 120° C. for 15 min. Solvent was removed under reduced pressure, the residue was purified by reverse phase HPLC to afford Intermediate 89 (0.064 g, 0.219 mmol, 64.1% yield) as a white solid. MS (ESI) m/z: 293.2 (M+H)$^+$. $^1$H-NMR (500 MHz, DMSO-d$_6$) δ ppm 8.35 (s, 1H), 7.94 (d, J=9.6 Hz, 1H), 7.61 (d, J=9.6 Hz, 1H), 4.29-4.22 (m, 1H), 3.83 (s, 2H), 1.46 (d, J=7.2 Hz, 6H), 1.26 (s, 6H).

INTERMEDIATE 90

Preparation of (R)-6-(2-hydroxypropoxy)pyrazolo[1,5-a]pyridine-3-carboxylic acid

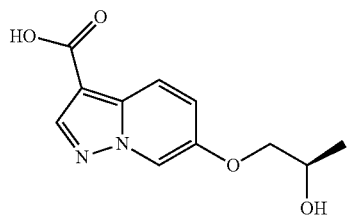 [SMILES: C[C@@H](O)COc1ccc2c(C(=O)O)cnn2c1]

INTERMEDIATE 90A

Preparation of (R)-methyl 6-(2-hydroxypropoxy)pyrazolo[1,5-a]pyridine-3-carboxylate

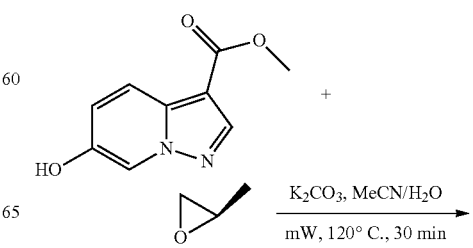

-continued

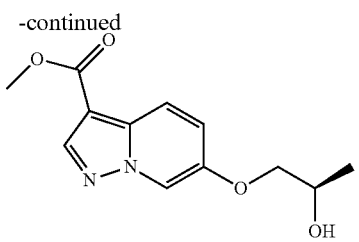

Methyl 6-hydroxypyrazolo[1,5-a]pyridine-3-carboxylate (0.500 g, 2.60 mmol) was suspended in MeCN (10.00 mL), then (R)-2-methyloxirane (1.83 mL, 26.0 mmol), $K_2CO_3$ (1.438 g, 10.41 mmol) and water (0.67 mL) were added. The reaction mixture was stirred under microwave irradiation at 120° C. for 30 min. The reaction mixture was diluted with EtOAc, Celite was added, and the reaction mixture was concentrated. The residue was purified by normal phase chromatography (solid loading on Celite; 20-100% EtOAc/hexanes gradient; eluted at ~90% EtOAc). Fractions were combined and concentrated under reduced pressure to give Intermediate 90A (0.615 g, 94% yield) as a white solid. MS (ESI) m/z: 251.0 (M+H)+. $^1$H-NMR (500 MHz, DMSO-$d_6$) δ ppm 8.32 (s, 1H), 8.13 (s, 1H), 8.06 (br d, J=9.6 Hz, 1H), 7.24 (d, J=9.6 Hz, 1H), 4.27 (quind, J=6.6, 3.3 Hz, 1H), 3.97 (dd, J=9.1, 3.0 Hz, 1H), 3.91 (s, 3H), 3.86 (dd, J=8.8, 7.4 Hz, 1H), 1.34 (d, J=6.3 Hz, 3H).

INTERMEDIATE 90

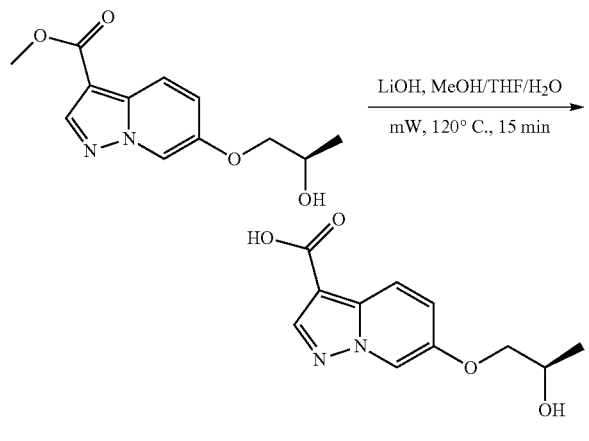

Intermediate 90A (250 mg, 0.999 mmol) was dissolved in MeOH (4.00 mL)/THF (4.00 mL), and LiOH (1 M aq.) (3.00 mL, 3.00 mmol) was added. The reaction mixture was stirred under microwave irradition at 120° C. for 15 min. Solvent was removed under reduced pressure, the residue was suspended water (50 mL), acidified to pH-2.0 with aq. HCl (1 M; ~2.7 mL) and extracted with EtOAc (3×50 mL). The combined organic fractions were washed with brine (1×50 mL), dried ($Na_2SO_4$) and filtered. EtOAc was removed under reduced pressure to afford Intermediate 90 (234 mg, 99% yield) as an off-white solid. MS (ESI) m/z: 237.0 (M+H)+. $^1$H-NMR (500 MHz, DMSO-$d_6$) δ ppm 12.34 (br s, 1H), 8.55 (d, J=2.2 Hz, 1H), 8.28 (s, 1H), 7.96 (d, J=9.6 Hz, 1H), 7.36 (dd, J=9.6, 2.2 Hz, 1H), 4.93 (br s, 1H), 4.01-3.95 (m, 1H), 3.94-3.86 (m, 2H), 1.16 (d, J=6.3 Hz, 3H).

INTERMEDIATE 91

Preparation of (S)-6-(2-hydroxypropoxy)pyrazolo[1,5-a]pyridine-3-carboxylic acid

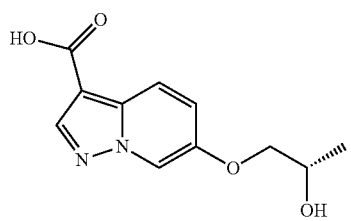 [SMILES: C[C@H](O)COc1ccc2c(C(=O)O)cnn2c1]

Intermediate 91 (227 mg, 96% yield) was prepared in an analogous manner as Intermediate 90 replacing commercially available (R)-2-methyloxirane with (S)-2-methyloxirane. MS (ESI) m/z: 237.0 (M+H)+. $^1$H-NMR (500 MHz, DMSO-$d_6$) 12.34 (br s, 1H), 8.55 (d, J=2.2 Hz, 1H), 8.28 (s, 1H), 7.96 (d, J=9.6 Hz, 1H), 7.36 (dd, J=9.6, 2.2 Hz, 1H), 4.93 (br s, 1H), 4.03-3.95 (m, 1H), 3.94-3.87 (m 2H), 1.16 (d, J=6.3 Hz, 3H).

INTERMEDIATE 92

Preparation of methyl 6-cyclobutoxypyrazolo[1,5-a]pyridine-3-carboxylate

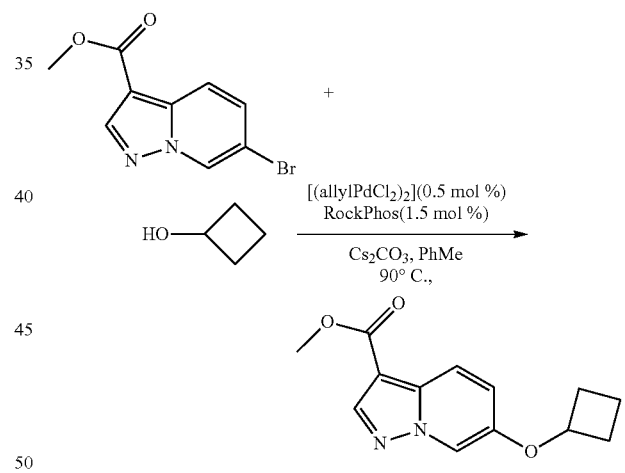

Methyl 6-bromopyrazolo[1,5-a]pyridine-3-carboxylate (0.100 g, 0.392 mmol), allylpalladium chloride dimer (2.9 mg, 7.84 µmol), RockPhos (0.011 g, 0.024 mmol) and cesium carbonate (0.192 g, 0.588 mmol) were placed in a pressure vial. The reaction mixture was degassed (3× vacuum/Ar), then cyclobutanol (0.037 g, 0.510 mmol) in toluene (1 mL) was added. The reaction mixture was degassed again, and stirred at 90° C. for 16 h. The reaction mixture was diluted with DCM (20 mL), Celite was added, and the solvent was removed under reduced pressure. The residue was purified by normal phase chromatography (solid loading on Celite; 0-60% EtOAc/DCM gradient; eluted at ~24% EtOAc). Fractions were combined and concentrated under reduced pressure to give Intermediate 92 (40 mg, 41% yield) as an off-white solid. MS (ESI) m/z: 247.0 (M+H)+. $^1$H-NMR (500 MHz, DMSO-$d_6$) δ ppm 8.31 (s, 1H), 8.04 (d, J=10.1 Hz, 1H), 7.97 (d, J=1.5 Hz, 1H), 7.17 (dd, J=9.5, 2.2 Hz, 1H), 4.63 (quin, J=6.9 Hz, 1H), 3.91 (s, 3H), 2.59-2.46 (m, 2H), 2.30-2.16 (m, 2H), 1.99-1.87 (m, 1H), 1.82-1.67 (m, 1H).

INTERMEDIATE 93

Preparation of methyl 7-cyclopropyl-6-(2-(2,2,2-trifluoroethoxy)ethoxy)pyrazolo[1,5-a]pyridine-3-carboxylate

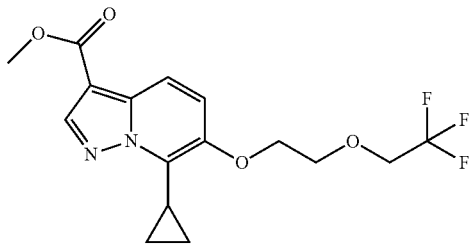 [SMILES: COC(=O)c1cnn2c(C3CC3)c(OCCOCC(F)(F)F)ccc12]

Intermediate 93 (0.109 g, 94% yield) was prepared in an analogous manner as Intermediate 27 utilizing commercially available 2-(2,2,2-trifluoroethoxy)ethanol. MS (ESI) m/z: 359.0 (M+H)$^+$. $^1$H-NMR (500 MHz, DMSO-d$_6$) δ ppm 8.41 (s, 1H), 7.91 (d, J=9.6 Hz, 1H), 7.61 (d, J=9.6 Hz, 1H), 4.26-4.23 (m, 2H), 4.16 (q, J=9.4 Hz, 2H), 3.95-3.91 (m, 2H), 3.82 (s, 3H), 2.60 (tt, J=8.8, 5.5 Hz, 1H), 1.52-1.47 (m, 2H), 1.10-1.02 (m, 2H). $^{19}$F-NMR: (471 MHz, DMSO-d$_6$) δ ppm −72.94 (s, 3F).

INTERMEDIATE 94

Preparation of methyl 7-cyclopropyl-6-((1,3-difluoropropan-2-yl)oxy)pyrazolo[1,5-a]pyridine-3-carboxylate

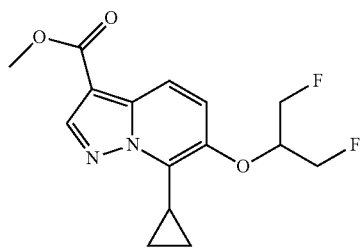 [SMILES: COC(=O)c1cnn2c(C3CC3)c(OC(CF)CF)ccc12]

Intermediate 94 (55.4 mg, 83% yield) was prepared in an analogous manner as Intermediate 27 utilizing commercially available 1,3-difluoropropan-2-ol. MS (ESI) m/z: 311.0 (M+H)$^+$. $^1$H-NMR (500 MHz, DMSO-d$_6$) δ ppm 8.40 (s, 1H), 8.03 (d, J=9.6 Hz, 1H), 7.30 (d, J=9.4 Hz, 1H), 4.81-4.73 (m, 2H), 4.71-4.64 (m, 2H), 4.55 (tquin, J=18.8, 4.6 Hz, 1H), 3.91 (s, 3H), 2.43 (tt, J=8.7, 5.6 Hz, 1H), 1.51-1.46 (m, 2H), 1.22-1.15 (m, 2H). $^{19}$F-NMR: (471 MHz, DMSO-d$_6$) δ ppm −232.01 (s, 2F).

INTERMEDIATE 95

Preparation of methyl 7-cyclopropyl-6-((tetrahydrofuran-2-yl)methoxy)pyrazolo[1,5-a]pyridine-3-carboxylate

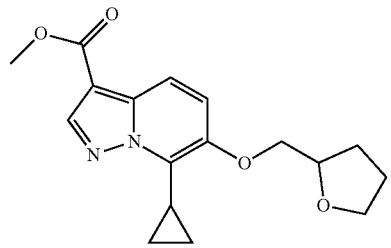 [SMILES: COC(=O)c1cnn2c(C3CC3)c(OCC3CCCO3)ccc12]

Intermediate 95 (44 mg, 65% yield) was prepared in an analogous manner as Intermediate 27 utilizing commercially available (tetrahydrofuran-2-yl)methanol. MS (ESI) m/z: 317.0 (M+H)$^+$. $^1$H-NMR (500 MHz, DMSO-d$_6$) δ ppm 8.38 (s, 1H), 7.99 (d, J=9.6 Hz, 1H), 7.32 (d, J=9.4 Hz, 1H), 4.28 (tdd, J=7.1, 5.4, 4.5 Hz, 1H), 4.04 (t, J=5.1 Hz, 2H), 3.95 (dt, J=8.3, 6.7 Hz, 1H), 3.90 (s, 3H), 3.89-3.82 (m, 1H), 2.53 (tt, J=8.8, 5.5 Hz, 1H), 2.16-2.07 (m, 1H), 2.05-1.92 (m 2H), 1.80 (ddt, J=12.1, 8.6, 7.2 Hz, 1H), 1.49-1.43 (m, 2H), 1.20-1.12 (m, 2H).

INTERMEDIATE 96

Preparation of methyl 7-cyclopropyl-6-(oxetan-3-yloxy)pyrazolo[1,5-a]pyridine-3-carboxylate

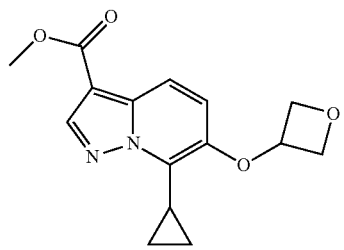 [SMILES: COC(=O)c1cnn2c(C3CC3)c(OC3COC3)ccc12]

Intermediate 96 (46 mg, 74% yield) was prepared in an analogous manner as Intermediate 27 utilizing commercially available oxetan-3-ol. MS (ESI) m/z: 289.0 (M+H)$^+$. $^1$H-NMR (500 MHz, DMSO-d$_6$) δ ppm 8.39 (s, 1H), 7.99 (d, J=9.6 Hz, 1H), 6.91 (d, J=9.6 Hz, 1H), 5.27-5.19 (m, 1H), 4.99-4.93 (m, 2H), 4.88-4.82 (m, 2H), 3.90 (s, 3H), 2.54 (tt, J=8.7, 5.6 Hz, 1H), 1.51-1.45 (m, 2H), 1.23-1.17 (m, 2H).

INTERMEDIATE 97

Preparation of methyl 7-cyclopropyl-6-(oxetan-2-ylmethoxy)pyrazolo[1,5-a]pyridine-3-carboxylate

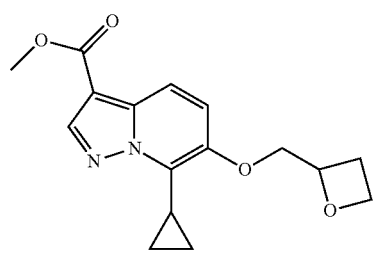 [SMILES: COC(=O)c1cnn2c(C3CC3)c(OCC3CCO3)ccc12]

Intermediate 97 (46.5 mg, 71% yield) was prepared in an analogous manner as Intermediate 27 utilizing commercially available oxetan-3-ol. MS (ESI) m/z: 303.0 (M+H)$^+$. $^1$H-NMR (500 MHz, DMSO-d$_6$) δ ppm 8.39 (s, 1H), 8.01 (d, J=9.6 Hz, 1H), 7.36 (d, J=9.6 Hz, 1H), 5.18-5.12 (m, 1H), 4.76 (ddd, J=8.5, 7.3, 5.9 Hz, 1H), 4.67 (dt, J=9.1, 6.1 Hz, 1H), 4.24-4.14 (m, 2H), 3.91 (s, 3H), 2.86-2.69 (m, 2H), 2.56 (tt, J=8.8, 5.5 Hz, 1H), 1.51-1.45 (m, 2H), 1.22-1.15 (m, 2H).

INTERMEDIATE 98

Preparation of methyl 6-(2-oxa-6-azaspiro[3.3]heptan-6-yl)pyrazolo[1,5-a]pyridine-3-carboxylate

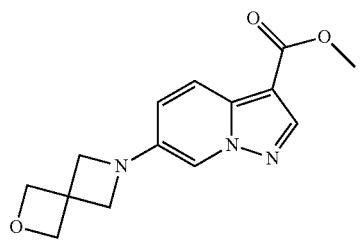 [SMILES: COC(=O)c1cnn2cc(N3CC4(COC4)C3)ccc12]

Intermediate 98 (0.195 g, 73% yield) was prepared in an analogous manner as Intermediate 21 utilizing commercially available 2-oxa-6-azaspiro[3.3]heptane, ½, oxalic acid salt. MS (ESI) m/z: 274.0 (M+H)$^+$. $^1$H-NMR (500 MHz, DMSO-d$_6$) δ ppm 8.26 (s, 1H), 7.99 (d, J=1.4 Hz, 1H), 7.94-7.88 (m, 1H), 7.09 (dd, J=9.4, 2.2 Hz, 1H), 4.72 (s, 4H), 4.04 (s, 4H), 3.79 (s, 3H).

INTERMEDIATE 99

Preparation of methyl 7-cyclopropyl-6-(1-methyl-1H-pyrazol-4-yl)pyrazolo[1,5-a]pyridine-3-carboxylate

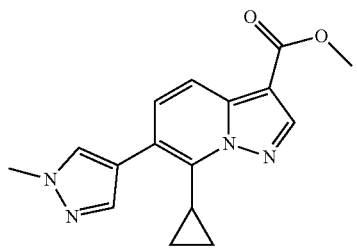

INTERMEDIATE 99A

Preparation of methyl 7-cyclopropyl-6-(((trifluoromethyl)sulfonyl)oxy)pyrazolo[1,5-a]pyridine-3-carboxylate

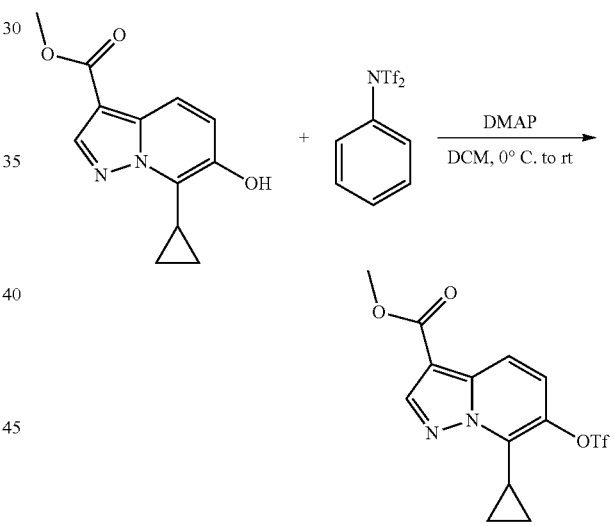

Intermediate 4B (200 mg, 0.861 mmol) was dissolved in DCM (15 mL) and THF (5 mL), and 1,1,1-trifluoro-N-phenyl-N-((trifluoromethyl)sulfonyl)methanesulfonamide (461 mg, 1.292 mmol) was added. The reaction mixture was cooled to 0° C., and DMAP (210 mg, 1.722 mmol) was added. The reaction mixture was stirred at 0° C. for 1 h. Then, ice bath was removed, and the reaction mixture was stirred at rt for 1 h. The reaction mixture was concentrated under reduced pressure, and the residue was purified by normal phase chromatography (0-20% EtOAc/DCM gradient: eluted at ~8% EtOAc). Fractions were combined and concentrated under reduced pressure to give Intermediate 99A (289 mg, 92% yield) as a white solid. MS (ESI) m/z: 365.0 (M+H)$^+$. $^1$H-NMR (500 MHz, CDCl$_3$) δ ppm 8.50 (s, 1H), 8.15 (d, J=9.6 Hz, 1H), 7.33 (d, J=9.6 Hz, 1H), 3.94 (s, 3H), 2.37-2.27 (m, 1H), 1.40-1.35 (m, 2H), 1.35-1.31 (m, 2H), 9F-NMR: (471 MHz, CDCl$_3$) δ ppm −73.14 (s, 3F).

INTERMEDIATE 99

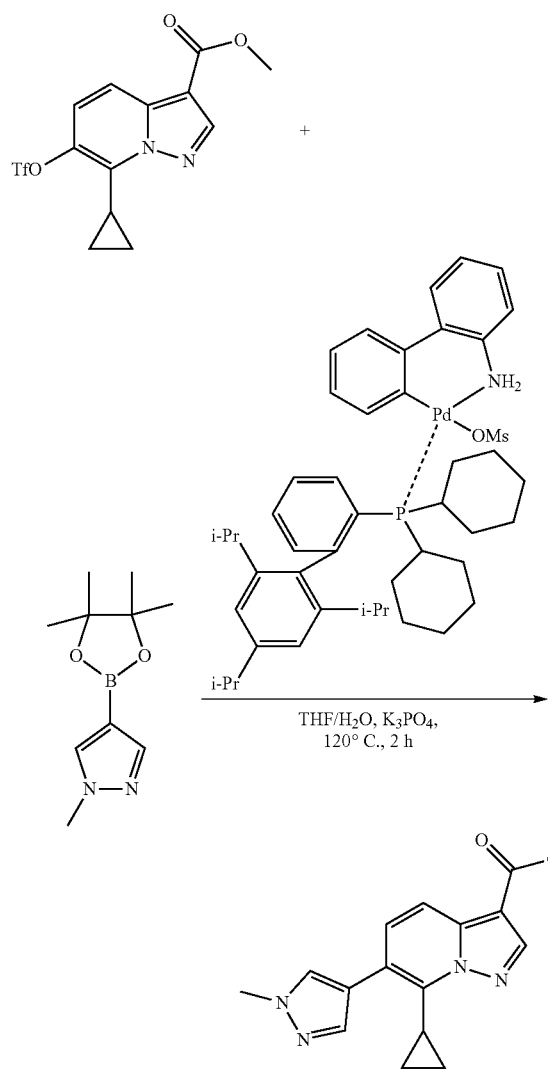

Intermediate 99A (50 mg, 0.137 mmol), 1-methyl-4-(4,4,5,5-tetramethyl-1,3,2-dioxaborolan-2-yl)-1H-pyrazole (86 mg, 0.412 mmol) and Pd-XPhos G3 (8.7 mg, 10.29 µmol) were placed in a pressure vial. Then THF (3 mL) and phosphoric acid, potassium salt (0.5 M aq.) (0.55 mL, 0.275 mmol) were added, and the reaction mixture was degassed (3×, vacuum/Ar). The pressure vial was capped, and the reaction mixture was stirred at 120° C. for 2 h. Most of the solvent was removed under reduced pressure, the obtained residue was purified by normal phase chromatography (0-80% EtOAc/DCM gradient; eluted at ~75% EtOAc). Fractions were combined and concentrated under reduced pressure to give Intermediate 99 (37 mg, 91% yield) as an amber syrup, which solidified upon standing to provide an off-white solid. MS (ESI) m/z: 297.1 (M+H)$^+$. 1H-NMR (500 MHz, CDCl$_3$) δ ppm 8.44 (s, 1H), 8.09 (dd, J=9.1, 0.8 Hz, 1H), 7.71 (s, 1H), 7.59 (s, 1H), 7.40 (d, J=9.1 Hz, 1H), 4.01 (s, 3H), 3.93 (s, 3H), 2.31 (tt, J=8.3, 5.8 Hz, 1H), 1.23-1.16 (m, 2H), 0.81-0.76 (m, 2H).

INTERMEDIATE 100

Preparation of 7-bromo-N-((aR)-6-((3-carbamoylpyridin-2-yl)oxy)spiro[3.3]heptan-2-yl)imidazo[1,2-a]pyridine-3-carboxamide

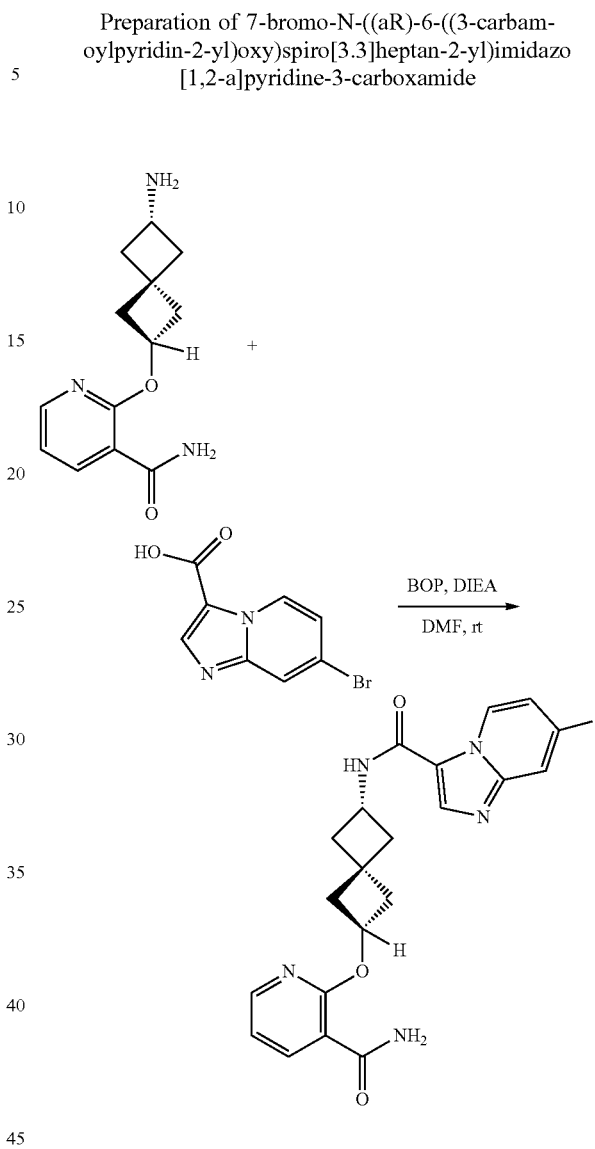

Example 42C (205 mg, 0.830 mmol) and 7-bromoimidazo[1,2-a]pyridine-3-carboxylic acid (200 mg, 0.830 mmol) were dissolved in anhydrous DMF (3 mL), then DIEA (0.73 mL, 4.15 mmol) was added, followed by BOP (477 mg, 1.079 mmol). The reaction mixture was stirred at rt for 1 h. The reaction mixture was quenched with MeOH (1.0 mL), and most for the solvent was removed under reduced pressure. To the obtained semi-solid residue, water was added portionwise with sonication (total volume ~25 mL), which resulted in white solid formation. The mixture was stirred at rt for 2 h, filtered using a filter cartridge, washed with water (3×5 mL), and dried in vacuum to afford Intermediate 100 (385 mg, 99% yield) as an off-white solid. MS (ESI) m/z: 469.9 (M+H)$^+$. $^1$H-NMR (500 MHz, DMSO-d$_6$) δ ppm 9.42 (d, J=7.4 Hz, 1H), 8.76 (d, J=7.4 Hz, 1H), 8.45 (s, 1H), 8.27 (dd, J=5.0, 1.9 Hz, 1H), 8.17 (dd, J=7.4, 2.2 Hz, 1H), 8.15 (d, J=1.4 Hz, 1H), 7.70 (br s, 1H), 7.59 (br s, 1H), 7.43 (dd, J=7.4, 1.9 Hz, 1H), 7.11 (dd, J=7.4, 5.0 Hz, 1H), 5.24 (quin, J=7.2 Hz, 1H), 4.39 (sxt, J=8.0 Hz, 1H), 2.72-2.65 (m, 1H), 2.42-2.36 (m, 1H), 2.29 (dd, J=11.3, 7.4 Hz, 1H), 2.26-2.22 (m, 1H), 2.22-2.15 (m, 2H).

INTERMEDIATE 101

Preparation of 6-bromo-N-((aR)-6-((3-carbamoylpyridin-2-yl)oxy)spiro[3.3]heptan-2-yl)-[1,2,3]triazolo[15-a]pyridine-3-carboxamide

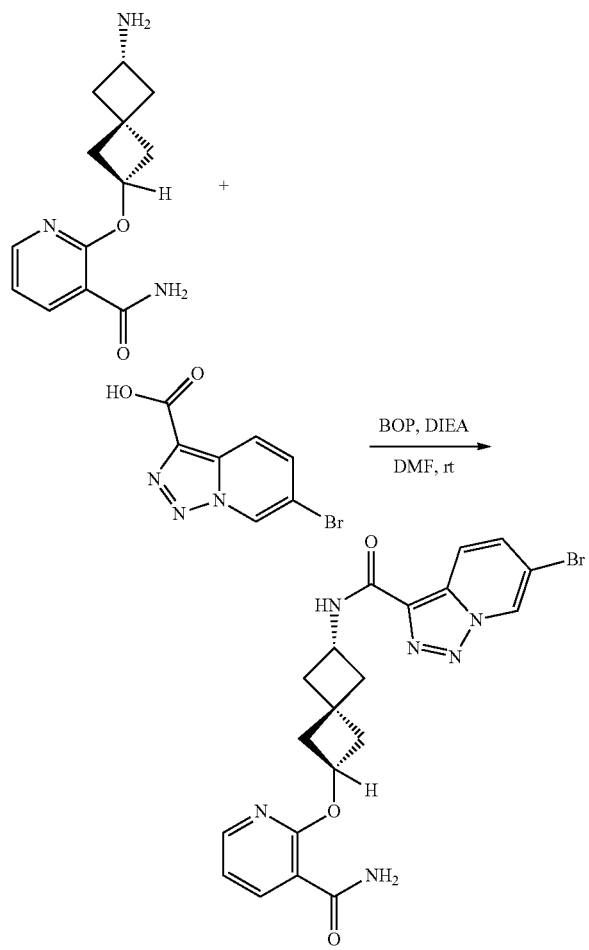

Example 42C (148 mg, 0.599 mmol) and 6-bromo-[1,2,3]triazolo[1,5-a]pyridine-3-carboxylic acid (145 mg, 0.599 mmol) were dissolved in anhydrous DMF (3 mL), then DIEA (0.52 mL, 3.00 mmol) was added, followed by BOP (344 mg, 0.779 mmol). The reaction mixture was stirred at rt for 1 h. The reaction mixture was quenched with MeOH (1.0 mL), and most for the solvent was removed under reduced pressure. To the obtained semi-solid residue, water was added portionwise with sonication (total volume ~25 mL), which resulted in white solid formation. The mixture was stirred at rt for 2 h, filtered using a filter cartridge, washed with water (3×5 mL), and dried in vacuum to afford Intermediate 101 (283 mg, 0.600 mmol, 100% yield) as an off-white solid. MS (ESI) m/z: 470.9 (M+H)+. 1H-NMR (500 MHz, DMSO-d6) δ ppm 9.65 (s, 1H), 8.95 (br d, J=8.0 Hz, 1H), 8.27 (br d, J=3.0 Hz, 1H), 8.21-8.09 (m, 2H), 7.75 (br d, J=9.1 Hz, 1H), 7.69 (br s, 1H), 7.58 (br s, 1H), 7.15-7.04 (m, 1H), 5.23 (br t, J=7.0 Hz, 1H), 4.53-4.34 (m, 1H), 2.81 (br d, J=10.7 Hz, 1H), 2.73-2.61 (m, 1H), 2.49-2.45 (m, 1H), 2.42 (br d, J=7.4 Hz, 1H), 2.29-2.23 (m, 1H), 2.21 (br dd, J=11.1, 7.8 Hz, 1H).

INTERMEDIATE 102

Preparation of methyl 6-morpholino-[1,2,3]triazolo[1,5-a]pyridine-3-carboxylate

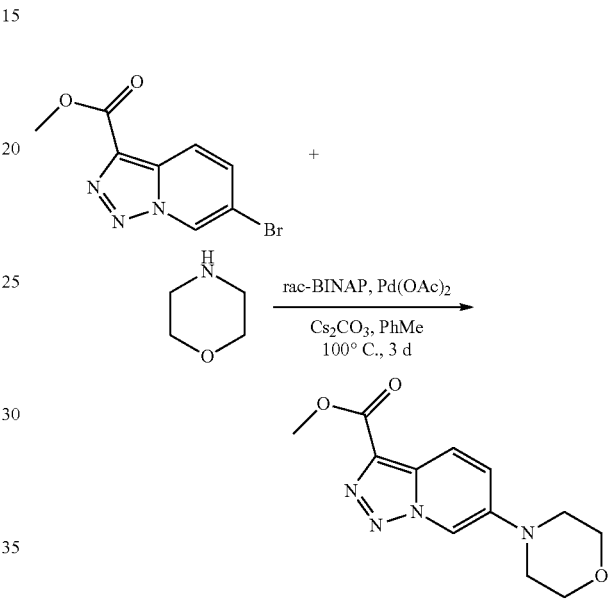

Methyl 6-bromo-[1,2,3]triazolo[1,5-a]pyridine-3-carboxylate (0.190 g, 0.742 mmol), palladium(II) acetate (10.0 mg, 0.045 mmol), BINAP (0.042 g, 0.067 mmol) and cesium carbonate (0.363 g, 1.113 mmol) were placed in a pressure vial. The reaction mixture was degassed (3× vacuum/Ar), then Toluene (2.473 mL) and morpholine (0.083 mL, 0.965 mmol) were added. The reaction mixture was degassed again, and stirred at 120° C. for 3 d Additional amounts of palladium(II) acetate (10.00 mg, 0.045 mmol), BINAP (0.042 g, 0.067 mmol), cesium carbonate (0.363 g, 1.113 mmol), morpholine (0.083 mL, 0.965 mmol) and toluene (2.473 mL) were added. The reaction mixture was degassed, and stirred at 130° C. for additional 16 h. Celite was added to the reaction mixture, and the solvent was removed under removed pressure. The crude product was purified by normal phase chromatography (0-100% EtOAc/hexanes gradient: eluted at ~65% EtOAc). Fractions were combined and concentrated under reduced pressure to give Intermediate 102 (0.020 g, 0.076 mmol, 10.28% yield) as a white solid. MS (ESI) m/z: 263.1 (M+H)+. 1H-NMR (500 MHz, DMSO-d6) δ ppm 8.61 (d, J=1.4 Hz, 1H), 8.02 (d, J=9.6 Hz, 1H), 7.79 (dd, J=9.6, 2.2 Hz, 1H), 3.91 (s, 3H), 3.82-3.74 (m, 4H), 3.26-3.19 (m, 4H).

INTERMEDIATE 103

Preparation of ethyl 1-(difluoromethyl)-6-morpholino-1H-indazole-3-carboxylate

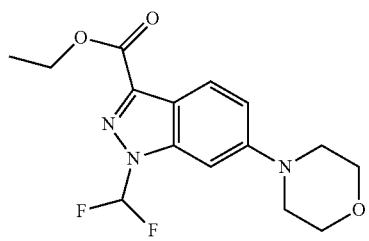 [SMILES: CCOC(=O)c1nn(C(F)F)c2cc(N3CCOCC3)ccc12]

INTERMEDIATE 103A

Preparation of 6-bromo-1-(difluoromethyl)-1H-indazole-3-carboxylate

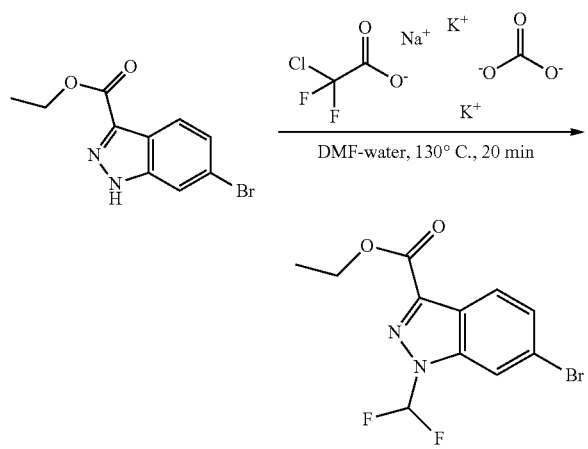

Ethyl 6-bromo-1H-indazole-3-carboxylate (0.150 g, 0.557 mmol), $K_2CO_3$ (0.154 g, 1.115 mmol), and sodium chlorodifluoroacetate (0.170 g, 1.115 mmol) were dissolved in DMF (2.53 mL) and water (0.25 mL). The reaction was stirred at 130° C. for 20 min (CAUTION: gas evolution observed; use open system w/ air condenser). Additional amounts of sodium chlorodifluoroacetate (0.170 g, 1.115 mmol) and $K_2CO_3$ (0.154 g, 1.115 mmol) were added, the reaction flask immersed into oil bath and stirred at 130° C. for additional 20 min. Reaction diluted with water (50 mL) and EtOAc (100 mL). Organic phase was separated, washed with water (3×25 mL), brine (1×25 mL) and dried ($Na_2SO_4$). EtOAc was removed under reduced pressure and the residue was purified by normal phase chromatography (0-75% EtOAc/hexanes gradient, eluted at ~25% EtOAc) to give Intermediate 103A (0.100 g, 56% yield) as a light-yellow solid. MS (ESI) m/z: 318.8 $(M+H)^+$. $^1$H-NMR (500 MHz, DMSO-$d_6$) δ ppm 8.14 (d, J=8.8 Hz, 1H), 8.02 (s, 1H), 7.56 (dd, J=8.7, 1.5 Hz, 1H), 7.52 (t, J=58.9 Hz, 1H), 4.55 (q, J=7.2 Hz, 2H), 1.50 (t, J=7.2 Hz, 3H).

INTERMEDIATE 103

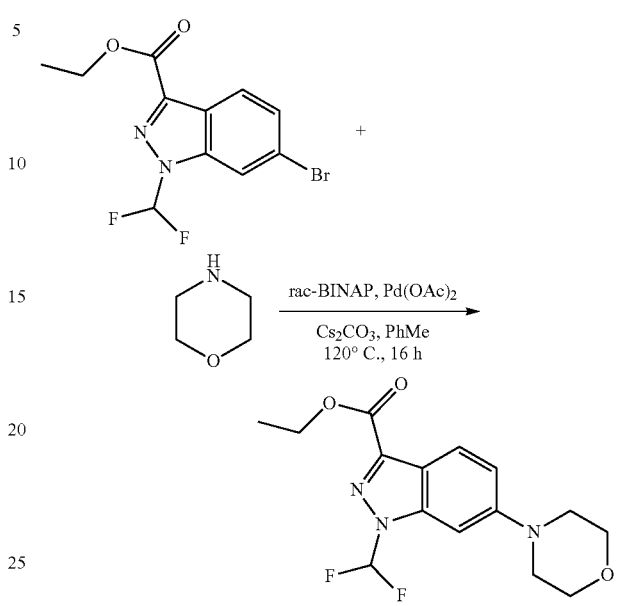

Intermediate 103A (0.100 g, 0.313 mmol), palladium(II) acetate (4.2 mg, 0.019 mmol), BINAP (0.018 g, 0.028 mmol) and cesium carbonate (0.153 g, 0.470 mmol) were placed in a pressure vial. The reaction mixture was degassed (3× vacuum/Ar), then toluene (1.05 mL) and morpholine (0.035 mL, 0.407 mmol) were added. The reaction mixture was degassed again, and stirred at 120° C. for 16 h. Celite was added to the reaction mixture, and the solvent was removed under removed pressure. The crude product was purified by normal phase chromatography (solid loading on Celite; 0-40% EtOAc/DCM gradient; eluted at ~22% EtOAc). Intermediate 103 (0.066 g, 65% yield). MS (ESI) m/z: 263.1 $(M+H)^+$. $^1$H-NMR (500 MHz, DMSO-$d_6$) δ ppm 8.07 (d, J=9.1 Hz, 1H), 7.50 (t, J=60.8 Hz, 1H), 7.13 (dd, J=9.1, 2.2 Hz, 1H), 7.06 (s, 1H), 4.53 (q, J=7.2 Hz, 2H), 3.97-3.86 (m, 4H), 3.35-3.26 (m, 4H), 1.49 (t, J=7.2 Hz, 3H). $^{19}$F-NMR: (471 MHz, DMSO-$d_6$) δ ppm −95.81 (s, 2F).

INTERMEDIATE 104

Preparation of ethyl 6-(benzyloxy)-7-chloro-[1,2,3]triazolo[1,5-a]pyridine-3-carboxylate

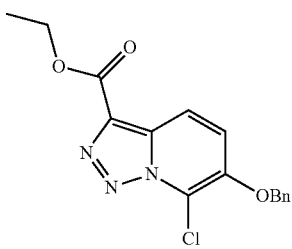 [SMILES: CCOC(=O)c1nnn2c(Cl)c(OCc3ccccc3)ccc12]

INTERMEDIATE 104A

Preparation of diethyl 2-(5-(benzyloxy)-6-chloropyridin-2-yl)malonate

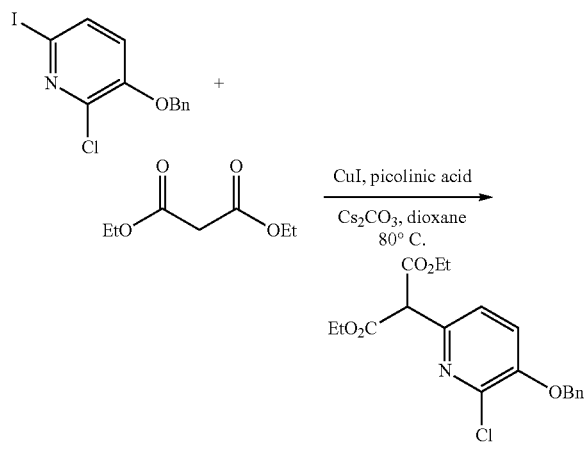

3-(benzyloxy)-2-chloro-6-iodopyridine (3.857 g, 11.2 mmol) dissolved in dioxane (75 mL). Added diethyl malonate (2.12 mL, 14.0 mmol), cesium carbonate (4.55 g, 14.0 mmol), and picolinic acid (0.275 g, 2.23 mmol). Degassed thoroughly. Added cuprous iodide (0.213 g, 1.12 mmol) and stirred at 80° C. for 16 hours. The reaction mixture was quenched with NH$_4$Cl (aq. std.; ~2.0 mL), Celite was added to the reaction mixture, and the solvent was removed under reduced pressure. The residue was purified by normal phase chromatography (0-50% EtOAc/hexanes gradient; eluted at ~33% EtOAc) to give diethyl Intermediate 104A (3.613 g, 86% yield) as a colorless oil. MS (ESI) m/z: 378.2 (M+H)$^+$. $^1$H-NMR (500 MHz, CDCl$_3$) δ ppm 7.71 (d, J=8.5 Hz, 1H), 7.50-7.46 (m, 2H), 7.45-7.39 (m, 3H), 7.38-7.33 (m, 1H), 5.27 (s, 2H), 5.04 (s, 1H), 4.21-4.12 (m, 4H), 1.18 (t, J=7.2 Hz, 6H).

INTERMEDIATE 104B

Preparation of ethyl 2-(5-(benzyloxy)-6-chloropyridin-2-yl)acetate

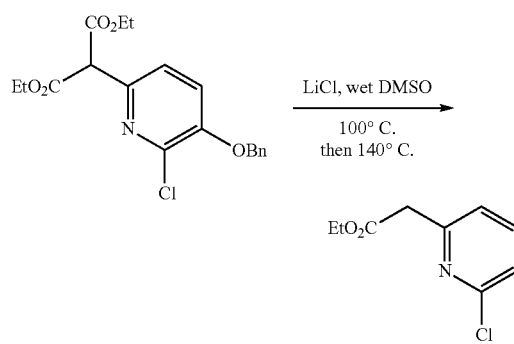

Intermediate 104A (3.613 g, 9.56 mmol) dissolved in DMSO (19.13 mL), then water (0.17 mL, 9.56 mmol) and lithium chloride (1.014 g, 23.91 mmol) were added. The reaction mixture was stirred at 100° C. for 16 hours. Additional amount of water (0.17 mL, 9.56 mmol) and lithium chloride (1.014 g, 23.91 mmol) were added, and the reaction mixture was stirred at 100° C. for additional 2 d. The reaction mixture was stirred at 140° C. for 3 h. The reaction mixture was diluted with EtOAc (300 mL), and water (100 mL). Organic phase was separated, washed with water (2×100 mL), brine (1×50 mL), and dried (Na$_2$SO$_4$). Solvent was removed under reduced pressure, and the residue was purified by normal phase chromatography (0-50% EtOAc/hexanes gradient; eluted at ~30% EtOAc). Fractions were combined and concentrated under reduced pressure to give Intermediate 104B (2.095 g, 72% yield) as a colorless oil. MS (ESI) m/z: 306.0 (M+H)$^+$. $^1$H-NMR (500 MHz, CDCl$_3$) δ ppm 7.49-7.43 (m, 2H), 7.43-7.38 (m, 2H), 7.37-7.32 (m, 1H), 7.23-7.15 (m, 2H), 5.18 (s, 2H), 4.18 (q, J=7.2 Hz, 2H), 3.76 (s, 2H), 1.27 (t, J=7.2 Hz, 3H).

INTERMEDIATE 104

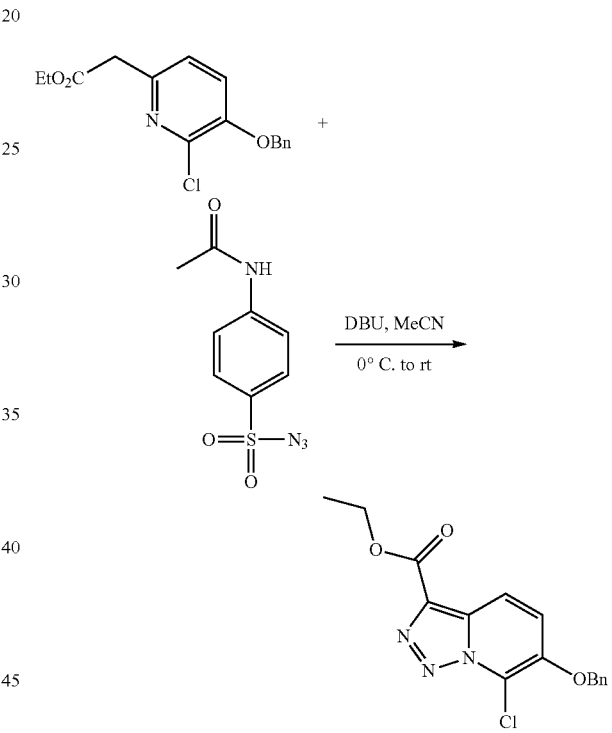

Intermediate 104B (1.037 g, 4.32 mmol) were dissolved in MeCN (10.3 mL) and the reaction mixture cooled to 0° C. before the addition of DBU (0.65 mL, 4.32 mmol) dropwise over 1 min. The stirred reaction mixture was stirred at 0° C. for 1 h. Cooling bath was removed, and the reaction mixture was stirred at rt for 14 h. The reaction mixture became heterogeneous. The reaction was quenched with saturated NH$_4$Cl (0.5 mL) and Celite was added. Solvent was removed under reduced pressure and the residue was purified by normal phase chromatography (solid loading on Celite; 0-40% EtOAc/hexanes gradient; eluted at ~24% EtOAc). Fractions were combined and concentrated under reduced pressure to give Intermediate 104 (0.847 g, 71% yield) as a white solid. MS (ESI) m/z: 331.9 (M+H)$^+$. $^1$H-NMR: (500 MHz, DMSO-d$_6$; 24° C.) δ ppm 8.23-7.98 (m, 1H), 7.94-7.70 (m, 1H), 7.49 (br d, J=6.6 Hz, 2H), 7.45-7.40 (m, 2H), 7.39-7.33 (m, 1H), 5.52-5.20 (m, 2H), 4.47-4.22 (m, 2H), 1.46-1.25 (m, 3H). $^1$H-NMR: (500 MHz, DMSO-d$_6$; 90° C.) δ ppm 7.94 (d, J=9.1 Hz, 1H), 7.79 (d, J=9.1 Hz, 1H), 7.51-7.46 (m, 2H), 7.44-7.38 (m, 2H), 7.38-7.32 (m, 1H), 5.31 (s, 2H), 4.37 (q, J=7.2 Hz, 2H), 1.34 (t, J=7.0 Hz, 3H).

INTERMEDIATE 105

Preparation of ethyl 6-(benzyloxy)-7-cyclopropyl-[1,2,3]triazolo[1,5-a]pyridine-3-carboxylate

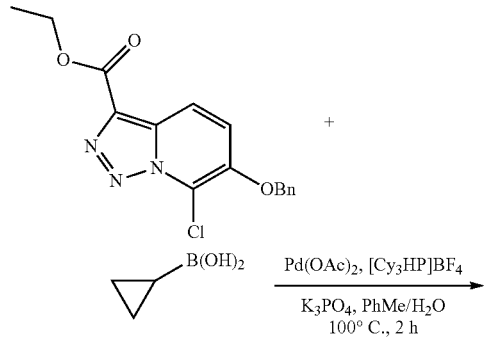

Intermediate 104 (300 mg, 0.904 mmol), cyclopropylboronic acid (311 mg, 3.62 mmol), palladium(II) acetate (10.2 mg, 0.045 mmol), tricyclohexylphosphonium tetrafluoroborate (33.3 mg, 0.090 mmol) and Phosphoric acid, potassium salt (576 mg, 2.71 mmol) were placed in a pressure vial, and the mixture was degassed (3× Ar/vacuum). Then, PhMe (5.0 mL) and water (0.1 mL) were added, and the reaction mixture was degassed again. Afterwards, the vial was capped, the reaction mixture was heated to 100° C. for 2 h. The reaction mixture was diluted with EtOAc, and Celite was added. Solvent was removed under reduced pressure, and the residue was purified by normal phase chromatography (solid loading on Celite; 0-20% EtOAc/DCM gradient; eluted at ~15% EtOAc). Fractions were combined and concentrated under reduced pressure to give Intermediate 105 (146 mg, 48% yield) as a white solid. MS (ESI) m/z: 338.1 (M+H)+. 1H-NMR: (500 MHz, DMSO-d6) δ ppm 8.03 (d, J=9.4 Hz, 1H), 7.88 (d, J=9.6 Hz, 1H), 7.50 (d, J=7.2 Hz, 2H), 7.46-7.35 (m, 3H), 5.28 (s, 2H), 4.39 (q, J=7.2 Hz, 2H), 2.60 (s, 1H), 1.47-1.40 (m, 2H), 1.37 (t, J=7.2 Hz, 3H), 1.17-1.12 (m, 2H).

INTERMEDIATE 106

Preparation of ethyl 6-(2-hydroxy-2-methyl-propoxy)-[1,2,3]triazolo[1,5-a]pyridine-3-carboxylate

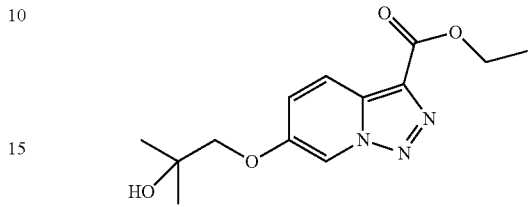

INTERMEDIATE 106A

Preparation of ethyl 6-hydroxy-[1,2,3]triazolo[1,5-a]pyridine-3-carboxylate

Intermediate 104 (300 mg, 0.904 mmol) was dissolved in THF (5 mL) and MeOH (5 mL), and TEA (1.26 mL, 9.04 mmol) was added. The reaction mixture was degassed (3× vacuum/Ar), then palladium on carbon (10 wt %) (28.9 mg, 0.027 mmol) was added.

The reaction mixture was degassed again, and it was stirred under dihydrogen atmosphere (1 atm; ballon) for 45 min. The reaction mixture was degassed again, and stirred under dihydrogen atmosphere (1 atm; ballon) for additional 75 min. Pd—C was filtered off using membrane filter, and the filtrate was concentrated to afford crude material containing Et3N—HCl. The residue was suspended in THF (5 mL), filtered through a pad of silica (~1 inch), pad washed with THF (3×5 mL). Combined organic fractions were concentrated to afford Intermediate 106A (168 mg, 90% yield) as a yellow solid. MS (ESI) m/z: 208.0 (M+H)+. 1H-NMR: (500 MHz, DMSO-d6) δ ppm 10.77-10.52 (br s, 1H), 8.58 (dd, J=1.9, 0.8 Hz, 1H), 8.05 (dd, J=9.5, 0.7 Hz, 1H), 7.46 (dd, J=9.4, 1.9 Hz, 1H), 4.38 (q, J=7.1 Hz, 2H), 1.37 (t, J=7.2 Hz, 3H).

INTERMEDIATE 106

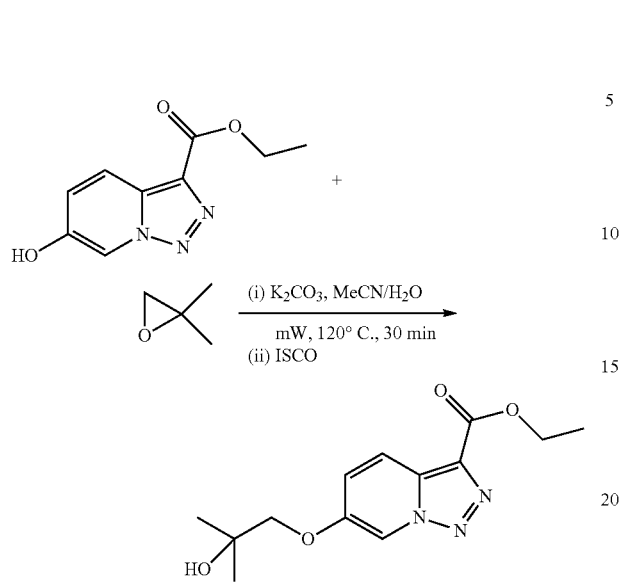

Intermediate 106A (0.168 g, 0.811 mmol) was suspended in MeCN (3.00 mL), then 2,2-dimethyloxirane (0.72 mL, 8.11 mmol), K$_2$CO$_3$ (0.448 g, 3.24 mmol) and water (0.200 mL) were added. The reaction mixture was stirred under microwave irradiation at 120° C. for 30 min. The reaction mixture was diluted with EtOAc, Celite was added, and the reaction mixture was concentrated. The residue was purified by normal phase chromatography (solid loading on Celite; 0-100% EtOAc/hexanes gradient; eluted at 100% EtOAc). Fractions were combined and concentrated under reduced pressure to give Intermediate 106 (0.022 g, 10% yield) as a white solid. MS (ESI) m's: 266.0 (M+H)$^+$.

INTERMEDIATE 107

Preparation of ethyl 6-(benzyloxy)-5-chloro-3-cyclopropylindolizine-1-carboxylate

INTERMEDIATE 108

Preparation of ethyl 6-(benzyloxy)-5-chloro-2-cyclopropylindolizine-1-carboxylate

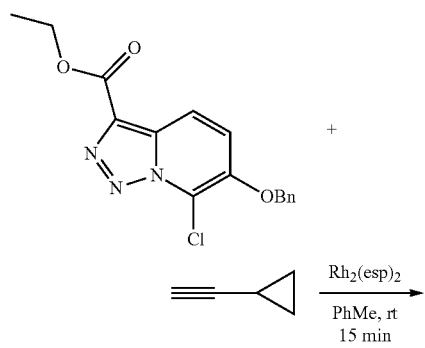

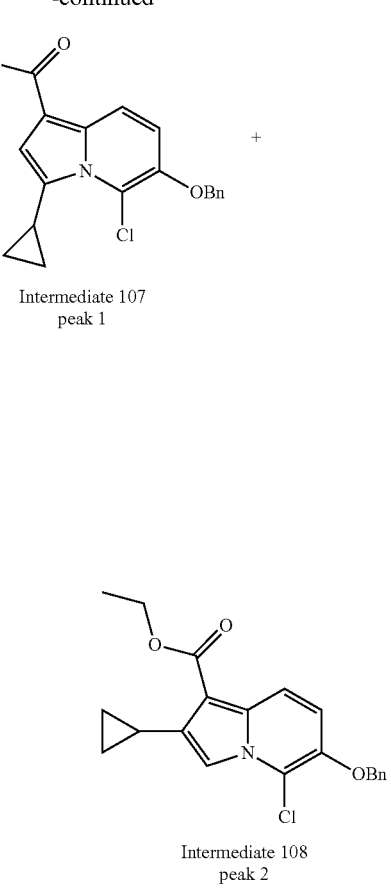

Intermediate 107
peak 1

Intermediate 108
peak 2

A round bottom flask containing a stirring bar was charged with Intermediate 104 (100 mg, 0.301 mmol), then dry toluene (2.5 mL) and ethynylcyclopropane (0.032 mL, 0.377 mmol) were added. The mixture was stirred for 5 min at rt (clear solution obtained), then bis[rhodium(α,α,α',α'-tetramethyl-1,3-benzenedipropionic acid)] (2.3 mg, 3.0 μmol) was added in one portion (immediately upon addition extensive bubbling was observed).

The reaction mixture was stirred at rt for 15 min. The reaction mixture was allowed to stir at rt overnight. The reaction mixture was concentrated under reduced pressure, and the residue was purified by flash chromatography (0-50% EtOAc/hexanes gradient) affording two products.

Intermediate 107 (25 mg, 22% yield) as a white solid eluted at ~26% EtOAc. MS (ESI) m/z: 370.0 (M+H)$^+$. $^1$H-NMR (500 MHz, DMSO-d$_6$) δ ppm 8.13 (d, J=9.6 Hz, 1H), 7.51-7.45 (m, 2H), 7.42-7.38 (m, 2H), 7.37-7.32 (m, 1H), 6.99 (d, J=1.1 Hz, 1H), 6.94 (d, J=9.6 Hz, 1H), 5.14 (s, 2H), 4.33 (q, J=7.0 Hz, 2H), 2.53 (ttd, J=8.1, 5.3, 0.8 Hz, 1H), 1.39 (t, J=7.2 Hz, 3H), 1.04-0.97 (m, 2H), 0.90-0.86 (m, 2H).

Intermediate 108 (48 mg, 43% yield) as a colorless syrup eluted at ~38% EtOAc. MS (ESI) m/z: 370.0 (M+H)$^+$. $^1$H-NMR (500 MHz, DMSO-d$_6$) δ ppm 7.48-7.44 (m, 2H), 7.42-7.38 (m, 2H), 7.36-7.33 (m, 1H), 7.31 (d, J=8.3 Hz, 1H), 7.16 (d, J=8.3 Hz, 1H), 6.52 (s, 1H), 5.16 (s, 2H), 4.23-4.09 (m, 2H), 1.88 (tt, J=7.9, 4.9 Hz, 1H), 1.23 (t, J=7.2 Hz, 3H), 1.00-0.95 (m, 1H), 0.92-0.88 (m, 1H), 0.87-0.82 (m, 2H).

INTERMEDIATE 109

Preparation of 1-(4-cyano-2-fluorophenyl)-5-methyl-1H-pyrazole-4-carboxylic acid

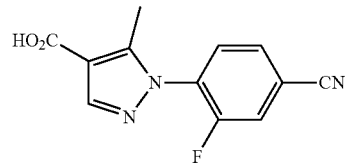 [SMILES: Cc1c(C(=O)O)cnn1-c1ccc(C#N)cc1F]

INTERMEDIATE 109A

Preparation of tert-butyl 1-(4-bromo-2-fluorophenyl)-5-methyl-1H-pyrazole-4-carboxylate

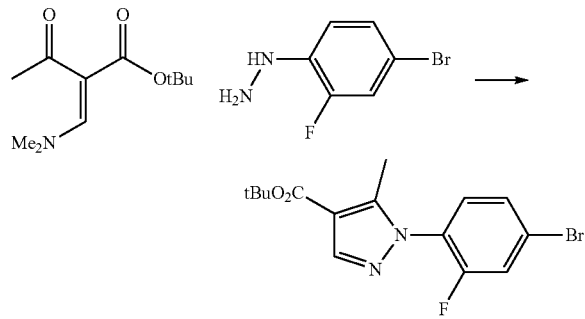

An acetonitrile solution of (E)-tert-butyl 2-((dimethylamino)methylene)-3-oxobutanoate (300 mg, 1.407 mmol) and TEA (196 μl, 1.407 mmol) was added to a solution of (4-bromo-2-fluorophenyl)hydrazine, HCl (340 mg, 1.407 mmol) in acetonitrile (7033 μl). The reaction mixture was stirred at rt overnight. The solution was concentrated and the residue was purified by silica gel flash column chromatography to give tert-butyl 1-(4-bromo-2-fluorophenyl)-5-methyl-1H-pyrazole-4-carboxylate (327 mg, 65%) as an orange colored oil. $^1$H NMR (400 MHz, CDCl$_3$) δ 8.03 (s, 1H), 7.54-7.43 (m, 2H), 7.38-7.31 (m, 1H), 2.45 (d, J=2.0 Hz, 3H), 1.67-1.54 (s, 9H). MS (ESI) m/z: 356.9 (M+H)$^+$.

INTERMEDIATE 109B

Preparation of tert-butyl 1-(4-cyano-2-fluorophenyl)-5-methyl-1H-pyrazole-4-carboxylate

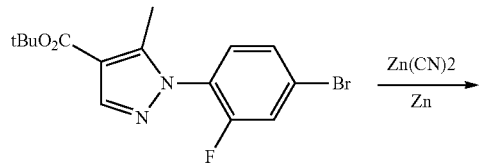

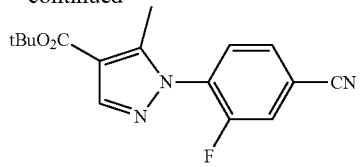

tert-Butyl 1-(4-bromo-2-fluorophenyl)-5-methyl-1H-pyrazole-4-carboxylate (110 mg, 0.310 mmol) in a microwave tube was added dicyanozinc (36.4 mg, 0.310 mmol), zinc (6.07 mg, 0.093 mmol) and DMF (3097 μl). The reaction was bubbled through Ar for several minutes. Bis(tri-t-butylphosphine)palladium(0) (15.83 mg, 0.031 mmol) was added and the reaction was sealed and heated at 80° C. overnight. The reaction mixture was filtered and concentrated. The residue was purified by silica gel flash column chromatography to give tert-butyl 1-(4-cyano-2-fluorophenyl)-5-methyl-1H-pyrazole-4-carboxylate (35 mg, 38%) as a colorless oil. (ESI) m/z: 302.0 (M+H)$^+$.

INTERMEDIATE 109

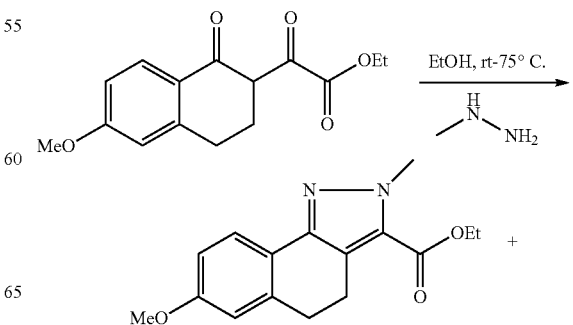

tert-Butyl 1-(4-cyano-2-fluorophenyl)-5-methyl-1H-pyrazole-4-carboxylate (35 mg, 0.116 mmol) in DCM (1162 μl) was added TFA (268 μl, 3.48 mmol). The reaction was stirred at rt overnight. The reaction was concentrated to give 1-(4-cyano-2-fluorophenyl)-5-methyl-1H-pyrazole-4-carboxylic acid as an off white solid. The material was used as is in the next step. MS (ESI) m/z: 246.0 (M+H)$^+$.

Preparation of ethyl 7-methoxy-2-methyl-4,5-dihydro-2H-benzo[g]indazole-3-carboxylate (Intermediate 110A) and ethyl 7-methoxy-1-methyl-4,5-dihydro-1H-benzo[g]indazole-3-carboxylate (Intermediate 11A)

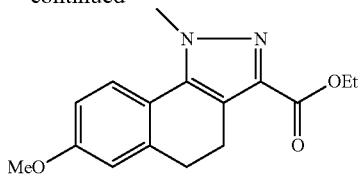

Ethyl 2-(6-methoxy-1-oxo-1,2,3,4-tetrahydronaphthalen-2-yl)-2-oxoacetate (5 g, 18.10 mmol) in Ethanol (20 mL) was added methylhydrazine (0.953 mL, 18.10 mmol) dropwise. The resulting dark brown solution was heated at 75° C. for 3 hr. The reaction mixture was cooled down to room temperature, diluted with EtOAc, washed with cold 1N HCl, then water and brine, dried over MgSO$_4$, filtered off solid, concentrated under vacuum which afforded an oily brown crude product. The aliquot was purified by prep HPLC to give Intermediate 110A (ethyl 7-methoxy-2-methyl-4,5-dihydro-2H-benzo[g]indazole-3-carboxylate) as a white solid. $^1$H NMR (500 MHz, CDCl$_3$) δ 7.75 (d, J=8.5 Hz, 1H), 6.83 (dd, J=8.4, 2.6 Hz, 1H), 6.80 (d, J=2.5 Hz, 1H), 4.39 (q, J=7.2 Hz, 2H), 4.20 (s, 3H), 3.84 (s, 3H), 3.04-2.97 (m, 2H), 2.96-2.91 (m, 2H), 1.42 (t, J=7.2 Hz, 3H). MS (ESI) m/z: 287.1 (M+H)$^+$ and Intermediate 111A (ethyl 7-methoxy-1-methyl-4,5-dihydro-1H-benzo[g]indazole-3-carboxylate). $^1$H NMR (500 MHz, CDCl$_3$) δ 7.51 (d, J=8.5 Hz, 1H), 6.91 (d, J=2.8 Hz, 1H), 6.85 (dd, J=8.5, 2.5 Hz, 1H), 4.42 (q, J=7.2 Hz, 2H), 4.21 (s, 3H), 3.85 (s, 3H), 3.04-2.97 (m, 2H), 2.94-2.88 (m, 2H), 1.42 (t, J=7.2 Hz, 3H). MS (ESI) m/z: 287.1 (M+H)$^+$.

Preparation of 7-methoxy-2-methyl-4,5-dihydro-2H-benzo[g]indazole-3-carboxylic acid (Intermediate 110) and methoxy-1-methyl-4,5-dihydro-1H-benzo[g]indazole-3-carboxylic acid (Intermediate 111)

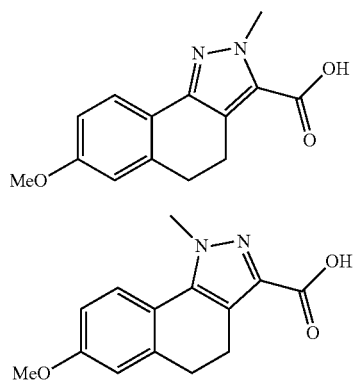

Intermediate 110

Intemediate 111

Intermediate 110 and Intermediate 11 were prepared by hydrolysis of Intermediate 110A and Intermediate 111A, respectively.

Intermediate 110; $^1$H NMR (500 MHz, CDCl$_3$) δ=7.79 (d, J=8.3 Hz, 1H), 6.85 (dd, J=2.6, 8.4 Hz, 1H), 6.82 (d, J=2.5 Hz, 1H), 4.24 (s, 3H), 3.86 (s, 3H), 3.12-3.07 (m, 2H), 3.00-2.95 (m, 2H). MS (ESI) m/z: 259.1 (M+H)$^+$.

Intermediate 111; $^1$H NMR (500 MHz, CDCl$_3$) δ=7.53 (d, J=8.5 Hz, 1H), 6.93 (d, J=2.5 Hz, 1H), 6.87 (dd, J=2.6, 8.7 Hz, 1H), 4.23 (s, 3H), 3.87 (s, 3H), 3.05-3.00 (m, 2H), 2.95-2.91 (m, 2H). MS (ESI) m/z: 259.1 (M+H)$^+$.

INTERMEDIATE 112

Preparation of 1-(1-amino-2-methyl-1-oxopropan-2-yl)-6-bromo-N-((aR)-6-((3-carbamoylpyridin-2-yl)oxy)spiro[3.3]heptan-2-yl)-1H-indazole-3-carboxamide

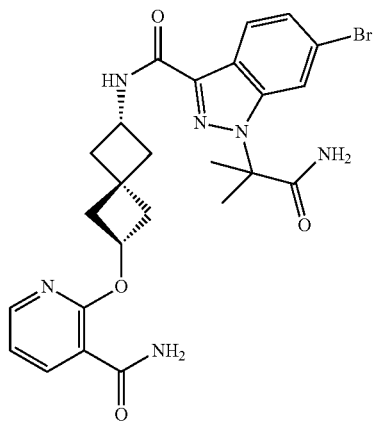

INTERMEDIATE 112A

Preparation of 6-bromo-1H-indazole-3-carboxylic acid

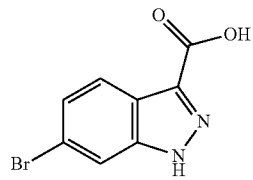 [SMILES: O=C(O)c1n[nH]c2cc(Br)ccc12]

To a round bottom flask containing 6-bromoindoline-2,3-dione (1 g, 4.42 mmol) was added NaOH (4.9 mL, 4.87 mmol) and stirred at 50° C. for 1 h. The reaction mixture is then brought to rt and cooled to 0° C. before adding a solution of NaNO$_2$ (0.31 g, 4.42 mmol) in H$_2$O (1.1 mL) dropwise over a period of 15 mins. The above mixture was then added to a solution of H$_2$O (9 mL) and H$_2$SO$_4$ (4.6 mL) that is precooled to 0° C. dropwise over a period of 15 mins. The crude mixture was then added to a mix of conc. HCl (4 mL) and SnCl$_2$.2H$_2$O (2.5 g, 11.06 mmol) at rt and continued to stir at rt for 1 h. The solids are then filtered and dried to give the crude product 6-bromo-1H-indazole-3-carboxylic acid (Intermediate 112A) (1.1 g, 93%) as a tan solid. The crude product was taken to the next step without further purification.

INTERMEDIATE 112B

Preparation of ethyl 6-bromo-1H-indazole-3-carboxylate

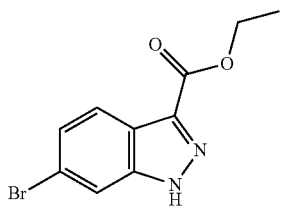

To a solution of Intermediate 112A (4.4 g, 18.25 mmol) in EtOH (100 mL) was added SOCl$_2$ (6.66 mL, 91 mmol) and refluxed for 3 h. The reaction mixture was concentrated and purified using flash column chromatography to afford ethyl 6-bromo-1H-indazole-3-carboxylate (Intermediate 112B) (2.1 g, 39%) as tan solid. MS(ESI) m/z: 270.9 (M+H)$^+$. $^1$H NMR (400 MHz, CDCl$_3$) δ 8.08 (d, J=8.6 Hz, 1H), 7.95 (s, 1H), 7.44 (d, J=8.6 Hz, 1H), 4.57 (q, J=7.0 Hz, 2H), 1.51 (t, J=7.2 Hz, 3H).

112C. Preparation of ethyl 1-(1-amino-2-methyl-1-oxopropan-2-yl)-6-bromo-1H-indazole-3-carboxylate

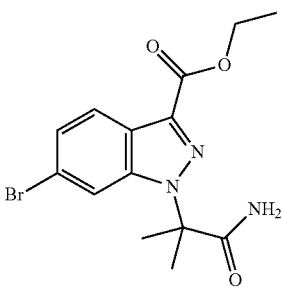 [SMILES: CCOC(=O)c1nn(C(C)(C)C(N)=O)c2cc(Br)ccc12]

DMF (12 mL) was added to a vial containing Intermediate 112B (2.1 g, 7.80 mmol), Cs$_2$CO$_3$ (2.54 g, 7.80 mmol), and 2-bromo-2-methylpropanamide (2.59 g, 15.61 mmol). The suspension was heated to 90° C. for 1 h, at which point the starting material had been consumed and a nonpolar product appeared on TLC. The reaction mixture was then concentrated and purified using flash column chromatography to afford ethyl 1-(1-amino-2-methyl-1-oxopropan-2-yl)-6-bromo-1H-indazole-3-carboxylate (Intermediate 112C) (1.74 g, 60%) as clear oil. MS(ESI) m/z: 355.9 (M+H, Bromine isotope peak). $^1$H NMR (400 MHz, CDCl$_3$) δ 8.07 (dd, J=8.7, 0.6 Hz, 1H), 7.69 (dd, J=1.4, 0.6 Hz, 1H), 7.43 (dd, J=8.7, 1.4 Hz, 1H), 4.51 (q, J=7.0 Hz, 2H), 1.97 (d, J=4.4 Hz, 6H), 1.53-1.45 (m, 3H).

INTERMEDIATE 112D

Preparation of 1-(1-amino-2-methyl-1-oxopropan-2-yl)-6-bromo-1H-indazole-3-carboxylic acid, HCl

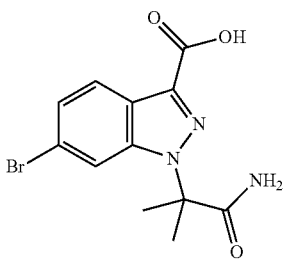 [SMILES: CC(C)(C(N)=O)n1nc(C(=O)O)c2ccc(Br)cc21]

To a solution of Intermediate 112C (1.74 g, 4.91 mmol) in THF (40 mL) was added LiOH (4.91 mL, 9.82 mmol) and stirred at rt for 4 h. The reaction mixture was then acidified with 1N HCl, extracted with EtOAc (30 mL) to afford 1-(1-amino-2-methyl-1-oxopropan-2-yl)-6-bromo-1H-indazole-3-carboxylic acid (Intermediate 112D) (1.47 g, 87%). MS(ESI) m/z: 327.9 (M+H, Bromine isotope peak). $^1$H NMR (400 MHz, DMSO-d$_6$) δ 8.09-8.04 (m, 1H), 7.61 (d, J=1.1 Hz, 1H), 7.54-7.43 (m, 3H), 3.31 (br. s., 1H), 1.84 (s, 3H), 1.79 (s, 3H).

INTERMEDIATE 112

Example 42C (15 mg, 0.061 mmol) and Intermediate 112D (19.86 mg, 0.061 mmol) were dissolved in anhydrous DMF (1.0 mL), then DIEA (0.053 mL, 0.303 mmol) was added, followed by BOP (29.5 mg, 0.067 mmol). The reaction mixture was stirred at rt for 1 h, quenched with MeOH (0.1 mL), diluted with DMF (2 mL total volume), filtered, and purified by reverse phase HPLC to give Intermediate 112 (15 mg, 42%). MS(ESI) m/z: 557.1 (M+H, Bromine isotope peak). $^1$H NMR (400 MHz, DMSO-d$_6$) δ 8.53 (br. s., 1H), 8.25 (d, J=4.8 Hz, 1H), 8.15 (d, J=6.0 Hz, 1H), 8.10 (d, J=8.6 Hz, 1H), 7.67 (d, J=13.9 Hz, 2H), 7.53 (s, 1H), 7.48 (d, J=16.2 Hz, 2H), 7.40 (d, J=8.7 Hz, 1H), 7.10 (dd, J=7.4, 4.9 Hz, 1H), 5.21 (t, J=7.1 Hz, 1H), 4.42 (m, 1H), 2.73-2.62 (m, 1H), 2.48-2.39 (m, 1H), 2.35-2.15 (m, 5H), 1.79 (s, 6H), 1.14 (t, J=7.3 Hz, 1H).

INTERMEDIATE 113

Preparation of 6-bromo-1-(2-cyanopropan-2-yl)-1H-indazole-3-carboxylic acid

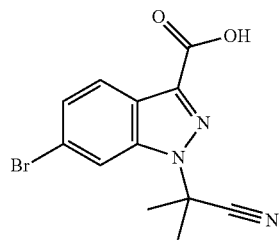 [SMILES: CC(C)(C#N)n1nc(C(=O)O)c2ccc(Br)cc21]

To a mixture of Intermediate 112C (815 mg, 2.25 mmol), pyridine (0.364 mL, 4.50 mmol) and trifluoroacetic anhydride (0.476 mL, 3.37 mmol) at 0° C. was added THF (20 mL) and stirred at the same temperature for 2 h. The reaction mixture was then raised to rt and stirred at rt o.n. The reaction mixture was concentrated and then acidified with 1N HCl, extracted with EtOAc (30 mL) to afford 6-bromo-1-(2-cyanopropan-2-yl)-1H-indazole-3-carboxylic acid (Intermediate 113) (0.69 g, 95%). MS(ESI) m/z: 308.0 (M+H, Bromine isotope peak).

INTERMEDIATE 114

Preparation of methyl 1-(1-amino-2-methyl-1-oxo-propan-2-yl)-6-(2-hydroxy-2-methylpropoxy)-1H-indazole-3-carboxylate

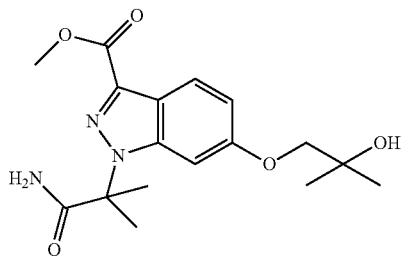 [SMILES: COC(=O)c1nn(C(C)(C)C(N)=O)c2cc(OCC(C)(C)O)ccc12]

INTERMEDIATE 114A

Preparation of methyl 1-(1-amino-2-methyl-1-oxo-propan-2-yl)-6-(benzyloxy)-1H-indazole-3-carboxylate

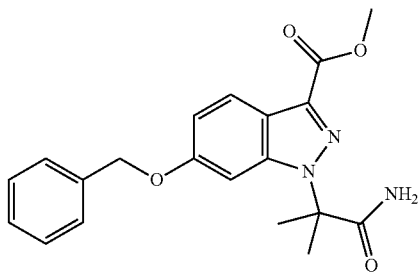 [SMILES: COC(=O)c1nn(C(C)(C)C(N)=O)c2cc(OCc3ccccc3)ccc12]

To a vial containing methyl 6-(benzyloxy)-1H-indazole-3-carboxylate (260 mg, 0.921 mmol), Cs$_2$CO$_3$ (300 mg, 0.921 mmol), and 2-bromo-2-methylpropanamide (306 mg, 1.842 mmol) was added DMF (2 mL). The suspension was heated to 90° C. for 1 h, at which point the starting material had been consumed and a nonpolar product appeared on TLC. The reaction mixture was then concentrated and purified using flash column chromatography to afford methyl 1-(1-amino-2-methyl-1-oxopropan-2-yl)-6-(benzyloxy)-1H-indazole-3-carboxylate (Intermediate 114A) (116 mg, 31%) as clear oil. MS(ESI) m/z: 368.2 (M+H).

INTERMEDIATE 114B

Preparation of methyl 1-(1-amino-2-methyl-1-oxo-propan-2-yl)-6-hydroxy-1H-indazole-3-carboxylate

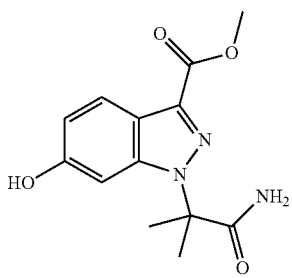 [SMILES: COC(=O)c1nn(C(C)(C)C(N)=O)c2cc(O)ccc12]

To a degassed solution of Intermediate 114A (116 mg, 0.316 mmol) in EtOH (10 mL) was added Pd—C (33.6 mg, 0.032 mmol) and stirred at 55 psi under hydrogen for 1 h. The reaction mix was then filtered over a pad of Celite® and concentrated to give the crude product, methyl 1-(1-amino-2-methyl-1-oxopropan-2-yl)-6-hydroxy-1H-indazole-3-carboxylate (Intermediate 114B) (88 mg, 100%/o) which is used as is in the next step. MS(ESI) m/z: 278.1 (M+H).

INTERMEDIATE 114

Intermediate 114B (75 mg, 0.270 mmol) was suspended in CH$_3$CN (4 mL), then 2,2-dimethyloxirane (0.241 mL, 2.70 mmol), K$_2$CO$_3$ (150 mg, 1.082 mmol) and H$_2$O (0.267 mL) were added. The reaction mixture was stirred under microwave irradiation at 120° C. for 30 min. The reaction mixture was concentrated and the residue was purified by flash column chromatography to afford methyl 1-(1-amino-2-methyl-1-oxopropan-2-yl)-6-(2-hydroxy-2-methyl-propoxy)-1H-indazole-3-carboxylate (Intermediate 114) (50 mg, 51%). MS(ESI) m/z: 350.1 (M+H).

INTERMEDIATE 115

Preparation of 2-bromo-N-((aR)-6-((3-carbam-oylpyridin-2-yl)oxy)spiro[3.3]heptan-2-yl)thiazole-5-carboxamide

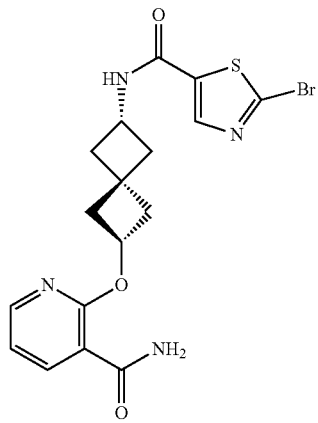

To a vial containing Example 42C (100 mg, 0.404 mmol) and 2-bromothiazole-5-carboxylic acid (84 mg, 0.404 mmol) was added anhydrous DMF (1.0 mL), DIEA (0.353 mL, 2.022 mmol), followed by BOP (197 mg, 0.445 mmol). The reaction mixture was stirred at rt for 1 h. The reaction mixture was then slowly added to ice cold water dropwise and the crashed product is filtered out to afford 2-bromo-N-((aR)-6-((3-carbamoylpyridin-2-yl)oxy)spiro[3.3]heptan-2-yl)thiazole-5-carboxamide (Intermediate 115) (740 mg, 66%) as tan solid. MS(ESI) m: 438.9 (M+H, Bromine isotope peak). $^1$H NMR (400 MHz, DMSO-$d_6$) δ 8.88 (d, J=7.3 Hz, 1H), 8.30-8.24 (m, 1H), 8.22 (s, 1H), 8.16 (dd, J=7.4, 2.1 Hz, 1H), 7.75-7.52 (m, 2H), 7.10 (dd, J=7.5, 4.8 Hz, 1H), 5.22 (quin. J=7.2 Hz, 1H), 4.34-4.21 (m, 1H), 2.65 (dt, J=11.5, 5.8 Hz, 1H), 2.47-2.40 (m, 2H), 2.38-2.30 (m, 1H), 2.29-2.08 (m, 4H).

INTERMEDIATE 116

Preparation of methyl 6-(benzyloxy)-3-((dimethylamino)methyl)imidazo[1,5-a]pyridine-1-carboxylate

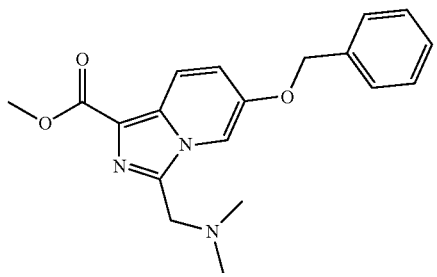 [SMILES: COC(=O)c1nc(CN(C)C)n2cc(OCc3ccccc3)ccc12]

INTERMEDIATE 116A

Preparation of methyl 6-(benzyloxy)imidazo[1,5-a]pyridine-1-carboxylate

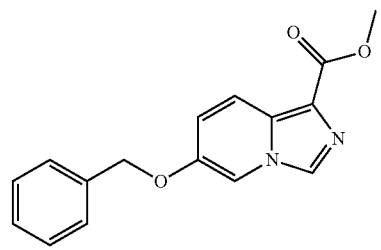 [SMILES: COC(=O)c1ncn2cc(OCc3ccccc3)ccc12]

A neat solution of methyl 2-amino-2-(5-(benzyloxy)pyridin-2-yl)acetate (500 mg, 1.836 mmol) in trimethyl orthoformate (5 mL, 45.2 mmol) was heated to 150° C. for 7 mins in a microwave vial. The reaction mixture was then allowed to cool down to rt, concentrated and purified using flash column chromatography to afford methyl 6-(benzyloxy) imidazo[1,5-a]pyridine-1-carboxylate (Intermediate 116A) (75 mg, 14%). MS(ESI) m/z: 283.0 (M+H).

INTERMEDIATE 116B

Preparation of methyl 6-(benzyloxy)-3-formylimidazo[1,5-a]pyridine-1-carboxylate

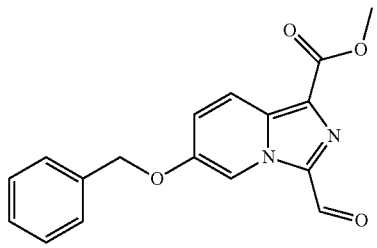 [SMILES: COC(=O)c1nc(C=O)n2cc(OCc3ccccc3)ccc12]

To a solution of Intermediate 116A (150 mg, 0.531 mmol) in DMF (3 mL) was added POCl$_3$ (0.099 mL, 1.063 mmol) and heated to 115° C. for 3 h. The reaction mixture was then slowly added to a solution of ice cold NaHCO$_3$ and then extracted with EtOAc. The crude product is then purified by flash column chromatography to afford methyl 6-(benzyloxy)-3-formylimidazo[1,5-a]pyridine-1-carboxylate (Intermediate 116B) (40 mg, 23%). MS(ESI) m/z: 311.0 (M+H).

INTERMEDIATE 116

To a solution of Intermediate 116B (40 mg, 0.129 mmol) in DCM (3 mL) was added dimethylamine in MeOH (0.097 mL, 0.193 mmol) and stirred at rt for 30 mins. To this mixture was then added sodium triacetoxyborohydride (54.6 mg, 0.258 mmol) and then stirred at rt for 6 h. The reaction mixture was quenched with brine, extracted with EtOAc and purified using flash column chromatography to afford methyl 6-(benzyloxy)-3-((dimethylamino)methyl)imidazo [1,5-a]pyridine-1-carboxylate (Intermediate 116) (28 mg, 61%). MS(ESI) m/z: 340.0 (M+H).

INTERMEDIATE 117

Preparation of 6-bromo-2-methyl-2H-indazole-4-carboxylic acid and 6-bromo-1-methyl-1H-indazole-4-carboxylic acid

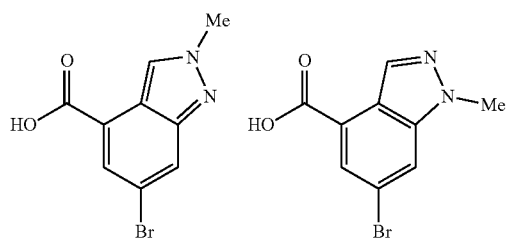 [SMILES: Cn1cc2c(C(=O)O)cc(Br)cc2n1 ; Cn1ncc2c(C(=O)O)cc(Br)cc21]

Methyl 6-bromo-1H-indazole-4-carboxylate (0.2 g, 0.784 mmol) and MeI (0.11 g, 0.784 mmol) dissolved in CH$_3$CN (5 mL). Cs$_2$CO$_3$ (0.255 g, 0.784 mmol) was added and the reaction was heated to 80° C. for 3 hours, at which point the indazole was methylated and the ester had converted to the acid. The reaction was cooled to rt and filtered and the filtrate was concentrated. The residue (0.14 g, 70% yield) was used as a crude mixture of 2 regioisomers. MS (ESI) m/z: 255.8 (M+H)$^+$.

INTERMEDIATE 118

Preparation of 6-bromo-3-(trifluoromethyl)imidazo[1,5-a]pyridine-1-carboxylic acid

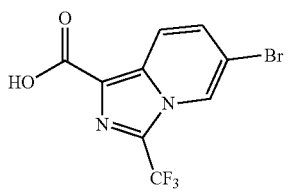 [SMILES: O=C(O)c1nc(C(F)(F)F)n2cc(Br)ccc12]

INTERMEDIATE 118A

Preparation of ethyl 2-(5-bromopyridin-2-yl)acetate

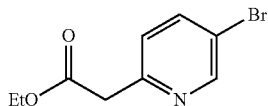

5-bromo-2-iodopyridine (20 g, 70.4 mmol) was dissolved in dioxane (90 mL). Diethyl malonate (13.54 g, 85 mmol), $Cs_2CO_3$ (34.4 g, 106 mmol), and picolinic acid (1.74 g, 14.09 mmol) were then added. The suspension was degassed thoroughly by 3 evacuation and nitrogen-back-fill cycles. Next, CuI (1.34 g, 7.04 mmol) was added and the reaction was stirred at 80° C. under nitrogen atmosphere for 5 hours. The reaction was then cooled to rt and diluted with 500 mL water and extracted with 100 mL EtOAc×4. The organic layers were concentrated and the residue was dissolved in DMSO (250 mL) and LiCl (2.99 g, 70.4 mmol) in 10 mL water was added. The reaction was heated to 150° C. for 3 hours (observation of gas evolution), adding LiCl (250 mg) in 1 mL water every 30 minutes until double decarboxylation was observed in LCMS. The reaction was cooled to rt and diluted with 500 mL water and extracted with EtOAc 2×200 mL. The combined organic layers were concentrated and the residue was purified by silica gel chromatography, eluting with a linear gradient of 0% to 100% EtOAc. Ethyl 2-(5-bromopyridin-2-yl)acetate (12 g, 49.2 mmol, 70% yield) was isolated as a yellow oil. MS (ESI) m/z: 245.9 $(M+H)^+$.

INTERMEDIATE 118B

Preparation of (Z)-ethyl 2-(5-bromopyridin-2-yl)-2-(hydroxyimino)acetate

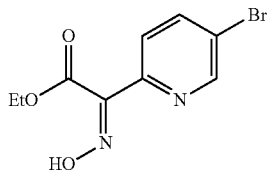 [SMILES: CCOC(=O)/C(=N\O)c1ccc(Br)cn1]

Ethyl 2-(5-bromopyridin-2-yl)acetate (12 g, 49.2 mmol) was dissolved in HOAc (60 mL). $NaNO_2$ (3.39 g, 49.2 mmol) in water (15 mL) was added dropwise to the ester. The reaction was stirred at rt for 1 hour and then concentrated to an oil. The residue was diluted with 500 mL water and potassium carbonate was added until a pH of 7-8 was obtained, at which point a white solid precipitated. The solid was filtered and dried to isolate (Z)-ethyl 2-(5-bromopyridin-2-yl)-2-(hydroxyimino)acetate (12 g, 43.9 mmol, 89% yield) as a white solid. MS (ESI) m/z: 275.0 $(M+H)^+$.

INTERMEDIATE 118C

Preparation of ethyl 6-bromo-3-(trifluoromethyl)imidazo[1,5-a]pyridine-1-carboxylate

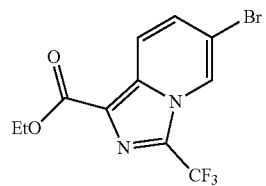 [SMILES: CCOC(=O)c1nc(C(F)(F)F)n2cc(Br)ccc12]

(E)-ethyl 2-(5-bromopyridin-2-yl)-2-(hydroxyimino)acetate (4.5 g, 16.48 mmol) was dissolved in THF (50 mL) and TFA (6.25 mL) was added. Zinc (2.16 g, 33.0 mmol) was added portionwise followed by TFAA (4.7 mL, 33.0 mmol) and the reaction stirred for 1 hour. The mixture was filtered through Celite® and concentrated. The residue was dissolved in pyridine (25 mL) and TFAA (4.7 mL, 33.0 mmol) was added. Following about 1 hour at 60° reaction was concentrated and purified by silica gel chromatography eluting with a linear gradient of 0% to 100% EtOAc in hexanes. Isolated ethyl 6-bromo-3-(trifluoromethyl)imidazo[1,5-a]pyridine-1-carboxylate (5 g, 14.83 mmol, 90% yield) as a yellow solid. MS (ESI) m/z: 337.0 $(M+H)^+$.

INTERMEDIATE 118

Ethyl 6-bromo-3-(trifluoromethyl)imidazo[1,5-a]pyridine-1-carboxylate (1.4 g, 4.15 mmol) was dissolved in MeOH (50 mL) and NaOH (0.166 g, 4.15 mmol) dissolved in water (10 mL) was carefully added. After 1 hour at rt, reaction was complete and solid had precipitated. The reaction was concentrated to about half of the original volume and filtered. The solid was dried under vacuum to yield 6-bromo-3-(trifluoromethyl)imidazo[1,5-a]pyridine-1-carboxylic acid (1.1 g, 3.56 mmol, 86% yield) as a white solid. MS (ESI) m/z: 310.8 $(M+H)^+$.

INTERMEDIATE 119

Preparation of 6-(benzyloxy)-3-(trifluoromethyl)imidazo[1,5-a]pyridine-1-carboxylic acid

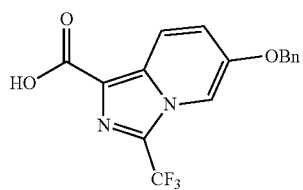 [SMILES: O=C(O)c1nc(C(F)(F)F)n2cc(OCc3ccccc3)ccc12]

INTERMEDIATE 119A

Preparation of methyl (Z)-2-(5-(benzyloxy)pyridin-2-yl)-2-(hydroxyimino)acetate

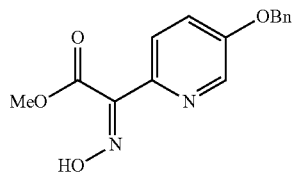 [SMILES: COC(=O)/C(=N\O)c1ccc(OCc2ccccc2)cn1]

Intermediate 119A was synthesized in the same was as Intermediate 118B, substituting 2-bromo-5-iodopyridine with 5-(benzyloxy)-2-bromopyridine and diethyl malonate with dimethyl malonate. MS (ESI) m/z: 287.0 (M+H)$^+$.

INTERMEDIATE 119B

Preparation of methyl 2-amino-2-(5-(benzyloxy)pyridin-2-yl)acetate

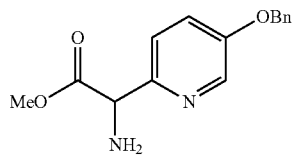 [SMILES: COC(=O)C(N)c1ccc(OCc2ccccc2)cn1]

(E)-methyl 2-(5-(benzyloxy)pyridin-2-yl)-2-(hydroxyimino)acetate (9 g, 31.4 mmol) was dissolved in MeOH (150 mL). TFA (6 mL, 79 mmol) was added followed by portionwise addition of zinc (4.1 g, 62.9 mmol). After 1 hour, the reaction was filtered through Celite® and concentrated. Methyl 2-amino-2-(5-(benzyloxy)pyridin-2-yl)acetate was isolated as a yellow, foaming solid and used crude in subsequent steps. MS (ESI) m/z: 273.1 (M+H)$^+$.

INTERMEDIATE 119C

Preparation of methyl 6-(benzyloxy)-3-(trifluoromethyl)imidazo[1,5-a]pyridine-1-carboxylate

Methyl 2-amino-2-(5-(benzyloxy)pyridin-2-yl)acetate (8.5 g, 31 mmol) was dissolved in CH$_2$Cl$_2$ (100 mL) and Et$_3$N (13.15 mL, 94 mmol) was added. The solution was cooled in an ice bath and TFAA (8.88 mL, 62.9 mmol) was added dropwise. After 2 hours, the reaction was warmed to rt and concentrated. The residue was purified by silica gel chromatography, eluting with a linear gradient of 0% to 100% EtOAc in hexanes. Methyl 6-(benzyloxy)-3-(trifluoromethyl)imidazo[1,5-a]pyridine-1-carboxylate (4 g, 11.42 mmol, 36.3% yield) isolated as a light yellow solid. MS (ESI) m/z: 351.0 (M+H)$^+$.

INTERMEDIATE 119

Intermediate 119 was synthesized just as Intermediate 118 was synthesized from Intermediate 118C. 6-(benzyloxy)-3-(trifluoromethyl)imidazo[1,5-a]pyridine-1-carboxylic acid was isolated as a white powder. MS (ESI) m/z: 337.0 (M+H)$^+$.

INTERMEDIATE 120

Preparation of methyl 3-(trifluoromethyl)imidazo[1,5-a]pyridine-1-carboxylate

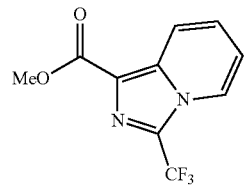

Intermediate 120 was synthesized in the same way as Intermediate 118C by substituting 5-bromo-2-iodopyridine with 2-iodopyridine. (ESI) m/z: 244.9 (M+H)$^+$.

INTERMEDIATE 121

Preparation of 6-bromo-3-(difluoromethyl)imidazo[1,5-a]pyridine-1-carboxylic acid

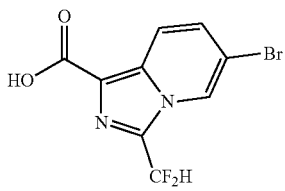 [SMILES: O=C(O)c1nc(C(F)F)n2cc(Br)ccc12]

Intermediate 121 was synthesized in a method analogous to Intermediate 118, however in the zinc reduction reaction, trifluoroacetic acid and trifluoroacetic anhydride were substituted with difluoroacetic acid and difluoroacetic anhydride, respectively. (ESI) m/z: 291.1 (M+H)$^+$.

INTERMEDIATE 122

Preparation of 6-(benzyloxy)-3-(difluoromethyl)imidazo[1,5-a]pyridine-1-carboxylic acid

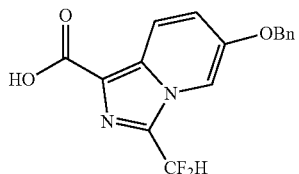

Intermediate 122 was synthesized in a method analogous to Intermediate 116, however in the zinc reduction reaction, trifluoroacetic acid and trifluoroacetic anhydride were substituted with difluoroacetic acid and difluoroacetic anhydride, respectively. (ESI) m/z: 319.0 (M+H)$^+$.

INTERMEDIATE 123

Preparation of 6-bromo-3-methylimidazo[1,5-a]pyridine-1-carboxylic acid

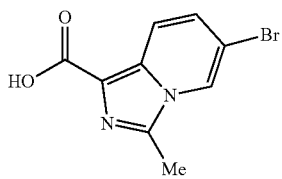 [SMILES: Cc1nc(C(=O)O)c2ccc(Br)cn12]

Intermediate 123 was synthesized in a method analogous to Intermediate 118, however in the zinc reduction reaction, trifluoroacetic acid and trifluoroacetic anhydride were substituted with acetic acid and acetic anhydride, respectively. (ESI) m/z: 256.9 (M+H)$^+$.

INTERMEDIATE 124

Ethyl 7-(pyrrolidin-1-yl)-[1,2,4]triazolo[4,3-a]pyridine-3-carboxylate

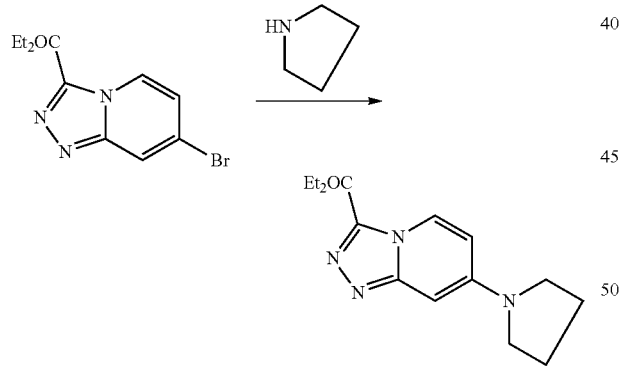

A slurry of ethyl 7-bromo-[1,2,4]triazolo[4,3-a]pyridine-3-carboxylate (0.100 g, 0.370 mmol), pyrrolidine (0.039 g, 0.56 mmol), (4,4'-di-tBu-2,2'-bipyridine)bis[3,5-difluoro-2-[5-trifluoromethyl-2-pyridinyl-κN)phenyl-κC]Ir(III) PF$_6$ (4 mg, 4 µmol), NiCl$_2$-DME (4.0 mg, 0.019 mmol) and DABCO (0.075 g, 0.67 mmol) in DMA (3.7 mL) was degassed, blanketed under N$_2$ and irradiated with blue LED (Kessil lamp). The reaction mixture was concentrated and the residue purified by silica gel chromatography to furnish ethyl 7-(pyrrolidin-1-yl)-[1,2,4]triazolo[4,3-a]pyridine-3-carboxylate (0.067 g, 0.26 mmol, 70% yield). MS (ESI) m/z: 261.0 (M+H)$^+$.

INTERMEDIATE 125

Ethyl 7-morpholino-[1,2,4]triazolo[4,3-a]pyridine-3-carboxylate

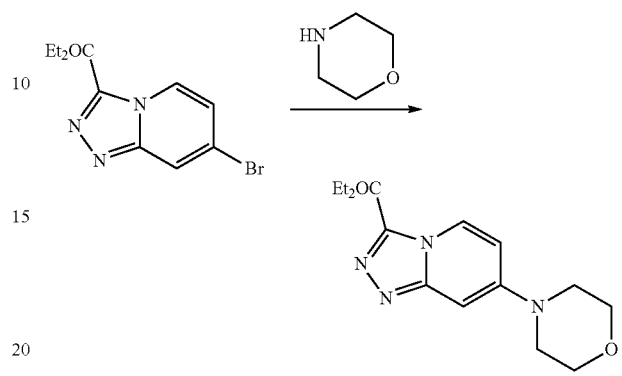

Prepared according to the procedure outlined for Intermediate 124 to furnish ethyl 7-morpholino-[1,2,4]triazolo[4,3-a]pyridine-3-carboxylate (0.074 g, 0.27 mmol, 72% yield). MS (ESI) m/z: 277.0 (M+H)$^+$.

INTERMEDIATE 126

2-(((aR)-6-aminospiro[3.3]heptan-2-yl)oxy)-6-methoxynicotinamide

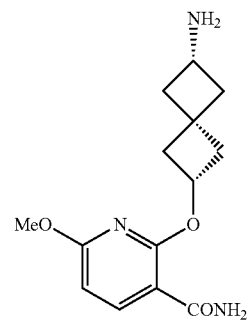

INTERMEDIATE 126A

Benzyl ((aR)-6-((3-cyano-6-methoxypyridin-2-yl)oxy)spiro[3.3]heptan-2-yl)carbamate

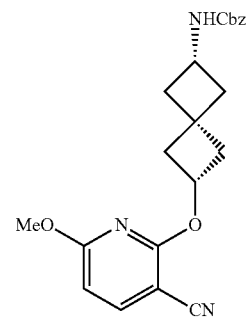

To a solution of benzyl ((aR)-6-hydroxyspiro[3.3]heptan-2-yl)carbamate (50 mg, 0.19 mmol) in THF (5 mL), was added NaH (60%, 10.1 mg. 0.42 mmol) and the reaction mixture was stirred at r.t. for 0.25 h, then 2-chloro-6-methoxynicotinonitrile (32 mg, 0.19 mmol) was added. The reaction mixture was stirred at r.t. overnight. Quenched the reaction with water (25 mL), and extracted with EtOAc (2×25 mL), dried and concentrated to an oil. Purified via flash chromatography (EtOAc/hexane gradient). The titled product was obtained as an oil (70 mg, 93%). LCMS m/z=394 (M+H)+. $^1$H NMR (400 MHz, CDCl$_3$) δ 7.70-7.65 (m, 1H), 7.3 (m 5H), 6.35-6.32 (m, 1H), 5.17-5.01 (m, 4H), 4.89-4.77 (m, 1H), 4.20-4.07 (m, 1H), 3.83 (s, 3H), 2.71-2.19 (m, 6H), 2.03-1.85 (m, 1H), 1.67-1.50 (m, 1H).

INTERMEDIATE 126

Intermediate 126A (70 mg, 0.18 mmol) was dissolved in DMSO (1 mL). To this solution was added potassium carbonate (123 mg, 0.89 mmol), followed by 37% H$_2$O$_2$ (0.2 mL, 1.96 mmol). The reaction mixture was stirred at r.t. overnight. LCMS confirmed the formation of the carboxamide intermediate. LCMS m/z=412.08 (M+H)+. Quenched the reaction with water (25 mL) and extracted organics with EtOAc (2×25 mL), dried (MgSO$_4$) and evaporated to an oil. Re-dissolved the oil in methanol (5 ml) and to this was added Pd/C (10%, 0.05 g) and hydrogenated at 60 psi for 4 h. Filtered and evaporated the solvents to afford the desired product as a semi-solid mass (50 mg, 100%). LCMS m/z=278.08 (M+H)+.

INTERMEDIATE 127

Preparation of methyl 7-cyclopropyl-6-((1-hydroxycyclobutyl)methoxy)pyrazolo[1,5-a]pyridine-3-carboxylate

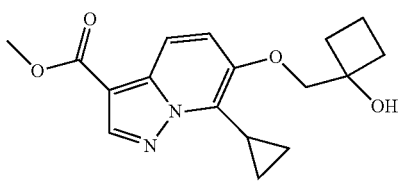 [SMILES: COC(=O)c1cnn2c(C3CC3)c(OCC3(O)CCC3)ccc12]

Intermediate 4B (0.100 g, 0.431 mmol) was suspended in MeCN (3.0 mL), then 1-oxaspiro[2.3]hexane (36.2 mg, 0.431 mmol), K$_2$CO$_3$ (0.238 g, 1.72 mmol) and water (0.2 mL) were added. The reaction mixture was stirred under microwave irradiation at 120° C. for 30 min. The reaction mixture was concentrated under reduced pressure, then the residue was purified by flash column chromatography to afford Intermediate 127 (0.096 g, 67% yield). MS (ESI) m/z: 317.1 (M+H)+.

EXAMPLE 1

Preparation of N-(6-(2-carbamoylphenoxy)spiro[3.3]heptan-2-yl)-5-methyl-1-phenyl-1H-pyrazole-4-carboxamide

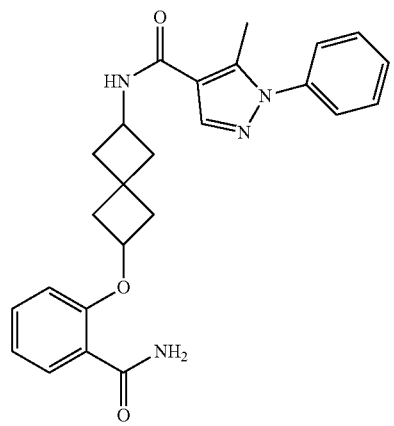 [SMILES: Cc1c(C(=O)NC2CC3(C2)CC(Oc2ccccc2C(N)=O)C3)cnn1-c1ccccc1]

Commercially available 5-methyl-1-phenyl-1H-pyrazole-4-carboxylic acid (12.31 mg, 0.061 mmol) was suspended in anhydrous DMF (1 mL), then DIEA (0.021 mL, 0.122 mmol) and HATU (19.30 mg, 0.051 mmol) were added. After stirring for 30 min, this solution was added to a solution of Intermediate 10 (10 mg, 0.041 mmol) and DIEA (0.021 mL, 0.122 mmol) in anhydrous DMF (0.5 mL). After 1 h, the reaction mixture was quenched with MeOH (0.1 mL) purified by reverse phase HPLC to give N-(6-(2-carbamoylphenoxy)spiro[3.3]heptan-2-yl)-5-methyl-1-phenyl-1H-pyrazole-4-carboxamide (6.9 mg, 38% yield). MS (ESI) m/z: 431.3 (M+H)+. $^1$H NMR (500 MHz, DMSO-d$_6$) δ 8.22 (br d, J=7.4 Hz, 1H), 8.09 (s, 1H), 7.80 (br d, J=7.6 Hz, 1H), 7.59-7.52 (m, 3H), 7.48 (br d, J=7.4 Hz, 4H), 7.45-7.39 (m, 1H), 7.01 (t, J=7.4 Hz, 1H), 6.95 (br d, J=8.2 Hz, 1H), 4.77 (br t, J=6.7 Hz, 1H), 4.37-4.26 (m, 1H), 2.76-2.66 (m, 1H), 2.47 (s, 3H), 2.45-2.40 (m, 1H), 2.32 (br s, 1H), 2.24-2.08 (m, 4H). Analytical HPLC RT=1.506 min and (Method A) 1.594 min (Method B), purity=97.9%.

EXAMPLE 2

Preparation of N-(6-(2-carbamoylphenoxy)spiro[3.3]heptan-2-yl)-1-methyl-1H-indazole-3-carboxamide

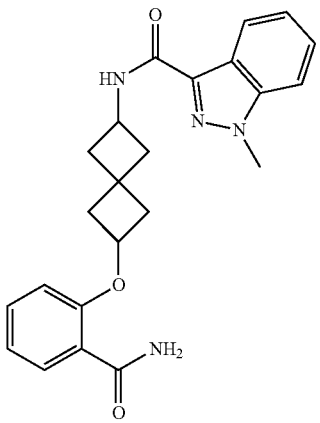 [SMILES: Cn1nc(C(=O)NC2CC3(C2)CC(Oc2ccccc2C(N)=O)C3)c2ccccc21]

According to the procedure for the preparation of Example 1, coupling of Intermediate 10 (10 mg, 0.041 mmol) and commercially available 1-methyl-1H-indazole-3-carboxylic acid (10.73 mg, 0.061 mmol) afforded N-(6-(2-carbamoylphenoxy)spiro-[3.3]heptan-2-yl)-1-methyl-1H-indazole-3-carboxamide (10.6 mg, 65% yield). MS (ESI) m-z: 405.2 (M+H)$^+$. $^1$H NMR (500 MHz, DMSO-d$_6$) δ ppm 8.52 (br d, J=8.0 Hz, 1H), 8.14 (d, J=8.2 Hz, 1H), 7.80 (br d, J=7.6 Hz, 1H), 7.71 (d, J=8.5 Hz, 1H), 7.53 (br d, J=16.0 Hz, 2H), 7.48-7.38 (m, 2H), 7.26 (t, J=7.5 Hz, 1H), 7.01 (t, J=7.4 Hz, 1H), 6.96 (d, J=8.2 Hz, 1H), 4.77 (quin, J=6.8 Hz, 1H), 4.49-4.35 (m, 1H), 4.12 (s, 3H), 2.72 (dt, J=11.0, 5.6 Hz, 1H), 2.46-2.38 (m, 1H), 2.29 (br t, J=9.0 Hz, 3H), 2.22 (br dd, J=11.1, 7.0 Hz, 1H), 2.17 (br dd. J=11.5, 7.0 Hz, 1H). Analytical HPLC RT=1.578 min (Method A) and 1.575 min (Method B), purity=100%.

EXAMPLE 3

Preparation of N-(6-(2-carbamoylphenoxy)spiro[3.3]heptan-2-yl)-6-(2-hydroxy-2-methylpropoxy)pyrazolo[1,5-a]pyridine-3-carboxamide

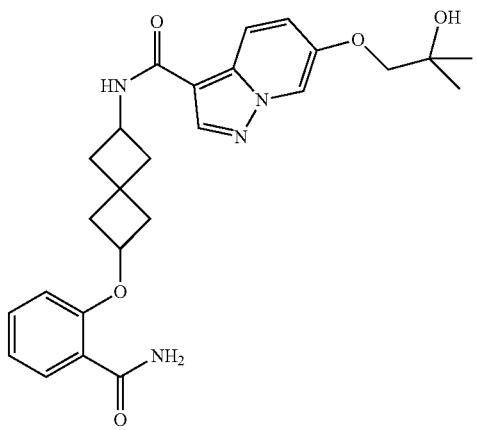 [SMILES: CC(C)(O)COc1ccc2c(C(=O)NC3CC4(C3)CC(Oc3ccccc3C(N)=O)C4)cnn2c1]

According to the procedure for the preparation of Example 1, coupling of Intermediate 10 (10 mg, 0.041 mmol) and Intermediate 2 (15.24 mg, 0.061 mmol) afforded N-(6-(2-carbamoylphenoxy)spiro[3.3]heptan-2-yl)-6-(2-hydroxy-2-methylpropoxy)pyrazolo[1,5-a]pyridine-3-carboxamide (11.8 mg, 60% yield). MS (ESI) m/z: 479.4 (M+H)$^+$. $^1$H NMR (500 MHz, DMSO-d$_6$) δ ppm 8.43 (br d, J=5.0 Hz, 2H), 8.26 (br d, J=7.5 Hz, 1H), 8.07 (d, J=9.6 Hz, 1H), 7.80 (br d, J=7.7 Hz, 1H), 7.53 (br d, J=14.2 Hz, 2H), 7.43 (br t, J=7.6 Hz, 1H), 7.27 (br d, J=9.8 Hz, 1H), 7.01 (t, J=7.4 Hz, 1H), 6.96 (d, J=8.2 Hz, 1H), 4.77 (br t, J=6.7 Hz, 1H), 4.72 (s, 1H), 4.43-4.29 (m, 1H), 3.79 (s, 2H), 2.77-2.66 (m, 1H), 2.38-2.30 (m, 1H), 2.26-2.20 (m, 1H), 2.20-2.10 (m, 3H), 1.21 (s, 6H). Analytical HPLC RT=1.321 min (Method A) and 1.401 min (Method B), purity=99.2%.

EXAMPLE 4

Preparation of N-(6-(2-carbamoylphenoxy)spiro[3.3]heptan-2-yl)-6-((tetrahydrofuran-3-yl)oxy)pyrazolo[1,5-a]pyridine-3-carboxamide

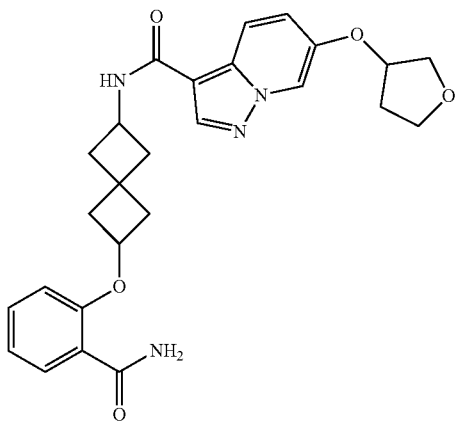 [SMILES: NC(=O)c1ccccc1OC1CC2(CC(NC(=O)c3cnn4cc(OC5CCOC5)ccc34)C2)C1]

According to the procedure for the preparation of Example 1, coupling of Intermediate 10 (10 mg, 0.041 mmol) and Intermediate 8 (15.12 mg, 0.061 mmol) afforded N-(6-(2-carbamoylphenoxy)spiro[3.3]heptan-2-yl)-6-((tetrahydrofuran-3-yl)oxy)pyrazolo[1,5-a]pyridine-3-carboxamide (10.1 mg, 0.021 mmol, 52% yield). MS (ESI) m/z: 477.0 (M+H)$^+$. $^1$H NMR (500 MHz, DMSO-d$_6$) δ ppm 8.45 (br d, J=4.0 Hz, 2H), 8.27 (br d, J=7.6 Hz, 1H), 8.08 (d, J=9.6 Hz, 1H), 7.80 (br d, J=7.2 Hz, 1H), 7.53 (br d, J=15.1 Hz, 2H), 7.43 (br t, J=7.3 Hz, 1H), 7.24 (br d, J=9.7 Hz, 1H), 7.01 (t, J=7.5 Hz, 1H), 6.96 (d, J=8.3 Hz, 1H), 5.08 (br s, 1H), 4.77 (br t, J=6.8 Hz, 1H), 4.43-4.30 (m, 1H), 3.92-3.81 (m, 3H), 3.79-3.71 (m, 1H), 2.77-2.67 (m, 1H), 2.47-2.42 (m, 1H), 2.38-2.30 (m, 1H), 2.29-2.20 (m, 2H), 2.19-2.11 (m, 3H), 2.06-1.95 (m, 1H). Analytical HPLC RT=1.345 min (Method A) and 1.434 min (Method B), purity=100%.

EXAMPLE 5

Preparation of N-(6-(2-carbamoylphenoxy)spiro[3.3]heptan-2-yl)-3-methoxy-4-(1H-pyrazol-4-yl)benzamide

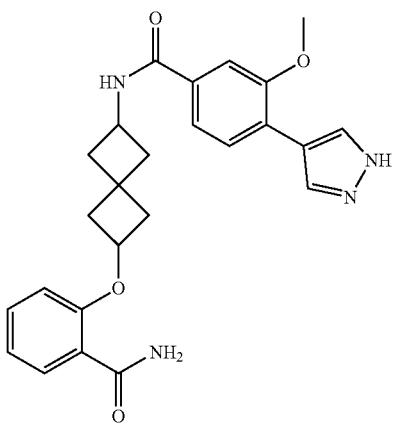 [SMILES: COc1cc(C(=O)NC2CC3(C2)CC(Oc2ccccc2C(N)=O)C3)ccc1-c1cn[nH]c1]

According to the procedure for the preparation of Example 1, coupling of Intermediate 10 (10 mg, 0.041 mmol) and Intermediate 9 (13.2 mg, 0.061 mmol) afforded N-(6-(2-carbamoylphenoxy)spiro[3.3]heptan-2-yl)-3-methoxy-4-(1H-pyrazol-4-yl)benzamide (2.3 mg, 12%6 yield). MS (ESI) m/z: 447.3 (M+H)$^+$. $^1$H NMR (500 MHz, DMSO-d$_6$) δ ppm 8.62 (br d, J=7.3 Hz, 1H), 8.11 (br s, 2H), 7.79 (br d, J=7.6 Hz, 1H), 7.69 (d, J=8.0 Hz, 1H), 7.59 (br s, 1H), 7.50 (br s, 1H), 7.48-7.37 (m, 3H), 7.01 (t, J=7.4 Hz, 1H), 6.95 (br d, J=8.2 Hz, 1H), 4.77 (br t. J=6.8 Hz, 1H), 4.40-4.29 (m, 1H), 3.91 (s, 3H), 2.72 (br s, 1H), 2.47-2.42 (m, 1H), 2.33 (br s, 1H), 2.19 (br t, J=9.9 Hz, 3H). Analytical HPLC RT=1.35 min (Method A) and 1.303 min (Method B), purity=96%.

EXAMPLE 6

Preparation of N-(6-((3-carbamoylpyridin-2-yl)oxy)spiro[3.3]heptan-2-yl)-6-(2-hydroxy-2-methyl-propoxy)pyrazolo[1,5-a]pyridine-3-carboxamide, trifluoroacetic acid salt

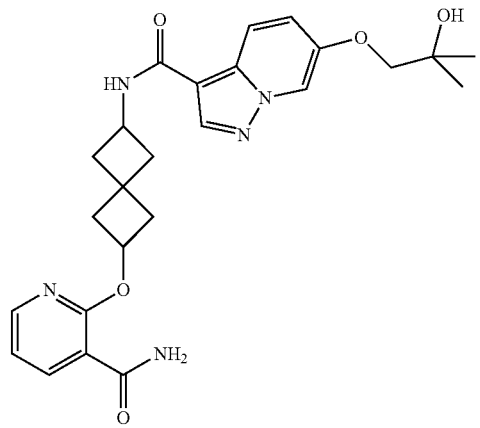 [SMILES: CC(C)(O)COc1ccc2c(C(=O)NC3CC4(C3)CC(Oc3ncccc3C(N)=O)C4)cnn2c1]

According to the procedure for the preparation of Example 3, replacing Intermediate 10 with Intermediate 11 afforded Example 6. MS (ESI) m/z: 480.3 (M+H)$^+$. $^1$H NMR (500 MHz, DMSO-d$_6$) δ ppm 8.47-8.41 (m, 2H), 8.30-8.25 (m, 2H), 8.17 (dd, J=7.5, 2.0 Hz, 1H), 8.08 (d, J=9.5 Hz, 1H), 7.70 (br. s., 1H), 7.61 (br. s., 1H), 7.28 (dd, J=9.8, 2.1 Hz, 1H), 7.11 (dd, J=7.3, 4.9 Hz, 1H), 5.24 (quin, J=7.2 Hz, 1H), 4.44-4.33 (m, 1H), 3.80 (s, 2H), 2.70-2.65 (m, 1H), 2.49-2.42 (m, 2H), 2.38-2.32 (m, 1H), 2.30-2.14 (m, 4H), 1.22 (s, 6H). Analytical HPLC RT=1.245 min (Method A) and 1.281 min (Method B), purity=98%.

EXAMPLE 7

Preparation of N-(6-((3-carbamoylpyrazin-2-yl)oxy)spiro[3.3]heptan-2-yl)-6-(2-hydroxy-2-methyl-propoxy)pyrazolo[1,5-a]pyridine-3-carboxamide

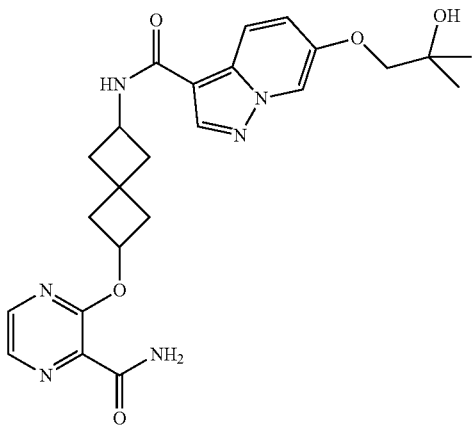 [SMILES: CC(C)(O)COc1ccc2c(C(=O)NC3CC4(C3)CC(Oc3nccnc3C(N)=O)C4)cnn2c1]

According to the procedure for the preparation of Example 3, replacing Intermediate 10 with Intermediate 12 afforded Example 7. MS (ESI) m/z: 481.3 (M+H)$^+$. $^1$H NMR (500 MHz, DMSO-d$_6$) δ ppm 8.44-8.40 (m, 2H), 8.28 (d, J=2.7 Hz, 2H), 8.19 (d, J=2.4 Hz, 1H), 8.07 (d, J=9.5 Hz, 1H), 7.91 (br. s., 1H), 7.63 (br. s., 1H), 7.28 (dd, J=9.6, 2.0 Hz, 1H), 5.13 (quin, J=7.1 Hz, 1H), 4.40-4.32 (m, 1H), 3.79 (s, 2H), 2.66 (dt, J=11.4, 5.9 Hz, 1H), 2.48-2.42 (m, 2H), 2.37-2.31 (m, 1H), 2.21-2.12 (m, 4H), 1.22 (s, 6H). Analytical HPLC RT=1.081 min (Method A) and 1.11 min (Method B), purity=94%.

EXAMPLE 8

Preparation of N-(6-((5-carbamoylpyrimidin-4-yl)oxy)spiro[3.3]heptan-2-yl)-6-(2-hydroxy-2-methylpropoxy)pyrazolo[1,5-a]pyridine-3-carboxamide

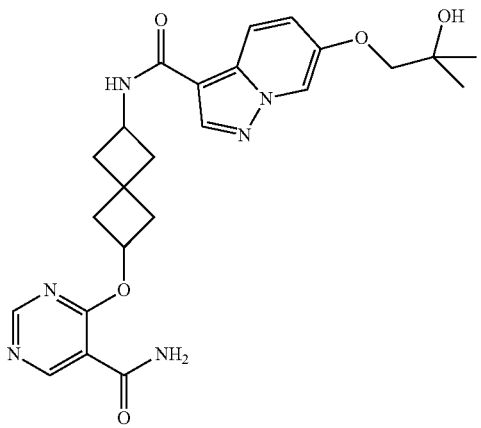 [SMILES: CC(C)(O)COc1ccc2c(C(=O)NC3CC4(C3)CC(Oc3ncncc3C(N)=O)C4)cnn2c1]

According to the procedure for the preparation of Example 3, replacing Intermediate 10 with Intermediate 14 afforded Example 8. MS (ESI) m/z: 481.0 (M+H)+. 1H NMR (500 MHz, DMSO-d6) δ ppm 8.81 (d, J=5.8 Hz, 2H), 8.45-8.39 (m, 2H), 8.31 (d, J=7.3 Hz, 1H), 8.06 (d, J=9.5 Hz, 1H), 7.80 (br. s., 1H), 7.63 (br. s., 1H), 7.28 (d, J=9.8 Hz, 1H), 5.26 (t, J=7.2 Hz, 1H), 4.40-4.32 (m, 1H), 3.17 (d, J=4.9 Hz, 1H), 2.66 (dd, J=11.4, 6.0 Hz, 2H), 2.44 (d, J=11.9 Hz, 1H), 2.38-2.23 (m, 3H), 2.19-2.11 (m, 2H), 1.21 (s, 6H). Analytical HPLC RT=1.082 min (Method A) and 1.061 min (Method B), purity=95%6.

EXAMPLE 9

Preparation of N-(6-((3-carbamoylpyridin-2-yl)oxy)spiro[3.3]heptan-2-yl)-6-((1,3-difluoropropan-2-yl)oxy)pyrazolo[1,5-a]pyridine-3-carboxamide, trifluoroacetic acid salt

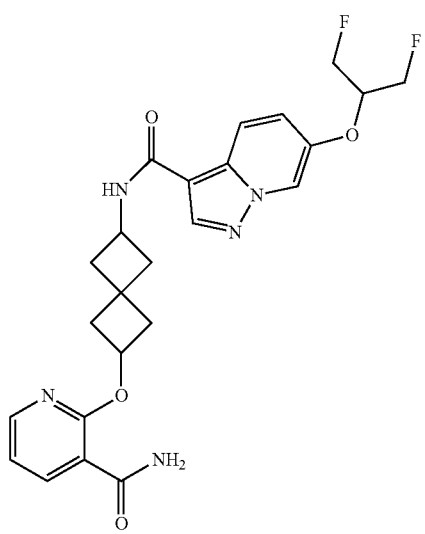 [SMILES: NC(=O)c1cccnc1OC1CC2(CC(NC(=O)c3cnn4cc(OC(CF)CF)ccc34)C2)C1]

Intermediate 11 (8 mg, 0.032 mmol) was suspended in anhydrous PhMe (1 mL), then Me3Al (2 M in PhMe) (0.049 mL, 0.097 mmol) was added dropwise. After stirring for 5 min. at rt, Intermediate 5 (11 mg, 0.042 mmol) was added, and the reaction mixture was stirred at 120° C. for 30 min. under microwave irradiation. The reaction was incomplete by LCMS. DCM (0.5 mL) and additional Me3Al (0.3 mL) was added and the reaction was heated 50° C. in an oil bath for 18 h. The reaction mixture was cooled to rt, and carefully quenched with TFA. Solvent was removed under reduced pressure, the residue was diluted with DMF (2 mL), filtered, and purified by reverse phase HPLC to afford 2.1 mg (11%) of desired product. MS (ESI) m/z: 486.2 (M+H)+. 1H NMR (500 MHz, DMSO-d6) δ ppm 8.64 (s, 1H), 8.46 (s, 1H), 8.33 (d, J=7.6 Hz, 1H), 8.29-8.22 (m, 1H), 8.16 (dd, J=7.5, 1.7 Hz, 1H), 8.11 (d, J=9.5 Hz, 1H), 7.74-7.58 (m, 2H), 7.34 (dd, J=9.8, 1.8 Hz, 1H), 7.11 (dd, J=7.3, 4.9 Hz, 1H), 5.22 (quin, J=7.0 Hz, 1H), 5.03-4.89 (m, 1H), 4.88-4.81 (m, 1H), 4.81-4.71 (m, 2H), 4.65 (dd, J=10.4, 5.2 Hz, 1H), 4.44-4.26 (m, 1H), 2.66 (dt, J=11.4, 5.5 Hz 1H), 2.47-2.41 (m, 1H), 2.40-2.29 (m, 2H), 2.27-2.22 (m, 1H), 2.22-2.10 (m, 3H). Analytical HPLC RT=1.384 min (Method A) and 1.378 (Method B) min, purity=99%.

EXAMPLE 10

Preparation of N-(6-((3-carbamoylpyridin-2-yl)oxy)spiro[3.3]heptan-2-yl)-6-(3,3,3-trifluoropropoxy)pyrazolo[1,5-a]pyridine-3-carboxamide, trifluoroacetic acid salt

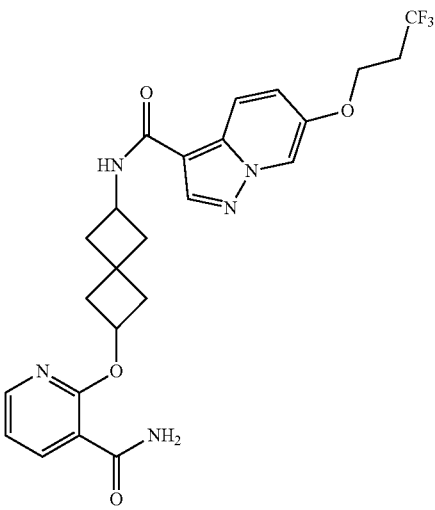 [SMILES: NC(=O)c1cccnc1OC1CC2(CC(NC(=O)c3cnn4cc(OCCC(F)(F)F)ccc34)C2)C1]

N-(6-((3-carbamoylpyridin-2-yl)oxy)spiro[3.3]heptan-2-yl)-6-(3,3,3-trifluoropropoxy)pyrazolo[1,5-a]pyridine-3-carboxamide (1.7 mg, 8%) was prepared in a similar manner as Example 9, substituting Intermediate 6 for Intermediate 5. MS (ESI) m/z: 504.2 (M+H)+. 1H NMR (500 MHz, DMSO-d6) δ ppm 8.54 (s, 1H), 8.46 (s, 1H), 8.31-8.23 (m, 2H), 8.17 (dd, J=7.5, 2.0 Hz, 1H), 8.09 (d, J=9.8 Hz, 1H), 7.69 (br. s., 1H), 7.61 (br. s., 1H), 7.33-7.22 (m, 1H), 7.11 (dd, J=7.6, 4.9 Hz, 1H), 5.24 (t, J=7.0 Hz, 1H), 4.45-4.36 (m, 1H), 4.36-4.25 (m, 2H), 2.94-2.78 (m, 2H), 2.67 (dd, J=11.1, 6.0 Hz, 1H), 2.48-2.41 (m, 2H), 2.36 (d, J=11.0 Hz, 1H), 2.30-2.25 (m, 1H), 2.21-2.11 (m, 3H). Analytical HPLC RT=1.568 min (Method A) and 1.570 min (Method B), purity=91%.

EXAMPLE 11

Preparation of N-(6-((3-carbamoylpyridin-2-yl)oxy)spiro[3.3]heptan-2-yl)-6-((tetrahydro-2H-pyran-4-yl)oxy)pyrazolo[1,5-a]pyridine-3-carboxamide, trifluoroacetic acid salt

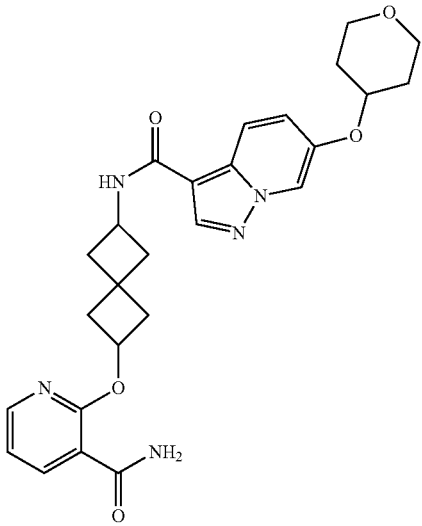 [SMILES: NC(=O)c1cccnc1OC1CC2(CC(NC(=O)c3cnn4cc(OC5CCOCC5)ccc34)C2)C1]

N-(6-((3-carbamoylpyridin-2-yl)oxy)spiro[3.3]heptan-2-yl)-6-((tetrahydro-2H-pyran-4-yl)oxy)pyrazolo[1,5-a]pyridine-3-carboxamide (3 mg, 14%) was prepared in a similar manner as Example 9, substituting Intermediate 7 for Intermediate 5. MS (ESI) m/z: 492.08 (M+H)$^+$. $^1$H NMR (500 MHz, DMSO-d$_6$) δ ppm 8.58 (s, 1H), 8.44 (s, 1H), 8.27 (d, J=6.7 Hz, 2H), 8.17 (d, J=5.5 Hz, 1H), 8.08 (d, J=9.8 Hz, 1H), 7.69 (br. s., 1H), 7.61 (br. s., 1H), 7.29 (d, J=9.8 Hz, 1H), 7.16-7.07 (m, 1H), 5.23 (t, J=7.0 Hz, 1H), 4.62 (br. s., 1H), 4.43-4.34 (m, 1H), 3.91-3.82 (m, 3H), 2.66 (d, J=11.6 Hz, 1H), 2.48-2.42 (m, 2H), 2.36 (d, J=11.9 Hz, 1H), 2.30-2.20 (m 2H), 2.20-2.12 (m, 2H), 2.08-1.97 (m, 2H), 1.61 (d, J=9.2 Hz, 2H). Analytical HPLC RT=1.337 min (Method A) and 1.337 min (Method B), purity=90%.

EXAMPLE 12

Preparation of N-(6-((3-carbamoylpyridin-2-yl)oxy)spiro[3.3]heptan-2-yl)indoline-1-carboxamide, trifluoroacetic acid salt

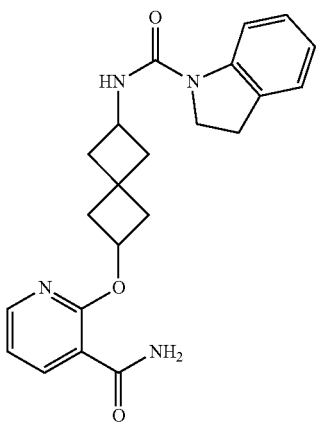 [SMILES: NC(=O)c1cccnc1OC1CC2(CC(NC(=O)N3CCc4ccccc43)C2)C1]

To Intermediate 13 (0.011 g, 0.027 mmol) in THF (0.5 mL), was added indoline (0.015 mL, 0.13 mmol), and DIEA (0.014 mL, 0.080 mmol). The reaction was heated to 50° C. Solvent was removed under reduced pressure, the residue was diluted with DMF (2 mL), filtered, and purified by reverse phase HPLC to afford 6.1 mg (40%) of desired product. MS (ESI) m/z: 393.1 (M+H)$^+$. $^1$H NMR (500 MHz, DMSO-d$_6$) δ ppm 8.26 (dd, J=4.7, 2.0 Hz, 1H), 8.16 (dd, J=7.5, 2.0 Hz, 1H), 7.78 (d, J=7.9 Hz, 1H), 7.68 (br. s., 1H), 7.62 (br. s., 1H), 7.17-7.07 (m, 2H), 7.05 (t, J=7.6 Hz, 1H), 6.82 (t, J=7.3 Hz, 1H), 6.76-6.71 (m, 1H), 5.21 (quin, J=7.1 Hz, 1H), 4.21-4.09 (m, 1H), 3.91-3.82 (m, 2H), 3.08 (t, J=8.7 Hz, 2H), 2.66-2.58 (m, 1H), 2.48-2.43 (m, 1H), 2.42-2.34 (m, 1H), 2.30-2.18 (m, 3H), 2.17-2.10 (m, 2H): 89%; RT=1.506 min (M+H) Analytical HPLC RT=1.505 min (Method A) and 1.506 min (Method B), purity=89%.

EXAMPLE 13

Preparation of N-(6-((3-carbamoylpyridin-2-yl)oxy)spiro[3.3]heptan-2-yl)-5-cyanoisoindoline-2-carboxamide, trifluoroacetic acid salt

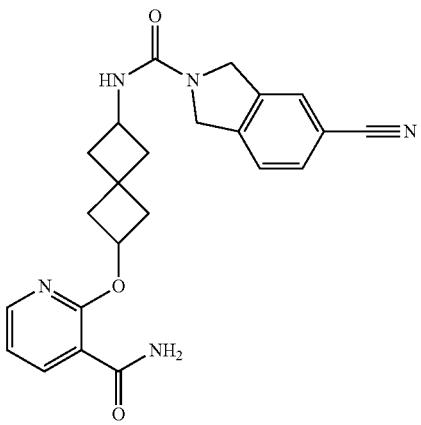 [SMILES: N#Cc1ccc2c(c1)CN(C(=O)NC1CC3(C1)CC(Oc1ncccc1C(N)=O)C3)C2]

N-(6-((3-carbamoylpyridin-2-yl)oxy)spiro[3.3]heptan-2-yl)-5-cyanoisoindoline-2-carboxamide (5.8 mg, 28%) was prepared in a similar manner as Example 12, substituting isoindoline-5-carbonitrile, HCl for indoline. MS (ESI) m/z: 418.1 (M+H)$^+$. $^1$H NMR (500 MHz, DMSO-d$_6$) δ ppm 8.26 (dd, J=4.6, 1.8 Hz, 1H), 8.16 (dd, J=7.3, 1.8 Hz, 1H), 7.81 (s, 1H), 7.74 (d, J=7.9 Hz, 1H), 7.67 (br. s., 1H), 7.61 (br. s., 1H), 7.53 (d, J=7.9 Hz, 1H), 7.10 (dd, J=7.3, 4.9 Hz, 1H), 6.57 (d, J=7.6 Hz, 1H), 5.20 (quin, J=7.1 Hz, 1H), 4.62 (d, J=15.0 Hz, 4H), 4.14-4.05 (m, 1H), 2.65-2.59 (m, 1H), 2.49-2.43 (m, 1H), 2.37 (t, J=11.6 Hz, 1H), 2.32-2.14 (m, 3H), 2.14-2.04 (m, 2H). Analytical HPLC (Method B) RT=1.296 min, purity=95%.

EXAMPLE 14

Preparation of Benzyl ((aR)-6-(2-carbamoylphenoxy)spiro[3.3]heptan-2-yl)carbamate (Peak 2)

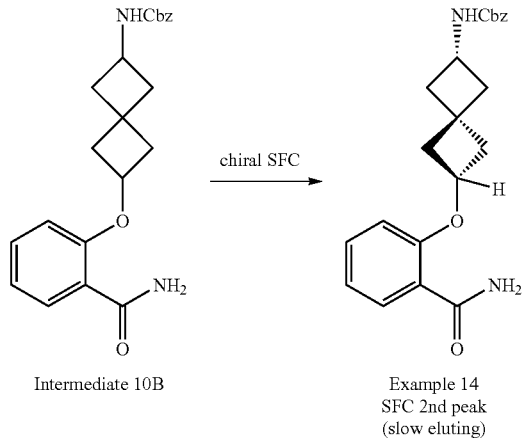

Intermediate 10B

Example 14
SFC 2nd peak
(slow eluting)

Intermediate 10B (0.849 g, 2.23 mmol) was separated on chiral SFC (Instrument: Berger Multigram II SFC: Column: CHIRALPAK® IC, 21×250 mm, 5μ; Mobile Phase: 35% Methanol/65% $CO_2$; Flow Conditions: 45 mL/min, 120 Bar, 40° C.; Detector wavelength: 235 nm). Collected 2nd peak and concentrated to afford Example 14 (396 mg, 47%) as a white solid. An analytical sample was obtained by purification by reverse phase HPLC. MS (ESI) m/z: 381.1 $(M+H)^+$; ee≥99%. $^1$H NMR (500 MHz, DMSO-$d_6$) δ ppm ppm 7.78 (br d, J=7.6 Hz, 1H), 7.56-7.45 (m, 3H), 7.41 (br t, J=7.2 Hz, 1H), 7.38-7.26 (m, 5H), 7.00 (t, J=7.5 Hz, 1H), 6.93 (br d, J=8.2 Hz, 1H), 4.98 (s, 2H), 4.72 (br t, J=6.9 Hz, 1H), 3.95-3.83 (m, 1H), 2.64 (br d, J=5.5 Hz, 1H), 2.48-2.41 (m, 1H), 2.36 (br s, 1H), 2.23 (br d, J=5.8 Hz, 1H), 2.19-2.07 (m, 2H), 1.99 (br t, J=9.2 Hz, 2H). Analytical HPLC RT=1.82 min (Method A) and 1.831 min (Method B), purity=100%.

EXAMPLE 15

Preparation of N-((aR)-6-(2-carbamoylphenoxy)spiro[3.3]heptan-2-yl)-7-cyclopropyl-6-(2-hydroxy-2-methylpropoxy)pyrazolo[1,5-a]pyridine-3-carboxamide

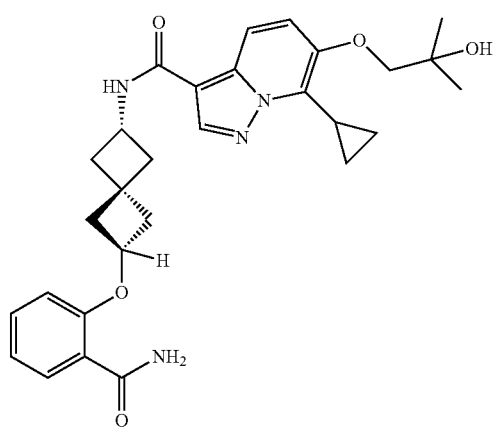

EXAMPLE 15A

Preparation of 2-(((aR)-6-aminospiro[3.3]heptan-2-yl)oxy)benzamide

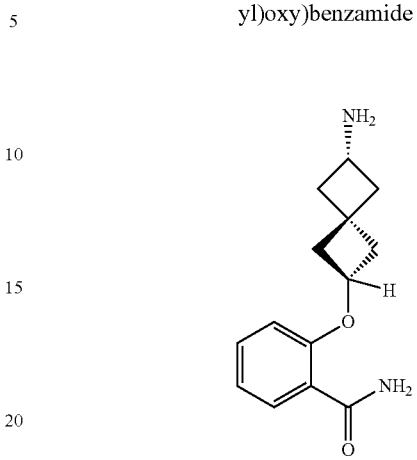

Example 14 (396 mg, 1.04 mmol) was dissolved in THF (15 mL) and MeOH (15 mL), and TEA (0.725 mL, 5.20 mmol) was added. The reaction mixture was degassed (3× vacuum/$N_2$), then Pd/C (10 wt %) (111 mg, 0.104 mmol) was added. The reaction mixture was subjected to a hydrogen atmosphere (1 atm; balloon). After 1 h, the suspension was filtered through a membrane filter and the filtrate concentrated to afford Example 15A (258 mg, 100% yield) as a colorless film, which solidified upon standing to give a white solid. $^1$H NMR (500 MHz, DMSO-$d_6$) δ ppm 7.80 (dd, J=7.7, 1.9 Hz, 1H), 7.50 (br. s., 2H), 7.41 (ddd, J=8.4, 7.3, 1.9 Hz, 1H), 7.00 (td. J=7.5, 1.0 Hz, 1H), 6.93 (d, J=8.3 Hz, 1H), 4.72 (quin, J=6.9 Hz, 1H), 3.28 (br. s, 2H), 3.24-3.16 (m, 1H), 2.58 (dt, J=11.3, 5.7 Hz, 1H), 2.47-2.42 (m, 1H), 2.35-2.29 (m 1H), 2.23-2.16 (m, 1H), 2.10 (dt, J=11.5, 7.3 Hz, 2H), 1.71 (dd, J=10.7, 8.5 Hz, 2H); MS (ESI) m/z: 247.1 $(M+H)^+$.

EXAMPLE 15

Example 15A (10 mg, 0.041 mmol) and Intermediate 4 (13 mg, 0.045 mmol) were dissolved in anhydrous DMF (1.5 mL), then DIEA (0.035 mL, 0.203 mmol) was added, followed by BOP (19.8 mg, 0.045 mmol). The reaction mixture was stirred at rt for 1 h. The reaction mixture was quenched with MeOH (0.1 mL), diluted with DMF (2 mL total volume), filtered, and purified by reverse phase HPLC to give Example 15 (11.7 mg, 56% yield). MS (ESI) m/z: 519.2 $(M+H)^+$. $^1$H NMR (500 MHz, DMSO-$d_6$) δ ppm 8.48 (s, 1H), 8.29 (br d, J=7.6 Hz, 1H), 8.01 (d, J=9.7 Hz, 1H), 7.79 (br d, J=6.9 Hz, 1H), 7.58 (br s, 1H), 7.51 (br s, 1H), 7.47-7.39 (m, 2H), 7.01 (t, J=7.4 Hz, 1H), 6.95 (d, J=8.3 Hz, 1H), 4.81-4.71 (m, 2H), 4.40-4.30 (m, 1H), 3.78 (s, 1H), 2.71 (br d, J=7.3 Hz, 1H), 2.62-2.55 (m, 1H), 2.55-2.52 (m, 1H), 2.48-2.40 (m, 1H), 2.36-2.28 (m, 1H), 2.25-2.19 (m, 1H), 2.19-2.10 (m, 3H), 1.45 (br d, J=3.5 Hz, 2H), 1.23 (s, 6H), 1.05 (br dd, J=8.6, 2.1 Hz, 2H). Analytical HPLC RT=1.520 min (Method A) and 1.529 min (Method B), purity=100%.

EXAMPLE 16

Preparation of N-((aR)-6-(2-carbamoylphenoxy)spiro[3.3]heptan-2-yl)-6-(2-hydroxy-2-methylpropoxy)pyrazolo[1,5-a]pyridine-3-carboxamide

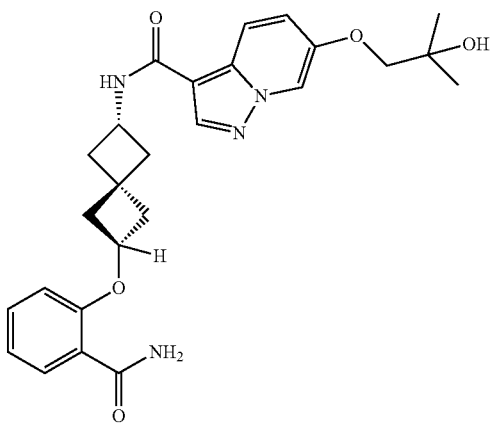

Example 16 (8.8 mg, 44%) was prepared in a analogous manner as Example 15 replacing Intermediate 4 with Intermediate 2 and coupling with Example 15A. MS (ESI) m/z: 479.4 (M+H)+. $^1$H NMR (500 MHz, DMSO-$d_6$) δ ppm 8.41 (br d, J=9.9 Hz, 2H), 8.32 (br d, J=7.4 Hz, 1H), 8.06 (br d, J=9.7 Hz, 1H), 7.79 (br d, J=7.6 Hz, 1H), 7.59 (br s, 1H), 7.51 (br s, 1H), 7.43 (br t, J=7.4 Hz, 1H), 7.27 (br d, J=9.6 Hz, 1H), 7.01 (br t, J=7.4 Hz, 1H), 6.95 (br d, J=8.2 Hz, 1H), 4.85 (s, 1H), 4.76 (br t, J=6.5 Hz, 1H), 4.40-4.28 (m, 1H), 3.77 (s, 1H), 2.72 (br s, 1H), 2.45 (br s, 1H), 2.32 (br s, 1H), 2.22 (br d, J=6.8 Hz, 1H), 2.18-2.08 (m, 3H), 1.20 (s, 6H). Analytical HPLC RT=1.310 min (Method A) and 1.320 min (Method B), purity=97%.

EXAMPLE 17

Preparation of N-((aR)-6-((3-carbamoylpyridin-2-yl)oxy)spiro[3.3]heptan-2-yl)-5-methoxyindoline-1-carboxamide, Trifluoroacetic Acid Salt

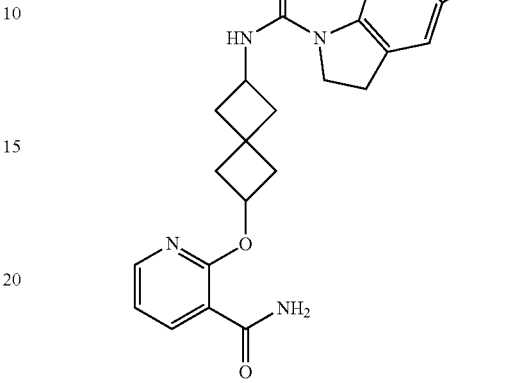

Example 17 (4.5 mg, 27%) was prepared in a similar manner as Example 12, substituting 5-methoxyindoline for indoline. MS (ESI) m % z: 423.1 (M+H)+. $^1$H NMR (500 MHz, DMSO-$d_6$) δ ppm 8.25 (d, J=3.2 Hz, 1H), 8.15 (d, J=6.1 Hz, 1H), 7.66 (m, 3H), 7.10 (dd, J=7.2, 5.0 Hz, 1H), 6.75 (br. s., 1H), 6.62 (d, J=7.6 Hz, 2H), 5.25-5.15 (m, 1H), 4.16-4.07 (m, 1H), 3.85-3.81 (m, 1H), 3.70-3.66 (m, 1H), 3.05 (t, J=8.4 Hz, 2H), 2.66-2.58 (m, 1H), 2.44 (d, J=5.7 Hz, 1H), 2.38-2.34 (m, 1H), 2.29-2.22 (m, 2H), 2.13-2.08 (m, 3H). Analytical HPLC RT=1.649 min (Method A) and 1.648 min (Method B), purity=94%.

The following examples in Table 1 were prepared using a similar procedure to that which was used in the preparation of Example 15. Example 15a was coupled with a carboxylic acid. Various bases could be used other than the one described in Example 15, such as TEA, DBU, or DABCO. Various coupling reagents could be used other than the one described in Example 15, such as EDCI, HATU, or T3P.

TABLE 1

| Example | R | Name | LCMS (M + H)+ | HPLC Method, RT (min.) | 1H NMR |
|---|---|---|---|---|---|
| 18 | 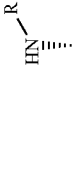 | N-[(aR)-6-(2-carbamoylphenoxy)spiro[3.3]heptan-2-yl]-7-(3,3,3-(trifluoropropoxy)imidazo[1,2-a]pyridine-3-carboxamide | 503.3 | A: 1.72 B: 1.43 | (500 MHz, DMSO-d6) δ ppm 9.29 (d, J = 7.6 Hz, 1H), 8.52 (d, J = 7.6 Hz, 1H), 8.24 (s, 1H), 7.80 (d, J = 7.6 Hz, 1H), 7.52 (d, J = 12.8 Hz, 2H), 7.43 (t, J = 7.8 Hz, 1H), 7.17 (d, J = 1.8 Hz, 1H), 7.01 (t, J = 7.5 Hz, 1H), 6.96 (d, J = 8.5 Hz, 1H), 6.84 (dd, J = 7.6, 2.4 Hz, 1H), 4.82-4.70 (m, 1H), 4.41-4.36 (m, 1H), 4.34 (t, J = 5.6 Hz, 2H), 2.85 (tt, J = 11.3, 5.5 Hz, 2H), 2.77-2.68 (m, 1H), 2.40-2.30 (m, 1H), 2.26-2.12 (m, 4H) |
| 19 | 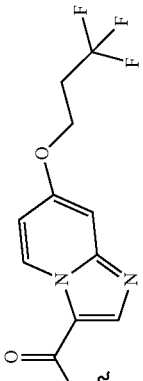 | N-[(aR)-6-(2-carbamoylphenoxy)spiro[3.3]heptan-2-yl]-6-(2-hydroxy-2-methylpropoxy)-7-(3,3,3-trifluoropropyl)pyrazolo[1,5-a]pyridine-3-carboxamide | 575.3 | A: 1.83 B: 1.82 | (500 MHz, DMSO-d6) δ ppm 8.55 (s, 1H), 8.30 (d, J = 7.6 Hz, 1H), 8.13 (d, J = 9.5 Hz, 1H), 7.81 (dd, J = 7.8, 1.7 Hz, 1H), 7.62-7.47 (m, 3H), 7.48-7.40 (m, 1H), 7.02 (t, J = 7.5 Hz, 1H), 6.97 (d, J = 8.2 Hz, 1H), 4.84-4.75 (m, 1H), 4.43-4.33 (m, 1H), 3.85 (s, 2H), 3.46 (t, J = 7.6 Hz, 1H), 2.78-2.65 (m, 4H), 2.48-2.43 (m, 1H), 2.40-2.30 (m, 1H), 2.28-2.12 (m, 4H), 1.25 (s, 6H) |

TABLE 1-continued

| | Name | Structure | MS | LC | NMR |
|---|---|---|---|---|---|
| 20 | N-[(aR)-6-(2-carbamoylphenoxy)spiro[3.3]heptan-2-yl]-5-[2-(morpholin-4-yl)ethoxy]pyrazolo[1,5-a]pyridine-3-carboxamide | (morpholine-ethoxy pyrazolopyridine structure) | 520.3 | A: 1.39 B: 1.19 | (500 MHz, DMSO-d$_6$) δ ppm 8.66 (d, J = 7.6 Hz, 1H), 8.49 (s, 1H), 8.24 (d, J = 7.0 Hz, 1H), 7.81 (d, J = 6.4 Hz, 1H), 7.58 (br. s., 1H), 7.54 (d, J = 7.0 Hz, 2H), 7.44 (t, J = 7.0 Hz, 1H), 7.02 (t, J = 7.6 Hz, 1H), 6.97 (d, J = 8.5 Hz, 1H), 6.80-6.73 (m, 1H), 4.79 (t, J = 6.7 Hz, 1H), 4.47 (br. s., 2H), 4.40-4.30 (m, 1H), 4.07-3.64 (m, 3H), 3.60 (br. s., 1H), 2.77-2.67 (m, 1H), 2.46 (br. s., 1H), 2.38-2.29 (m, 1H), 2.27-2.11 (m, 4H) |
| 21 | N-[(aR)-6-(2-carbamoylphenoxy)spiro[3.3]heptan-2-yl]-6-[2-(pyrrolidin-1-yl)ethoxy]pyrazolo[1,5-a]pyridine-3-carboxamide | (pyrrolidine-ethoxy pyrazolopyridine structure) | 504.2 | A: 1.18 B: 1.13 | (5000 MHz, DMSO-d$_6$) δ ppm 8.47-8.40 (m, 2H), 8.29 (d, J = 7.6 Hz, 1H), 8.06 (d, J = 9.8 Hz, 1H), 7.80 (d, J = 7.6 Hz, 1H), 7.56 (br. s., 1H), 7.50 (br. s., 1H), 7.44 (t, J = 7.0 Hz, 1H), 7.25 (dd, J = 9.8, 1.8 Hz, 1H), 7.02 (t, J = 7.3 Hz, 1H), 6.97 (d, J = 8.5 Hz, 1H), 4.82-4.76 (m, 1H), 4.82-4.73 (m, 1H), 4.41-4.32 (m, 1H), 4.12 (t, J = 5.5 Hz, 2H), 2.81 (t, J = 5.5 Hz, 2H), 2.75-2.69 (m, 1H), 2.48-2.42 (m, 1H), 2.38-2.30 (m, 1H), 2.27-2.11 (m, 4H), 1.85 (s, 2H), 1.68 (br. s., 4H) |
| 22 | N-[(aR)-6-(2-carbamoylphenoxy)spiro[3.3]heptan-2-yl]-6-(2,2-difluoromethoxy)pyrazolo[1,5-a]pyridine-3-carboxamide | (difluoroethoxy pyrazolopyridine structure) | 471.1 | A: 1.58 B: 1.60 | (500 MHz, DMSO-d$_6$) δ ppm 8.60 (s, 1H), 8.47 (s, 1H), 8.30 (d, J = 7.6 Hz, 1H), 8.10 (d, J = 9.5 Hz, 1H), 7.81 (d, J = 7.6 Hz, 1H), 7.60-7.48 (m, 2H), 7.44 (t, J = 7.8 Hz, 1H), 7.33 (d, J = 9.5 Hz, 1H), 7.02 (t, J = 7.3 Hz, 1H), 6.97 (d, J = 8.2 Hz, 1H), 6.43 (t, J = 54.4 Hz, 1H), 4.82-4.73 (m, 1H), 4.47-4.33 (m, 3H), 2.78-2.67 (m, 1H), 2.49-2.44 (m, 1H), 2.38-2.30 (m, 1H), 2.26-2.12 (m, 4H) |

TABLE 1-continued

| | Name | Structure | Mass | LC | NMR |
|---|---|---|---|---|---|
| 23 | N-[(aR)-6-(2-carbamoylphenoxy)spiro[3.3]heptan-2-yl]-6-(3,3-difluoropyrrolidin-1-yl)pyrazolo[1,5-a]pyridine-3-carboxamide | | 496.3 | A: 1.68<br>B: 1.61 | (500 MHz, DMSO-d₆) δ ppm 8.37 (s, 1H), 8.21 (d, J = 7.3 Hz, 1H), 8.05 (d, J = 9.8 Hz, 1H), 7.99 (s, 1H), 7.84-7.76 (m, 1H), 7.55 (br. s., 1H), 7.51 (br. s., 1H), 7.44 (t, J = 7.0 Hz, 1H), 7.26 (dd, J = 9.6, 1.7 Hz, 1H), 7.02 (t, J = 7.5 Hz, 1H), 6.97 (d, J = 8.2 Hz, 1H), 4.78 (quin, J = 6.9 Hz, 1H), 4.37 (sxt, J = 8.0 Hz, 1H), 3.73 (t, J = 13.3 Hz, 2H), 3.51 (t, J = 7.2 Hz, 1H), 2.77-2.69 (m, 1H), 2.60-2.52 (m, 3H), 2.46 (dd, J = 11.1, 7.2 Hz, 1H), 2.38-2.29 (m, 1H), 2.27-2.10 (m, 4H) |
| 24 | N-[(aR)-6-(2-carbamoylphenoxy)spiro[3.3]heptan-2-yl]-6-(difluoromethoxy)pyrazolo[1,5-a]pyridine-3-carboxamide | | 457.3 | A: 1.60<br>B: 1.64 | (500 MHz, DMSO-d₆) 8.88 (s, 1H), 8.58 (s, 1H), 8.37 (br d, J = 7.6 Hz, 1H), 8.21 (d, J = 9.5 Hz, 1H), 7.80 (dd, J = 7.6, 1.5 Hz, 1H), 7.53 (br d, J = 10.4 Hz, 2H), 7.47-7.42 (m, 2H), 7.12 (t, J = 77.5 Hz, 1H), 7.01 (t, J = 7.5 Hz, 1H), 6.96 (d, J = 8.2 Hz, 1H), 4.78 (quin, J = 6.8 Hz, 1H), 4.44-4.32 (m, 1H), 2.73 (dt, J = 11.1, 5.6 Hz, 1H), 2.57 (br s, 1H), 2.40-2.31 (m, 1H), 2.26-2.21 (m, 1H), 2.20-2.10 (m, 3H) |
| 25 | N-[(aR)-6-(2-carbamoylphenoxy)spiro[3.3]heptan-2-yl]-7-(3,3-difluoropyrrolidin-1-yl)imidazo[1,2-a]pyridine-3-carboxamide | | 496.0 | A: 1.65<br>B: 1.42 | (500 MHz, DMSO-d₆) δ ppm 9.20 (d, J = 7.7 Hz, 1H), 8.35 (d, J = 7.5 Hz, 1H), 8.12 (br. s., 1H), 7.80 (d, J = 7.6 Hz, 1H), 7.56 (br. s., 2H), 7.44 (t, J = 7.3 Hz, 1H), 7.02 (t, J = 7.4 Hz, 1H), 6.97 (d, J = 8.3 Hz, 1H), 6.74 (d, J = 7.8 Hz, 1H), 6.50 (br. s., 1H), 4.78 (t, J = 6.8 Hz, 1H), 4.43-4.30 (m, 1H), 3.87-3.76 (m, 2H), 3.60 (t, J = 7.2 Hz, 1H), 2.77-2.67 (m, 1H), 2.64-2.56 (m, 2H), 2.49-2.42 (m, 1H), 2.39-2.28 (m, 1H), 2.27-2.12 (m, 4H) |
| 26 | N-[(aR)-6-(2-carbamoylphenoxy)spiro[3.3]heptan-2-yl]-7-(2-(pyrrolidin-1-yl)ethoxy)imidazo[1,2-a]pyridine-3-carboxamide | | 504.0 | A: 1.34<br>B: 1.09 | (500 MHz, DMSO-d6) δ ppm 9.26 (d, J = 7.6 Hz, 1H), 8.48 (br d, J = 7.5 Hz, 1H), 8.20 (s, 1H), 7.80 (br d, J = 7.3 Hz, 1H), 7.54 (br s, 2H), 7.43 (br t, J = 7.6 Hz, 1H), 7.10 (br s, 1H), 7.01 (t, J = 7.4 Hz, 1H), 6.96 (d, J = 8.2 Hz, 1H), 6.83 (br d, J = 7.6 Hz, 1H), 4.77 (br t, J = 6.8 Hz, 1H), 4.42-4.32 (m, 1H), 4.23 (br s, 2H), 3.16 (br d, J = 3.5 Hz, 1H), 2.78-2.67 (m, 2H), 2.35 (br d, J = 6.6 Hz, 1H), 2.26-2.20 (m, 1H), 2.21-2.12 (m, 2H), 1.90 (s, 4H), 1.75 (br s, 4H) |

EXAMPLE 27

Preparation of methyl 3-((3-(((aR)-6-(2-carbamoyl-phenoxy)spiro[3.3]heptan-2-yl)carbamoyl)pyrazolo[1,5-a]pyridin-6-yl)oxy)azetidine-1-carboxylate

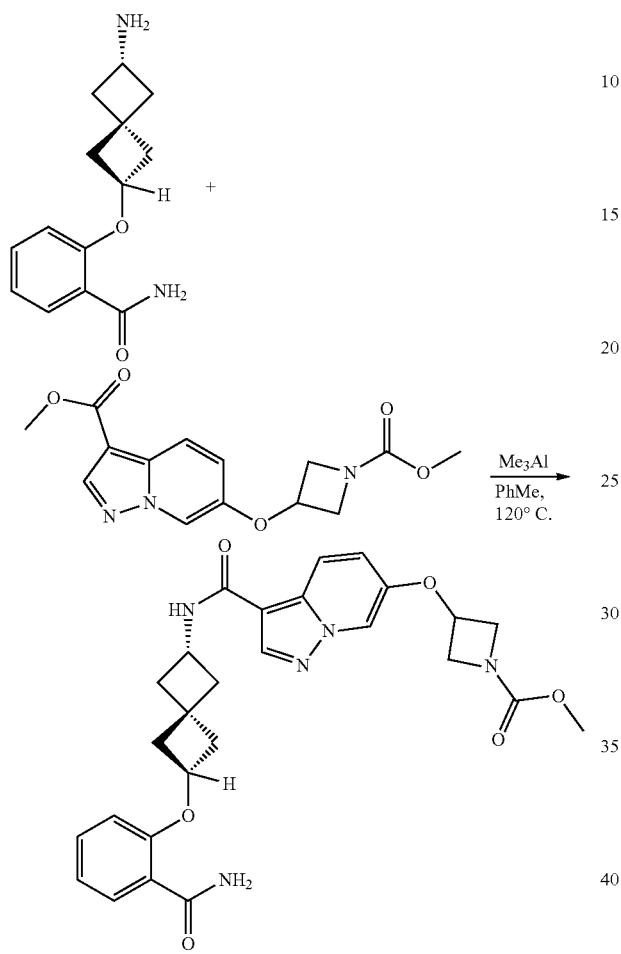

Example 15A (10 mg, 0.041 mmol) was suspended in anhydrous PhMe (1 mL), then trimethylaluminum (2 M in PhMe) (0.061 mL, 0.12 mmol) was added dropwise. After stirring for 5 min at rt (clear solution obtained), methyl 6-((1-(methoxycarbonyl)azetidin-3-yl)oxy)pyrazolo[1,5-a]pyridine-3-carboxylate (14.9 mg, 0.049 mmol) was added, and the reaction mixture was stirred at 120° C. for 30 min. The reaction mixture was cooled to rt, and carefully quenched with TFA. Solvent was removed under reduced pressure, the residue was diluted with DMF (2 mL), filtered, and purified by prep HPLC to afford Example 27 (2.1 mg, 10% yield). MS (ESI) m/z: 520.2 (M+H)$^+$. $^1$H NMR (500 MHz, DMSO-d$_6$) δ ppm 8.46 (s, 1H), 8.31 (s, 1H), 8.28 (br d, J=7.3 Hz, 1H), 8.10 (d, J=9.5 Hz, 1H), 7.83-7.77 (m, 1H), 7.52 (br d, J=14.0 Hz, 2H), 7.46-7.39 (m, 1H), 7.27 (dd, J=9.6, 2.0 Hz, 1H), 7.01 (t, J=7.3 Hz, 1H), 6.96 (d, J=8.2 Hz, 1H), 5.09 (br s, 1H), 4.77 (br t, J=6.7 Hz, 1H), 4.47-4.32 (m, 2H), 3.93 (br s, 1H), 3.58 (s, 3H), 2.72 (br d, J=5.2 Hz, 1H), 2.35 (br d, J=11.6 Hz, 1H), 2.26-2.13 (m, 4H), 1.84 (br s, 4H). Analytical HPLC RT=1.52 min (Method A) and 1.50 min (Method B), purity=100%.

The following examples in Table 2 were prepared using a similar procedure as shown in Example 27. Example 15a was coupled with an ester using trimethylaluminum.

TABLE 2

| Example | R | Name | LCMS (M + H)+ | HPLC Method, RT (min.) | 1H NMR |
|---|---|---|---|---|---|
| 28 | (acyl-pyrazolo[1,5-a]pyridine with 6-[(1,1-dioxo-1λ6-thian-4-yl)oxy] substituent) | N-[(aR)-6-(2-carbamoyl-phenoxy)spiro[3.3]heptan-2-yl]-6-[(1,1-dioxo-1λ6-thian-4-yl)oxy]pyrazolo[1,5-a]pyridine-3-carboxamide | 539.2 | A: 1.39 B: 1.40 | (500 MHz, DMSO-$d_6$) δ ppm 8.70 (s, 1H), 8.47 (s, 1H), 8.28 (d, J = 7.3 Hz, 1H), 8.11 (d, J = 9.8 Hz, 1H), 7.81 (d, J = 7.6 Hz, 1H), 7.55 (br. s., 1H), 7.52 (br. s., 1H), 7.44 (t, J = 7.2 Hz, 1H), 7.38 (d, J = 9.8 Hz, 1H), 7.02 (t, J = 7.3 Hz, 1H), 6.97 (d, J = 8.5 Hz, 1H), 4.83-4.70 (m, 2H), 4.43-4.32 (m, 1H), 3.32-3.22 (m, 2H), 3.15 (d, J = 14.0 Hz, 2H), 2.73 (s, 1H), 2.48-2.43 (m, 1H), 2.39-2.30 (m, 1H), 2.30-2.21 (m, 5H), 2.20-2.09 (m, 3H) |
| 29 | (acyl-imidazo[1,2-a]pyridine with 7-morpholinyl substituent) | N-[(aR)-6-(2-carbamoyl-phenoxy)spiro[3.3]heptan-2-yl]-7-(morpholin-4-yl)imidazo[1,2-a]pyridine-3-carboxamide | 476.2 | A: 1.41 B: 1.27 | (500 MHz, DMSO-$d_6$) δ ppm 9.24 (d, J = 7.6 Hz, 1H), 8.75 (d, J = 7.3 Hz, 1H), 8.36 (br. s., 2H), 7.80 (d, J = 7.6 Hz, 1H), 7.53 (d, J = 7.0 Hz, 2H), 7.44 (t, J = 7.8 Hz, 1H), 7.31-7.23 (m, 1H), 7.02 (t, J = 7.5 Hz, 1H), 6.96 (d, J = 8.2 Hz, 1H), 6.92 (br. s., 1H), 4.78 (quin, J = 6.8 Hz, 1H), 4.42-4.31 (m, 1H), 3.75 (d, J = 4.9 Hz, 4H), 3.46-3.31 (m, 2H), 2.98-2.87 (m, 2H), 2.77-2.69 (m, 1H), 2.41-2.33 (m, 1H), 2.28-2.12 (m, 5H) |
| 30 | (acyl-pyrazolo[1,5-a]pyridine with 7-cyclopropyl-6-(3-methanesulfonylpropoxy)) | N-[(aR)-6-(2-carbamoyl-phenoxy)spiro[3.3]heptan-2-yl]-7-cyclopropyl-6-(3-methanesulfonyl-propoxy)pyrazolo[1,5-a]pyridine-3-carboxamide | 566.9 | A: 1.52 B: 1.53 | (500 MHz, DMSO-$d_6$) 8.50 (s, 1H), 8.27 (br d, J = 7.6 Hz, 1H), 8.04 (d, J = 9.8 Hz, 1H), 7.80 (br d, J = 7.6 Hz, 1H), 7.55 (br s, 1H), 7.50 (br s, 1H), 7.46 (d, J = 9.8 Hz, 1H), 7.43-7.38 (m, 1H), 7.01 (t, J = 7.5 Hz, 1H), 6.96 (d, J = 8.2 Hz, 1H), 4.77 (quin, J = 6.7 Hz, 1H), 4.43-4.29 (m, 1H), 4.15 (t, J = 6.1 Hz, 2H), 3.34-3.25 (m, 2H), 3.02 (s, 3H), 2.76-2.68 (m, 1H), 2.39-2.31 (m, 1H), 2.25-2.20 (m, 1H), 2.20-2.09 (m, 5H), 1.42-1.31 (m, 2H), 1.13-1.02 (m, 2H) |
| 31 | (acyl-pyrazolo[1,5-a]pyridine with 7-cyclopropyl-6-(2-hydroxyethoxy)) | N-[(aR)-6-(2-carbamoyl-phenoxy)spiro[3.3]heptan-2-yl]-7-cyclopropyl-6-(2-hydroxy-ethoxy)pyrazolo[1,5-a]pyridine-3-carboxamide | 491.0 | A: 1.49 B: 1.50 | (500 MHz, DMSO-$d_6$) δ ppm 8.49 (s, 1H), 8.27 (d, J = 7.6 Hz, 2H), 8.02 (d, J = 9.8 Hz, 1H), 7.81 (d, J = 7.6 Hz, 1H), 7.56 (br. s., 1H), 7.51 (br. s., 1H), 7.49-7.38 (m, 2H), 7.02 (t, J = 7.5 Hz, 1H), 6.97 (d, J = 8.2 Hz, 1H), 4.78 (t, J = 6.7 Hz, 1H), 4.42-4.33 (m, 1H), 4.06 (t, J = 4.7 Hz, 2H), 3.71 (br. s., 2H), 2.92 (br. s., 5H), 2.26-2.10 (m, 4H), 1.51 (d, J = 3.4 Hz, 2H), 1.03 (dd, J = 8.7, 2.3 Hz, 2H) |

TABLE 2-continued

| | | | | |
|---|---|---|---|---|
| 32 | | N-[(aR)-6-(2-carbamoyl-phenoxy)spiro[3.3]heptan-2-yl]-7-cyclopropyl-6-(3,3,3-trifluoro-propoxy)pyrazolo[1,5-a]pyridine-3-carboxamide | 542.9 | A: 1.97 B: 1.99 (500 MHz, DMSO-$d_6$) 8.51 (s, 1H), 8.27 (br d, J = 7.6 Hz, 1H), 8.04 (d, J = 9.8 Hz, 1H), 7.80 (br d, J = 7.6 Hz, 1H), 7.54 (br s, 1H), 7.49 (br d, J = 9.8 Hz, 2H), 7.43 (br t, J = 7.6 Hz, 1H), 7.04-7.00 (m, 1H), 6.96 (d, J = 8.2 Hz, 1H), 4.78 (br t, J = 6.9 Hz, 1H), 4.44-4.33 (m, 1H), 4.26 (t, J = 5.8 Hz, 2H), 2.81 (tt, J = 11.3, 5.5 Hz, 2H), 2.72 (br d, J = 5.5 Hz, 1H), 2.46 (br s, 1H), 2.38-2.27 (m, 1H), 2.25-2.20 (m, 1H), 2.20-2.10 (m, 3H), 1.40 (br d, J = 3.7 Hz, 2H), 1.12-1.00 (m, 2H) |
| 33 | | N-[(aR)-6-(2-carbamoyl-phenoxy)spiro[3.3]heptan-2-yl]-6-(3,3,3-trifluoro-propoxy)pyrazolo[1,5-a]pyridine-3-carboxamide | 503.2 | A: 1.73 B: 1.73 (500 MHz, DMSO-$d_6$) δ ppm 8.55 (s, 1H), 8.46 (s, 1H), 8.28 (d, J = 7.6 Hz, 1H), 8.09 (d, J = 9.8 Hz, 1H), 7.84-7.77 (m, 1H), 7.55 (br. s., 1H), 7.52 (br. s., 1H), 7.44 (t, J = 6.9 Hz, 1H), 7.25 (dd, J = 9.6, 2.0 Hz, 1H), 7.02 (t, J = 7.3 Hz, 1H), 6.97 (d, J = 8.2 Hz, 1H), 4.83-4.73 (m, 1H), 4.42-4.34 (m, 1H), 4.29 (t, J = 5.8 Hz, 2H), 2.91-2.77 (m, 2H), 2.77-2.69 (m, 1H), 2.49-2.42 (m, 1H), 2.39-2.29 (m, 1H), 2.27-2.12 (m, 4H) |
| 34 | | N-[(aR)-6-(2-carbamoyl-phenoxy)spiro[3.3]heptan-2-yl]-7-(1-methyl-1H-pyrazol-4-yl)imidazo[1,2-a]pyridine-3-carboxamide | 471.2 | A: 1.40 B: 1.15 (500 MHz, DMSO-$d_6$) δ ppm 9.48 (br. s., 1H), 8.82 (d, J = 7.2 Hz, 1H), 8.47 (s, 1H), 8.16 (s, 1H), 7.98 (d, J = 15.1 Hz, 1H), 7.85-7.72 (m, 1H), 7.62-7.51 (m, 2H), 7.44 (t, J = 7.2 Hz, 1H), 7.12-6.93 (m, 3H), 4.79 (t, J = 6.8 Hz, 1H), 4.45-4.34 (m, 1H), 3.91 (s, 3H), 2.74 (dd, J = 11.2, 5.6 Hz, 1H), 2.59-2.55 (m, 1H), 2.42-2.33 (m, 1H), 2.28-2.15 (m, 4H) |
| 35 | | N-[(aR)-6-(2-carbamoyl-phenoxy)spiro[3.3]heptan-2-yl]-7-cyclopropyl-6-[(1,1-dioxo-1λ⁶-thian-4-yl)oxy]pyrazolo[1,5-a]pyridine-3-carboxamide | 578.9 | A: 1.60 B: 1.60 (500 MHz, DMSO-$d_6$) δ ppm 8.52 (s, 1H), 8.30 (d, J = 7.6 Hz, 1H), 8.06 (d, J = 9.6 Hz, 1H), 7.81 (d, J = 7.7 Hz, 1H), 7.55 (br. s., 2H), 7.50 (d, J = 9.7 Hz, 1H), 7.44 (t, J = 7.2 Hz, 1H), 7.02 (t, J = 7.4 Hz, 1H), 6.97 (d, J = 8.2 Hz, 1H), 4.78 (t, J = 6.8 Hz, 1H), 4.65 (br. s., 1H), 4.42-4.33 (m, 1H), 3.30-3.13 (m, 3H), 2.77-2.67 (m, 1H), 2.48-2.44 (m, 1H), 2.41 (d, J = 5.5 Hz, 1H), 2.37-2.31 (m, 1H), 2.29-2.12 (m, 8H), 1.35 (d, J = 3.8 Hz, 2H), 1.16 (t, J = 7.2 Hz, 1H), 1.10 (d, J = 6.6 Hz, 2H) |
| 36 | | N-[(aR)-6-(2-carbamoyl-phenoxy)spiro[3.3]heptan-2-yl]-7-(4-methyl-piperazin-1-yl)imidazo[1,2-a]pyridine-3-carboxamide | 489.3 | A: 1.34 B: 1.08 (500 MHz, DMSO-$d_6$) □ 9.29 (br d, J = 7.9 Hz, 1H), 8.84 (br d, J = 6.8 Hz, 1H), 8.42 (s, 1H), 7.79 (br d, J = 7.4 Hz, 1H), 7.54 (br s, 2H), 7.43 (br t, J = 7.4 Hz, 1H), 7.21 (br d, J = 51.0 Hz, 1H), 7.06 (br d, J = 12.7 Hz, 1H), 7.02-6.98 (m, 1H), 6.95 (br d, J = 8.2 Hz, 1H), 4.77 (br t, J = 6.8 Hz, 1H), 4.45-4.28 (m, 1H), 2.86 (s, 3H), 2.72 (br s, 1H), 2.54 (s, 8H), 2.37 (br s, 1H), 2.27-2.11 (m, 4H) |

EXAMPLE 37

Preparation of N-((aR)-6-(2-carbamoylphenoxy)spiro[3.3]heptan-2-yl)indoline-1-carboxamide

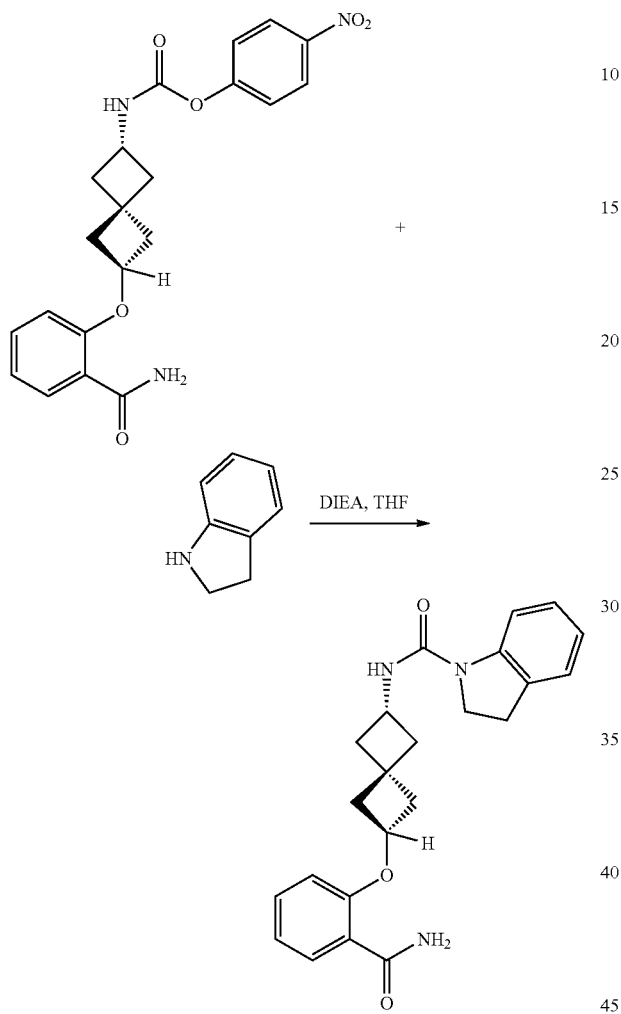

To a solution of indoline (0.011 mL, 0.10 mmol) and DIEA (0.021 mL, 0.12 mmol) in anhydrous THF (0.5 mL), a solution of Intermediate 15 (16.8 mg, 0.041 mmol) was added. The reaction mixture was stirred at rt for 5 min, and then at 50° C. for 15 min. The reaction mixture was concentrated, diluted with DMF, filtered and purified by prep HPLC to afford Example 36 (10 mg, 63%). MS (ESI) m/z: 392.2 (M+H)$^+$. $^1$H NMR (500 MHz, DMSO-d$_6$) δ ppm 7.84-7.76 (m, 2H), 7.54 (br. s., 2H), 7.43 (t, J=7.6 Hz, 1H), 7.13 (d, J=7.2 Hz, 1H), 7.09-6.99 (m, 2H), 6.96 (d, J=8.3 Hz, 1H), 6.82 (t, J=7.4 Hz, 1H), 6.71 (d, J=7.4 Hz, 1H), 4.77 (quin, J=6.8 Hz, 1H), 4.21-4.09 (m, 1H), 3.87 (t, J=8.6 Hz, 2H), 3.09 (t, J=8.5 Hz, 2H), 2.73-2.66 (m, 1H), 2.44-2.36 (m, 1H), 2.32-2.24 (m, 1H), 2.23-2.10 (m, 4H). Analytical HPLC RT=1.73 min (Method A) and 1.74 min (Method B), purity=99.5%.

The following examples in Table 3 were prepared by using a similar procedure to that used in the preparation of Example 37. Intermediate 15 was coupled with an amine in the presence of base. Various bases could be used other than the one described in Example 15, such as TEA.

TABLE 3

| Example | R | Name | LCMS (M + H)+ | HPLC Method, RT (min.) | 1H NMR |
|---|---|---|---|---|---|
| 38 | (acyl-5-methoxy-2,3-dihydroindoline-1-carbonyl) | N-[(aR)-6-(2-carbamoyl-phenoxy)spiro[3.3]heptan-2-yl]-5-methoxy-2,3-dihydro-1H-indole-1-carboxamide | 422.0 | A: 1.69 B: 1.70 | (500 MHz, DMSO-d6) δ ppm 7.80 (d, J = 6.6 Hz, 1H), 7.69 (d, J = 8.8 Hz, 1H), 7.54 (br. s., 2H), 7.43 (t, J = 7.1 Hz, 1H), 7.02 (t, J = 7.5 Hz, 1H), 6.96 (d, J = 8.3 Hz, 1H), 6.76 (s, 1H), 6.66-6.57 (m, 2H), 4.76 (t, J = 6.8 Hz, 1H), 4.19-4.09 (m, 1H), 3.85 (t, J = 8.6 Hz, 2H), 3.68 (s, 3H), 3.06 (t, J = 8.5 Hz, 2H), 2.72-2.65 (m, 1H), 2.44-2.35 (m, 1H), 2.31-2.22 (m, 1H), 2.23-2.09 (m, 5H) |
| 39 | (5-methanesulfonyl-2,3-dihydroindoline-1-carbonyl) | N-[(aR)-6-(2-carbamoyl-phenoxy)spiro[3.3]heptan-2-yl]-5-methane-sulfonyl-2,3-dihydro-1H-indole-1-carboxamide | 469.9 | A: 1.48 B: 1.48 | (500 MHz, DMSO-d6) δ ppm 7.96 (d, J = 8.3 Hz, 1H), 7.80 (d, J = 6.9 Hz, 1H), 7.66-7.60 (m, 2H), 7.54 (br. s., 2H), 7.47-7.39 (m, 1H), 7.05-6.98 (m, 2H), 6.96 (d, J = 8.4 Hz, 1H), 4.77 (t, J = 6.8 Hz, 1H), 4.20-4.11 (m, 1H), 3.98 (t, J = 8.8 Hz, 2H), 3.18 (t, J = 8.6 Hz, 1H), 3.12 (s, 3H), 2.97-2.88 (m, 1H), 2.73-2.66 (m, 1H), 2.45-2.38 (m, 1H), 2.33-2.26 (m, 1H), 2.24-2.13 (m, 4H) |
| 40 | ((4-methoxyphenyl)carbamoyl-acetyl) | 2-[((aR)-6-{[(4-methoxy-phenyl)carbamoyl]amino}spiro[3.3]heptan-2-yl)oxy]benzamide | 395.9 | A: 1.52 B: 1.53 | (500 MHz, DMSO-d6) δ ppm 8.12 (s, 1H), 7.80 (d, J = 7.6 Hz, 1H), 7.54 (br. s., 2H), 7.43 (t, J = 7.7 Hz, 1H), 7.26 (d, J = 8.6 Hz, 2H), 7.01 (t, J = 7.4 Hz, 1H), 6.95 (d, J = 8.2 Hz, 1H), 6.80 (d, J = 8.6 Hz, 2H), 6.28 (d, J = 7.8 Hz, 1H), 4.75 (t, J = 6.8 Hz, 1H), 4.11-3.98 (m, 1H), 3.74-3.65 (m, 3H), 2.71-2.62 (m, 1H), 2.43 (br. s., 1H), 2.34-2.25 (m, 1H), 2.17 (ddd, J = 17.7, 11.1, 7.1 Hz, 2H), 1.94 (t, J = 8.9 Hz, 2H) |
| 41 | (isoindoline-2-carbonyl) | N-[(aR)-6-(2-carbamoyl-phenoxy)spiro[3.3]heptan-2-yl]-2,3-dihydro-1H-isoindole-2-carboxamide | 392.0 | A: 1.58 B: 1.59 | (500 MHz, DMSO-d6) δ ppm 7.81 (dd, J = 7.6, 1.5 Hz, 1H), 7.55 (br. s., 1H), 7.51 (br. s., 1H), 7.46-7.39 (m, 1H), 7.34-7.22 (m, 4H), 7.02 (t, J = 7.5 Hz, 1H), 6.96 (d, J = 8.5 Hz, 1H), 6.48 (d, J = 7.6 Hz, 1H), 4.76 (quin, J = 6.8 Hz, 1H), 4.57 (s, 4H), 4.16-4.05 (m, 1H), 2.68 (dt, J = 11.1, 5.7 Hz, 1H), 2.43-2.34 (m, 1H), 2.30-2.22 (m, 1H), 2.22-2.13 (m, 2H), 2.13-2.06 (m, 2H) |

EXAMPLE 42

Preparation of N-((aR)-6-((3-carbamoylpyridin-2-yl)oxy)spiro[3.3]heptan-2-yl)-7-cyclopropyl-6-(2-hydroxy-2-methylpropoxy)pyrazolo[1,5-a]pyridine-3-carboxamide

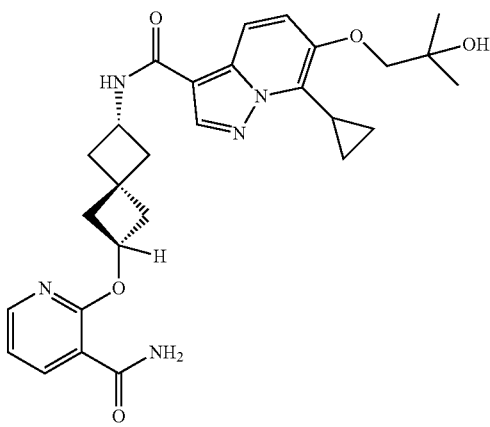

EXAMPLE 42A

Preparation of benzyl (6-((3-cyanopyridin-2-yl)oxy)spiro[3.3]heptan-2-yl)carbamate

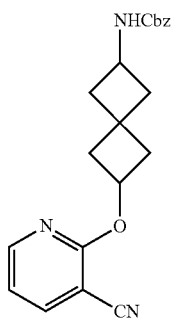 [SMILES: N#Cc1cccnc1OC1CC2(CC(NC(=O)OCc3ccccc3)C2)C1]

To a solution of Intermediate 1 (0.48 g, 1.837 mmol) in anhydrous THF (14 mL) at 0° C., was added 60% NaH (0.162 g, 4.04 mmol). The reaction mixture was stirred at rt until becoming mostly homogeneous (~30 min), then, 2-chloronicotinonitrile (0.5 g, 3.61 mmol) was added in one portion, and the reaction mixture was allowed to stir for 16 h. The reaction mixture was quenched with sat. NH$_4$Cl and evaporated. The residue was partitioned between water (20 mL) and ethyl acetate (50 mL). The aqueous layer was extracted with ethyl acetate (2×20 mL). The combined organic layers were washed with sat. NaHCO$_3$ and brine, dried (MgSO$_4$) and concentrated. The residue was purified via flash chromatography to afford benzyl (6-((3-cyanopyridin-2-yl)oxy)spiro[3.3]heptan-2-yl)carbamate (0.52 g, 78% yield), as a clear oil. MS (ESI) m/z: 364.1 (M+H)$^+$; $^1$H NMR (400 MHz, CDCl$_3$) δ 8.31 (dd, J=5.1, 2.0 Hz, 1H), 7.86 (dd, J=7.5, 2.0 Hz, 1H), 7.42-7.29 (m, 5H), 6.95 (dd, J=7.6, 5.0 Hz, 1H), 5.23 (quin, J=7.2 Hz, 1H), 5.09 (s, 2H), 4.83 (br. s., 1H), 2.74-2.61 (m, 1H), 2.59-2.38 (m, 3H), 2.27 (dt, J=11.8, 7.3 Hz, 2H), 2.02-1.91 (m, 2H).

EXAMPLE 42B

Preparation of benzyl ((aR)-6-((3-carbamoylpyridin-2-yl)oxy)spiro[3.3]heptan-2-yl)carbamate

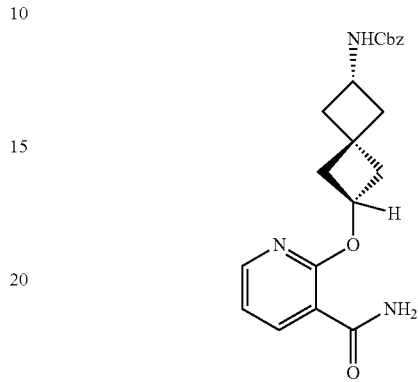

To a solution of Example 42A (0.52 g, 1.431 mmol) in DMSO (12 mL), were added K$_2$CO$_3$ (0.593 g, 4.29 mmol) and magnesium oxide (0.288 g, 7.15 mmol). To the reaction was added 30% aq. hydrogen peroxide (1.61 mL, 15.7 mmol) dropwise over 5 min (slight exotherm), and the reaction mixture was stirred at rt. The reaction mixture was diluted with EtOAc (80 mL) and dilute HCl (25 mL). Organic phase was separated, washed with sat. NaHCO$_3$ (2×25 mL) and brine (1×25 mL), dried (MgSO$_4$) and filtered. Solvent was removed under reduced pressure. The racemic product was subjected to chiral prep HPLC (Instrument: Berger MGII Prep SFC (Column: Chiralpak IC, 21×250 mm, 5 micron; Mobile Phase: 35% MeOH/65% CO$_2$; Flow Conditions: 45 mL/min, 110 Bar, 40° C.; Detector Wavelength: 220 nm; Injection Details: 0.5 mL of 12 mg/mL in Methanol) and the second peak was collected to afford Example 42B (229 mg, 42% yield). MS (ESI) m/z: 382.1 (M+H)$^+$.

EXAMPLE 42C

Preparation of 2-(((aR)-6-aminospiro[3.3]heptan-2-yl)oxy)nicotinamide

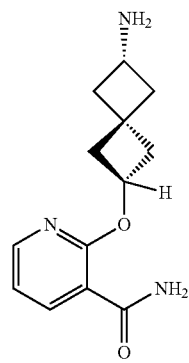

Example 42B (229 mg, 0.601 mmol) in MeOH/EtOH and 90 mg (50% water) Pd/C was hydrogenated at 50 psi. The mixture was filtered and concentrated to afford Example 42C (146 mg, 98% yield). MS (ESI) m/z: 248.1 (M+H)$^+$.

EXAMPLE 42

To 7-cyclopropyl-6-(2-hydroxy-2-methylpropoxy)pyrazolo[1,5-a]pyridine-3-carboxylic acid (17 mg, 0.059 mmol) and HATU (22.3 mg, 0.059 mmol) in DMF (0.5 mL), was added DIEA (39 μl, 0.23 mmol). After 10 min, Example 42C (11.1 mg, 0.045 mmol) was added. The mixture was stirred at rt for 18 h, then the reaction was quenched with MeOH and TFA, filtered and purified by preparative HPLC to afford Example 42 (14 mg, 48%/o yield). MS (ESI) m/z: 392.2 (M+H)$^+$. $^1$H NMR (500 MHz, DMSO-d$_6$) δ 8.50 (s, 1H), 8.33-8.21 (m, 2H), 8.17 (d, J=7.6 Hz, 1H), 8.03 (d, J=9.8 Hz, 1H), 7.71 (br. s., 1H), 7.60 (br. s., 1H), 7.46 (d, J=9.8 Hz, 1H), 7.18-7.05 (m, 1H), 5.31-5.16 (m, 1H), 4.39 (d, J=7.9 Hz, 1H), 2.73-2.59 (m, 2H), 2.48-2.41 (m, 1H), 2.35 (br. s., 1H), 2.30-2.12 (m, 4H), 1.56-1.43 (m, 2H), 1.24 (s, 6H), 1.11-1.00 (m, 2H); Analytical HPLC RT=1.59 min (Method A) and 1.58 min (Method B), purity=97.5%.

EXAMPLE 43

Preparation of N-((aR)-6-((3-carbamoylpyridin-2-yl)oxy)spiro[3.3]heptan-2-yl)-6-(2-hydroxy-2-methylpropoxy)-7-(3,3,3-trifluoropropyl)pyrazolo[1,5-a]pyridine-3-carboxamide, trifluoroacetic acid salt

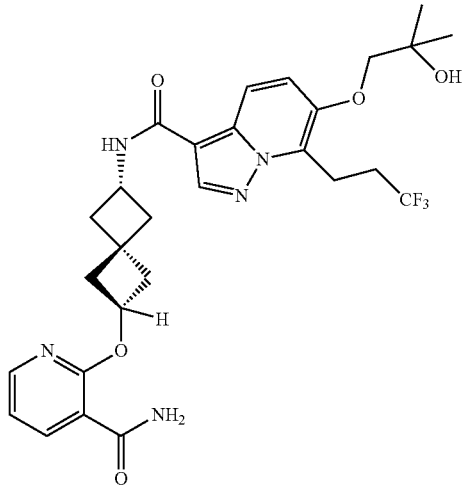

Example 43 (5.2 mg, 95%) was prepared in a manner similar to Example 42, using Bop and substituting Intermediate 17 for Intermediate 4. MS (ESI) m/z: 576.0 (M+H)$^+$. $^1$H NMR (500 MHz, DMSO-d$_6$) δ 8.56 (s, 1H), 8.33 (d, J=7.5 Hz, 1H), 8.27 (d, J=3.1 Hz, 1H), 8.17 (d, J=7.4 Hz, 1H), 8.13 (d, J=9.6 Hz, 1H), 7.73 (br. s., 1H), 7.61 (br. s., 1H), 7.57 (d, J=9.7 Hz, 1H), 7.11 (dd, J=7.3, 5.0 Hz, 1H), 5.23 (quin, J=7.0 Hz, 1H), 4.45-4.33 (m, 1H), 3.85 (s, 2H), 2.77-2.63 (m, 3H), 2.49-2.42 (m, 2H), 2.40-2.30 (m, 1H), 2.30-2.12 (m, 4H), 1.24 (s, 6H). Analytical HPLC RT=1.83 min (Method A) and 1.84 min (Method B), purity=95.5%.

EXAMPLE 44

Preparation of N-((aR)-6-((3-carbamoylpyridin-4-yl)oxy)spiro[3.3]heptan-2-yl)-6-(2-hydroxy-2-methylpropoxy)pyrazolo[1,5-a]pyridine-3-carboxamide, trifluoracetate

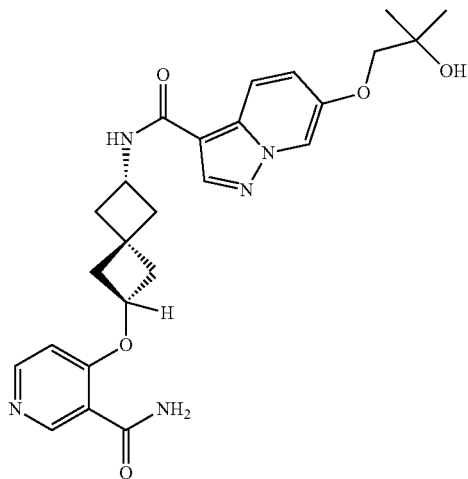

EXAMPLE 44A

Preparation of benzyl ((aR)-6-((3-cyanopyridin-4-yl)oxy)spiro[3.3]heptan-2-yl)carbamate

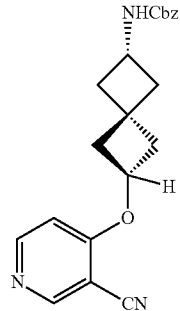

Intermediate 35 (0.10 g, 0.383 mmol) was dissolved in anhydrous THF (3.99 mL), and NaH (60%/0 wt. in mineral oil) (0.034 g, 0.842 mmol) was added in one portion at 0° C. After 30 min, 4-chloronicotinonitrile (0.133 g, 0.957 mmol) and was added in one portion, and the reaction mixture was allowed to reach rt overnight (16 h). Afterwards, the reaction mixture was quenched with NH$_4$Cl (2 mL), diluted with EtOAc (50 mL), washed with water (2×10 mL), brine (1×20 mL), dried (Na$_2$SO$_4$), filtered, concentrated, and purified by normal phase chromatography to give Example 44A (138 mg, 99%). MS (ESI) m/z: 364.1 (M+H)$^+$.

EXAMPLE 44B

Preparation of 4-((aR)-6-aminospiro[3.3]heptan-2-yl)oxy)nicotinamide

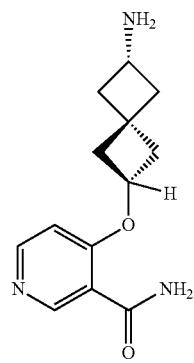

Example 44A (138 mg, 0.38 mmol) was dissolved in DMSO (3.5 mL), then K$_2$CO$_3$ (157 mg, 1.14 mmol) and MgO (77 mg, 1.899 mmol) were added. Afterwards, hydrogen peroxide (35% wt. aq) (366 µl, 4.18 mmol) dropwise over 5 min (slight exotherm), and the reaction mixture was stirred at rt overnight. The reaction mixture was diluted with EtOAc (50 mL) and HCl (1 M, aq., 10 mL). Organic phase was separated, washed with brine (1×25 mL), dried (Na$_2$SO$_4$), filtered and concentrated. The CBz group was removed by dissolving in MeOH/THF (4 mL/4 mL), treating with TEA (265 µl, 1.899 mmol) followed by Pd—C (10%) (40.4 mg, 0.038 mmol) and subjecting to a hydrogen atmosphere (55 psi) for 2 h. Pd—C was filtered off using membrane filter, and the filtrate concentrated to afford Example 44B (59 mg, 62.8% yield) as a white solid. MS (ESI) m/z: 248.1 (M+H)$^+$.

EXAMPLE 44

A solution of Example 44B (0.015 g, 0.061 mmol) and Intermediate 2 (0.020 g, 0.079 mmol) in DMF (1.0 mL) was treated with DIEA (0.053 mL, 0.303 mmol) followed by BOP (0.030 g, 0.067 mmol). The reaction mixture was stirred at rt for 1 h. The reaction mixture was quenched with MeOH (0.1 mL), diluted with DMF (2 mL total volume), filtered, and purified by reverse phase HPLC to give Example 44 (14.6 mg, 36.9% yield). MS (ESI) m/z: 480.0 (M+H)$^+$. $^1$H NMR (500 MHz, DMSO-d$_6$) δ 8.43 (br s, 2H), 8.28 (br d, J=7.5 Hz, 1H), 8.07 (d, J=9.6 Hz, 1H), 7.83 (br s, 1H), 7.53 (br s, 1H), 7.29-7.22 (m, 2H), 7.16-7.01 (m, 1H), 4.84 (br s, 1H), 4.41-4.32 (m, 1H), 3.78 (s, 2H), 3.45-3.37 (m, 1H), 2.73 (br s, 1H), 2.47-2.43 (m, 1H), 2.36-2.12 (m, 5H), 1.21 (s, 6H). Analytical HPLC RT=1.061 min (Method A) and 0.891 min (Method B), purity=95%.

EXAMPLE 45

Preparation of N-((aR)-6-((4-carbamoylpyridin-3-yl)oxy)spiro[3.3]heptan-2-yl)-6-(2-hydroxy-2-methylpropoxy)pyrazolo[1,5-a]pyridine-3-carboxamide, trifluoracetate

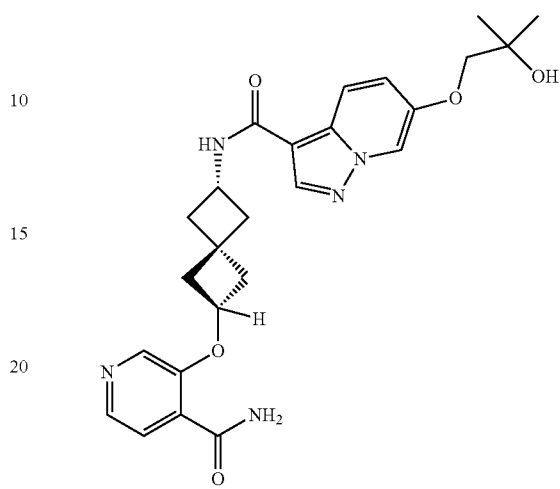

N-((aR)-6-((4-carbamoylpyridin-3-yl)oxy)spiro[3.3]heptan-2-yl)-6-(2-hydroxy-2-methylpropoxy)pyrazolo[1,5-a]pyridine-3-carboxamide (5.8 mg, 28%) was prepared in a similar manner as Example 44, substituting 3-chloroisonicotinonitrile for 4-chloronicotinonitrile. MS (ESI) m/z: 480.1 (M+H)$^+$. $^1$H NMR (500 MHz, DMSO-d$_6$) δ 8.43 (br d, J=6.5 Hz, 2H), 8.29 (br d, J=7.5 Hz, 1H), 8.07 (br d, J=9.6 Hz, 1H), 7.78 (br s, 1H), 7.66 (br s, 1H), 7.28-7.22 (m, 2H), 4.91 (br s, 1H), 4.42-4.31 (m, 1H), 3.78 (s, 2H), 3.45 (br d, J=10.3 Hz, 1H), 2.74 (br s, 1H), 2.48-2.42 (m, 1H), 2.33 (br s, 1H), 2.25-2.11 (m, 5H), 1.21 (s, 6H). Analytical HPLC RT=1.106 min (Method A) and 0.948 min (Method B), purity=92%.

EXAMPLE 46

Preparation of N-((aR)-6-((3-carbamoylpyridin-2-yl)oxy)spiro[3.3]heptan-2-yl)-1-(2-hydroxy-2-methylpropyl)-6-(1-methyl-1H-pyrazol-4-yl)-1H-indazole-3-carboxamide, trifluoracetate

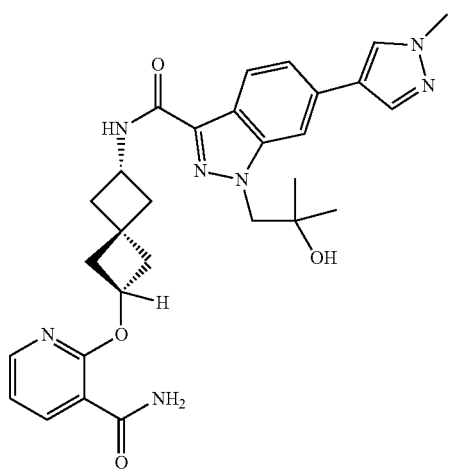

A solution of Example 81 (0.018 g, 0.027 mmol), 1-methyl-4-(4,4,5,5-tetramethyl-1,3,2-dioxaborolan-2-yl)-1H-pyrazole (0.011 g, 0.055 mmol), and solution of Na₂CO₃ (0.015 g, 0.137 mmol) dissolved in H₂O (0.169 mL) were added to dioxane (0.846 mL). After purging with nitrogen for 5 min, tetrakis(triphenylphosphine)palladium (0) (3.17 mg, 2.74 µmol) was added and the reaction mixture irradiated at 120° C. for 30 min. The reaction was cooled to rt, diluted with water, extracted with EtOAc, dried over Na₂SO₄, filtered, and concentrated. The residue was purified by reverse phase chromatography to give the desired product (7.9 mg, 43.8%). MS (ESI) m/z: 544.0 (M+H)⁺. ¹H NMR (500 MHz, DMSO-d₆) δ 8.40 (d, J=7.9 Hz, 1H), 8.28 (d, J=4.6 Hz, 1H), 8.24-8.16 (m, 2H), 8.07 (d, J=8.5 Hz, 1H), 7.95 (d, J=16.2 Hz, 2H), 7.70 (br. s., 1H), 7.61 (br. s., 1H), 7.47 (d, J=8.5 Hz, 1H), 7.12 (dd, J=7.2, 5.0 Hz, 1H), 5.30-5.19 (m, 1H), 4.49-4.41 (m, 1H), 4.39 (s, 2H), 3.89 (s, 3H), 2.68 (dd, J=10.8, 5.6 Hz, 1H), 2.50-2.41 (m, 2H), 2.38-2.19 (m, 5H), 1.18 (s, 6H). Analytical HPLC RT=1.480 min (Method A) and 1.454 min (Method B), purity=100%.

EXAMPLE 47

Preparation of N-((aR)-6-((3-carbamoylpyridin-2-yl)oxy)spiro[3.3]heptan-2-yl)-8-cyclopropyl-7-(2-fluoro-2-methylpropoxy)imidazo[1,2-a]pyridine-3-carboxamide, trifluoracetate

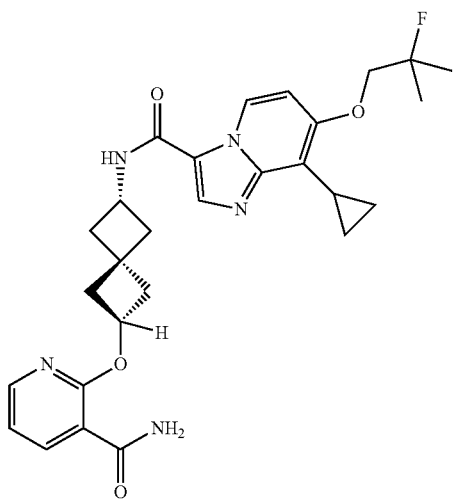

Example 65 (0.014 g, 0.027 mmol) was suspended in anhydrous DCM (5 mL), and the reaction mixture was cooled to −78° C. DAST (0.018 mL, 0.135 mmol) was added in one portion, and the reaction mixture allowed to reach rt over 14 h. The reaction mixture was cooled to 0° C., quenched with MeOH (1 mL), concentrated, and purified by reverse phase chromatography to give the desired product (6.3 mg, 36.8%). MS (ESI) m/z: 522.0 (M+H)⁺. ¹H NMR (500 MHz, DMSO-d6) 9.41 (d, J=7.6 Hz, 1H), 8.80 (d, J=6.4 Hz, 1H), 8.49 (s, 1H), 8.26 (br. s., 1H), 8.17 (d, J=7.0 Hz, 1H), 7.69 (br. s., 1H), 7.62 (br. s., 1H), 7.36 (d, J=7.6 Hz, 1H), 7.26 (s, 1H), 7.16 (s, 1H), 7.11 (d, J=5.2 Hz, 1H), 7.06 (s, 1H), 5.23 (t, J=7.0 Hz, 1H), 4.42-4.34 (m, 1H), 2.73-2.64 (m, 1H), 2.49-2.45 (m, 1H), 2.38 (br. s., 1H), 2.31-2.15 (m, 4H), 2.07 (d, J=9.2 Hz, 1H), 1.50 (s, 3H), 1.46 (s, 3H), 1.16-1.08 (m, 2H), 1.04 (d, J=7.6 Hz, 2H). Analytical HPLC RT=1.830 min (Method A) and 1.436 min (Method B), purity=100%.

EXAMPLE 48

Preparation of N-((aR)-6-((4-carbamoylpyridazin-3-yl)oxy)spiro[3,3]heptan-2-yl)-6-(2-hydroxy-2-methylpropoxy)pyrazolo[1,5-a]pyridine-3-carboxamide, trifluoracetate

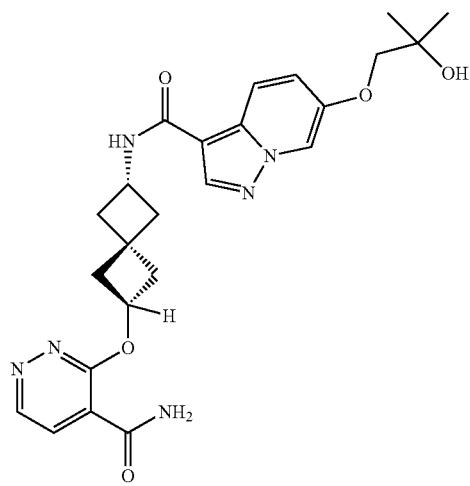

N-((aR)-6-((4-carbamoylpyridazin-3-yl)oxy)spiro[3.3]heptan-2-yl)-6-(2-hydroxy-2-methylpropoxy)pyrazolo[1,5-a]pyridine-3-carboxamide (4.0 mg, 16.2%) was prepared in a similar manner as Example 64 substituting 4-chloroisonicotinonitrile with 3-chloropyridazine-4-carbonitrile. MS (ESI) m/z: 503.3 (M+H)⁺. ¹H NMR (500 MHz, DMSO-d6) δ 8.99 (d, J=4.5 Hz, 1H), 8.42 (br d, J=8.7 Hz, 2H), 8.30 (br d, J=7.6 Hz, 1H), 8.07 (d, J=9.7 Hz, 1H), 7.95 (br s, 1H), 7.84 (br s, 1H), 7.76 (d, J=4.5 Hz, 1H), 7.27 (br d, J=9.8 Hz, 1H), 5.33 (quin, J=7.1 Hz, 1H), 4.42-4.34 (m, 1H), 3.78 (s, 2H), 2.73-2.67 (m, 1H), 2.44 (br s, 1H), 2.37-2.15 (m, 6H), 1.21 (s, 6H). Analytical HPLC RT=1.301 min (Method A) and 1.308 min (Method B), purity=97.1%.

EXAMPLE 49

Preparation of N-((aR)-6-((3-carbamoylpyridin-2-yl)oxy)spiro[3.3]heptan-2-yl)-7-cyclopropyl-6-(2-fluoro-2-methylpropoxy)pyrazolo[1,5-a]pyridine-3-carboxamide, trifluoroacetate

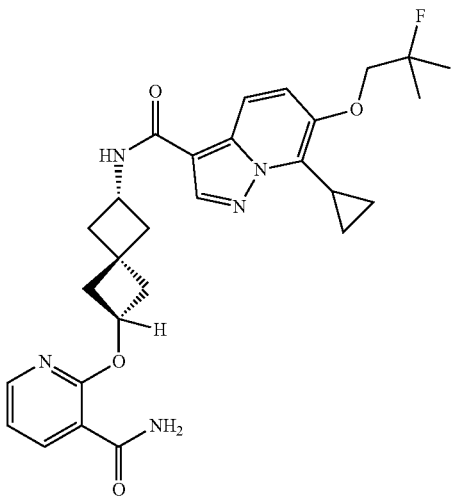

Example 42 (0.010 g, 0.016 mmol) was suspended in anhydrous DCM (5 mL), and the reaction mixture was cooled to −78° C. DAST (10.43 µl, 0.079 mmol) was added in one portion, and the reaction mixture allowed to reach rt over 14 h. The reaction mixture was cooled to 0° C., quenched with MeOH (1 mL), concentrated, and purified by reverse phase chromatography to give the desired product (3.4 mg, 32.5%). MS (ESI) m/z: 522.2 (M+H)$^+$. $^1$H NMR (500 MHz, DMSO-d6) δ 8.51 (s, 1H), 8.28-8.25 (m, 2H), 8.16 (br d, J=7.3 Hz, 1H), 8.04 (d, J=9.8 Hz, 1H), 7.69 (br s, 1H), 7.60 (br s, 1H), 7.46 (d, J=9.8 Hz, 1H), 7.11-7.08 (m, 1H), 5.23 (quin, J=7.0 Hz, 1H), 4.41-4.34 (m, 1H), 4.10-4.05 (m, 2H), 2.69-2.63 (m, 1H), 2.46-2.42 (m, 1H), 2.37-2.32 (m, 1H), 2.29-2.13 (m, 5H), 1.47 (s, 3H), 1.43-1.40 (m, 5H), 1.09-1.05 (m, 2H). Analytical HPLC RT=1.842 min (Method A) and 1.837 min (Method B), purity=96%.

EXAMPLE 50

Preparation of N-((aR)-6-((3-carbamoylpyridin-2-yl)oxy)spiro[3.3]heptan-2-yl)-1-(2-hydroxy-2-methylpropyl)-5-(1-methyl-1H-pyrazol-4-yl)-1H-indazole-3-carboxamide, trifluoroacetate

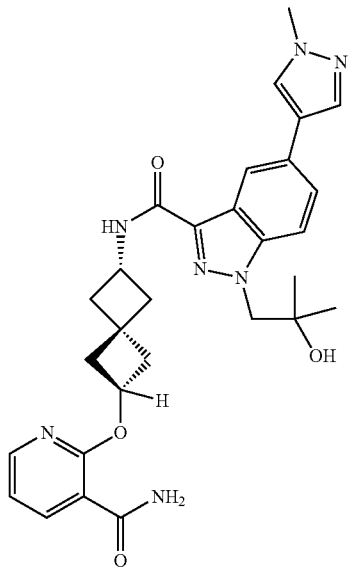

A solution of Example 93 (17.7 mg, 0.033 mmol), 1-methyl-4-(4,4,5,5-tetramethyl-1,3,2-dioxaborolan-2-yl)-1H-pyrazole (0.014 g, 0.065 mmol), and solution of Na$_2$CO$_3$ (0.017 g, 0.163 mmol) dissolved in H$_2$O (0.201 mL) were added to dioxane (1.007 mL). After purging with nitrogen for 5 min, pallidiumtetrakis (3.77 mg, 3.26 µmol) was added and the reaction mixture irradiated at 120° C. for 30 min before diluting with H$_2$O, extracted with EtOAc, dried over Na$_2$SO$_4$, filtered, concentrated, and purifying by reverse phase chromatography to give the desired product (9.7 mg, 43.8%). MS (ESI) m/z: 544.3 (M+H)$^+$. $^1$H NMR (500 MHz, DMSO-d6) δ 8.44 (br d, J=7.7 Hz, 1H), 8.29-8.22 (m, 2H), 8.19-8.13 (m, 2H), 7.85 (s, 1H), 7.79-7.70 (m, 2H), 7.64 (br d, J=7.8 Hz, 2H), 7.28 (br s, 1H), 7.18 (br s, 1H), 7.13-7.05 (m, 2H), 5.23 (br t, J=6.8 Hz, 1H), 4.48-4.41 (m, 1H), 4.36 (br s, 2H), 3.88 (s, 3H), 2.46-2.41 (m, 1H), 2.34-2.19 (m, 5H), 1.18-1.12 (m, 6H). Analytical HPLC RT=1.409 min (Method A) and 1.458 min (Method B), purity=96%.

EXAMPLE 51

Preparation of 2-((aR)-6-(3-(1-(difluoromethyl)-1H-pyrazol-4-yl)-5-(methylsulfonyl)benzamido)spiro[3.3]heptan-2-yl)oxy)nicotinamide trifluoroacetate

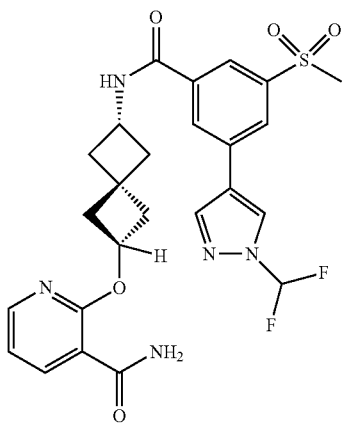

Example 119 (0.015 g, 0.024 mmol), 1-(difluoromethyl)-4-(4,4,5,5-tetramethyl-1,3,2-dioxaborolan-2-yl)-1H-pyrazole (7.06 mg, 0.029 mmol), and Na$_2$CO$_3$ (0.013 g, 0.120 mmol) in H$_2$O (0.149 mL) were added to dioxane (0.744 mL) and degassed with a stream of N$_2$. After purging with nitrogen for 5 min, pallidiumtetrakis (2.78 mg, 2.410 µmol) was added and the reaction mixture irradiated at 120° C. for 30 min before diluting with H$_2$O, extracted with EtOAc, dried over Na$_2$SO$_4$, filtered, concentrated, and purifying by reverse phase chromatography to give the desired product (13 mg, 82%). MS (ESI) m/z: 546.2 (M+H)$^+$. $^1$H NMR (500 MHz, DMSO-d$_6$) δ 8.95-8.89 (m, 2H), 8.46-8.39 (m, 2H), 8.35-8.22 (m, 2H), 8.16 (br d, J=6.7 Hz, 1H), 7.98-7.72 (m, 1H), 7.66 (br s, 1H), 7.62 (br s, 1H), 7.10 (dd, J=7.0, 5.2 Hz, 1H), 5.23 (quin, J=7.0 Hz, 1H), 4.44-4.34 (m, 1H), 3.34-3.20 (m, 3H), 2.68 (dt, J=11.4, 5.5 Hz, 1H), 2.41-2.35 (m, 1H), 2.30-2.17 (m, 4H). Analytical HPLC RT=1.489 min (Method A) and 1.489 min (Method B), purity=100%.

EXAMPLE 52

Preparation of 2-((aR)-6-(3-(1-methyl-1H-pyrazol-4-yl)-5-(methylsulfonyl)benzamido)spiro[3.3]heptan-2-yl)oxy)nicotinamide trifluoroacetate

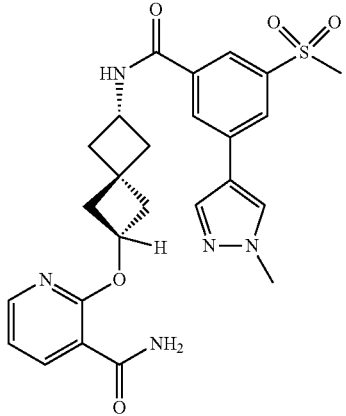

2-((aR)-6-(3-(1-methyl-1H-pyrazol-4-yl)-5-(methylsulfonyl)benzamido)spiro[3.3]heptan-2-yl)oxy)nicotinamide, trifluoroacetate (12.9 mg, 85%) was prepared in a similar manner as Example 51, substituting 1-(difluoromethyl)-4-(4,4,5,5-tetramethyl-1,3,2-dioxaborolan-2-yl)-1H-pyrazole with 1-methyl-4-(4,4,5,5-tetramethyl-1,3,2-dioxaborolan-2-yl)-1H-pyrazole. MS (ESI) m/z: 510.1 (M+H)+. 1H NMR (500 MHz, DMSO-d6) δ 8.88 (d, J=7.3 Hz, 1H), 8.39-8.34 (m, 1H), 8.30-8.25 (m, 2H), 8.20-8.13 (m, 2H), 8.06-8.02 (m, 1H), 7.72-7.66 (m, 1H), 7.61 (br s, 1H), 7.10 (dd, J=7.5, 5.0 Hz, 1H), 5.23 (quin, J=7.1 Hz, 1H), 4.39 (sxt, J=8.0 Hz, 1H), 3.92-3.85 (m, 3H), 2.72-2.65 (m, 1H), 2.47-2.41 (m, 1H), 2.41-2.35 (m, 1H), 2.30-2.18 (m, 4H). Analytical HPLC RT=1.248 min (Method A) and 1.343 min (Method B), purity=99%.

EXAMPLE 53

Preparation of 2-{[(4s)-6-{3-methanesulfonyl-5-[1-(2H3)methyl-1H-pyrazol-4-yl]benzamido}spiro[3.3]heptan-2-yl]oxy}pyridine-3-carboxamide, trifluoroacetate

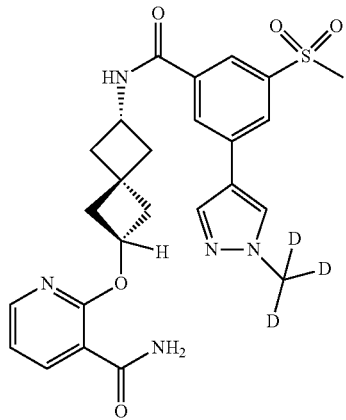

2-{[(4s)-6-{3-methanesulfonyl-5-[1-(2H3)methyl-1H-pyrazol-4-yl]benzamido}spiro[3.3]heptan-2-yl]oxy}pyridine-3-carboxamide, trifluoroacetate (14.6 mg, 97%) was prepared in a similar manner as Example 51, substituting 1-(difluoromethyl)-4-(4,4,5,5-tetramethyl-1,3,2-dioxaborolan-2-yl)-1H-pyrazole with 1-(2H3)methyl-4-(tetramethyl-1,3,2-dioxaborolan-2-yl)-1H-pyrazole. MS (ESI) m/z: 513.2 (M+H)+. 1H NMR (500 MHz, DMSO-d6) δ 8.96 (br d, J=5.9 Hz, 1H), 8.29-8.23 (m, 3H), 8.17-8.12 (m, 2H), 8.11-8.08 (m, 1H), 8.03-7.98 (m, 1H), 7.72-7.66 (m, 1H), 7.64 (br s, 1H), 7.10 (dd, J=7.4, 4.9 Hz, 1H), 5.23-5.16 (m, 1H), 4.39-4.31 (m, 1H), 3.26-3.21 (m, 3H), 2.68-2.63 (m, 1H), 2.46-2.43 (m, 1H), 2.38-2.32 (m, 1H), 2.25-2.15 (m, 4H). Analytical HPLC RT=1.334 min (Method A) and 1.330 min (Method B), purity=100%.

EXAMPLE 54

Preparation of 2-((aR)-6-(3-(1-methyl-1H-pyrazol-4-yl)benzamido)spiro[3.3]heptan-2-yl)oxy)nicotinamide, trifluoroacetate

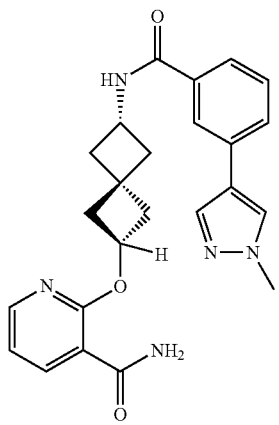

EXAMPLE 54A

Preparation of 2-((aR)-6-(3-bromobenzamido)spiro-[3.3]heptan-2-yl)oxy)nicotinamide

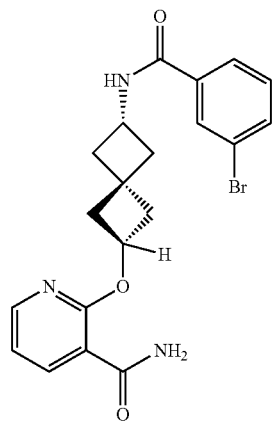

To a solution of Example 42C (0.09 g, 0.364 mmol) and 3-bromobenzoic acid (0.088 g, 0.437 mmol) in DMF (1.0 mL) was treated with DIEA (0.318 mL, 1.82 mmol) followed by BOP (0.177 g, 0.400 mmol). After stirring overnight, the crude material was purified by reverse phase chromatography to give 2-((aR)-6-(3-bromobenzamido)spiro-[3.3]heptan-2-yl)oxy)nicotinamide, TFA (0.057 g, 28.9% yield) as a tan solid. MS (ESI) min: 430.0 (M+H)+.

EXAMPLE 54

2-((aR)-6-(3-bromobenzamido)spiro-[3.3]heptan-2-yl)oxy)nicotinamide, TFA (0.015 g, 0.028 mmol), 1-methyl-4-(4,4,5,5-tetramethyl-1,3,2-dioxaborolan-2-yl)-1H-pyrazole (0.011 g, 0.055 mmol), and Na2CO3 (0.138 mL, 0.138 mmol) in H2O (0.170 mL) were added to dioxane (0.851 mL) and degassed with a stream of N2. After purging with nitrogen for 5 min, pallidiumtetrakis (3.18 mg, 2.76 μmol) was added and the reaction mixture irradiated at 120° C. for 30 min before diluting with H₂O, extracted with EtOAc, dried over Na₂SO₄, filtered, concentrated, and purifying by reverse phase chromatography to give the desired product (8 mg, 50.6%). MS (ESI) m/z: 432.2 (M+H)⁺. ¹H NMR (400 MHz, Methanol-d4) δ 8.36 (dd, J=7.6, 2.1 Hz, 1H), 8.31 (dd, J=4.8, 2.0 Hz, 1H), 8.07-8.01 (m, 2H), 7.91 (s, 1H), 7.75-7.67 (m, 2H), 7.50-7.44 (m, 1H), 7.12 (dd, J=7.5, 4.8 Hz, 1H), 5.36 (quin, J=7.2 Hz, 1H), 4.50 (quin, J=8.3 Hz, 1H), 3.97 (s, 3H), 2.82 (dt, J=11.6, 6.0 Hz, 1H), 2.67-2.59 (m, 2H), 2.55-2.47 (m, 1H), 2.40-2.25 (m, 4H). Analytical HPLC RT=4.70 min (Method C) and 6.74 min (Method D), purity=95%.

EXAMPLE 55

Preparation of 2-((aR)-6-(3'-(methylsulfonyl)-[1,1'-biphenyl]-3-ylcarboxamido)spiro[3.3]heptan-2-yl)oxy)nicotinamide, trifluoroacetate

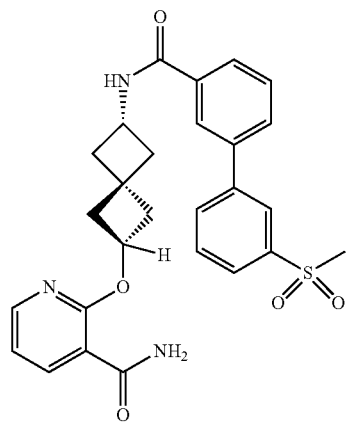

2-((aR)-6-(3'-(Methyl sulfonyl)-[1,1'-biphenyl]-3-ylcarboxamido)spiro[3.3]heptan-2-yl)oxy)nicotinamide, trifluoroacetate (8.1 mg, 45.1%) was prepared in a similar manner as Example 54, substituting 1-methyl-4-(4,4,5,5-tetramethyl-1,3,2-dioxaborolan-2-yl)-1H-pyrazole with 3-(methylsulfonyl)phenylboronic acid. MS (ESI) m/z: 506.2 (M+H)⁺. ¹H NMR (400 MHz, Methanol-d4) δ 8.36 (dd, J=7.5, 2.0 Hz, 1H), 8.30 (td, J=4.6, 1.9 Hz, 2H), 8.18 (t, J=1.7 Hz, 1H), 8.10-8.06 (m, 1H), 8.03-7.99 (m, 1H), 7.93-7.89 (m, 2H), 7.81-7.76 (m, 1H), 7.66-7.61 (m, 1H), 7.12 (dd, J=7.6, 5.0 Hz, 1H), 5.37 (quin, J=7.1 Hz, 1H), 4.57-4.48 (m, 1H), 3.22 (s, 3H), 2.83 (dt, J=11.7, 5.8 Hz, 1H), 2.67-2.60 (m, 2H), 2.55-2.49 (m, 1H), 2.40-2.27 (m, 4H). Analytical HPLC RT=4.60 min (Method C) and 6.71 min (Method D), purity=95%.

EXAMPLE 56

Preparation of 2-((aR)-6-(3-bromo-5-(3,3,3-trifluoropropoxy)benzamido)spiro[3.3]heptan-2-yl)oxy)nicotinamide, trifluoroacetate

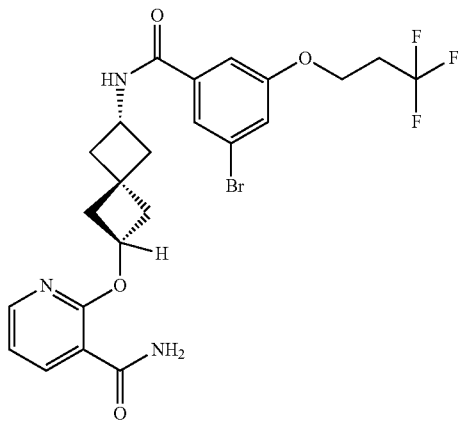

EXAMPLE 56A

Preparation of Methyl 3-bromo-5-(3,3,3-trifluoropropoxy)-benzoate

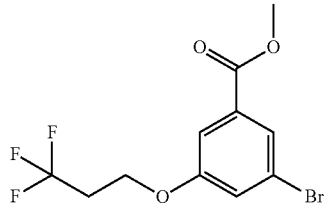 [SMILES: COC(=O)c1cc(Br)cc(OCCC(F)(F)F)c1]

Methyl 3-bromo-5-hydroxybenzoate (0.30 g, 1.298 mmol), 3,3,3-trifluoropropan-1-ol (0.239 mL, 2.60 mmol), and and 1,1'-(azodicarbonyl)dipiperidine (0.983 g, 3.90 mmol) were placed in a pressure vial. Then, anhydrous toluene (12.98 mL) and tri-N-butylphosphine (0.973 mL, 3.90 mmol) were added, and the reaction mixture was irradiated at 140° C. for 20 min. The reaction mixture was quenched with MeOH (5 mL), concentrated, and purified by normal phase chromatography to give methyl 3-bromo-5-(3,3,3-trifluoropropoxy)benzoate (0.27 g, 64.4%) as a yellow oil. MS (ESI) m/z: 328 (M+H)⁺.

EXAMPLE 56B

Preparation of 3-bromo-5-(3,3,3-trifluoropropoxy)benzoic acid

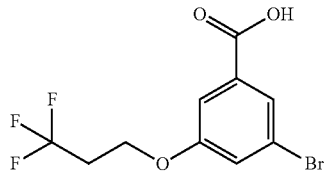 [SMILES: O=C(O)c1cc(Br)cc(OCCC(F)(F)F)c1]

Methyl 3-bromo-5-(3,3,3-trifluoropropoxy)benzoate (0.2735 g, 0.836 mmol) was dissolved in MeOH (4.0 mL)/THF (4.0 mL), treated with 1.0M LiOH (2.508 mL, 2.508 mmol), and irradiated at 100° C. for 15 min. The reaction mixture was diluted with water, acidified with 1.0N HCl solution, extracted with EtOAc, washed with brine, dried over sodium sulfate, filtered, and concentrated to give 3-bromo-5-(3,3,3-trifluoropropoxy)benzoic acid (0.156 g, 0.498 mmol, 59.6% yield) as a yellow solid. MS (ESI) m/z: 312.9 (M+H)+. $^1$H NMR (400 MHz, CDCl$_3$) δ 7.88 (t, J=1.5 Hz, 1H), 7.56 (dd, J=2.4, 1.3 Hz, 1H), 7.32 (t, J=2.1 Hz, 1H), 4.25 (t, J=6.5 Hz, 2H), 2.66 (qt, J=10.4, 6.5 Hz, 2H).

EXAMPLE 56

To a solution of Example 42C (0.10 g, 0.404 mmol) and 3-bromo-5-(3,3,3-trifluoropropoxy)benzoic acid (0.127 g, 0.404 mmol) in DMF (1.0 mL) was treated with DIEA (0.353 mL, 2.022 mmol) followed by BOP (0.197 g, 0.445 mmol). After 2 h, the crude material was purified by reverse phase chromatography gave the desired product (0.147 g, 52.6%) as a white solid. MS (ESI) m/z: 544.1 (M+H)+. H NMR (500 MHz, Methanol-d4) δ 8.35 (dd, J=7.6, 2.1 Hz, 1H), 8.29 (dd, J=4.8, 2.1 Hz, 1H), 7.61 (t, J=1.5 Hz, 1H), 7.39 (dd, J=2.5, 1.4 Hz, 1H), 7.33-7.29 (m, 1H), 7.11 (dd, J=7.6, 4.8 Hz, 1H), 5.35 (quin, J=7.2 Hz, 1H), 4.48-4.40 (m, 1H), 4.30 (t, J=6.1 Hz, 2H), 2.84-2.69 (m, 3H), 2.64-2.57 (m, 2H), 2.51-2.44 (m, 1H), 2.34 (dd, J=11.4, 7.3 Hz, 1H), 2.30-2.22 (m, 3H). Analytical HPLC RT=9.45 min (Method C) and 10.43 min (Method D), purity=97.3%.

EXAMPLE 57

Preparation of 2-((aR)-6-(3-(1-methyl-1H-pyrazol-4-yl)-5-(3,3,3-trifluoropropoxy)benzamido)spiro[3.3]heptan-2-yl)oxy)nicotinamide, trifluoroacetate

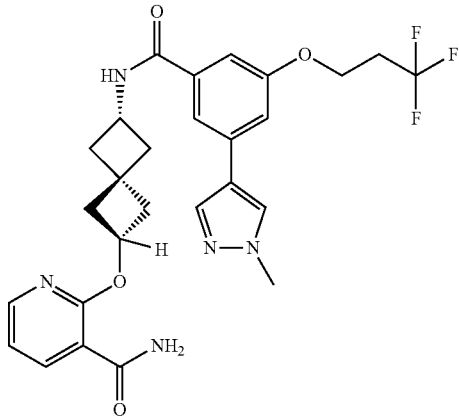

Example 57 (0.015 g, 0.023 mmol), 1-methyl-4-(4,4,5,5-tetramethyl-1,3,2-dioxaborolan-2-yl)-1H-pyrazole (9.51 mg, 0.046 mmol), and Na$_2$CO$_3$ (0.114 mL, 0.114 mmol) in H$_2$O (0.141 mL) were added to dioxane (0.705 mL) and degassed with a stream of N2. After purging for 5 min, pallidiumtetrakis (2.64 mg, 2.285 μmol) was added, and the mixture irradiated at 120° C. for 30 min before diluting with H$_2$O, extracted with EtOAc, dried over Na$_2$SO$_4$, filtered, concentrated, and purifying by reverse phase chromatography to give the desired product (9.6 mg, 63.9%). MS (ESI) m/z: 544.2 (M+H)+. $^1$H NMR (500 MHz, DMSO-d6) δ 8.65-8.59 (m, 1H), 8.28-8.25 (m, 1H), 8.23-8.19 (m, 1H), 8.18-8.14 (m, 1H), 7.93 (s, 1H), 7.75-7.68 (m, 1H), 7.65-7.59 (m, 2H), 7.29-7.25 (m, 1H), 7.20 (br s, 1H), 7.10 (dd, J=7.4, 4.9 Hz, 1H), 5.22 (br t, J=7.1 Hz, 1H), 4.40-4.32 (m, 1H), 4.28 (br t, J=5.6 Hz, 2H), 3.86 (s, 3H), 2.85-2.75 (m, 2H), 2.69-2.64 (m, 1H), 2.48-2.45 (m, 1H), 2.34 (br d, J=4.4 Hz, 1H), 2.28-2.16 (m, 4H). Analytical HPLC RT=1.661 min (Method A) and 1.613 min (Method B), purity=100%.

EXAMPLE 58

Preparation of 2-((aR)-6-(3'-(methylsulfonyl)-5-(3,3,3-trifluoropropoxy)-[1,1'-biphenyl]-3-ylcarboxamido)spiro[3.3]heptan-2-yl)oxy)nicotinamide, trifluoroacetate

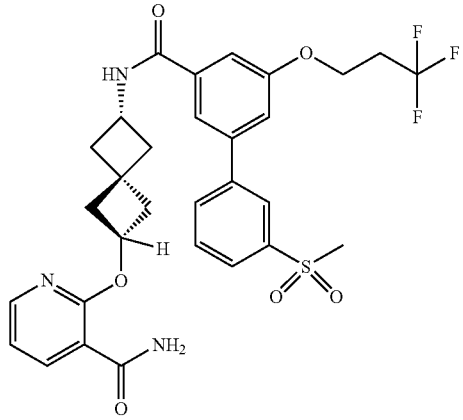

2-((aR)-6-(3'-(methyl sulfonyl)-5-(3,3,3-trifluoropropoxy)-[1,1'-biphenyl]-3-ylcarboxamido)spiro[3.3]heptan-2-yl)oxy)nicotinamide, trifluoroacetate (13.3 mg, 78%) was prepared in a similar manner as Example 57, substituting 1-methyl-4-(4,4,5,5-tetramethyl-1,3,2-dioxaborolan-2-yl)-1H-pyrazole with 3-(methylsulfonyl)phenylboronic acid. MS (ESI) m/z: 618.1 (M+H)+. $^1$H NMR (500 MHz, DMSO-d6) δ 8.78 (br d, J=6.1 Hz, 1H), 8.25 (br d, J=4.5 Hz, 1H), 8.19 (br s, 1H), 8.15 (br d, J=7.4 Hz, 1H), 8.09 (br d, J=7.7 Hz, 1H), 7.94 (br d, J=7.8 Hz, 1H), 7.79-7.75 (m, 2H), 7.68 (br s, 1H), 7.64 (br s, 1H), 7.44 (br d, J=5.7 Hz, 2H), 7.10 (dd, J=7.4, 4.9 Hz, 1H), 5.24-5.18 (m, 1H), 4.40-4.32 (m, 3H), 3.28 (s, 3H), 2.85-2.77 (m, 2H), 2.67-2.63 (m, 1H), 2.47-2.44 (m, 1H), 2.38-2.32 (m, 1H), 2.28-2.16 (m, 4H). Analytical HPLC RT=1.814 min (Method A) and 1.763 min (Method B), purity=98%.

EXAMPLE 59

Preparation of N-((aR)-6-((3-carbamoylpyridin-2-yl)oxy)spiro[3.3]heptan-2-yl)-6-methoxyimidazo[1,2-b]pyridazine-2-carboxamide, TFA

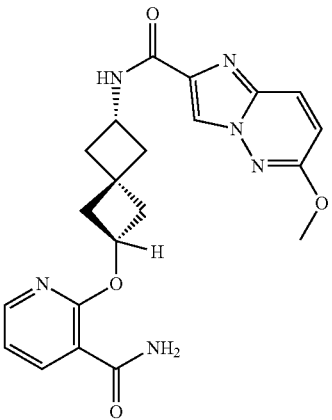

INTERMEDIATE 59A

Preparation of 6-methoxyimidazo[1,2-b]pyridazine-2-carboxylic acid

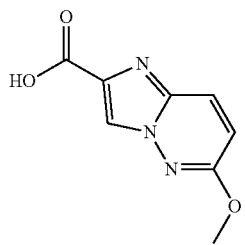

Combined ethyl 6-chloroimidazo[1,2-b]pyridazine-2-carboxylate (0.298 g, 1.321 mmol) and LiOH.H$_2$O (2.64 mL, 2.64 mmol) in MeOH (4 mL)/H$_2$O (4 mL) and heated to 100° C. in microwave for 15 min. The solvents were reduced and remainder was acidified with 1 N HCl and the resultant tan solid was collected by filtration to afford 6-methoxyimidazo[1,2-b]pyridazine-2-carboxylic acid (0.195 g, 1.01 mmol, 76% yield). LCMS(ESI) m/z: 194.0 [M+H]$^+$ $^1$H NMR (400 MHz, DMSO-d$_6$) δ 13.14-12.50 (m, 1H), 8.54 (d, J=0.7 Hz, 1H), 8.07 (dd, J=9.7, 0.7 Hz, 1H), 7.02 (d, J=9.7 Hz, 1H), 3.97 (s, 3H).

EXAMPLE 59

Combined Example 42C (12 mg, 0.049 mmol) with Intermediate 59A (9.37 mg, 0.049 mmol), BOP (21.46 mg, 0.049 mmol), DMF (0.25 mL) and DIEA (0.042 mL, 0.243 mmol). After 30 min, the reaction was complete by LCMS and the mixture was acidified with TFA, diluted with DMF, filtered and purified by reverse phase HPLC to afford Example 59 (7.9 mg, 0.014 mmol, 29.0% yield). LCMS (ESI) m/z: 423.2 (M+H)$^+$. $^1$H NMR (500 MHz, DMSO-d$_6$) δ 8.52 (br d, J=8.2 Hz, 1H), 8.35 (s, 1H), 8.25 (br d, J=3.4 Hz, 1H), 8.16 (br d, J=7.3 Hz, 1H), 7.97 (d, J=9.8 Hz, 1H), 7.67 (br s, 1H), 7.62 (br s, 1H), 7.11 (dd, J=7.3, 5.2 Hz, 1H), 6.98 (d, J=9.8 Hz, 1H), 5.24-5.12 (m, 1H), 4.41-4.27 (m, 1H), 3.94 (s, 2H), 3.16 (br d, J=4.3 Hz, 1H), 2.69-2.59 (m, 1H), 2.44-2.38 (m, 1H), 2.35-2.27 (m, 1H), 2.27-2.08 (m, 3H). Analytical HPLC: RT=1.31 min (Method A) and RT=1.28 min (Method B), purity 95.5%.

EXAMPLE 60

Preparation of N-((aR)-6-((3-carbamoylpyridin-2-yl)oxy)spiro[3.3]heptan-2-yl)-6-chloro-8-methoxyimidazo[1,2-b]pyridazine-3-carboxamide, TFA

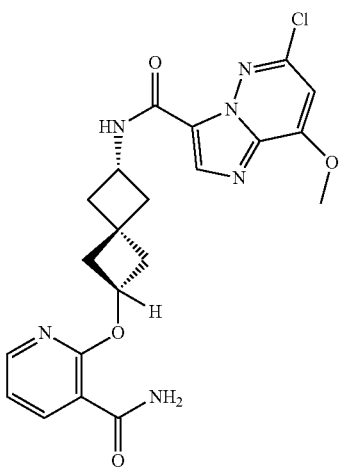

EXAMPLE 60A

Ethyl 6,8-dichloroimidazo[1,2-b]pyridazine-3-carboxylate

To ethyl 6,8-dichloroimidazo[1,2-b]pyridazine-3-carboxylate (0.336 g, 1.292 mmol) in THF (5 mL)/MeOH (3 mL)/water (2 mL) was added LiOH.H$_2$O (0.163 g, 3.88 mmol). After 18 h, the solvents were concentrated and the aqueous layer was washed with Et$_2$O, acidified w/ 1 N HCl, extracted with EtOAc (3×25 mL), dried (MgSO$_4$), filtered and concentrated to afford 331A (0.155 g, 0.681 mmol, 52.7% yield) white solid. LCMS(ESI) m/z: 457.0 (M+H)$^+$. $^1$H NMR (400 MHz, Methanol-d$_4$) δ 8.24 (s, 1H), 7.08 (s, 1H), 4.20 (s, 3H).

EXAMPLE 60

Combined Example 42C (19.0 mg, 0.077 mmol) with Intermediate 60A (17.4 mg, 0.077 mmol), BOP (34.0 mg, 0.077 mmol), DMF (0.25 mL) and DIEA (0.067 mL, 0.384 mmol). After 30 min, the reaction was complete by LCMS and the mixture was acidified with TFA, diluted with DMF, filtered and purified by reverse phase HPLC to afford Example 60 (26.9 mg, 0.047 mmol, 61.3% yield). LCMS (ESI) m/z: 457.0 (M+H)$^+$. $^1$H NMR (500 MHz, DMSO-d$_6$) δ 8.58 (br d, J=7.6 Hz, 1H), 8.36-8.19 (m, 1H), 8.23-8.10 (m, 1H), 8.07 (s, 1H), 7.69 (br s, 1H), 7.61 (br s, 1H), 7.10 (dd, J=7.5, 5.0 Hz, 1H), 7.06 (s, 1H), 5.20 (quin, J=7.2 Hz, 1H), 4.35 (sxt, J=7.5 Hz, 1H), 4.08 (s, 3H), 2.70-2.61 (m, 1H), 2.55 (s, 2H), 2.47-2.37 (m, 1H), 2.30-2.17 (m, 2H), 2.16-

2.05 (m, 2H). Analytical HPLC: RT=1.31 min (Method A) and RT=1.29 min (Method B), purity 100%.

EXAMPLE 61

Preparation of N-((aR)-6-((3-carbamoylpyridin-2-yl)oxy)spiro[3.3]heptan-2-yl)-6-(2,2,2-trifluoroethoxy)imidazo[1,2-b]pyridazine-2-carboxamide, TFA

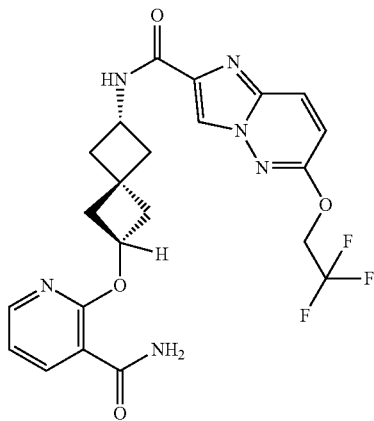

INTERMEDIATE 61A

Preparation of 6-(2,2,2-trifluoroethoxy)imidazo[1,2-b]pyridazine-2-carboxylic acid and 6-chloroimidazo[1,2-b]pyridazine-2-carboxylic acid

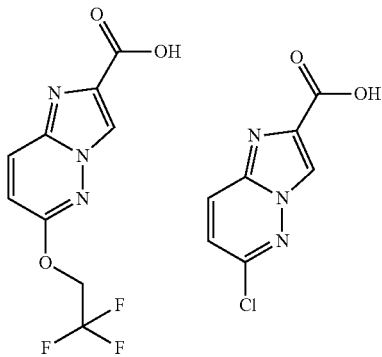 [SMILES: O=C(O)c1cn2nc(OCC(F)(F)F)ccc2n1 ; O=C(O)c1cn2nc(Cl)ccc2n1]

To ethyl 6-chloroimidazo[1,2-b]pyridazine-2-carboxylate (0.206 g, 0.913 mmol) was added LiOH.H₂O (1.826 mL, 1.826 mmol) in 2,2,2-trifluoroethanol (2 mL, 27.8 mmol)/H₂O (7 mL) and the mixture was heated to 100° C. in microwave for 15 min. The reaction produced desired ether product and hydrolysized starting material. The reaction mixture was concentrated, acidified with 1H HCl and solid filtered to collect 0.2 g brown solid mixture of 2 products. LCMS(ESI) m/z: 198.0-199.9 and 262.0 (M+H)⁺. The mixture was carried onto the next step as is.

EXAMPLE 61

Combined Example 42C (13 mg, 0.053 mmol) with a mixture of 6-(2,2,2-trifluoroethoxy)imidazo[1,2-b]pyridazine-2-carboxylic acid and 6-(-chloroimidazo[1,2-b]pyridazine-2-carboxylic acid (13.73 mg, 0.053 mmol), BOP (23.25 mg, 0.053 mmol), DMF (0.25 mL) and DIEA (0.046 mL, 0.263 mmol). After stirring 18 h, the reaction was acidified with TFA, diluted with DMF, filtered and purified by reverse phase HPLC to afford 2 products, one was Example 61 (8.3 mg, 0.014 mmol, 26.1% yield). LCMS (ESI) m/z: 491.2 (M+H)⁺. ¹H NMR (500 MHz, DMSO-d₆) δ 8.56 (br d, J=7.9 Hz, 1H), 8.42 (s, 1H), 8.33-8.24 (m, 1H), 8.17 (dd, J=7.3, 1.5 Hz, 1H), 8.13 (d, J=10.1 Hz, 1H), 7.68 (br s, 1H), 7.61 (br s, 1H), 7.16 (d, J=9.8 Hz, 1H), 7.11 (dd, J=7.5, 5.0 Hz, 1H), 5.22 (quin, J=7.0 Hz, 1H), 5.05 (q, J=8.9 Hz, 2H), 4.38 (sxt, J=8.3 Hz, 1H), 2.66 (dt, J=11.5, 5.7 Hz, 1H), 2.47 (br d, J=5.8 Hz, 1H), 2.41 (br dd, J=10.8, 7.2 Hz, 1H), 2.34-2.22 (m, 3H), 2.19 (br dd, J=1.7, 7.5 Hz, 1H). Analytical HPLC: RT=1.56 min (Method A) and RT=1.56 min (Method B), purity 100%.

EXAMPLE 62

Preparation of N-((aR)-6-((3-carbamoylpyridin-2-yl)oxy)spiro[3.3]heptan-2-yl)-6-chloroimidazo[1,2-b]pyridazine-2-carboxamide, TFA

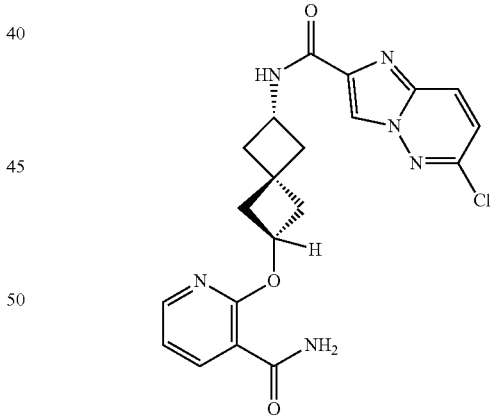

Example 62 (9 mg, 0.016 mmol, 30.1% yield) was separated from the reaction mixture of Example 61 during purification. LCMS(ESI) m/z: 426.9 (M+H)⁺. ¹H NMR (500 MHz, DMSO-d₆) δ 8.68 (br d, J=8.2 Hz, 1H), 8.66 (s, 1H), 8.30-8.25 (m, 1H), 8.23 (d, J=9.5 Hz, 1H), 8.19-8.12 (m, 1H), 7.68 (br s, 1H), 7.60 (br s, 1H), 7.47 (d, J=9.8 Hz, 1H), 7.11 (dd, J=7.3, 4.9 Hz, 1H), 5.28-5.15 (m, 1H), 4.40 (dq, J=16.3, 8.2 Hz, 1H), 3.60-3.35 (m, 1H), 2.66 (dt, J=11.4, 5.8 Hz, 1H), 2.47-2.37 (m, 2H), 2.35-2.23 (m, 4H), 2.19 (br dd, J=11.9, 7.6 Hz, 1H). Analytical HPLC: RT=1.26 min (Method A) and RT=1.27 min (Method B), purity 95%.

EXAMPLE 63

Preparation of N²-((aR)-6-((3-carbamoylpyridin-2-yl)oxy)spiro[3.3]heptan-2-yl)imidazo[1,2-a]pyridine-2,6-dicarboxamide, TFA

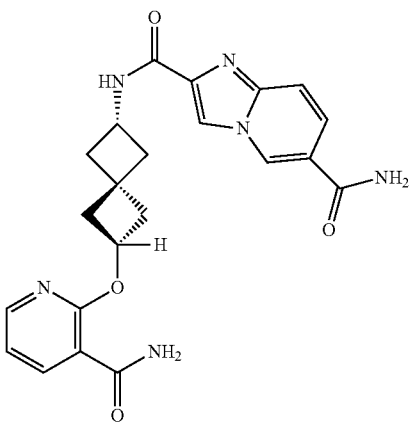

EXAMPLE 63A

Preparation of 6-carbamoylimidazo[1,2-a]pyridine-2-carboxylic

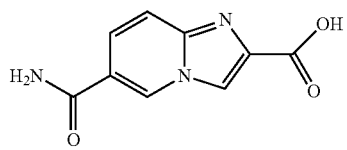 [SMILES: NC(=O)c1ccc2nc(C(=O)O)cn2c1]

To ethyl 6-cyanoimidazo[1,2-a]pyridine-2-carboxylate (100 mg, 0.465 mmol) in 2 mL THF and 1 mL MeOH was added LiOH (1M, 929 μl, 0.929 mmol). The reaction mixture was heated in microwave for 20 min at 120° C. Heating was aborted at 12 min., but LCMS showed reaction complete. The solvents were concentrated, 1N HCl was added and the resultant tan solid was filtered off to afford 6-carbamoylimidazo[1,2-a]pyridine-2-carboxylic acid (53 mg, 0.258 mmol, 55.6% yield). LCMS(ESI) m/z: 206.0 (M+H)⁺. ¹H NMR (400 MHz, DMSO-d₆) δ 13.49-12.70 (m, 1H), 8.65-8.41 (m, 1H), 8.14 (br s, 1H), 7.78 (dd, J=9.5, 1.8 Hz, 1H), 7.66 (d, J=9.7 Hz, 2H), 7.60 (br s, 1H).

EXAMPLE 63

Combined Example 42C (12 mg, 0.049 mmol) with 6-carbamoylimidazo[1,2-a]pyridine-2-carboxylic acid (9.96 mg, 0.049 mmol), BOP (21.4 mg, 0.049 mmol) in DMF (0.25 mL) and DIEA (0.042 mL, 0.243 mmol) was then added. After 3 h, the reaction was complete by LCMS. The reaction mixture was quenched with TFA, diluted with DMF, filtered and purified by reverse phase HPLC. Collected N²-(6-((3-carbamoylpyridin-2-yl)oxy)spiro[3.3]heptan-2-yl)imidazo[1,2-a]pyridine-2,6-dicarboxamide, TFA (2.4 mg, 4.38 μmol, 9.02% yield). LCMS(ESI) m/z: 435.3 (M+H)⁺. ¹H NMR (500 MHz, DMSO-d₆) δ 9.18 (br s, 1H), 8.60 (br s, 1H), 8.45 (br s, 1H), 8.33-8.23 (m, 1H), 8.20-8.16 (m, 1H), 8.18 (br dd, J=7.3, 1.5 Hz, 1H), 8.14 (br s, 1H), 7.78 (br d, J=8.5 Hz, 1H), 7.71 (br s, 1H), 7.60 (br s, 3H), 7.11 (dd, J=7.3, 4.9 Hz, 1H), 5.23 (quin, J=7.1 Hz, 1H), 4.47-4.33 (m, 1H), 2.77-2.62 (m, 1H), 2.42 (br d, J=4.6 Hz, 1H), 2.38-2.16 (m, 4H). Analytical HPLC: RT=1.13 min (Method A) and RT=1.08 min (Method B), purity 100%.

The following examples in Table 4 were prepared using a similar procedure to that which was used in the preparation of Example 42. Example 42C was coupled with a carboxylic acid.

The carboxylic acids were commercially available or synthesized as described previously. Various bases could be used other than the one described in Example 42, such as TEA, DBU, or DABCO. Various coupling reagents could be used other than the one described in Example 42, such as EDCI, BOP, or T3P.

TABLE 4

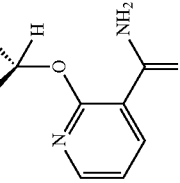

| Example | R | Name | LCMS (M + H)+ | HPLC Method, RT (min.) | 1H NMR |
|---|---|---|---|---|---|
| 64 | 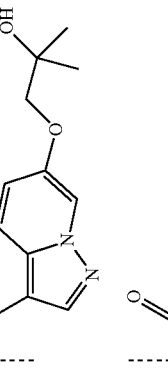 | N-((aR)-6-((3-carbamoylpyridin-2-yl)oxy)spiro[3.3]-heptan-2-yl)-6-(2-hydroxy-2-methylpropoxy)pyrazolo-[1,5-a]pyridine-3-carboxamide, trifluoroacetate | 480.0 | C: 5.48 D: 6.77 | 1H NMR (400 MHz, DMSO-d6) δ 8.47-8.43 (m, 2H), 8.33-8.23 (m, 2H), 8.18 (dd, J = 7.4, 2.1 Hz, 1H), 8.09 (d, J = 9.5 Hz, 1H), 7.71 (br. s., 1H), 7.60 (br. s, 1H), 7.28 (dd, J = 9.7, 2.2 Hz, 1H), 7.12 (dd, J = 7.5, 4.8 Hz, 1H), 5.26 (quin, J = 7.1 Hz, 1H), 4.45-4.36 (m, 1H), 2.73-2.65 (m, 2H), 2.50-2.42 (m, 1H), 2.40-2.14 (m, 6H), 1.23 (s, 6H) |
| 65 | 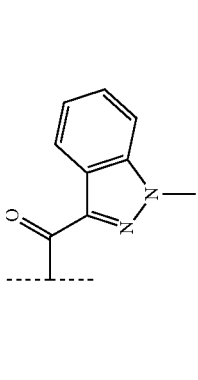 | N-((aR)-6-((3-carbamoylpyridin-2-yl)oxy)spiro[3.3]heptan-2-yl)-8-cyclopropyl-7-(2-hydroxy-2-methylpropoxy)imidazo[1,2-a]pyridine-3-carboxamide, trifluoroacetate | 520.2 | C: 4.25 D: 6.69 | 1H NMR (400 MHz, Methanol-d4) δ 9.57 (d, J = 7.9 Hz, 1H), 8.35-8.26 (m, 2H), 7.46 (d, J = 7.9 Hz, 1H), 7.09 (dd, J = 7.5, 4.8 Hz, 1H), 5.39-5.29 (m, 1H), 4.53-4.43 (m, 1H), 4.10 (s, 2H), 2.89 (d, J = 10.6 Hz, 1H), 2.84-2.78 (m, 1H), 2.65-2.58 (m, 2H), 2.52-2.47 (m, 1H), 2.36-2.20 (m, 5H), 1.94-1.88 (m, 1H), 1.40 (s, 6H), 1.23-1.18 (m, 2H), 0.93-0.86 (m, 2H) |
| 66 | | N-((aR)-6-((3-carbamoylpyridin-2-yl)oxy)spiro[3.3]-heptan-2-yl)-1-methyl-3a,7a-dihydro-1H-indazole-3-carboxamide, trifluoroacetate | 406.2 | A: 1.487 B: 1.529 | 1H NMR (400 MHz, DMSO-d6) δ 8.54 (br d, J = 8.1 Hz, 1H), 8.27-8.26 (m, 1H), 8.18-8.13 (m, 2H), 7.71 (br d, J = 8.4 Hz, 2H), 7.61 (br s, 1H), 7.45 (t, J = 7.6 Hz, 1H), 7.26 (t, J = 7.5 Hz, 1H), 7.10 (dd, J = 7.4, 5.0 Hz, 1H), 5.21 (quin, J = 7.1 Hz, 1H), 4.42 (sxt, J = 8.2 Hz, 1H), 4.12 (s, 3H), 2.69-2.64 (m, 1H), 2.47-2.39 (m, 2H), 2.33-2.17 (m, 6H) |

| # | Structure | Name | | NMR |
|---|---|---|---|---|
| 67 | (5-fluoro-indazole with neopentyl-OH N-substituent) | N-((aR)-6-((3-carbamoylpyridin-2-yl)oxy)spiro[3.3]heptan-2-yl)-5-fluoro-1-(2-hydroxy-2-methylpropyl)-3a,7a-dihydro-1H-indazole-3-carboxamide, trifluoroacetate | 481.1 | C: 7.01  D: 8.26 | ¹H NMR (400 MHz, Methanol-d₄) δ 8.36 (dd, J = 7.5, 2.0 Hz, 1H), 8.31 (dd, J = 4.8, 2.0 Hz, 1H), 7.84 (dd, J = 9.0, 2.0 Hz, 1H), 7.74 (dd, J = 9.2, 4.0 Hz, 1H), 7.27 (d, J = 2.4 Hz, 1H), 7.13 (dd, J = 7.6, 5.0 Hz, 1H), 5.37 (quin, J = 7.1 Hz, 1H), 4.59-4.50 (m, 1H), 4.47 (s, 2H), 2.84 (dt, J = 11.8, 6.0 Hz, 1H), 2.68-2.61 (m, 2H), 2.56-2.49 (m, 1H), 2.40-2.28 (m, 4H), 1.27 (s, 6H) |
| 68 | (1-methyl-indazol-5-yl) | N-((aR)-6-((3-carbamoylpyridin-2-yl)oxy)spiro[3.3]heptan-2-yl)-1-methyl-1H-indazole-5-carboxamide, trifluoroacetate | 406.2 | A: 1.33  B: 1.23 | ¹H NMR (500 MHz, DMSO-d₆) δ 8.63 (br d, J = 7.4 Hz, 1H), 8.32-8.26 (m, 2H), 8.18-8.15 (m, 2H), 7.88 (br d, J = 8.8 Hz, 1H), 7.72-7.61 (m, 3H), 7.10 (dd, J = 7.4, 4.9 Hz, 1H), 5.22 (quin, J = 7.1 Hz, 1H), 4.38 (sxt, J = 8.0 Hz, 1H), 4.05 (s, 3H), 2.69-2.63 (m, 1H), 2.45 (br d, J = 7.8 Hz, 1H), 2.36-2.32 (m, 1H), 2.28-2.16 (m, 5H) |
| 69 | (pyrazolopyridine with 2-hydroxy-2-methylpropoxy and oxopiperidinyl) | N-((aR)-6-((3-carbamoylpyridin-2-yl)oxy)spiro[3.3]heptan-2-yl)-6-(2-hydroxy-2-methylpropoxy)-7-(2-oxopiperidin-1-yl)pyrazolo[1,5-a]pyridine-3-carboxamide, trifluoroacetate | 577.2 | A: 1.311  B: 1.297 | ¹H NMR (500 MHz, DMSO-d₆) δ 8.48 (s, 1H), 8.35-8.25 (m, 2H), 8.17-8.14 (m, 2H), 7.72 (br s, 1H), 7.61 (s, 1H), 7.10 (dd, J .2, 5.0 Hz, 1H), 5.23 (quin, J = 7.1 Hz, 1H), 4.41-4.35 (m, 1H), 3.85-3.77 (m, 2H), 3.68-3.58 (m, 1H), 2.69-2.64 (m, 1H), 2.47-2.38 (m, 3H), 2.35 (m, 1H), 1.21 (s, 3H), 1.18 (s, 3H) |
| 70 | (1-methyl-indole-2-yl) | N-((aR)-6-((3-carbamoylpyridin-2-yl)oxy)spiro[3.3]heptan-2-yl)-1-methyl-1H-indole-2-carboxamide, trifluoroacetate | 405.3 | A: 1.716  B: 1.720 | ¹H NMR (500 MHz, DMSO-d₆) δ 8.67 (d, J = 7.6 Hz, 1H), 8.31-8.25 (m, 2H), 8.17 (d, J = 7.4 Hz, 1H), 7.72 (br. s., 1H), 7.63 (d, J = 7.5 Hz, 2H), 7.51 (d, J = 8.4 Hz, 1H), 7.27 (t, J = 7.6 Hz, 1H), 7.13-7.05 (m, 3H), 5.23 (quin, J = 7.1 Hz, 1H), 4.41-4.31 (m, 1H), 3.96 (s, 3H), 2.67 (dt, J = 11.1, 5.8 Hz, 1H), 2.48-2.42 (m, 2H), 2.38-2.32 (m, 1H), 2.28-2.18 (m, 4H) |
| 71 | (imidazo[1,2-a]pyridin-7-yl) | N-((aR)-6-((3-carbamoylpyridin-2-yl)oxy)spiro[3.3]heptan-2-yl)imidazo[1,2-a]pyridine-7-carboxamide, trifluoroacetate | 392.1 | A: 1.047  B: 0.821 | ¹H NMR (500 MHz, DMSO-d₆) δ 8.94 (d, J = 7.3 Hz, 1H), 8.71 (d, J = 7.0 Hz, 1H), 8.27-8.25 (m, 1H), 8.18 (d, J = 14.6 Hz, 2H), 7.90 (s, 1H), 7.68 (br. s., 1H), 7.62 (br. s., 1H), 7.48 (d, J = 7.0 Hz, 1H), 7.27 (s, 1H), 7.13-7.10 (m, 1H), 5.25-5.19 (m, 1H), 4.43-4.33 (m, 1H), 2.95-2.90 (m, 2H), 2.67 (dd, J = 10.7, 5.8 Hz, 1H), 2.42-2.34 (m, 4H) |

TABLE 4-continued

| | | | | |
|---|---|---|---|---|
| 72 |  | N-((aR)-6-((3-carbamoylpyridin-2-yl)oxy)spiro[3.3]-heptan-2-yl)oxy)quinoline-3-carboxamide, trifluoroacetate | 403.2 | A: 1.335<br>B: 1.100 | $^{1}$H NMR (400 MHz, DMSO-d$_{6}$) δ 9.27 (d, J = 1.5 Hz, 1H), 8.99 (d, J = 7.2 Hz, 1H), 8.82 (s, 1H), 8.28 (d, J = 3.2 Hz, 2H), 7.87 (t, J = 7.5 Hz, 1H), 8.09 (t, J = 7.4 Hz, 2H), 7.62 (br. s., 1H), 7.11 (dd, J = 7.7 Hz, 1H), 7.77-7.68 (m, 2H), 5.24 (quin, J = 7.1 Hz, 1H), 4.48-4.40 (m, 1H), 2.69 (dt, J = 11.3, 5.7 Hz, 1H), 2.43-2.37 (m, 1H), 2.34-2.21 (m, 4H) |
| 73 |  | 2-((aR)-6-(1-phenyl-1H-pyrazole-4-carboxamido)spiro[3.3]-heptan-2-yl)oxy)nicotinamide, trifluoroacetate | 418 | A: 1.470<br>B: 1.471 | $^{1}$H NMR (500 MHz, DMSO-d$_{6}$) δ 8.87 (s, 1H), 8.36 (d, J = 7.3 Hz, 1H), 8.27 (dd, J = 4.9, 1.8 Hz, 1H), 8.17 (dd, J = 7.5, 1.7 Hz, 1H), 8.13 (s, 1H), 7.83 (d, J = 7.9 Hz, 2H), 7.69 (br. s., 1H), 7.61 (br. s., 1H), 7.53 (t, J = 7.8 Hz, 2H), 7.37 (t, J = 7.3 Hz, 1H), 7.11 (dd, J = 7.5, 5.0 Hz, 1H), 5.23 (quin, J = 7.1 Hz, 1H), 4.39-4.30 (m, 1H), 3.48-3.43 (m, 1H), 2.67 (dt, J = 11.4, 5.8 Hz, 1H), 2.48-2.44 (m, 1H), 2.38-2.32 (m, 1H), 2.29-2.20 (m, 1H), 2.17-2.12 (m, 2H) |
| 74 |  | 2-((aR)-6-(4-(1H-pyrazol-1-yl)benzamido)spiro[3.3]heptan-2-yl)oxy)nicotinamide, trifluoroacetate | 418.2 | A: 1.388<br>B: 1.350 | $^{1}$H NMR (500 MHz, DMSO-d$_{6}$) δ 8.65 (d, J = 7.3 Hz, 1H), 8.59 (d, J = 2.1 Hz, 1H), 8.31-8.25 (m, 1H), 8.17 (dd, J = 7.6, 1.8 Hz, 1H), 8.01-7.91 (m, 4H), 7.79 (s, 1H), 7.70 (br. s., 1H), 7.60 (br. s., 1H), 7.11 (dd, J = 7.5, 5.0 Hz, 1H), 6.59 (s, 1H), 5.24 (quin, J = 7.2 Hz, 1H), 4.46-4.35 (m, 1H), 2.67 (dt, J = 11.2, 5.8 Hz, 1H), 2.50-2.42 (m, 2H), 2.39-2.32 (m, 1H), 2.30-2.17 (m, 4H) |
| 75 |  | N-((aR)-6-((3-carbamoylpyridin-2-yl)oxy)spiro[3.3]-heptan-2-yl)imidazo[1,2-a]pyridine-2-carboxamide, trifluoroacetate | 392.1 | A: 1.188<br>B: 0.890 | $^{1}$H NMR (500 MHz, DMSO-d$_{6}$) δ 8.76-8.66 (m, 2H), 8.44 (br. s., 1H), 8.27 (d, J = 3.2 Hz, 1H), 8.16 (d, J = 6.0 Hz, 1H), 7.72 (br. s., 1H), 7.66-7.60 (m, 1H), 7.50 (t, J = 7.7 Hz, 1H), 7.28-7.03 (m, 4H), 5.22 (t, J = 7.1 Hz, 1H), 4.39 (d, J = 8.2 Hz, 1H), 2.92 (d, J = 6.0 Hz, 1H), 2.70-2.64 (m, 1H), 2.42 (d, J = 11.4 Hz, 1H), 2.35-2.18 (m, 4H) |
| 76 |  | N-((aR)-6-((3-carbamoylpyridin-2-yl)oxy)spiro-[3.3]heptan-2-yl)-6-cyanoimidazo-[1,2-a]pyridine-2-carboxamide, trifluoroacetate | 417.2 | A: 1.220<br>B: 1.187 | $^{1}$H NMR (500 MHz, DMSO-d$_{6}$) δ 9.37 (s, 1H), 8.72 (d, J = 8.2 Hz, 1H), 8.41 (s, 1H), 8.27 (d, J = 3.0 Hz, 1H), 8.19-8.14 (m, 1H), 7.75 (d, J = 9.4 Hz, 1H), 7.63-7.57 (m, 2H), 7.11 (dd, J = 7.4, 4.9 Hz, 1H), 5.21 (t, J = 7.2 Hz, 1H), 4.45-4.34 (m, 1H), 2.70-2.63 (m, 1H), 2.46 (d, J = 5.5 Hz, 2H), 2.41 (d, J = 7.3 Hz, 1H), 2.31-2.17 (m, 4H) |

| | | | | |
|---|---|---|---|---|
| 77 | 2-((αR)-6-(3-(tert-butyl)-1-methyl-1H-pyrazole-5-carboxamido)spiro[3.3]heptan-2-yl)oxy)nicotinamide, trifluoroacetate | [structure] | 412.0 | A: 1.705<br>B: 1.696 | ¹H NMR (500 MHz, DMSO-d₆) δ 8.50 (d, J = 7.6 Hz, 1H), 8.26 (d, J = 3.1 Hz, 1H), 8.20-8.12 (m, 1H), 7.67 (br. s., 1H), 7.61 (t, J = 7.2 Hz, 1H), 7.29-7.04 (m, 3H), 6.72 (s, 1H), 5.21 (t, J = 7.2 Hz, 1H), 4.34-4.26 (m, 1H), 3.94 (s, 3H), 2.64 (dd, J = 10.8, 5.6 Hz, 1H), 2.55 (s, 9H), 2.34-2.29 (m, 1H), 2.27-2.12 (m, 4H). |
| 78 | N-((αR)-6-((3-carbamoylpyridin-2-yl)oxy)spiro[3.3]heptan-2-yl)-1-(2-(2-methoxyethoxy)ethyl)-1H-indazole-3-carboxamide, trifluoroacetate | [structure] | 494.3 | A: 1.529<br>B: 1.514 | ¹H NMR (500 MHz, DMSO-d₆) δ 8.48 (d, J = 7.9 Hz, 1H), 8.28-8.25 (m, 1H), 8.15 (dd, J = 18.3, 7.6 Hz, 2H), 7.74 (d, J = 8.5 Hz, 1H), 7.68 (br. s., 1H), 7.62 (br. s., 1H), 7.43 (t, J = 7.6 Hz, 1H), 7.25 (t, J = 7.5 Hz, 1H), 7.11 (dd, J = 7.3, 4.9 Hz, 1H), 5.23 (quin, J = 7.1 Hz, 1H), 4.62 (t, J = 5.2 Hz, 2H), 4.47-4.37 (m, 1H), 3.89 (t, J = 5.2 Hz, 2H), 3.33-3.28 (m, 2H), 3.12 (s, 3H), 2.92 (q, J = 7.1 Hz, 1H), 2.67 (dd, J = 11.0, 5.8 Hz, 1H), 2.43 (q, J = 3.4 Hz, 1H), 2.34-2.25 (m, 4H), 2.20 (dd, J = 11.6, 7.6 Hz, 1H), 1.16 (t, J = 7.3 Hz, 2H). |
| 79 | 2-((αR)-6-(3-methoxy-4-(4-methyl-1H-imidazol-1-yl)benzamido)spiro[3.3]heptan-2-yl)oxy)nicotinamide, trifluoroacetate | [structure] | 462.0 | A: 1.380<br>B: 1.161 | ¹H NMR (500 MHz, DMSO-d₆) δ 8.71 (d, J = 7.3 Hz, 1H), 8.27 (d, J = 4.7 Hz, 1H), 8.16 (d, J = 7.4 Hz, 1H), 7.86 (s, 1H), 7.75-7.67 (m, 1H), 7.62 (br. s., 2H), 7.55 (d, J = 9.1 Hz, 1H), 7.47 (d, J = 8.2 Hz, 1H), 7.20 (s, 1H), 7.11 (dd, J = 7.3, 5.0 Hz, 1H), 5.28-5.19 (m, 1H), 4.43-4.33 (m, 1H), 3.90 (s, 3H), 2.67 (dd, J = 10.6, 4.8 Hz, 1H), 2.35 (d, J = 6.0 Hz, 1H), 2.30-2.13 (m, 7H). |
| 80 | N-((αR)-6-((3-carbamoylpyridin-2-yl)oxy)spiro[3.3]heptan-2-yl)-6-(2-(dimethylamino)ethoxy)pyrazolo[1,5-a]pyridine-3-carboxamide, trifluoroacetate | [structure] | 479.0 | A: 1.097<br>B: 1.078 | ¹H NMR (500 MHz, DMSO-d₆) δ 8.52-8.45 (m, 2H), 8.33 (d, J = 7.5 Hz, 1H), 8.27 (d, J = 3.1 Hz, 1H), 8.16 (d, J = 7.4 Hz, 1H), 8.09 (d, J = 9.7 Hz, 1H), 7.71 (br. s., 1H), 7.63 (br. s., 1H), 7.27 (d, J = 9.8 Hz, 1H), 7.11 (d, J = 7.2, 5.0 Hz, 1H), 5.22 (quin, J = 7.1 Hz, 1H), 4.42-4.33 (m, 1H), 4.21 (t, J = 5.0 Hz, 2H), 3.03-2.96 (m, 1H), 2.69-2.63 (m, 1H), 2.47 (br. s., 6H), 2.36-2.31 (m, 1H), 2.29-2.13 (m, 4H). |

TABLE 4-continued

| | | | | |
|---|---|---|---|---|
| 81 | ![structure] | 6-bromo-N-((aR)-6-((3-carbamoylpyridin-2-yl)oxy)spiro[3.3]heptan-2-yl)-1-(2-hydroxy-2-methylpropyl)-1H-indazole-3-carboxamide, trifluoroacetate | 542.0 | A: 1.796<br>B: 1.714 | $^1$H NMR (500 MHz, DMSO-d$_6$) δ 8.51 (br d, J = 7.9 Hz, 1H), 8.26 (br d, J = 4.6 Hz, 1H), 8.16 (br d, J = 7.3 Hz, 1H), 8.08-8.03 (m, 2H), 7.68-7.60 (m, 1H), 7.35 (br d, J = 8.5 Hz, 1H), 7.10 (dd, J = 7.0, 4.9 Hz, 1H), 5.22 (quin, J = 7.1 Hz, 1H), 4.45-4.38 (m, 1H), 4.36 (s, 2H), 3.48 (br s, 1H), 2.66 (dt, J = 10.8, 5.6 Hz, 1H), 2.46-2.41 (m, 1H), 2.35-2.17 (m, 5H), 1.13 (s, 6H) |
| 82 | ![structure] | N-((aR)-6-((3-carbamoylpyridin-2-yl)oxy)spiro[3.3]heptan-2-yl)-6-(3,3,3-trifluoropropoxy)pyrazolo[1,5-a]pyridine-3-carboxamide, trifluoroacetate | 504.2 | C: 8.87<br>D: 7.48 | $^1$H NMR: (500 MHz, DMSO-d$_6$) δ 8.54 (d, J = 1.7 Hz, 1H), 8.46-8.44 (m, 1H), 8.27-8.23 (m, 2H), 8.16 (dd, J = 7.4, 1.9 Hz, 1H), 8.08 (d, J = 9.9 Hz, 1H), 7.68 (br s, 1H), 7.58 (d, J = 7.4, 4.7 Hz, 1H), 7.23 (dd, J = 9.6, 2.2 Hz, 1H), 7.09 (dd, J = 7.4, 4.7 Hz, 1H), 5.23 (quin, J = 7.2 Hz, 1H), 4.37 (sxt, J = 8.1 Hz, 1H), 4.28 (t, J = 5.8 Hz, 2H), 2.83 (qt, J = 11.3, 5.8 Hz, 2H), 2.68-2.63 (m, 1H), 2.47-2.43 (m, 2H), 2.36-2.31 (m, 1H), 2.28-2.13 (m, 4H) |
| 83 | ![structure] | 2-((aR)-6-(1,3-dimethyl-1H-pyrazole-5-carboxamido)spiro[3.3]heptan-2-yl)oxy)nicotinamide, trifluoroacetate | 370.0 | A: 1.201<br>B: 1.176 | $^1$H NMR (500 MHz, DMSO-d$_6$) δ 8.49 (d, J = 7.6 Hz, 1H), 8.27 (d, J = 3.1 Hz, 1H), 8.17 (d, J = 6.4 Hz, 1H), 7.69 (br. s., 1H), 7.60 (br. s., 1H), 6.61 (s, 1H), 5.22 (t, J = 7.0 Hz, 1H), 4.35-4.25 (m, 1H), 3.94 (s, 3H), 2.72-2.62 (m, 1H), 2.49-2.38 (m, 2H), 2.37-2.29 (m, 1H), 2.29-2.11 (m, 7H) |
| 84 | ![structure] | 2-((aR)-6-(5-(cyclopropylmethoxy)-1-methyl-1H-pyrazole-3-carboxamido)spiro[3.3]heptan-2-yl)oxy)nicotinamide, trifluoroacetate | 426.0 | A: 1.599<br>B: 1.616 | $^1$H NMR (500 MHz, DMSO-d$_6$) δ 8.27-8.23 (m, 1H), 8.16-8.08 (m, 2H), 7.70-7.55 (m, 2H), 7.15-7.03 (m, 2H), 5.24-5.17 (m, 1H), 4.35-4.25 (m, 1H), 3.93 (d, J = 7.3 Hz, 2H), 3.60 (s, 3H), 2.62 (dt, J = 10.9, 5.7 Hz, 1H), 2.44 (dt, J = 11.4, 5.9 Hz, 1H), 2.39-2.34 (m, 1H), 2.26-2.15 (m, 5H), 1.27-1.20 (m, 1H), 0.57 (br d, J = 7.0 Hz, 2H), 0.34 (br d, J = 4.6 Hz, 2H) |
| 85 | ![structure] | 2-((aR)-6-(3-cyclopropyl-1-methyl-1H-pyrazole-5-carboxamido)spiro[3.3]heptan-2-yl)oxy)nicotinamide, trifluoroacetate | 396.0 | A: 1.460<br>B: 1.338 | $^1$H NMR (500 MHz, DMSO-d$_6$) δ 8.46 (d, J = 7.3 Hz, 1H), 8.30-8.24 (m, 1H), 8.16 (dd, J = 7.3, 1.5 Hz, 1H), 7.68 (br. s., 1H), 7.60 (br. s., 1H), 6.52 (s, 1H), 5.21 (quin, J = 7.1 Hz, 1H), 4.37-4.24 (m, 1H), 3.91 (s, 3H), 2.64 (dt, J = 11.1, 5.7 Hz, 1H), 2.49-2.38 (m, 2H), 2.34-2.14 (m, 4H), 1.90-1.79 (m, 1H), 0.89-0.83 (m, 2H), 0.62-0.54 (m, 2H) |

| | Structure | Name | Mass | A/B | ¹H NMR |
|---|---|---|---|---|---|
| 86 | (pyrazole with CF₃) | 2-((aR)-6-(1-methyl-3-(trifluoromethyl)-1H-pyrazole-5-carboxamido)spiro[3.3]heptan-2-yl)oxy)nicotinamide, trifluoroacetate | 422.1 | A: 1.662 B: 1.663 | ¹H NMR (500 MHz, DMSO-d₆) δ 8.79 (d, J = 7.3 Hz, 1H), 8.26 (d, J = 3.4 Hz, 1H), 8.16 (d, J = 7.3 Hz, 1H), 7.69 (br. s., 1H), 7.59 (t, J = 7.3 Hz, 1H), 7.13-7.07 (m, 1H), 5.22 (br. s., 1H), 4.34-4.24 (m, 1H), 4.11 (s, 3H), 2.69-2.62 (m, 1H), 2.48-2.42 (m, 2H), 2.34 (d, J = 4.9 Hz, 1H), 2.30-2.11 (m, 4H) |
| 87 | (pyrazole with OCH₂CF₂CHF₂) | 2-((aR)-6-(1-methyl-5-(2,2,3,3-tetrafluoropropoxy)-1H-pyrazole-3-carboxamido)spiro[3.3]heptan-2-yl)oxy)nicotinamide, trifluoroacetate | 486.1 | A: 1.569 B: 1.511 | ¹H NMR (500 MHz, DMSO-d₆) δ 8.26-8.24 (m, 1H), 8.21-8.14 (m, 2H), 7.67 (br s, 1H), 7.59 (br. s., 1H), 7.09 (dd, J = 7.3, 4.9 Hz, 1H), 6.80-6.57 (m, 1H), 5.20 (quin, J = 7.1 Hz, 1H), 4.74 (br t, J = 13.3 Hz, 2H), 4.30 (sxt, J = 8.1 Hz, 1H), 3.64 (s, 3H), 2.65-2.60 (m, 1H), 2.47-2.42 (m, 1H), 2.39-2.34 (m, 1H), 2.28-2.14 (m, 6H) |
| 88 | (methylthiazole-pyridine) | N-((aR)-6-((3-carbamoylpyridin-2-yl)oxy)spiro[3.3]heptan-2-yl)-4-methyl-2-(pyridin-2-yl)thiazole-5-carboxamide, trifluoroacetate | 449.9 | A: 1.583 B: 1.568 | ¹H NMR (500 MHz, DMSO-d₆) δ 8.64 (d, J = 4.5 Hz, 1H), 8.56 (d, J = 7.2 Hz, 1H), 8.27 (d, J = 4.6 Hz, 1H), 8.19-8.10 (m, 2H), 7.98 (t, J = 7.7 Hz, 1H), 7.72 (br. s., 1H), 7.62 (br. s., 1H), 7.56-7.50 (m, 1H), 7.11 (dd, J = 7.2, 5.0 Hz, 1H), 5.22 (quin, J = 7.1 Hz, 1H), 4.36-4.26 (m, 1H), 2.65 (dt, J = 11.2, 5.7 Hz, 1H), 2.55 (s, 3H), 2.49-2.41 (m, 2H), 2.37-2.31 (m, 1H), 2.28-2.14 (m, 4H) |
| 89 | (3-phenyl pyrazole) | 2-((aR)-6-(1-methyl-3-phenyl-1H-pyrazole-5-carboxamido)spiro[3.3]heptan-2-yl)oxy)nicotinamide, trifluoroacetate | 432.2 | A: 1.702 B: 1.705 | ¹H NMR (500 MHz, DMSO-d₆) δ 8.70 (d, J = 7.4 Hz, 1H), 8.27 (d, J = 3.4 Hz, 1H), 8.17 (d, J = 7.3 Hz, 1H), 7.76 (d, J = 7.7 Hz, 2H), 7.72 (br. s., 1H), 7.62 (br. s., 1H), 7.43 (t, J = 7.7 Hz, 2H), 7.36-7.31 (m, 1H), 7.27 (s, 1H), 7.11 (dd, J = 7.2, 5.0 Hz, 1H), 5.23 (quin, J = 7.1 Hz, 1H), 4.38-4.28 (m, 1H), 4.07 (s, 3H), 2.66 (dd, J = 11.4, 5.9 Hz, 1H), 2.48-2.42 (m, 2H), 2.39-2.32 (m, 1H), 2.30-2.15 (m, 4H) |
| 90 | (difluoroazetidinyl methylthiazole) | N-((aR)-6-((3-carbamoylpyridin-2-yl)oxy)spiro[3.3]heptan-2-yl)-2-(3,3-difluoroazetidin-1-yl)-4-methylthiazole-5-carboxamide, trifluoroacetate | 462.1 | A: 1.494 B: 1.443 | ¹H NMR (500 MHz, DMSO-d6) δ 8.25 (br d, J = 3.8 Hz, 1H), 8.15 (br d, J = 7.2 Hz, 1H), 7.98 (br d, J = 7.3 Hz, 1H), 7.69 (br s, 1H), 7.60 (br s, 1H), 5.22-5.16 (m, 1H), 4.49 (br t, J = 12.1 Hz, 4H), 4.26-4.19 (m, 1H), 2.61 (dt, J = 11.1, 5.7 Hz, 1H), 2.45 (m, 1H), 2.38 (s, 4H), 2.29-2.11 (m, 5H) |

TABLE 4-continued

| # | Structure | Name | Mass | A/B | ¹H NMR |
|---|---|---|---|---|---|
| 91 | 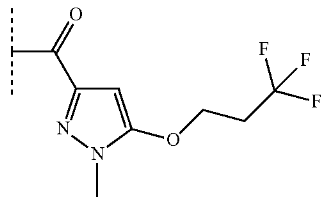 | 2-((aR)-6-(1-methyl-5-(3,3,3-trifluoropropoxy)-1H-pyrazole-3-carboxamido)spiro[3.3]heptan-2-yl)oxy)nicotinamide, trifluoroacetate | 468.0 | A: 1.649 B: 1.639 | ¹H NMR (500 MHz, DMSO-d₆) δ 8.25-8.22 (m, 2H), 8.15 (dd, J = 7.4, 1.6 Hz, 1H), 7.66 (br d, J = 14.9 Hz, 2H), 7.10 (dd, J = 7.4, 5.0 Hz, 1H), 6.10 (s, 1H), 5.17 (quin, J = 7.1 Hz, 1H), 4.34-4.24 (m, 3H), 3.57 (s, 3H), 2.81-2.72 (m, 2H), 2.65-2.61 (m, 1H), 2.47-2.42 (m, 1H), 2.39-2.35 (m, 1H), 2.28-2.12 (m, 5H) |
| 92 | 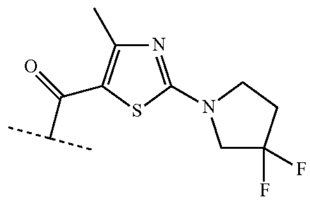 | N-((aR)-6-((3-carbamoylpyridin-2-yl)oxy)spiro[3.3]heptan-2-yl)-2-(3,3-difluoropyrrolidin-1-yl)-4-methylthiazole-5-carboxamide, trifluoroacetate | 478.0 | A: 1.460 B: 1.284 | ¹H NMR (500 MHz, DMSO-d₆) δ 8.26 (br d, J = 4.3 Hz, 1H), 8.15 (br d, J = 7.3 Hz, 1H), 7.87 (br d, J = 7.3 Hz, 1H), 7.70 (br s, 1H), 7.60 (br s, 1H), 7.10 (br t, J = 5.8 Hz, 1H), 5.19 (quin, J = 6.9 Hz, 1H), 4.27-4.21 (m, 1H), 3.90-3.80 (m, 2H), 3.59 (br t, J = 6.9 Hz, 1H), 3.48-3.40 (m, 2H), 2.63-2.56 (m, 2H), 2.45 (br dd, J = 11.7, 5.8 Hz, 1H), 2.38 (s, 3H), 2.28-2.10 (m, 6H) |
| 93 | 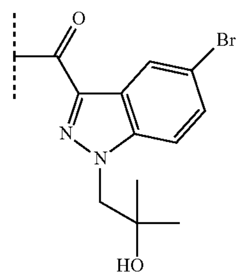 | 5-bromo-N-((aR)-6-((3-carbamoylpyridin-2-yl)oxy)spiro[3.3]heptan-2-yl)-1-(2-hydroxy-2-methylpropyl)-1H-indazole-3-carboxamide, trifluoroacetate | 542.0 | A: 1.730 B: 1.726 | ¹H NMR (500 MHz, DMSO-d₆) δ 8.54 (br d, J = 7.9 Hz, 1H), 8.16 (br d, J = 7.3 Hz, 1H), 7.78 (br d, J = 9.0 Hz, 1H), 7.72 (br s, 1H), 7.61 (br s, 1H), 7.54 (br d, J = 8.8 Hz, 1H), 7.24-7.01 (m, 3H), 5.25-5.19 (m, 1H), 4.47-4.40 (m, 1H), 4.37 (s, 2H), 2.70-2.64 (m, 1H), 2.45-2.40 (m, 1H), 2.34-2.25 (m, 4H), 2.20 (br dd, J = 11.4, 7.5 Hz, 1H), 1.13 (s, 6H) |
| 94 | 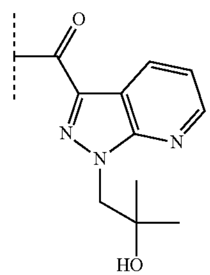 | N-((aR)-6-((3-carbamoylpyridin-2-yl)oxy)spiro[3.3]heptan-2-yl)-1-(2-hydroxy-2-methylpropyl)-1H-pyrazolo[3,4-b]pyridine-3-carboxamide, trifluoroacetate | 464.2 | A: 1.256 B: 1.156 | ¹H NMR (500 MHz, DMSO-d₆) δ 8.44 (br d, J = 7.7 Hz, 1H), 8.16 (br d, J = 7.4 Hz, 1H), 7.72 (br s, 1H), 7.61 (br s, 1H), 7.22-7.01 (m, 4H), 5.26-5.18 (m, 1H), 4.44-4.35 (m, 1H), 4.21 (s, 2H), 2.66 (br dd, J = 11.4, 6.0 Hz, 1H), 2.46 (br d, J = 6.1 Hz, 1H), 2.36-2.30 (m, 1H), 2.29-2.14 (m, 5H), 1.06 (s, 6H) |

| | Name | Structure | MS | RT | 1H NMR |
|---|---|---|---|---|---|
| 95 | 2((aR)-6-(5-(2,2-difluoroethoxy)-1-methyl-1H-pyrazole-3-carboxamido)spiro[3.3]heptan-2-yl)oxy)nicotinamide, trifluoroacetate | | 436.0 | A: 1.359 B: 1.329 | 1H NMR (500 MHz, DMSO-d6) δ 8.24 (br d, J = 6.1 Hz, 2H), 8.14 (br d, J = 7.4 Hz, 1H), 7.65 (br s, 2H), 7.12-7.06 (m, 1H), 6.46-6.20 (m, 1H), 6.15-6.11 (m, 1H), 5.21-5.13 (m, 1H), 4.42 (br t, J = 14.9 Hz, 2H), 4.31-4.22 (m, 1H), 3.72 (br s, 3H), 2.65-2.58 (m, 1H), 2.46-2.42 (m, 1H), 2.37-2.33 (m, 1H), 2.26-2.11 (m, 5H) |
| 96 | N-((aR)-6-(3-carbamoylpyridin-2-yl)oxy)spiro[3.3]heptan-2-yl)-4-methyl-2-phenylthiazole-5-carboxamide, trifluoroacetate | | 449.2 | A: 1.714 B: 1.706 | 1H NMR (500 MHz, DMSO-d6) δ 8.53 (br d, J = 7.0 Hz, 1H), 8.26 (br d, J = 3.6 Hz, 1H), 8.15 (br d, J = 7.4 Hz, 1H), 7.92 (br s, 2H), 7.69 (br s, 1H), 7.62 (br s, 1H), 7.52 (br s, 3H), 7.12-7.09 (m, 1H), 5.24-5.17 (m, 1H), 4.33-4.26 (m, 1H), 2.67-2.62 (m, 1H), 2.60-2.55 (m, 3H), 2.46-2.41 (m, 1H), 2.36-2.29 (m, 1H), 2.26-2.13 (m, 4H) |
| 97 | N-((aR)-6-(3-carbamoylpyridin-2-yl)oxy)spiro[3.3]heptan-2-yl)-6-fluoro-1-(2-hydroxy-2-methylpropyl)-1H-indazole-3-carboxamide, trifluoroacetate | | 482.2 | A: 1.609 B: 1.601 | 1H NMR (500 MHz, DMSO-d6) δ 8.47 (br d, J = 7.6 Hz, 1H), 8.26 (br d, J = 3.1 Hz, 1H), 8.17-8.09 (m, 2H), 7.70-7.57 (m, 3H), 7.23-7.02 (m, 3H), 5.25-5.18 (m, 1H), 4.45-4.37 (m, 1H), 4.33 (s, 2H), 2.69-2.63 (m, 1H), 2.43 (br dd, J = 11.0, 7.0 Hz, 1H), 2.32-2.16 (m, 5H), 1.16-1.12 (m, 6H) |
| 98 | N-((aR)-6-(3-carbamoylpyridin-2-yl)oxy)spiro[3.3]heptan-2-yl)-1-(2-hydroxy-2-methylpropyl)-6-(trifluoromethoxy)-1H-indazole-3-carboxamide, trifluoroacetate | | 548.2 | A: 1.866 B: 1.859 | 1H NMR (500 MHz, DMSO-d6) δ 8.57 (br d, J = 8.0 Hz, 1H), 8.28-8.13 (m, 3H), 7.84 (s, 1H), 7.71 (br s, 1H), 7.62 (br s, 1H), 7.22 (br d, J = 8.8 Hz, 1H), 7.10 (dd, J = 7.2, 5.0 Hz, 1H), 5.22 (quin, J = 7.1 Hz, 1H), 4.46-4.40 (m, 1H), 4.39 (s, 2H), 2.70-2.62 (m, 1H), 2.46-2.41 (m, 1H), 2.34-2.18 (m, 5H), 1.13 (s, 6H) |

| # | Name | Structure | Mass | Ret. time | 1H NMR |
|---|---|---|---|---|---|
| 99 | N-((aR)-6-((3-carbamoylpyridin-2-yl)oxy)spiro[3.3]heptan-2-yl)-6-methoxy-7-(3,3,3-trifluoropropyl)pyrazolo[1,5-a]pyridine-3-carboxamide, trifluoroacetate | | 518.1 | A: 1.809 B: 1.804 | 1H NMR (500 MHz, DMSO-d6) δ 8.52 (s, 1H), 8.34 (br d, J = 7.3 Hz, 1H), 8.25 (br d, J = 3.4 Hz, 1H), 8.17-8.11 (m, 2H), 7.64 (br d, J = 10.7 Hz, 1H), 7.58 (d, J = 9.8 Hz, 1H), 7.16-7.05 (m, 1H), 5.21 (quin, J = 7.0 Hz, 1H), 4.41-4.32 (m, 1H), 3.88 (s, 3H), 3.62 (br d, J = 7.9 Hz, 2H), 3.38 (br t, J = 7.5 Hz, 2H), 2.69-2.62 (m, 3H), 2.45-2.41 (m, 1H), 2.36-2.31 (m, 1H), 2.26-2.12 (m, 4H) |
| 100 | N-((aR)-6-((3-carbamoylpyridin-2-yl)oxy)spiro[3.3]heptan-2-yl)-6-methoxypyrazolo[1,5-a]pyridine-3-carboxamide, trifluoroacetate | | 443.9 | A: 1.428 B: 1.424 | 1H NMR (500 MHz, DMSO-d6) δ 8.41 (br d, J = 12.8 Hz, 2H), 8.32-8.24 (m, 2H), 8.17-8.14 (m, 1H), 8.05 (d, J = 9.8 Hz, 1H), 7.64 (br d, J = 16.2 Hz, 2H), 7.24 (br d, J = 11.3 Hz, 1H), 7.13-7.07 (m, 1H), 5.21 (quin, J = 7.1 Hz, 1H), 4.39-4.31 (m, 1H), 3.82 (s, 3H), 2.65 (dt, J = 11.3, 6.0 Hz, 1H), 2.46-2.42 (m, 1H), 2.35-2.30 (m, 1H), 2.26-2.11 (m, 4H) |
| 101 | N-((aR)-6-((3-carbamoylpyridin-2-yl)oxy)spiro[3.3]heptan-2-yl)-6-(2-hydroxy-2-methylpropoxy)-7-(1-methyl-1H-pyrazol-4-yl)pyrazolo[1,5-a]pyridine-3-carboxamide, trifluoroacetate | | 560.0 | A: 1.415 B: 1.415 | 1H NMR (500 MHz, DMSO-d6) δ 8.89 (s, 1H), 8.57 (d, J = 3.7 Hz, 2H), 8.34 (br d, J = 7.6 Hz, 1H), 8.26 (br d, J = 3.1 Hz, 1H), 8.17-8.08 (m, 2H), 7.68-7.60 (m, 3H), 7.10 (dd, J = 7.5, 5.0 Hz, 1H), 5.26-5.20 (m, 1H), 4.38 (q, J = 8.0 Hz, 1H), 3.97-3.94 (m, 3H), 3.56 (s, 3H), 3.28-3.23 (m, 1H), 3.18-3.14 (m, 1H), 2.69-2.64 (m, 1H), 2.35 (br d, J = 11.6 Hz, 1H), 2.29-2.14 (m, 4H), 1.24 (s, 6H) |
| 102 | N-((aR)-6-((3-carbamoylpyridin-2-yl)oxy)spiro[3.3]heptan-2-yl)-1-(2-hydroxy-2-methylpropyl)-1H-indazole-3-carboxamide, trifluoroacetate | | 464.2 | A: 1.518 B: 1.520 | 1H NMR (500 MHz, DMSO-d6) δ 8.44-8.39 (m, 1H), 8.29-8.25 (m, 1H), 8.18-8.10 (m, 2H), 7.79-7.74 (m, 1H), 7.72-7.66 (m, 1H), 7.62-7.58 (m, 1H), 7.40 (br t, J = 7.6 Hz, 1H), 7.25-7.20 (m, 1H), 7.10 (dd, J = 7.3, 4.9 Hz, 1H), 5.25-5.19 (m, 1H), 4.47-4.40 (m, 1H), 4.39-4.34 (m, 2H), 2.70-2.64 (m, 1H), 2.45-2.40 (m, 1H), 2.33-2.17 (m, 5H), 1.13 (s, 6H) |

| # | Structure | Name | MS | LC | ¹H NMR |
|---|---|---|---|---|---|
| 103 | 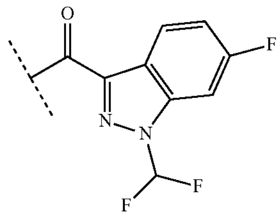 | N-((aR)-6-(3-carbamoylpyridin-2-yl)oxy)spiro[3.3]heptan-2-yl)-1-(difluoromethyl)-6-fluoro-1H-indazole-3-carboxamide, trifluoroacetate | 459.9 | A: 1.948 B: 1.916 | ¹H NMR (500 MHz, DMSO-d₆) δ 9.02-8.96 (m, 1H), 8.33-8.05 (m, 4H), 7.79-7.62 (m, 3H), 7.37-7.05 (m, 3H), 5.21 (quin, J = 6.9 Hz, 1H), 4.41 (sxt, J = 8.0 Hz, 1H), 2.66 (br d, J = 11.3, 5.6 Hz, 1H), 2.46 (br dd, J = 13.1, 7.4 Hz, 1H), 2.34-2.17 (m, 5H) |
| 104 | 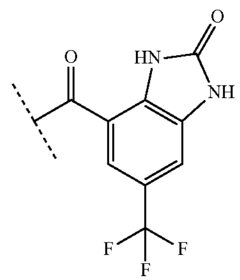 | N-((aR)-6-(3-carbamoylpyridin-2-yl)oxy)spiro[3.3]heptan-2-yl)-2-oxo-6-(trifluoromethyl)-2,3-dihydro-1H-benzo[d]imidazole-4-carboxamide, trifluoroacetate | 476.2 | A: 1.411 B: 1.393 | ¹H NMR (500 MHz, DMSO-d₆) δ 11.20 (br s, 1H), 10.77 (br s, 1H), 8.86 (br d, J = 6.8 Hz, 1H), 8.26 (br d, J = 4.2 Hz, 1H), 8.16 (br d, J = 7.3 Hz, 1H), 7.90-7.79 (m, 1H), 7.76-7.57 (m, 2H), 7.29 (br s, 1H), 7.10 (dd, J = 7.1, 5.2 Hz, 1H), 5.22 (br t, J = 6.8 Hz, 1H), 4.41-4.34 (m, 1H), 2.66 (br dd, J = 10.9, 6.0 Hz, 1H), 2.43 (br s, 1H), 2.37-2.31 (m, 1H), 2.29-2.19 (m, 4H) |
| 105 | 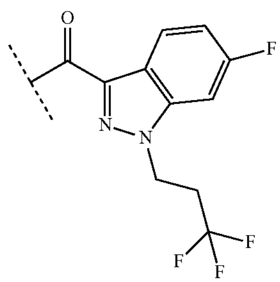 | N-((aR)-6-(3-carbamoylpyridin-2-yl)oxy)spiro[3.3]heptan-2-yl)-6-fluoro-1-(3,3,3-trifluoropropyl)-1H-indazole-3-carboxamide, trifluoroacetate | 506.1 | A: 1.905 B: 1.919 | ¹H NMR (500 MHz, DMSO-d₆) δ 8.57 (br d, J = 7.9 Hz, 1H), 8.26 (br d, J = 3.1 Hz, 1H), 8.18-8.12 (m, 2H), 7.73-7.59 (m, 3H), 7.17-7.09 (m, 2H), 5.22 (quin, J = 7.1 Hz, 1H), 4.70 (br t, J = 6.7 Hz, 2H), 4.44-4.38 (m, 1H), 3.05-2.97 (m, 2H), 2.70-2.64 (m, 1H), 2.46-2.41 (m, 1H), 2.34-2.18 (m, 5H) |
| 106 | 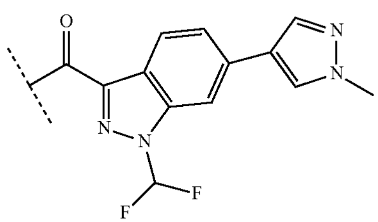 | N-((aR)-6-(3-carbamoylpyridin-2-yl)oxy)spiro[3.3]heptan-2-yl)-1-(difluoromethyl)-6-(1-methyl-1H-pyrazol-4-yl)-1H-indazole-3-carboxamide, trifluoroacetate | 522.1 | A: 1.595 B: 1.558 | ¹H NMR (500 MHz, DMSO-d₆) δ 8.88 (br d, J = 7.9 Hz, 1H), 8.29-8.25 (m, 2H), 8.15 (br s, 1H), 7.99 (s, 2H), 7.68-7.61 (m, 3H), 7.29-7.05 (m, 2H), 5.24-5.17 (m, 1H), 4.45-4.36 (m, 1H), 3.87 (s, 3H), 2.69-2.63 (m, 1H), 2.45-2.41 (m, 1H), 2.34-2.15 (m, 5H) |

TABLE 4-continued

| # | Structure | Name | Mass | LC | ¹H NMR |
|---|---|---|---|---|---|
| 107 | 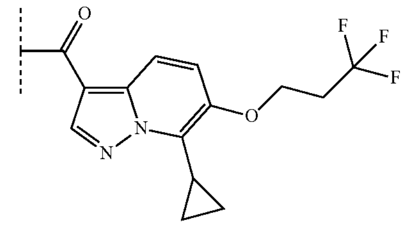 | N-((aR)-6-((3-carbamoylpyridin-2-yl)oxy)spiro[3.3]heptan-2-yl)-7-cyclopropyl-6-(3,3,3-trifluoropropoxy)pyrazolo[1,5-a]pyridine-3-carboxamide, trifluoroacetate | 544.1 | C: 8.65 D: 9.70 | ¹H NMR (400 MHz, DMSO-d₆) δ 8.53 (s, 1H), 8.31-8.26 (m, 2H), 8.18 (dd, J = 7.5, 2.0 Hz, 1H), 8.07 (d, J = 9.5 Hz, 1H), 7.72 (br. s., 1H), 7.61 (br. s., 1H), 7.52 (d, J = 9.7 Hz, 1H), 7.12 (dd, J = 7.5, 4.8 Hz, 1H), 5.25 (t, J = 7.2 Hz, 1H), 2.84 (tt, J = 11.4, 5.6 Hz, 2H), 2.72-2.65 (m, 1H), 2.49-2.42 (m, 2H), 2.41-2.12 (m, 6H), 1.47-1.39 (m, 2H), 1.10-1.03 (m, 2H) |
| 108 | 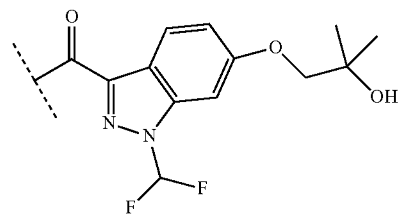 | N-((aR)-6-((3-carbamoylpyridin-2-yl)oxy)spiro[3.3]heptan-2-yl)-1-(difluoromethyl)-6-(2-hydroxy-2-methylpropoxy)-1H-indazole-3-carboxamide, trifluoroacetate | 530.1 | C: 8.77 D: 7.51 | ¹H NMR (400 MHz, DMSO-d₆) δ 8.80 (d, J = 8.1 Hz, 1H), 8.38-8.04 (m, 4H), 7.70 (br s, 1H), 7.59 (br s, 1H), 7.38 (d, J = 1.8 Hz, 1H), 7.12-7.06 (m, 2H), 5.23 (quin, J = 7.2 Hz, 1H), 4.48-4.38 (m, 1H), 3.84 (s, 2H), 2.72-2.63 (m, 1H), 2.47-2.39 (m, 2H), 2.36-2.20 (m, 5H), 1.24 (s, 6H) |
| 109 | 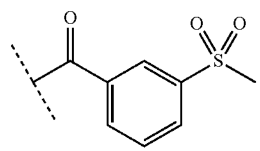 | 2-((aR)-6-((3-carbamoylpyridin-2-yl)oxy)spiro[3.3]heptan-2-yl)oxy)nicotinamide, trifluoroacetate | 430.1 | A: 1.280 B: 1.276 | ¹H NMR (500 MHz, DMSO-d₆) δ 8.92 (d, J = 7.0 Hz, 1H), 8.37 (br. s., 1H), 8.27 (d, J = 4.9 Hz, 1H), 8.17 (d, J = 7.6 Hz, 2H), 8.07 (d, J = 7.3 Hz, 1H), 7.76 (t, J = 7.8 Hz, 1H), 7.69 (br. s., 1H), 7.62 (br. s., 1H), 7.13-7.08 (m, 1H), 5.27-5.21 (m, 1H), 4.42-4.34 (m, 1H), 3.25 (s, 3H), 3.18 (d, J = 4.6 Hz, 1H), 2.68 (br. s., 1H), 2.37 (br. s., 1H), 2.30-2.17 (m, 4H) |
| 110 | 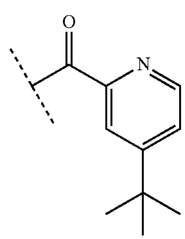 | 4-(tert-butyl)-N-((aR)-6-((3-carbamoylpyridin-2-yl)oxy)spiro[3.3]heptan-2-yl)oxy)picolinamide, bis trifluoroacetate | 409.4 | A: 1.870 B: 1.719 | ¹H NMR (500 MHz, DMSO-d₆) δ 8.87 (d, J = 7.9 Hz, 1H), 8.54 (d, J = 4.9 Hz, 1H), 8.27 (d, J = 2.7 Hz, 1H), 8.17 (d, J = 7.3 Hz, 1H), 8.00 (s, 1H), 7.69-7.60 (m, 3H), 7.11 (dd, J = 7.3, 4.9 Hz, 1H), 5.22 (t, J = 7.0 Hz, 1H), 4.41-4.35 (m, 1H), 2.66 (dt, J = 11.3, 5.6 Hz, 1H), 2.42 (br. s., 1H), 2.31-2.19 (m, 4H), 1.30 (s, 9H) |
| 111 | 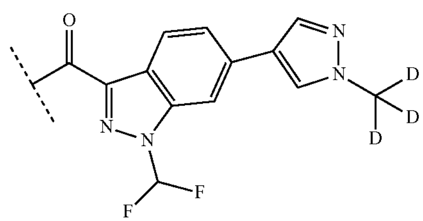 | 1-(difluoromethyl)-6-[1-(²H₃)methyl-1H-pyrazol-4-yl]-N-[(4s)-6-[(3-carbamoylpyridin-2-yl)oxy]spiro[3.3]heptan-2-yl]-1H-indazole-3-carboxamide, trifluoroacetate | 525.4 | A: 1.573 B: 1.520 | ¹H NMR (500 MHz, DMSO-d₆) δ 8.93-8.88 (m, 1H), 8.33-8.09 (m, 5H), 8.02 (d, J = 13.5 Hz, 2H), 7.73-7.59 (m, 3H), 7.10 (dd, J = 7.4, 4.9 Hz, 1H), 5.21 (quin, J = 7.0 Hz, 1H), 4.42 (sxt, J = 8.1 Hz, 1H), 2.69-2.64 (m, 1H), 2.47-2.41 (m, 1H), 2.34-2.16 (m, 5H) |

| | | | | |
|---|---|---|---|---|
| 112 | N-((aR)-6-((3-carbamoylpyridin-2-yl)oxy)spiro[3.3]heptan-2-yl)-1-(difluoromethyl)-6-(1-(difluoromethyl)-1H-pyrazol-4-yl)-1H-indaozle-3-carboxamide, trifluoroacetate | 558.0 | A: 1.783 B: 1.805 | ¹H NMR (500 MHz, DMSO-d₆) δ 8.99-8.94 (m, 1H), 8.90-8.85 (m, 1H), 8.44-8.39 (m, 1H), 8.30-8.14 (m, 5H), 7.84-7.76 (m, 2H), 7.71-7.63 (m, 2H), 7.10 (dd, J = 7.3, 5.0 Hz, 1H), 5.20 (quin, J = 6.8 Hz, 1H), 4.46-4.37 (m, 1H), 2.68-2.63 (m, 1H), 2.47-2.43 (m, 1H), 2.35-2.16 (m, 5H) |
| 113 | 2-((aR)-6-(3-(tert-butyl)-1H-pyrazole-5-carboxamido)spiro[3.3]heptan-2-yl)oxy)nicotinamide, trifluoroacetate | 462.1 | A: 1.937 B: 1.931 | ¹H NMR (500 MHz, DMSO-d₆) δ 8.65 (br d, J = 6.6 Hz, 1H), 8.26-8.24 (m, 1H), 8.15 (dd, J = 7.4, 1.6 Hz, 1H), 7.69 (br s, 1H), 7.62 (br s, 1H), 7.10 (dd, J = 7.4, 4.9 Hz, 1H), 6.86-6.82 (m, 1H), 6.36-6.14 (m, 1H), 5.23-5.16 (m, 1H), 4.86 (br t, J = 14.0 Hz, 2H), 4.31-4.23 (m, 1H), 2.66-2.62 (m, 1H), 2.46-2.41 (m, 1H), 2.33-2.28 (m, 1H), 2.26-2.12 (m, 4H), 1.23 (s, 9H) |
| 114 | 2-((aR)-6-(3-(tert-butyl)-1-(3,3,3-trifluoropropyl)-1H-pyrazole-5-carboxamido)spiro[3.3]heptan-2-yl)oxy)nicotinamide, trifluoroacetate | 494.4 | A: 2.007 B: 1.985 | ¹H NMR (500 MHz, DMSO-d₆) δ 8.58 (br d, J = 7.2 Hz, 1H), 8.28-8.25 (m, 1H), 8.15 (br d, J = 6.1 Hz, 1H), 7.71 (br s, 1H), 7.60 (br s, 1H), 7.10 (dd, J = 7.3, 5.0 Hz, 1H), 6.83-6.78 (m, 1H), 5.20 (quin, J = 7.1 Hz, 1H), 4.65 (br t, J = 7.0 Hz, 2H), 4.30 (sxt, J = 8.0 Hz, 1H), 2.92 (q, J = 7.2 Hz, 1H), 2.78-2.68 (m, 2H), 2.67-2.62 (m, 1H), 2.46-2.40 (m, 1H), 2.32-2.13 (m, 5H), 1.23 (s, 9H) |
| 115 | N-((aR)-6-((3-carbamoylpyridin-2-yl)oxy)spiro[3.3]heptan-2-yl)-6-(3,3,3-trifluoropropoxy)-7-(3,3,3-trifluoropropyl)pyrazolo[1,5-a]pyridine-3-carboxamide, trifluoroacetate | 600.1 | A: 2.051 B: 2.045 | ¹H NMR (500 MHz, DMSO-d₆) δ 8.53 (s, 1H), 8.40 (br d, J = 5.1 Hz, 1H), 8.24 (br d, J = 3.2 Hz, 1H), 8.16-8.10 (m, 2H), 7.66 (br s, 2H), 7.58 (br d, J = 9.7 Hz, 1H), 7.10 (dd, J = 7.3, 5.0 Hz, 1H), 5.24-5.16 (m, 1H), 4.38-4.29 (m, 3H), 2.78 (m, J = 10.9, 5.4 Hz, 2H), 2.68-2.59 (m, 3H), 2.47-2.38 (m, 2H), 2.35-2.29 (m, 1H), 2.26-2.10 (m, 4H) |

TABLE 4-continued

| | Name | Structure | MS | IC50 | NMR |
|---|---|---|---|---|---|
| 116 | N-((aR)-6-((3-carbamoylpyridin-2-yl)oxy)spiro[3.3]heptan-2-yl)-6-((E)-3,3,3-trifluoroprop-1-en-1-yl)pyrazolo[1,5-a]pyridine-3-carboxamide, trifluoroacetate | | 484.1 | A: 2.433 B: 2.426 | $^1$H NMR (500 MHz, DMSO-d$_6$) δ 9.10 (br s, 1H), 8.60 (br s, 1H), 8.44 (br s, 1H), 8.28-8.24 (m, 1H), 8.18-8.14 (m, 1H), 7.86 (br s, 1H), 7.70 (br s, 1H), 7.62 (br s, 1H), 7.42 (br d, J = 15.8 Hz, 1H), 7.10 (dd, J = 7.4, 4.9 Hz, 1H), 6.91-6.82 (m, 1H), 5.21 (br t, J = 7.1 Hz, 1H), 4.42-4.33 (m, 1H), 2.65 (br dd, J = 10.9, 5.8 Hz, 1H), 2.46-2.42 (m, 1H), 2.33 (br d, J = 5.9 Hz, 1H), 2.28-2.12 (m, 4H) |
| 117 | N-((aR)-6-((3-carbamoylpyridin-2-yl)oxy)spiro[3.3]heptan-2-yl)-6-(3,3,3-trifluoropropoxy)-1H-indazole-3-carboxamide, trifluoroacetate | | 599.9 | A: 1.987 B: 2.016 | $^1$H NMR (500 MHz, DMSO-d$_6$) δ 8.49 (br s, 1H), 8.26 (br d, J = 2.9 Hz, 1H), 8.15 (br d, J = 7.3 Hz, 1H), 7.97 (br d, J = 8.8 Hz, 1H), 7.69 (br s, 1H), 7.63 (br s, 1H), 7.30 (br s, H), 7.17-7.05 (m, 2H), 6.88 (br d, J = 8.9 Hz, 1H), 5.24-5.18 (m, 1H), 4.70-4.64 (m, 2H), 4.43-4.35 (m, 1H), 4.29 (br t, J = 5.4 Hz, 2H), 2.99 (br d, J = 5.4 Hz, 2H), 2.87-2.80 (m, 2H), 2.69-2.63 (m, 1H), 2.48-2.38 (m, 2H), 2.33-2.17 (m, 5H) |
| 118 | N-((aR)-6-((3-carbamoylpyridin-2-yl)oxy)spiro[3.3]heptan-2-yl)-6-(3,3,3-trifluoropropyl)pyrazolo[1,5-a]pyridine-3-carboxamide, trifluoroacetate | | 488.2 | A: 1.664 B: 1.663 | $^1$H NMR (500 MHz, DMSO-d$_6$) δ 8.73 (s, 1H), 8.51 (s, 1H), 8.33-8.25 (m, 2H), 8.19-8.10 (m, 2H), 7.72 (br s, 1H), 7.61 (br s, 1H), 7.45 (br d, J = 9.1 Hz, 1H), 7.26 (s, 1H), 7.17-7.06 (m, 2H), 5.22 (quin, J = 7.0 Hz, 1H), 4.38 (sxt, J = 8.0 Hz, 1H), 2.92-2.87 (m, 2H), 2.66 (br dd, J = 10.7, 6.1 Hz, 2H), 2.46 (br s, 1H), 2.37-2.32 (m, 1H), 2.28-2.13 (m, 4H) |
| 119 | 2-((aR)-6-(3-bromo-5-(methylsulfonyl)benzamido)spiro[3.3]heptan-2-yl)oxy)nicotinamide, trifluoroacetate | | 510.2 | A: 1.453 B: 1.409 | $^1$H NMR (500 MHz, DMSO-d$_6$) δ 8.99 (br d, J = 7.0 Hz, 1H), 8.34 (br s, 2H), 8.27-8.22 (m, 2H), 8.16 (br d, J = 6.4 Hz, 1H), 7.67 (br s, 1H), 7.60 (br s, 1H), 7.10 (dd, J = 7.3, 4.9 Hz, 1H), 5.25-5.19 (m, 1H), 4.35 (dq, J = 15.7, 7.9 Hz, 1H), 2.70-2.63 (m, 1H), 2.47-2.43 (m, 1H), 2.39-2.32 (m, 1H), 2.28-2.15 (m, 4H) |

| # | Name | Structure | Mass | LCMS | 1H NMR |
|---|---|---|---|---|---|
| 120 | 6-(2-(1H-imidazol-1-yl)ethoxy)-N-((aR)-6-((3-carbamoylpyridin-2-yl)oxy)spiro[3.3]heptan-2-yl)pyrazolo[1,5-a]pyridine-3-carboxamide, trifluoroacetate | | 502.2 | C: 3.74 D: 5.85 | 1H NMR (500 MHz, Methanol-d4) δ 9.11 (t, J = 1.4 Hz, 1H), 8.40 (s, 1H), 8.37-8.34 (m, 2H), 8.29 (dd, J = 4.8, 2.1 Hz, 1H), 8.15 (d, J = 9.6 Hz, 1H), 7.80 (t, J = 1.8 Hz, 1H), 7.65-7.61 (m, 1H), 7.30-7.26 (m, 1H), 7.12-7.10 (m, 1H), 5.39-5.33 (m, 1H), 4.78-4.74 (m, 2H), 4.53-4.45 (m, 3H), 2.81 (dt, J = 11.6, 5.9 Hz, 1H), 2.64-2.58 (m, 2H), 2.51-2.46 (m, 1H), 2.35 (dd, J = 11.6, 7.2 Hz, 1H), 2.31-2.22 (m, 3H) |
| 121 | N-((aR)-6-((3-carbamoylpyridin-2-yl)oxy)spiro[3.3]heptan-2-yl)-6-(2-(2-methoxyethoxy)ethoxy)pyrazolo[1,5-a]pyridine-3-carboxamide, trifluoroacetate | | 510.1 | A: 1.301 B: 1.253 | 1H NMR (500 MHz, DMSO-d6) δ 8.49-8.39 (m, 2H), 8.29-8.24 (m, 2H), 8.16 (br d, J = 6.1 Hz, 1H), 8.06 (br d, J = 9.8 Hz, 1H), 7.67 (br s, 1H), 7.61 (br s, 1H), 7.26 (br d, J = 7.9 Hz, 1H), 7.10 (dd, J = 7.3, 5.2 Hz, 1H), 5.25-5.19 (m, 1H), 4.40-4.33 (m, 1H), 4.15 (br s, 2H), 3.75 (br s, 1H), 3.27-3.13 (m, 2H), 2.66 (dt, J = 11.4, 5.6 Hz, 1H), 2.47-2.39 (m, 2H), 2.36-2.30 (m, 1H), 2.27-2.11 (m, 4H) |
| 122 | N-((aR)-6-((3-carbamoylpyridin-2-yl)oxy)spiro[3.3]heptan-2-yl)-6-(4,4,4-trifluorobutoxy)pyrazolo[1,5-a]pyridine-3-carboxamide, trifluoroacetate | | 518.4 | A: 1.742 B: 1.684 | 1H NMR (500 MHz, DMSO-d6) δ 8.43 (s, 2H), 8.33 (br d, J = 6.4 Hz, 1H), 8.25 (dd, J = 4.7, 1.7 Hz, 1H), 8.15 (dd, J = 7.4, 1.6 Hz, 1H), 8.06 (d, J = 9.6 Hz, 1H), 7.69 (br s, 1H), 7.63 (br s, 1H), 7.26 (dd, J = 9.6, 1.8 Hz, 1H), 7.10 (dd, J = 7.4, 4.9 Hz, 1H), 4.20 (quin, J = 7.1 Hz, 1H), 4.08 (br t, J = 5.9 Hz, 2H), 2.65 (dt, J = 11.1, 5.7 Hz, 1H), 2.47-2.38 (m, 3H), 2.34-2.29 (m, 1H), 2.26-2.11 (m, 4H), 1.99-1.92 (m, 2H) |
| 123 | N-((aR)-6-((3-carbamoylpyridin-2-yl)oxy)spiro[3.3]heptan-2-yl)-6-(3-hydroxy-3-methylbutoxy)pyrazolo[1,5-a]pyridine-3-carboxamide, trifluoroacetate | | 508.2 | A: 1.557 B: 1.565 | 1H NMR (500 MHz, DMSO-d6) δ 8.42-8.37 (m, 2H), 8.33 (br d, J = 7.6 Hz, 1H), 8.24 (dd, J = 4.6, 1.5 Hz, 1H), 8.15 (dd, J = 7.5, 1.7 Hz, 1H), 8.04 (d, J = 9.5 Hz, 1H), 7.65 (br s, 1H), 7.62 (br s, 1H), 7.21 (dd, J = 9.6, 1.7 Hz, 1H), 7.11-7.08 (m, 1H), 5.19 (quin, J = 7.1 Hz, 1H), 4.33 (sxt, J = 8.2 Hz, 1H), 4.04 (br t, J = 6.9 Hz, 2H), 2.64 (dt, J = 11.2, 5.8 Hz, 1H), 2.47-2.39 (m, 2H), 2.34-2.30 (m, 1H), 2.26-2.11 (m, 4H), 1.92 (t, J = 6.9 Hz, 2H), 1.18-1.13 (m, 6H) |
| 124 | N-((aR)-6-((3-carbamoylpyridin-2-yl)oxy)spiro[3.3]heptan-2-yl)-6-(3-(2-oxopyrrolidin-1-yl)propoxy)pyrazolo[1,5-a]pyridine-3-carboxamide, trifluoroacetate | | 533.3 | A: 1.216 B: 1.223 | 1H NMR (500 MHz, DMSO-d6) δ 8.42-8.32 (m, 3H), 8.28-8.23 (m, 1H), 8.19-8.14 (m, 1H), 8.04 (d, J = 9.8 Hz, 1H), 7.70-7.60 (m, 2H), 7.27-7.22 (m, 1H), 7.12-7.08 (m, 1H), 5.23-5.16 (m, 1H), 4.38-4.27 (m, 1H), 3.37-3.30 (m, 4H), 2.64 (dt, J = 11.0, 5.8 Hz, 1H), 2.47-2.38 (m, 2H), 2.35-2.28 (m, 1H), 2.26-2.10 (m, 6H), 1.95-1.86 (m, 4H) |

TABLE 4-continued

| | Name | | MS | Rt | 1H NMR |
|---|---|---|---|---|---|
| 125 | N-((aR)-6-((3-carbamoylpyridin-2-yl)oxy)spiro[3.3]heptan-2-yl)-6-(2-(trifluoromethoxy)ethoxy)pyrazolo[1,5-a]pyridine-3-carboxamide, trifluoroacetate | | 520.2 | C: 9.01 D: 7.66 | 1H NMR (500 MHz, DMSO-d6) δ 8.55-8.50 (m, 1H), 8.45 (s, 1H), 8.29-8.22 (m, 2H), 8.16 (dd, J = 7.5, 2.0 Hz, 1H), 8.09 (d, J = 9.7 Hz, 1H), 7.69 (br s, 1H), 7.58 (br s, 1H), 7.28 (dd, J = 9.7, 2.2 Hz, 1H), 7.10 (dd, J = 7.5, 4.8 Hz, 1H), 5.23 (quin, J = 7.2 Hz, 1H), 4.48-4.30 (m, 5H), 2.70-2.61 (m, 1H), 2.47-2.41 (m, 5H), 2.38-2.12 (m, 5H). |
| 126 | N-((aR)-6-((3-carbamoylpyridin-2-yl)oxy)spiro[3.3]heptan-2-yl)-6-(2-((S)-2-oxooxazolidin-4-yl)ethoxy)pyrazolo[1,5-a]pyridine-3-carboxamide, trifluoroacetate | | 521.2 | C: 6.81 D: 5.26 | 1H NMR (500 MHz, DMSO-d6) δ 8.44-8.42 (m, 2H), 8.26 (dd, J = 5.0, 2.2 Hz, 1H), 8.23 (d, J = 7.7 Hz, 1H), 8.16 (dd, J = 7.4, 1.9 Hz, 1H), 8.07 (d, J = 9.6 Hz, 1H), 7.79 (s, 1H), 7.68 (br s, 1H), 7.58 (br s, 1H), 7.26 (dd, J = 9.6, 2.2 Hz, 1H), 7.10 (dd, J = 7.4, 4.7 Hz, 1H), 5.23 (quin, J = 7.2 Hz, 1H), 4.44 (t, J = 8.3 Hz, 1H), 4.41-4.33 (m, 1H), 4.15-3.95 (m, 5H), 2.68-2.62 (m, 1H), 2.46-2.42 (m, 1H), 2.36-2.32 (m, 1H), 2.28-2.13 (m, 4H), 2.03-1.96 (m, 1H), 1.94-1.88 (m, 1H) |
| 127 | N-((aR)-6-((3-carbamoylpyridin-2-yl)oxy)spiro[3.3]heptan-2-yl)-6-(2-hydroxypropoxy)-1-(2-hydroxy-2-methylpropyl)-1H-indazole-3-carboxamide, trifluoroacetate | | 552.3 | A: 1.395 B: 1.395 | 1H NMR (500 MHz, DMSO-d6) δ 8.39-8.34 (m, 1H), 8.29-8.23 (m, 1H), 8.20-8.12 (m, 1H), 7.98-7.92 (m, 1H), 7.70-7.64 (m, 1H), 7.63-7.60 (m, 1H), 7.21-7.15 (m, 1H), 7.13-7.07 (m, 1H), 6.89-6.85 (m, 1H), 5.21 (quin, J = 7.1 Hz, 1H), 4.39 (dq, J = 16.3, 8.1 Hz, 1H), 4.30 (s, 2H), 2.70-2.62 (m, 1H), 2.47-2.38 (m, 2H), 2.35-2.15 (m, 5H), 1.23 (s, 6H), 1.13 (s, 6H) |
| 128 | N-((aR)-6-((3-carbamoylpyridin-2-yl)oxy)spiro[3.3]heptan-2-yl)-6-(2-(4-methylthiazol-5-yl)ethoxy)pyrazolo[1,5-a]pyridine-3-carboxamide, trifluoroacetate | | 533.0 | A: 1.426 B: 1.198 | 1H NMR (500 MHz, DMSO-d6) δ 8.81 (s, 1H), 8.47-8.40 (m, 2H), 8.38-8.33 (m, 1H), 8.27-8.22 (m, 1H), 8.15 (dd, J = 7.4, 1.6 Hz, 1H), 8.08-8.02 (m, 1H), 7.71-7.61 (m, 2H), 7.26-7.20 (m, 1H), 7.13-7.08 (m, 1H), 5.24-5.16 (m, 1H), 4.39-4.29 (m, 1H), 4.20 (br t, J = 5.6 Hz, 2H), 3.27-3.21 (m, 2H), 2.64 (dt, J = 11.0, 5.6 Hz, 1H), 2.46-2.42 (m, 1H), 2.35-2.10 (m, 8H) |
| 129 | 2-(((aR)-6-(1-(pyridin-2-yl)-5-(trifluoromethyl)-1H-pyrazole-4-carboxamido)spiro[3.3]heptan-2-yl)oxy)nicotinamide | | 487.2 | A: 1.38 B: 1.41 | 1H NMR (500 MHz, DMSO-d6) δ 8.93-8.78 (m, 1H), 8.57 (d, J = 3.6 Hz, 1H), 8.26 (d, J = 3.0 Hz, 1H), 8.19-8.06 (m, 3H), 7.76 (d, J = 8.0 Hz, 1H), 7.69 (br. s., 1H), 7.65 (br s., 1H), 7.60 (d, J = 5.0 Hz, 1H), 7.11 (dd, J = 7.3, 5.0 Hz, 1H), 5.20 (s, 1H), 4.36-4.20 (m, 2H), 2.72-2.58 (m, 1H), 2.48-2.42 (m, 2H), 2.38-2.31 |

| | | | | |
|---|---|---|---|---|
| | | | | (m, 1H), 2.27-2.16 (m, 2H), 2.11 (d, J = 10.4 Hz, 2H) |
| 130 | N-((aR)-6-((3-carbamoylpyridin-2-yl)oxy)spiro[3.3]heptan-2-yl)-2-(pyridin-2-yl)thiazole-4-carboxamide, bis-trifluoroacetate | 436.1 | A: 1.46 B: 1.47 | 1H NMR (500 MHz, DMSO-d6) δ 8.73-8.62 (m, 2H), 8.40-8.32 (m, 2H), 8.28 (d, J = 2.9 Hz, 1H), 8.17 (d, J = 6.0 Hz, 1H), 8.03 (t, J = 7.2 Hz, 1H), 7.72 (br. s., 1H), 7.63 (br. s., 1H), 7.61-7.51 (m, 1H), 7.11 (dd, J = 7.3, 5.0 Hz, 1H), 5.23 (t, J = 7.2 Hz, 1H), 4.55-4.30 (m, 1H), 2.74-2.63 (m, 1H), 2.46 (br. s., 1H), 2.38-2.19 (m, 5H) |
| 131 | 2-(((aR)-6-(3-(N-methyl-N-phenylsulfamoyl)benzamido)spiro[3.3]heptan-2-yl)oxy)nicotinamide, trifluoroacetate | 521.2 | A: 1.74 B: 1.74 | 1H NMR (500 MHz, DMSO-d6) δ 8.87 (d, J = 7.3 Hz, 1H), 8.27 (d, J = 3.1 Hz, 1H), 8.16 (t, J = 7.9 Hz, 2H), 8.04 (s, 1H), 7.74-7.50 (m, 4H), 7.39-7.26 (m, 3H), 7.15-7.02 (m, 3H), 5.23 (t, J = 7.0 Hz, 1H), 4.43-4.27 (m, 1H), 3.21-3.12 (m, 3H), 2.66 (dd, J = 11.4, 6.0 Hz, 1H), 2.49-2.43 (m, 2H), 2.38-2.31 (m, 1H), 2.31-2.15 (m, 4H) |
| 132 | 1-benzyl-N-((aR)-6-((3-carbamoylpyridin-2-yl)oxy)spiro[3.3]heptan-2-yl)-1H-indazole-3-carboxamide, trifluoroacetate | 482.1 | A: 1.88 B: 1.90 | 1H NMR (500 MHz, DMSO-d6) δ 8.57 (d, J = 7.9 Hz, 1H), 8.28 (d, J = 4.3 Hz, 1H), 8.17 (d, J = 7.9 Hz, 2H), 7.74 (d, J = 8.2 Hz, 1H), 7.69 (br. s., 1H), 7.61 (br. s., 1H), 7.43 (t, J = 7.6 Hz, 1H), 7.37-7.30 (m, 2H), 7.30-7.20 (m, 4H), 7.16-7.08 (m, 1H), 5.75 (s, 2H), 5.23 (t, J = 7.2 Hz, 1H), 4.51-4.38 (m, 1H), 2.67 (dd, J = 11.4, 5.6 Hz, 1H), 2.52-2.40 (m, 3H), 2.37-2.25 (m, 3H), 2.25 (s, 1H) |

| | | | | |
|---|---|---|---|---|
| 133 | [structure: 3-(2-methylthiazol-4-yl)phenyl ketone] | 2-(((aR)-6-(3-(2-methylthiazol-4-yl)benzamido)spiro[3.3]heptan-2-yl)oxy)nicotinamide, trifluoroacetate | 499.1 | A: 1.51 B: 1.50 | 1H NMR (500 MHz, DMSO-d6) δ 8.74 (br d, J = 7.2 Hz, 1H), 8.37-8.23 (m, 2H), 8.21-7.89 (m, 3H), 7.85-7.63 (m, 3H), 7.51 (t, J = 7.8 Hz, 1H), 7.11 (dd, J = 7.4, 5.0 Hz, 1H), 5.21 (br t, J = 7.0 Hz, 1H), 4.49-4.26 (m, 1H), 2.72 (s, 3H), 2.68-2.60 (m, 1H), 2.39-2.30 (m, 1H), 2.26-2.09 (m, 4H); |
| 134 | [structure: 3-(1H-pyrazol-1-yl)phenyl ketone] | 2-(((aR)-6-(3-(1H-pyrazol-1-yl)benzamido)spiro[3.3]heptan-2-yl)oxy)nicotinamide, trifluoroacetate | 418.1 | A: 1.35 B: 1.37 | 1H NMR (500 MHz, DMSO-d6) δ 8.78 (d, J = 7.3 Hz, 1H), 8.49 (d, J = 2.1 Hz, 1H), 8.34-8.08 (m, 3H), 7.95 (br d, J = 8.2 Hz, 1H), 7.85-7.74 (m, 1H), 7.71-7.52 (m, 3H), 7.11 (dd, J = 7.3, 4.9 Hz, 1H), 6.58 (s, 1H), 5.22 (quin, J = 7.1 Hz, 1H), 4.48-4.22 (m, 1H), 3.71-3.55 (m, 1H), 2.81-2.64 (m, 1H), 2.40-2.13 (m, 4H) |
| 135 | [structure: 4-methyl-2-(pyridin-3-yl)thiazol-5-yl ketone] | N-((aR)-6-((3-carbamoylpyridin-2-yl)oxy)spiro[3.3]heptan-2-yl)-4-methyl-2-(pyridin-3-yl)thiazole-5-carboxamide, bis-trifluoroacetate | 450.1 | A: 1.26 B: 1.09 | 1H NMR (500 MHz, DMSO-d6) δ 9.10 (s, 1H), 8.77-8.51 (m, 2H), 8.38-8.23 (m, 2H), 8.16 (dd, J = 7.3, 1.8 Hz, 1H), 7.64 (br d, J = 9.5 Hz, 2H), 7.56 (dd, J = 7.6, 4.9 Hz, 1H), 7.11 (dd, J = 7.3, 4.9 Hz, 1H), 5.21 (t, J = 7.0 Hz, 1H), 4.41-4.18 (m, 1H), 2.73-2.56 (m, 3H), 2.26-1.93 (m, 3H) |
| 136 | [structure: 2-(4-methoxyphenyl)thiazol-4-yl ketone] | N-((aR)-6-((3-carbamoylpyridin-2-yl)oxy)spiro[3.3]heptan-2-yl)-2-(4-methoxyphenyl)thiazole-4-carboxamide, trifluoroacetate | 465.1 | A: 1.74 B: 1.77 | ¹H NMR (500 MHz, DMSO-d₆) δ 8.63 (br d, J = 7.7 Hz, 1H), 8.34-7.94 (m, 5H), 7.67 (br d, J = 16.0 Hz, 2H), 7.22-6.85 (m, 3H), 5.21 (br t, J = 7.1 Hz, 1H), 4.49-4.28 (m, 1H), 3.82 (s, 3H), 3.16 (d, J = 5.1 Hz, 1H), 2.67 (dt, J = 11.0, 5.7 Hz, 1H), 2.39-2.12 (m, 5H) |

| | | | | |
|---|---|---|---|---|
| 138 | [structure: 2-(N-isopropylsulfamoyl)benzoyl] | 2-(((aR)-6-(2-(N-isopropylsulfamoyl)benzamido)spiro[3.3]heptan-2-yl)oxy)nicotinamide, trifluoroacetate | 473.0 A: 1.52 B: 1.53 | $^1$H NMR (500 MHz, DMSO-d6) δ 8.96 (br d, J = 6.5 Hz, 1H), 8.27 (dd, J = 4.8, 1.9 Hz, 1H), 8.16 (dd, J = 7.4, 1.8 Hz, 1H), 7.89 (d, J = 7.6 Hz, 1H), 7.80-7.47 (m, 6H), 7.11 (dd, J = 7.4, 4.9 Hz, 1H), 5.44-5.07 (m, 1H), 4.47-4.13 (m, 1H), 3.30 (dt, J = 12.9, 6.6 Hz, 1H), 2.78-2.61 (m, 2H), 2.41-2.06 (m, 6H), 0.96 (d, J = 6.4 Hz, 6H) |
| 139 | [structure: 2-(trifluoromethyl)-6-chloroimidazo[1,2-a]pyridine-3-carbonyl] | N-((aR)-6-(3-carbamoylpyridin-2-yl)oxy)spiro[3.3]heptan-2-yl)-6-chloro-2-(trifluoromethyl)imidazo[1,2-a]pyridine-3-carboxamide, trifluoroacetate | 494.1 A: 1.58 B: 1.61 | $^1$H NMR (500 MHz, DMSO-d6) δ 9.09 (br d, J = 7.0 Hz, 1H), 8.62 (s, 1H), 8.32-8.11 (m, 2H), 7.81 (d, J = 9.8 Hz, 1H), 7.70-7.54 (m, 3H), 7.11 (dd, J = 7.3, 4.9 Hz, 1H), 5.21 (quin, J = 7.1 Hz, 1H), 4.44-4.27 (m, 1H), 3.70 (br d, J = 5.8 Hz, 1H), 2.66 (dt, J = 12.1, 6.2 Hz, 1H), 2.31-2.08 (m, 4H), 1.20-1.10 (m, 2H) |
| 140 | [structure: 1H-benzo[d]imidazol-2-yl benzoyl] | 2-(((aR)-6-(2-(1H-benzo[d]imidazol-2-yl)benzamido)spiro[3.3]heptan-2-yl)oxy)nicotinamide, trifluoroacetate | 467.9 A:1.54 B:1.42 | $^1$H NMR (500 MHz, DMSO-d6) δ 8.54 (br d, J = 7.3 Hz, 1H), 8.26 (dd, J = 4.6, 1.8 Hz, 1H), 8.17 (dd, J = 7.3, 1.8 Hz, 1H), 7.87 (d, J J = .6 Hz, 1H), 7.77-7.44 (m, 8H), 7.21 (br s, 2H), 7.10 (dd, J = 7.3, 4.9 Hz, 1H), 5.17 (quin, J = 7.2 Hz, 1H), 4.39-4.04 (m, 1H), 2.61 (dt, J = 11.3, 5.6 Hz, 1H), 2.41-2.31 (m, 2H), 2.32-2.23 (m, 1H), 2.20 (br dd, J = 11.4, 7.5 Hz, 1H), 2.12-1.95 (m, 3H) |
| 141 | [structure: 3-((1H-imidazol-1-yl)methyl)benzoyl] | 2-(((aR)-6-(3-((1H-imidazol-1-yl)methyl)benzamido)spiro[3.3]heptan-2-yl)oxy)nicotinamide, trifluoroacetate | 432.1 A: 1.14 B: 0.92 | $^1$H NMR (500 MHz, DMSO-d6) δ 8.66 (br d, J = 6.6 Hz, 1H), 8.26 (dd, J = 4.8, 1.8 Hz, 1H), 8.15 (dd, J = 7.4, 1.7 Hz, 1H), 7.87-7.59 (m, 4H), 7.53-7.31 (m, 2H), 7.11 (dd, J = 7.4, 4.9 Hz, 2H), 5.45-5.04 (m, 3H), 4.54-4.21 (m, 1H), 3.85 (br s, 1H), 2.75-2.58 (m, 1H), 2.48-2.39 (m, 1H), 2.36-2.28 (m, 1H), 2.27-2.11 (m, 3H), add'l peaks under water/dmso |

TABLE 4-continued

| | | | | |
|---|---|---|---|---|
| 142 | 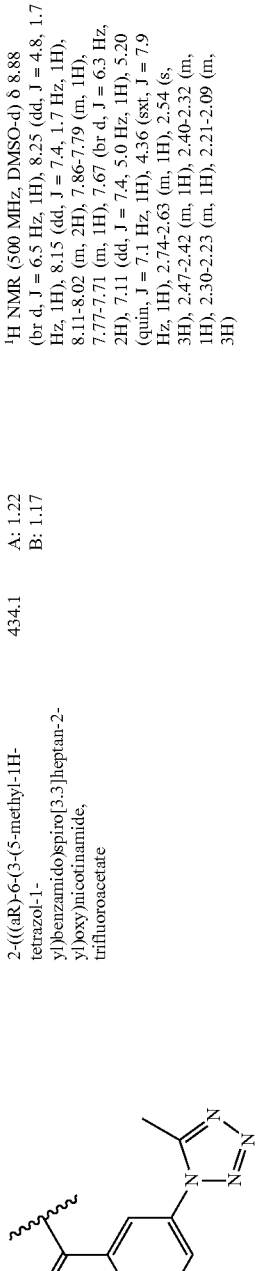 | 2-(((aR)-6-(3-(5-methyl-1H-tetrazol-1-yl)benzamido)spiro[3.3]heptan-2-yl)oxy)nicotinamide, trifluoroacetate | 434.1 | A: 1.22<br>B: 1.17 | $^1$H NMR (500 MHz, DMSO-d) δ 8.88 (br d, J = 6.5 Hz, 1H), 8.25 (dd, J = 4.8, 1.7 Hz, 1H), 8.15 (dd, J = 7.4, 1.7 Hz, 1H), 8.11-8.02 (m, 2H), 7.86-7.79 (m, 1H), 7.77-7.71 (m, 1H), 7.67 (br d, J = 6.3 Hz, 2H), 7.11 (dd, J = 7.4, 5.0 Hz, 1H), 5.20 (quin, J = 7.1 Hz, 1H), 4.36 (sxt, J = 7.9 Hz, 1H), 2.74-2.63 (m, 1H), 2.54 (s, 3H), 2.47-2.42 (m, 1H), 2.40-2.32 (m, 1H), 2.30-2.23 (m, 1H), 2.21-2.09 (m, 3H) |
| 143 | 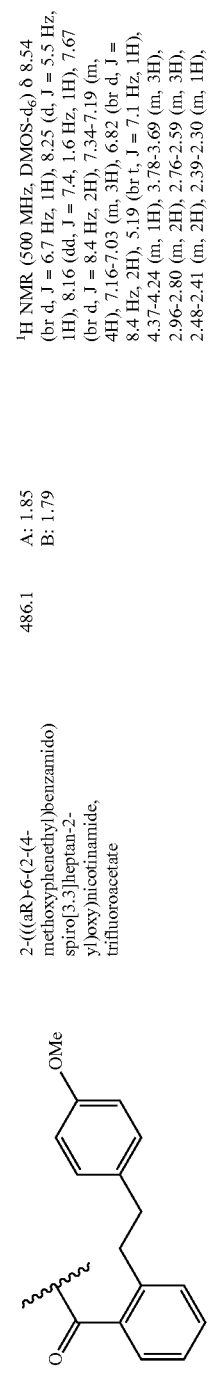 | 2-(((aR)-6-(2-(4-methoxyphenethyl)benzamido)spiro[3.3]heptan-2-yl)oxy)nicotinamide, trifluoroacetate | 486.1 | A: 1.85<br>B: 1.79 | $^1$H NMR (500 MHz, DMOS-d$_6$) δ 8.54 (br d, J = 6.7 Hz, 1H), 8.25 (d, J = 5.5 Hz, 1H), 8.16 (dd, J = 7.4, 1.6 Hz, 1H), 7.67 (br d, J = 8.4 Hz, 2H), 7.34-7.19 (m, 4H), 7.16-7.03 (m, 3H), 6.82 (br d, J = 8.4 Hz, 2H), 5.19 (br t, J = 7.1 Hz, 1H), 4.37-4.24 (m, 1H), 3.78-3.69 (m, 3H), 2.96-2.80 (m, 2H), 2.76-2.59 (m, 3H), 2.48-2.41 (m, 2H), 2.39-2.30 (m, 1H), 2.23 (br dd, J = 11.2, 7.4 Hz, 1H), 2.19-2.04 (m, 3H) |
| 144 | 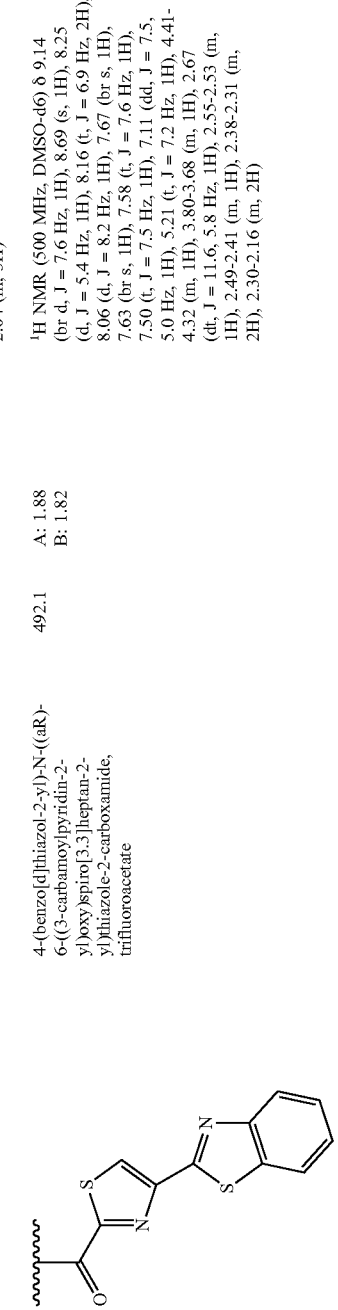 | 4-(benzo[d]thiazol-2-yl)-N-((aR)-6-((3-carbamoylpyridin-2-yl)oxy)spiro[3.3]heptan-2-yl)thiazole-2-carboxamide, trifluoroacetate | 492.1 | A: 1.88<br>B: 1.82 | $^1$H NMR (500 MHz, DMSO-d6) δ 9.14 (br d, J = 7.6 Hz, 1H), 8.69 (s, 1H), 8.25 (d, J = 5.4 Hz, 1H), 8.16 (t, J = 6.9 Hz, 2H), 8.06 (d, J = 8.2 Hz, 1H), 7.67 (br s, 1H), 7.63 (br s, 1H), 7.58 (t, J = 7.6 Hz, 1H), 7.50 (t, J = 7.5 Hz, 1H), 7.11 (dd, J = 7.5, 5.0 Hz, 1H), 5.21 (t, J = 7.2 Hz, 1H), 4.41-4.32 (m, 1H), 3.80-3.68 (m, 1H), 2.67 (dt, J = 11.6, 5.8 Hz, 1H), 2.55-2.53 (m, 1H), 2.49-2.41 (m, 1H), 2.38-2.31 (m, 2H), 2.30-2.16 (m, 2H) |
| 145 | 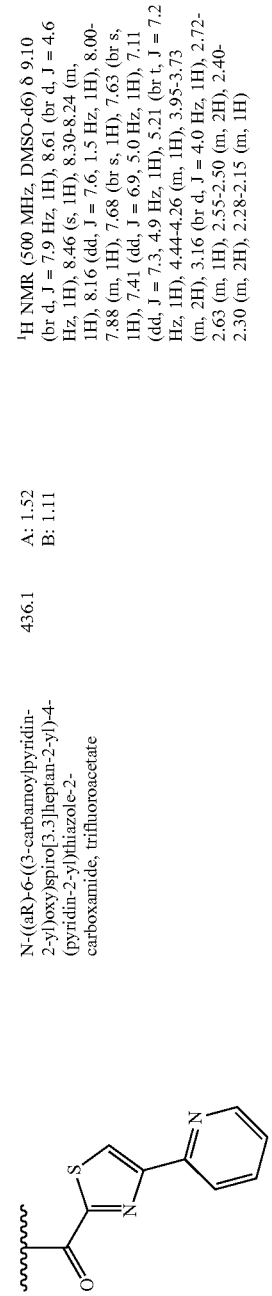 | N-((aR)-6-((3-carbamoylpyridin-2-yl)oxy)spiro[3.3]heptan-2-yl)-4-(pyridin-2-yl)thiazole-2-carboxamide, trifluoroacetate | 436.1 | A: 1.52<br>B: 1.11 | $^1$H NMR (500 MHz, DMSO-d6) δ 9.10 (br d, J = 7.9 Hz, 1H), 8.61 (br d, J = 4.6 Hz, 1H), 8.46 (s, 1H), 8.30-8.24 (m, 1H), 8.16 (dd, J = 7.6, 1.5 Hz, 1H), 8.00-7.88 (m, 1H), 7.68 (br s, 1H), 7.63 (br s, 1H), 7.41 (dd, J = 6.9, 5.0 Hz, 1H), 7.11 (dd, J = 7.3, 4.9 Hz, 1H), 5.21 (br t, J = 7.2 Hz, 1H), 4.44-4.26 (m, 1H), 3.95-3.73 (m, 2H), 3.16 (br d, J = 4.0 Hz, 1H), 2.72-2.63 (m, 1H), 2.55-2.50 (m, 2H), 2.40-2.30 (m, 2H), 2.28-2.15 (m, 1H) |

TABLE 4-continued

| | Name | Structure | MS | NMR |
|---|---|---|---|---|
| 146 | N-((aR)-6-((3-carbamoylpyridin-2-yl)oxy)spiro[3.3]heptan-2-yl)-2-(1-methyl-1H-benzo[d]imidazol-2-yl)thiazole-4-carboxamide, trifluoroacetate | | 489.2 | A: 1.57<br>B: 1.50 | ¹H NMR (500 MHz, DMSO-d₆) δ 9.01 (br d, J = 5.6 Hz, 1H), 8.56 (s, 1H), 8.27 (br d, J = 3.0 Hz, 1H), 8.22-8.10 (m, 1H), 7.83-7.66 (m, 3H), 7.63 (br s, 1H), 7.45-7.37 (m, 1H), 7.35-7.28 (m, 1H), 7.11 (dd, J = 7.3, 5.0 Hz, 1H), 5.23 (quin, J = 6.9 Hz, 1H), 4.39-4.30 (m, 1H), 4.26 (s, 3H), 2.74-2.61 (m, 1H), 2.55 (s, 2H), 2.42-2.33 (m, 1H), 2.31-2.14 (m, 4H) |
| 147 | 2-(((aR)-6-(3-methyl-1,2,4-oxadiazol-5-yl)benzamido)spiro[3.3]heptan-2-yl)oxy)nicotinamide, trifluoroacetate | | 434.1 | A: 1.46<br>B: 1.40 | ¹H NMR (500 MHz, DMSO-d6) δ 8.93 (br d, J = 7.3 Hz, 1H), 8.55 (s, 1H), 8.29-8.11 (m, 4H), 7.76-7.59 (m, 3H), 7.11 (dd, J = 7.3, 4.9 Hz, 1H), 5.23 (quin, J = 7.1 Hz, 1H), 4.44-4.33 (m, 1H), 3.66-3.55 (m, 1H), 2.67 (dt, J = 11.2, 5.8 Hz, 1H), 2.55-2.49 (m, 6H), 2.41-2.32 (m, 1H), 2.30-2.17 (m, 4H) |
| 148 | 2-(((aR)-6-(2-chloro-4-fluoro-5-sulfamoylbenzamido)spiro[3.3]heptan-2-yl)oxy)nicotinamide, trifluoroacetate | | 482.8 | A: 1.19<br>B: 1.14 | ¹H NMR (500 MHz, DMSO-d6) δ 8.88 (d, J = 7.3 Hz, 1H), 8.25 (dd, J = 4.9, 1.8 Hz, 1H), 8.15 (dd, J = 7.3, 1.8 Hz, 1H), 7.86 (s, 1H), 7.80-7.70 (m, 2H), 7.64 (br s, 2H), 7.10 (dd, J = 7.3, 4.9 Hz, 1H), 5.20 (quin, J = 7.1 Hz, 1H), 4.25 (sxt, J = 7.8 Hz, 1H), 2.64 (dt, J = 11.2, 5.8 Hz, 1H), 2.55 (s, 1H), 2.49-2.41 (m, 2H), 2.40-2.29 (m, 1H), 2.23 (br dd, J = 11.4, 7.2 Hz, 1H), 2.18 (br dd, J = 11.7, 7.5 Hz, 1H), 2.12-2.01 (m, 2H) |
| 149 | N-((aR)-6-((3-carbamoylpyridin-2-yl)oxy)spiro[3.3]heptan-2-yl)-3-oxo-2,3-dihydrobenzo[d]isothiazole-6-carboxamide 1,1-dioxide, trifluoroacetate | | 457.2 | A: 1.05<br>B: 1.11 | ¹H NMR (500 MHz, DMSO-d₆) δ 8.96 (br d, J = 7.3 Hz, 1H), 8.32-8.23 (m, 2H), 8.16 (d, J = 7.6 Hz, 1H), 7.85 (d, J = 7.9 Hz, 1H), 7.66 (br s, 1H), 7.63 (br s, 1H), 7.24 (s, 1H), 7.14 (s, 1H), 7.11 (dd, J = 7.3, 4.9 Hz, 1H), 7.04 (s, 1H), 5.22 (quin, J = 7.1 Hz, 1H), 4.45-4.24 (m, 1H), 2.66 (br dd, J = 11.4, 6.0 Hz, 1H), 2.41-2.33 (m, 1H), 2.28-2.10 (m, 4H). |

TABLE 4-continued

| | | | | |
|---|---|---|---|---|
| 150 | 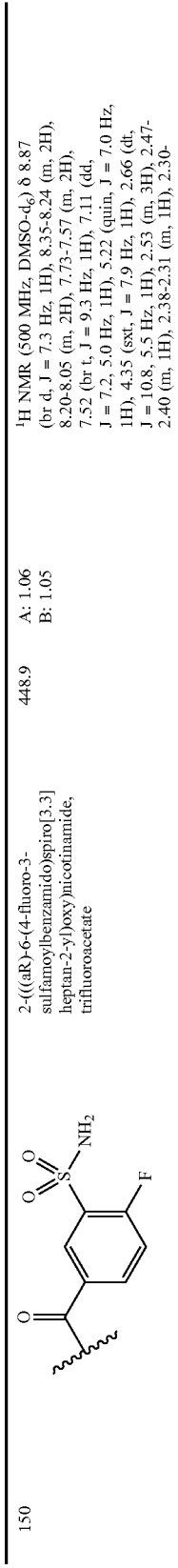 | 2-(((aR)-6-(4-fluoro-3-sulfamoylbenzamido)spiro[3.3]heptan-2-yl)oxy)nicotinamide, trifluoroacetate | 448.9 | A: 1.06 B: 1.05 | 1H NMR (500 MHz, DMSO-d6) δ 8.87 (br d, J = 7.3 Hz, 1H), 8.35-8.24 (m, 2H), 8.20-8.05 (m, 2H), 7.73-7.57 (m, 2H), 7.52 (br t, J = 9.3 Hz, 1H), 7.11 (dd, J = 7.2, 5.0 Hz, 1H), 5.22 (quin, J = 7.0 Hz, 1H), 4.35 (sxt, J = 7.9 Hz, 1H), 2.66 (dt, J = 10.8, 5.5 Hz, 1H), 2.53 (m, 3H), 2.47-2.40 (m, 1H), 2.38-2.31 (m, 1H), 2.30-2.12 (m, 4H) |
| 151 | 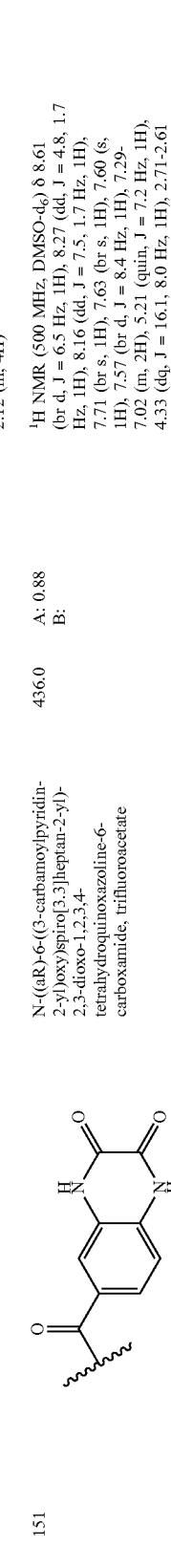 | N-((aR)-6-((3-carbamoylpyridin-2-yl)oxy)spiro[3.3]heptan-2-yl)-2,3-dioxo-1,2,3,4-tetrahydroquinoxaline-6-carboxamide, trifluoroacetate | 436.0 | A: 0.88 B: | 1H NMR (500 MHz, DMSO-d6) δ 8.61 (br d, J = 6.5 Hz, 1H), 8.27 (dd, J = 4.8, 1.7 Hz, 1H), 8.16 (dd, J = 7.5, 1.7 Hz, 1H), 7.71 (br s, 1H), 7.63 (br s, 1H), 7.60 (s, 1H), 7.57 (br d, J = 8.4 Hz, 1H), 7.29-7.02 (m, 2H), 5.21 (quin, J = 7.2 Hz, 1H), 4.33 (dq, J = 16.1, 8.0 Hz, 1H), 2.71-2.61 (m, 1H), 2.49-2.38 (m, 2H), 2.37-2.30 (m, 1H), 2.29-2.21 (m, 1H), 2.21-2.10 (m, 3H) |
| 152 | 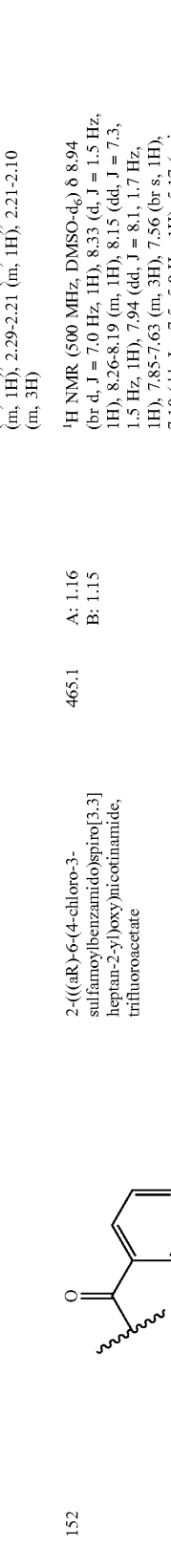 | 2-(((aR)-6-(4-chloro-3-sulfamoylbenzamido)spiro[3.3]heptan-2-yl)oxy)nicotinamide, trifluoroacetate | 465.1 | A: 1.16 B: 1.15 | 1H NMR (500 MHz, DMSO-d6) δ 8.94 (br d, J = 7.0 Hz, 1H), 8.33 (d, J = 1.5 Hz, 1H), 8.26-8.19 (m, 1H), 8.15 (dd, J = 7.3, 1.5 Hz, 1H), 7.94 (dd, J = 8.1, 1.7 Hz, 1H), 7.85-7.63 (m, 3H), 7.56 (br s, 1H), 7.10 (dd, J = 7.5, 5.0 Hz, 1H), 5.17 (quin, J = 7.0 Hz, 1H), 4.41-4.20 (m, 1H), 2.79-2.62 (m, 1H), 2.62 (br s, 1H), 2.49-2.38 (m, 2H), 2.37-2.28 (m, 1H), 2.21 (br dd, J = 11.4, 7.5 Hz, 1H), 2.18-2.06 (m, 3H) |
| 153 | 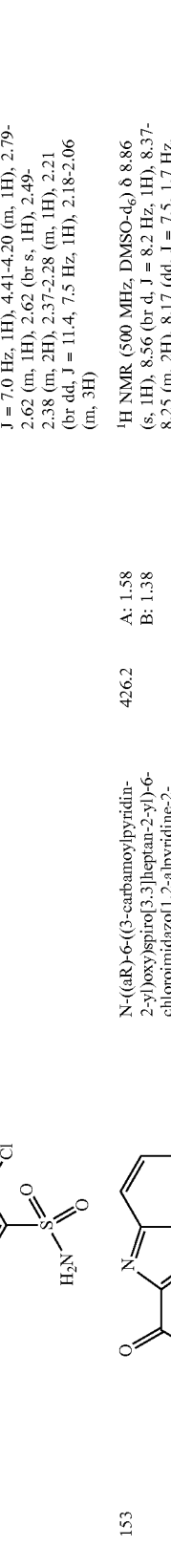 | N-((aR)-6-((3-carbamoylpyridin-2-yl)oxy)spiro[3.3]heptan-2-yl)-6-chloroimidazo[1,2-a]pyridine-2-carboxamide, trifluoroacetate | 426.2 | A: 1.58 B: 1.38 | 1H NMR (500 MHz, DMSO-d6) δ 8.86 (s, 1H), 8.56 (br d, J = 8.2 Hz, 1H), 8.37-8.25 (m, 2H), 8.17 (dd, J = 7.5, 1.7 Hz, 1H), 7.89-7.55 (m, 3H), 7.40 (dd, J = 9.6, 1.7 Hz, 1H), 7.11 (dd, J = 7.3, 4.9 Hz, 1H), 5.22 (quin, J = 7.2 Hz, 1H), 4.53-4.24 (m, 1H), 3.60-3.35 (m, 1H), 2.66 (dt, J = 11.2, 5.5 Hz, 1H), 2.48-2.44 (m, 1H), 2.41 (br dd, J = 10.7, 7.3 Hz, 1H), 2.33-2.09 (m, 4H) |
| 154 | 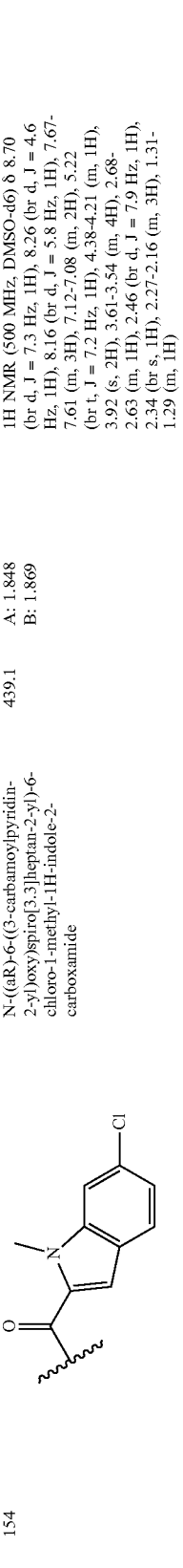 | N-((aR)-6-((3-carbamoylpyridin-2-yl)oxy)spiro[3.3]heptan-2-yl)-6-chloro-1-methyl-1H-indole-2-carboxamide | 439.1 | A: 1.848 B: 1.869 | 1H NMR (500 MHz, DMSO-d6) δ 8.70 (br d, J = 7.3 Hz, 1H), 8.26 (br d, J = 4.6 Hz, 1H), 8.16 (br d, J = 5.8 Hz, 1H), 7.67-7.61 (m, 3H), 7.12-7.08 (m, 2H), 5.22 (br t, J = 7.2 Hz, 1H), 4.38-4.21 (m, 1H), 3.92 (s, 2H), 3.61-3.54 (m, 4H), 2.68-2.63 (m, 1H), 2.46 (br d, J = 7.9 Hz, 1H), 2.34 (br s, 1H), 2.27-2.16 (m, 3H), 1.31-1.29 (m, 1H) |

| # | Structure | Name | Mass | LCMS | 1H NMR |
|---|---|---|---|---|---|
| 155 | (2-fluoro-5-cyanobenzoyl) | 2-(((aR)-6-(5-cyano-2-fluorobenzamido)spiro[3.3]heptan-2-yl)oxy)nicotinamide | 395.0 | A: 1.295 B: 1.275 | 1H NMR (500 MHz, DMOS-d6) δ 8.86-8.79 (m, 1H), 8.29-8.23 (m, 1H), 8.18-8.12 (m, 1H), 8.06-7.97 (m, 1H), 7.74-7.60 (m, 1H), 7.52 (br t, J = 9.0 Hz, 1H), 7.11 (dd, J = 7.4, 4.9 Hz, 1H), 5.20 (br t, J = 7.1 Hz, 1H), 4.34-4.24 (m, 1H), 3.67-3.57 (m, 4H), 2.55-2.47 (m, 1H), 2.49-2.44 (m, 1H), 2.38-2.32 (m, 1H), 2.27-2.08 (m, 1H) |
| 156 | (4-fluoro-3-cyanobenzoyl) | 2-(((aR)-6-(3-cyano-4-fluorobenzamido)spiro[3.3]heptan-2-yl)oxy)nicotinamide | 395.1 | A: 1.388 B: 1.363 | 1H NMR (500 MHz, DMOS-d6) δ 8.84 (br d, J = 6.6 Hz, 1H), 8.39-8.30 (m, 1H), 8.29-8.23 (m, 1H), 8.22-8.14 (m, 2H), 7.69 (br s, 1H), 7.66-7.58 (m, 2H), 7.11 (dd, J = 7.4, 4.9 Hz, 1H), 5.21 (br t, J = 7.1 Hz, 1H), 4.38-4.26 (m, 1H), 3.89 (s, 1H), 2.89-2.59 (m, 1H), 2.49-2.42 (m, 2H), 2.39-2.30 (m, 1H), 2.28-2.13 (m, 4H) |
| 157 | (3-cyano-5-fluorobenzoyl) | 2-(((aR)-6-(3-cyano-5-fluorobenzamido)spiro[3.3]heptan-2-yl)oxy)nicotinamide | 395.1 | A: 1.416 B: 1.388 | 1H NMR (500 MHz, DMSO-d6) δ 8.89 (br d, J = 6.6 Hz, 1H), 8.26 (d, J = 5.5 Hz, 1H), 8.19-8.12 (m, 1H), 8.04 (br d, J = 7.4 Hz, 1H), 7.98 (br d, J = 9.3 Hz, 1H), 7.71 (br s, 1H), 7.62 (br s, 1H), 7.11 (dd, J = 7.4, 4.9 Hz, 1H), 5.22 (quin, J = 7.1 Hz, 1H), 4.40-4.29 (m, 1H), 2.66 (dt, J = 11.1, 5.5 Hz, 1H), 2.58-2.53 (m, 3H), 2.40-2.33 (m, 1H), 2.49-2.32 (m, 1H), 2.29-2.14 (m, 2H) |
| 158 | (3-cyanobenzoyl) | 2-(((aR)-6-(3-cyanobenzamido)spiro[3.3]heptan-2-yl)oxy)nicotinamide | 377.1 | A: 1.308 B: 1.302 | 1H NMR (500 MHz, DMSO-d6) δ 8.84-8.75 (m, 1H), 8.24 (br s, 1H), 8.19-8.10 (m, 1H), 7.97 (br d, J = 7.3 Hz, 1H), 7.67 (br d, J = 6.1 Hz, 2H), 7.09 (br d, J = 4.9 Hz, 2H), 5.21 (br d, J = 5.8 Hz, 1H), 2.71-2.63 (m, 2H), 2.38-2.09 (m, 6H) |
| 159 | (isoquinoline-3-carbonyl) | N-((aR)-6-(3-carbamoylpyridin-2-yl)oxy)spiro[3.3]heptan-2-yl)isoquinoline-3-carboxamide | 403.3 | A: 1.745 B: 1.734 | 1H NMR (500 MHz, DMSO-d6) δ 9.10 (br d, J = 7.9 Hz, 1H), 8.50 (d, J = 8.5 Hz, 1H), 8.24 (br d, J = 3.1 Hz, 1H), 8.18-8.13 (m, 2H), 8.07 (d, J = 8.3 Hz, 1H), 8.02 (d, J = 8.0 Hz, 1H), 7.85 (t, J = 7.5 Hz, 1H), 7.75 (br s, 1H), 7.69 (t, J = 7.6 Hz, 1H), 7.58 (br s, 1H), 7.11 (dd, J = 7.3, 4.9 Hz, 1H), 5.19 (t, J = 7.0 Hz, 1H), 4.45-4.33 (m, 1H), 3.16 (d, J = 4.3 Hz, 1H), 2.67 (dt, J = 11.4, 5.8 Hz, 1H), 2.48-2.43 (m, 1H), 2.3-2.33 (m, 1H), 2.31-2.15 (m, 4H) |

| # | Structure | Name | Mass | A/B | 1H NMR |
|---|---|---|---|---|---|
| 160 | (3-cyanobiphenyl ketone) | 2-(((aR)-6-(3'-cyano-[1,1'-biphenyl]-4-ylcarboxamido)spiro[3.3]heptan-2-yl)oxy)nicotinamide | 453.3 | A: 1.733 B: 1.737 | 1H NMR (500 MHz, DMSO-d6) δ 8.74 (br d, J = 7.3 Hz, 1H), 8.26 (br d, J = 3.4 Hz, 1H), 8.22-8.12 (m, 3H), 8.08 (br d, J = 7.9 Hz, 1H), 7.94-7.81 (m, 3H), 7.74-7.56 (m, 3H), 7.11 (dd, J = 7.3, 5.2 Hz, 1H), 5.23 (quin, J = 7.1 Hz, 1H), 4.53-4.34 (m, 1H), 2.75-2.60 (m, 1H), 2.49-2.44 (m, 1H), 2.37 (br t, J = 11.6 Hz, 1H), 2.30-2.16 (m, 4H) |
| 161 | (4-cyanophenyl pyridine) | N-((aR)-6-((3-carbamoylpyridin-2-yl)oxy)spiro[3.3]heptan-2-yl)-6-(4-cyanophenyl)nicotinamide | 454.4 | A: 1.418 B: 1.469 | 1H NMR (500 MHz, DMSO-d6) δ 9.06 (s, 1H), 9.00 (s, 1H), 8.95 (br d, J = 7.0 Hz, 1H), 8.49 (s, 1H), 8.26 (br d, J = 3.4 Hz, 1H), 8.16 (br d, J = 7.3 Hz, 1H), 8.04-7.95 (m, 4H), 7.66 (s, 1H), 7.64 (br s, 1H), 7.11 (t, J = 6.5 Hz, 1H), 5.35-5.17 (m, 1H), 4.47-4.27 (m, 1H), 2.75-2.60 (m, 1H), 2.45-2.34 (m, 1H), 2.31-2.14 (m, 4H) |
| 162 | (3-fluorobiphenyl ketone) | 2-(((aR)-6-(3'-fluoro-[1,1'-biphenyl]-4-ylcarboxamido)spiro[3.3]heptan-2-yl)oxy)nicotinamide | 446.3 | A: 1.847 | 1H NMR (500 MHz, DMSO-d6) δ 8.75 (br d, J = 7.3 Hz, 1H), 8.26 (br d, J = 3.1 Hz, 1H), 8.16 (br d, J = 7.3 Hz, 1H), 8.10 (s, 1H), 7.84 (br d, J = 7.6 Hz, 2H), 7.65 (br s, 2H), 7.62-7.51 (m, 4H), 7.23 (br t, J = 7.9 Hz, 1H), 7.11 (dd, J = 7.3, 5.2 Hz, 1H), 5.22 (br t, J = 7.2 Hz, 1H), 4.44-4.27 (m, 1H), 3.17 (d, J = 4.9 Hz, 1H), 2.67 (br dd, J = 11.7, 6.0 Hz, 1H), 2.49-2.42 (m, 1H), 2.36 (br d, J = 5.2 Hz, 1H), 2.29-2.14 (m, 4H) |
| 163 | (2,2-dimethyl-2,3-dihydrobenzofuran) | 2-(((aR)-6-(2,2-dimethyl-2,3-dihydrobenzofuran-7-carboxamido)spiro[3.3]heptan-2-yl)oxy)nicotinamide | 422.0 | A: 1.766 B: 1.727 | 1H NMR (500 MHz, DMSO-d6) δ 8.27 (br d, J = 2.7 Hz, 1H), 8.17 (br d, J = 7.3 Hz, 1H), 7.87 (br d, J = 7.3 Hz, 1H), 7.69 (br s, 1H), 7.59 (br d, J = 7.9 Hz, 2H), 7.35 (br d, J = 7.0 Hz, 1H), 7.11 (dd, J = 7.5, 5.0 Hz, 1H), 6.91 (t, J = 7.6 Hz, 1H), 5.23 (quin, J = 6.9 Hz, 1H), 4.37-4.28 (m, 1H), 3.07 (s, 2H), 2.74-2.59 (m, 1H), 2.48-2.37 (m, 1H), 2.31-2.20 (m, 2H), 2.12-2.02 (m, 2H), 1.50 (br d, J = 4.0 Hz, 6H) |

TABLE 4-continued

| | | | | |
|---|---|---|---|---|
| 164 | 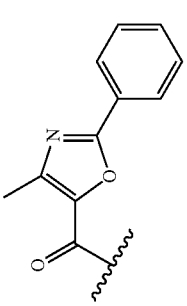 N-((aR)-6-((3-carbamoylpyridin-2-yl)oxy)spiro[3.3]heptan-2-yl)-4-methyl-2-phenyloxazole-5-carboxamide | 433.1 | A: 1.649 B: 1.612 | 1H NMR (500 MHz, DMSO-d6) Shift 8.64 (br d, J = 7.6 Hz, 1H), 8.27 (br d, J = 2.7 Hz, 1H), 8.17 (br d, J = 5.5 Hz, 2H), 7.69 (br s, 1H), 7.64-7.54 (m, 3H), 7.11 (dd, J = 7.3, 5.2 Hz, 1H), 5.24 (quin, J = 7.1 Hz, 1H), 4.51-4.31 (m, 1H), 2.74-2.60 (m, 1H), 2.42 (s, 3H), 2.38-2.20 (m, 4H), 1.00 (d, J = 6.4 Hz, 1H) |
| 165 | 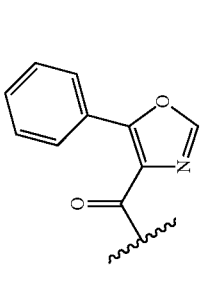 N-((aR)-6-((3-carbamoylpyridin-2-yl)oxy)spiro[3.3]heptan-2-yl)-5-phenyloxazole-4-carboxamide | 419.3 | A: 1.743 B: 1.723 | 1H NMR (500 MHz, DMSO-d6) δ 8.60-8.48 (m, 1H), 8.33-8.22 (m, 1H), 8.17 (br d, J = 7.6 Hz, 3H), 7.69-7.60 (br s, 1H), 7.54-7.44 (m, 2H), 7.11 (dd, J = 7.5, 5.0 Hz, 1H), 5.22 (quin, J = 7.2 Hz, 1H), 4.42-4.30 (m, 1H), 2.65 (dt, J = 11.2, 5.8 Hz, 1H), 2.34-2.16 (m, 5H), 1.23 (s, 2H) |
| 166 | 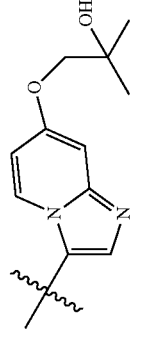 N-((aR)-6-((3-carbamoylpyridin-2-yl)oxy)spiro[3.3]heptan-2-yl)-7-(2-hydroxy-2-methylpropoxy)imidazo[1,2-a]pyridine-3-carboxamide | 480.43 | A: 1.22 B: 1.01 | 1H NMR (500 MHz, DMSO-d6) δ 9.25 (d, J = 7.6 Hz, 1H), 8.49 (br. d, J = 7.6 Hz, 1H), 8.27 (dd, J = 4.9, 1.8 Hz, 1H), 8.20-8.10 (m, 2H), 7.74-7.55 (m, 2H), 7.11 (dd, J = 7.3, 4.9 Hz, 1H), 7.01 (d, J = 2.1 Hz, 1H), 6.83 (dd, J = 7.6, 2.1 Hz, 1H), 5.23 (quin, J = 7.1 Hz, 1H), 4.45-4.28 (m, 1H), 3.83 (s, 2H), 2.66 (br dd, J = 11.9, 5.8 Hz, 1H), 2.50-2.41 (m, 2H), 2.40-2.31 (m, 1H), 2.30-2.10 (m, 4H), 1.91 (s, 1H), 1.22 (s, 6H) |

The following examples in Table 5 were prepared using a similar procedure to that which was used in the preparation of Example 42. Intermediate 126 was coupled with a carboxylic acid. The carboxylic acids were commercially available or synthesized as described previously. Various bases could be used other than the one described in Example 42, such as TEA, DBU, or DABCO. Various coupling reagents could be used other than the one described in Example 42, such as EDCI, BOP, or T3P.

TABLE 5

| Example | R | Name | LCMS (M + H)+ | HPLC Method, RT (min.) | 1H NMR |
|---|---|---|---|---|---|
| 167 | | N-((aR)-6-((3-carbamoyl-6-methoxypyridin-2-yl)oxy)spiro[3.3]heptan-2-yl)-7-cyclopropyl-6-(2-hydroxy-2-methylpropoxy)pyrazolo[1,5-a]pyridine-3-carboxamide | 550.3 | A: 1.649 B: 1.661 | 1H NMR (500 MHz, DMSO-d6) δ 8.49 (s, 1H), 8.27 (br d, J = 7.5 Hz, 1H), 8.16 (d, J = 8.3 Hz, 1H), 8.02 (d, J = 9.6 Hz, 1H), 7.55-7.51 (m, 1H), 7.45 (d, J = 9.7 Hz, 1H), 7.40-7.35 (m, 1H), 6.48 (d, J = 8.3 Hz, 1H), 5.19 (s, 1H), 4.42-4.33 (m, 1H), 3.89 (s, 3H), 3.78 (s, 2H), 3.46-3.40 (m, 1H), 2.76-2.69 (m, 1H), 2.59 (br s, 1H), 2.45-2.41 (m, 1H), 2.38-2.24 (m, 3H), 2.16 (s, 2H), 1.51-1.41 (m, 2H), 1.23 (s, 6H), 1.07-1.01 (m, 2H) |
| 168 | | N-((aR)-6-((3-carbamoyl-6-methoxypyridin-2-ypoxy)spiro[3.3]heptan-2-yl)-6-(2-hydroxy-2-methylpropoxy)-7-(3,3,3-trifluoropropyl)pyrazolo[1,5-a]pyridine-3-carboxamide | 606.1 | A: 1.842 B: 1.862 | 1H NMR (500 MHz, DMSO-d6) δ 8.56 (s, 1H), 8.32 (br d, J = 7.5 Hz, 1H), 8.17 (d, J = 8.3 Hz, 1H), 8.13 (d, J = 9.7 Hz, 1H), 7.59-7.55 (m, 2H), 7.38 (br s, 1H), 6.49 (d, J = 8.3 Hz, 1H), 5.20 (t, J = 7.1 Hz, 1H), 4.42-4.37 (m, 1H), 3.91 (s, 3H), 3.85 (s, 2H), 2.76-2.67 (m, 3H), 2.56-2.53 (m, 1H), 2.48-2.45 (m, 1H), 2.38-2.27 (m, 3H), 2.18 (br t, J = 9.9 Hz, 2H), 1.24 (s, 6H) |
| 169 | | N-((aR)-6-((3-carbamoyl-6-methoxypyridin-2-yl)oxy)spiro[3.3]heptan-2-yl)-5-fluoro-1-(2-hydroxy-2-methylpropyl)-1H-indazole-3-carboxamide | 512.11 | A: 1.678 B: 1.743 | 1H NMR (500 MHz, DMSO-d6) δ 8.50 (d, J = 8.0 Hz, 1H), 8.16 (d, J = 8.3 Hz, 1H), 7.83 (dd, J = 9.1, 4.2 Hz, 1H), 7.75 (br d, J = 6.9 Hz, 1H), 7.53 (br s, 1H), 7.39 (br s, 1H) 7.33 (t, J = 8.8 Hz, 1H), 6.49 (d, J = 8.4 Hz, 1H), 5.19 (t, J = 7.1 Hz, 1H), 4.45-4.37 (m, 2H), 3.90 (s, 2H), 2.75-2.70 (m, 1H), 2.56-2.53 (m, 4H), 2.47-2.42 (m, 1H), 2.35-2.24 (m, 4H), 1.23 (s, 2H), 1.17-1.11 (m, 6H) |

EXAMPLE 170

Preparation of N-((aR)-6-((3-carbamoylpyridin-2-yl)oxy)spiro[3.3]heptan-2-yl)-8-cyclopropylimidazo[1,2-a]pyridine-3-carboxamide, trifluoroacetate

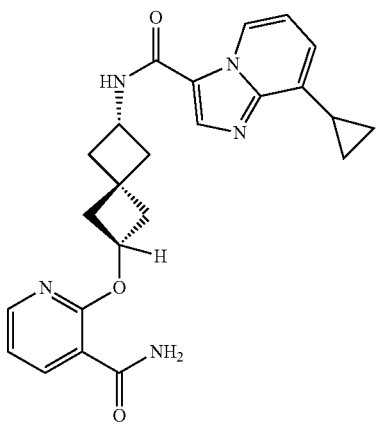

Example 42C (10 mg, 0.040 mmol) was suspended in anhydrous toluene (1 mL), then trimethylaluminum (2.0 M in toluene) (0.061 mL, 0.121 mmol) was added dropwise at rt. After 5 min, ethyl 8-cyclopropylimidazo[1,2-a]pyridine-3-carboxylate (11.2 mg, 0.049 mmol) was added and the complete mixture was stirred at 120° C. for 30 min. Afterwards, the reaction was cooled to rt, carefully quenched with TFA, concentrated, and purified by reverse phase chromatography to give the desired product (1.3 mg, 5.9%). MS (ESI) m/z: 430.3 (M+H)$^+$. $^1$H NMR (500 MHz, DMSO-d$_6$) δ 9.31 (d, J=6.2 Hz, 1H), 8.70 (d, J=7.1 Hz, 1H), 8.44 (s, 1H), 8.28 (d, J=4.6 Hz, 1H), 8.17 (d, J=6.5 Hz, 1H), 7.73 (br. s., 1H), 7.61 (br. s., 1H), 7.27 (s, 1H), 7.17 (s, 1H), 7.13-7.05 (m, 4H), 5.30-5.20 (m, 1H), 4.45-4.37 (m, 1H), 2.74-2.63 (m, 1H), 2.37 (br. s., 1H), 2.31-2.17 (m, 4H), 1.08 (d, J=7.9 Hz, 2H), 0.97 (d, J=3.8 Hz, 2H). Analytical HPLC RT=1.517 min (Method A) and 1.206 min (Method B), purity=100%.

The following examples in Table 6 were prepared using a similar procedure to that which was used in the preparation of Example 170. Example 42C was coupled with an ester using trimethylaluminum.

TABLE 6

| Example | R | Name | LCMS (M + H)$^+$ | HPLC Method, RT (min.) | $^1$H NMR |
|---|---|---|---|---|---|
| 171 | (3-(benzyloxy)-1-(difluoromethyl)-1H-indazol-3-yl)carbonyl | 6-(benzyloxy)-N-((aR)-6-((3-carbamoylpyridin-2-yl)oxy)spiro[3.3]heptan-2-yl)-1-(difluoromethyl)-1H-indazole-3-carboxamide, trifluoroacetate | 548.7 | A: 2.142 B: 2.148 | $^1$H NMR (500 MHz, DMSO-d$_6$) δ 8.82 (br d, J = 7.9 Hz, 1H), 8.25 (br d, J = 2.7 Hz, 1H), 8.15 (dd, J = 7.2, 5.3 Hz, 1H), 8.07-8.02 (m, 1H), 7.64 (br d, J = 10.4 Hz, 2H), 7.48 (br d, J = 7 Hz, 2H), 7.43-7.38 (m, 3H), 7.35 (br d, J = 7.0 Hz, 1H), 7.13-7.08 (m, 2H), 5.24-5.17 (m, 3H), 4.42-4.36 (m, 1H), 2.65 (dt, J = 10.9, 5.4 Hz, 1H), 2.45-2.40 (m, 1H), 2.34-2.15 (m, 6H) |
| 172 | (6-bromo-1-(difluoromethyl)-1H-indazol-3-yl)carbonyl | 6-bromo-N-((aR)-6-((3-carbamoylpyridin-2-yl)oxy)spiro[3.3]heptan-2-yl)-1-(difluoromethyl)-1H-indazole-3-carboxamide, trifluoroacetate | 520.2 | A: 2.020 B: 2.019 | $^1$H NMR (500 MHz, DMSO-d$_6$) δ 8.96 (br d, J = 7.6 Hz, 1H), 8.25-8.10 (m, 4H), 7.67-7.59 (m, 2H), 7.26-7.03 (m, 3H), 5.21 (br t, J = 7.2 Hz, 1H), 4.45-4.37 (m, 1H), 2.66 (br dd, J = 11.4, 6.0 Hz, 1H), 2.46-2.41 (m, 1H), 2.34-2.17 (m, 5H) |

TABLE 6-continued

| | | | | | |
|---|---|---|---|---|---|
| 173 | | N-((aR)-6-((3-carbamoylpyridin-2-yl)oxy)spiro[3.3]heptan-2-yl)-6-fluoro-1-methyl-1H-indazole-3-carboxamide, trifluoroacetate | 424.1 | A: 1.669<br>B: 1.658 | $^1$H NMR (500 MHz, DMSO-d$_6$) δ 8.56 (br d, J = 7.9 Hz, 1H), 8.25 (br d, J = 3.1 Hz, 1H), 8.16-8.09 (m, 2H), 7.64 (br s, 2H), 7.55 (br d, J = 8.5 Hz, 1H), 7.15-7.08 (m, 2H) 5.19 (quin, J = 7.0 Hz 1H), 4.38 (sxt, J = 8.1 Hz, 1H), 4.05 (s, 3H), 2.65 (dt, J = 11.1, 5.7 Hz, 1H), 2.47-2.35 (m, 2H), 2.32-2.14 (m, 5H) |
| 174 | | 6-fluoro-1-($^2$H$_3$) methyl-N-[(aR)-6-[(3-carbamoylpyridin-2-yl)oxy]spiro[3.3]heptan-2-yl]-1H-indazole-3-carboxamide, trifluoroacetate | 427.1 | A: 1.673<br>B: 1.656 | $^1$H NMR (500 MHz, DMSO-d$_6$) δ 8.55 (br d, J = 7.9 Hz, 1H), 8.26-8.23 (m, 1H), 8.17-8.09 (m, 2H), 7.64 (br s, 2H), 7.57-7.53 (m, 1H), 7.15-70.8 (m, 2H), 522- 5.16 (m, 1H), 4.42-4.34 (m, 1H), 2.65 (dt, J = 11.0, 5.8 Hz, 1H), 2.46- 2.38 (m, 2H), 2.33-2.15 (m, 5H) |
| 175 | | N-((aR)-6-((3-carbamoylpyridin-2-yl)oxy)spiro[3.3]heptan-2-yl)-1-(2,2-difluoroethyl)-6-fluoro-1H-indazole-3-carboxamide, trifluoroacetate | 474.1 | A: 1.742<br>B: 1.647 | $^1$H NMR (500 MHz, DMSO-d$_6$) δ 8.61 (br d, J = 7.9 Hz, 1H), 8.26 (br d, J = 3.1 Hz, 1H), 8.18-8.14 (m, 2H), 7.71-7.58 (m, 3H), 7.18 (br t, J = 9.0 Hz, 1H), 7.10 (dd, J = 7.0, 5.2 Hz, 1H), 6.59-6.34 (m, 1H), 5.25-5.18 (m, 1H), 5.01-4.94 (m, 2H), 4.41 (sxt, J = 8.1 Hz, 1H), 2.66 (dt, J = 10.9, 5.7 Hz, 1H), 2.47-2.38 (m, 2H), 2.33-2.17 (m, 5H) |
| 176 | | 6-fluoro-2-($^2$H$_3$) methyl-N-[(aR)-6-[(3-carbamoylpyridin-2-yl)oxy]spiro[3.3]heptan-2-yl]-2H-indazole-3-carboxamide, trifluoroacetate | 427.2 | A: 1.451<br>B: 1.421 | $^1$H NMR (500 MHz, DMSO-d$_6$) δ 8.89 (br d, J = 7.0 Hz, 1H), 8.26 (br d, J = 3.1 Hz, 1H), 8.16 (br d, J = 7.3 Hz, 1H), 7.79 (br dd, J = 9.0, 5.3 Hz, 1H), 7.70-7.64 (m, 1H), 7.62 (br s, 1H), 7.40 (br d, J = 9.2 Hz, 1H), 7.16-7.04 (m, 3H), 5.26-5.19 (m, 1H), 4.45-4.37 (m, 1H), 2.71-2.64 (m, 1H), 2.42-2.36 (m, 1H), 2.29-2.18 (m, 4H) |
| 177 | | N-((aR)-6-((3-carbamoylpyridin-2-yl)oxy)spiro[3.3]heptan-2-yl)-1-(difluoromethyl)-6-(3-methoxyphenyl)-1H-indazole-3-carboxamide, trifluoroacetate | 548.1 | A: 2.139<br>B: 2.146 | $^1$H NMR (500 MHz, DMSO-d$_6$) δ 8.93 (br d, J = 7.9 Hz, 1H), 8.46-8.20 (m, 3H), 8.17 (br s, 2H), 7.77 (br d, J = 8.2 Hz, 1H), 7.68 (br s, 1H), 7.61 (br s, 1H), 7.47-7.42 (m, 1H), 7.37-7.30 (m, 2H), 7.10 (dd, J = 7.3, 4.9 Hz, 1H), 7.02 (br d, J = 7.9 Hz, 1H), 5.23 (quin, J = 7.0 Hz, 1H), 4.49-4.41 (m, 1H), 3.85 (s, 3H), 2.68 (dt, J = 10.8, 5.6 Hz, 1H), 2.47-2.42 (m, 1H), 2.36-2.18 (m, 5H) |
| 178 | | N-((aR)-6-((3-carbamoylpyridin-2-yl)oxy)spiro[3.3]heptan-2-yl)-7-(pyrrolidin-1-yl)-[1,2,4]triazolo[4,3-a]pyridine-3-carboxamide | 462.02 | A: 1.48<br>B: 1.15 | $^1$H NMR (500 MHz, DMSO-d$_6$) δ 9.07 (br s, 1H), 8.87 (br d, J = 7.7 Hz, 1H), 8.34-8.20 (m, 1H), 8.16 (dd, J = 7.4, 1.7 Hz, 1H), 7.84-7.54 (m, 2H), 7.11 (dd, J = 7.4, 4.9 Hz, 1H), 6.81 (br d, J = 7.7 Hz, 1H), 6.38 (br s, 1H), 5.20 (quin, J = 6.9 Hz, 1H), 4.52-4.24 (m, 1H), 3.35 (br s, 4H), 2.70-2.62 (m, 1H), 2.48-2.38 (m, 2H), 2.34-2.13 (m, 5H), 1.97 (br s, 4H) |
| 179 | | N-((aR)-6-((3-carbamoylpyridin-2-yl)oxy)spiro[3.3]heptan-2-yl)-7-morpholino-[1,2,4]triazolo[4,3-a]pyridine-3-carboxamide | 478.41 | A: 1.18<br>B: 1.02 | $^1$H NMR (500 MHz, DMSO-d$_6$) δ 9.24-9.06 (m, 1H), 8.90 (d, J = 7.9 Hz, 1H), 8.26 (br d, J = 3.1 Hz, 1H), 8.19-8.12 (m, 1H), 7.64 (br d, J = 17.7 Hz, 2H), 7.19-7.06 (m, 2H), 6.88 (s, 1H), 5.21 (quin, J = 7.1 Hz, 1H), 4.39 (dq, J = 16.2, 8.0 Hz, 1H), 3.87-3.64 (m, 4H), 3.32 (br d, J = 4.3 Hz, 4H), 2.66 (dt, J = 11.1, 5.4 Hz, 1H), 2.48-2.39 (m, 2H), 2.36-2.11 (m, 5H) |

EXAMPLE 180

Preparation of 2-(((aR)-6-(3-cyano-5-(2-methylthiazol-5-yl)benzamido)spiro[3.3]heptan-2-yl)oxy)nicotinamide, TFA

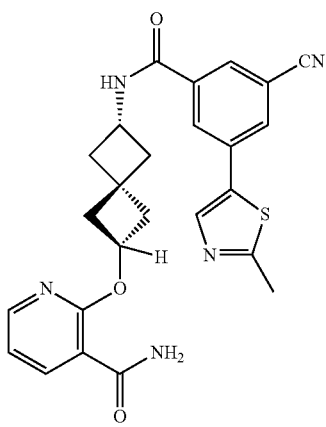

EXAMPLE 180A

Preparation of 2-(((aR)-6-(3-bromo-5-cyanobenzamido)spiro[3.3]heptan-2-yl)oxy)nicotinamide

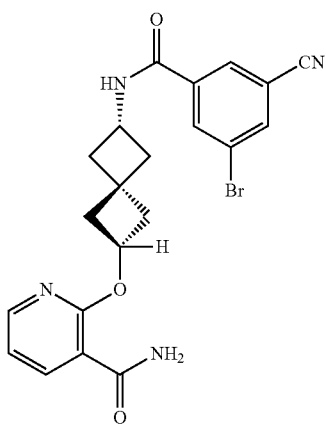

In a small vial, Example 42C (0.361 g, 1.460 mmol) was combined with 3-bromo-5-cyanobenzoic acid (0.33 g, 1.46 mmol), DMF (5 mL) and DIEA (1.275 mL, 7.30 mmol). After 24 h, the reaction was partitioned with water (20 mL) and ethyl acetate (50 mL). The aqueous layer was extracted with ethyl acetate (2×20 mL). The combined organic layers were washed with water (15 mL), brine (15 mL) and dried ($Na_2SO_4$). The residue was purified via silica gel chromatography (0-100% EtOAc in DCM gradient) to afford 2-((6-(3-bromo-5-cyanobenzamido)spiro[3.3]heptan-2-yl)oxy)nicotinamide (0.67 g, 100% yield) as white foam containing a small amount of DMF. LCMS(ESI) m/z: 457.0 $[M+H]^+$ $^1$H NMR (400 MHz, $CDCl_3$) δ 8.53 (dd, J=7.5, 2.0 Hz, 1H), 8.29 (dd, J=4.8, 2.0 Hz, 1H), 8.16 (t, J=1.8 Hz, 1H), 8.00 (t, J=1.4 Hz, 1H), 7.93 (t, J=1.7 Hz, 1H), 7.79 (br s, 1H), 7.08 (dd, J=7.7, 4.8 Hz, 1H), 6.32 (br d, J=7.3 Hz, 1H), 5.82 (br s, 1H), 5.38 (quin, J=7.2 Hz, 1H), 4.64-4.49 (m, 1H), 2.83 (dt, J=12.0, 5.9 Hz, 1H), 2.77-2.53 (m, 3H), 2.38-2.24 (m, 2H), 2.20-2.11 (m, 2H).

EXAMPLE 180

In a microwave vial, combined Example 180A (24 mg, 0.053 mmol), $K_3PO_4$ (3 M aq.) (53 µl, 158 mmol) in Dioxane (1.0 mL), degassed with $N_2$, added chloro-(2-dicyclohexylphosphino-2',4',6'-tri-i-propyl-1,1'-biphenyl)(2'-amino-1,1'-biphenyl-2-yl) palladium (II) (4.15 mg, 5.27 µmol), sealed and heated to 120° C. in microwave for 30 min. The solvent was removed under reduced pressure, and residue was dissolved in DMF (2 mL), filtered and purified by reverse phase chromatography to give Example 180 (9.9 mg, 32.0% yield). LCMS(ESI) m/z: 474.2. $^1$H NMR (500 MHz, DMSO-$d_6$) δ 8.98 (br d, J=7.0 Hz, 1H), 8.23 (br d, J=3.1 Hz, 1H), 8.20 (s, 1H), 8.15 (br d, J=7.3 Hz, 1H), 8.12 (s, 1H), 8.09 (s, 1H), 7.75 (br s, 1H), 7.57 (br s, 1H), 7.17-7.04 (m, 1H), 5.24-5.12 (m, 1H), 3.16 (br d, J=4.6 Hz, 1H), 2.67 (s, 4H), 2.59-2.55 (m, 3H), 2.48-2.42 (m, 1H), 2.36 (br d, J=7.9 Hz, 1H), 2.22 (br dd, J 11.3, 7.3 Hz, 1H), 2.21-2.09 (m, 2H). Analytical HPLC 1.50 min (Method A) and 1.40 min. (Method B), purity 100%.

The following examples in Table 7 were prepared using commercially available boronic acids or boronates and a similar procedure to that which was used in the preparation of Example 180. Various protecting groups were deprotected with the appropriate reagents such as TFA.

TABLE 7

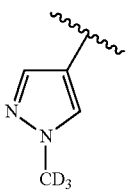

| Example | R | Name | LCMS (M + H)+ | HPLC Method, RT (min.) | 1H NMR |
|---|---|---|---|---|---|
| 181 | 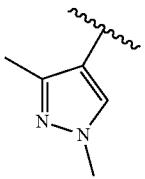 [SMILES: *c1cn(C)nc1C] | 2-(((aR)-6-(3-cyano-5-(1-(methyl-d3)-1H-pyrazol-4-yl)benzamido)spiro[3.3]heptan-2-yl)oxy)nicotinamide, trifluoroacetate | 460.2 | A: 1.35 B: 1.35 | 1H NMR (500 MHz, DMSO-d6) δ 8.80 (br d, J = 7.3 Hz, 1H), 8.32 (s, 1H), 8.27 (br s, 2H), 8.21 (s, 1H), 8.19-8.12 (m, 1H), 8.03 (br d, J = 7.3 Hz, 2H), 7.69 (br s, 1H), 7.61 (br s, 1H), 7.11 (dd, J = 7.3, 4.9 Hz, 1H), 5.31-5.13 (m, 1H), 4.48-4.25 (m, 1H), 3.55-3.37 (m, 1H), 2.68 (dt, J = 10.9, 5.7 Hz, 1H), 2.43-2.32 (m, 1H), 2.32-2.12 (m, 4H) |
| 182 | 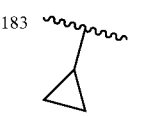 | 2-(((aR)-6-(3-cyano-5-(1,3-dimethyl-1H-pyrazol-4-yl)benzamido)spiro[3.3]heptan-2-yl)oxy)nicotinamide, trifluoroacetate | 471.2 | A: 1.42 B: 1.40 | 1H NMR 500 MHz, DMSO-d6) δ 8.81 (br d, J = 7.0 Hz, 1H), 8.27 (dd, J = 4.7, 1.7 Hz, 1H), 8.23-8.13 (m, 2H), 8.09 (s, 2H), 8.00 (s, 1H), 7.70 (br s, 1H), 7.60 (br s, 1H), 7.11 (dd, J = 7.3, 4.9 Hz, 1H), 5.24 (quin, J = 7.2 Hz, 1H), 4.42-4.29 (m, 1H), 3.81 (s, 3H), 3.21-3.09 (m, 1H), 2.75-2.63 (m, 1H), 2.42-2.36 (m, 1H), 2.34 (s, 3H), 2.30-2.15 (m, 4H) |
| 183 | 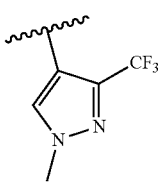 [SMILES: *c1cn(C)nc1C(F)(F)F] | 2-(((aR)-6-(3-cyano-5-cyclopropylbenzamido)spiro[3.3]heptan-2-yl)oxy)nicotinamide, trifluoroacetate | 417.2 | A: 1.63 B: 1.62 | 1H NMR (500 MHz, DMSO-d6) δ 8.75 (br d, J = 7.3 Hz, 1H), 8.39-8.24 (m, 1H), 8.17 (dd, J = 7.3, 1.5 Hz, 1H), 8.00 (s, 1H), 7.81 (s, 1H), 7.74-7.64 (m, 1H), 7.60 (br s, 1H), 7.11 (dd, J = 7.3, 4.9 Hz, 1H), 5.23 (quin, J = 7.1 Hz, 1H), 4.35 (sxt, J = 7.9 Hz, 1H), 2.67 (dt, J = 11.5, 5.7 Hz, 1H), 2.42-2.30 (m, 1H), 2.32-2.11 (m, 3H), 2.07-1.96 (m, 1H), 1.24 (s, 2H), 1.12-0.94 (m, 4H), 0.90-0.67 (m, 2H) |
| 184 | 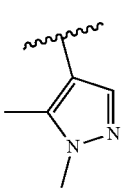 [SMILES: *c1cnn(C)c1C] | 2-(((aR)-6-(3-cyano-5-(1-methyl-3-(trifluoromethyl)-1H-pyrazol-4-yl)benzamido)spiro[3.3]heptan-2-yl)oxy)nicotinamide, trifluoroacetate | 525.2 | A: 1.68 B: 1.66 | 1H NMR (500 MHz, DMSO-d6) δ 8.86 (br d, J = 7.0 Hz, 1H), 8.27 (br d, J = 14.0 Hz, 3H), 8.21-8.07 (m, 2H), 7.96 (s, 1H), 7.67 (br s, 1H), 7.62 (br s, 1H), 7.11 (dd, J = 7.3, 4.9 Hz, 1H), 5.22 (quin, J = 7.1 Hz, 1H), 4.45-4.24 (m, 1H), 3.98 (s, 3H), 3.68-3.44 (m, 1H), 2.66 (br dd, J = 11.0, 6.1 Hz, 1H), 2.48-2.41 (m, 1H), 2.40-2.30 (m, 1H), 2.29-2.13 (m, 4H) |
| 185 | | 2-(((aR)-6-(3-cyano-5-(1,5-dimethyl-1H-pyrazol-4-yl)benzamido)spiro[3.3]heptan-2-yl)oxy)nicotinamide, trifluoroacetate | 471.3 | A: 1.43 B: 1.40 | 1H NMR (500 MHz, DMSO-d6) δ 8.82 (br d, J = 7.3 Hz, 1H), 8.47-8.23 (m, 1H), 8.17 (dd, J = 7.5, 1.7 Hz, 1H), 8.16-7.92 (m, 3H), 7.75 (s, 1H), 7.69 (br s, 1H), 7.61 (br s, 1H), 7.11 (dd, J = 7.5, 5.0 Hz, 1H), 5.23 (quin, J = 7.1 Hz, 1H), 4.52-4.24 (m, 1H), 3.82 (s, 3H), 2.75-2.62 (m, 1H), 2.55 (s, 3H), 2.48-2.44 (m, 1H), 2.43-2.33 (m, 3H), 2.32-2.23 (m, 1H), 2.23-2.11 (m, 2H) |

TABLE 7-continued

| | | | | | |
|---|---|---|---|---|---|
| 186 | (2-methylbenzo[d]thiazol-5-yl, structure) | 2-(((aR)-6-(3-cyano-5-(2-methylbenzo[d]thiazol-5-yl)benzamido)spiro[3.3]heptan-2-yl)oxy)nicotinamide, trifluoroacetate | 524.2 | A: 1.73<br>B: 1.71 | $^1$H NMR (500 MHz, DMSO-d$_6$) δ 8.92 (br d, J = 7.3 Hz, 1H), 8.51 (s, 1H), 8.47 (s, 1H), 8.39 (s, 1H), 8.27 (br d, J = 3.1 Hz, 1H), 8.2.3 (s, 1H), 8.19-8.12 (m, 1H), 8.03 (d, J = 8.5 Hz, 1H), 7.92 (br d, J = 8.5 Hz, 1H), 7.69 (br s, 1H), 7.62 (br s, 1H), 7.11 (dd, J = 7.3, 4.9 Hz, 1H), 5.24 (quin, J = 7.2 Hz, 1H), 4.40 (sxt, J = 7.7 Hz, 1H), 3.56-3.40 (m, 1H), 2.84 (s, 3H), 2.74-2.62 (m, 1H), 2.45-2.35 (m, 1H), 2.33-2.17 (m, 4H) |
| 187 | (1-isobutyl-1H-pyrazol-4-yl, structure) | 2-((aR)-6-(3-cyano-5-(1-isobutyl-1H-pyrazol-4-yl)benzamido)spiro[3.3]heptan-2-yl)oxy)nicotinamide, trifluoroacetate | 499.0 | A: 1.809<br>B: 1.789 | $^1$H NMR (500 MHz, DMSO-d$_6$) δ 8.84-8.79 (m, 1H), 8.35-8.31 (m, 1H), 8.27-8.24 (m, 2H), 8.22-8.19 (m, 1H), 8.18-8.14 (m, 1H), 8.06-8.03 (m, 1H), 8.01-7.97 (m, 1H), 7.66 (br s, 1H), 7.62 (br s, 1H), 7.10 (dd, J = 7.3, 4.9 Hz, 1H), 5.22 (quin, J = 7.1 Hz, 1H), 4.35 (sxt, J = 7.9 Hz, 1H), 3.93 (br d, J = 7.3 Hz, 2H), 2.69-2.63 (m, 1H), 2.47-2.44 (m, 1.H), 2.39-2.33 (m, 1H), 2.28-2.10 (m, 5H), 0.87-0.82 (m, 6H) |
| 188 | (4-methyl-2-(4-(trifluoromethyl)phenyl)thiazol-5-yl, structure) | 2-((aR)-6-(3-cyano-5-(4-methyl-2-(4-(trifluoromethyl)phenyl)thiazol-5-yl)benzamido)spiro[3.3]heptan-2-yl)oxy)nicotinainide, trifluoroacetate | 618.1 | A: 2.357<br>B: 2.346 | $^1$H NMR (500 MHz, DMSO-d$_6$) δ 8.91 (br d, J = 7.3 Hz, 1H), 8.31-8.13 (m, 7H), 7.88 (br d, J = 8.2 Hz, 2H), 7.67 (br s, 1H), 7.60 (br s, 1H), 7.10 (dd, J = 7.3, 4.9 Hz, 1H), 5.22 (quin, J = 7.1 Hz, 1H), 4.40-4.33 (m, 1H), 2.69-2.62 (m, 1H), 2.56-2.53 (m, 3H), 2.48-2.43 (m, 1H), 2.40-2.33 (m, 1H), 2.29- 2.16 (m, 4H) |
| 189 | (2-oxo-1,2,3,4-tetrahydroquinolin-6-yl, structure) | 2-((aR)-6-(3-cyano-5-(2-oxo-1,2,3,4-tetrahydroquinolin-6-yl)benzamido)spiro[3.3]heptan-2-yl)oxy)nicotinamide, trifluoroacetate | 522.0 | A: 1.631<br>B: 1.576 | $^1$H NMR (500 MHz, DMSO-d$_6$) δ 10.30-10.24 (m, 1H), 8.97-8.87 (m, 1H), 8.33 (br s, 1H) 8.29-8.23 (m, 2H), 8.18-8.13 (m, 2H), 7.74-7.59 (m, 4H), 7.10 (dd, J = 7.4, 4.9 Hz, 1H), 6.97 (d, J = 8.2 Hz, 1H), 5.26-5.19 (m, 1H), 4.42-4.34 (m, 1H), 3.00-2.93 (m, 2H), 2.72-2.63 (m, 1H), 2.47-2.43 (m, 1H), 2.41-2.33 (m, 1H), 2.30-2.17 (m, 4H) |
| 190 | (3,5-dimethylisoxazol-4-yl, structure) | 2-((aR)-6-(3-cyano-5-(3,5-dimethylisoxazol-4-yl)benzamido)spiro[3.3]heptan-2-yl)oxy)nicotinamide, trifluoroacetate | 471.9 | A: 1.724<br>B: 1.665 | $^1$H NMR (500 MHz, DMSO-d$_6$) δ 8.89-8.85 (m, 1H), 8.26-8.21 (m, 2H), 8.16-8.13 (m, 1H), 8.08-8.04 (m, 1H), 8.03-8.00 (m, 1H), 7.13-7.06 (m, 1H), 5.20 (quin, J = 7.1 Hz, 1H), 4.33 (sxt, J = 8.0 Hz, 1H), 2.68-2.62 (m, 1H), 2.48-2.42 (m, 2H), 2.41-2.38 (m, 3H), 2.37-2.32 (m, 1H), 2.28-2.14 (m, 7H) |
| 191 | (6-cyanopyridin-3-yl, structure) | 2-(((aR)-6-(3-cyano-5-(6-cyanopyridin-3-yl)benzamido)spiro[3.3]heptan-2-yl)oxy)nicatinamide, trifluoroacetate | 479.2 | A: 1.688<br>B: 1.636 | $^1$H NMR (500 MHz, DMSO-d$_6$) δ 9.22 (s, 1H), 8.90 (br d, J = 7.0 Hz, 1H), 8.52-8.48 (m, 3H), 8.35-8.31 (m, 1H), 8.28-8.24 (m, 1H), 8.22-8.19 (m, 1H), 8.18-8.14 (m, 1H), 7.69 (br s, 1H), 7.60 (br s, 1H), 7.10 (dd, J = 7.3, 4.9 Hz, 1H), 5.26-5.20 (m, 1H), 4.39 (sxt, J = 8.1 Hz, 1H), 2.71-2.63 (m, 1H), 2.48-2.43 (m, 1H), 2.42-2.35 (m, 1H), 2.30-2.16 (m, 4H) |
| 192 | (1-methyl-2-oxo-1,2-dihydropyridin-4-yl, structure) | 2-(((aR)-6-(3-cyano-5-(1-methyl-2-oxo-1,2-dihydropyridin-4-yl)benzamido)spiro[3.3]heptan-2-yl)oxy)nicotinamide, trifluoroacetate | 484.1 | A: 1.237<br>B: 1.223 | $^1$H NMR (500 MHz, DMSO-d$_6$) δ 8.91 (br d, J = 7.0 Hz, 1H), 8.39 (br d, J = 19.5 Hz, 2H), 8.31-8.25 (m, 2H), 8.16 (br d, J = 7.0 Hz, 1H), 7.85 (br d, J = 7.0 Hz, 1H), 7.76-7.68 (m, 1H), 7.59 (br s, 1H), 7.11 (br d, J = 4.6 Hz, 1H), 7.23-7.01 (m, 1H), 6.91 (br s, 1H), 6.71 (br d, J = 6.7 Hz, 1H), 5.28-5.20 (m, 1H), 4.43-4.33 (m, 1H), 2.73-2.65 (m, 1H), 2.54 (s, 3H), 2.43-2.34 (m, 1H), 2.33-2.18 (m, 4H) |

| | | | | | |
|---|---|---|---|---|---|
| 193 | (3-(trifluoromethyl)-1H-pyrazol-4-yl) | 2-(((aR)-6-(3-cyano-5-(3-(trifluoromethyl)-1H-pyrazol-4-yl)benzamido)spiro[3.3]heptan-2-yl)oxy)nicatinamide, trifluoroacetate | 511.2 | A: 1.541<br>B: 1.532 | $^1$H NMR (500 MHz, DMSO-d$_6$) δ 8.84 (br d, J = 7.3 Hz, 1H), 8.42-8.34 (m, 1H), 8.30-8.24 (m, 2H), 8.19-8.12 (m, 2H), 8.00 (s, H), 7.71-7.66 (m, 1H), 7.64-7.52 (m, 3H), 7.10 (dd, J = 7.3, 4.9 Hz, 1H), 5.22 (quin, J = 7.1 Hz, 1H), 4.36 (sxt, J = 7.8 Hz, 1H), 2.71-2.63 (m, 1H), 2.47-2.44 (m, 1H), 2.41-2.33 (m, 1H), 2.28-2.14 (m, 4H) |
| 194 | (1-methyl-2-oxo-1,2-dihydropyridin-3-yl) | 2-(((aR)-6-(3-cyano-5-(1-methyl-2-oxo-1,2-dihydropyridin-3-yl)benzamido)spiro[3.3]heptan-2-yl)oxy)nicotinamide, trifluoroacetate | 484.0 | A: 1.284<br>B: 1.273 | $^1$H NMR (500 MHz, DMSO-d$_6$) δ 8.84-8.78 (m, 1H), 8.45-8.40 (m, 1H), 8.35-8.31 (m, 1H), 8.29-8.24 (m, 1H), 8.19-8.13 (m, 2H), 7.86-7.81 (m, 2H), 7.72-7.66 (m, 1H), 7.63-7.57 (m, 1H), 7.10 (dd, J = 7.3, 5.2 Hz, 1H), 6.40 (t, J = 6.7 Hz, 1H), 5.23 (quin, J = 7.0 Hz, 1H), 4.41-4.33 (m, 1H), 2.70-2.63 (m, 1H), 2.54 (s, 3H), 2.47-2.43 (m, 1H), 2.40-2.34 (m, 1H), 2.29-2.15 (m, 4H) |
| 195 | (1-methyl-1H-pyrazol-4-yl) | 2-(((aR)-6-(3-cyano-5-(1-methyl-1H-pyrazol-4-yl)benzamido)spiro[3.3]heptan-2-yl)oxy)nicotinamide | 454.9 | A: 1.458<br>B: 1.455 | 1H NMR (500 MHz, DMSO-d6) δ 8.81 (br d, J = 7.3 Hz, 1H), 8.31 (s, 1H), 8.26 (br s, 2H), 8.20 (s, 1H), 8.18-8.15 (m, 1H), 8.02 (d, J = 7.9 Hz, 2H), 7.68 (br s, 1H), 7.62 (br s, 1H), 7.11 (dd, J = 7.3, 4.9 Hz, 1H), 5.23 (br t, J = 7.2 Hz, 1H), 4.47-4.28 (m, 1H), 3.53 (br s, 1H), 2.67 (br dd, J = 11.1, 5.6 Hz, 1H), 2.56-2.54 (m, 3H), 2.46-2.33 (m, 2H), 2.30-2.15 (m, 4H) |
| 196 | (2-(methylsulfonyl)phenyl) | 2-(((aR)-6-(5-cyano-2'-(methylsulfonyl)-[1,1'-biphenyl]-3-ylcarboxamidospiro[3.3]heptan-2-yl)oxy)nicotinamide | 531.4 | A: 1.485<br>B: 1.484 | 1H NMR (500 MHz, DMSO-d6) δ 9.01 (br d, J = 7.3 Hz, 1H), 8.37 (s, 1H), 8.34 (br s, 1H), 8.25-8.13 (m, 2H), 8.09 (br d, J = 7.9 Hz, 1H), 7.97 (br d, J = 7.6 Hz, 1H), 7.87-7.67 (m, 2H), 7.57 (br s, 1H), 7.10 (dd, J = 7.3, 4.9 Hz, 1H), 5.18 (t, J = 7.0 Hz, 1H), 4.48-4.26 (m, 1H), 2.73-2.59 (s, 3H), 2.56-2.53 (m, 1.H), 2.49-2.44 (m, 1H), 2.42-2.31 (m, 1H), 2.25-2.13 (m, 4H) |
| 197 | (1-methyl-1H-pyrazol-5-yl) | 2-(((aR)-6-(3-cyano-5-(1-methyl-1H-pyrazol-5-yl)benzamido)spiro[3.3]heptan-2-yl)oxy)nicotinamide | 457.0 | A: 1.394<br>B: 1.470 | 1H NMR (500 MHz, DMSO-d6) δ 8.88 (br d, J = 7.0 Hz, 1H), 8.31-8.15 (m, 2H), 7.69 (br s, 1H), 7.60 (br s, 1H), 7.53 (s, 1H), 7.11 (dd, J = 7.5, 5.0 Hz, 1H), 6.60 (s, 1H), 5.23 (t, J = 7.2 Hz, 1H), 4.48-4.27 (m, 1H), 3.00 (s, 1H), 2.83-2.60 (m, 1H), 2.56-2.53 (s, 3H), 2.49-2.44 (m, 1H), 2.42-2.33 (m, 1H), 2.32-2.15 (m, 4H) |
| 198 | (1-(difluoromethyl)-1H-pyrazol-4-yl) | 2-(((aR)-6-(3-cyano-5-(1-(difluoromethyl)-1H-pyrazol-4-yl)benzamido)spiro[3.3]heptan-2-yl)oxy)nicotinamide | 493.4 | A: 1.536<br>B: 1.571 | 1H NMR (500 MHz, DMSO-d6) δ 8.90 (br d, J = 6.6 Hz, 1H), 8.83 (s, 1H), 8.41-8.30 (m, 3H), 8.25 (dd, J = 4.8, 1.8 Hz, 1H), 8.15 (dd, J = 7.4, 1.7 Hz, 1H), 8.08 (s, 1H), 7.94-7.93 (m, 1H), 7.79 (s, 1H), 7.68 (br s, 2H), 7.11 (dd, J = 7.5, 4.9 Hz, 1H), 5.20 (quin, J = 7.1 Hz, 1H), 4.50-4.30 (m, 1H), 3.81 (s, 1H), 2.66 (dt, J = 11.4, 5.7 Hz, 1H), 2.57-2.54 (m, 1H), 2.49-2.44 (m, 1H), 2.41-2.31 (m, 1H), 2.28-2.14 (m, 4H) |

EXAMPLE 199

Preparation of 2-(((aR)-6-(3-cyano-5-(4,5,6,7-tetrahydrothiazolo[5,4-c]pyridin-2-yl)benzamido)spiro[3.3]heptan-2-yl)oxy)nicotinamide, 2TFA

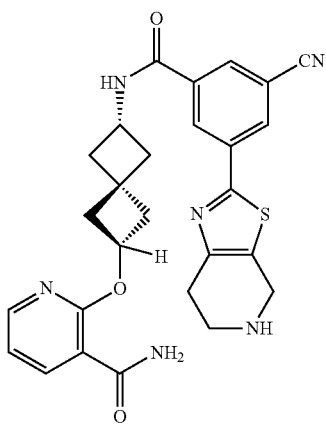

EXAMPLE 199A

Preparation of 2-(((aR)-6-(3-cyano-5-(5,5-dimethyl-1,3,2-dioxaborinan-2-yl)benzamido)spiro[3.3]heptan-2-yl)oxy)nicotinamide

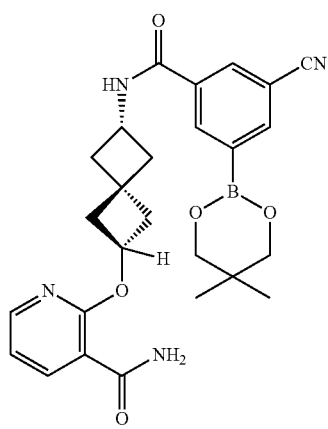

Combined Example 180A (0.2 g, 0.439 mmol), 5,5,5',5'-tetramethyl-2,2'-bi(1,3,2-dioxaborinane) (0.109 g, 0.483 mmol), potassium acetate (0.129 g, 1.318 mmol) in Dioxane (5 mL). The mixture was degassed with $N_2$, added $PdCl_2$ (dppf)-$CH_2Cl_2$ Adduct (0.018 g, 0.022 mmol) and heated in oil bath to 90° C. After 18 h, the reaction mixture was filtered through cotton/0.45 μM frit and partitioned with water (10 mL) and ethyl acetate (30 mL). The aqueous layer was extracted with ethyl acetate (2×20 mL). The combined organic layers were washed with brine (15 m) and dried ($Na_2SO_4$), filtered and concentrated to 0.31 g of a dark residue that was used as is in subsequent steps. LCMS(ESI) m/z: 421.1 $[M+H]^+$

EXAMPLE 199

Combined crude 2-(((aR)-6-(3-cyano-5-(5,5-dimethyl-1,3,2-dioxaborinan-2-yl)benzamido)spiro[3.3]heptan-2-yl)oxy)nicotinamide (20 mg, 0.041 mmol), tert-butyl 2-bromo-6,7-dihydrothiazolo[5,4-c]pyridine-5(4H)-carboxylate (13.0 mg, 0.041 mmol), 3M $K_3PO_4$ (0.04 mL, 0.123 mmol) in Dioxane (1.0 mL), degassed with $N_2$, added chloro-(2-dicyclohexylphosphino-2',4'6'-tri-1-propyl-1,1'-biphenyl X)(2'-amino-1,1'-biphenyl-2-yl) palladium(II) (3.22 mg, 4.10 μmol), sealed and heated to 120° C. in microwave for 30 min. LCMS(ESI) m/z: 615.1$[M+H]^+$. The reaction mixture was concentrated and the residue was treated with excess DCM/TFA for 30 min. The solvents were removed and residue diluted with DMF, filtered and purified by reverse phase HPLC to afford 2-(((2S,4s,6S)-6-(3-cyano-5-(4,5,6,7-tetrahydrothiazolo[5,4-c]pyridin-2-yl)benzamido)spiro[3.3]heptan-2-yl)oxy)nicotinamide, 2TFA (1.6 mg, 5.2% yield). LCMS(ESI) m/z: 515.1 $[M+H]^+$. $^1$H NMR (500 MHz, DMSO-$d_6$) δ 9.02 (br d, J=6.7 Hz, 1H), 8.59 (s, 1H), 8.46 (s, 1H), 8.36 (s, 1H), 8.26 (br d, J=3.1 Hz, 1H), 8.17 (br d, J=6.4 Hz, 1H), 7.68 (br s, 1H), 7.63 (br s, 1H), 7.11 (br dd, J=7.0, 5.2 Hz, 1H), 5.23 (quin, J=7.0 Hz, 1H), 4.49 (br s, 2H), 4.42-4.28 (m, 1H), 3.70-3.47 (m, 1H), 3.23-3.13 (m, 1H), 3.10 (br s, 1H), 2.76-2.63 (m, 1H), 2.59-2.55 (m, 4H), 2.43-2.33 (m, 1H), 2.31-2.15 (m, 4H). Analytical HPLC 1.13 min (Method A) and 1.06 min. (Method B), purity 100%.

The following examples in Table 8 were prepared using commercially available compounds and a similar procedure to that which was used in the preparation of Example 199.

Various protecting groups were deprotected with the appropriate reagents such as TFA.

TABLE 8

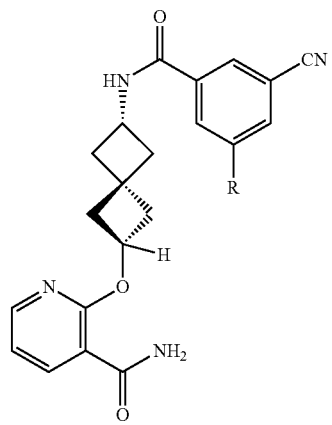

| Example | R | Name | LCMS (M + H)+ | HPLC Method, RT (min.) | 1H NMR |
|---|---|---|---|---|---|
| 200 | (5-methyl-4,5,6,7-tetrahydrothiazolo[5,4-c]pyridin-2-yl) | 2-(((aR)-6-(3-cyano-5-(5-methyl-4,5,6,7-tetrahydrothiazolo[5,4-c]pyridin-2-yl)benzamido)spiro[3.3]heptan-2-yl)oxy)nicotinamide, bis-trifluoroacetate | 529.2 | A: 1.44 B: 1.07 | 1H NMR (500 MHz, DMSO-$d_6$) δ 9.02 (br d, J = 7.0 Hz, 1H), 8.61 (s, 1H), 8.49 (s, 1H), 8.39 (s, 1H), 8.27 (br d, J = 3.1 Hz, 1H), 8.17 (dd, J = 7.3, 1.5 Hz, 1H), 7.70 (br s, 1H), 7.60 (br s, 1H), 7.28 (br s, 1H), 7.18 (br s, 1H), 7.13-6.93 (m, 1H), 5.24 (quin, J = 7.0 Hz, 1H), 4.61 (br s, 1H), 4.41-4.24 (m, 1H), 3.18 (s, 3H), 2.98 (s, 2H), 2.76-2.62 (m, 2H), 2.45-2.41 (m, 2H), 2.31-2.08 (m, 4H) |
| 201 | (2,4-dimethylthiazol-5-yl) | 2-(((aR)-6-(3-cyano-5-(2,4-dimethylthiazol-5-yl)benzamido)spiro[3.3]heptan-2-yl)oxy)nicotinamide, trifluoroacetate | 488.1 | A: 1.55 B: 1.46 | 1H NMR (500 MHz, DMSO-$d_6$) δ 8.88 (br d, J = 7.0 Hz, 1H), 8.27 (dd, J = 4.9, 1.8 Hz, 1H), 8.25 (s, 1H), 8.17 (dd, J = 7.5, 1.7 Hz, 1H), 8.13 (s, 1H), 8.09 (s, 1H), 7.69 (br s, 1H), 7.61 (br s, 1H), 7.11 (dd, J = 7.3, 4.9 Hz, 1H), 5.23 (quin, J = 7.1 Hz, 1H), 4.44-4.28 (m, 1H), 3.59-3.35 (m, 1H), 2.75-2.61 (m, 3H), 2.48-2.43 (m, 2H), 2.43-2.32 (m, 3H), 2.32-2.10 (m, 4H) |
| 202 | (2-(trifluoromethyl)thiazol-5-yl) | 2-(((aR)-6-(3-cyano-5-(2-(trifluoromethyl)thiazol-5-yl)benzamido)spiro[3.3]heptan-2-yl)oxy)nicotinamide, trifluoroacetate | 528.1 | A: 1.86 B: 1.86 | 1H NMR (500 MHz, DMSO-$d_6$) δ 8.91 (br d, J = 7.0 Hz, 1H), 8.72 (s, 1H), 8.52 (s, 1H), 8.43 (s, 1H), 8.31 (s, 1H), 8.27 (br d, J = 3.1 Hz, 1H), 8.17 (br d, J = 7.6 Hz, 1H), 7.69 (br s, 1H), 7.61 (br s, 1H), 7.11 (dd, J = 7.2, 5.0 Hz, 1H), 5.24 (quin, J = 7.2 Hz, 1H), 4.47-4.26 (m, 1H), 2.75-2.62 (m, 1H), 2.57-2.55 (m, 1H), 2.38 (br d, J = 5.2 Hz, 1H), 2.32-2.14 (m, 4H) |
| 203 | (2-methylthiazol-4-yl) | 2-(((aR)-6-(3-cyano-5-(2-methylthiazol-4-yl)benzamido)spiro[3.3]heptan-2-yl)oxy)nicotinamide, trifluoroacetate | 474.4 | A: 1.57 B: 1.56 | 1H NMR (500 MHz, DMSO-$d_6$) δ 8.96 (br d, J = 7.0 Hz, 1H), 8.92 (s, 1H), 8.35 (s, 1H), 8.29-8.21 (m, 1H), 8.19-8.05 (m, 3H), 7.73 (br s, 1H), 7.58 (br s, 1H), 7.11 (dd, J = 7.3, 4.9 Hz, 1H), 5.18 (quin, J = 7.2 Hz, 1H), 4.40-4.25 (m, 1H), 3.16 (d, J = 4.9 Hz, 1H), 2.73-2.60 (m, 1H), 2.57 (s, 3H), 2.47-2.41 (m, 1H), 2.40-2.31 (m, 1H), 2.22 (br dd, J = 11.1, 7.5 Hz, 1H), 2.18-2.05 (m, 2H) |

EXAMPLE 204

Preparation of 2-(((2S,4s,6S)-6-(3-cyano-5-isopropylbenzamido)spiro[3.3]heptan-2-yl)oxy)nicotinamide, TFA salt

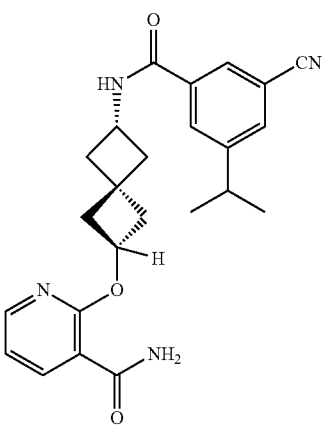

In a vial, combined Example 180A (30 mg, 0.066 mmol), 2-bromopropane (8.1 mg, 0.066 mmol), (4,4'-di-t-butyl-2,2'-bipyridine)bis[3,5-difluoro-2-[5-trifluoromethyl-2-pyridinyl-kappan)phenyl-kappac]iridium(III) hexafluorophosphate (0.68 mg, 0.66 μmol), nickel(II) chloride ethylene glycol dimethyl ether complex (0.72 mg, 3.3 μmol) and tris(trimethylsilyl)silane (20 μl, 0.06 mmol) in degassed DME (1.3 mL) was blanketed under $N_2$ and irradiated with blue LED for 72 h. The reaction was concentrated, diluted with DMF, filtered and purified by reverse phase HPLC to afford Example 204 (5.2 mg, 14% yield). LCMS(ESI) m/z: 419.4. $^1$H NMR (500 MHz, DMSO-$d_6$) δ 8.77 (br d, J=7.3 Hz, 1H), 8.27 (br d, J=3.1 Hz, 1H), 8.17 (br d, J=7.6 Hz, 1H), 8.07 (s, 1H), 8.01 (s, 1H), 7.88 (s, 1H), 7.68 (br s, 1H), 7.61 (br s, 1H), 7.11 (dd, J=7.2, 5.0 Hz, 1H), 5.31-5.14 (m, 1H), 4.35 (dq, J=15.8, 7.7 Hz, 1H), 3.17 (br s, 1H), 3.02 (dt, J=13.5, 6.8 Hz, 1H), 2.66 (br dd, J=11.7, 6.0 Hz, 1H), 2.47 (m, 1H), 2.42-2.31 (m, 1H), 2.28-2.13 (m, 4H), 1.23 (br d, J=7.0 Hz, 6H). Analytical HPLC 1.74 min (Method A) and 1.72 min. (Method B), purity 96%.

The following compounds in Table 9 were prepared in a similar manner as Example 204 using Example 180A.

TABLE 9

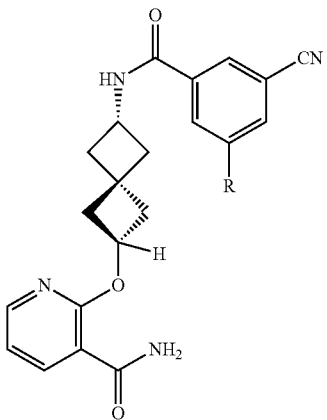

| Example | R | Name | LCMS (M + H)+ | HPLC Method, RT (min.) | $^1$H NMR |
|---|---|---|---|---|---|
| 205 | ~~~CF3 | 2-(((aR)-6-(3-cyano-5-(3,3,3-trifluoropropyl)benzamido)spiro[3.3]heptan-2-yl)oxy)nicotinamide, trifluoroacetate | 472.8 | A: 1.70<br>B: 1.72 | $^1$H NMR (500 MHz, DMSO-$d_6$) δ 8.76 (br d, J = 7.3 Hz, 1H), 8.27 (dd, J = 4.7, 1.7 Hz, 1H), 8.17 (dd, J = 7.5, 1.7 Hz, 1H), 8.12 (s, 1H), 8.07 (s, 1H), 7.97 (s, 1H), 7.69 (br s, 1H), 7.61 (br s, 1H), 7.11 (dd, J = 7.5, 5.0 Hz, 1H), 5.23 (quin, J = 7.1 Hz, 1H), 4.36 (dq, J = 16.0, 8.2 Hz, 1H), 3.02-2.88 (m, 2H), 2.75-2.60 (m, 3H), 2.49-2.42 (m, 2H), 2.40-2.31 (m, 1H), 2.30-2.12 (m, 4H) |
| 206 | (tetrahydro-2H-pyran-4-yl)methyl | 2-((6(aR)-(3-cyano-5-((tetrahydro-2H-pyran-4-yl)methyl)benzamido)spiro[3.3]heptan-2-yl)oxy)nicotinamide, trifluoroacetate | 475.1 | A: 1.55<br>B: 1.53 | $^1$H NMR (500 MHz, DMSO-$d_6$) δ 8.76 (br d, J = 7.3 Hz, 1H), 8.30-8.24 (m, 1H), 8.17 (dd, J = 7.5, 1.7 Hz, 1H), 8.09 (s, 1H), 7.96 (s, 1H), 7.82 (s, 1H), 7.68 (br s, 1H), 7.61 (br s, 1H), 7.11 (dd, J = 7.3, 4.9 Hz, 1H), 5.23 (quin, J = 7.2 Hz, 1H), 4.42-4.27 (m, 1H), 3.87-3.75 (m, 2H), 3.27-3.18 (m, 2H), 2.73-2.65 (m, 1H), 2.62 (br d, J = 7.3 Hz, 2H), 2.48-2.41 (m, 1H), 2.39-2.31 (m, 1H), 2.30-2.10 (m, 4H), 1.78 (br dd, J = 7.3, 3.7 Hz, 1H), 1.43 (br d, J = 12.2 Hz, 2H), 1.30-1.14 (m, 3H) |

EXAMPLE 207

Preparation of 2-(((aR)-6-(3-(1,3-dimethyl-1H-pyrazol-4-yl)-5-(1H-tetrazol-1-yl)benzamido)spiro[3.3]heptan-2-yl)oxy)nicotinamide, TFA

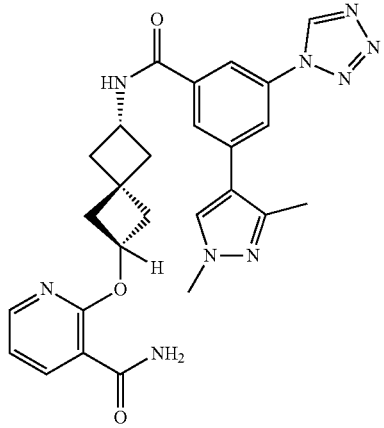

EXAMPLE 207A

Preparation of 2-(((aR)-6-(3-amino-5-bromobenzamido)spiro[3.3]heptan-2-yl)oxy)nicotinamide

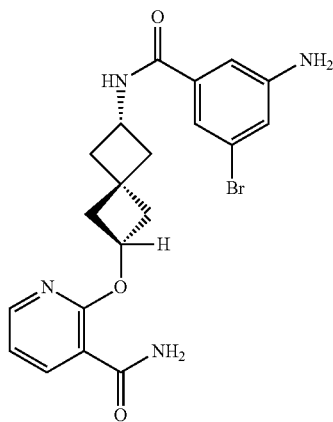

Combined Example 42C (85 mg, 0.344 mmol) with 3-amino-5-bromobenzoic acid (74.3 mg, 0.344 mmol), BOP (152 mg, 0.344 mmol), DMF (5 mL) and DIEA (0.300 mL, 1.719 mmol). After 72 h, the reaction was partitioned with water (20 mL) and ethyl acetate (50 mL). The aqueous layer was extracted with ethyl acetate (2×20 mL). The combined organic layers were washed with water (15 mL), brine (15 mL) and dried (Na$_2$SO$_4$). After filtration and concentration, the crude was purified via silica gel chromatography, eluting with DCM/0-100% ethyl acetate, then product flushed off with 10% MeOH/DCM to afford 0.16 g (105%) orange solid. LCMS(ESI) m/z: 445.0 [M+H]$^+$. $^1$H NMR (400 MHz, CDCl$_3$) δ 8.40 (br d, J=7.7 Hz, 1H), 8.26-8.03 (m, 1H), 7.76 (br s, 1H), 7.33-7.21 (m, 1H), 7.02 (s, 2H), 7.01-6.89 (m, 1H), 6.84 (d, J=1.5 Hz, 1H), 6.72 (br s, 1H), 5.48-5.08 (m, 1H), 4.64-4.34 (m, 1H), 4.12-3.86 (m, 1H), 2.69-2.63 (m, 1H), 2.48 (br dd, J=11.0, 5.5 Hz, 2H), 2.42-2.36 (m, 1H), 2.24-2.05 (m, 4H).

EXAMPLE 207B

Preparation 2-(((aR)-6-(3-bromo-5-(1H-tetrazol-1-yl)benzamido)spiro[3.3]heptan-2-yl)oxy)nicotinamide

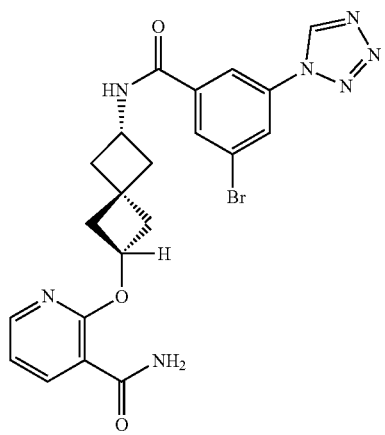

To Example 207A (0.15 g, 0.337 mmol), in AcOH (3 mL) and trimethyl orthoformate (0.372 mL, 3.37 mmol), cooled to 0° C., was added sodium azide (0.065 g, 1 mmol). After 48 h, the solvents was removed and the residue purified via silica gel chromatography, eluting with DCM 0-10% MeOH to afford Intermediate 207B (0.120 g, 71.5% yield). LCMS (ESI) m/z: 498-500.0 [M+H]$^+$. $^1$H NMR (400 MHz, CDCl$_3$) δ 9.11 (s, 1H), 8.54 (dd, J=7.5, 2.0 Hz, 1H), 8.29 (dd, J=4.8, 2.0 Hz, 1H), 8.18-8.05 (m, 2H), 8.03 (s, 1H), 7.79 (br d, J=3.3 Hz, 1H), 7.09 (dd, J=7.5, 4.8 Hz, 1H), 6.35 (br d, J=7.7 Hz, 1H), 5.79 (br s, 1H), 5.49-5.30 (m, 1H), 4.70-4.51 (m, 1H), 2.95-2.79 (m, 1H), 2.77-2.47 (m, 3H), 2.45-2.25 (m, 2H), 2.22-2.09 (m, 2H).

EXAMPLE 207

Combined Example 207B (25 mg, 0.050 mmol), 1,3-dimethyl-4-(4,4,5,5-tetramethyl-1,3,2-dioxaborolan-2-yl)-1H-pyrazole (11.5 mg, 0.050 mmol), 3M K$_3$PO$_4$ (31.9 mg, 0.151 mmol) in Dioxane (1.0 mL), the mixture was degassed with N$_2$, chloro-(2-dicyclohexylphosphino-2',4',6'-tri-i-propyl-1,1'-biphenyl)(2'-amino-1,1'-biphenyl-2-yl) palladium (II) (3.95 mg, 5.02 µmol) was added and the reaction was heated to 120° C. in microwave for 30 min. LCMS(ESI) m/z: 514.2 [M+H]$^+$. The reaction mixture was concentrated diluted with DMF, filtered and purified by reverse phase HPLC to afford Example 207 (12.6 mg, 0.020 mmol, 39.4% yield), $^1$H NMR (500 MHz, DMSO-d$_6$) δ 10.15 (s, 1H), 8.86 (br d, J=7.3 Hz, 1H), 8.27 (dd, J=4.6, 1.8 Hz, 1H), 8.20-8.13 (m, 2H), 8.10 (s, 1H), 8.06 (s, 1H), 8.04 (s, 1H), 7.69 (br s, 1H), 7.62 (br s, 1H), 7.11 (dd, J=7.5, 5.0 Hz, 1H), 5.24 (quin, J=7.1 Hz, 1H), 4.53-4.32 (m, 1H), 3.83 (s, 3H), 3.57-3.40 (m, 1H), 2.93 (q, J=7.3 Hz, 1H), 2.79-2.64 (m, 1H), 2.38 (s, 4H), 2.32-2.13 (m, 4H). Analytical HPLC 1.32 min (Method A) and 1.29 min. (Method B), purity 98%.

EXAMPLE 208

Preparation of N-(6-(2-carbamoyl-6-methoxyphenoxy)spiro[3.3]heptan-2-yl)-7-cyclopropyl-6-(2-hydroxy-2-methylpropoxy)pyrazolo[1,5-a]pyridine-3-carboxamide

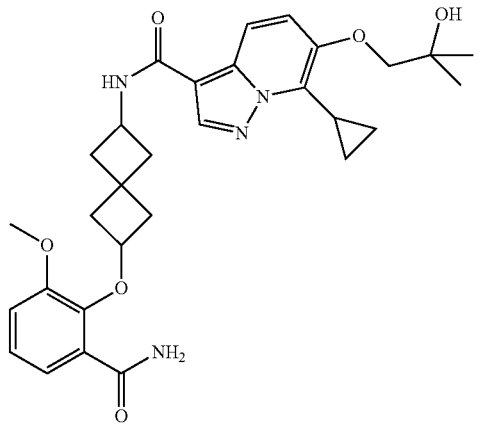 [SMILES: COc1cccc(C(N)=O)c1OC1CC2(CC(NC(=O)c3cnn4c(C5CC5)c(OCC(C)(C)O)ccc34)C2)C1]

EXAMPLE 208A

Preparation of benzyl (6-(2-cyano-6-methoxyphenoxy)spiro[3.3]heptan-2-yl)carbamate

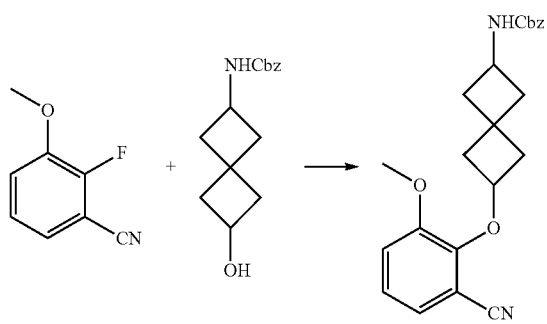 [SMILES: COc1cccc(C#N)c1F ; O=C(NC1CC2(CC(O)C2)C1)OCc1ccccc1 ; COc1cccc(C#N)c1OC1CC2(CC(NC(=O)OCc3ccccc3)C2)C1]

Intermediate 1 (93 mg, 0.36 mmol) was dissolved in anhydrous THF (2 mL). The reaction mixture was cooled in ice bath, and potassium tert-butoxide (1M in THF, 0.36 mL, 0.36 mmol) was added. An insoluble gum was formed. After 30 min, 2-fluoro-3-methoxybenzonitrile (134 mg, 0.89 mmol) was added in one portion. The ice bath was removed and the reaction was stirred at rt for 2 h, then put in the freezer o.n. The reaction was quenched with water (0.5 mL), concentrated and purified by flash chromatography (0-100% EtOAc/hexanes gradient) to give Example 208A (110 mg, 79%) as a clear oil. MS(ESI) m/z: 393.1 (M+H)$^+$. $^1$H NMR (400 MHz, CDCl$_3$) δ 7.43-7.28 (m, 5H), 7.16-7.02 (m, 3H), 5.07 (s, 2H), 4.82 (d, J=5.1 Hz, 1a), 4.72 (quin, J=7.2 Hz, 1H), 4.23-4.00 (m, 1H), 3.85 (s, 3H), 2.54-2.21 (m, 6H), 1.95 (t, J=10.1 Hz, 1H), 1.86 (t, J=9.7 Hz, 1H).

EXAMPLE 208B

Preparation of benzyl (6-(2-carbamoyl-6-methoxyphenoxy)spiro[3.3]heptan-2-yl)carbamate

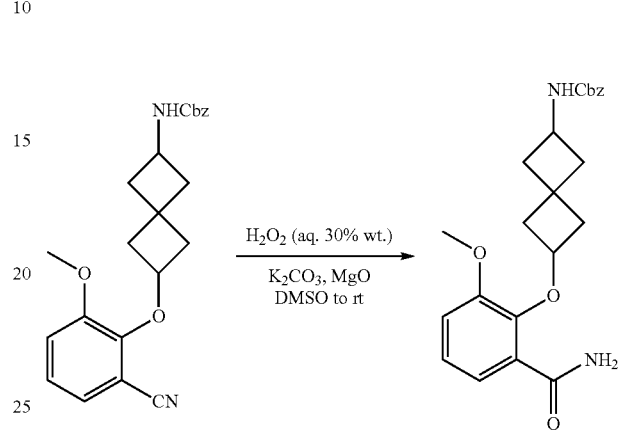

To a solution of Example 208A (110 mg, 0.28 mmol) in DMSO (2 mL) was added potassium carbonate (116 mg, 0.84 mmol), magnesium oxide (57.9 mg, 1.40 mmol) followed by hydrogen peroxide (0.32 mL, 3.08 mmol) dropwise. (Exotherm, ice bath should be used on larger scale). The reaction was stirred at rt o.n, diluted with EtOAc and acidified with 1N HCl. The organic phase was separated, washed with brine, dried (MgSO$_4$) and filtered. Solvent was removed under reduced pressure to afford Example 208B (115 mg, 100%) as a colorless oil. MS(ESI) m/z: 411.1 (M+H)$^+$.

EXAMPLE 208C

Preparation of 2-((6-aminospiro[3.3]heptan-2-yl)oxy)-3-methoxybenzamide

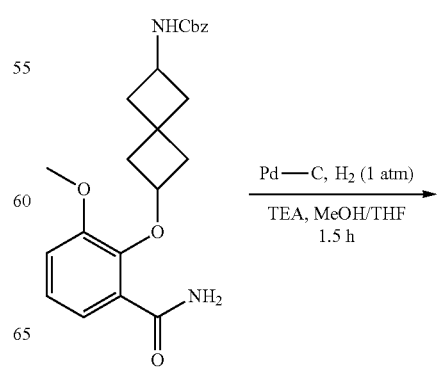

-continued

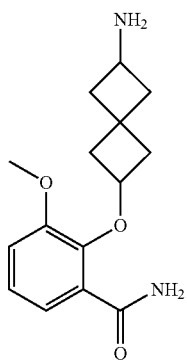

To a solution of Example 208B (115 mg, 0.28 mmol) and TEA (0.20 mL, 1.40 mmol) in THF (3 mL), and MeOH (3 mL) under N₂ was added Pd—C (10 wt %) (29.8 mg, 0.03 mmol). The reaction hydrogenated under H₂ atmosphere (balloon) for 125 h. The mixture was filtered and the filtrate was concentrated to afford Example 208C (62 mg, 80%) as a white solid. MS(ESI) m/z: 277.0 (M+H)⁺.

EXAMPLE 208

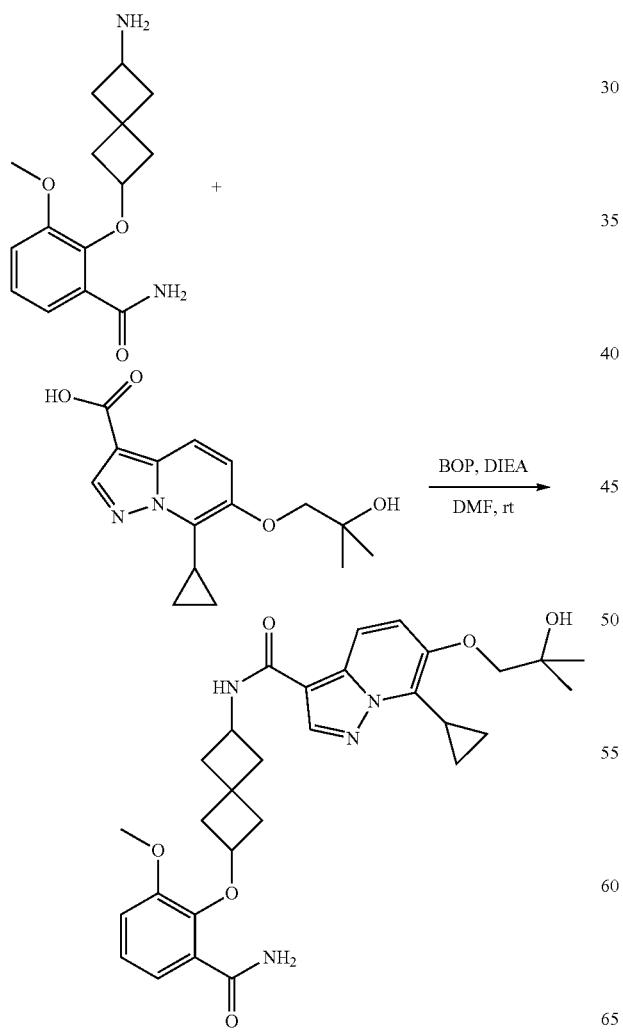

Example 208C (10 mg, 0.04 mmol) and Intermediate 4 (10.5 mg, 0.04 mmol) were dissolved in anhydrous DMF (1.5 mL), then DIEA (0.034 mL, 0.18 mmol) was added, followed by BOP (17.6 mg, 0.04 mmol). The reaction mixture was stirred at rt for 1 h, quenched with MeOH (0.1 mL), diluted with DMF (2 mL total volume), filtered, and purified by reverse phase HPLC to give Example 208 (11.9 mg, 60%). MS (ESI) m/z: 549.3 (M+H)⁺. ¹H NMR (500 MHz, DMSO-d₆) δ 8.48 (s, 1H), 8.25 (d, J=7.6 Hz, 1H), 8.02 (d, J=9.6 Hz, 1H), 7.64-7.49 (m, 2H), 7.45 (d, J=9.7 Hz, 1H), 7.23-7.05 (m, 3H), 4.56 (quin, J=7.2 Hz, 1H), 4.38-4.27 (m, 1H), 3.84-3.75 (m, 4H), 2.64-2.57 (m, 1H), 2.46-2.39 (m, 1H), 2.36-2.14 (m, 5H), 2.14-1.99 (m, 2H), 1.47 (d, J=3.6 Hz, 2H), 1.24 (s, 6H), 1.05 (dd, J=8.7, 2.2 Hz, 2H). Analytical HPLC RT=1.700 min (Method A) and 1.695 min (Method B), purity 100%.

EXAMPLE 209

Preparation of N-(6-(2-carbamoyl-6-methoxyphenoxy)spiro[3.3]heptan-2-yl)-6-(2-hydroxy-2-methylpropoxy)pyrazolo[1,5-a]pyridine-3-carboxamide

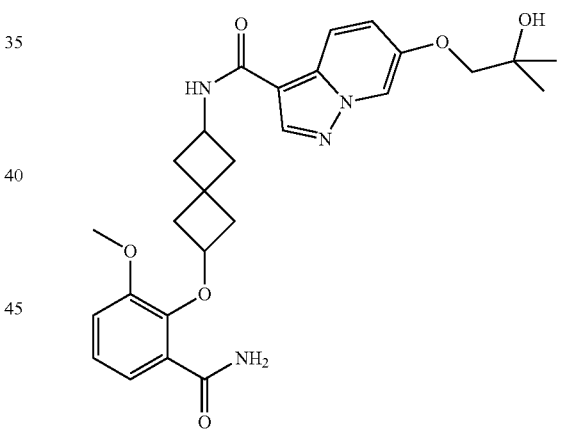

Example 209 (14.5 mg, 79%) was prepared in an analogous manner as Example 208 replacing Intermediate 4 with Intermediate 2 and coupling with Example 208C. MS (ESI) m/z: 508.9 (M+H)⁺. ¹H NMR (500 MHz, DMSO-d₆) δ 8.43 (s, 2H), 8.24 (d, J=7.3 Hz, 1H), 8.07 (d, J=9.6 Hz, 1H), 7.66-7.47 (m, 2H), 7.33-7.05 (m, 4H), 4.56 (t, J=7.2 Hz, 1H), 4.40-4.28 (m, 1H), 3.87-3.72 (m, 4H), 2.43 (d, J=5.1 Hz, 1H), 2.34-2.16 (m, 5H), 2.14-1.98 (m, 2H), 1.22 (s, 6H). Analytical HPLC RT=1.426 min (Method A) and 1.445 min (Method B), purity 100%.

EXAMPLE 210

Preparation of N-(6-(2-carbamoyl-5-methoxyphenoxy)spiro[3.3]heptan-2-yl)-6-(2-hydroxy-2-methylpropoxy)pyrazolo[1,5-a]pyridine-3-carboxamide

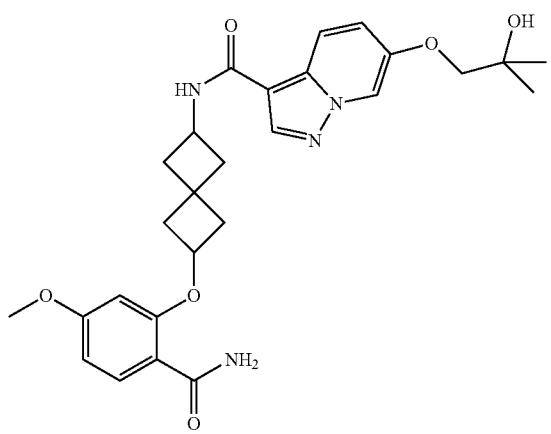 [SMILES: COc1ccc(C(N)=O)c(OC2CC3(CC(NC(=O)c4cnn5cc(OCC(C)(C)O)ccc45)C3)C2)c1]

Example 210 (10.8 mg, 56%) was prepared in an analogous manner as Example 208 replacing commercially available 2-fluoro-3-methoxybenzonitrile with 2-fluoro-4-methoxybenzonitrile and replacing Intermediate 4 with Intermediate 2.

MS (ESI) m/z: 508.9 (M+H)$^+$. $^1$H NMR (500 MHz, DMSO-d$_6$) δ 8.44 (d, J=2.9 Hz, 2H), 8.28 (d, J=7.2 Hz, 1H), 8.08 (d, J=9.6 Hz, 1H), 7.85 (d, J=8.7 Hz, 1H), 7.41 (d, J=5.7 Hz, 2H), 7.28 (d, J=9.6 Hz, 1H), 6.62 (d, J=8.7 Hz, 1H), 6.44 (s, 1H), 4.82 (t, J=6.6 Hz, 1H), 4.50-4.31 (m, 1H), 3.87-3.73 (m, 4H), 2.74 (br. s., 1H), 2.34 (br. s., 1H), 2.28-2.06 (m, 4H), 1.29-1.15 (m, 6H). Analytical HPLC RT=1.442 min (Method A) and 1.472 min (Method B), purity 96%.

EXAMPLE 211

Preparation of N-(6-(2-carbamoyl-5-methoxyphenoxy)spiro[3.3]heptan-2-yl)-7-cyclopropyl-6-(2-hydroxy-2-methylpropoxy)pyrazolo[1,5-a]pyridine-3-carboxamide

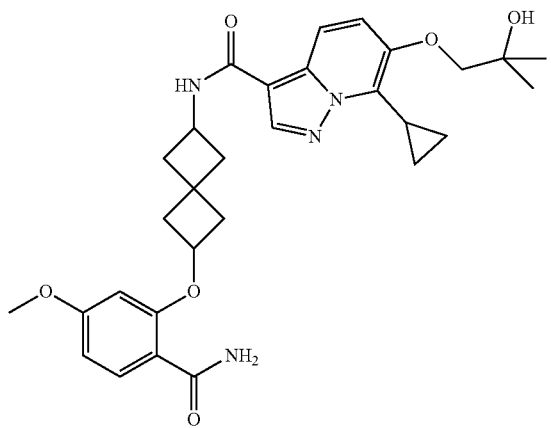 [SMILES: COc1ccc(C(N)=O)c(OC2CC3(CC(NC(=O)c4cnn5c(C6CC6)c(OCC(C)(C)O)ccc45)C3)C2)c1]

Example 211 (10.8 mg, 53%) was prepared in an analogous manner as Example 208 replacing commercially available 2-fluoro-3-methoxybenzonitrile with 2-fluoro-4-methoxybenzonitrile. MS (ESI) m/z: 549.2 (M+H)$^+$. $^1$H NMR (500 MHz, DMSO-d$_6$) δ 8.50 (s, 1H), 8.27 (d, J=7.5 Hz, 1H), 8.03 (d, J=9.6 Hz, 1H), 7.86 (d, J=8.8 Hz, 1H), 7.46 (d, J=9.8 Hz, 1H), 7.41 (br. s., 2H), 6.62 (d, J=8.6 Hz, 1H), 6.44 (s, 1H), 4.82 (t, J=6.8 Hz, 1H), 4.42-4.31 (m, 1H), 3.83-3.75 (m, 4H), 2.78-2.68 (m, 1H), 2.64-2.57 (m, 1H), 2.38-2.29 (m, 1H), 2.27-2.10 (m, 4H), 1.48 (d, J=3.6 Hz, 2H), 1.24 (s, 6H), 1.09-1.00 (m, 2H). Analytical HPLC RT=1.655 min (Method A) and 1.678 min (Method B), purity 98%.

EXAMPLE 212

Preparation of N-(6-(2-carbamoyl-4-methoxyphenoxy)spiro[3.3]heptan-2-yl)-6-(2-hydroxy-2-methylpropoxy)pyrazolo[1,5-a]pyridine-3-carboxamide

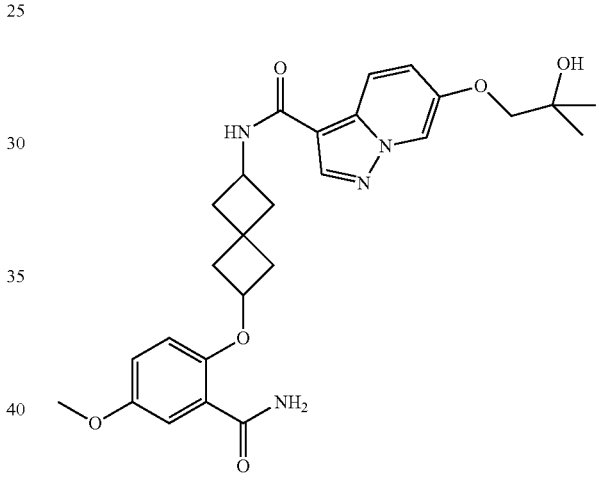

Example 212 (2.6 mg, 27%) was prepared in an analogous manner as Example 208 replacing commercially available 2-fluoro-3-methoxybenzonitrile with 2-fluoro-5-methoxybenzonitrile, and Intermediate 4 with Intermediate 2. MS (ESI) m/z: 509.0 (M+H)$^+$. $^1$H NMR (500 MHz, DMSO-d$_6$) δ 8.43 (d, J=3.2 Hz, 2H), 8.29 (d, J=7.7 Hz, 1H), 8.07 (d, J=9.7 Hz, 1H), 7.61 (d, J=9.3 Hz, 2H), 7.37 (d, J=3.2 Hz, 1H), 7.28 (dd, J=9.6, 1.8 Hz, 1H), 7.02 (dd, J=8.9, 3.1 Hz, 1H), 6.92 (d, J=9.0 Hz, 1H), 4.71 (t, J=6.8 Hz, 1H), 4.41-4.31 (m, 1H), 3.79 (s, 2H), 3.73 (s, 3H), 2.69 (dt, J=11.0, 5.6 Hz, 1H), 2.46-2.39 (m, 1H), 2.37-2.25 (m, 1H), 2.23-2.09 (m, 4H), 1.25-1.18 (m, 6H). Analytical HPLC RT=1.500 min (Method A) and 1.504 min (Method B), purity 95%.

EXAMPLE 213

Preparation of N-(6-(2-carbamoyl-4-methoxyphenoxy)spiro[3.3]heptan-2-yl)-7-cyclopropyl-6-(2-hydroxy-2-methylpropoxy)pyrazolo[1,5-a]pyridine-3-carboxamide

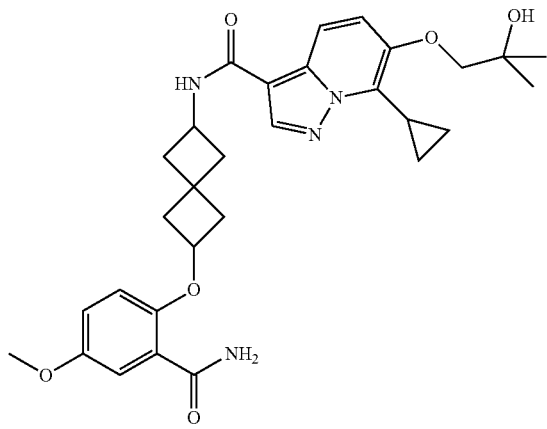 [SMILES: COc1ccc(OC2CC3(CC(NC(=O)c4cnn5c(C6CC6)c(OCC(C)(C)O)ccc45)C3)C2)c(C(N)=O)c1]

Example 213 (2.8 mg, 27%) was prepared in an analogous manner as Example 208 replacing commercially available 2-fluoro-3-methoxybenzonitrile with 2-fluoro-5-methoxybenzonitrile MS (ESI) m/z: 549.4 (M+H)$^+$. $^1$H NMR (500 MHz, DMSO-d$_6$) δ 8.50 (s, 1H), 8.27 (d, J=7.7 Hz, 1H), 8.03 (d, J=9.7 Hz, 1H), 7.61 (d, J=7.6 Hz, 2H), 7.46 (d, J=9.7 Hz, 1H), 7.37 (d, J=3.3 Hz, 1H), 7.02 (dd, J=9.0, 3.2 Hz, 1H), 6.93 (d, J=9.0 Hz, 1H), 4.72-4.66 (m, 1H), 4.42-4.32 (m, 1H), 3.79 (s, 2H), 3.73 (s, 3H), 2.73-2.65 (m, 1H), 2.64-2.56 (m, 1H), 2.46-2.40 (m, 1H), 2.37-2.25 (m, 1H), 2.24-2.11 (m, 4H), 1.52-1.44 (m, 2H), 1.29-1.19 (m, 6H), 1.05 (dd, J=8.8, 2.4 Hz, 2H). Analytical HPLC RT=1.590 min (Method A) and 1.619 min (Method B), purity 96%.

EXAMPLE 214

Preparation of N-(6-(2-carbamoyl-6-methylphenoxy)spiro[3.3]heptan-2-yl)-7-cyclopropyl-6-(2-hydroxy-2-methylpropoxy)pyrazolo[1,5-a]pyridine-3-carboxamide

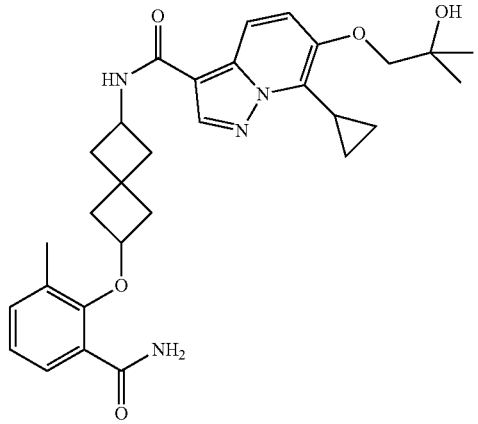 [SMILES: Cc1cccc(C(N)=O)c1OC1CC2(CC(NC(=O)c3cnn4c(C5CC5)c(OCC(C)(C)O)ccc34)C2)C1]

Example 214 (7.3 mg, 97%) was prepared in an analogous manner as Example 208 replacing commercially available 2-fluoro-3-methoxybenzonitrile with 2-fluoro-3-methylbenzonitrile. MS (ESI) m/z: 533.1 (M+H)$^+$. $^1$H NMR (500 MHz, DMSO-d$_6$) δ 8.49 (s, 1H), 8.25 (d, J=7.6 Hz, 1H), 8.02 (d, J=9.6 Hz, 1H), 7.56 (s, 1H), 7.51-7.42 (m, 2H), 7.37 (d, J=7.5 Hz, 1H), 7.30 (d, J=7.2 Hz, 1H), 7.05 (t, J=7.5 Hz, 1H), 4.39-4.27 (m, 2H), 3.79 (s, 2H), 2.64-2.57 (m, 1H), 2.48-2.43 (m, 1H), 2.33-2.17 (m, 8H), 2.15-1.99 (m, 2H), 1.52-1.42 (m, 2H), 1.24 (s, 6H), 1.08-1.01 (m, 2H). Analytical HPLC RT=1.634 min (Method A) and 1.675 min (Method B), purity 97%.

EXAMPLE 215

Preparation of N-(6-(2-carbamoyl-5-methylphenoxy)spiro[3.3]heptan-2-yl)-6-(2-hydroxy-2-methylpropoxy)pyrazolo[1,5-a]pyridine-3-carboxamide

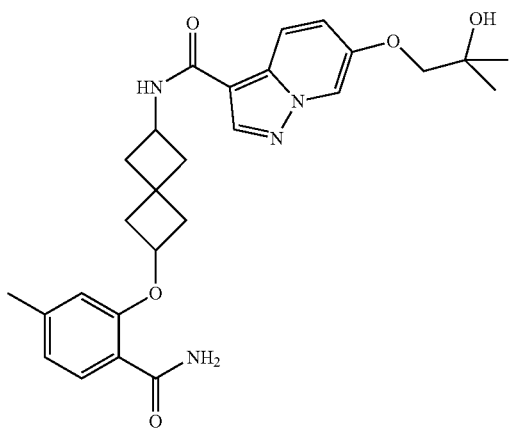 [SMILES: Cc1ccc(C(N)=O)c(OC2CC3(CC(NC(=O)c4cnn5cc(OCC(C)(C)O)ccc45)C3)C2)c1]

Example 215 (6.8 mg, 31%) was prepared in an analogous manner as Example 208 replacing commercially available 2-fluoro-3-methoxybenzonitrile with 2-fluoro-4-methylbenzonitrile and Intermediate 4 with Intermediate 2. MS (ESI) m/z: 493.3 (M+H)$^+$. $^1$H NMR (500 MHz, DMSO-d$_6$) δ 8.51-8.37 (m, 1H), 8.29 (d, J=7.6 Hz, 1H), 8.08 (d, J=9.6 Hz, 1H), 7.74 (d, J=7.9 Hz, 1H), 7.49 (d, J=13.0 Hz, 2H), 7.28 (dd, J=9.6, 1.8 Hz, 1H), 6.84 (d, J=7.9 Hz, 1H), 6.79 (s, 1H), 4.83-4.74 (m, 2H), 4.43-4.31 (m, 1H), 3.79 (s, 2H), 2.75 (dt, J=11.1, 5.8 Hz, 1H), 2.39-2.28 (m, 4H), 2.26-2.12 (m, 4H), 1.28-1.17 (m, 6H). Analytical HPLC RT=1.449 min (Method A) and 1.484 min (Method B), purity 95%.

EXAMPLE 216

Preparation of N-(6-(2-carbamoyl-4-methylphenoxy)spiro[3.3]heptan-2-yl)-7-cyclopropyl-6-(2-hydroxy-2-methylpropoxy)pyrazolo[1,5-a]pyridine-3-carboxamide

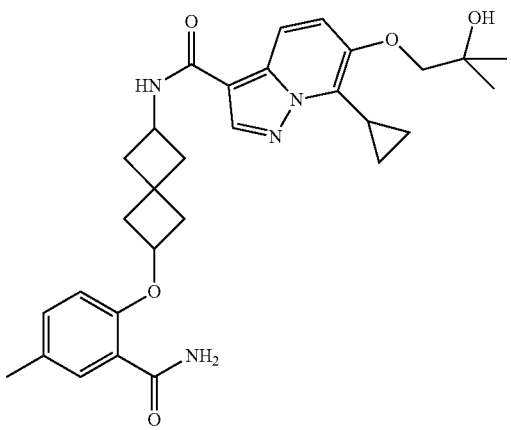 [SMILES: Cc1ccc(OC2CC3(CC(NC(=O)c4cnn5c(C6CC6)c(OCC(C)(C)O)ccc45)C3)C2)c(C(N)=O)c1]

Example 216 (8 mg, 35%) was prepared in an analogous manner as Example 208 replacing commercially available 2-fluoro-3-methoxybenzonitrile with 2-fluoro-5-methylbenzonitrile. MS (ESI) m/z: 533.3 (M+H)$^+$. $^1$H NMR (500 MHz, DMSO-d$_6$) δ 8.49 (s, 1H), 8.29 (d, J=7.6 Hz, 1H), 8.02 (d, J=9.6 Hz, 1H), 7.62 (s, 1H), 7.57 (br. s., 1H), 7.50 (br. s., 1H), 7.46 (d, J=9.7 Hz, 1H), 7.26-7.20 (m, 1H), 6.86 (d, J=8.4 Hz, 1H), 4.73 (t, J=6.8 Hz, 1H), 4.40-4.32 (m, 1H), 3.78 (s, 1H), 2.73-2.65 (m, 1H), 2.63-2.57 (m, 1H), 2.47-2.41 (m, 1H), 2.32 (dt, J=11.7, 5.9 Hz, 1H), 2.25 (s, 3H), 2.18-2.09 (m, 3H), 1.49-1.43 (m, 2H), 1.27-1.20 (m, 6H), 1.09-1.01 (m, 2H). Analytical HPLC RT=1.772 min (Method A) and 1.782 min (Method B), purity 97%.

EXAMPLE 217

Preparation of N-(6-(2-carbamoyl-5-methylphenoxy)spiro[3.3]heptan-2-yl)-7-cyclopropyl-6-(2-hydroxy-2-methylpropoxy)pyrazolo[1,5-a]pyridine-3-carboxamide

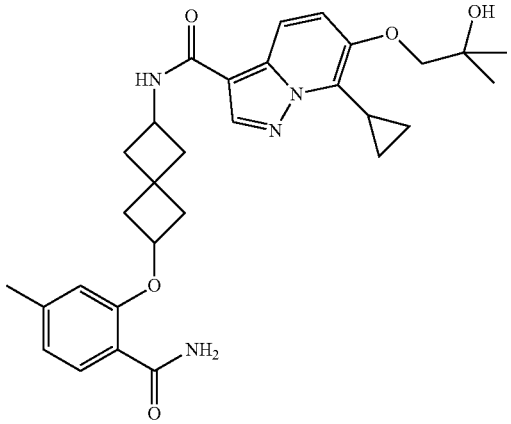 [SMILES: Cc1ccc(C(N)=O)c(OC2CC3(CC(NC(=O)c4cnn5c(C6CC6)c(OCC(C)(C)O)ccc45)C3)C2)c1]

Example 217 (7.3 mg, 32%) was prepared in an analogous manner as Example 208 replacing commercially available 2-fluoro-3-methoxybenzonitrile with 2-fluoro-4-methylbenzonitrile. MS (ESI) m/z: 533.4 (M+H)$^+$. $^1$H NMR (500 MHz, DMSO-d$_6$) δ 8.50 (s, 1H), 8.28 (d, J=7.6 Hz, 1H), 8.03 (d, J=9.6 Hz, 1H), 7.74 (d, J=7.9 Hz, 1H), 7.55-7.42 (m, 3H), 6.84 (d, J=7.9 Hz, 1H), 6.79 (s, 1H), 4.78 (t, J=6.8 Hz, 1H), 4.45-4.31 (m, 1H), 3.79 (s, 2H), 2.79-2.70 (m, 1H), 2.65-2.57 (m, 1H), 2.33 (s, 4H), 2.28-2.09 (m, 4H), 1.52-1.43 (m, 2H), 1.29-1.18 (m, 6H), 1.06 (dd, J=8.7, 2.3 Hz, 2H). Analytical HPLC RT=1.657 min (Method A) and 1.677 min (Method B), purity 97%.

EXAMPLE 218

Preparation of N-(6-(2-carbamoyl-4-methylphenoxy)spiro[3.3]heptan-2-yl)-6-(2-hydroxy-2-methylpropoxy)pyrazolo[1,5-a]pyridine-3-carboxamide

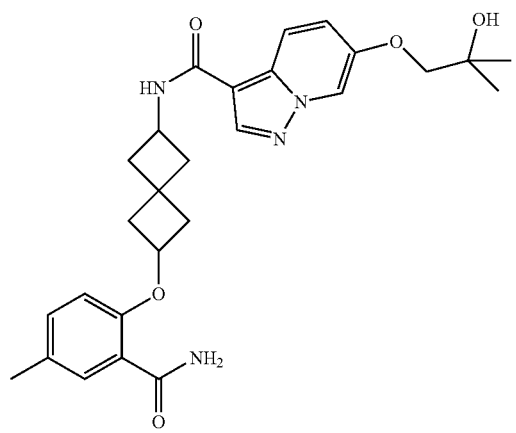 [SMILES: Cc1ccc(OC2CC3(CC(NC(=O)c4cnn5cc(OCC(C)(C)O)ccc45)C3)C2)c(C(N)=O)c1]

Example 218 (4.9 mg, 23%) was prepared in an analogous manner as Example 208 replacing commercially available 2-fluoro-3-methoxybenzonitrile with 2-fluoro-5-methylbenzonitrile and Intermediate 4 with Intermediate 2. MS (ESI) m/z: 493.2 (M+H)$^+$. $^1$H NMR (500 MHz, DMSO-d$_6$) δ 8.45-8.39 (m, 2H), 8.30 (d, J=7.6 Hz, 1H), 8.07 (d, J=9.6 Hz, 1H), 7.62 (s, 1H), 7.56 (br. s., 1H), 7.50 (br. s., 1H), 7.33-7.20 (m, 2H), 6.86 (d, J=8.4 Hz, 1H), 4.73 (t, J=6.9 Hz, 1H), 4.41-4.30 (m, 1H), 3.79 (s, 2H), 2.70 (dd, J=10.7, 5.3 Hz, 1H), 2.48-2.41 (m, 1H), 2.32 (d, J=5.0 Hz, 1H), 2.25 (s, 3H), 2.21-2.09 (m, 4H), 1.21 (s, 6H). Analytical HPLC RT=1.558 min (Method A) and 1.558 min (Method B), purity 97%.

EXAMPLE 219

Preparation of N-(6-(2-carbamoyl-5-(difluoromethoxy)phenoxy)spiro[3.3]heptan-2-yl)-6-(2-hydroxy-2-methylpropoxy)pyrazolo[1,5-a]pyridine-3-carboxamide

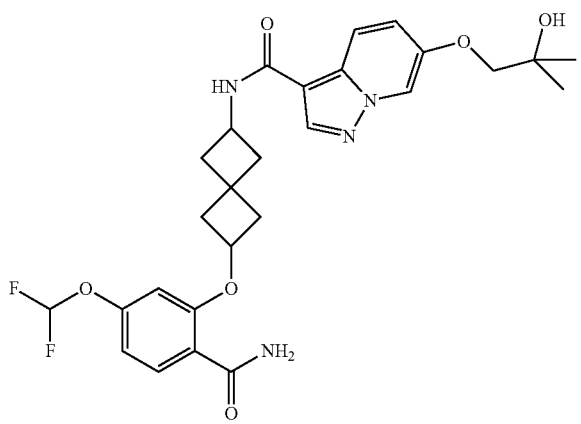 [SMILES: CC(C)(O)COc1ccc2c(C(=O)NC3CC4(C3)CC(Oc3cc(OC(F)F)ccc3C(N)=O)C4)cnn2c1]

Example 219 (7.5 mg, 52%) was prepared in an analogous manner as Example 208 replacing commercially available 2-fluoro-3-methoxybenzonitrile with 2-fluoro-4-(difluoromethoxy)benzonitrile and Intermediate 4 with Intermediate 2. MS (ESI) m/z: 544.9 (M+H)$^+$. $^1$H NMR (500 MHz, DMSO-d$_6$) δ 8.44 (br. s., 2H), 8.28 (d, J=7.6 Hz, 1H), 8.08 (d, J=9.7 Hz, 1H), 7.86 (d, J=8.6 Hz, 1H), 7.58 (br. s., 1H), 7.49 (br. s., 1H), 7.37 (s, 1H), 7.28 (dd, J=9.6, 1.9 Hz, 1H), 6.82 (d, J=8.6 Hz, 1H), 6.73 (d, J=1.9 Hz, 1H), 4.82 (quin, J=6.8 Hz, 1H), 4.73 (s, 1H), 4.43-4.31 (m, 1H), 3.79 (s, 2H), 2.74 (dt, J=10.9, 5.6 Hz, 1H), 2.39-2.30 (m, 1H), 2.28-2.11 (m, 4H), 1.29-1.17 (m, 6H). Analytical HPLC RT=1.563 min (Method A) and 1.548 min (Method B), purity 97%.

EXAMPLE 220

Preparation of N-(6-(2-carbamoyl-5-chlorophenoxy)spiro[3.3]heptan-2-yl)-6-(2-hydroxy-2-methylpropoxy)pyrazolo[1,5-a]pyridine-3-carboxamide

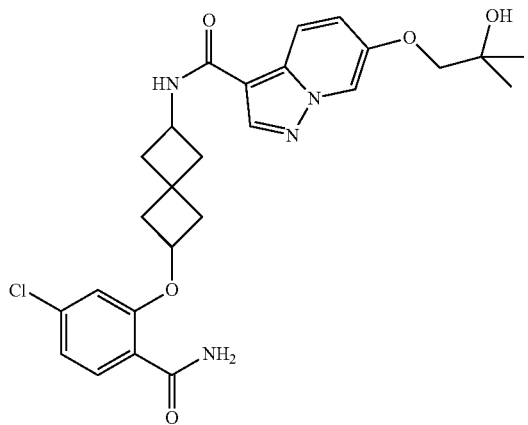 [SMILES: CC(C)(O)COc1ccc2c(C(=O)NC3CC4(C3)CC(Oc3cc(Cl)ccc3C(N)=O)C4)cnn2c1]

Example 220 (2.6 mg, 20%) was prepared in an analogous manner as Example 208 replacing commercially available 2-fluoro-3-methoxybenzonitrile with 4-chloro-2-fluorobenzonitrile and Intermediate 4 with Intermediate 2. TMSI was used for Cbz deprotection analogous to Example 221C. MS (ESI) m/z: 513.1 (M+H)$^+$. $^1$H NMR (500 MHz, DMSO-d$_6$) δ 8.46-8.39 (m, 2H), 8.30 (d, J=7.5 Hz, 1H), 8.07 (d, J=9.6 Hz, 1H), 7.77 (d, J=8.3 Hz, 1H), 7.61 (br. s., 1H), 7.53 (br. s., 1H), 7.28 (d, J=9.8 Hz, 1H), 7.08 (d, J=8.3 Hz, 1H), 7.02 (s, 1H), 4.83 (t, J=6.9 Hz, 1H), 4.80 (s, 1H), 4.41-4.30 (m, 1H), 3.79 (s, 2H), 2.76-2.67 (m, 1H), 2.33 (d, J=5.0 Hz, 1H), 2.26-2.10 (m, 4H), 1.26-1.17 (m, 6H). Analytical HPLC RT=1.601 min (Method A) and 1.587 min (Method B), purity 960%.

EXAMPLE 221

Preparation of N-(6-(2-carbamoyl-5-chlorophenoxy)spiro[3.3]heptan-2-yl)-6-(2-hydroxy-2-methylpropoxy)pyrazolo[1,5-a]pyridine-3-carboxamide

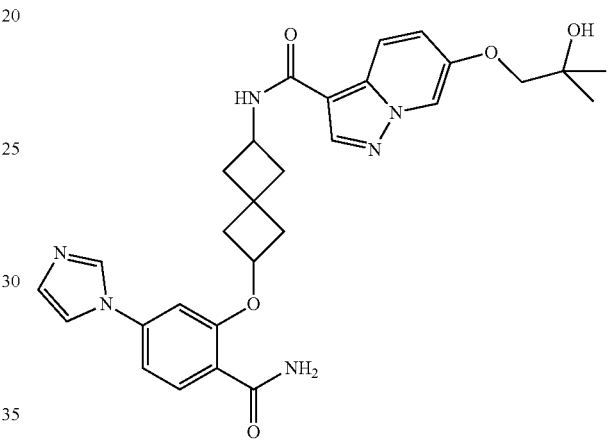

EXAMPLE 221A

Preparation of benzyl (6-(2-cyano-5-(1H-imidazol-1-yl)phenoxy)spiro[3.3]heptan-2-yl)carbamate

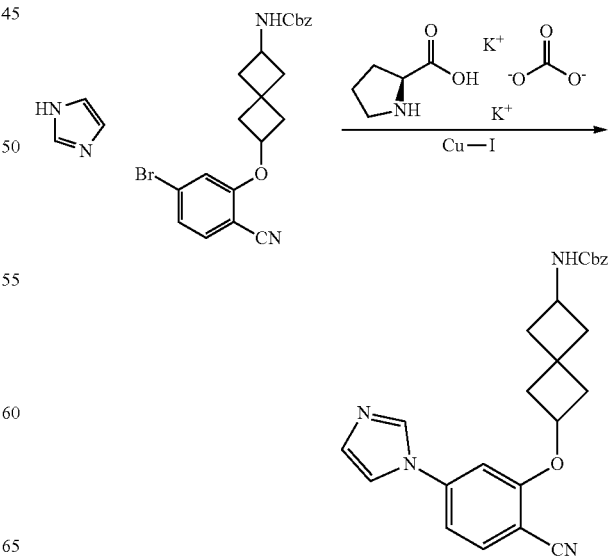

A mixture of benzyl (6-(5-bromo-2-cyanophenoxy)spiro[3.3]heptan-2-yl)carbamate (Intermediate 209A) (50 mg, 0.11 mmol), imidazole (7.0 mg, 0.10 mmol), K$_2$CO$_3$ (28.5 mg, 0.21 mmol), L-proline (11.9 mg, 0.10 mmol) and copper(I) iodide (3.9 mg, 0.02 mmol) in DMSO (5 mL) was heated at 130° C. for 2 h then stirred at it o.n. Water was added and the mixture was extracted with EtOAc (3×). The combined organic layer was concentrated and purified by flash chromatography (0-100% EtOAc/hexanes, then 0-10% MeOH/CH$_2$Cl$_2$ gradient) to give Example 221A (38 mg, 86%). MS(ESI) m/z: 429.0 (M+H)$^+$. $^1$H NMR (400 MHz, CDCl$_3$) δ 7.88 (br s, 1H), 7.66 (d, J=8.4 Hz, 1H), 7.41-7.21 (m, 6H), 7.03 (dd, J=8.4, 2.0 Hz, 1H), 6.75 (d, J=1.5 Hz, 1H), 5.08 (s, 2H), 5.03 (br d, J=6.8 Hz, 1H), 4.73 (br t, J=6.7 Hz, 1H), 4.19-4.08 (m, 1H), 2.75-2.65 (m, 1H), 2.57-2.26 (m, 5H), 2.08-1.96 (m, 2H).

EXAMPLE 221B

Preparation of benzyl (6-(2-carbamoyl-5-(1H-imidazol-1-yl)phenoxy)spiro[3.3]heptan-2-yl)carbamate

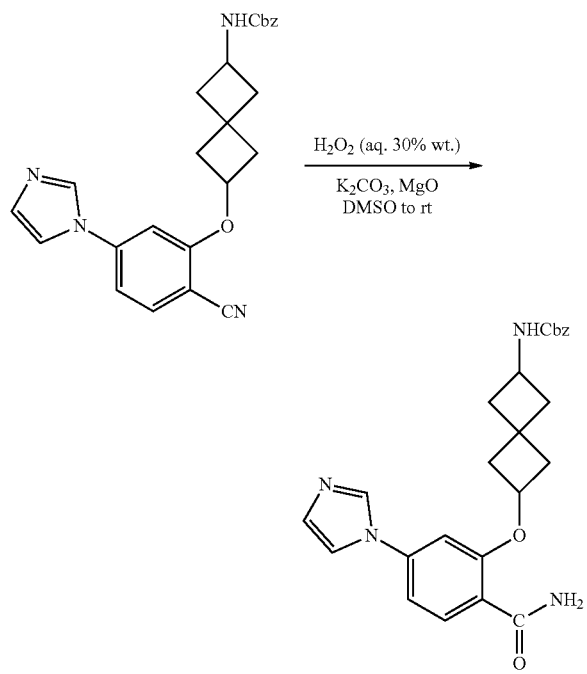

To a solution of Example 221A (38 mg, 0.089 mmol) in DMSO (1 mL) was added potassium carbonate (36.8 mg, 0.27 mmol), magnesium oxide (18.3 mg, 0.44 mmol) followed by hydrogen peroxide (400 μL, 3.92 mmol) dropwise. After 2 h, the reaction mixture was diluted with water and 1N HCl to dissolve MgO, extracted with EtOAc (3×). The combined organic layer was concentrated. Residual DMSO was removed by adding and decanting with water (1 mL), then the residue was dried to give Example 221B (27 mg, 68%) as a sticky white solid that was used without further purification. MS(ESI) m/z: 447.1 (M+H)$^+$.

EXAMPLE 221C

Preparation of 2-((6-aminospiro[3.3]heptan-2-yl)oxy)-4-(1H-imidazol-1-yl)benzamide

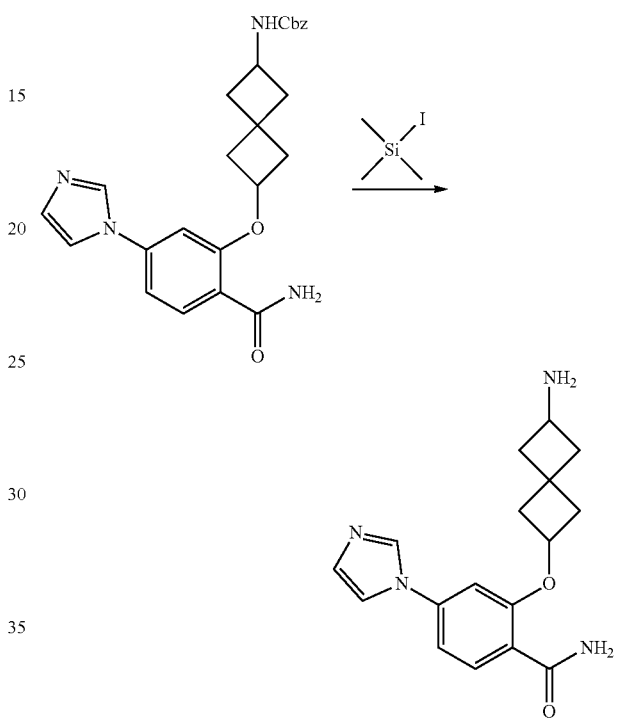

To a solution of Example 221B (17 mg, 0.04 mmol) in CH$_2$Cl$_2$ (1 mL) at 0° C. was added iodotrimethylsilane (20 μL, 0.15 mmol) under N$_2$. After 2 h at 0° C., the reaction was diluted with CH$_2$Cl$_2$, basified with NaHCO$_3$ (sat) and extracted with CH$_2$Cl$_2$ (2×). The combined organic layer was concentrated to dryness to give Example 221C (11.89 mg, 100%) as a yellow glass which was used without further purification. MS(ESI) m/z: 313.1 (M+H)$^+$.

EXAMPLE 221

Example 221 (1.7 mg, 9%) was prepared in an analogous manner as Example 208 replacing Intermediate 4 with Intermediate 2 and coupling with Example 221C. MS (ESI) m/z: 545.2 (M+H)$^+$. $^1$H NMR (500 MHz, DMSO-d$_6$) δ 8.47-8.37 (m, 3H), 8.30 (d, J=7.5 Hz, 1H), 8.08 (d, J=9.7 Hz, 1H), 7.94-7.89 (m, 1H), 7.86 (s, 1H), 7.63 (br. s., 1H), 7.57 (br. s., 1H), 7.35-7.24 (m, 2H), 7.15 (br. s., 2H), 4.99 (t, J=6.8 Hz, 1H), 4.43-4.34 (m, 1H), 3.79 (s, 2H), 3.43 (br. s., 1H), 2.85-2.74 (m, 1H), 2.63-2.57 (m, 1H), 2.39-2.30 (m, 1H), 2.28-2.12 (m, 4H), 1.22 (s, 6H). Analytical HPLC RT=1.139 min (Method A) and 0.977 min (Method B), purity 91%.

EXAMPLE 222

Preparation of N-(6-(2-carbamoyl-5-(pyrimidin-2-yl)phenoxy)spiro[3.3]heptan-2-yl)-6-(2-hydroxy-2-methylpropoxy)pyrazolo[1,5-a]pyridine-3-carboxamide

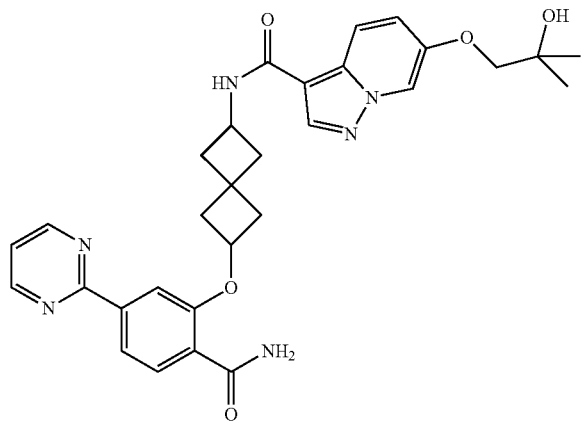 [SMILES: CC(C)(O)COc1ccc2c(C(=O)NC3CC4(C3)CC(Oc3cc(-c5ncccn5)ccc3C(N)=O)C4)cnn2c1]

EXAMPLE 222A

Preparation of 2-fluoro-pyrimidin-2-yl)benzonitrile

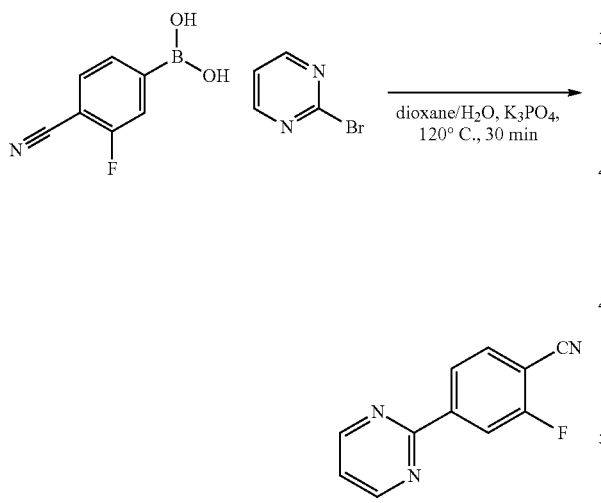

A solution of 2-bromopyrimidine (38.6 mg, 0.24 mmol), (4-cyano-3-fluorophenyl)boronic acid (40 mg, 0.24 mmol) and phosphoric acid, potassium salt (3 M aq.) (0.40 mL, 1.21 mmol) in dioxane (3 mL) was purged with $N_2$. Pd-XPhos G3 (2.05 mg, 2.43 μmol) was added. The reaction mixture was microwaved at 120° C. for 30 min. Water was added and the mixture was extracted with EtOAc. The organic layer was concentrated then purified by flash chromatography (0-10% EtOAc/hexanes gradient) to give Example 222A (35 mg, 73%). MS(ESI) m/z: 200.0 (M+H)$^+$. $^1$H NMR (400 MHz, CDCl$_3$) δ 8.86 (d, J=4.8 Hz, 2H), 8.45-8.29 (m, 2H), 7.74 (dd, J=8.1, 6.4 Hz, 1H), 7.36-7.28 (m, 1H).

EXAMPLE 222

Example 222 (6.4 mg, 25%) was prepared in an analogous manner as Example 208 replacing commercially available 2-fluoro-3-methoxybenzonitrile with Example 222A and Intermediate 4 with Intermediate 2. MS (ESI) m/z: 557.2 (M+H)$^+$. $^1$H NMR (500 MHz, DMSO-d$_6$) δ 8.96 (d, J=4.9 Hz, 2H), 8.51-8.37 (m, 2H), 8.31 (d, J=7.6 Hz, 1H), 8.06 (dd, J=16.5, 9.0 Hz, 2H), 7.96-7.85 (m, 2H), 7.65 (br. s., 2H), 7.51 (t, J=4.8 Hz, 1H), 7.36-7.20 (m, 1H), 4.90 (t, J=6.8 Hz, 1H), 4.47-4.32 (m, 1H), 3.79 (s, 2H), 2.83-2.70 (m, 1H), 2.63-2.56 (m, 1H), 2.42-2.30 (m, 2H), 2.27 (dd, J=11.7, 6.9 Hz, 1H), 2.22-2.11 (m, 2H), 1.22 (s, 6H). Analytical HPLC RT=1.288 min (Method A) and 1.343 min (Method B), purity 99%.

EXAMPLE 223

Preparation of N-(6-(2-carbamoyl-5-(1H-pyrazol-1-yl)phenoxy)spiro[3.3]heptan-2-yl)-6-(2-hydroxy-2-methylpropoxy)pyrazolo[1,5-a]pyridine-3-carboxamide

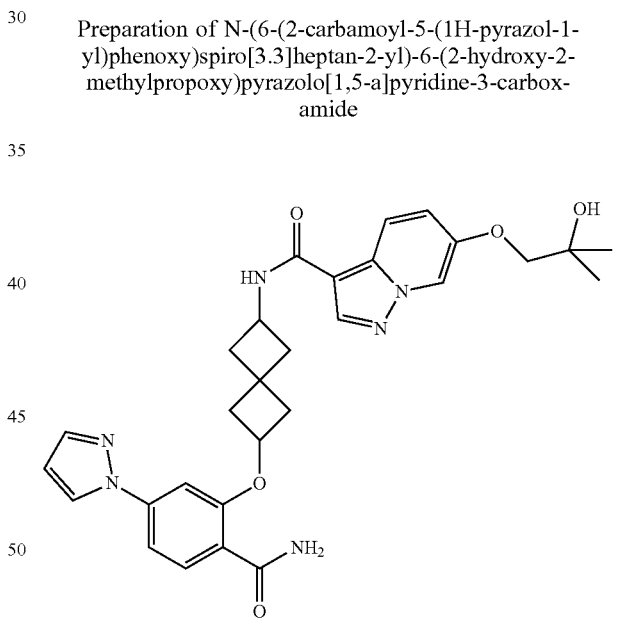

Example 223 (13.3 mg, 28%) was prepared in an analogous manner as Example 221 replacing commercially available imidazole with 1H-pyrazole and Pd/C H$_2$ was used for Cbz deprotection analogous to Example 208. MS (ESI) m/z: 545.1 (M+H)$^+$. $^1$H NMR (500 MHz, DMSO-d$_6$) δ 8.64 (d, J=2.4 Hz, 1H), 8.49-8.41 (m, 2H), 8.26 (d, J=7.6 Hz, 1H), 8.09 (d, J=9.5 Hz, 1H), 7.94 (d, J=8.5 Hz, 1H), 7.81 (s, 1H), 7.62-7.47 (m, 3H), 7.39 (s, 1H), 7.28 (dd, J=9.6, 2.0 Hz, 1H), 6.60 (s, 1H), 4.95 (t, J=6.7 Hz, 1H), 4.45-4.33 (m, 1H), 3.80 (s, 2H), 2.84-2.73 (m, 1H), 2.64-2.56 (m, 1H), 2.42-2.33 (m, 1H), 2.33-2.23 (m, 2H), 2.22-2.13 (m, 2H), 1.22 (s, 6H). Analytical HPLC RT=1.357 min (Method A) and 1.388 min (Method B), purity 100%.

EXAMPLE 224

Preparation of N-(6-(2-carbamoyl-5-(4-methylpiperazin-1-yl)phenoxy)spiro[3.3]heptan-2-yl)-6-(2-hydroxy-2-methylpropoxy)pyrazolo[1,5-a]pyridine-3-carboxamide

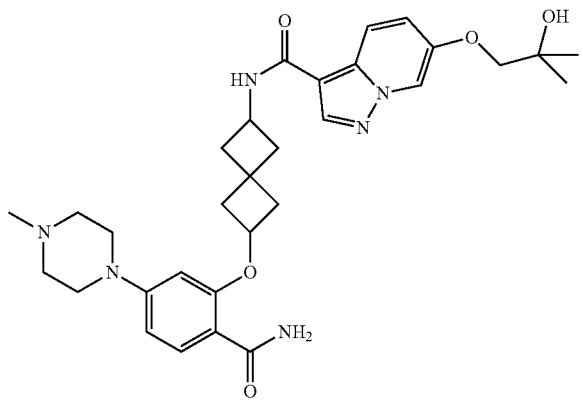 [SMILES: CN1CCN(c2ccc(C(N)=O)c(OC3CC4(CC(NC(=O)c5cnn6cc(OCC(C)(C)O)ccc56)C4)C3)c2)CC1]

EXAMPLE 224A

Preparation of benzyl (6-(2-cyano-5-(4-methylpiperazin-1-yl)phenoxy)spiro[3.3]heptan-2-yl)carbamate

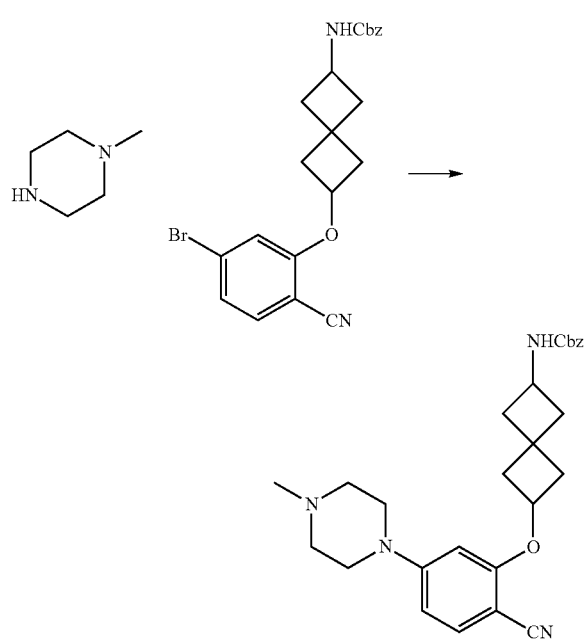

A solution of Intermediate 85A (100 mg, 0.23 mmol), 1-methylpiperazine (0.035 mL, 0.32 mmol), Cs$_2$CO$_3$ (103 mg, 0.32 mmol) and BINAP (28.2 mg, 0.05 mmol) in toluene (2 mL) was purged with N$_2$. Pd$_2$(dba)$_3$ (20.8 mg, 0.02 mmol) was added and the mixture was heated at 110° C. o.n. Water was added and the mixture was extracted with EtOAc (3×). The combined organic layer was concentrated and purified by flash chromatography (0-100% EtOAc/hexanes then 0-15% MeOH/CH$_2$Cl$_2$ gradient) to give Example 224A (57 mg, 54.6%) as a brown oil. MS(ESI) m/z: 461.1 (M+H)$^+$.

EXAMPLE 224

Example 224 (17.1 mg, 65%) was prepared in an analogous manner as Example 208 replacing Example 208A with Example 224A and Intermediate 4 with Intermediate 2. MS (ESI) m/z: 577.4 (M+H)$^+$. $^1$H NMR (500 MHz, DMSO-d$_6$) δ 8.43 (d, J=3.7 Hz, 2H), 8.25 (d, J=7.6 Hz, 1H), 8.08 (d, J=9.8 Hz, 1H), 7.76 (d, J=8.9 Hz, 1H), 7.36 (br. s., 1H), 7.28 (d, J=9.5 Hz, 1H), 7.21 (br. s., 1H), 6.57 (d, J=8.9 Hz, 1H), 6.30 (s, 1H), 4.84 (t, J=6.9 Hz, 1H), 4.44-4.32 (m, 1H), 3.80 (s, 2H), 3.26 (m, 3H), 2.80-2.70 (m, 1H), 2.45 (m, 4H), 2.38-2.29 (m, 2H), 2.27-2.10 (m, 7H), 1.22 (s, 6H). Analytical HPLC RT=1.294 min (Method A) and 0.975 min (Method B), purity 96%.

EXAMPLE 225

Preparation of N-(6-(2-carbamoyl-5-(pyridin-4-yl)phenoxy)spiro[3.3]heptan-2-yl)-6-(2-hydroxy-2-methylpropoxy)pyrazolo[1,5-a]pyridine-3-carboxamide

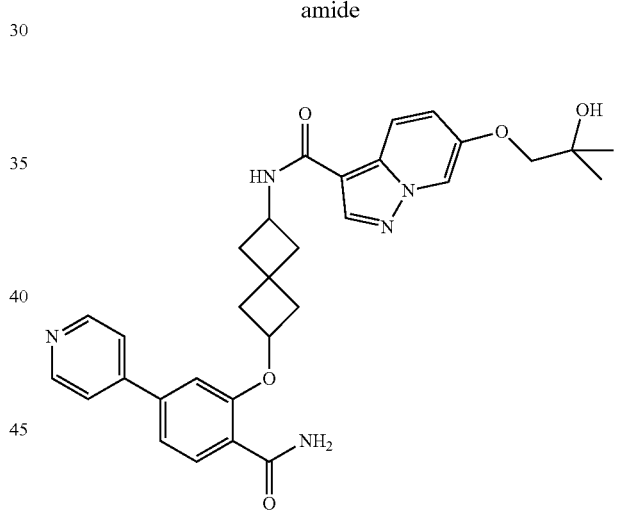

Example 225 (8.4 mg, 31%) was prepared in an analogous manner as Example 222 replacing commercially available (4-cyano-3-fluorophenyl)boronic acid with pyridine-4-boronic acid pinacol ester and 2-bromopyrimidine with Intermediate 85A. MS (ESI) m/z: 556.0 (M+H)$^+$. $^1$H NMR (500 MHz, DMSO-d$_6$) δ 8.67 (d, J=3.8 Hz, 2H), 8.42 (d, J=8.3 Hz, 2H), 8.31 (d, J=7.1 Hz, 1H), 8.07 (d, J=9.5 Hz, 1H), 7.91 (d, J=7.9 Hz, 1H), 7.76 (d, J=3.9 Hz, 2H), 7.63 (br. s., 2H), 7.44 (d, J=7.9 Hz, 1H), 7.31-7.22 (m, 2H), 4.99 (t, J=6.4 Hz, 1H), 4.43-4.30 (m, 1H), 3.78 (s, 1H), 2.79 (br. s., 1H), 2.58 (d, J=5.5 Hz, 1H), 2.34 (br. s., 1H), 2.29-2.12 (m, 4H), 1.21 (s, 6H). Analytical HPLC RT=1.438 min (Method A) and 1.158 min (Method B), purity 95%.

EXAMPLE 226

Preparation of N-(6-(5-(azetidin-3-yl)-2-carbamoylphenoxy)spiro[3.3]heptan-2-yl)-6-(2-hydroxy-2-methylpropoxy)pyrazolo[1,5-a]pyridine-3-carboxamide

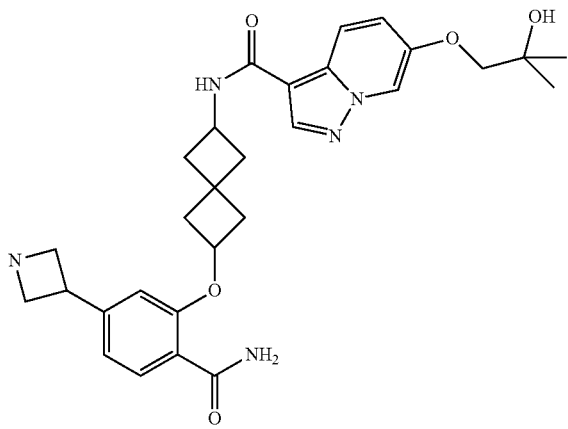 [SMILES: CC(C)(O)COc1ccc2c(C(=O)NC3CC4(C3)CC(Oc3cc(C5CNC5)ccc3C(N)=O)C4)cnn2c1]

EXAMPLE 226A tert-butyl 3-(3-((6-(((benzyloxy)carbonyl)amino)spiro[3.3]heptan-2-yl)oxy)-4-cyanophenyl)azetidine-1-carboxylate

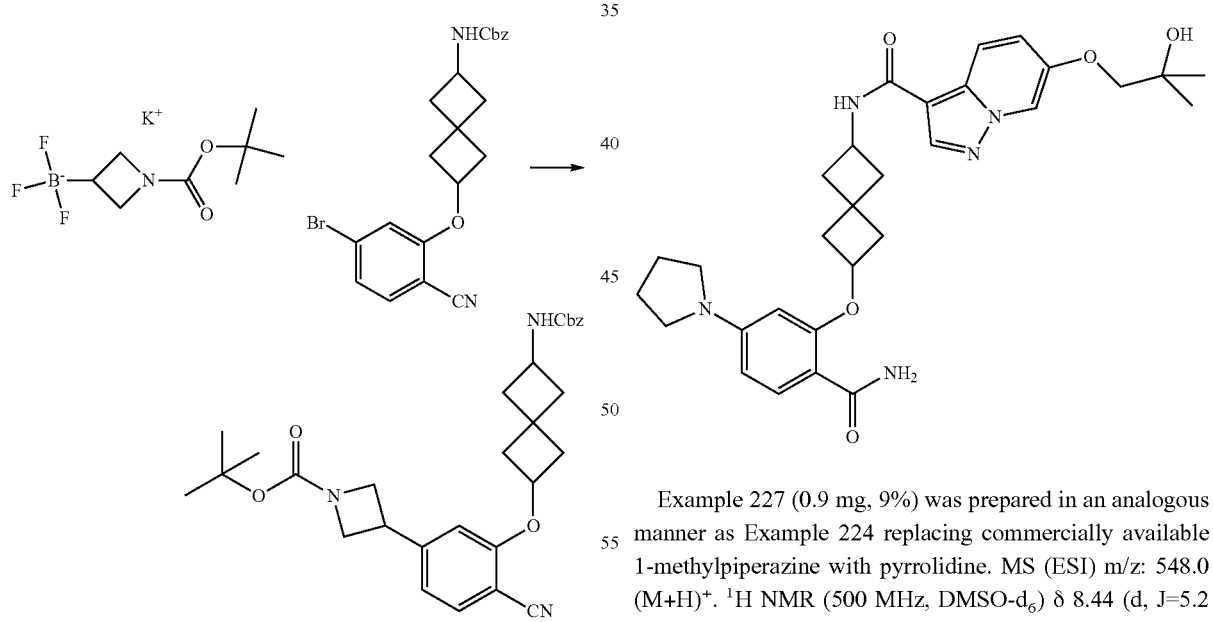

A mixture of potassium (1-(tert-butoxycarbonyl)azetidin-3-yl)trifluoroborate (48.5 mg, 0.18 mmol), Intermediate 85A (74 mg, 0.17 mmol), Cs$_2$CO$_3$ (164 mg, 0.50 mmol) in toluene (2 mL) and water (0.68 mL) was purged with N$_2$. PdCl$_2$(dppf)-CH$_2$Cl$_2$ Adduct (13.69 mg, 0.017 mmol) was added. The reaction was heated at 80° C. o.n. NH$_4$Cl (sat.) was added and the mixture was extracted with EtOAc (3×). The combined organic layer was concentrated then purified by flash chromatography (0-100% EtOAc/hexanes gradient) to give Example 226A (37 mg, 43%). MS(ESI) m/z: 518.0 (M+H)$^+$.

EXAMPLE 226

Example 226 (1.2 mg, 2%) was prepared in an analogous manner as Example 208 replacing Example 208A with Example 226A and Intermediate 4 with Intermediate 2. The Boc group was deprotected using 1:1 TFA in CH$_2$Cl$_2$ (1 mL) for 1 h at it. MS (ESI) m/z: 534.3 (M+H)$^+$. $^1$H NMR (500 MHz, DMSO-d$_6$) δ 8.44 (d, J=6.4 Hz, 2H), 8.29 (d, J=7.6 Hz, 1H), 8.08 (d, J=9.6 Hz, 1H), 7.80 (d, J=7.8 Hz, 1H), 7.52 (br. s., 2H), 7.28 (d, J=9.3 Hz, 1H), 7.03 (d, J=7.8 Hz, 1H), 6.94 (br. s., 1H), 4.84 (t, J=6.6 Hz, 1H), 4.49-4.29 (m, 1H), 3.90 (s, 1H), 3.79 (s, 2H), 3.17 (s, 1H), 2.77 (br. s., 1H), 2.40-2.27 (m, 1H), 2.27-2.10 (m, 4H), 1.95-1.71 (m, 2H), 1.29-1.15 (m, 9H). Analytical HPLC RT=1.379 min (Method A) and 1.125 min (Method B), purity 97%.

EXAMPLE 227

Preparation of N-(6-(2-carbamoyl-5-(pyrrolidin-1-yl)phenoxy)spiro[3.3]heptan-2-yl)-6-(2-hydroxy-2-methylpropoxy)pyrazolo[1,5-a]pyridine-3-carboxamide Example 227 (0.9 mg, 9%) was prepared in an analogous manner as Example 224 replacing commercially available 1-methylpiperazine with pyrrolidine. MS (ESI) m/z: 548.0 (M+H)$^+$. $^1$H NMR (500 MHz, DMSO-d$_6$) δ 8.44 (d, J=5.2 Hz, 2H), 8.29 (d, J=7.6 Hz, 1H), 8.08 (d, J=9.6 Hz, 1H), 7.76 (d, J=8.8 Hz, 1H), 7.32 (br. s., 1H), 7.28 (d, J=9.6 Hz, 1H), 7.11 (br. s., 1H), 6.19 (d, J=8.4 Hz, 1H), 5.90 (s, 1H), 4.88-4.77 (m, 1H), 4.42-4.33 (m, 1H), 3.91 (s, 1H), 3.83-3.74 (m, 2H), 3.29 (br. s., 1H), 3.17 (s, 2H), 2.76 (br. s., 1H), 2.40-2.11 (m, 6H), 1.96 (br. s., 4H), 1.23-1.22 (m, 1H), 1.23 (d, J=8.2 Hz, 6H). Analytical HPLC RT=1.651 min (Method A) and 1.631 min (Method B), purity 100%.

EXAMPLE 228

Preparation of N-(6-((4-carbamoyl-2'-(trifluoromethyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide

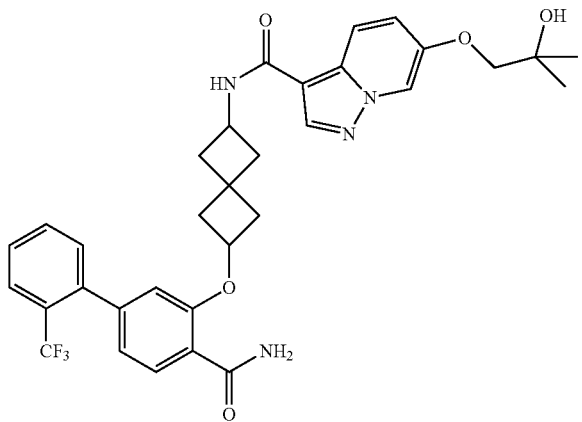 [SMILES: CC(C)(O)COc1ccc2c(C(=O)NC3CC4(C3)CC(Oc3cc(-c5ccccc5C(F)(F)F)ccc3C(N)=O)C4)cnn2c1]

Example 228 (9.5 mg, 39%) was prepared in an analogous manner as Example 222 replacing commercially available (4-cyano-3-fluorophenyl)boronic acid with (2-(trifluoromethyl)phenyl)boronic acid and 2-bromopyrimidine with Intermediate 85A. MS (ESI) m/z: 623.2 (M+H)$^+$. $^1$H NMR (500 MHz, DMSO-d$_6$) δ 8.41 (s, 2H), 8.25 (d, J=7.6 Hz, 1H), 8.06 (d, J=9.8 Hz, 1H), 7.90-7.81 (m, 2H), 7.78-7.71 (m, 1H), 7.69-7.53 (m, 3H), 7.43 (d, J=7.6 Hz, 1H), 7.27 (dd, J=9.5, 1.8 Hz, 1H), 6.96 (d, J=7.9 Hz, 1H), 6.87 (s, 1H), 4.80 (t, J=6.7 Hz, 1H), 4.39-4.28 (m, 1H), 3.79 (s, 2H), 2.75-2.61 (m, 1H), 2.41 (br. s., 1H), 2.36-2.29 (m, 1H), 2.27-2.04 (m, 4H), 1.21 (s, 6H). Analytical HPLC RT=1.816 min (Method A) and 1.803 min (Method B), purity 97%.

EXAMPLE 229

Preparation of N-6-((4-carbamoyl-2'-fluoro-[1,1'-biphenyl]-3-yl)oxy)spiro[3.3]heptan-2-yl)-6-(2-hydroxy-2-methylpropoxy)pyrazolo[1,5-a]pyridine-3-carboxamide

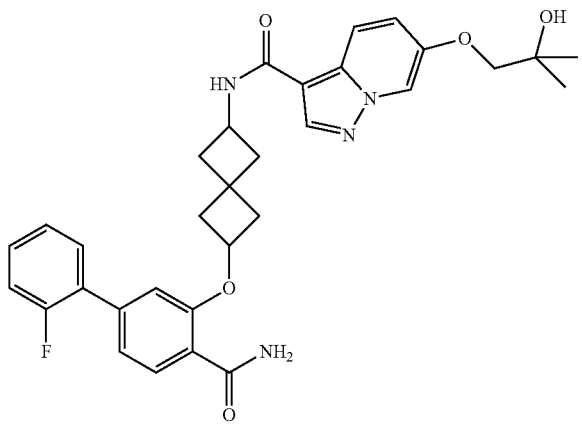

Example 229 (9 mg, 35%) was prepared in an analogous manner as Example 222 replacing commercially available (4-cyano-3-fluorophenyl)boronic acid with (2-fluorophenyl)boronic acid and 2-bromopyrimidine with Intermediate 85A. MS (ESI) m/z: 573.3 (M+H)$^+$. $^1$H NMR (500 MHz, DMSO-d$_6$) δ 8.46-8.39 (m, 2H), 8.27 (d, J=7.6 Hz, 1H), 8.07 (d, J=9.5 Hz, 1H), 7.89 (d, J=7.9 Hz, 1H), 7.59 (d, J=10.1 Hz, 3H), 7.51-7.42 (m, 1H), 7.38-7.30 (m, 2H), 7.27 (dd, J=9.8, 1.8 Hz, 1H), 7.20 (d, J=7.9 Hz, 1H), 7.08 (s, 1H), 4.88 (t, J=6.9 Hz, 1H), 4.43-4.30 (m, 1H), 3.79 (s, 2H), 2.78-2.69 (m, 1H), 2.49-2.42 (m, 1H), 2.39-2.31 (m, 1H), 2.30-2.20 (m, 2H), 2.20-2.11 (m, 2H), 1.22 (s, 6H). Analytical HPLC RT=1.706 min (Method A) and 1.693 min (Method B), purity 97%.

EXAMPLE 230

Preparation of N-(6-(2-carbamoyl-5-morpholinophenoxy)spiro[3.3]heptan-2-yl)-6-(2-hydroxy-2-methylpropoxy)pyrazolo[1,5-a]pyridine-3-carboxamide

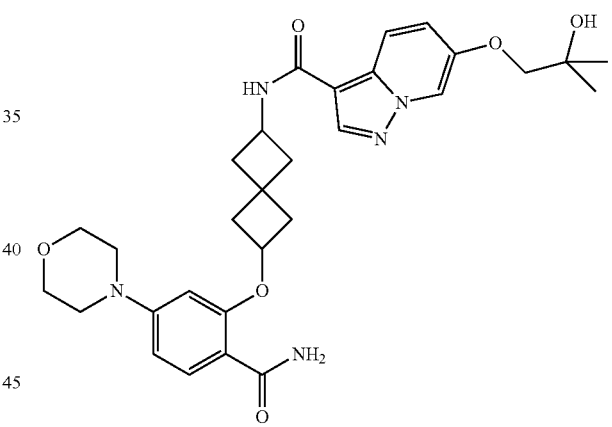

Example 230 (4.4 mg, 16%) was prepared in an analogous manner as Example 224 replacing commercially available 1-methylpiperazine with morpholine. MS (ESI) m/z: 564.1 (M+H)$^+$. $^1$H NMR (500 MHz, DMSO-d$_6$) δ 8.44 (s, 2H), 8.27 (d, J=7.6 Hz, 1H), 8.08 (d, J=9.7 Hz, 1H), 7.78 (d, J=8.8 Hz, 1H), 7.38 (br. s., 1H), 7.31-7.21 (m, 2H), 6.58 (d, J=8.6 Hz, 1H), 6.32 (s, 1H), 4.84 (t, J=6.7 Hz, 1H), 4.44-4.31 (m, 1H), 3.85-3.68 (m, 5H), 3.37 (br. s., 3H), 3.22 (br. s., 2H), 2.76 (br. s., 1H), 2.34 (br. s., 1H), 2.26-2.10 (m, 4H), 1.22 (s, 6H). Analytical HPLC RT=1.315 min (Method A) and 1.276 min (Method B), purity 100%.

EXAMPLE 231

Preparation of N-(6-(2-carbamoyl-5-(6-fluoropyridin-2-yl)phenoxy)spiro[3.3]heptan-2-yl)-6-(2-hydroxy-2-methylpropoxy)pyrazolo[1,5-a]pyridine-3-carboxamide

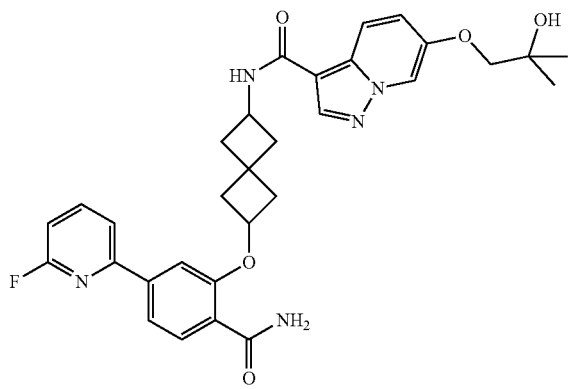 [SMILES: CC(C)(O)COc1ccc2c(C(=O)NC3CC4(C3)CC(Oc3cc(-c5cccc(F)n5)ccc3C(N)=O)C4)cnn2c1]

Example 231 (13.8 mg, 55%) was prepared in an analogous manner as Example 222 replacing commercially available (4-cyano-3-fluorophenyl)boronic acid with 6-fluoropyridine-2-boronic acid pinacol ester and 2-bromopyrimidine with Intermediate 85A. MS (ESI) m/z: 574.4 (M+H)$^+$. $^1$H NMR (500 MHz, DMSO-d$_6$) δ 8.44 (d, J=4.6 Hz, 2H), 8.29 (d, J=7.5 Hz, 1H), 8.17-8.01 (m, 3H), 7.91 (d, J=8.1 Hz, 1H), 7.72 (d, J=8.1 Hz, 1H), 7.63 (d, J=15.5 Hz, 2H), 7.56 (s, 1H), 7.28 (d, J=9.6 Hz, 1H), 7.21 (d, J=8.0 Hz, 1H), 4.96 (t, J=6.8 Hz, 1H), 4.45-4.34 (m, 1H), 3.79 (s, 2H), 2.83-2.73 (m, 1H), 2.63-2.56 (m, 1H), 2.41-2.33 (m, 1H), 2.33-2.23 (m, 2H), 2.22-2.12 (m, 2H), 1.22 (s, 6H). Analytical HPLC RT=1.556 min (Method A) and 1.552 min (Method B), purity 100%.

EXAMPLE 232

Preparation of methyl 5-(4-carbamoyl-3-((6-(6-(2-hydroxy-2-methylpropoxy)pyrazolo[1,5-a]pyridine-3-carboxamido)spiro[3.3]heptan-2-yl)oxy)phenyl)nicotinate

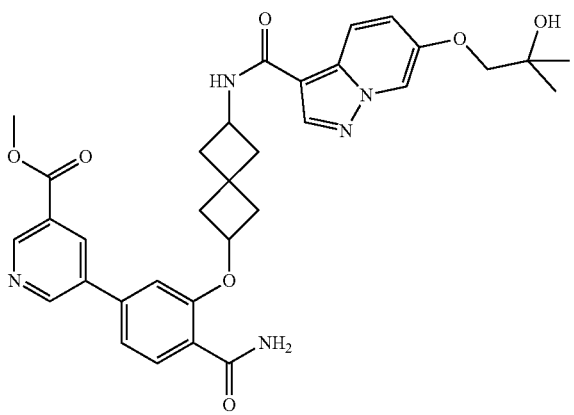 [SMILES: COC(=O)c1cncc(-c2ccc(C(N)=O)c(OC3CC4(CC(NC(=O)c5cnn6cc(OCC(C)(C)O)ccc56)C4)C3)c2)c1]

Example 232 (4.2 mg, 11%) was prepared in an analogous manner as Example 222 replacing commercially available (4-cyano-3-fluorophenyl)boronic acid with (5-(methoxycarbonyl)pyridin-3-yl)boronic acid and 2-bromopyrimidine with Intermediate 85B. MS (ESI) m/z: 614.0 (M+H)$^+$. $^1$H NMR (500 MHz, DMSO-d$_6$) δ 9.30-9.03 (m, 2H), 8.50 (br. s., 1H), 8.42 (d, J=10.1 Hz, 2H), 8.29 (d, J=7.3 Hz, 1H), 8.07 (d, J=9.8 Hz, 1H), 7.94 (d, J=7.9 Hz, 1H), 7.62 (d, J=18.3 Hz, 2H), 7.42 (d, J=7.0 Hz, 1H), 7.33-7.24 (m, 2H), 5.08-4.97 (m, 1H), 4.43-4.32 (m, 1H), 3.94 (s, 3H), 3.79 (s, 2H), 2.78 (br. s., 1H), 2.35 (br. s., 1H), 2.30-2.11 (m, 4H), 1.22 (s, 6H). Analytical HPLC RT=1.443 min (Method A) and 1.392 min (Method B), purity 96%.

EXAMPLE 233

Preparation of 2-methoxyethyl (5-(4-carbamoyl-3-((6-(6-(2-hydroxy-2-methylpropoxy)pyrazolo[1,5-a]pyridine-3-carboxamido)spiro[3.3]heptan-2-yl)oxy)phenyl)pyridin-2-yl)carbamate

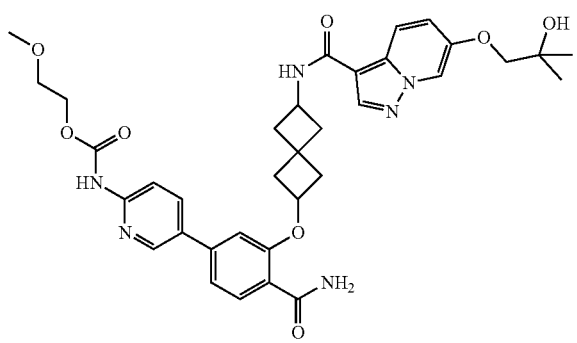 [SMILES: COCCOC(=O)Nc1ccc(-c2ccc(C(N)=O)c(OC3CC4(CC(NC(=O)c5cnn6cc(OCC(C)(C)O)ccc56)C4)C3)c2)cn1]

Example 233 (5.8 mg, 31%) was prepared in an analogous manner as Example 222 replacing commercially available (4-cyano-3-fluorophenyl)boronic acid with 2-methoxyethyl (5-(4,4,5,5-tetramethyl-1,3,2-dioxaborolan-2-yl)pyridin-2-yl)carbamate and 2-bromopyrimidine with Intermediate 85B. MS (ESI) m/z: 673.2 (M+H)$^+$. $^1$H NMR (500 MHz, DMSO-d$_6$) δ 10.33 (s, 1H), 8.65 (s, 1H), 8.42 (d, J=1-1.0 Hz, 2H), 8.29 (d, J=7.6 Hz, 1H), 8.14 (d, J=8.9 Hz, 1H), 8.08 (d, J=9.8 Hz, 1H), 7.92 (t, J=8.7 Hz, 2H), 7.64-7.51 (m, 2H), 7.35 (d, J=7.9 Hz, 1H), 7.28 (d, J=9.8 Hz, 1H), 7.18 (s, 1H), 4.99 (t, J=6.9 Hz, 1H), 4.44-4.32 (m, 1H), 4.29-4.21 (m, 2H), 3.79 (s, 2H), 3.62-3.56 (m, 1H), 3.29 (s, 3H), 3.17 (d, J=4.3 Hz, 1H), 2.79 (d, J=5.2 Hz, 1H), 2.65-2.57 (m, 1H), 2.35 (br. s., 1H), 2.29-2.12 (m, 4H), 1.20-1.20 (m, 1H), 1.22 (s, 6H). Analytical HPLC 1.322 min (Method B), purity 98%.

EXAMPLE 234

Preparation of N-(6-(2-carbamoyl-5-(6-(2-hydroxy-propan-2-yl)pyridin-3-yl)phenoxy)spiro[3.3]heptan-2-yl)-6-(2-hydroxy-2-methylpropoxy)pyrazolo[1,5-a]pyridine-3-carboxamide

EXAMPLE 235

Preparation of N-(6-(2-carbamoyl-5-(6-methoxy-pyridin-2-yl)phenoxy)spiro[3.3]heptan-2-yl)-6-(2-hydroxy-2-methylpropoxy)pyrazolo[1,5-a]pyridine-3-carboxamide

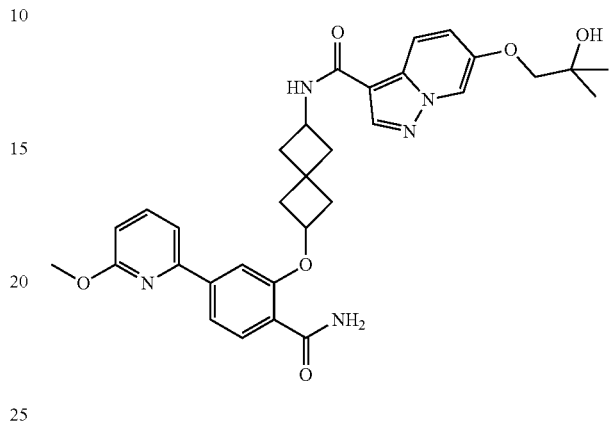

Intermediate 85 (7.5 mg, 0.01 mmol), (6-methoxypyridin-2-yl)boronic acid (6.2 mg, 0.040 mmol) and Pd-XPhos G3 (0.9 mg, 1.01 µmol) were placed in a pressure vial. Then THF (1.5 mL) and phosphoric acid, potassium salt (0.5 M aq.) (9 µL, 0.03 mmol) were added. The reaction mixture was purged with $N_2$. The pressure vial was capped, and the reaction mixture was stirred at 100° C. for 1 h. The solvent was removed under reduced pressure, and residue was dissolved in DMF (2 mL), filtered and purified by reverse phase chromatography to give Example 235 (4.1 mg, 50%). MS (ESI) m/z: 586.2 (M+H)$^+$. $^1$H NMR (500 MHz, DMSO-d$_6$) δ 8.45 (d, J=3.2 Hz, 2H), 8.28 (d, J=7.6 Hz, 1H), 8.08 (d, J=9.5 Hz, 1H), 7.91 (d, J=8.1 Hz, 1H), 7.83 (t, J=7.8 Hz, 1H), 7.74 (d, J=8.2 Hz, 1H), 7.71-7.57 (m, 4H), 7.28 (d, J=9.6 Hz, 1H), 6.85 (d, J=8.2 Hz, 1H), 4.94 (t, J=6.8 Hz, 1H), 4.47-4.34 (m, 1H), 4.00 (s, 3H), 3.80 (s, 2H), 2.83-2.75 (m, 1H), 2.66-2.56 (m, 1H), 2.41-2.24 (m, 3H), 2.19 (t, J=9.8 Hz, 2H), 1.22 (s, 6H). Analytical HPLC 1.696 min (Method A) and 1.649 min (Method B), purity 96%.

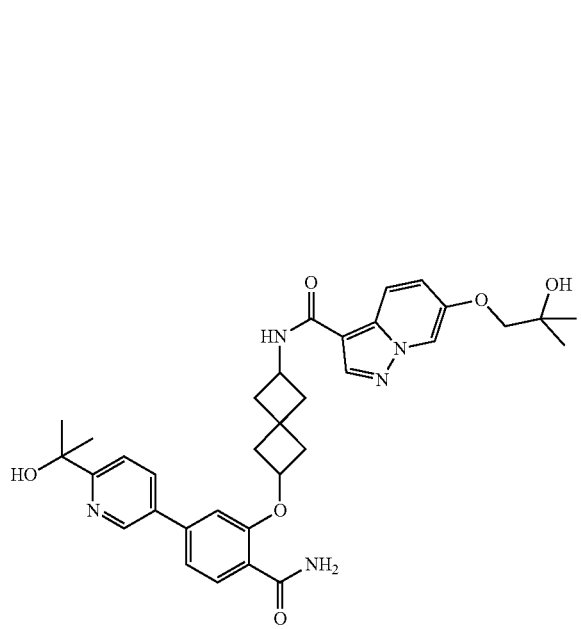 [SMILES: CC(C)(O)COc1ccc2c(C(=O)NC3CC4(C3)CC(Oc3cc(-c5ccc(C(C)(C)O)nc5)ccc3C(N)=O)C4)cnn2c1]

Example 234 (27.6 mg, 58%) was prepared in an analogous manner as Example 222 replacing commercially available (4-cyano-3-fluorophenyl)boronic acid with 5-(4,4,5,5-tetramethyl-1,3,2-dioxaborolan-2-yl)-2-(2-((trimethylsilyl)oxy)propan-2-yl)pyridine and 2-bromopyrimidine with Intermediate 85B. The trimethylsilyl group was deprotected in TBAF (1M in THF, 0.1 mL, 0.10 mmol) and THF (1 mL) for 2 h at rt. MS (ESI) m/z: 614.2 (M+H)$^+$. $^1$H NMR (500 MHz, DMSO-d$_6$) δ 8.85 (s, 1H), 8.44 (d, J=6.5 Hz, 2H), 8.29 (d, J=7.5 Hz, 1H), 8.10 (dd, J=15.7, 9.0 Hz, 2H), 7.91 (d, J=8.0 Hz, 1H), 7.77 (d, J=8.2 Hz, 1H), 7.60 (br. s., 2H), 7.36 (d, J=8.1 Hz, 1H), 7.27 (d, J=9.7 Hz, 1H), 7.23 (s, 1H), 5.00 (t, J=6.8 Hz, 1H), 4.45-4.31 (m, 1H), 3.79 (s, 2H), 2.84-2.74 (m, 1H), 2.63-2.56 (m, 1H), 2.34 (d, J=5.0 Hz, 1H), 2.25 (td, J=12.9, 7.0 Hz, 2H), 2.17 (t, J=9.8 Hz, 2H), 1.49 (s, 6H), 1.22 (s, 6H). Analytical HPLC 1.424 min (Method A) and 1.077 min (Method B), purity 99%.

The following examples in Table 10 were prepared using a similar procedure to that which was used in the preparation of Example 235 utilizing the appropriate boronic acids/boronate esters/potassium trifluoroborates. Longer time and higher temperature maybe used to drive the reaction. Microwave conditions (120° C. for 30 min) were also used. Various protecting groups were deprotected with the appropriate reagents such as TFA and TMSI.

TABLE 10

| Example | R | Name | MS (M + H)+ | HPLC Method, RT (min.) | 1H NMR |
|---|---|---|---|---|---|
| 236 | [2-amino-pyridin-6-yl, H2N-pyridine] | N-(6-(5-(6-aminopyridin-2-yl)-2-carbamoylphenoxy)spiro[3.3]heptan-2-yl)-6-(2-hydroxy-2-methylpropoxy)pyrazolo[1,5-a]pyridine-3-carboxamide | 571.0 | A: 1.416 | 1H NMR (500 MHz, DMSO-d6) δ 8.45 (br. s., 2H), 8.29 (d, J = 7.5 Hz, 1H), 8.08 (d, J = 9.6 Hz, 1H), 7.89 (d, J = 8.0 Hz, 1H), 7.70-7.52 (m, 4H), 7.47 (br. s., 1H), 7.32-7.13 (m, 3H), 5.00-4.81 (m, 1H), 4.47-4.33 (m, 1H), 3.80 (s, 2H), 2.88-2.75 (m, 1H), 2.63-2.57 (m, 2H), 2.40-2.33 (m, 1H), 2.32-2.23 (m, 2H), 2.19 (br. s., 2H), 1.22 (s, 6H) |
| 237 | [pyridin-2-yl] | N-(6-(2-carbamoyl-5-(pyridin-2-yl)phenoxy)spiro[3.3]heptan-2-yl)-6-(2-hydroxy-2-methylpropoxy)pyrazolo[1,5-a]pyridine-3-carboxamide | 556.2 | A: 1.411 B: 1.152 | 1H NMR (500 MHz, DMSO-d6) δ 8.70 (br. s., 1H), 8.42 (d, J = 9.0 Hz, 2H), 8.33 (d, J = 7.3 Hz, 1H), 8.05 (dd, J = 17.5, 8.9 Hz, 2H), 7.97-7.88 (m, 2H), 7.71 (d, J = 8.1 Hz, 1H), 7.65-7.57 (m, 3H), 7.41 (d, J = 5.3 Hz, 1H), 7.28 (d, J = 10.0 Hz, 1H), 4.94 (t, J = 6.5 Hz, 1H), 4.45-4.33 (m, 1H), 3.89 (s, 2H), 3.78 (s, 1H), 2.78 (br. s., 1H), 2.59 (br. s., 1H), 2.40-2.10 (m, 5H), 1.21 (s, 6H) |
| 238 | [3-(2,2,2-trifluoroethoxy)phenyl, F3C-CH2-O-phenyl] | N-(6-((4-carbamoyl-3'-(2,2,2-trifluoroethoxy)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 653.2 | A: 1.867 B: 1.881 | 1H NMR (500 MHz, DMSO-d6) δ 8.42 (d, J = 8.2 Hz, 2H), 8.31 (d, J = 7.6 Hz, 1H), 8.07 (d, J = 9.7 Hz, 1H), 7.90 (d, J = 8.0 Hz, 1H), 7.60 (d, J = 10.7 Hz, 2H), 7.49-7.43 (m, 1H), 7.39 (d, J = 7.7 Hz, 1H), 7.36 (m, 2H), 7.27 (d, J = 9.7 Hz, 1H), 7.15 (s, 1H), 7.11 (d, J = 8.0 Hz, 1H), 6.02-6.02 (m, 1H), 5.00 (t, J = 6.8 Hz, 1H), 4.87 (q, J = 8.9 Hz, 2H), 4.43-4.31 (m, 1H), 3.79 (s, 2H), 2.82-2.73 (m, 1H), 2.57 (m, 1H), 2.35 (d, J = 4.5 Hz, 1H), 2.30-2.20 (m, 2H), 2.17 (t, J = 8.5 Hz, 2H), 1.21 (s, 6H) |
| 239 | [3-methoxyphenyl] | N-(6-((4-carbamoyl-3'-methoxy-[1,1'-biphenyl]-3-yl)oxy)spiro[3.3]heptan-2-yl)-6-(2-hydroxy-2-methylpropoxy)pyrazolo[1,5-a]pyridine-3-carboxamide | 585.3 | A: 1.759 B: 1.757 | 1H NMR (500 MHz, DMSO-d6) δ 8.43 (d, J = 6.0 Hz, 2H), 8.29 (d, J = 7.5 Hz, 1H), 8.08 (d, J = 9.7 Hz, 1H), 7.89 (d, J = 8.1 Hz, 1H), 7.59 (br. s., 2H), 7.48-7.37 (m, 1H), 7.35-7.24 (m, 3H), 7.22 (br. s., 1H), 7.14 (s, 1H), 7.00 (d, J = 8.2 Hz, 1H), 4.99 (t, J = 6.7 Hz, 1H), 4.44-4.32 (m, 1H), 3.84 (s, 3H), 3.79 (s, 2H), 3.42 (m, 1H), 2.81-2.71 (m, 1H), 2.58 (d, J = 5.6 Hz, 1H), 2.35 (m, 1H), 2.31-2.20 (m, 2H), 2.17 (t, J = 9.0 Hz, 2H), 1.22 (s, 6H) |
| 240 | [3-hydroxyphenyl] | N-(6-((4-carbamoyl-3'-hydroxy-[1,1'-biphenyl]-3-yl)oxy)spiro[3.3]heptan-2-yl)-6-(2-hydroxy-2-methylpropoxy)pyrazolo[1,5-a]pyridine-3-carboxamide | 571.2 | A: 1.428 B: 1.412 | 1H NMR (500 MHz, DMSO-d6) δ 8.43 (d, J = 6.9 Hz, 2H), 8.30 (d, J = 7.5 Hz, 1H), 8.08 (d, J = 9.7 Hz, 1H), 7.88 (d, J = 8.1 Hz, 1H), 7.58 (d, J = 6.4 Hz, 2H), 7.33-7.21 (m, 3H), 7.16-7.02 (m, 3H), 6.82 (d, J = 8.2 Hz, 1H), 4.96 (t, J = 6.8 Hz, 1H), 4.45-4.32 (m, 1H), 3.79 (s, 2H), 3.44 (br. s., 2H), 2.77 (m, 1H), 2.58 (m, 1H), 2.35 (m, 1H), 2.26 (ddd, J = 18.9, 11.5, 7.1 Hz, 2H), 2.17 (t, J = 9.9 Hz, 2H), 1.27-1.15 (m, 6H) |

TABLE 10-continued

| | | | | |
|---|---|---|---|---|
| 241 | (structure: 3-(difluoromethyl)phenyl) | N-(6-((4-carbamoyl-3'-(difluoromethyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 605.1 | A: 1.742<br>B: 1.772 | $^1$H NMR (500 MHz, DMSO-$d_6$) δ 8.44 (d, J = 4.1 Hz, 2H), 8.29 (d, J = 7.6 Hz, 1H), 8.08 (d, J = 9.6 Hz, 1H), 7.96-7.85 (m, 3H), 7.71-7.56 (m, 4H), 7.35 (d, J = 8.1 Hz, 1H), 7.27 (d, J = 9.7 Hz, 1H), 7.19 (s, 1H), 5.00 (t, J = 6.7 Hz, 1H), 4.43-4.33 (m, 1H), 3.79 (s, 2H), 2.82-2.75 (m, 1H), 2.62-2.56 (m, 1H), 2.36 (m, 1H), 2.31-2.22 (m, 2H), 2.18 (t, J = 9.9 Hz, 2H), 1.22 (s, 6H) |
| 242 | (structure: 3-fluorophenyl) | N-(6-((4-carbamoyl-3'-fluoro-[1,1'-biphenyl]-3-yl)oxy)spiro[3.3]heptan-2-yl)-6-(2-hydroxy-2-methylpropoxy)pyrazol[1,5-a]pyridine-3-carboxamide | 573.2 | A: 1.855<br>B: 1.815 | $^1$H NMR (500 MHz, DMSO-$d_6$) δ 8.42 (d, J = 5.5 Hz, 2H), 8.24 (d, J = 7.6 Hz, 1H), 8.06 (d, J = 9.8 Hz, 1H), 7.88 (d, J = 7.9 Hz, 1H), 7.68-7.46 (m, 5H), 7.34 (d, J = 8.2 Hz, 1H), 7.29-7.21 (m, 2H), 7.17 (s, 1H), 5.00 (t, J = 6.9 Hz, 1H), 4.46-4.26 (m, 1H), 3.78 (s, 2H), 2.84-2.70 (m, 1H), 2.63-2.55 (m, 1H), 2.34 (m, 1H), 2.28-2.09 (m, 4H), 1.20 (s, 6H) |
| 243 | (structure: 3-(trifluoromethyl)phenyl, F$_3$C) | N-(6-((4-carbamoyl-3'-(trifluoromethyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 623.3 | A: 1.889<br>B: 1.885 | $^1$H NMR (500 MHz, DMSO-$d_6$) δ 8.43 (d, J = 6.1 Hz, 2H), 8.29 (d, J = 7.6 Hz, 1H), 8.12-8.02 (m, 2H), 8.00 (s, 1H), 7.92 (d, J = 8.1 Hz, 1H), 7.84-7.70 (m, 2H), 7.62 (br. s., 2H), 7.39 (d, J = 8.1 Hz, 1H), 7.27 (d, J = 9.7 Hz, 1H), 7.22 (s, 1H), 5.08-4.96 (m, 1H), 4.77 (s, 1H), 4.47-4.31 (m, 1H), 3.79 (s, 2H), 2.82-2.70 (m, 1H), 2.62-2.56 (m, 1H), 2.35 (d, J = 5.7 Hz, 1H), 2.31-2.20 (m, 2H), 2.17 (t, J = 9.8 Hz, 2H), 1.22 (s, 6H) |
| 244 | (structure: 3-cyanophenyl, NC) | N-(6-((4-carbamoyl-3'-cyano-[1,1'-biphenyl]-3-yl)oxy)spiro[3.3]heptan-2-yl)-6-(2-hydroxy-2-methylpropoxy)pyrazolo[1,5-a]pyridine-3-carboxamide | 580.2 | A: 1.655<br>B: 1.650 | $^1$H NMR (500 MHz, DMSO-$d_6$) δ 8.43 (d, J = 6.4 Hz, 2H), 8.30-8.19 (m, 2H), 8.07 (d, J = 9.2 Hz, 2H), 7.89 (dd, J = 12.4, 8.1 Hz, 2H), 7.70 (t, J = 7.8 Hz, 1H), 7.60 (br. s., 2H), 7.39 (d, J = 7.9 Hz, 1H), 7.30-7.20 (m, 2H), 5.02 (t, J = 6.7 Hz, 1H), 4.44-4.32 (m, 1H), 3.79 (s, 2H), 2.84-2.74 (m, 1H), 2.59 (dd, J = 11.1, 6.0 Hz, 1H), 2.35 (m, 1H), 2.30-2.11 (m, 4H), 1.22 (s, 6H) |
| 245 | (structure: 3-(methoxymethyl)phenyl) | N-(6-((4-carbamoyl-3'-(methoxymethyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 598.9 | A: 1.674<br>B: 1.639 | $^1$H NMR (500 MHz, DMSO-$d_6$) δ 8.49-8.39 (m, 2H), 8.29 (br. s., 1H), 8.08 (d, J = 9.6 Hz, 1H), 7.91 (d, J = 8.0 Hz, 1H), 7.71-7.55 (m, 4H), 7.49 (t, J = 7.6 Hz, 1H), 7.38 (d, J = 7.6 Hz, 1H), 7.29 (dd, J = 18.6, 8.9 Hz, 2H), 7.15 (s, 1H), 4.99 (t, J = 6.7 Hz, 1H), 4.51 (s, 2H), 4.43-4.33 (m, 1H), 3.79 (s, 2H), 3.34 (s, 2H), 2.83-2.72 (m, 1H), 2.62-2.55 (m, 1H), 2.35 (d, J = 6.1 Hz, 1H), 2.32-2.21 (m, 2H), 2.17 (t, J = 9.9 Hz, 2H), 1.22 (s, 6H) |
| 246 | (structure: 5-amino-4-cyano-3-methyl-1H-pyrazol-1-yl, NC, NH$_2$) | N-(6-((3'-(5-amino-4-cyano-3-methyl-1H-pyrazol-1-yl)-4-carbamoyl-[1,1'-biphenyl]-3-yl)oxy)spiro[3.3]heptan-2-yl)-6-(2-hydroxy-2-methylpropoxy)pyrazolo[1,5-a]pyridine-3-carboxamide | 675.3 | A: 1.522<br>B: 1.486 | $^1$H NMR (500 MHz, DMSO-$d_6$) δ 8.41 (d, J = 11.3 Hz, 2H), 8.29 (d, J = 7.3 Hz, 1H), 8.07 (d, J = 9.8 Hz, 1H), 7.91 (d, J = 7.9 Hz, 1H), 7.76-7.70 (m, 2H), 7.67-7.59 (m, 2H), 7.57-7.48 (m, 2H), 7.36 (d, J = 7.9 Hz, 1H), 7.27 (d, J = 8.9 Hz, 1H), 7.20 (s, 1H), 6.75 (s, 2H), 4.98 (m, 1H), 4.50-4.29 (m, 1H), 3.78 (s, 2H), 2.77 (m, 1H), 2.35 (m, 1H), 2.29-2.09 (m, 7H), 1.21 (s, 6H) |
| 247 | (structure: 3-(hydroxymethyl)phenyl, HO) | N-(6-((4-carbamoyl-3'-(hydroxymethyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 585.2 | A: 1.404<br>B: 1.398 | $^1$H NMR (500 MHz, DMSO-$d_6$) δ 8.44 (d, J = 7.2 Hz, 2H), 8.29 (d, J = 6.2 Hz, 1H), 8.08 (d, J = 9.6 Hz, 1H), 7.91 (d, J = 8.1 Hz, 1H), 7.66-7.55 (m, 4H), 7.46 (t, J = 7.6 Hz, 1H), 7.37 (d, J = 7.5 Hz, 1H), 7.33-7.25 (m, 2H), 7.13 (s, 1H), 4.97 (m, 1H), 4.60 (s, 2H), 4.39 (m, 1H), 3.79 (s, 2H), 2.78 (m, 1H), 2.36 (m, 1H), 2.32-2.21 (m, 2H), 2.18 (t, J = 9.8 Hz, 2H), 1.22 (s, 6H) |
| 248 | (structure: 6-chloropyridin-2-yl, Cl, N) | N-(6-(2-carbamoyl-5-(6-chloropyridin-2-yl)phenoxy)spiro[3.3]heptan-2-yl)-6-(2-hydroxy-2-methylpropoxy)pyrazolo[1,5-a]pyridine-3-carboxamide | 590.4 | A: 1.663<br>B: 1.644 | $^1$H NMR (500 MHz, DMSO-$d_6$) δ 8.44 (d, J = 4.3 Hz, 1H), 8.29 (d, J = 7.3 Hz, 1H), 8.11-8.06 (m, 2H), 8.00 (t, J = 7.8 Hz, 1H), 7.91 (d, J = 8.1 Hz, 1H), 7.72 (d, J = 8.2 Hz, 1H), 7.66 (br. s., 1H), 7.62 (br. s., 1H), 7.58-7.52 (m, 2H), 7.28 (d, J = 9.6 Hz, 1H), 4.96 (t, J = 6.8 Hz, 1H), 4.46-4.34 (m, 1H), 3.79 (s, 2H), 2.81-2.74 (m, 1H), 2.62-2.56 (m, 1H), 2.41-2.23 (m, 3H), 2.23-2.14 (m, 2H), 1.22 (s, 6H) |

TABLE 10-continued

| | | | | |
|---|---|---|---|---|
| 249 | | 3-((((4'-carbamoyl-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3-yl)methoxy)carbonyl)amino) propanoic acid | 700.2 | A: 1.236<br>B: 1.422 | $^1$H NMR (500 MHz, DMSO-d$_6$) δ 8.44 (s, 1H), 8.41 (s, 1H), 8.35 (d, J = 6.1 Hz, 1H), 8.07 (d, J = 9.6 Hz, 1H), 7.90 (d, J = 8.0 Hz, 1H), 7.68-7.54 (m, 4H), 7.49 (t, J = 7.7 Hz, 1H), 7.41-7.24 (m, 4H), 7.12 (s, 1H), 5.10 (s, 2H), 5.01-4.92 (m, 1H), 4.42-4.32 (m, 1H), 3.78 (s, 2H), 3.22 (m, 2H), 2.77 (m, 1H), 2.43-2.32 (m, 3H), 2.31-2.12 (m, 4H), 1.21 (s, 6H) |
| 250 | | tert-butyl 3-((((4'-carbamoyl-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3-yl)methoxy)carbonyl)amino) propanoate | | A: 1.854<br>B: 1.817 | $^1$H NMR (500 MHz, DMSO-d$_6$) δ 8.42 (d, J = 9.1 Hz, 2H), 8.32 (d, J = 6.1 Hz, 1H), 8.07 (d, J = 9.6 Hz, 1H), 7.90 (d, J = 8.0 Hz, 1H), 7.69-7.55 (m, 4H), 7.49 (t, J = 7.9 Hz, 1H), 7.41-7.25 (m, 4H), 7.12 (s, 1H), 5.10 (s, 2H), 4.96 (t, J = 6.6 Hz, 1H), 4.42-4.33 (m, 1H), 3.78 (s, 2H), 3.25-3.18 (m, 2H), 2.77 (m, 1H), 2.36 (m, 3H), 2.30-2.20 (m, 2H), 2.17 (m, 2H), 1.34 (s, 9H), 1.21 (s, 6H) |
| 251 | | 5-fluoro-3'-((6-(6-(2-hydroxy-2-methylpropoxy)pyrazolo[1,5-a]pyridine-3-carboxamido)spiro[3.3]heptan-2-yl)oxy)-N3-propyl-[1,1'-biphenyl]-3,4'-dicarboxamide | 658.5 | A: 1.580<br>B: 1.566 | $^1$H NMR (500 MHz, DMSO-d$_6$) δ 8.46-8.37 (m, 2H), 8.34 (br. s., 1H), 8.06 (d, J = 9.6 Hz, 1H), 7.97 (br. s., 1H), 7.91 (d, J = 8.1 Hz, 1H), 7.76 (d, J = 9.4 Hz, 1H), 7.68-7.57 (m, 3H), 7.41 (d, J = 8.0 Hz, 1H), 7.28 (d, J = 9.8 Hz, 1H), 7.21 (br. s., 1H), 5.05-4.96 (m, 1H), 4.42-4.30 (m, 1H), 3.78 (br. s., 2H), 3.25 (q, J = 6.4 Hz, 2H), 2.77 (br. s., 1H), 2.58 (br. s., 1H), 2.34 (br. s., 1H), 2.29-2.11 (m, 4H), 1.60-1.50 (m, 2H), 1.21 (s, 6H), 0.90 (t, J = 7.2 Hz, 3H) |
| 252 | | N-(6-((3'-(aminomethyl)-4-carbamoyl-[1,1'-biphenyl]-3-yl)oxy)spiro[3.3]heptan-2-yl)-6-(2-hydroxy-2-methylpropoxy)pyrazolo[1,5-a]pyridine-3-carboxamide | 584.4 | A: 1.097<br>B: 1.097 | $^1$H NMR (500 MHz, DMSO-d$_6$) δ 8.45-8.38 (m, 2H), 8.35 (br. s., 1H), 8.06 (d, J = 9.5 Hz, 1H), 7.91 (d, J = 8.0 Hz, 1H), 7.79-7.67 (m, 2H), 7.63 (br. s., 2H), 7.57 (br. s., 1H), 7.47 (t, J = 7.5 Hz, 1H), 7.41 (d, J = 6.8 Hz, 1H), 7.33 (d, J = 7.7 Hz, 1H), 7.28 (d, J = 9.7 Hz, 1H), 7.14 (s, 1H), 5.00-4.91 (m, 1H), 4.36 (d, J = 7.3 Hz, 1H), 3.91 (br. s., 1H), 3.88 (br. s., 2H), 2.77 (d, J = 5.7 Hz, 1H), 2.35 (br. s., 1H), 2.29-2.21 (m, 2H), 2.16 (t, J = 9.9 Hz, 2H), 1.21 (s, 6H) |
| 253 | | N-(6-((4-carbamoyl-3'-cyano-5'-fluoro-[1,1'-biphenyl]-3-yl)oxy)spiro[3.3]heptan-2-yl)-6-(2-hydroxy-2-methylpropoxy)pyrazolo[1,5-a]pyridine-3-carboxamide | 598.3 | A: 1.576<br>B: 1.720 | $^1$H NMR (500 MHz, DMSO-d$_6$) δ 8.41 (d, J = 12.5 Hz, 2H), 8.30 (d, J = 7.3 Hz, 1H), 8.10 (s, 1H), 8.06 (d, J = 9.5 Hz, 1H), 7.99 (d, J = 10.1 Hz, 1H), 7.89 (d, J = 8.2 Hz, 1H), 7.85 (d, J = 7.9 Hz, 1H), 7.63 (br. s., 1H), 7.59 (br. s., 1H), 7.42 (d, J = 7.9 Hz, 1H), 7.27 (d, J = 9.8 Hz, 1H), 7.24 (s, 1H), 5.03 (t, J = 6.6 Hz, 1H), 4.81 (s, 1H), 4.42-4.33 (m, 1H), 3.78 (s, 2H), 2.83-2.73 (m, 1H), 2.62-2.57 (m, 1H), 2.34 (d, J = 5.8 Hz, 1H), 2.27-2.11 (m, 4H), 1.21 (s, 6H) |

TABLE 10-continued

| | | | | | |
|---|---|---|---|---|---|
| 254 | 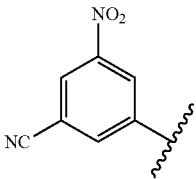 [SMILES: *c1cc(C#N)cc([N+](=O)[O-])c1] | N-(6-((4-carbamoyl-3'-cyano-5'-nitro-[1,1'-biphenyl]-3-yl)oxy)spiro[3.3]heptan-2-yl)-6-(2-hydroxy-2-methylpropoxy)pyrazolo[1,5-a]pyridine-3-carboxamide | 625.3 | A: 1.674<br>B: 1.646 | $^1$H NMR (500 MHz, DMSO-$d_6$) δ 8.85-8.62 (m, 3H), 8.42 (d, J = 7.0 Hz, 2H), 8.26 (d, J = 7.3 Hz, 1H), 8.07 (d, J = 9.8 Hz, 1H), 7.92 (d, J = 7.9 Hz, 1H), 7.63 (br. s., 2H), 7.49 (d, J = 8.2 Hz, 1H), 7.34 (s, 1H), 7.27 (d, J = 9.8 Hz, 1H), 5.05 (t, J = 6.6 Hz, 1H), 4.73 (s, 1H), 4.45-4.32 (m, 1H), 3.79 (s, 2H), 2.79 (m, 1H), 2.60 (m, 1H), 2.36 (m, 1H), 2.30-2.10 (m, 4H), 1.33-1.14 (m, 6H) |
| 255 | 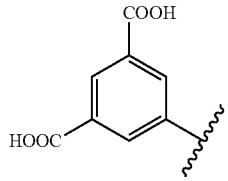 [SMILES: *c1cc(C(=O)O)cc(C(=O)O)c1] | 4'-carbamoyl-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3,5-dicarboxylic acid | 643.4 | A: 0.770<br>B: 1.199 | $^1$H NMR (500 MHz, DMSO-$d_6$) δ 8.50 (s, 1H), 8.42 (d, J = 9.5 Hz, 2H), 8.38 (s, 2H), 8.30 (d, J = 7.6 Hz, 1H), 8.07 (d, J = 9.8 Hz, 1H), 7.94 (d, J = 7.9 Hz, 1H), 7.63 (br. s., 1H), 7.59 (br. s., 1H), 7.37 (d, J = 7.9 Hz, 1H), 7.28 (d, J = 9.8 Hz, 1H), 7.21 (s, 1H), 5.02 (t, J = 6.7 Hz, 1H), 4.42-4.33 (m, 1H), 3.79 (s, 2H), 2.99 (s, 1H), 2.75 (br. s., 1H), 2.37 (m, 1H), 2.33-2.28 (m, 1H), 2.24 (dd, J = 11.4, 6.6 Hz, 1H), 2.18 (t, J = 9.8 Hz, 2H), 1.22 (s, 6H) |

EXAMPLE 256

Preparation of N-(6-(2-carbamoyl-5-(pyridin-3-yl)phenoxy)spiro[3.3]heptan-2-yl)-6-(2-hydroxy-2-methylpropoxy)pyrazolo[1,5-a]pyridine-3-carboxamide

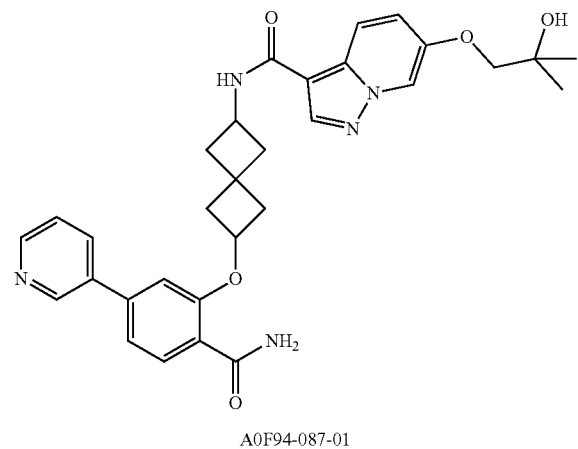 [SMILES: CC(C)(O)COc1ccc2c(C(=O)NC3CC4(C3)CC(Oc3cc(-c5cccnc5)ccc3C(N)=O)C4)cnn2c1]

A0F94-087-01

EXAMPLE 256A

Preparation of 2-fluoro-4-(pyridin-3-yl)benzonitrile

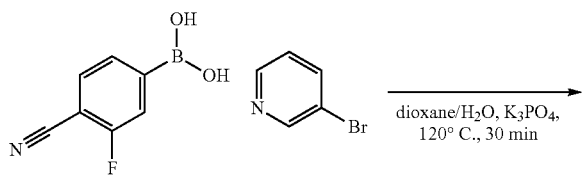

-continued

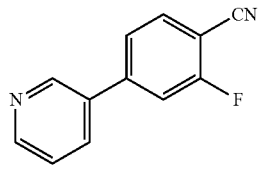

A0D48-073-01

Example 256A (63 mg, 87%) was prepared in an analogous manner as Example 222A replacing commercially available 2-bromopyrimidine with 3-bromopyridine. MS(ESI) m/z: 198.9. $^1$H NMR (400 MHz, CDCl$_3$) δ 8.88-8.84 (m, 1H), 8.70 (dd, J=4.8, 1.5 Hz, 1H), 7.90-7.84 (m, 1H), 7.75 (dd, J=7.9, 6.6 Hz, 1H), 7.49 (dd, J=8.0, 1.7 Hz, 1H), 7.47-7.40 (m, 2H).

EXAMPLE 256

Example 256 (3.6 mg, 21%) was prepared in an analogous manner as Example 208 replacing commercially available 2-fluoro-3-methoxybenzonitrile with 2-fluoro-4-(pyridin-3-yl)benzonitrile and replacing Intermediate 4 with Intermediate 2. MS (ESI) m/z: 556.1 (M+H)$^+$. $^1$H NMR (500 MHz, DMSO-$d_6$) δ 8.95 (s, 1H), 8.62 (d, J=4.4 Hz, 1H), 8.43 (d, J=6.8 Hz, 2H), 8.30 (d, J=7.5 Hz, 1H), 8.14 (d, J=7.8 Hz, 1H), 8.07 (d, J=9.6 Hz, 1H), 7.92 (d, J=8.0 Hz, 1H), 7.61 (br. s., 2H), 7.53 (dd, J=7.7, 4.9 Hz, 1H), 7.38 (d, J=8.0 Hz, 1H), 7.28 (d, J=9.8 Hz, 1H), 7.23 (s, 1H), 5.01 (t, J=6.8 Hz, 1H), 4.42-4.31 (m, 1H), 3.79 (s, 2H), 2.84-2.74 (m, 1H), 2.63-2.56 (m, 1H), 2.35 (br. s., 1H), 2.30-2.11 (m, 4H), 1.22 (s, 6H). Analytical HPLC RT=1.373 min (Method A) and 1.174 min (Method B), purity 98%.

EXAMPLE 257

Preparation of 2-amino-2-(4'-carbamoyl-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3-yl)acetic acid

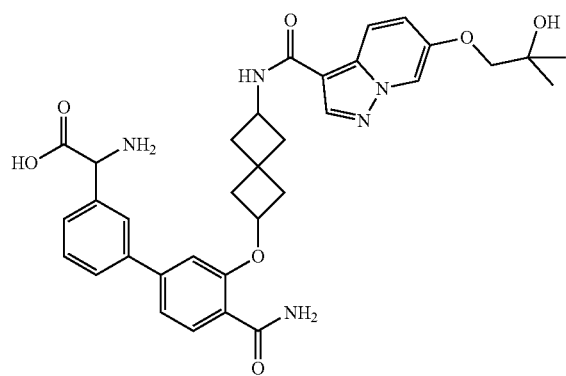 [SMILES: CC(C)(O)COc1ccc2c(C(=O)NC3CC4(C3)CC(Oc3cc(-c5cccc(C(N)C(=O)O)c5)ccc3C(N)=O)C4)cnn2c1]

EXAMPLE 257A

Preparation of N-(6-(2-carbamoyl-5-(4,4,5,5-tetramethyl-1,3,2-dioxaborolan-2-yl)phenoxy)spiro[3.3]heptan-2-yl)-6-(2-hydroxy-2-methylpropoxy)pyrazolo[1,5-a]pyridine-3-carboxamide

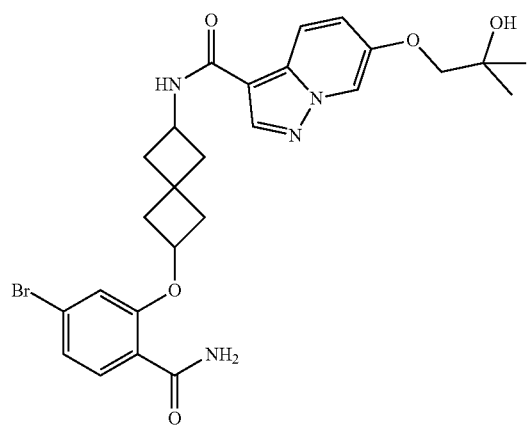

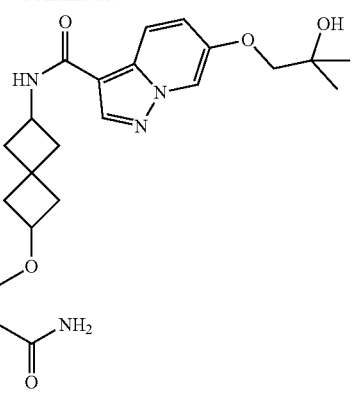

A mixture Intermediate 85A (20 mg, 0.04 mmol), 4,4,4',4',5,5,5',5'-octamethyl-2,2'-bi(1,3,2-dioxaborolane) (15 mg, 0.06 mmol), potassium acetate (15 mg, 0.15 mmol), and PdCl$_2$(dppf)-CH$_2$Cl$_2$ Adduct (2.1 mg, 2.5 µmol) in 1,4-Dioxane (1 mL) was purged with N$_2$. The reaction was heated at 100° C. for 2.5 h, then 80° C. o.n. The mixture was filtered and used without purification. MS (ESI) m/z: 605.2 (M+H)$^+$.

EXAMPLE 257

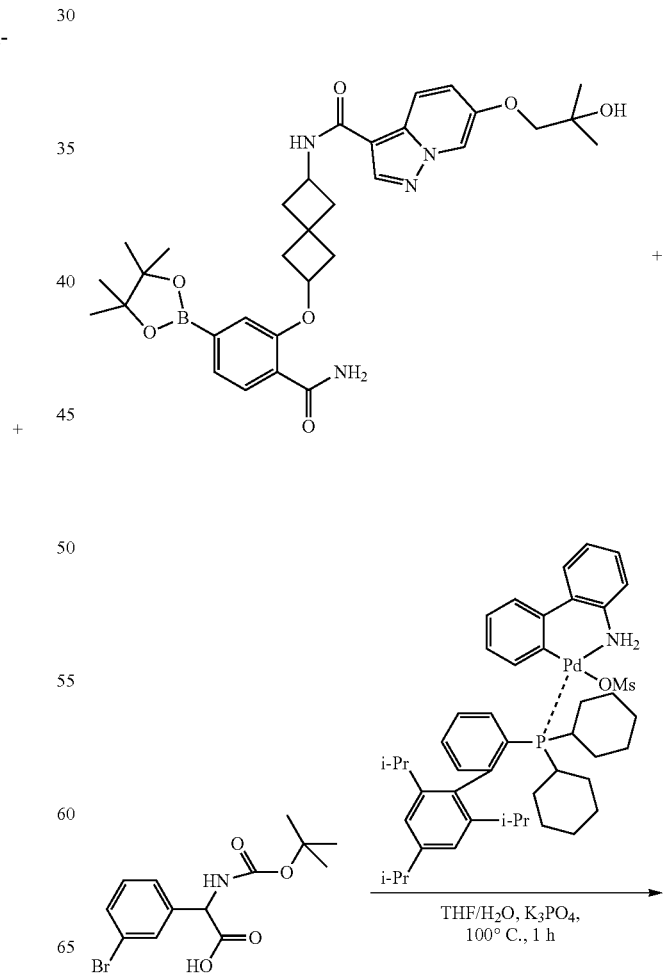

-continued

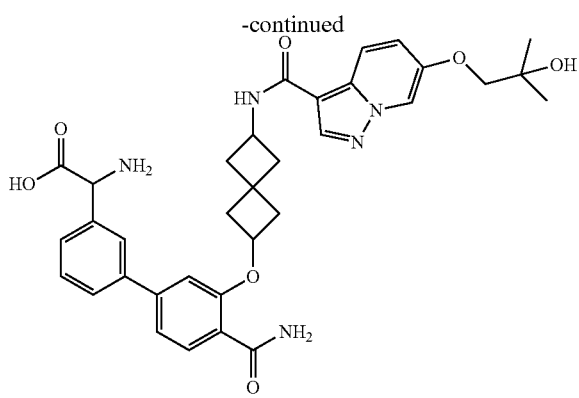

A reaction mixture containing half of crude solution of Example 257A (10 mg, 0.02 mmol), (3-bromophenyl)[(tert-butoxycarbonyl)amino]acetic acid (16.4 mg, 0.05 mmol), phosphoric acid, potassium salt (3M) (40 µL, 0.12 mmol) and THF (1.5 mL) was purged with $N_2$. Pd-XPhos G3 (1.1 mg, 1.2 µmol) was added. The reaction was heated at 100° C. for 3.5 h. The mixture was filtered, and the solvent was removed under reduced pressure. The residue was dissolved in TFA:$CH_2Cl_2$ 1:1 (1 mL) and stirred at rt for 1 h. The reaction was concentrated and purified by reverse phase HPLC to give Example 257 (3.1 mg, 29%). MS (ESI) m/z: 626.1 (M+H)$^+$. $^1$H NMR (500 MHz, DMSO-d$_6$) δ 8.43 (d, J=9.8 Hz, 2H), 8.28 (d, J=7.6 Hz, 1H), 8.08 (d, J=9.8 Hz, 1H), 7.92 (d, J=7.9 Hz, 1H), 7.76 (br. s., 1H), 7.65 (d, J=6.1 Hz, 1H), 7.58 (br. s., 2H), 7.50-7.42 (m, 2H), 7.33 (d, J=7.9 Hz, 1H), 7.27 (d, J=9.8 Hz, 1H), 7.15 (s, 1H), 5.06-4.88 (m, 1H), 4.37 (m, 2H), 3.79 (s, 2H), 2.78 (m, 1H), 2.59 (m, 1H), 2.40-2.13 (m, 5H), 1.30-1.16 (m, 6H). Analytical HPLC RT=1.132 min (Method A) and 1.229 min (Method B), purity 96%.

EXAMPLE 258

Preparation of N-6-((4-carbamoyl-3',5'-bis(hydroxymethyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide

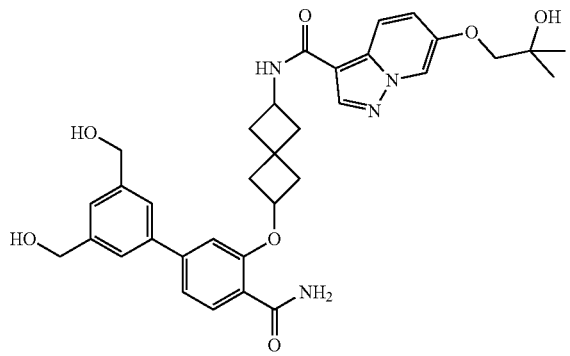 [SMILES: CC(C)(O)COc1ccc2c(C(=O)NC3CC4(C3)CC(Oc3cc(-c5cc(CO)cc(CO)c5)ccc3C(N)=O)C4)cnn2c1]

Example 258 (5.2 mg, 48%) was prepared in an analogous manner as Example 257 replacing commercially available (3-bromophenyl)[(tert-butoxycarbonyl)amino]acetic acid with (5-bromo-1,3-phenylene)dimethanol. MS (ESI) m/z: 615.2 (M+H)$^+$. H NMR (500 MHz, DMSO-d$_6$) δ 8.42 (d, J=7.6 Hz, 2H), 8.27 (d, J=7.6 Hz, 1H), 8.07 (d, J=9.5 Hz, 1H), 7.91 (d, J=8.2 Hz, 1H), 7.57 (d, J=19.5 Hz, 2H), 7.49 (s, 2H), 7.40-7.20 (m, 3H), 7.11 (s, 1H), 5.31 (t, J=5.6 Hz, 1H), 4.96 (t, J=6.7 Hz, 1H), 4.58 (d, J=5.8 Hz, 4H), 4.43-4.31 (m, 1H), 3.79 (s, 2H), 2.80-2.73 (m, 1H), 2.62-2.56 (m, 1H), 2.41-2.12 (m, 5H), 1.27-1.16 (m, 6H). Analytical HPLC RT=1.199 min (Method A) and 1.179 min (Method B), purity 93%.

EXAMPLE 259

Preparation of N-(6-(2-carbamoyl-5-hydroxyphenoxy)spiro[3.3]heptan-2-yl)-6-(2-hydroxy-2-methylpropoxy)pyrazolo[1,5-a]pyridine-3-carboxamide

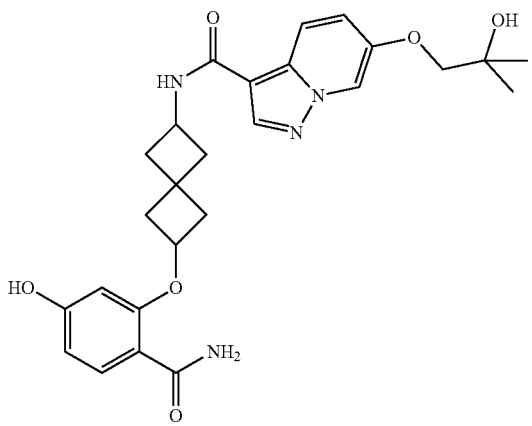 [SMILES: CC(C)(O)COc1ccc2c(C(=O)NC3CC4(C3)CC(Oc3cc(O)ccc3C(N)=O)C4)cnn2c1]

Example 259 (0.8 mg, 7%) was isolated as a side product in the preparation of 5-(aminomethyl)-4'-carbamoyl-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3-carboxylic acid prepared in an analogous manner as Example 257 replacing commercially available (3-bromophenyl)[(tert-butoxycarbonyl)amino]acetic acid with 3-(aminomethyl)-5-bromobenzoic acid as a side product. MS (ESI) m/z: 495.5 (M+H)$^+$. $^1$H NMR (500 MHz, DMSO-d$_6$) δ 8.45 (d, J=7.3 Hz, 2H), 8.27 (d, J=7.3 Hz, 1H), 8.09 (d, J=9.8 Hz, 1H), 7.74 (d, J=8.5 Hz, 1H), 7.37-7.18 (m, 3H), 6.40 (d, J=9.5 Hz, 1H), 6.32 (s, 1H), 4.70 (t, J=6.9 Hz, 1H), 4.43-4.32 (m, 1H), 3.80 (s, 2H), 2.76-2.67 (m, 1H), 2.47-2.41 (m, 1H), 2.35 (br. s., 1H), 2.28-2.11 (m, 4H), 1.67 (s, 1H), 1.23 (s, 6H) Analytical HPLC RT=1.108 min (Method A) and 1.141 min (Method B), purity 95%.

EXAMPLE 260

Preparation of N-(6-(5-(3-aminoazetidin-1-yl)-2-carbamoylphenoxy)spiro[3.3]heptan-2-yl)-6-(2-hydroxy-2-methylpropoxy)pyrazolo[1,5-a]pyridine-3-carboxamide, TFA

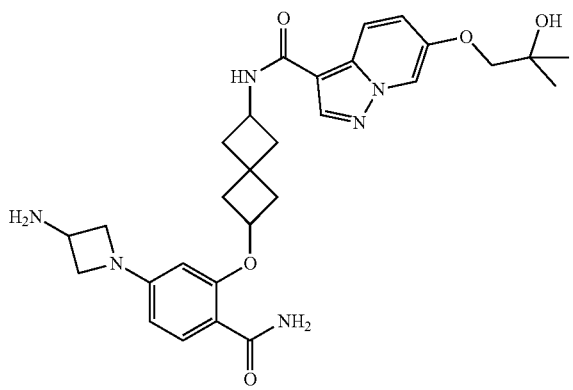 [SMILES: CC(C)(O)COc1ccc2c(C(=O)NC3CC4(C3)CC(Oc3cc(N5CC(N)C5)ccc3C(N)=O)C4)cnn2c1]

Example 260 (1.0 mg, 8%) was prepared in an analogous manner as Example 224 replacing commercially available 1-methyl piperazine with 3-N-Boc-amino-azetidine and Intermediate 85A with Intermediate 85. The Boc group was deprotected using 1:1 TFA in CH$_2$Cl$_2$ for 0.5 h at rt. MS (ESI) m/z: 549.4 (M+H)$^+$. $^1$H NMR (500 MHz, DMSO-d$_6$) δ 8.45 (d, J=4.6 Hz, 4H), 8.27 (d, J=7.3 Hz, 1H), 8.08 (d, J=9.5 Hz, 1H), 7.79 (d, J=8.9 Hz, 1H), 7.38-7.12 (m, 5H), 7.06 (br. s., 1H), 6.14 (d, J=7.3 Hz, 1H), 5.89 (s, 1H), 4.84 (t, J=6.7 Hz, 1H), 4.38 (d, J=7.9 Hz, 1H), 4.19 (d, J=7.9 Hz, 3H), 3.88 (br. s., 2H), 3.80 (s, 2H), 2.74 (br. s., 1H), 2.35 (br. s., 1H), 2.27-2.13 (m, 4H), 1.23 (s, 6H). Analytical HPLC RT=1.001 min (Method A) and 0.964 min (Method B), purity 94%.

EXAMPLE 261

Preparation of N-(6-((3'-(2-aminoethyl-4-carbamoyl-[1,1'-biphenyl]-3-yl)oxy)spiro[3.3]heptan-2-yl)-6-(2-hydroxy-2-methylpropoxy)pyrazolo[1,5-a]pyridine-3-carboxamide

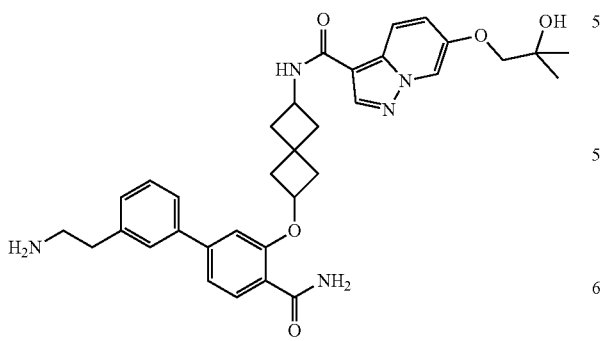

Example 261 (2.7 mg, 22%) was prepared in an analogous manner as Example 257 replacing commercially available (3-bromophenyl)[(ter-butoxycarbonyl)amino]acetic acid with tert-butyl 3-bromophenethylcarbamate. The Boc group was deprotected using 1:1 TFA in CH$_2$Cl$_2$ for 0.5 h at rt. MS (ESI) m/z: 598.6 (M+H)$^+$. $^1$H NMR (500 MHz, DMSO-d$_6$) δ 8.43 (d, J=9.5 Hz, 2H), 8.30 (d, J=7.6 Hz, 1H), 8.08 (d, J=9.8 Hz, 1H), 7.91 (d, J=7.9 Hz, 1H), 7.63-7.49 (m, 4H), 7.44 (t, J=7.6 Hz, 1H), 7.35-7.23 (m, 3H), 7.14 (s, 1H), 4.98 (t, J=6.7 Hz, 1H), 4.42-4.31 (m, 1H), 3.79 (s, 2H), 3.50 (m, 2H), 2.99-2.72 (m, 4H), 2.42-2.12 (m, 5H), 1.22 (s, 6H). Analytical HPLC RT=1.123 min (Method A) and 1.200 min (Method B), purity 93%.

EXAMPLE 262

Preparation of N-(6-(2-carbamoyl-5-(3-(dimethylamino)propyl)phenoxy)spiro[3.3]heptan-2-yl)-6-(2-hydroxy-2-methylpropoxy)pyrazolo[1,5-a]pyridine-3-carboxamide

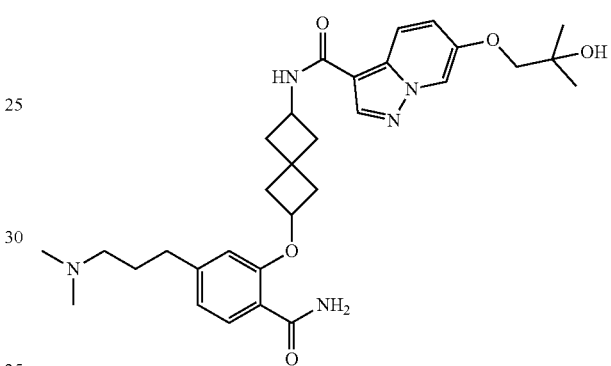

EXAMPLE 262A

Preparation of benzyl benzyl (6-(2-cyano-5-(3-(dimethylamino)propyl)phenoxy)spiro[3.3]heptan-2-yl) carbamate

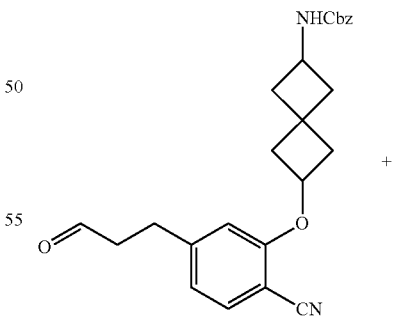

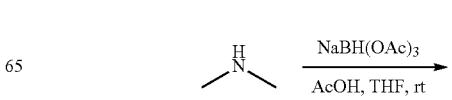

-continued

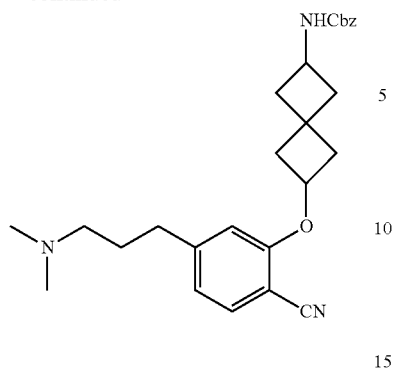

To a solution of Intermediate 84 (50 mg, 0.119 mmol), dimethylamine (2 M in THF) (0.24 mL, 0.478 mmol) and acetic acid (0.014 mL, 0.239 mmol) in anhydrous THF (3 mL) was added sodium triacetoxyborohydride (152 mg, 0.717 mmol), and the reaction mixture was stirred at rt for 1 h. The reaction mixture was quenched by NH₄Cl (aq. saturated; ~0.5 mL), and most of the solvent was removed under reduced pressure. The residue was diluted with EtOAc (50 mL) and K₂CO₃ (aq. saturated; 25 mL); organic phase was separated, washed with water (1×25 mL), brine (1×25 mL), dried (Na₂SO₄) and filtered. Solvent was removed under reduced pressure to afford Example 262A (39 mg, 73% yield) as a colorless film. MS (ESI) m/z: 448.1 (M+H)⁺. ¹H NMR (500 MHz, CDCl₃) δ ppm 7.45 (d, J=8.0 Hz, 1H), 7.36 (s, 3H), 6.81 (dd, J=8.0, 1.4 Hz, 1H), 6.59 (s, 1H), 5.09 (br s, 2H), 4.85 (br s, 1H), 4.66 (t, J=6.9 Hz, 1H), 4.13 (br s, 1H), 2.70-2.62 (m, 3H), 2.56-2.40 (m, 3H), 2.29 (br d, J=9.6 Hz, 6H), 2.04-1.94 (m, 2H), 1.82 (br s, 2H), 1.27 (s, 6H).

EXAMPLE 262B

Preparation of benzyl benzyl (6-(2-cyano-5-(3-(dimethylamino)propyl)phenoxy)spiro[3.3]heptan-2-yl) carbamate

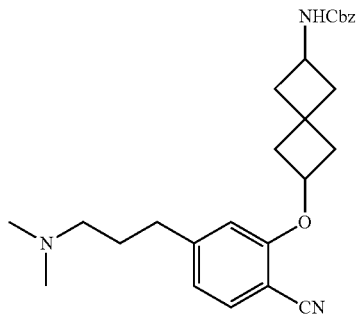

-continued

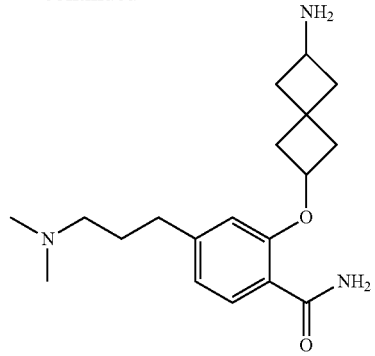

Intermediate 84A (39 mg, 0.087 mmol) was dissolved in DMSO (2.0 mL), then K₂CO₃ (36 mg, 0.261 mmol) and magnesium oxide (17.56 mg, 0.436 mmol) were added at rt. To the reaction was added hydrogen peroxide (30% wt. aq) (0.098 mL, 0.959 mmol) dropwise over 5 min (slight exotherm), and the reaction mixture was stirred at rt for 1 h. Additional amount of hydrogen peroxide (30% wt. aq) (0.098 mL, 0.959 mmol) were added. The reaction mixture was stirred at rt for additional 16 h. The reaction mixture was diluted with EtOAc (50 mL) then quenched with HCl (1 M aq.) (1.39 mL, 1.394 mmol), and Na₂CO₃ (saturated, aq. 1×25 mL), was added. Organic phase was separated, washed brine (1×25 mL), dried (Na₂SO₄) and filtered. Solvent was removed under reduced pressure. The obtained material was dissolved in was dissolved in THF (2 mL) and MeOH (2 mL), and TEA (0.06 mL, 0.436 mmol) was added. The reaction mixture was degassed (3× vacuum/Ar), then palladium on carbon (10% wt.) (9.3 mg, 8.71 μmol) was added. The reaction mixture was degassed again, and it was stirred under dihydrogen atmosphere (1 atm; ballon) for 2 h. Pd—C was filtered off using membrane filter, and the filtrate was concentrated to afford Example 262B (28 mg, 97% yield) as a colorless film. MS (ESI) m/z: 332.1 (M+H)⁺.

EXAMPLE 262

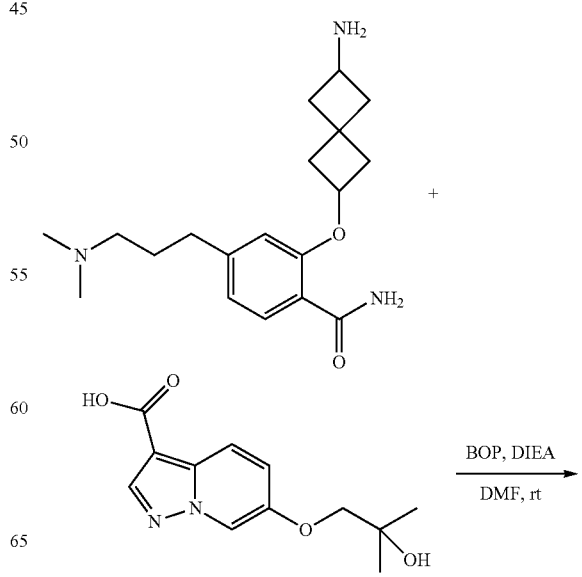

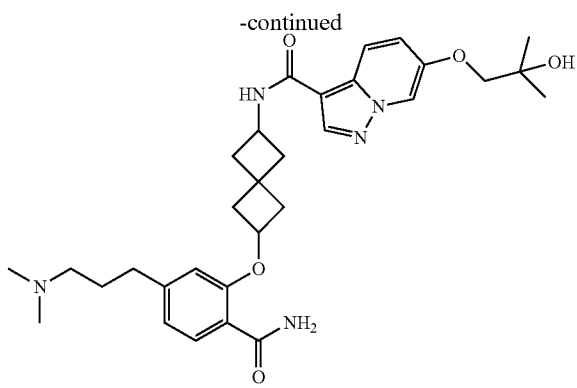

Example 262B (14 mg, 0.042 mmol) and Intermediate 2 (11.6 mg, 0.046 mmol) were dissolved in anhydrous DMF (1.5 mL), then DIEA (0.037 mL, 0.211 mmol) was added, followed by BOP (20.6 mg, 0.046 mmol). The reaction mixture was stirred at rt for 1 h. The reaction mixture was quenched with MeOH (0.1 mL), diluted with DMF (2 mL total volume), filtered, and purified by reverse phase HPLC to afford Example 262 (7.3 mg, 31% yield). MS (ESI) m/z: 564.0 (M+H)$^+$. $^1$H-NMR: (500 MHz, DMSO-d$_6$) δ ppm 8.38 (s, 1H), 8.37 (s, 1H), 8.26 (br d, J=7.6 Hz, 1H), 8.02 (d, J=9.7 Hz, 1H), 7.70 (d, J=7.9 Hz, 1H), 7.48 (br s, 1H), 7.41 (br s, 1H), 7.23 (dd, J=9.6, 1.9 Hz, 1H), 6.81 (d, J=7.9 Hz, 1H), 6.73 (s, 1H), 4.75 (quin, J=6.8 Hz, 1H), 4.38-4.27 (m, 1H), 2.72-2.65 (m, 1H), 2.55 (br t, J=7.5 Hz, 2H), 2.35-2.24 (m, 1H), 2.22-2.15 (m, 3H), 2.10 (s, 6H), 1.70-1.60 (m, 2H), 1.17 (s, 10H). Analytical HPLC RT=1.352 min (Method A) and 1.165 min (Method B), purity 100%.

EXAMPLE 263

Preparation of N-(6-(2-carbamoyl-5-(3-(dimethylamino)propyl)phenoxy)spiro[3.3]heptan-2-yl)-7-cyclopropyl-6-(2-hydroxy-2-methylpropoxy)pyrazolo[1,5-a]pyridine-3-carboxamide

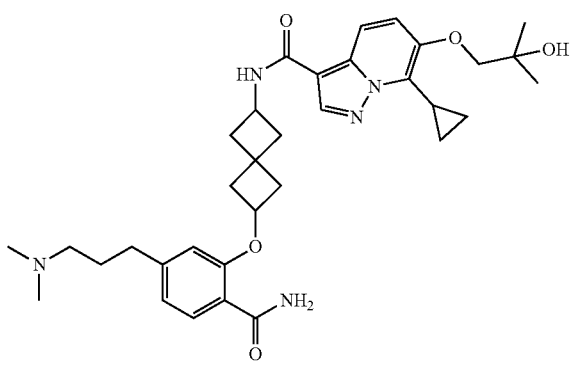 [SMILES: CN(C)CCCc1ccc(C(N)=O)c(OC2CC3(CC(NC(=O)c4cnn5c(C6CC6)c(OCC(C)(C)O)ccc45)C3)C2)c1]

Example 263 (6.4 mg, 22% yield) was prepared in a similar manner as Example 262 replacing Intermediate 2 with Intermediate 4 and coupling with Example 262B. MS (ESI) m/z: 604.3 (M+H)$^+$. $^1$H-NMR: (500 MHz, DMSO-d$_6$) 8.48 (s, 1H), 8.29 (br d, J=7.5 Hz, 1H), 8.01 (d, J=9.6 Hz, 1H), 7.74 (d, J=7.9 Hz, 1H), 7.52 (br s, 1H), 7.45 (br d, J=9.4 Hz, 2H), 6.85 (br d, J=7.9 Hz, 1H), 6.77 (s, 1H), 4.79 (br t, J=6.8 Hz, 1H), 4.40-4.31 (m, 1H), 3.54 (br s, 1H), 2.77-2.69 (m, 1H), 2.63-2.55 (m, 3H), 2.47 (br s, 2H), 2.37-2.28 (m, 1H), 2.28-2.19 (m, 3H), 2.15 (s, 6H), 1.70 (quin, J=7.3 Hz, 2H), 1.48-1.41 (m, 2H), 1.23 (s, 6H), 1.10-1.00 (m, 2H). Analytical HPLC RT=1.224 min (Method A) and 1.206 min (Method B), purity 87%.

EXAMPLE 264

Preparation N-(6-(2-carbamoyl-5-(3-morpholinopropyl)phenoxy)spiro[3.3]heptan-2-yl)-6-(2-hydroxy-2-methylpropoxy)pyrazolo[1,5-a]pyridine-3-carboxamide

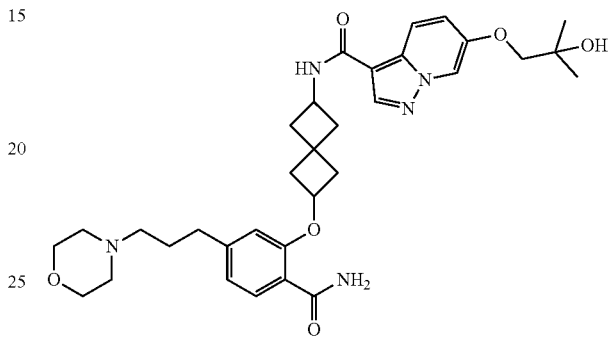

Example 264 (2.4 mg, 6% yield) was prepared in a similar manner as Example 262 replacing dimethylamine with morpholine and coupling with Intermediate 2. MS (ESI) m/z: 606.4. (M+H)$^+$. $^1$H-NMR: (500 MHz, DMSO-d$_6$) 8.42 (br d, J=6.6 Hz, 2H), 8.30 (br d, J=7.3 Hz, 1H), 8.07 (br d, J=9.7 Hz, 1H), 7.74 (br d, J=7.9 Hz, 1H), 7.51 (br s, 1H), 7.45 (br s, 1H), 7.27 (br d, J=9.8 Hz, 1H), 6.86 (br d, J=7.9 Hz, 1H), 6.78 (s, 1H), 4.83-4.72 (m, 1H), 4.43-4.31 (m, 1H), 3.78 (s, 2H), 2.72 (br s, 1H), 2.60 (br t, J=7.4 Hz, 2H), 2.32 (br s, 4H), 2.27-2.21 (m, 3H), 2.20-2.09 (m, 4H), 1.80-1.65 (m, 2H), 1.21 (s, 6H). Analytical HPLC RT=1.038 min (Method A) and 1.311 min (Method B), purity 94%.

EXAMPLE 265

Preparation N-(6-(2-carbamoyl-5-(3-morpholinopropyl)phenoxy)spiro[3.3]heptan-2-yl)-7-cyclopropyl-6-(2-hydroxy-2-methylpropoxy)pyrazolo[1,5-a]pyridine-3-carboxamide

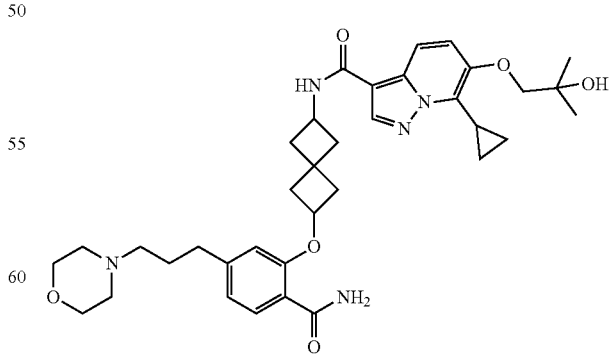

Example 265 (1.3 mg, 3% yield) was prepared in a similar manner as Example 262 replacing dimethylamine with morpholine and coupling with Intermediate 4. MS (ESI) m/z:

646.3. (M+H)⁺. ¹H-NMR: (500 MHz, DMSO-d₆) δ ppm 8.45 (s, 1H), 8.21 (br d, J=7.3 Hz, 1H), 7.98 (d, J=9.8 Hz, 1H), 7.71 (d, J=7.9 Hz, 1H), 7.45 (br s, 1H), 7.41 (br d, J=10.1 Hz, 2H), 6.82 (br d, J=7.6 Hz, 1H), 6.74 (s, 1H), 4.75 (br t, J=6.6 Hz, 1H), 4.39-4.27 (m, 1H), 3.75 (s, 2H), 3.53 (br s, 3H), 2.69 (br s, 1H), 2.61-2.52 (m, 3H), 2.28 (br s, 5H), 2.25-2.17 (m, 3H), 2.16-2.06 (m, 3H), 1.79 (br s, 1H), 1.72-1.61 (m, 2H), 1.44 (br d, J=3.7 Hz, 2H), 1.20 (s, 6H), 1.07-0.95 (m, 2H). Analytical HPLC RT=1.470 min (Method A) and 1.226 min (Method B), purity 100%.

EXAMPLE 266

Preparation N-(6-(2-carbamoyl-5-(3-(4-methylpiperazin-1-yl)propyl)phenoxy)spiro[3.3]heptan-2-yl)-6-(2-hydroxy-2-methylpropoxy)pyrazolo[1,5-a]pyridine-3-carboxamide

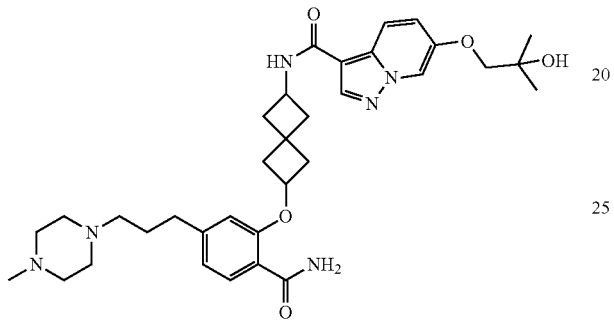

Example 266 (2.4 mg, 6% yield) was prepared in a similar manner as Example 262 replacing dimethylamine with piperazine and coupling with Intermediate 2. MS (ESI) m/z: 619.2. (M+H)⁺. ¹H-NMR: (500 MHz, DMSO-d₆) δ ppm 8.44 (br d, J=5.6 Hz, 2H), 8.30 (br d, J=7.3 Hz, 1H), 8.07 (br d, J=9.6 Hz, 1H), 7.77 (br d, J=7.8 Hz, 1H), 7.50 (br s, 2H), 7.31-7.21 (m, 2H), 7.17 (s, 1H), 7.07 (s, 1H), 6.88 (br d, J=8.0 Hz, 1H), 6.79 (s, 1H), 4.79 (br t, J=6.7 Hz, 1H), 4.42-4.31 (m, 1H), 3.79 (s, 2H), 2.86 (br d, J=22.4 Hz, 1H), 2.80-2.69 (m, 4H), 2.63 (br d, J=7.1 Hz, 2H), 2.33 (br s, 1H), 2.26-2.10 (m, 4H), 1.87 (br s, 2H), 1.21 (s, 6H). Analytical HPLC RT=1.158 min (Method A) and 1.042 min (Method B), purity 97%.

EXAMPLE 267

N-(6-(2-carbamoyl-5-(3-(4-methylpiperazin-1-yl)propyl)phenoxy)spiro[3.3]heptan-2-yl)-7-cyclopropyl-6-(2-hydroxy-2-methylpropoxy)pyrazolo[1,5-a]pyridine-3-carboxamide

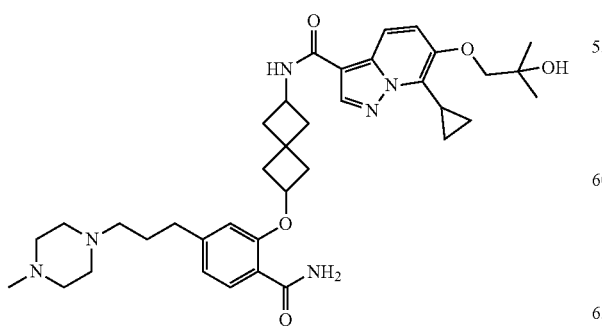

Example 267 (1.3 mg, 3% yield) was prepared in a similar manner as Example 262 replacing dimethylamine with piperazine and coupling with Intermediate 4. MS (ESI) m/z: 659.1. (M+H)⁺. ¹H-NMR: (500 MHz, DMSO-d₆) δ ppm 8.50 (s, 1H), 8.26 (br d, J=7.6 Hz, 1H), 8.03 (d, J=9.7 Hz, 1H), 7.74 (d, J=7.9 Hz, 1H), 7.52-7.42 (m, 3H), 6.85 (br d, J=7.8 Hz, 1H), 6.78 (s, 1H), 4.84-4.71 (m, 1H), 4.43-4.31 (m, 1H), 2.73 (br s, 1H), 2.65-2.56 (m, 4H), 2.35 (br d, J=10.9 Hz, 5H), 2.27-2.20 (m, 51H), 2.17-2.09 (m, 6H), 1.70 (br d, J=7.5 Hz, 2H), 1.49 (br d, J=3.7 Hz, 3H), 1.24 (s, 5H), 1.09-1.03 (m, 2H). Analytical HPLC RT=1.400 min (Method A) and 1.264 min (Method B), purity 84%.

EXAMPLE 268

Preparation of N-(6-(2-carbamoyl-4,6-difluorophenoxy)spiro[3.3]heptan-2-yl)-6-(2-hydroxy-2-methylpropoxy)pyrazolo[1,5-a]pyridine-3-carboxamide

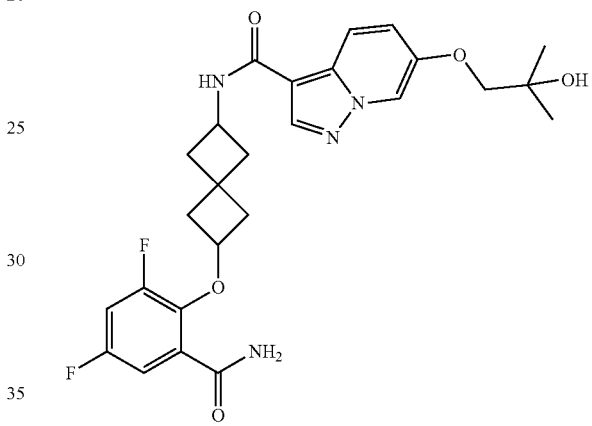

EXAMPLE 268A

Preparation of benzyl (6-(2-cyano-4,6-difluorophenoxy)spiro[3.3]heptan-2-yl)carbamate

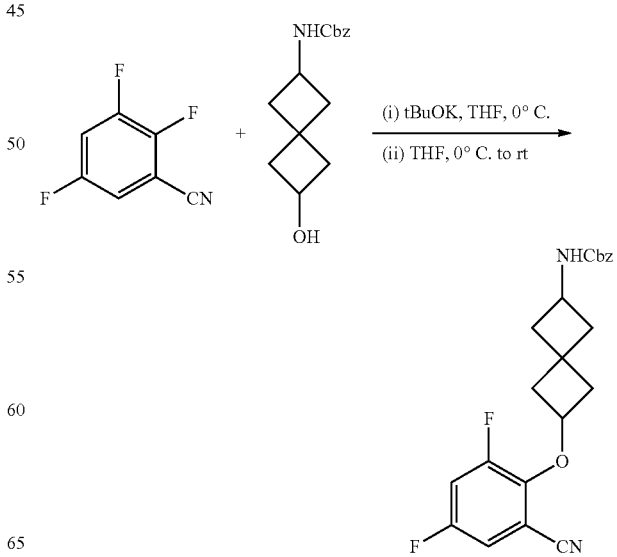

Benzyl (6-hydroxyspiro[3.3]heptan-2-yl)carbamate Intermediate 1 (100 mg, 0.383 mmol) was dissolved to anhydrous THF (3.0 mL), and the reaction mixture was cooled 0° C. Potassium tert-butoxide (45.1 mg, 0.402 mmol) was added in one portion, and the reaction mixture was stirred at 0° C. for 30 min. Thereafter, 2,3,5-trifluorobenzonitrile (0.11 mL, 0.957 mmol) was added, cooling bath was removed, and the reaction mixture was stirred at rt for 1 h. The reaction mixture was quenched with water (0.2 mL), and concentrated. The residue was purified by normal phase chromatography (0-75% EtOAc/hexanes gradient; eluted at ~40% EtOAc). Fractions were combined and concentrated under reduced pressure to give Example 268A (32 mg, 21% yield) as a white solid. MS (ESI) m/z: 399.0 (M+H)$^+$. $^1$H-NMR: (500 MHz, CDCl$_3$) ppm 7.35 (s, 5H), 7.13-7.06 (m, 2H), 5.08 (s, 2H), 4.81 (br s, 1H), 4.73 (quind, J=7.0, 1.9 Hz, 1H), 4.17-4.07 (m, 1H), 2.54 (dt, J=11.4, 5.8 Hz, 1H), 2.50-2.40 (m, 2H), 2.39-2.28 (m, 3H), 1.98 (br t, J=10.3 Hz, 1H), 1.90 (br t, J=9.8 Hz, 1H). $^{19}$F-NMR: (471 MHz, CDCl$_3$) δ ppm -114.18 (br s, 1F), -122.49 (br s, 1F).

EXAMPLE 268B

Preparation of 2-((6-aminospiro[3.3]heptan-2-yl)oxy)-3,5-difluorobenzamide

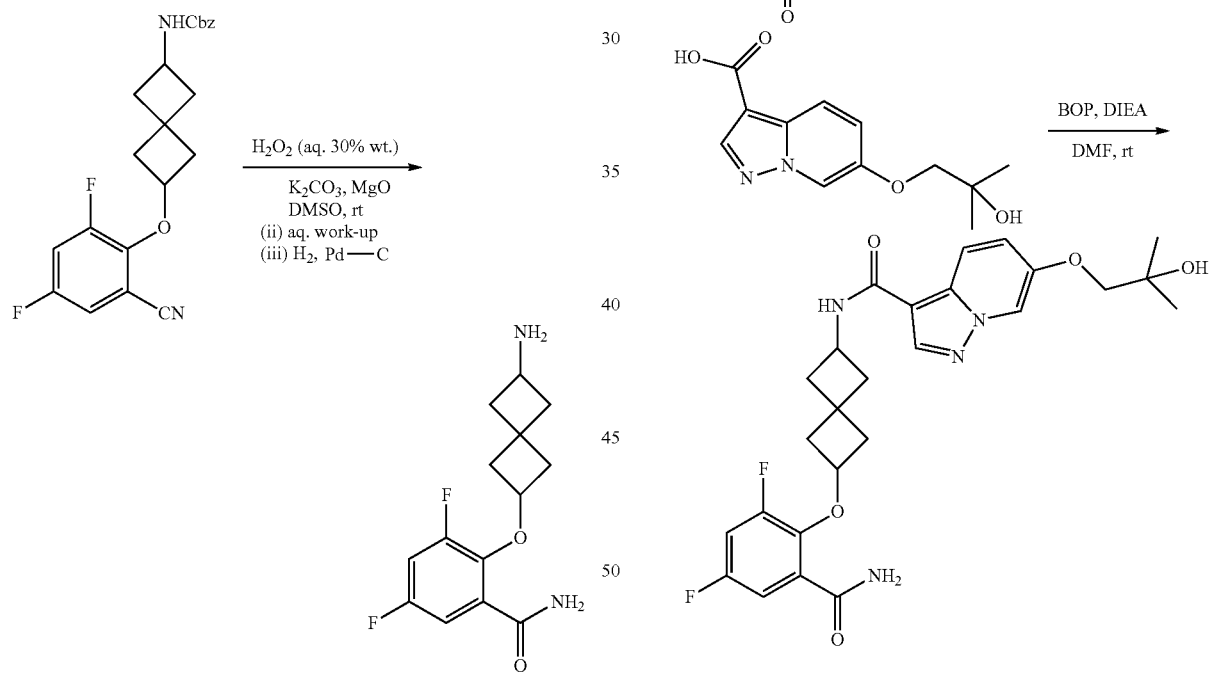

Example 268A (32 mg, 0.080 mmol) was dissolved in DMSO (2.0 mL), then K$_2$CO$_3$ (33.3 mg, 0.241 mmol) and magnesium oxide (16.2 mg, 0.402 mmol) were added at rt. To the reaction was added hydrogen peroxide (30% wt. aq) (0.180 mL, 1.77 mmol) dropwise over 5 min (slight exotherm), and the reaction mixture was stirred at rt for 1 h. Additional amount of hydrogen peroxide (30% wt. aq) (0.180 mL, 1.77 mmol) were added. The reaction mixture was stirred at rt for additional 16 h. The reaction mixture was diluted with EtOAc (50 mL) then quenched with HCl (1 M aq.) (1.29 mL, 1.285 mmol). Organic phase was separated, washed brine (1×25 mL), dried (Na$_2$SO$_4$) and filtered. Solvent was removed under reduced pressure to afford NHCbz protected product as a white solid. The obtained material was dissolved in THF (2 mL), then MeOH (2 mL), and TEA (0.056 mL, 0.402 mmol) was added. The reaction mixture was degassed (3× vacuum/Ar), then palladium on carbon (10% wt.) (8.6 mg, 8.0 μmol) was added. The reaction mixture was degassed again, and it was stirred under dihydrogen atmosphere (1 atm; ballon) for 2 h. Pd—C was filtered off using membrane filter, and the filtrate was concentrated to afford Example 268B (21 mg, 93% yield) as a colorless film. MS (ESI) m/z: 283.0 (M+H)$^+$.

EXAMPLE 268

Example 268B (10.5 mg, 0.037 mmol) and Intermediate 2 (10.2 mg, 0.041 mmol) were dissolved in anhydrous DMF (1.5 mL), then DIEA (0.032 mL, 0.186 mmol) was added, followed by BOP (18.1 mg, 0.041 mmol). The reaction mixture was stirred at rt for 1 h The reaction mixture was quenched with MeOH (0.1 mL), diluted with DMF (2 mL total volume), filtered, and purified by reverse phase HPLC to afford Example 268 (12.0 mg, 61% yield). MS (ESI) m/z: 515.2 (M+H)$^+$. $^1$H-NMR: (500 MHz, DMSO-d$_6$) δ ppm 8.42 (s, 2H), 8.25 (br d, J=7.7 Hz, 1H), 8.06 (d, J=9.6 Hz, 1H), 7.77 (br s, 1H), 7.73 (br s, 1H), 7.46 (ddd, J=11.1, 8.4, 3.0 Hz, 1H), 7.26 (dd, J=9.7, 1.9 Hz, 1H), 7.21 (br d, J=8.6 Hz, 1H), 4.74 (s, 1H), 4.54 (quin, J=7.0 Hz, 1H), 4.33 (sxt, J=8.1

Hz, 1H), 3.78 (s, 2H), 2.49-2.43 (m, 1H), 2.35-2.25 (m, 3H), 2.24-2.15 (m, 2H), 2.11 (br t, J=9.9 Hz, 1H), 2.06 (br t, J=9.7 Hz, 1H), 1.21 (s, 6H). Analytical HPLC RT=1.485 min (Method A) and 1.501 min (Method B), purity=98%.

EXAMPLE 269

Preparation of N-(6-(2-carbamoyl-4,6-difluorophenoxy)spiro[3.3]heptan-2-yl)-7-cyclopropyl-6-(2-hydroxy-2-methylpropoxy)pyrazolo[1,5-a]pyridine-3-carboxamide

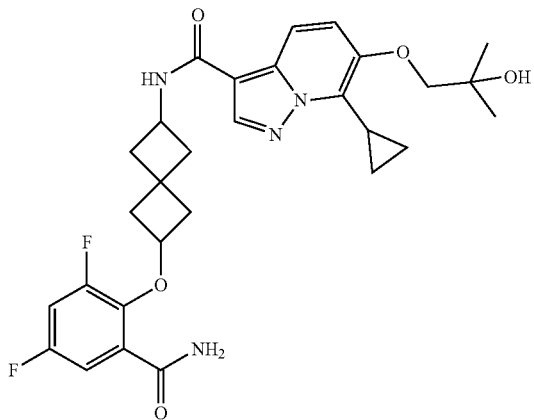 [SMILES: CC(C)(O)COc1ccc2c(C(=O)NC3CC4(C3)CC(Oc3c(F)cc(F)cc3C(N)=O)C4)cnn2c1C1CC1]

Example 269 (8.4 mg, 41% yield) was prepared in an analogous manner as Example 268 replacing Intermediate 2 with Intermediate 4. MS (ESI) m/z: 555.3 (M+H)$^+$. $^1$H-NMR (500 MHz, DMSO-d$_6$) δ ppm 8.47 (s, 1H), 8.26 (br d, J=7.6 Hz, 1H), 8.00 (d, J=9.6 Hz, 1H), 7.75 (br d, J=7.7 Hz, 2H), 7.49-7.40 (m, 2H), 7.20 (br d, J=8.3 Hz, 1H), 4.53 (quin, J=6.9 Hz, 1H), 4.38-4.27 (m, 1H), 3.77 (s, 2H), 3.16 (d, J=5.2 Hz, 1H), 2.62-2.55 (m, 1H), 2.48-2.42 (m, 1H), 2.35-2.23 (m, 3H), 2.23-2.14 (m, 2H), 2.11 (br t, J=9.9 Hz, 1H), 2.05 (br t, J=9.8 Hz, 1H), 1.45 (br d, J=3.5 Hz, 2H), 1.22 (s, 6H), 1.07-1.00 (m, 2H). Analytical HPLC RT=1.687 min (Method A) and 1.694 min (Method B), purity=100%.

EXAMPLE 270

Preparation of N-(6-(2-carbamoyl-4-fluorophenoxy)spiro[3.3]heptan-2-yl)-6-(2-hydroxy-2-methylpropoxy)pyrazolo[1,5-a]pyridine-3-carboxamide

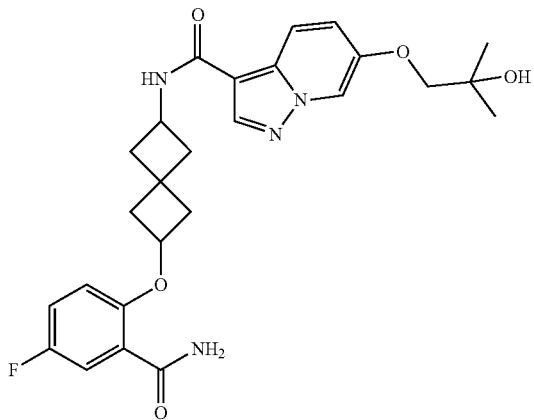 [SMILES: CC(C)(O)COc1ccc2c(C(=O)NC3CC4(C3)CC(Oc3ccc(F)cc3C(N)=O)C4)cnn2c1]

Example 270 (9.4 mg, 39% yield) was prepared in an analogous manner as Example 268 replacing commercially available 2,3,5-trifluorobenzonitrile with 2,5-difluorobenzonitrile. MS (ESI) m/z: 497.0 (M+H)$^+$. $^1$H-NMR (500 MHz, DMSO-d$_6$) δ ppm 8.44-8.38 (m, 2H), 8.30 (br d, J=7.6 Hz, 1H), 8.06 (d, J=9.6 Hz, 1H), 7.68 (br s, 1H), 7.64 (br s, 1H), 7.51 (dd, J=9.4, 3.2 Hz, 1H), 7.32-7.22 (m, 2H), 6.99 (dd, J=9.0, 4.2 Hz, 1H), 4.74 (quin, J=6.8 Hz, 1H), 4.41-4.29 (m, 1H), 3.77 (s, 2H), 3.16 (d, J=5.1 Hz, 1H), 2.69 (br dd, J=10.9, 5.4 Hz, 1H), 2.47-2.39 (m, 1H), 2.36-2.27 (m, 1H), 2.23-2.08 (m, 4H), 1.20 (s, 6H). Analytical HPLC RT=1.403 min (Method A) and 1.429 min (Method B), purity=98%.

EXAMPLE 271

Preparation of N-(6-(2-carbamoyl-4-fluorophenoxy)spiro[3.3]heptan-2-yl)-7-cyclopropyl-6-(2-hydroxy-2-methylpropoxy)pyrazolo[1,5-a]pyridine-3-carboxamide

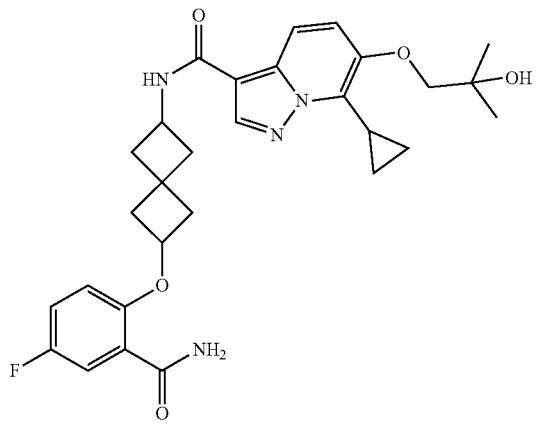 [SMILES: CC(C)(O)COc1ccc2c(C(=O)NC3CC4(C3)CC(Oc3ccc(F)cc3C(N)=O)C4)cnn2c1C1CC1]

Example 271 (8.5 mg, 33% yield) was prepared in an analogous manner as Example 268 replacing commercially available 2,3,5-trifluorobenzonitrile with 2,5-difluorobenzonitrile and Intermediate 2 with Intermediate 4. MS (ESI) m/z: 537.3 (M+H)$^+$. $^1$H-NMR (500 MHz, DMSO-d$_6$) δ ppm 8.49 (s, 1H), 8.27 (br d, J=7.7 Hz, 1H), 8.02 (d, J=9.6 Hz, 1H), 7.70 (br s, 1H), 7.62 (br s, 1H), 7.52 (dd, J=9.3, 3.3 Hz, 1H), 7.45 (d, J=9.8 Hz, 1H), 7.28 (td, J=8.4, 3.3 Hz, 1H), 7.00 (dd, J=9.0, 4.3 Hz, 1H), 4.80-4.72 (m, 1H), 4.72 (s, 1H), 4.41-4.30 (m, 1H), 3.78 (s, 2H), 2.70 (dt, J=11.1, 5.7 Hz, 1H), 2.64-2.56 (m, 1H), 2.47-2.40 (m, 1H), 2.38-2.27 (m, 1H), 2.25-2.09 (m, 4H), 1.52-1.44 (m, 2H), 1.23 (s, 6H), 1.10-1.00 (m, 2H). Analytical HPLC RT=1.621 min (Method A) and 1.603 min (Method B), purity=98%.

EXAMPLE 272

Preparation of N-(6-(5-bromo-2-carbamoylphenoxy)spiro[3.3]heptan-2-yl)-6-(2-hydroxy-2-methylpropoxy)pyrazolo[1,5-a]pyridine-3-carboxamide

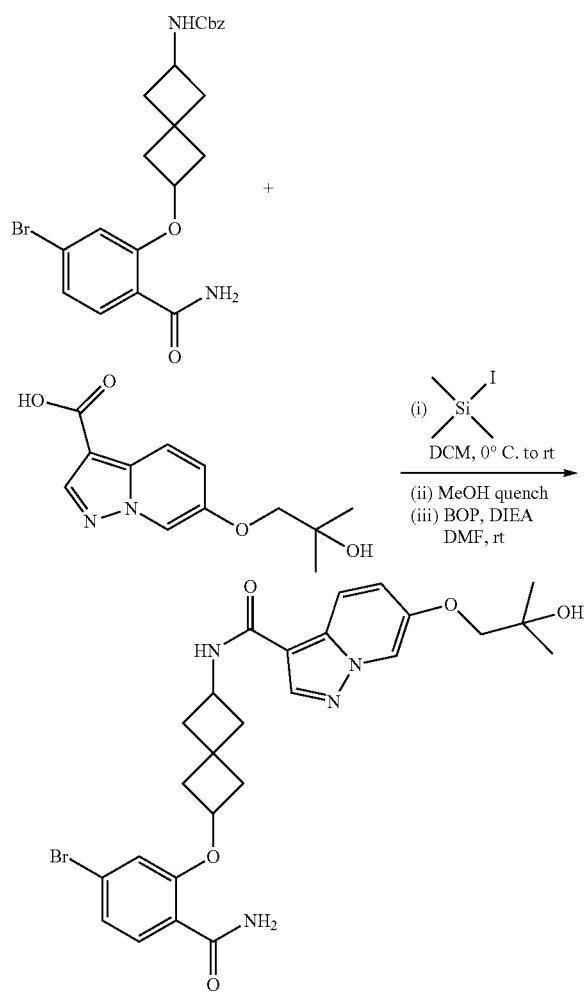

Intermediate 85B (100 mg, 0.218 mmol) was dissolved in DCM (5 mL). The reaction mixture was cooled to 0° C., and iodotrimethylsilane (0.09 mL, 0.653 mmol) was added dropwise under dinitrogen gas. The reaction mixture was stirred at 0° C. for 30 min, then the cooling bath was removed, and the reaction was further stirred at rt for 30 min. The reaction mixture was quenched with MeOH (1 mL), volatiles were removed under reduced pressure, and the residue was pumped under high vacuum for 30 min. The obtained residue was dissolved in anhydrous DMF (2.5 mL), then DIEA (0.19 mL, 1.089 mmol), Intermediate 2 (60 mg, 0.239 mmol) and BOP (125 mg, 0.283 mmol) were added sequentially. The reaction mixture was stirred at rt for 1 h. The reaction mixture was quenched with NH₄Cl (aq. std.), filtered and purified by reverse phase HPLC to afford Example 272 (17.3 mg, 14% yield) was obtained. MS (ESI) m/z: 557.0 (M+H)⁺. $^1$H-NMR (500 MHz, DMSO-$d_6$) δ ppm 8.43 (s, 1H), 8.43 (d, J=2.2 Hz, 1H), 8.23 (d, J=7.4 Hz, 1H), 8.07 (d, J=9.9 Hz, 1H), 7.69 (d, J=8.3 Hz, 1H), 7.60 (br s, 1H), 7.49 (br s, 1H), 7.27 (dd, J=9.6, 2.2 Hz, 1H), 7.22 (dd, J=8.3, 1.9 Hz, 1H), 7.15 (d, J=1.7 Hz, 1H), 4.84 (quin, J=6.9 Hz, 1H), 4.37 (dq, J=16.1, 8.1 Hz, 1H), 3.79 (s, 2H), 2.72 (dt, J=11.2, 5.8 Hz, 1H), 2.57-2.52 (m, 1H), 2.47 (br dd, J=7.2, 5.0 Hz, 1H), 2.38-2.30 (m, 1H), 2.26-2.10 (m, 4H), 1.22 (s, 6H). Analytical HPLC RT=1.606 min (Method A) and 1.610 min (Method B), purity=100%.

EXAMPLE 273

Preparation of N-(6-(2-carbamoyl-5-cyclopropylphenoxy)spiro[3.3]heptan-2-yl)-6-(2-hydroxy-2-methylpropoxy)pyrazolo[1,5-a]pyridine-3-carboxamide

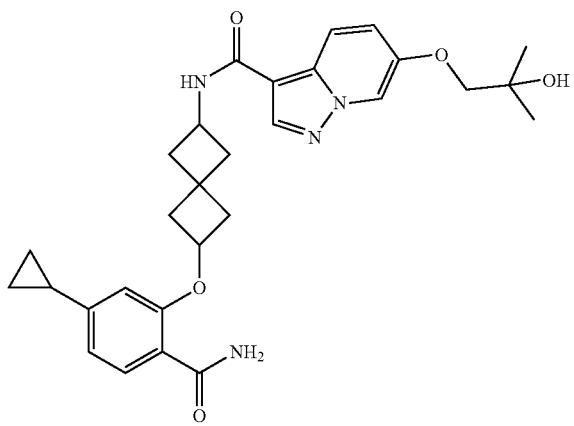 [SMILES: CC(C)(O)COc1ccc2c(C(=O)NC3CC4(C3)CC(Oc3cc(C5CC5)ccc3C(N)=O)C4)cnn2c1]

EXAMPLE 273A

Preparation of benzyl (6-(2-cyano-5-cyclopropylphenoxy)spiro[3.3]heptan-2-yl)carbamate

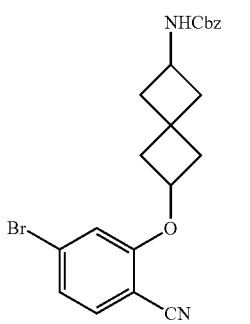

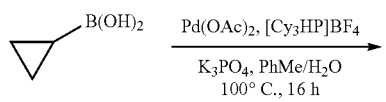

-continued

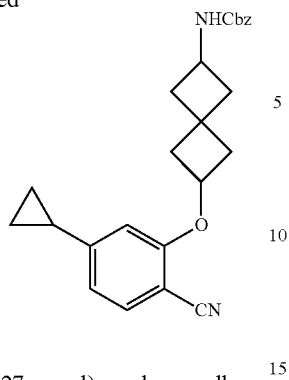

Intermediate 85A (100 mg, 0.227 mmol), cyclopropylboronic acid (78 mg, 0.906 mmol), palladium(ii) acetate (2.5 mg, 0.011 mmol), tricyclohexylphosphonium tetrafluoroborate (8.3 mg, 0.023 mmol) and phosphoric acid, potassium salt (144 mg, 0.680 mmol) were placed in a pressure vial, and the mixture was degassed (3× Ar/vacuum). Then, PhMe (3.0 mL) and Water (0.3 mL) were added, and the reaction mixture was degassed again. Afterwards, the vial was capped, the reaction mixture was heated to 100° C. for 16 h. The reaction mixture was diluted with EtOAc, and Celite was added. Solvent was removed under reduced pressure, and the residue was purified by normal phase chromatography (0-75% EtOAc/hexanes gradient; eluted at ~55% EtOAc). Fractions were combined and concentrated under reduced pressure to give Example 273A (79 mg, 87% yield) as colorless film. MS (ESI) m/z: 403.1 (M+H)$^+$. $^1$H-NMR (500 MHz, DMSO-d$_6$) δ ppm 7.40 (d, J=8.0 Hz, 1H), 7.39-7.30 (m, 5H), 6.62 (dd, J=8.0, 1.4 Hz, 1H), 6.45 (d, J=1.1 Hz, 1H), 5.09 (s, 2H), 4.83 (br s, 1H), 4.65 (quin, J=6.8 Hz, 1H), 4.20-4.08 (m, 1H), 2.64 (br dd, J=11.6, 5.5 Hz, 1H), 2.52 (br d, J=11.0 Hz, 1H), 2.50-2.42 (m, 2H), 2.35-2.25 (m, 2H), 2.02-1.94 (m, 2H), 1.89 (tt, J=8.3, 5.0 Hz, 1H), 1.11-1.04 (m, 2H), 0.77-0.71 (m, 2H).

EXAMPLE 273B

Preparation of 2-((6-aminospiro[3.3]heptan-2-yl)oxy)-4-cyclopropylbenzamide

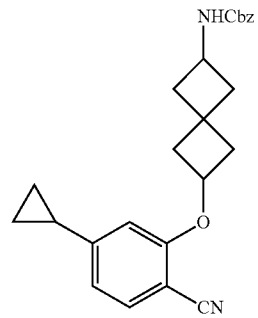

-continued

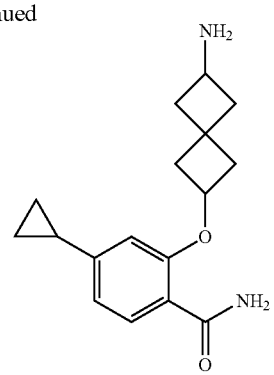

Example 273A (79 mg, 0.196 mmol) was dissolved in DMSO (3.0 mL), then K$_2$CO$_3$ (81 mg, 0.589 mmol) and magnesium oxide (40 mg, 0.981 mmol) were added at rt. To the reaction was added hydrogen peroxide (30% wt. aq) (0.441 mL, 4.32 mmol) dropwise over 5 min (slight exotherm), and the reaction mixture was stirred at rt for 1 h. Additional amount of hydrogen peroxide (30% wt. aq) (0.44 mL, 4.32 mmol) were added. The reaction mixture was stirred at rt for additional 16 h. The reaction mixture was diluted with EtOAc (50 mL) then quenched with HCl (1 M aq.) (3.14 mL, 3.14 mmol). Organic phase was separated, washed brine (1×25 mL), dried (Na$_2$SO$_4$) and filtered. Solvent was removed under reduced pressure. The obtained material was dissolved in THF (2 mL) and MeOH (2 mL), and TEA (0.41 mL, 2.94 mmol) was added.

The reaction mixture was degassed (3× vacuum/Ar), then palladium on carbon (100% wt.) (21 mg, 0.020 mmol) was added. The reaction mixture was degassed again, and it was stirred under dihydrogen atmosphere (1 atm; ballon) for 2 h. Pd—C was filtered off using a membrane filter, and the filtrate was concentrated to afford Example 273B (50 mg, 89% yield) as a colorless film. MS (ESI) m/z: 287.1 (M+H)$^+$.

EXAMPLE 273

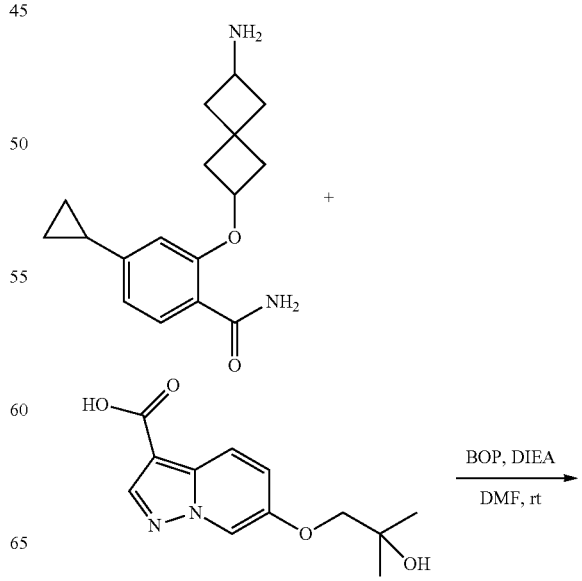

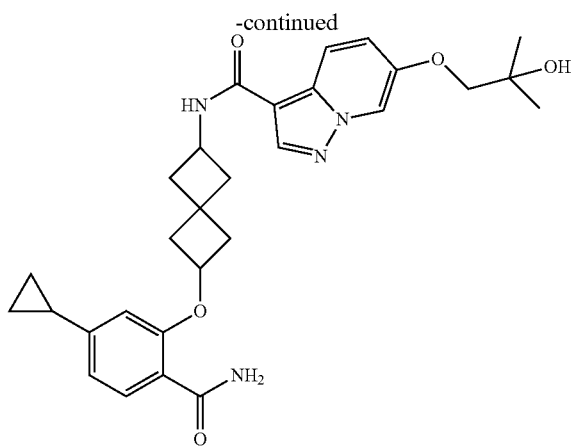

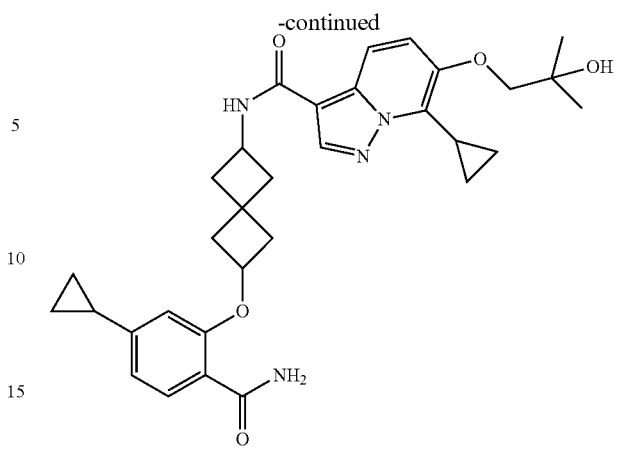

Example 219B (25 mg, 0.087 mmol) and Intermediate 2 (22 mg, 0.087 mmol) were dissolved in anhydrous DMF (1.5 mL), then DIEA (0.08 mL, 0.437 mmol) was added, followed by BOP (42.5 mg, 0.096 mmol). The reaction mixture was stirred at rt for 1 h. The reaction mixture was quenched with MeOH (0.1 mL), diluted with DMF, filtered, and purified by reverse phase HPLC to afford Example 273 (11.4 mg, 25% yield). MS (ESI) min: 519.1 (M+H)$^+$. $^1$H-NMR (500 MHz, DMSO-d$_6$) δ ppm 8.45-8.39 (m, 2H), 8.29 (br d, J=7.6 Hz, 1H), 8.07 (d, J=9.7 Hz, 1H), 7.72 (d, J=8.1 Hz, 1H), 7.49 (br s, 1H), 7.43 (br s, 1H), 7.27 (dd, J=9.6, 1.9 Hz, 1H), 6.67 (d, J=8.2 Hz, 1H), 6.63 (s, 1H), 4.85-4.80 (m, 1H), 4.79 (s, 1H), 4.42-4.29 (m, 1H), 3.78 (s, 2H), 2.76-2.68 (m, 1H), 2.53 (br d, J=4.8 Hz, 1H), 2.37-2.29 (m, 1H), 2.23-2.09 (m, 4H), 2.00-1.91 (m, 1H), 1.21 (s, 6H), 1.03-0.94 (m, 2H), 0.77-0.67 (m, 2H). Analytical HPLC RT=1.555 min (Method A) and 1.508 min (Method B), purity=99%.

EXAMPLE 274

Preparation of N-6-(2-carbamoyl-5-cyclopropylphenoxy)spiro[3.3]heptan-2-yl)-7-cyclopropyl-6-(2-hydroxy-2-methylpropoxy)pyrazolo[1,5-a]pyridine-3-carboxamide

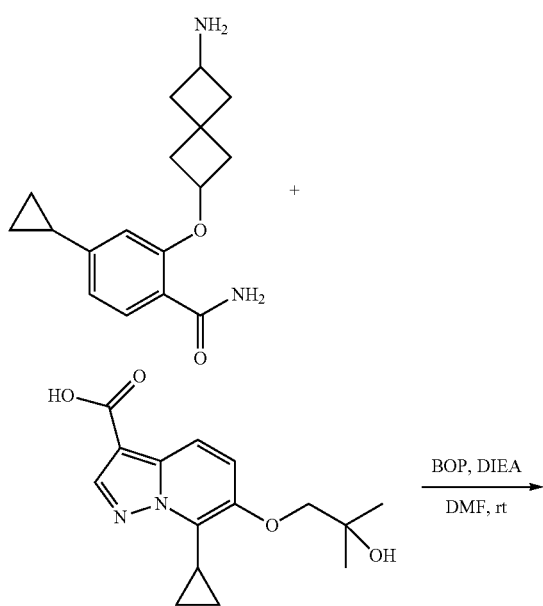

Example 274 ((10.0 mg, 20% yield) was prepared in an analogous manner as Example 273 replacing Intermediate 2 with Intermediate 4. MS (ESI) m/z: 559.1 (M+H)$^+$. $^1$H-NMR (500 MHz, DMSO-d$_6$) δ ppm 8.50 (s, 1H), 8.26 (br d, J=7.5 Hz, 1H), 8.03 (d, J=9.7 Hz, 1H), 7.72 (d, J=8.0 Hz, 1H), 7.46 (br d, J=9.8 Hz, 3H), 6.67 (d, J=8.4 Hz, 1H), 6.64 (s, 1H), 4.82 (quin, J=6.8 Hz, 1H), 4.70 (s, 1H), 4.37 (sxt, J=8.2 Hz, 1H), 3.78 (s, 2H), 2.73 (dt, J=11.0, 5.6 Hz, 1H), 2.64-2.57 (m, 1H), 2.37-2.29 (m, 1H), 2.25-2.09 (m, 4H), 2.00-1.91 (m, 1H), 1.52-1.44 (m, 2H), 1.23 (s, 6H), 1.09-1.02 (m, 2H), 1.03-0.95 (m, 2H), 0.76-0.69 (m, 2H). Analytical HPLC RT=1.770 min (Method A) and 1.791 min (Method B), purity=96%.

EXAMPLE 275

Preparation of N-(6-(2-carbamoyl-5-(1-methyl-1H-pyrazol-4-yl)phenoxy)spiro[3.3]heptan-2-yl)-6-(2-hydroxy-2-methylpropoxy)pyrazolo[1,5-a]pyridine-3-carboxamide

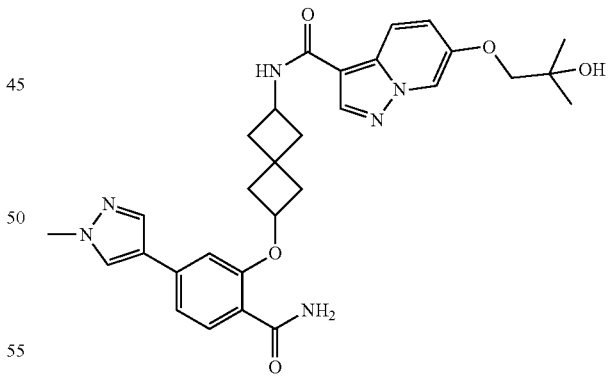

Example 275 (26.6 mg, 36% yield) was prepared in an analogous manner as Example 274 replacing commercially available cyclopropylboronic acid with 1-methyl-4-(4,4,5,5-tetramethyl-1,3,2-dioxaborolan-2-yl)-1H-pyrazole. MS (ESI) m/z: 559.1 (M+H)$^+$. $^1$H-NMR (500 MHz, DMSO-d$_6$) δ ppm 8.47-8.41 (m, 2H), 8.31-8.24 (m, 2H), 8.08 (d, J=9.6 Hz, 1H), 7.82 (d, J=8.1 Hz, 1H), 7.51 (br s, 2H), 7.27 (dd, J=9.6, 2.0 Hz, 1H), 7.22 (d, J=8.9 Hz, 1H), 7.05 (s, 1H), 4.90 (quin, J=6.8 Hz, 1H), 4.72 (s, 1H), 4.44-4.33 (m, 1H), 3.88 (s, 3H), 3.79 (s, 2H), 2.86-2.77 (m, 1H), 2.59 (dt, J=11.3, 5.8

Hz, 1H), 2.40-2.30 (m, 1H), 2.27-2.14 (m, 4H), 1.21 (s, 6H). Analytical HPLC RT=1.232 min (Method A) and 1.297 min (Method B), purity=95%.

EXAMPLE 276

Preparation of N-((aR)-6-(2-carbamoyl-5-(1-methyl-1H-pyrazol-4-yl)phenoxy)spiro[3.3]heptan-2-yl)-6-(2-hydroxy-2-methylpropoxy)pyrazolo[1,5-a]pyridine-3-carboxamide

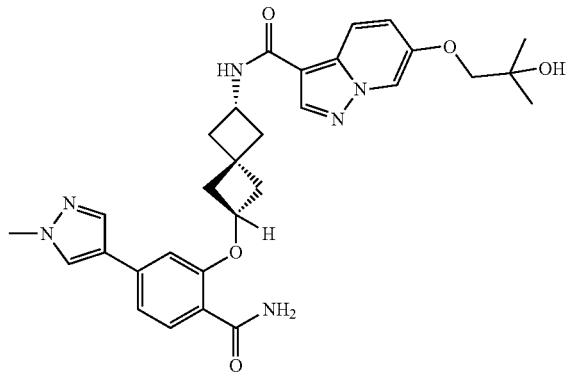

Example 275 (21 mg, 0.038 mmol) was separated using chiral SFC (Instrument: Waters 100 Prep SFC; Column: Chiralcel OD, 30×250 mm, 5 micron; Mobile Phase: 50S CO2/50% Methanol-0.1% DEA (isocratic), Flow Conditions: 100 mL/min, 120 Bar, 40° C.; Detector wavelength: 220 nm). Collected 2nd peak at 4.41 min, concentrated to afford Example 276 (5.0 mg, 22% yield). MS (ESI) m/z: 559.1 (M+H)$^+$. ee=98%. $^1$H-NMR (500 MHz, DMSO-d$_6$) δ ppm 8.42 (s, 1H), 8.39 (s, 1H), 8.31 (br d, J=7.3 Hz, 1H), 8.24 (s, 1H), 8.06 (d, J=9.5 Hz, 1H), 7.96 (s, 1H), 7.81 (d, J=7.9 Hz, 1H), 7.55 (br s, 1H), 7.42 (br s, 1H), 7.27 (br d, J=9.8 Hz, 1H), 7.22 (br d, J=8.2 Hz, 1H), 7.03 (s, 1H), 4.89 (br t, J=6.9 Hz, 1H), 4.40-4.32 (m, 1H), 3.86 (s, 3H), 3.16 (d, J=4.9 Hz, 2H), 2.79 (br s, 1H), 2.58 (br s, 1H), 2.37-2.28 (m, 1H), 2.25-2.10 (m, 4H), 1.21 (s, 6H). Analytical HPLC RT=1.248 min (Method A) and 1.306 min (Method B), purity=96%.

The following examples in Table 11 were prepared using a similar procedure to that which was used in the preparation of Example 235 utilizing the appropriate boronic acids/boronate esters/potassium trifluoroborates. Longer time and higher temperature maybe used to drive the reaction. Microwave conditions (120° C. for 30 min) were also used. Where appropriate, hydrogenation of unsaturated moieties was performed using a variety of conditions including, but not limited to, H$_2$/Pd—C in THF. Various protecting groups were deprotected with the appropriate reagents such as TFA, HCl and TMSI.

TABLE 11

| Example | R | Name | LCMS (M + H)$^+$ | HPLC Method, RT (min.) | $^1$H NMR |
|---|---|---|---|---|---|
| 277 | (1-cyclopropyl-1H-pyrazol-4-yl) | N-(6-(2-carbamoyl-5-(1-cyclopropyl-1H-pyrazol-4-yl)phenoxy)spiro[3.3]heptan-2-yl)-6-(2-hydroxy-2-methylpropoxy)pyrazolo[1,5-a]pyridine-3-carboxamide | 585.2 | A: 1.438 B: 1.411 | (500 MHz, DMSO-d$_6$) δ ppm 8.43 (s, 1H), 8.41 (s, 1H), 8.35 (s, 1H), 8.28 (br d, J = 7.3 Hz, 1H), 8.07 (d, J = 9.8 Hz, 1H), 7.96 (s, 1H), 7.82 (d, J = 7.9 Hz, 1H), 7.53 (br s, 1H), 7.45 (br s, 1H), 7.27 (br d, J = 9.8 Hz, 1H), 7.24 (br d, J = 8.2 Hz, 1H), 7.06 (s, 1H), 4.95-4.86 (m, 1H), 4.76 (s, 1H), 4.43-4.32 (m, 1H), 3.78 (s, 2H), 3.74 (dt, J = 7.2, 3.7 Hz, 1H), 2.85-2.76 (m, 1H), 2.66-2.57 (m, 1H), 2.37-2.30 (m, 1H), 2.27-2.10 (m, 4H), 1.21 (s, 6H), 1.08 (br d, J = 3.1 Hz, 2H), 1.01-0.94 (m, 2H) |
| 278 | (1-(tetrahydro-2H-pyran-4-yl)-1H-pyrazol-4-yl) | N-(6-(2-carbamoyl-5-(1-(tetrahydro-2H-pyran-4-yl)-1H-pyrazol-4-yl)phenoxy)spiro[3.3]heptan-2-yl)-6-(2-hydroxy-2-methylpropoxy)pyrazolo[1,5-a]pyridine-3-carboxamide | 629.1 | A: 1.432 B: 1.425 | (500 MHz, DMSO-d$_6$) δ ppm 8.43 (s, 1H), 8.41 (s, 1H), 8.38 (s, 1H), 8.27 (br d, J = 7.6 Hz, 1H), 8.07 (d, J = 9.8 Hz, 1H), 8.01 (s, 1H), 7.83 (d, J = 8.2 Hz, 1H), 7.52 (br s, 1H), 7.46 (br s, 1H), 7.26 (br t, J = 8.7 Hz, 2H), 7.07 (s, 1H), 4.91 (br t, J = 6.9 Hz, 1H), 4.74 (s, 1H), 4.47-4.33 (m, 2H), 3.98 (br d, J = 11.0 Hz, 2H), 3.79 (s, 2H), 2.85- |

TABLE 11-continued

| | | | | | |
|---|---|---|---|---|---|
| | | | | | 2.76 (m, 1H), 2.64-2.57 (m, 1H), 2.34 (br d, J = 5.2 Hz, 1H), 2.28-2.13 (m, 4H), 2.04-1.93 (m, 4H), 1.21 (s, 6H) |
| 279 | | N-(6-(2-carbamoyl-5-(1-(2-hydroxy-2-methylpropyl)-1H-pyrazol-4-yl)phenoxy)spiro[3.3]heptan-2-yl)-6-(2-hydroxy-2-methylpropoxy)pyrazolo[1,5-a]pyridine-3-carboxamide | 617.2 | A: 1.276 B: 1.279 | (500 MHz, DMSO-d$_6$) δ ppm 8.43 (br d, J = 5.1 Hz, 2H), 8.28 (br d, J = 7.6 Hz, 1H), 8.21 (s, 1H), 8.07 (d, J = 9.6 Hz, 1H), 8.00 (s, 1H), 7.83 (s, 1H), 7.74 (s, 1H), 7.51 (br d, J = 5.7 Hz, 2H), 7.27 (br d, J = 9.7 Hz, 1H), 7.24 (br d, J = 8.2 Hz, 1H), 7.07 (s, 1H), 4.92 (br t, J = 6.7 Hz, 1H), 4.79 (s, 1H), 4.74 (s, 1H), 4.44-4.33 (m, 1H), 4.07-4.02 (m, 2H), 3.79 (s, 2H), 2.80 (br d, J = 5.1 Hz, 1H), 2.64-2.57 (m, 1H), 2.34 (br s, 1H), 2.28-2.20 (m, 2H), 2.20-2.13 (m, 2H), 1.21 (s, 6H), 1.10 (s, 6H) |
| 280 | | 3-fluoro-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-4,4'-dicarboxamide | 616.1 | A: 1.276 B: 1.277 | (500 MHz, DMSO-d$_6$) δ ppm 8.42 (s, 1H), 8.40 (br s, 1H), 8.28 (br d, J = 7.6 Hz, 1H), 8.06 (br d, J = 9.5 Hz, 1H), 7.89 (br d, J = 7.9 Hz, 1H), 7.81-7.72 (m, 2H), 7.71-7.65 (m, 2H), 7.65-7.53 (m, 3H), 7.38 (br d, J = 7.9 Hz, 1H), 7.27 (br d, J = 9.5 Hz, 1H), 7.20 (s, 1H), 5.00 (br t, J = 6.7 Hz, 1H), 4.42-4.31 (m, 1H), 3.78 (s, 2H), 3.52 (br d, J = 6.1 Hz, 1H), 2.77 (br d, J = 4.6 Hz, 1H), 2.57 (br s, 1H), 2.34 (br s, 1H), 2.28-2.11 (m, 4H), 1.21 (s, 6H) |
| 281 | | N-(6-(2-carbamoyl-5-(5-(morpholinomethyl)thiophen-2-yl)phenoxy)spiro[3.3]heptan-2-yl)-6-(2-hydroxy-2-methylpropoxy)pyrazolo[1,5-a]pyridine-3-carboxamide | 659.9 | A: 1.56 B: 1.104 | (500 MHz, DMSO-d$_6$) δ ppm 8.42 (s, 1H), 8.39 (s, 1H), 8.33 (br d, J = 7.5 Hz, 1H), 8.06 (d, J = 9.7 Hz, 1H), 7.83 (d, J = 8.1 Hz, 1H), 7.57 (br s, 1H), 7.53 (br s, 1H), 7.49 (d, J = 3.4 Hz, 1H), 7.26 (br t, J = 9.8 Hz, 2H), 7.06 (s, 1H), 7.01 (d, J = 3.2 Hz, 1H), 4.91 (br t, J = 6.7 Hz, 1H), 4.41-4.31 (m, 1H), 3.77 (s, 1H), 3.66-3.53 (m, 7H), 2.75 (br d, J = 5.2 Hz, 1H), 2.56 (br s, 1H), 2.41 (br s, 4H), 2.35 (br d, J = 11.9 Hz, 1H), 2.29-2.19 (m, 2H), 2.19-2.10 (m, 2H), 1.20 (s, 6H) |
| 282 | | ethyl 2-(4'-carbamoyl-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3-yl)acetate | 641.0 | A: 1.802 B: 1.810 | (500 MHz, DMSO-d$_6$) δ ppm 8.42 (s, 1H), 8.39 (s, 1H), 8.29 (br d, J = 7.3 Hz, 1H), 8.06 (d, J = 9.5 Hz, 1H), 7.90 (d, J = 7.9 Hz, 1H), 7.59 (br d, J = 8.5 Hz, 3H), 7.53 (br s, 1H), 7.44 (t, J = 7.6 Hz, 1H), 7.34-7.24 (m, 3H), 7.11 (s, 1H), 4.95 (br t, J = 6.7 Hz, 1H), 4.42-4.30 (m, 1H), 4.09 (q, J = 7.2 Hz, 2H), 3.78 (s, 2H), 3.75 (s, 2H), 2.80-2.72 (m, 1H), 2.56 (br d, J = 5.8 Hz, 1H), 2.35 (br s, 1H), 2.27 (br dd, J = 11.3, 7.3 Hz, 1H), 2.23 (br dd, J = 11.9, 7.0 Hz, 1H), 2.16 (br t, J = 9.9 Hz, 2H), 1.21 (s, 6H), 1.20-1.16 (m, 3H) |
| 283 | | N-(6-((4-carbamoyl-3',4',5'-trifluoro-[1,1'-biphenyl]-3-yl)oxy)spiro[3.3]heptan-2-yl)-6-(2-hydroxy-2-methylpropoxy)pyrazolo[1,5-a]pyridine-3-carboxamide | 609.3 | A: 1.907 B: 1.869 | (500 MHz, DMSO-d$_6$) δ ppm 8.41 (s, 1H), 8.37 (s, 1H), 8.31 (br d, J = 7.3 Hz, 1H), 8.05 (d, J = 9.5 Hz, 1H), 7.87 (d, J = 8.2 Hz, 1H), 7.75-7.67 (m, 2H), 7.62 (br s, 1H), 7.55 (br s, 1H), 7.34 (br d, J = 8.2 Hz, 1H), 7.27 (br d, J = 9.8 Hz, 1H), 7.14 (s, 1H), 4.99 (br t, J = 6.7 Hz, 1H), 4.40-4.30 (m, 1H), 3.71-3.67 (m, 1H), 2.81-2.73 (m, 1H), 2.60-2.55 (m, 1H), 2.39-2.29 (m, 1H), 2.26-2.20 (m, 1H), 2.20-2.09 (m, 3H), 1.20 (s, 6H) |
| 284 | | N-(6-((4-carbamoyl-3'-(methylsulfonyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 633.2 | A: 1.421 B: 1.378 | (500 MHz, DMSO-d$_6$) δ ppm 8.42 (s, 1H), 8.39 (s, 1H), 8.31 (br d, J = 7.6 Hz, 1H), 8.15 (s, 1H), 8.10-8.07 (m, 1H), 8.05 (s, 1H), 7.96 (br d, J = 7.6 Hz, 1H), 7.93 (br d, J = 7.9 Hz, 1H), 7.79 (t, J = 7.9 Hz, 1H), 7.64 (br s, 1H), 7.57 (br s, 1H), 7.40 (br d, J = 7.9 Hz, 1H), 7.27 (br d, J = 9.8 Hz, 1H), 7.20 (s, 1H), 4.99 (br t, J = 6.9 Hz, 1H), 4.43-4.31 (m, 1H), 3.78 (s, 2H), 3.65-3.61 (m, 1H), 3.29 (s, 3H), 2.76 (br dd, J = 10.7, 5.5 Hz, 1H), 2.62-2.56 (m, 1H), 2.35 (br s, 1H), 2.28 (br dd, J = 11.1, 6.9 Hz, 1H), 2.23 (br dd, J = 11.7, 6.9 Hz, 1H), 2.16 (br t, J = 9.8 Hz, 2H), 1.21 (s, 6H) |
| 285 | | N3-(2-dimethylamino)ethyl)-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3,4'-dicarboxamide | 669.2 | A: 1.143 B: 1.121 | (500 MHz, DMSO-d$_6$) δ ppm 8.58 (br s, 1H), 8.41 (s, 1H), 8.39 (s, 1H), 8.30 (br d, J = 7.3 Hz, 1H), 8.09 (s, 1H), 8.06 (d, J = 9.5 Hz, 1H), 7.95-7.89 (m, 2H), 7.85 (br t, J = 6.3 Hz, 2H), 7.62 (br s, 1H), 7.58 (br t, J = 7.8 Hz, 1H), 7.55 (br s, 1H), 7.37 (br d, J = 7.9 Hz, 1H), 7.27 (br d, J = 9.5 Hz, 1H), 7.18 (s, 1H), 4.97 (br t, J = 6.7 Hz, 1H), 4.41-4.30 (m, 1H), 3.40 (br d, J = 6.1 Hz, 2H), 2.88 (s, |

TABLE 11-continued

| | | | | | |
|---|---|---|---|---|---|
| | | | | | 3H), 2.81-2.74 (m, 1H), 2.72 (s, 3H), 2.57 (br d, J = 6.1 Hz, 1H), 2.48-2.43 (m, 2H), 2.34 (br d, J = 4.6 Hz, 1H), 2.30-2.25 (m, 1H), 2.20 (s, 6H), 2.18-2.11 (m, 2H) |
| 286 | | N-(6-((4-carbamoyl-4'-(methylsulfonyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 633.1 | A: 1.429 B: 1.431 | (500 MHz, DMSO-$d_6$) δ ppm 8.43 (br s, 1H), 8.42 (br s, 1H), 8.29 (br d, J = 7.5 Hz, 1H), 8.07 (br d, J = 9.7 Hz, 1H), 8.04-8.01 (m, 2H), 8.00-7.95 (m, 2H), 7.91 (br d, J = 8.0 Hz, 1H), 7.62 (br s, 2H), 7.39 (br d, J = 8.0 Hz, 1H), 7.27 (br d, J = 9.8 Hz, 1H), 7.22 (s, 1H), 4.99 (br t, J = 6.8 Hz, 1H), 4.77 (s, 1H), 4.42-4.32 (m, 1H), 3.26 (s, 2H), 3.16 (d, J = 5.2 Hz, 1H), 2.79 (br s, 1H), 2.57 (br d, J = 5.3 Hz, 1H), 2.34 (br s, 1H), 2.25 (br t, J = 16.7 Hz, 2H), 2.16 (br t, J = 9.9 Hz, 2H), 1.21 (s, 6H) |
| 287 | | 3'-((6-(6-(2-hydroxy-2-methylpropoxy)pyrazolo[1,5-a]pyridine-3-carboxamido)spiro[3.3]heptan-2-yl)oxy)-N3-methyl-[1,1'-biphenyl]-3,4'-dicarboxamide | 612.4 | A: 1.333 B: 1.342 | (500 MHz, DMSO-$d_6$) δ ppm 8.61 (br d, J = 4.4 Hz, 1H), 8.42 (s, 1H), 8.41 (s, 1H), 8.30 (br d, J = 7.4 Hz, 1H), 8.09 (s, 1H), 8.06 (d, J = 9.7 Hz, 1H), 7.91 (d, J = 8.0 Hz, 1H), 7.85 (br t, J = 7.1 Hz, 2H), 7.61 (br s, 1H), 7.60-7.54 (m, 2H), 7.37 (br d, J = 8.2 Hz, 1H), 7.27 (br d, J = 9.6 Hz, 1H), 7.18 (s, 1H), 4.98 (br t, J = 6.8 Hz, 1H), 4.41-4.32 (m, 1H), 3.78 (s, 2H), 3.29-3.21 (m, 2H), 2.82 (d, J = 4.4 Hz, 3H), 2.77 (br d, J = 4.8 Hz, 1H), 2.57 (br d, J = 6.4 Hz, 1H), 2.38-2.33 (m, 1H), 2.30-2.25 (m, 1H), 2.22 (br dd, J = 11.6, 7.3 Hz, 1H), 2.16 (br t, J = 9.6 Hz, 2H), 1.21 (s, 6H) |
| 288 | | N-(6-((3'-(3-aminopropoxy)-4-carbamoyl-[1,1'-biphenyl]-3-yl)oxy)spiro[3.3]heptan-2-yl)-6-(2-hydroxy-2-methylpropoxy)pyrazolo[1,5-a]pyridine-3-carboxamide | 628.2 | A: 1.221 B: 1.223 | (500 MHz, DMSO-$d_6$) δ ppm 8.43 (s, 1H), 8.41 (s, 1H), 8.32 (br d, J = 7.5 Hz, 1H), 8.06 (d, J = 9.6 Hz, 1H), 7.88 (d, J = 8.1 Hz, 1H), 7.60 (br s, 1H), 7.57 (br s, 1H), 7.45-7.37 (m, 1H), 7.30 (br d, J = 8.1 Hz, 1H), 7.28 (br s, 1H), 7.26 (s, 1H), 7.20 (br s, 1H), 7.11 (s, 1H), 6.99 (br d, J = 8.1 Hz, 1H), 4.98 (br t, J = 6.7 Hz, 1H), 4.42-4.32 (m, 1H), 4.12 (br t, J = 6.0 Hz, 2H), 3.78 (s, 2H), 2.82 (br s, 2H), 2.78-2.72 (m, 1H), 2.59-2.55 (m, 1H), 2.34 (br s, 1H), 2.29-2.24 (m, 1H), 2.24-2.20 (m, 1H), 2.16 (br t, J = 9.9 Hz, 2H), 1.96-1.87 (m, 2H), 1.77 (br s, 4H), 1.21 (s, 6H) |
| 289 | | 3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3,4'-dicarboxamide | 598.2 | A: 1.258 B: 1.241 | (500 MHz, DMSO-$d_6$) δ ppm 8.43 (s, 1H), 8.42 (s, 1H), 8.29 (br d, J = 7.5 Hz, 1H), 8.17 (br s, 1H), 8.15 (s, 1H), 8.07 (d, J = 9.7 Hz, 1H), 7.90 (t, J = 8.2 Hz, 2H), 7.86 (s, 1H), 7.64-7.55 (m, 3H), 7.49 (br s, 1H), 7.38 (br d, J = 8.2 Hz, 1H), 7.27 (br d, J = 9.8 Hz, 1H), 7.19 (s, 1H), 4.99 (br t, J = 6.7 Hz, 1H), 4.43-4.32 (m, 1H), 3.78 (s, 2H), 2.82-2.74 (m, 1H), 2.58 (br dd, J = 11.1, 5.8 Hz, 1H), 2.35 (br s, 1H), 2.28 (br dd, J = 11.1, 7.0 Hz, 1H), 2.23 (br dd, J = 11.7, 6.8 Hz, 1H), 2.20-2.12 (m, 2H), 1.21 (s, 6H) |
| 290 | | (E)-N-(6-(2-carbamoyl-5-(4-hydroxybut-1-en-1-yl)phenoxy)spiro[3.3]heptan-2-yl)-6-(2-hydroxy-2-methylpropoxy)pyrazolo[1,5-a]pyridine-3-carboxamide | 549.2 | A: 1.249 B: 1.240 | (500 MHz, DMSO-$d_6$) δ ppm 8.43 (br s, 1H), 8.43 (br s, 1H), 8.28 (br d, J = 7.5 Hz, 1H), 8.07 (d, J = 9.6 Hz, 1H), 7.77 (d, J = 8.0 Hz, 1H), 7.50 (br s, 2H), 7.27 (br d, J = 9.8 Hz, 1H), 7.07 (br d, J = 8.1 Hz, 1H), 6.90 (s, 1H), 6.51-6.37 (m, 2H), 4.83 (br t, J = 6.7 Hz, 1H), 4.75 (s, 1H), 4.67 (t, J = 5.3 Hz, 1H), 4.44-4.30 (m, 1H), 3.78 (s, 2H), 3.54 (q, J = 6.2 Hz, 1H), 2.80-2.71 (m, 1H), 2.56 (br d, J = 5.8 Hz, 1H), 2.36 (q, J = 6.5 Hz, 3H), 2.26-2.10 (m, 4H), 1.21 (s, 6H) |
| 291 | | (E)-3-(4'-carbamoyl-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3-yl)acrylic acid | 625.0 | A: 1.439 B: 1.597 | (500 MHz, DMSO-$d_6$) δ ppm 8.43 (s, 1H), 8.41 (s, 1H), 8.26 (br d, J = 7.3 Hz, 1H), 8.07 (d, J = 9.5 Hz, 1H), 7.99 (s, 1H), 7.90 (d, J = 7.9 Hz, 1H), 7.75 (br s, 2H), 7.71 (br d, J = 15.9 Hz, 1H), 7.58 (br d, J = 15.0 Hz, 2H), 7.56-7.49 (m, 1H), 7.38 (br d, J = 7.9 Hz, 1H), 7.26 (br d, J = 9.5 Hz, 1H), 7.20 (s, 1H), 6.67 (d, J = 16.2 Hz, 1H), 5.01 (br t, J = 6.7 Hz, 1H), 4.43-4.32 (m, 1H), 3.78 (s, 2H), 2.78 (br d, J = 4.9 Hz, 1H), 2.58 (br d, J = 5.5 Hz, 1H), 2.35 (br s, 1H), 2.28 (br dd, J = 11.1, 6.9 Hz, 1H), 2.25-2.21 (m, 1H), 2.20-2.12 (m, 2H), 1.21 (s, 6H) |

TABLE 11-continued

| # | Structure | Name | MS | LC | NMR |
|---|---|---|---|---|---|
| 292 | (4-fluoro-benzamide structure) | 4-fluoro-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3,4'-dicarboxamide | 616.2 | A: 1.439 B: 1.355 | (500 MHz, DMSO-$d_6$) δ ppm 8.43 (br s, 1H), 8.42 (br s, 1H), 8.29 (br d, J = 7.4 Hz, 1H), 8.07 (d, J = 9.6 Hz, 1H), 7.94-7.83 (m, 4H), 7.73 (br s, 1H), 7.59 (br s, 2H), 7.40 (br t, J = 9.4 Hz, 1H), 7.32 (br d, J = 8.2 Hz, 1H), 7.27 (br d, J = 9.8 Hz, 1H), 7.15 (s, 1H), 4.99 (br t, J = 6.6 Hz, 1H), 4.42-4.33 (m, 1H), 3.78 (s, 2H), 2.77 (br s, 1H), 2.56 (br s, 1H), 2.35 (br s, 1H), 2.30-2.25 (m, 1H), 2.22 (br dd, J = 11.7, 6.9 Hz, 1H), 2.16 (br s, 2H), 1.21 (s, 6H) |
| 293 | (methoxyethyl benzamide structure) | 3'-((6-(6-(2-hydroxy-2-methylpropoxy)pyrazolo[1,5-a]pyridine-3-carboxamido)spiro[3.3]heptan-2-yl)oxy)-N3-(2-methoxyethyl)-[1,1'-biphenyl]-3,4'-dicarboxamide | 656.1 | A: 1.489 B: 1.488 | (500 MHz, DMSO-$d_6$) δ ppm 8.69 (br s, 1H), 8.42 (s, 1H), 8.40 (s, 1H), 8.29 (br d, J = 7.3 Hz, 1H), 8.11 (s, 1H), 8.06 (d, J = 9.5 Hz, 1H), 7.92 (d, J = 7.9 Hz, 1H), 7.87 (br d, J = 7.6 Hz, 2H), 7.65-7.52 (m, 3H), 7.38 (br d, J = 7.9 Hz, 1H), 7.27 (br d, J = 9.8 Hz, 1H), 7.18 (s, 1H), 4.98 (br t, J = 6.9 Hz, 1H), 4.41-4.31 (m, 1H), 3.78 (s, 2H), 3.59-3.50 (m, 3H), 3.50-3.42 (m, 2H), 3.27 (s, 3H), 2.77 (br d, J = 4.6 Hz, 1H), 2.57 (br d, J = 6.1 Hz, 1H), 2.35 (br s, 1H), 2.25 (ddd, J = 23.3, 11.5, 6.7 Hz, 2H), 2.16 (br t, J = 9.8 Hz, 2H), 1.21 (s, 6H) |
| 294 | (morpholine-carbonyl structure) | N-(6-((4-carbamoyl-3'-(morpholine-4-carbonyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 668.3 | A: 1.443 B: 1.447 | (500 MHz, DMSO-$d_6$) δ ppm 8.42 (br d, J = 8.5 Hz, 2H), 8.28 (br d, J = 7.3 Hz, 1H), 8.07 (d, J = 9.5 Hz, 1H), 7.91 (d, J = 7.9 Hz, 1H), 7.81 (br d, J = 7.9 Hz, 1H), 7.71 (s, 1H), 7.62-7.53 (m, 2H), 7.45 (br d, J = 7.3 Hz, 1H), 7.34 (br d, J = 8.2 Hz, 1H), 7.27 (br d, J = 9.8 Hz, 1H), 7.24 (s, 1H), 7.15 (br d, J = 10.4 Hz, 1H), 5.00 (br t, J = 6.7 Hz, 1H), 4.41-4.32 (m, 1H), 3.79 (s, 2H), 2.81-2.72 (m, 1H), 2.56 (br s, 1H), 2.34 (br d, J = 8.5 Hz, 1H), 2.26 (ddd, J = 22.8, 11.5, 6.6 Hz, 3H), 2.17 (br t, J = 9.0 Hz, 2H), 1.21 (s, 8H) |
| 295 | (4-fluoro-N-methyl-benzamide structure) | 4-fluoro-3'-((6-(6-(2-hydroxy-2-methylpropoxy)pyrazolo[1,5-a]pyridine-3-carboxamido)spiro[3.3]heptan-2-yl)oxy)-N3-methyl-[1,1'-biphenyl]-3,4'-dicarboxamide | 630.0 | A: 1.492 B: 1.490 | (500 MHz, DMSO-$d_6$) δ ppm 8.40 (br d, J = 11.9 Hz, 3H), 8.30 (br d, J = 7.3 Hz, 1H), 8.06 (d, J = 9.8 Hz, 1H), 7.91-7.81 (m, 3H), 7.61 (br s, 1H), 7.53 (br s, 1H), 7.39 (t, J = 9.3 Hz, 1H), 7.31 (br d, J = 7.9 Hz, 1H), 7.27 (br d, J = 9.5 Hz, 1H), 7.13 (s, 1H), 4.98 (br t, J = 6.9 Hz, 1H), 4.41-4.31 (m, 1H), 3.77 (s, 2H), 3.16 (d, J = 4.9 Hz, 2H), 2.80 (d, J = 4.6 Hz, 3H), 2.75 (br s, 1H), 2.56 (br d, J = 6.1 Hz, 1H), 2.34 (br s, 1H), 2.26 (br dd, J = 11.9, 6.4 Hz, 1H), 2.22 (br d, J = 6.7 Hz, 1H), 2.18-2.13 (m, 2H), 1.20 (s, 6H) |
| 296 | (benzoic acid structure) | 4'-carbamoyl-3'-((6-(6-(2-hydroxy-2-methylpropoxy)pyrazolo[1,5-a]pyridine-3-carboxamido)spiro[3.3]heptan-2-yl)oxy)-[1,1'-biphenyl]-3-carboxylic acid | 599.1 | A: 1.434 B: 1.104 | (500 MHz, DMSO-$d_6$) δ ppm 8.44-8.36 (m, 2H), 8.34 (br s, 1H), 8.17 (br s, 1H), 8.05 (br d, J = 9.7 Hz, 1H), 8.00-7.93 (m, 2H), 7.91 (br d, J = 8.0 Hz, 1H), 7.68-7.60 (m, 2H), 7.57 (br s, 1H), 7.33 (br d, J = 8.1 Hz, 1H), 7.27 (br d, J = 9.6 Hz, 1H), 7.15 (br s, 1H), 4.97 (br s, 1H), 4.35 (br d, J = 7.1 Hz, 1H), 2.75 (br s, 1H), 2.60-2.55 (m, 1H), 2.34 (br s, 1H), 2.30-2.24 (m, 1H), 2.22 (br s, 1H), 2.17-2.10 (m, 1H), 1.20 (s, 6H) |
| 297 | (hydroxyethylsulfamoyl structure) | N-(6-((4-carbamoyl-3'-(N-(2-hydroxyethyl)sulfamoyl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 678.4 | A: 1.293 B: 1.279 | (500 MHz, DMSO-$d_6$) δ ppm 8.45-8.39 (m, 2H), 8.33 (br s, 1H), 8.10-8.04 (m, 2H), 7.99 (br d, J = 7.7 Hz, 1H), 7.93 (d, J = 8.0 Hz, 1H), 7.84 (br d, J = 7.7 Hz, 1H), 7.77-7.70 (m, 1H), 7.63 (br d, J = 12.0 Hz, 2H), 7.35 (br d, J = 8.1 Hz, 1H), 7.28 (br d, J = 9.6 Hz, 1H), 7.17 (br s, 1H), 4.98 (br t, J = 6.4 Hz, 1H), 4.37 (br d, J = 7.6 Hz, 1H), 3.40 (br d, J = 4.9 Hz, 2H), 2.85 (br s, 2H), 2.77 (br s, 1H), 2.61-2.57 (m, 1H), 2.35 (br s, 1H), 2.27 (br dd, J = 20.8, 10.9 Hz, 2H), 2.17 (br t, J = 9.8 Hz, 2H), 1.21 (s, 6H) |
| 298 | (sulfamoyl structure) | N-(6-((4-carbamoyl-3'-sulfamoyl-[1,1'-biphenyl]-3-yl)oxy)spiro[3.3]heptan-2-yl)-6-(2-hydroxy-2-methylpropoxy)pyrazolo[1,5-a]pyridine-3-carboxamide | 634.4 | A: 1.299 B: 1.284 | (500 MHz, DMSO-$d_6$) δ ppm 8.43 (s, 1H), 8.41 (s, 1H), 8.28 (br d, J = 7.6 Hz, 1H), 8.11 (s, 1H), 8.07 (d, J = 9.8 Hz, 1H), 7.99-7.90 (m, 2H), 7.86 (br d, J = 7.9 Hz, 1H), 7.70 (t, J = 7.8 Hz, 1H), 7.60 (br d, J = 7.6 Hz, 2H), 7.35 (br d, J = 7.9 Hz, 1H), 7.27 (br d, J = 11.0 Hz, 1H), 7.17 (s, 1H), 4.98 (br t, J = 6.7 Hz, 1H), 4.43-4.32 (m, 1H), 3.79 (s, 2H), 2.77 (br d, J = 4.9 Hz, 1H), 2.58 (br d, J = 5.8 Hz, 1H), 2.36 (br s, 1H), 2.27 (ddd, J = 23.0, 11.4, |

TABLE 11-continued

| | | | | |
|---|---|---|---|---|
| | | | | 7.0 Hz, 2H), 2.17 (br t, J = 9.3 Hz, 2H), 1.21 (s, 6H) |
| 299 | 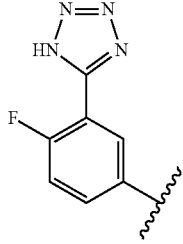 | N-(6-((4-carbamoyl-4'-fluoro-3'-(1H-tetrazol-5-yl)-[1,1'-biphenyl]-3-yl)oxy)spiro[3.3]heptan-2-yl)-6-(2-hydroxy-2-methylpropoxy)pyrazolo[1,5-a]pyridine-3-carboxamide | 641.0 | A: 1.142 B: 1.352 | (500 MHz, DMSO-$d_6$) δ ppm 8.45 (s, 1H), 8.44 (br s, 1H), 8.27 (br d, J = 7.6 Hz, 1H), 8.24 (br d, J = 5.2 Hz, 1H), 8.09 (br d, J = 9.5 Hz, 1H), 7.92 (br d, J = 7.9 Hz, 1H), 7.67 (br s, 1H), 7.58 (br d, J = 13.7 Hz, 2H), 7.41-7.30 (m, 2H), 7.28 (br d, J = 9.5 Hz, 1H), 7.17 (s, 1H), 5.01 (br t, J = 6.9 Hz, 1H), 4.45-4.35 (m, 1H), 3.80 (s, 2H), 2.78 (br s, 1H), 2.62 (br s, 1H), 2.38 (br s, 1H), 2.35-2.29 (m, 1H), 2.28-2.14 (m, 3H), 1.23 (s, 6H) |
| 300 | 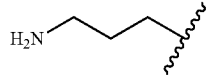 [SMILES: *CCCN] | N-(6-(5-(3-aminopropyl)-2-carbamoylphenoxy)spiro[3.3]heptan-2-yl)-6-(2-hydroxy-2-methylpropoxy)pyrazolo[1,5-a]pyridine-3-carboxamide | 536.3 | A: 1.206 B: 1.159 | (500 MHz, DMSO-$d_6$) δ ppm 8.41 (s, 1H), 8.39 (s, 1H), 8.32 (br d, J = 7.3 Hz, 1H), 8.05 (d, J = 9.8 Hz, 1H), 7.75 (d, J = 7.6 Hz, 1H), 7.54 (br s, 1H), 7.41 (br s, 1H), 7.27 (br d, J = 9.5 Hz, 1H), 6.86 (br d, J = 7.9 Hz, 1H), 6.78 (s, 1H), 4.78 (br t, J = 6.7 Hz, 1H), 4.40-4.28 (m, 1H), 3.77 (s, 2H), 2.76-2.72 (m, 1H), 2.68 (br s, 2H), 2.63 (br t, J = 7.5 Hz, 2H), 2.32 (br s, 1H), 2.23-2.10 (m, 4H), 1.81-1.74 (m, 2H), 1.73 (s, 4H), 1.20 (s, 6H) |
| 301 | 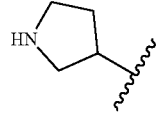 | N-(6-(2-carbamoyl-5-(pyrrolidin-3-yl)phenoxy)spiro[3.3]heptan-2-yl)-6-(2-hydroxy-2-methylpropoxy)pyrazolo[1,5-a]pyridine-3-carboxamide | 548.4 | A: 0.982 B: 0.966 | (500 MHz, DMSO-$d_6$) δ ppm 8.41 (s, 1H), 8.38 (s, 1H), 8.32 (br d, J = 7.3 Hz, 1H), 8.05 (br d, J = 9.8 Hz, 1H), 7.76 (br d, J = 7.9 Hz, 1H), 7.56 (br s, 1H), 7.43 (br s, 1H), 7.27 (br d, J = 8.9 Hz, 1H), 6.96 (br d, J = 7.9 Hz, 1H), 6.83 (s, 1H), 4.81 (br t, J = 6.7 Hz, 1H), 4.40-4.29 (m, 1H), 3.48-3.40 (m, 1H), 3.40-3.29 (m, 1H), 3.24 (br s, 1H), 3.12-3.03 (m, 1H), 2.91 (br t, J = 9.9 Hz, 1H), 2.72 (br d, J = 6.7 Hz, 1H), 2.49-2.43 (m, 2H), 2.32 (br s, 1H), 2.26 (br s, 1H), 2.22-2.09 (m, 4H), 1.89-1.81 (m, 1H), 1.79 (s, 3H), 1.20 (s, 6H) |

EXAMPLE 302

Preparation of N-((aR)-6-(5-bromo-2-carbamoylphenoxy)spiro[3.3]heptan-2-yl)-6-(2-hydroxy-2-methylpropoxy)pyrazolo[1,5-a]pyridine-3-carboxamide

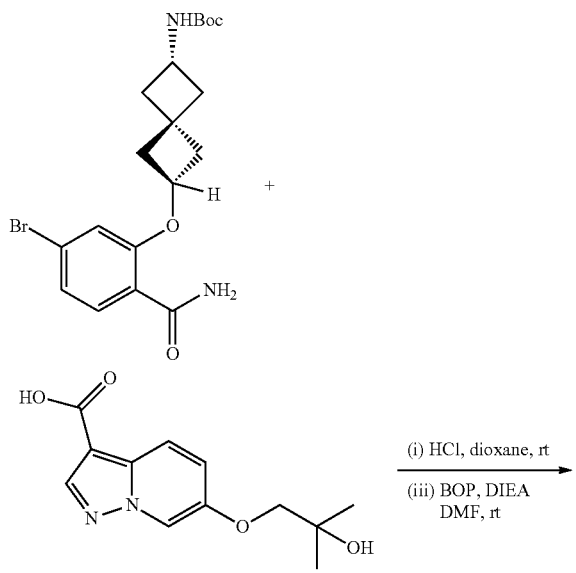

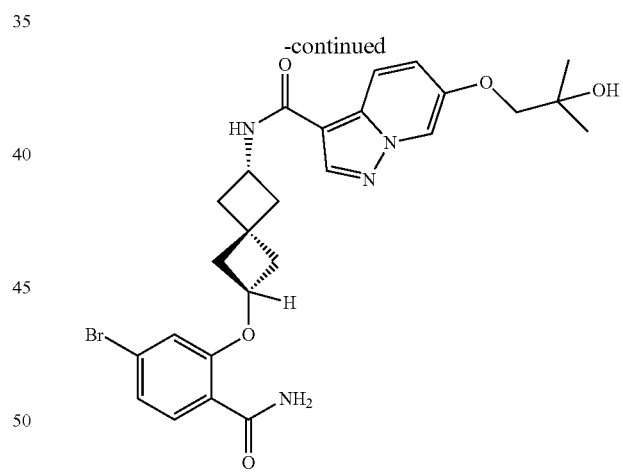

Intermediate 87 (15 mg, 0.035 mmol) was dissolved in HCl (4 M in dioxane) (0.25 mL, 1.000 mmol). The reaction mixture was stirred at rt for 15 min. Solvent was removed under reduced pressure, the residue was suspended in anhydrous DMF (1.5 mL), then DIEA (0.03 mL, 0.176 mmol), Intermediate 2 (9.7 mg, 0.039 mmol) and BOP (20.3 mg, 0.046 mmol) were added sequentially. The reaction mixture was stirred at rt for 30 min. The reaction mixture was quenched with MeOH (0.1 mL), diluted with DMF to 2 mL, filtered and purified by reverse phase HPLC to afford Example 302 (10.8 mg, 53% yield). MS (ESI) min: 557.2 (M+H)$^+$. $^1$H-NMR (500 MHz, DMSO-$d_6$) δ ppm 8.43 (s, 1H), 8.42 (s, 1H), 8.26 (br d, J=7.6 Hz, 1H), 8.08 (d, J=9.5 Hz, 1H), 7.70 (d, J=8.2 Hz, 1H), 7.59 (br s, 1H), 7.51 (br s, 1H), 7.27 (br d, J=9.8 Hz, 1H), 7.22 (br d, J=8.2 Hz, 1H), 7.14 (s, 1H), 4.84 (br t, J=6.7 Hz, 1H), 4.74 (s, 1H), 4.42-4.31 (m, 1H), 3.79 (s, 2H), 2.75-2.68 (m, 1H), 2.54 (br d, J=6.1 Hz, 1H), 2.39-2.30 (m, 1H), 2.27-2.21 (m, 1H), 2.20-2.10 (m, 3H), 1.22 (s, 6H). Analytical HPLC RT=1.526 min (Method A) and 1.511 min (Method B), purity=98%.

EXAMPLE 303

Preparation of N-((aR)-6-(2-carbamoylphenoxy) spiro[3.3]heptan-2-yl)pyrazolo[1,5-a]pyridine-3-carboxamide

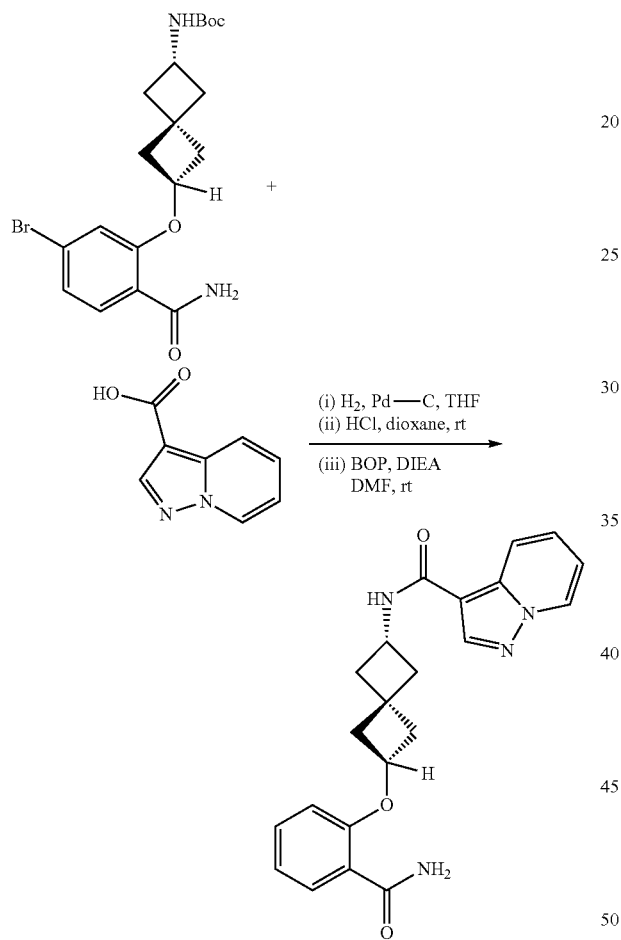

Intermediate 87 (20 mg, 0.047 mmol) was dissolved in THF (2 mL), and the reaction mixture was degassed (3× vacuum/N$_2$), Pd—C (5.0 mg, 4.70 µmol) was added. The reaction mixture was degassed again (3× vacuum/N$_2$), and stirred under H$_2$ (1 atm; balloon) for 14 h. The reaction mixture was filtered via a membrane filter, and the solvent was remove under reduced pressure. The residue was dissolved in HCl (4 M in dioxane) (0.25 mL, 1.0 mmol). The reaction mixture was stirred at rt for 15 min. Solvent was removed under reduced pressure, the residue was suspended in anhydrous DMF (1.5 mL), then DIEA (0.04 mL, 0.235 mmol), Intermediate 1 (8.4 mg, 0.052 mmol) and BOP (27.0 mg, 0.061 mmol) were added sequentially. The reaction mixture was stirred at rt for 30 min. The reaction mixture was quenched with MeOH (0.1 mL), diluted with DMF to 2 mL, filtered and purified by reverse phase HPLC to afford Example 303 (6.8 mg, 36% yield). MS (ESI) min: 391.0 (M+H)$^+$. $^1$H-NMR (500 MHz, DMSO-d$_6$) δ ppm 8.70 (br d, J=6.7 Hz, 1H), 8.51 (s, 1H), 8.36 (br d, J=7.3 Hz, 1H), 8.15 (br d, J=8.9 Hz, 1H), 7.79 (br d, J=7.6 Hz, 1H), 7.60 (br s, 1H), 7.50-7.36 (m, 3H), 7.03 (dt, J=13.8, 7.0 Hz, 2H), 6.95 (br d, J=8.2 Hz, 1H), 4.76 (br t, J=6.9 Hz, 1H), 4.40-4.29 (m, 1H), 2.71 (br d, J=5.2 Hz, 1H), 2.46 (br s, 1H), 2.33 (br s, 1H), 2.20 (br dd, J=11.0, 7.0 Hz, 1H), 2.18-2.08 (m, 3H). Analytical HPLC RT=1.308 min (Method A) and 1.282 min (Method B), purity=97%.

EXAMPLE 304

Preparation of N-(6-(2-carbamoyl-5-(pyrrolidin-3-ylmethyl)phenoxy)spiro[3.3]heptan-2-yl)-6-(2-hydroxy-2-methylpropoxy)pyrazolo[1,5-a]pyridine-3-carboxamide

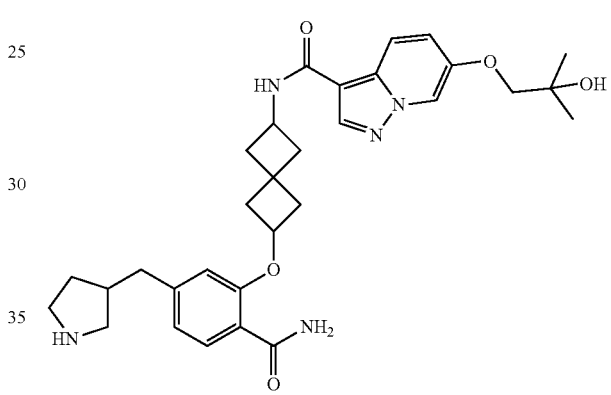

EXAMPLE 304A

Preparation of (4-carbamoyl-3-((6-(6-(2-hydroxy-2-methylpropoxy)pyrazolo[1,5-a]pyridine-3-carboxamido)spiro[3.3]heptan-2-yl)oxy)phenyl)boronic acid

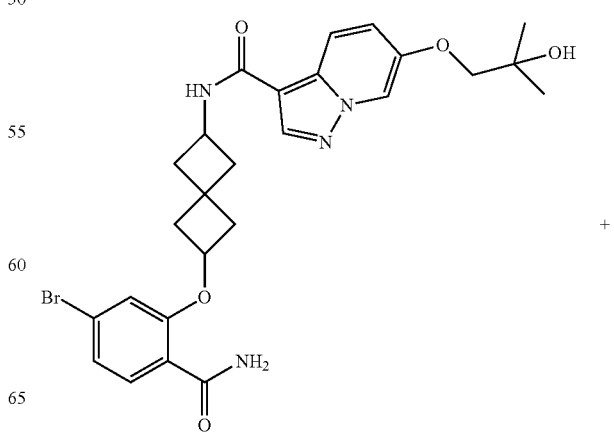

-continued

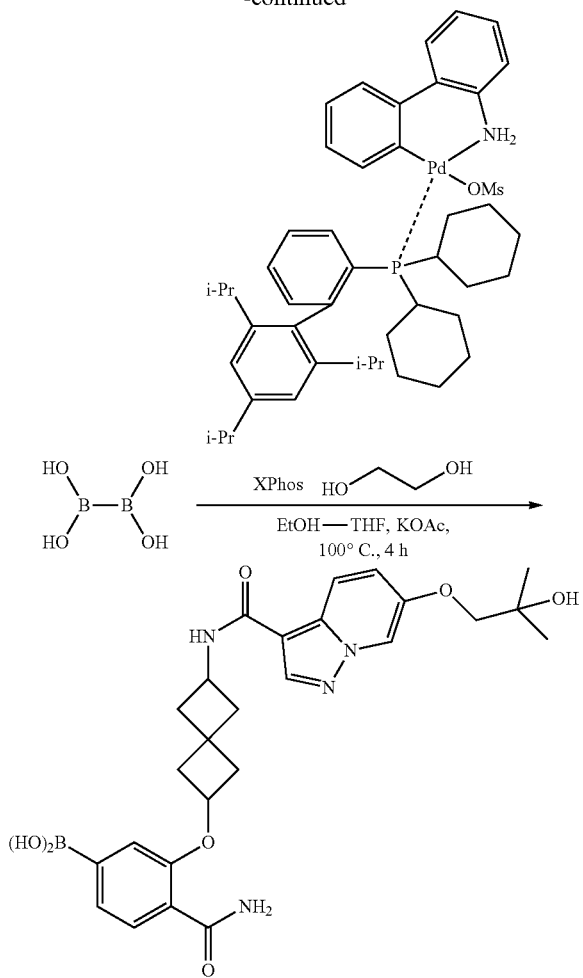

Intermediate 85 (75 mg, 0.135 mmol), hypodiboric acid (36.2 mg, 0.404 mmol), 2-(dicyclohexylphosphino)-2',4',6'-triisopropylbiphenyl (XPhos) (2.6 mg, 5.38 μmol), Pd-XPhos G3 (2.3 mg, 2.69 μmol) and potassium acetate (79 mg, 0.807 mmol) were placed in a pressure vial. Then EtOH (2.0 mL), THF (1.0 mL) and ethane-1,2-diol (0.045 mL, 0.807 mmol) were added, and the reaction mixture was degassed (3×, vacuum/$N_2$). The pressure vial was capped, and the reaction mixture was stirred at 80° C. for 16 h. Additional amounts of hypodiboric acid (36.2 mg, 0.404 mmol), Pd-XPhos G3 (2.3 mg, 2.69 μmol), 2-(dicyclohexylphosphino)-2',4',6'-triisopropylbiphenyl (XPhos) (2.57 mg, 5.38 μmol) and potassium acetate (79 mg, 0.807 mmol) were added, and the reaction mixture was degassed (3× vacuum/$N_2$). Then, ethane-1,2-diol (0.045 mL, 0.807 mmol) was added, the reaction mixture was degassed again, and stirred at 100° C. for 4 h. The reaction mixture was diluted with THF (2 mL), filtered (to remove Pd-black), the filtrate was concentrated under reduced pressure, the residue was triturated with water (10 mL) and HCl (3 mL; aq. 1 M) and stirred at rt for 15 min. The resulting solid was filtered, washed with water (3×5 mL), and dried under lyophilizer vacuum to afford Example 304A (56 mg, 80% yield) as a light-grey solid. MS (ESI) m/z: 523.2 (M+H)$^+$.

EXAMPLE 304

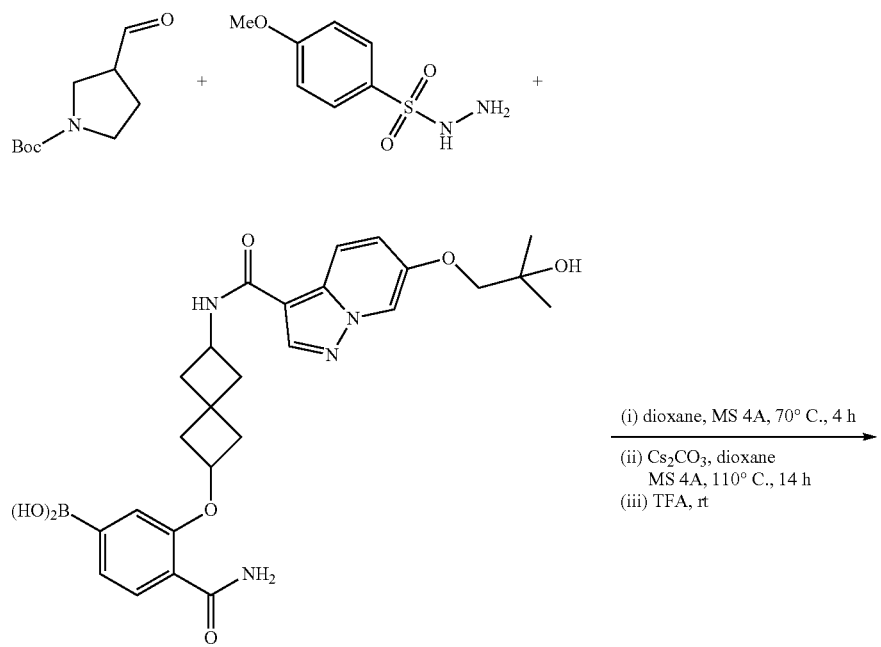

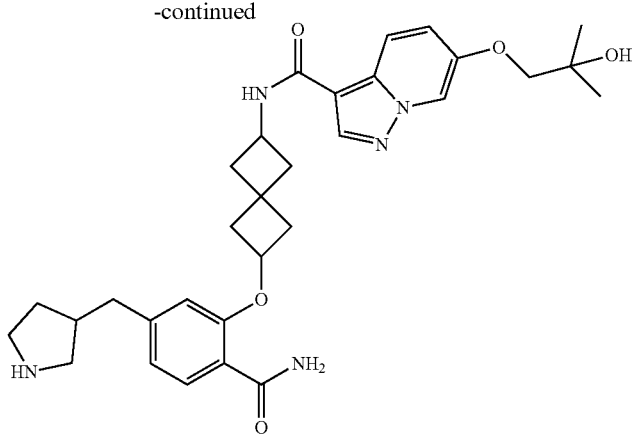

Tert-butyl 3-formylpyrrolidine-1-carboxylate (64.1 mg, 0.322 mmol) and 4-methoxybenzenesulfonohydrazide (68.3 mg, 0.338 mmol) were dissolved in anhydrous dioxane (3.0 mL), and activated MS 4A (30 mg) were added. The reaction mixture degassed (3× vacuum/$N_2$), and then was stirred at 70° C. for 2 h under $N_2$. The reaction mixture was degassed again, and was stirred at 70° C. for 2 h under $N_2$. The reaction mixture was cooled down to rt, and Example 304A (56 mg, 0.107 mmol), cesium carbonate (157 mg, 0.482 mmol) and activated MS 4A (30 mg) were added. The mixture was degassed again (3× vacuum/$N_2$), and the reaction mixture was stirred at 110° C. under $N_2$ for 14 h (CAUTION: dinitrogen gas is generated during the reaction). Solvent was removed under a stream of nitrogen, and the residue was treated with TFA (2 mL) for 15 min at rt. Most of TFA was removed under reduced pressure, the residue was dissolved in DMF (2 mL), filtered and purified by reverse phase HPLC to afford Example 304 (0.9 mg, 2% yield). MS (ESI) m: 562.0 (M+H)$^+$. $^1$H-NMR (500 MHz, DMSO-$d_6$) δ ppm 8.43 (br d, J=7.0 Hz, 2H), 8.25 (br s, 1H), 8.07 (br d, J=9.8 Hz, 1H), 7.75 (br d, J=7.6 Hz, 1H), 7.47 (br d, J=13.4 Hz, 2H), 7.27 (br d, J=9.5 Hz, 2H), 6.86 (br d, J=7.6 Hz, 1H), 4.80 (br d, J=6.7 Hz, 1H), 4.37 (br s, 1H), 3.79 (s, 2H), 3.53 (br s, 1H), 3.42-3.32 (m, 1H), 3.27 (br dd, J=25.6, 5.5 Hz, 1H), 2.98 (br s, 1H), 2.90 (br s, 1H), 2.74 (br s, 1H), 2.65 (br s, 1H), 2.34 (br s, 3H), 2.17 (br d, J=9.2 Hz, 4H), 1.56-1.47 (m, 1H), 1.43 (br s, 1H), 1.22 (s, 6H), 0.83 (br s, 2H). Analytical HPLC RT=1.159 min (Method A) and 1.159 min (Method B), purity=100%.

EXAMPLE 305

Preparation of N-(6-(5-(4-aminobutyl)-2-carbamoylphenoxy)spiro[3.3]heptan-2-yl)-6-(2-hydroxy-2-methylpropoxy)pyrazolo[1,5-a]pyridine-3-carboxamide

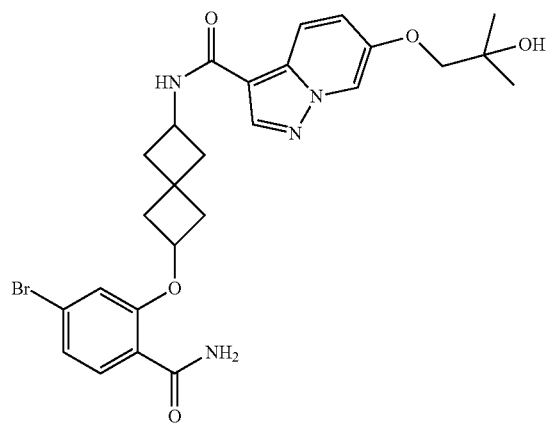

+

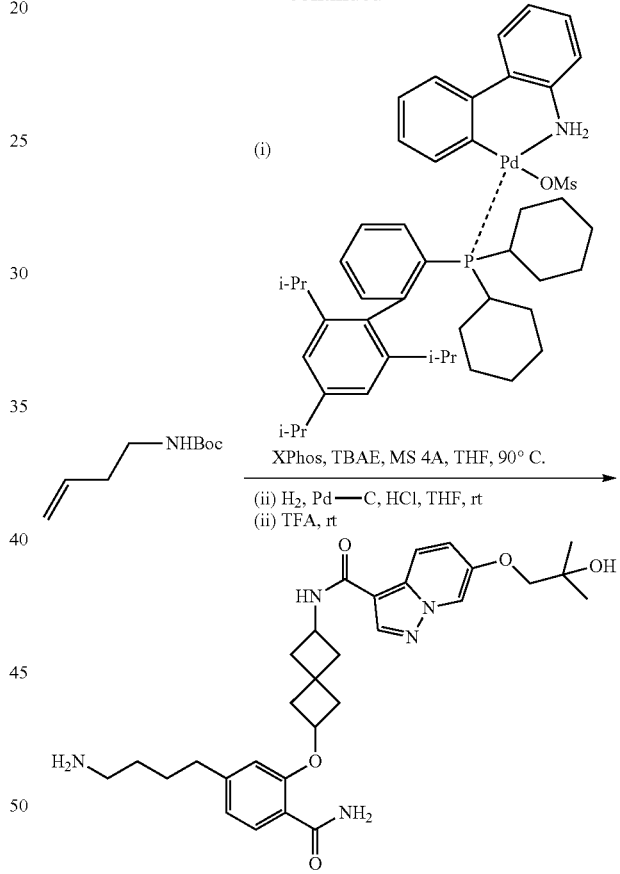

Intermediate 85 (50 mg, 0.090 mmol), 2-(dicyclohexylphosphino)-2',4',6'-triisopropylbiphenyl (XPhos) (2.6 mg, 5.38 μmol), Pd-XPhos G3 (2.3 mg, 2.69 μmol) were placed in a pressure vial. Then THF (2.0 mL), tert-butyl but-3-en-1-ylcarbamate (0.050 mL, 0.269 mmol) and tetrabutylammonium acetate (67.6 mg, 0.224 mmol) were added, along with activated MS 4 Å (~50 mg), and the reaction mixture was degassed (3×, vacuum/$N_2$). The pressure vial was capped, and the reaction mixture was stirred at 90° C. for 14 h. The reaction mixture was diluted with THF (6 mL) and filtered via a membrane filter. The mixture was degassed (3×, vacuum/$N_2$), Pd—C (10% wt.) (9.6 mg, 8.97 μmol) was added, the reaction mixture was degassed again and was stirred under dihydrogen atmosphere (1 atm, balloon) for 2 h. The reaction mixture was degassed, then Pd—C (10% wt.) (9.55 mg, 8.97 μmol) and HCl (1 M aq.) (0.224 mL, 0.224 mmol) were added. The reaction mixture was degassed again, and was stirred under dihydrogen atmosphere (1 atm, balloon) for 14 h. The reaction mixture was filtered via a membrane filter, and the solvent was removed under reduced pressure. The residue was treated with TFA (2 mL) for 15 min at rt. TFA was removed under reduced pressure, the residue was dissolved in DMF (2 mL), filtered and purified by reverse phase HPLC to afford Example 305 (2.5 mg, 5% yield). MS (ESI) m/z: 550.2 (M+H)$^+$. $^1$H-NMR (500 MHz, DMSO-d$_6$) δ ppm 8.42 (s, 1H), 8.39 (br s, 1H), 8.35 (br s, 1H), 8.05 (d, J=9.6 Hz, 1H), 7.75 (d, J=7.9 Hz, 1H), 7.54 (br s, 1H), 7.44 (br s, 1H), 7.27 (br d, J=11.2 Hz, 1a), 6.86 (br d, J=7.9 Hz, 1H), 6.77 (s, 1H), 4.78 (br t, J=6.7 Hz, 1H), 4.40-4.28 (m, 1H), 2.71 (br s, 3H), 2.59 (br t, J=7.4 Hz, 2H), 2.32 (br s, 1H), 2.24-2.09 (m, 4H), 1.70 (br s, 4H), 1.64-1.54 (m, 2H), 1.47 (br s, 2H), 1.20 (s, 6H). Analytical HPLC RT=1.004 min (Method A) and 1.015 min (Method B), purity=99%.

EXAMPLE 306

Preparation of N-(6-((2-(2-aminoethoxy)-5-carbamoylpyrimidin-4-yl)oxy)spiro[3.3]heptan-2-yl)-7-cyclopropyl-6-(2-hydroxy-2-methylpropoxy)pyrazolo[1,5-a]pyridine-3-carboxamide

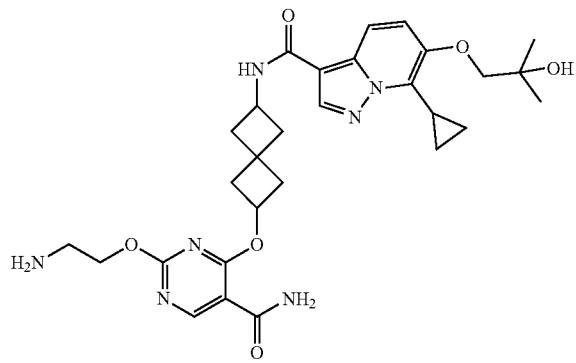 [SMILES: CC(C)(O)COc1ccc2c(C(=O)NC3CC4(C3)CC(Oc3nc(OCCN)ncc3C(N)=O)C4)cnn2c1C1CC1]

EXAMPLE 306A

Preparation of benzyl (6-((5-cyano-2-(methylthio)pyrimidin-4-yl)oxy)spiro[3.3]heptan-2-yl)carbamate

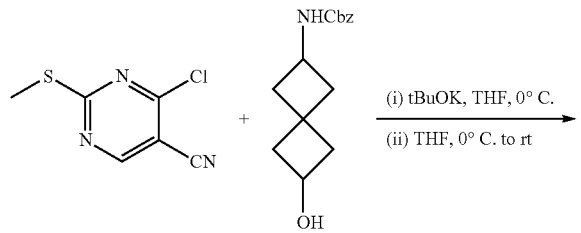

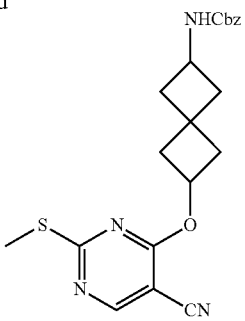

Intermediate 1 (300 mg, 1.15 mmol) was dissolved to anhydrous THF (8.0 mL), and the reaction mixture was cooled 0° C. Potassium tert-butoxide (135 mg, 1.21 mmol) was added in one portion, and the reaction mixture was stirred at 0° C. for 30 min. Thereafter, 4-chloro-2-(methylthio)pyrimidine-5-carbonitrile (266 mg, 1.44 mmol) was added, cooling bath was removed, and the reaction mixture was stirred at rt for 16 h. The reaction mixture was quenched with water (0.2 mL), and concentrated. The residue was purified by normal phase chromatography (20-100% EtOAc/hexanes gradient; eluted at ~50% EtOAc). Fractions were combined and concentrated under reduced pressure to give Example 306A (225 mg, 48% yield) as a colorless foam. MS (ESI) m/z: 411.0 (M+H)$^+$. $^1$H-NMR (500 MHz, DMSO-d$_6$) δ ppm 8.47 (s, 1H), 7.36 (s, 5H), 5.26 (t, J=7.3 Hz, 1H), 5.09 (s, 2H), 4.83 (br s, 1H), 4.13 (q, J=7.0 Hz, 1H), 2.74-2.62 (m, 1H), 2.56 (s, 3H), 2.55-2.41 (m, 3H), 2.31 (dt, J=12.0, 7.5 Hz, 2H), 2.04-1.92 (m, 2H).

EXAMPLE 306B

Preparation of benzyl (6-((5-cyano-2-(methylsulfonyl)pyrimidin-4-yl)oxy)spiro[3.3]heptan-2-yl)carbamate

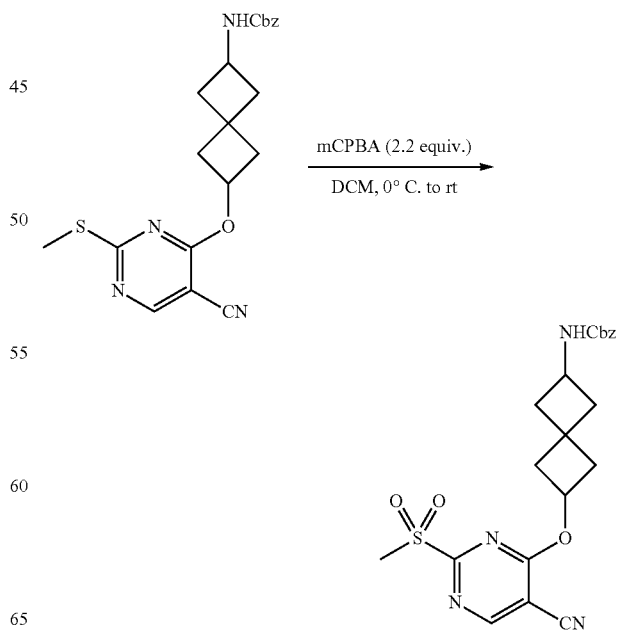

Example 306A (225 mg, 0.548 mmol) was dissolved in anhydrous DCM (10 mL). The reaction mixture was cooled to 0° C., m-CPBA (77% wt.) (270 mg, 1.206 mmol) was added, and the reaction mixture was stirred at 0° C. for 15 min, then cooling bath was removed and the reaction mixture was stirred at rt for 1 h. DCM was removed under reduced pressure, and the residue was purified by normal phase chromatography (20-100% EtOAc/hexanes gradient; eluted at ~68% EtOAc). Fractions were combined and concentrated under reduced pressure to give Example 306B (188 mg, 78% yield) as a colorless film. MS (ESI) m/z: 443.0 (M+H)$^+$. $^1$H-NMR (500 MHz, DMSO-d$_6$) δ ppm 8.84 (s, 1H), 7.40-7.33 (m, 5H), 5.42 (quin, J=7.2 Hz, 1H), 5.09 (br s, 2H), 4.84 (br s, 1H), 3.35 (s, 3H), 2.75 (dt, J=11.8, 6.1 Hz, 1H), 2.60 (dt, J=12.3, 6.1 Hz, 1H), 2.55 (br dd, J=10.7, 6.6 Hz, 1H), 2.51-2.43 (m, 1H), 2.39 (br dd, J=11.7, 7.6 Hz, 1H), 2.34 (dd, J=12.4, 7.2 Hz, 1H), 2.04-1.96 (m, 2H).

EXAMPLE 306C

Preparation of N-(6-{[2-(2-({[(tert-butoxy)carbonyl]amino}ethoxy)-5-cyanopyrimidin-4-yl]oxy}spiro[3.3]heptan-2-yl)carbamate

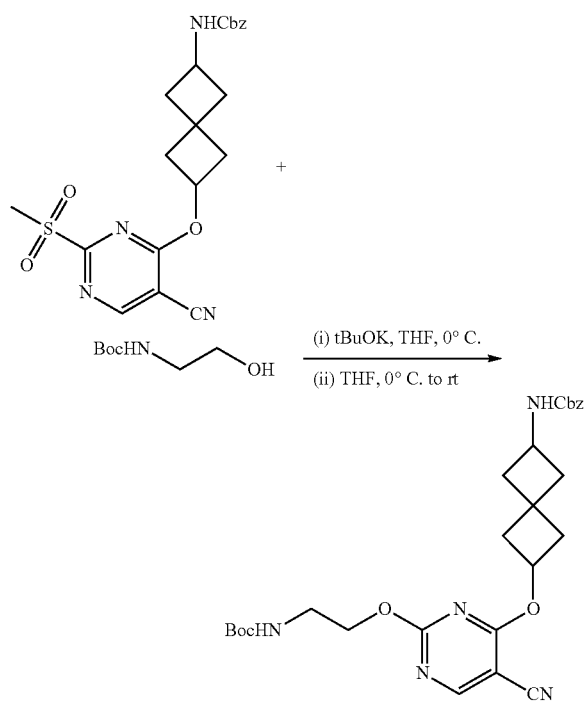

Tert-butyl (2-hydroxyethyl)carbamate (0.03 mL, 0.166 mmol) was dissolved to anhydrous THF (1.0 mL), and the reaction mixture was cooled 0° C. Potassium tert-butoxide (18.6 mg, 0.166 mmol) was added in one portion, and the reaction mixture was stirred at 0° C. for 15 min. Thereafter, Example 306B (70 mg, 0.158 mmol) solution in anhydrous THF (1 mL) was added, stirred at 0° C. for 15 min, cooling bath was removed, and the reaction mixture was stirred at rt for 1 h. The reaction mixture was quenched with water (0.2 mL), and concentrated. The residue was purified by normal phase chromatography (solid loading on Celite; 0-100% EtOAc/hexanes gradient, eluted at ~72% EtOAc). Fractions were combined and concentrated under reduced pressure to give 306C (40 mg, 48° % yield). MS (ESI) m/z: 524.2 (M+H)$^+$. $^1$H-NMR (500 MHz, DMSO-d$_6$) δ ppm 8.85 (s, 1H), 7.51 (br d, J=7.7 Hz, 1H), 7.41-7.23 (m, 5H), 7.01 (br t, J=5.4 Hz, 1H), 6.65 (br s, 1H), 5.18 (quin, J=7.1 Hz, 1H), 4.54 (t, J=5.6 Hz, 1H), 4.39-4.29 (m, 2H), 3.96-3.83 (m, 1H), 3.35 (q, J=6.3 Hz, 3H), 2.97 (q, J=6.2 Hz, 2H), 2.68-2.58 (m, 1H), 2.48-2.41 (m, 1H), 2.39-2.32 (m, 1H), 2.29-2.14 (m, 3H), 2.02-1.94 (m, 2H), 1.37 (s, 9H).

EXAMPLE 306D

Preparation of tert-butyl (2-((4-((6-aminospiro[3.3]heptan-2-yl)oxy)-5-carbamoylpyrimidin-2-yl)oxy)ethyl)carbamate

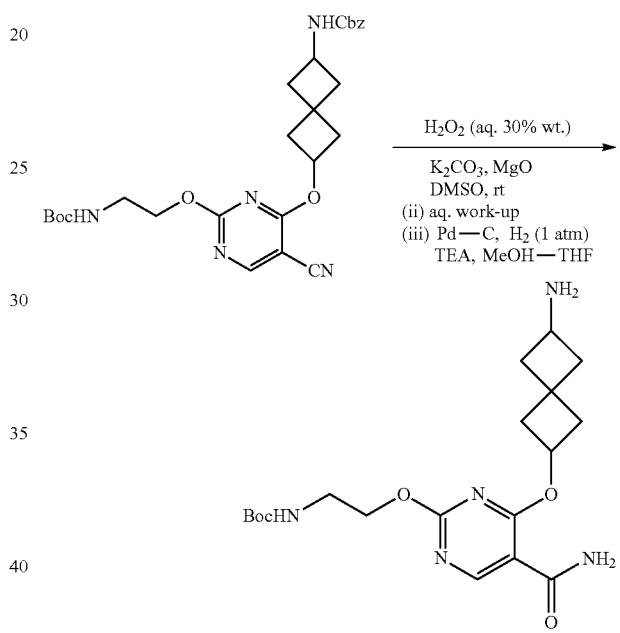

Example 306C (40 mg, 0.076 mmol) was dissolved in DMSO (2.50 mL), then K$_2$CO$_3$ (31.7 mg, 0.229 mmol) and magnesium oxide (15.4 mg, 0.382 mmol) were added at rt. To the reaction was added hydrogen peroxide (30% wt. aq) (0.26 mL, 2.52 mmol) dropwise over 5 min (slight exotherm), and the reaction mixture was stirred at rt for 1 h. The reaction mixture was diluted with EtOAc (50 mL), quenched with HCl (1 M aq.) (1.222 mL, 1.222 mmol), then Na$_2$CO$_3$ (saturated, aq. 1×25 mL) was added. Organic phase was separated, washed brine (1×25 mL), dried (Na$_2$SO$_4$) and filtered. Solvent was removed under reduced pressure to afford NHCbz protected product as a white foam. The material was dissolved in was dissolved in THF (2 mL) and MeOH (2 mL). The reaction mixture was degassed (3× vacuum/Ar), then Pd—C (10% wt. Degussa type E101) (8.1 mg, 7.64 μmol) was added. The reaction mixture was degassed again, and it was stirred under dihydrogen atmosphere (1 atm; ballon) for 14 h. Pd—C was filtered off using membrane filter, and the filtrate was concentrated to Example 306D (31.1 mg, 100% yield) as a colorless film. MS (ESI) m/z: 408.2 (M+H)$^+$.

EXAMPLE 306

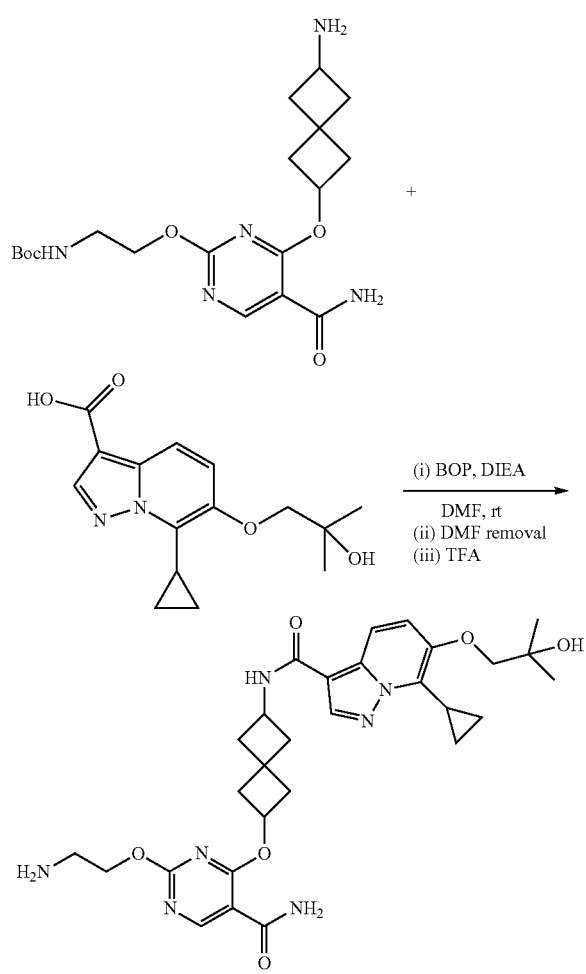

Example 306D (15.5 mg, 0.038 mmol) and Intermediate 4 (12.2 mg, 0.042 mmol) were dissolved in anhydrous DMF (1.5 mL), then DIEA (0.033 mL, 0.190 mmol) was added, followed by BOP (18.51 mg, 0.042 mmol). The reaction mixture was stirred at rt for 1 h The reaction mixture was diluted with MeOH (1 mL), and most of the solvent was evaporated. The residue was treated with TFA (1.5 mL) for 15 min at rt. TFA was removed under reduced pressure, the residue was diluted with DMF (2 mL total volume), filtered, and was purified by reverse phase HPLC to afford Example 306 (3.4 mg, 15% yield). MS (ESI) m/z: 580.0 (M+H)$^+$. $^1$H-NMR (500 MHz, DMSO-d$_6$) δ ppm 8.48 (s, 1H), 8.01 (br d, J=9.6 Hz, 1H), 7.45 (br d, J=9.6 Hz, 1H), 7.32 (br s, 1H), 7.07 (br s, 1H), 5.22-5.09 (m, 1H), 4.43-4.28 (m, 1H), 3.53 (br s, 3H), 3.36 (br d, J=5.7 Hz, 1H), 2.66 (br s, 1H), 2.58 (br s, 1H), 2.38-2.21 (m, 3H), 2.15 (br t, J=10.0 Hz, 2H), 1.45 (br d, J=3.2 Hz, 2H), 1.23 (s, 6H), 1.05 (br d, J=6.6 Hz, 2H). Analytical HPLC RT=1.359 min (Method A) and 1.200 min (Method B), purity=100%.

EXAMPLE 307

Preparation of 7-bromo-N-((aR)-6-((3-carbamoylpyridin-2-yl)oxy)spiro[3.3]heptan-2-yl)-6-(2,2-difluoropropoxy)pyrazolo[1,5-a]pyridine-3-carboxamide

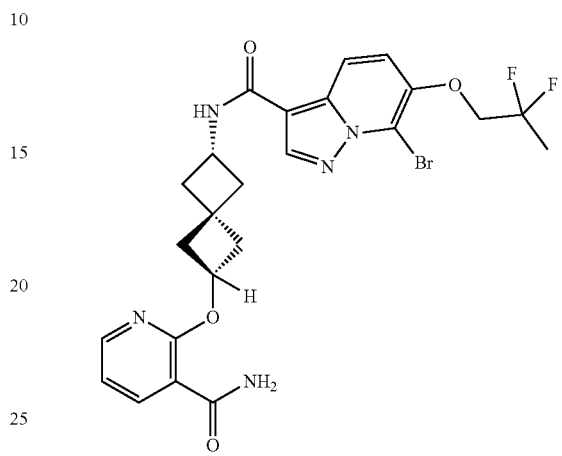

Intermediate 88 (15 mg, 0.027 mmol) was dissolved in anhydrous DMF (2 mL), and purified by reverse phase HPLC to afford Example 307 (5.5 mg, 36% yield). MS (ESI) m/z: 564.3 (M+H)$^+$. $^1$H-NMR (500 MHz, DMSO-d$_6$) δ ppm 8.61 (s, 1H), 8.47 (br d, J=7.1 Hz, 1H), 8.26 (dd, J=4.7, 1.6 Hz, 1H), 8.20 (d, J=9.7 Hz, 1H), 8.18-8.13 (m, 1H), 7.74-7.58 (m, 3H), 7.11 (dd, J=7.3, 5.0 Hz, 1H), 5.22 (quin, J=7.0 Hz, 1H), 4.48 (t, J=12.5 Hz, 2H), 4.37 (dq, J=16.0, 8.2 Hz, 1H), 2.66 (dt, J=11.0, 5.6 Hz, 1H), 2.49-2.42 (m, 2H), 2.38-2.29 (m, 1H), 2.26 (br dd, J=11.1, 7.4 Hz, 1H), 2.23-2.19 (m, 1H), 2.19-2.11 (m, 2H), 1.78 (t, J=19.3 Hz, 3H). Analytical HPLC RT=1.602 min (Method A) and 1.629 min (Method B), purity=97%.

EXAMPLE 308

Preparation of N-((aR)-6-((3-carbamoylpyridin-2-yl)oxy)spiro[3.3]heptan-2-yl)-6-(2,2-difluoropropoxy)pyrazolo[1,5-a]pyridine-3-carboxamide

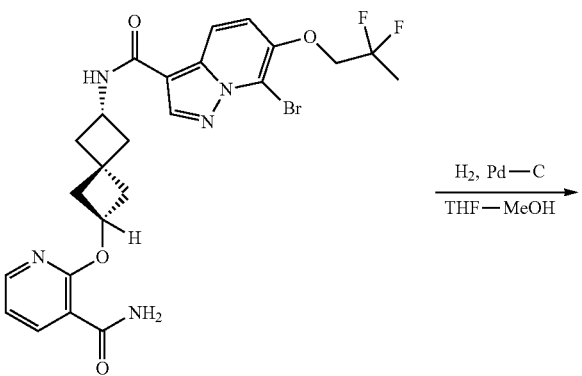

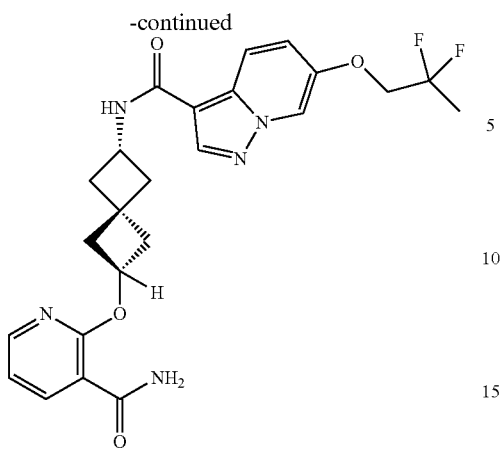

Intermediate 88 (30 mg, 0.053 mmol) and TEA (0.04 mL, 0.266 mmol) was dissolved in THF (2 mL), and the reaction mixture was degassed (3× vacuum/N₂), Pd—C (5.7 mg, 5.32 µmol) was added. The reaction mixture was degassed again (3× vacuum/N₂), and stirred under H2 (1 atm; balloon) for 14 h. The reaction mixture was filtered, concentrated, and the residue was re-dissolved in MeOH (3 mL)/THF (1 mL). The reaction mixture was degassed (3× vacuum/N₂), Pd—C (5.7 mg, 5.32 µmol) was added. The reaction mixture was degassed again (3× vacuum/N₂), and stirred under H₂ (1 atm; balloon) for 3 h. The reaction mixture was filtered via a membrane filter, and the solvent was remove under reduced pressure. The residue was diluted with DMF to 2 mL, filtered and purified by reverse phase HPLC to afford Example 308 (8.9 mg, 33° % yield). MS (ESI) m/z: 486.4 (M+H)⁺. ¹H-NMR (500 MHz, DMSO-d₆) δ ppm 8.59 (s, 1H), 8.47 (s, 1H), 8.33-8.23 (m, 2H), 8.17 (dd, J=7.6, 1.8 Hz, 1H), 8.10 (d, J=9.8 Hz, 1H), 7.69 (br s, 1H), 7.60 (br s, 1H), 7.33 (dd, J=9.8, 2.1 Hz, 1H), 7.11 (dd, J=7.6, 4.9 Hz, 1H), 5.23 (quin, J=7.2 Hz, 1H), 4.42-4.33 (m, 3H), 2.67 (dt, J=11.2, 5.8 Hz, 1H), 2.49-2.41 (m, 2H), 2.39-2.31 (m, 1H), 2.27 (br dd, J=11.1, 7.5 Hz, 1H), 2.22 (br dd, J=11.6, 7.3 Hz, 1H), 2.19-2.12 (m, 2H), 1.76 (t, J=19.2 Hz, 3H). Analytical HPLC RT=1.512 min (Method A) and 1.490 min (Method B), purity=95%.

EXAMPLE 309

Preparation of N-((aR)-6-((3-carbamoylpyridin-2-yl)oxy)spiro[3.3]heptan-2-yl)-7-cyclopropyl-6-(2,2-difluoropropoxy)pyrazolo[1,5-a]pyridine-3-carboxamide

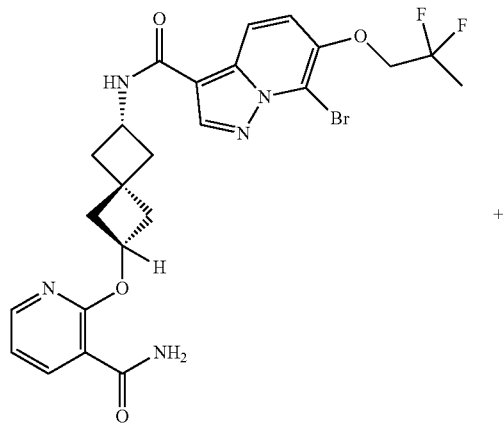

+

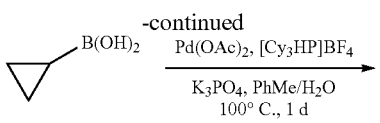

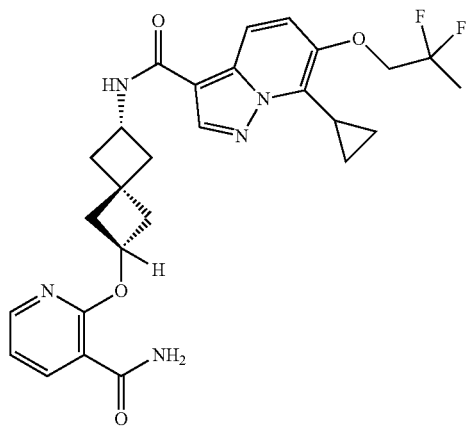

Intermediate 88 (25 mg, 0.044 mmol), cyclopropylboronic acid (15.2 mg, 0.177 mmol), palladium(ii) acetate (0.50 mg, 2.215 µmol), tricyclohexylphosphonium tetrafluoroborate (1.6 mg, 4.43 µmol) and phosphoric acid, potassium salt (28.2 mg, 0.133 mmol) were placed in a pressure vial, and the mixture was degassed (3× Ar/vacuum). Then, PhMe (1.0 mL) and water (0.1 mL) were added, and the reaction mixture was degassed again. Afterwards, the vial was capped, the reaction mixture was heated to 100° C. for 1 d. Most of the solvent was removed under reduced pressure, and the residue was dissolved in DMF (2 mL), filtered and purified by reverse phase HPLC to afford Example 309 (5.6 mg, 23% yield). MS (ESI) m/z: 526.5 (M+H)⁺. ¹H-NMR (500 MHz, DMSO-d₆) δ ppm 8.51 (s, 1H), 8.35 (br d, J=6.9 Hz, 1H), 8.28-8.21 (m, 1H), 8.15 (dd, J=7.5, 1.8 Hz, 1H), 8.03 (d, J=9.6 Hz, 1H), 7.68 (br s, 1H), 7.64 (br s, 1H), 7.47 (d, J=9.7 Hz, 1H), 7.10 (dd, J=7.4, 4.9 Hz, 1H), 5.20 (quin, J=7.0 Hz, 1H), 4.42-4.28 (m, 3H), 2.65 (dt, J=10.9, 5.7 Hz, 1H), 2.48-2.39 (m, 2H), 2.37-2.28 (m, 1H), 2.27-2.17 (m, 2H), 2.17-2.08 (m, 2H), 1.74 (br t, J=19.3 Hz, 3H), 1.34 (br d, J=3.5 Hz, 2H), 1.13-1.03 (m, 2H). Analytical HPLC RT=1.751 min (Method A) and 1.728 min (Method B), purity=96%.

EXAMPLE 310

Preparation of N-((aR)-6-((3-carbamoylpyridin-2-yl)oxy)spiro[3.3]heptan-2-yl)-6-(2,2-difluoropropoxy)-7-(1H-pyrazol-4-yl)pyrazolo[1,5-a]pyridine-3-carboxamide

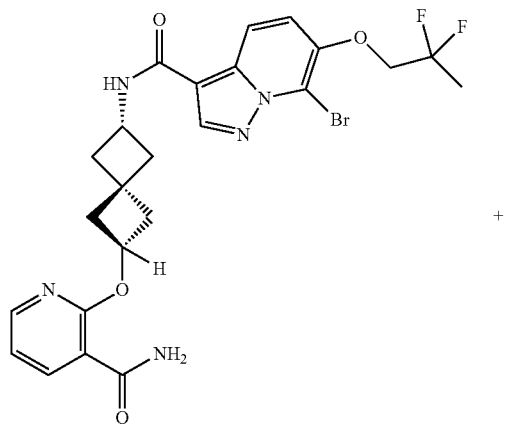

+

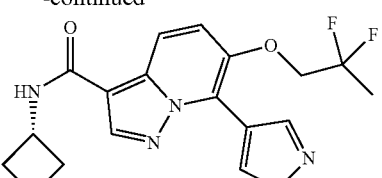

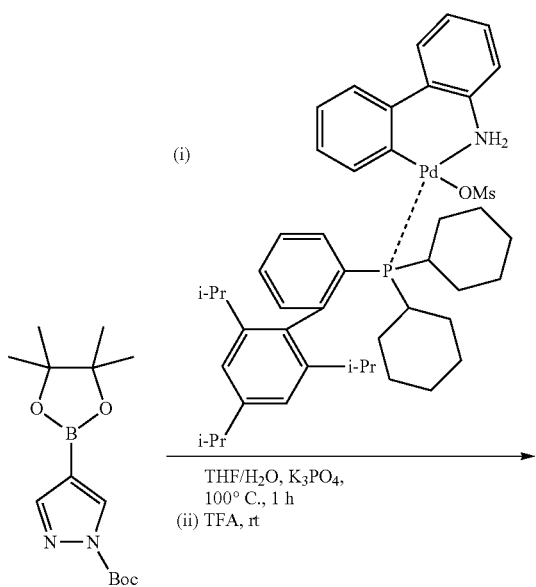

Intermediate 88 (25 mg, 0.044 mmol), tert-butyl 4-(4,4,5,5-tetramethyl-1,3,2-dioxaborolan-2-yl)-1H-pyrazole-1-carboxylate (39.1 mg, 0.133 mmol) and Pd-XPhos G3 (2.8 mg, 3.32 μmol) were placed in a pressure vial. Then THF (1.5 mL) and phosphoric acid, potassium salt (0.5 M aq.) (0.18 mL, 0.089 mmol) were added, and the reaction mixture was degassed (3×, vacuum/Ar). The pressure vial was capped, and the reaction mixture was stirred at 100° C. for 1 h. Most of the solvent was removed under reduced pressure, and the residue was treated with TFA (1 mL) at rt for 15 min. TFA was removed under reduced pressure, the obtained residue was dissolved in DMF (2 mL), filtered and purified by reverse phase HPLC to afford Example 310 (7.1 mg, 28% yield). MS (ESI) m/z: 552.4 (M+H)$^+$. $^1$H-NMR (500 MHz, DMSO-d$_6$) δ ppm 8.63-8.55 (m, 1H), 8.40 (br d, J=7.2 Hz, 1H), 8.26 (br d, J=2.4 Hz, 1H), 8.19-8.08 (m, 2H), 7.74-7.60 (m, 3H), 7.14-7.04 (m, 1H), 5.27-5.16 (m, 1H), 4.49 (br t, J=13.0 Hz, 2H), 4.43-4.30 (m, 1H), 2.65 (br dd, J=11.0, 5.6 Hz, 1H), 2.47 (br s, 2H), 2.34 (br d, J=4.7 Hz, 1H), 2.29-2.23 (m, 1H), 2.23-2.09 (m, 3H), 1.73 (br t, J=19.2 Hz, 3H). Analytical HPLC RT=1.404 min (Method A) and 1.387 min (Method B), purity=97%.

The following examples in Table 12 were prepared using a similar procedure to that which was used in the preparation of Example 43. Example 42C was coupled with a carboxylic acid. Various bases could be used other than the one described in Example 42, such as TEA, DBU, or DABCO. Various coupling reagents could be used other than the one described in Example 43, such as EDCI, HATU, or T3P.

TABLE 12

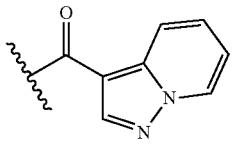 [SMILES: *C(=O)c1cnn2ccccc12]

| Example | R | Name | LCMS (M + H)+ | HPLC Method, RT (min.) | ¹H NMR |
|---|---|---|---|---|---|
| 311 | 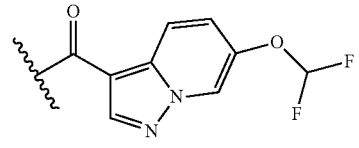 [SMILES: *C(=O)c1cnn2cc(OC(F)F)ccc12] | N-((aR)-6-((3-carbamoylpyridin-2-yl)oxy)spiro[3.3]heptan-2-yl)pyrazolo[1,5-a]pyridine-3-carboxamide | 392.2 | A: 1.185 B: 1.133 | (500 MHz, DMSO-$d_6$) δ ppm 8.74 (br d, J = 6.7 Hz, 1H), 8.54 (s, 1H), 8.33 (br d, J = 6.0 Hz, 1H), 8.26 (dd, J = 4.7, 1.8 Hz, 1H), 8.19-8.12 (m, 2H), 7.71 (br s, 1H), 7.62 (br s, 1H), 7.48-7.39 (m, 1H), 7.10 (dd, J = 7.4, 4.9 Hz, 1H), 7.04 (t, J = 6.7 Hz, 1H), 5.22 (quin, J = 6.9 Hz, 1H), 4.38 (sxt, J = 7.9 Hz, 1H), 2.66 (dt, J = 11.5, 5.8 Hz, 1H), 2.39-2.33 (m, 1H), 2.29-2.24 (m, 1H), 2.22 (br d, J = 7.5 Hz, 1H), 2.19-2.11 (m, 2H) |
| 312 | 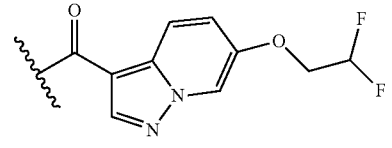 [SMILES: *C(=O)c1cnn2cc(OCC(F)F)ccc12] | N-((aR)-6-((3-carbamoylpyridin-2-yl)oxy)spiro[3.3]heptan-2-yl)-6-(difluoromethoxy)-pyrazolo[1,5-a]pyridine-3-carboxamide | 458.4 | A: 1.381 B: 1.435 | (500 MHz, DMSO-$d_6$) δ ppm 8.86 (s, 1H), 8.57 (s, 1H), 8.39 (br d, J = 7.6 Hz, 1H), 8.26 (dd, J = 4.6, 1.8 Hz, 1H), 8.21 (d, J = 9.8 Hz, 1H), 8.16 (dd, J = 7.3, 1.8 Hz, 1H), 7.67 (br s, 1H), 7.61 (br s, 1H), 7.48-7.41 (m, 1H), 7.10 (dd, J = 7.2, 4.7 Hz, 1H), 5.27-5.16 (m, 1H), 4.37 (sxt, J = 8.1 Hz, 1H), 2.71-2.60 (m, 1H), 2.49-2.40 (m, 2H), 2.38-2.30 (m, 1H), 2.26 (br dd, J = 11.3, 7.3 Hz, 1H), 2.23-2.18 (m, 1H), 2.18-2.12 (m, 2H) |
| 313 | 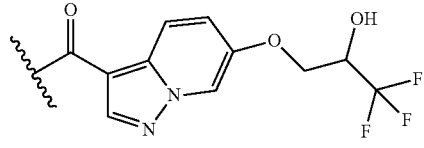 [SMILES: *C(=O)c1cnn2cc(OCC(O)C(F)(F)F)ccc12] | N-((aR)-6-((3-carbamoylpyridin-2-yl)oxy)spiro[3.3]heptan-2-yl)-6-(2,2-difluoroethoxy)-pyrazolo[1,5-a]pyridine-3-carboxamide | 472.1 | A: 1.428 B: 1.373 | (500 MHz, DMSO-$d_6$) δ ppm 8.58 (br s, 1H), 8.46 (s, 1H), 8.34 (br s, 1H), 8.29-8.22 (m, 1H), 8.15 (br d, J = 6.8 Hz, 1H), 8.09 (d, J = 9.7 Hz, 1H), 7.70 (br s, 1H), 7.63 (br s, 1H), 7.31 (dd, J = 9.7, 1.7 Hz, 1H), 7.10 (dd, J = 7.4, 4.9 Hz, 1H), 6.58-6.25 (m, 1H), 5.21 (br t, J = 6.9 Hz, 1H), 4.47-4.30 (m, 3H), 2.69-2.60 (m, 1H), 2.49-2.40 (m, 2H), 2.37-2.29 (m, 1H), 2.25 (br t, J = 8.8 Hz, 1H), 2.21-2.10 (m, 3H) |
| 314 |  | N-((aR)-6-((3-carbamoylpyridin-2-yl)oxy)spiro[3.3]heptan-2-yl)-6-(3,3,3-trifluoro-2-hydroxypropoxy)-pyrazolo[1,5-a]pyridine-3-carboxamide | 520.2 | A: 1.381 B: 1.329 | (500 MHz, DMSO-$d_6$) δ ppm 8.54 (s, 1H), 8.44 (s, 1H), 8.30 (br d, J = 7.3 Hz, 1H), 8.26 (dd, J = 4.7, 1.7 Hz, 1H), 8.16 (dd, J = 7.5, 1.7 Hz, 1H), 8.08 (d, J = 9.8 Hz, 1H), 7.67 (br s, 1H), 7.61 (br s, 1H), 7.27 (dd, J = 9.8, 1.8 Hz, 1H), 7.10 (dd, J = 7.6, 4.9 Hz, 1H), 5.22 (quin, J = 7.1 Hz, 1H), 4.49-4.40 (m, 1H), 4.41-4.31 (m, 1H), 4.26 (dd, J = 10.7, 3.7 Hz, 1H), 4.15 (dd, J = 10.5, 6.6 Hz, 1H), 2.65 (dt, J = 11.0, 5.2 Hz, 1H), 2.49-2.40 (m, 2H), 2.37-2.29 (m, 1H), |

TABLE 12-continued

| | | | | | |
|---|---|---|---|---|---|
| | | | | | 2.25 (br dd, J = 11.1, 7.5 Hz, 1H), 2.22-2.18 (m, 1H), 2.19-2.13 (m, 2H) |
| 315 | | N-((aR)-6-((3-carbamoylpyridin-2-yl)oxy)spiro[3.3]heptan-2-yl)-6-(3,3,3-trifluoro-2-hydroxy-2-(trifluoromethyl)-propoxy)-pyrazolo[1,5-a]pyridine-3-carboxamide | 588.0 | A: 1.689 B: 1.717 | (500 MHz, DMSO-d₆) δ ppm 8.62 (br s, 1H), 8.45 (s, 1H), 8.42-8.35 (m, 1H), 8.25 (br d, J = 4.0 Hz, 1H), 8.15 (br d, J = 7.3 Hz, 1H), 8.09 (d, J = 9.7 Hz, 1H), 7.66 (br s, 2H), 7.27 (br d, J = 9.7 Hz, 1H), 7.10 (dd, J = 7.2, 5.2 Hz, 1H), 5.20 (quin, J = 7.0 Hz, 1H), 4.48 (s, 2H), 4.34 (dq, J = 16.1, 7.9 Hz, 1H), 3.15 (d, J = 5.0 Hz, 1H), 2.68-2.60 (m, 1H), 2.48-2.39 (m, 2H), 2.37-2.27 (m, 1H), 2.25-2.21 (m, 1H), 2.20-2.09 (m, 3H) |
| 316 | | N-((aR)-6-((3-carbamoylpyridin-2-yl)oxy)spiro[3.3]heptan-2-yl)-6-(4,4-difluoropiperidin-1-yl)pyrazolo[1,5-a]pyridine-3-carboxamide | 511.3 | A: 1.546 B: 1.613 | (500 MHz, DMSO-d₆) δ ppm 8.40 (s, 1H), 8.26 (br d, J = 3.1 Hz, 1H), 8.24-8.20 (m, 2H), 8.16 (br d, J = 7.3 Hz, 1H), 8.03 (d, J = 9.5 Hz, 1H), 7.69 (br s, 1H), 7.60 (br s, 1H), 7.48 (br d, J = 9.5 Hz, 1H), 7.10 (dd, J = 7.2, 5.0 Hz, 1H), 5.23 (quin, J = 7.0 Hz, 1H), 4.37 (dq, J = 16.0, 8.2 Hz, 1H), 3.27 (br d, J = 4.9 Hz, 2H), 2.65 (br dd, J = 11.1, 6.0 Hz, 1H), 2.48-2.40 (m, 2H), 2.37-2.30 (m, 1H), 2.26 (br dd, J = 11.0, 7.9 Hz, 1H), 2.21 (br dd, J = 11.6, 7.6 Hz, 1H), 2.18-2.05 (m, 6H) |
| 317 | | N-((aR)-6-((3-carbamoylpyridin-2-yl)oxy)spiro[3.3]heptan-2-yl)-6-morpholino-pyrazolo[1,5-a]pyridine-3-carboxamide | 477.4 | A: 1.233 B: 1.204 | (500 MHz, DMSO-d₆) δ ppm 8.40 (s, 1H), 8.26 (br d, J = 3.1 Hz, 1H), 8.23 (br d, J = 7.6 Hz, 1H), 8.16 (br d, J = 7.3 Hz, 1H), 8.11 (s, 1H), 8.03 (d, J = 9.8 Hz, 1H), 7.68 (br s, 1H), 7.60 (br s, 1H), 7.47 (br d, J = 9.8 Hz, 1H), 7.10 (dd, J = 7.2, 5.0 Hz, 1H), 5.23 (quin, J = 6.9 Hz, 1H), 4.36 (dq, J = 16.0, 8.1 Hz, 1H), 3.75 (br s, 3H), 3.09 (br s, 3H), 2.92 (q, J = 7.3 Hz, 2H), 2.70-2.61 (m, 1H), 2.48-2.40 (m, 2H), 2.37-2.29 (m, 1H), 2.26 (br dd, J = 11.0, 7.6 Hz, 1H), 2.21 (br dd, J = 11.4, 7.8 Hz, 1H), 2.18-2.10 (m, 2H) |
| 318 | | N-((aR)-6-((3-carbamoylpyridin-2-yl)oxy)spiro[3.3]heptan-2-yl)-6-((R)-3-fluoropyrrolidin-1-yl)pyrazolo[1,5-a]pyridine-3-carboxamide | 479.3 | A: 1.426 B: 1.406 | (500 MHz, DMSO-d₆) δ ppm 8.33 (s, 1H), 8.26 (br d, J = 3.4 Hz, 1H), 8.17 (br t, J = 7.9 Hz, 2H), 8.03 (d, J = 9.8 Hz, 1H), 7.88 (s, 1H), 7.68 (br s, 1H), 7.60 (br s, 1H), 7.21 (br d, J = 9.2 Hz, 1H), 7.10 (dd, J = 7.2, 5.0 Hz, 1H), 5.46 (d, J = 53.7 Hz, 1H), 5.22 (quin, J = 7.0 Hz, 1H), 4.36 (dq, J = 15.9, 7.9 Hz, 1H), 2.65 (br dd, J = 10.8, 5.3 Hz, 1H), 2.48-2.39 (m, 2H), 2.37-2.30 (m, 1H), 2.27 (br d, J = 6.1 Hz, 2H), 2.24-2.19 (m, 2H), 2.19-2.09 (m, 3H) |

TABLE 12-continued

| # | Structure | Name | Mass | LC | NMR |
|---|---|---|---|---|---|
| 319 | 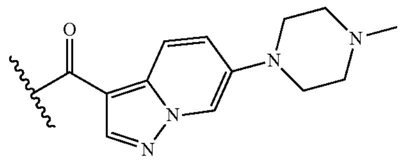 [SMILES: *C(=O)c1cnn2cc(N3CCN(C)CC3)ccc12] | N-((aR)-6-((3-carbamoylpyridin-2-yl)oxy)spiro[3.3]heptan-2-yl)-6-(4-methylpiperazin-1-yl)pyrazolo[1,5-a]pyridine-3-carboxamide | 490.5 | A: 1.104 B: 0.918 | (500 MHz, DMSO-$d_6$) δ ppm 8.37 (s, 1H), 8.28-8.21 (m, 2H), 8.16 (br d, J = 7.3 Hz, 1H), 8.08 (s, 1H), 8.01 (d, J = 9.5 Hz, 1H), 7.66 (br s, 1H), 7.61 (br s, 1H), 7.45 (br d, J = 9.8 Hz, 1H), 7.10 (dd, J = 7.3, 4.9 Hz, 1H), 5.22 (quin, J = 7.2 Hz, 1H), 4.35 (sxt, J = 7.9 Hz, 1H), 3.10 (br s, 3H), 2.65 (dt, J = 11.3, 5.6 Hz, 1H), 2.48-2.39 (m, 2H), 2.37-2.28 (m, 1H), 2.24 (s, 3H), 2.22-2.18 (m, 1H), 2.17-2.10 (m, 2H) |
| 320 | 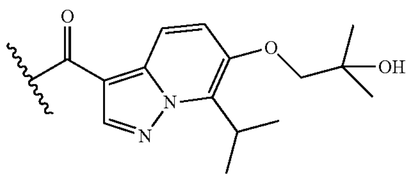 [SMILES: *C(=O)c1cnn2c(C(C)C)c(OCC(C)(C)O)ccc12] | N-((aR)-6-((3-carbamoylpyridin-2-yl)oxy)spiro[3.3]heptan-2-yl)-6-(2-hydroxy-2-methylpropoxy)-7-isopropyl-pyrazolo[1,5-a]pyridine-3-carboxamide | 522.2 | A: 1.631 B: 1.656 | (500 MHz, DMSO-$d_6$) δ ppm 8.49 (s, 1H), 8.29-8.22 (m, 2H), 8.16 (br d, J = 7.6 Hz, 1H), 8.06 (d, J = 9.8 Hz, 1H), 7.68 (br s, 1H), 7.60 (br s, 1H), 7.49 (d, J = 9.8 Hz, 1H), 7.10 (dd, J = 7.3, 5.2 Hz, 1H), 5.23 (quin, J = 7.2 Hz, 1H), 4.37 (dq, J = 16.0, 8.0 Hz, 1H), 4.21 (dt, J = 14.0, 7.0 Hz, 1H), 3.80 (s, 2H), 3.16 (d, J = 5.2 Hz, 1H), 2.70-2.62 (m, 1H), 2.48-2.41 (m, 2H), 2.38-2.31 (m, 1H), 2.26 (br dd, J = 11.1, 7.8 Hz, 1H), 2.21 (br d, J = 11.6, 7.6 Hz, 1H), 2.18-2.11 (m, 2H), 1.45 (d, J = 7.0 Hz, 6H), 1.25 (s, 6H) |
| 321 | 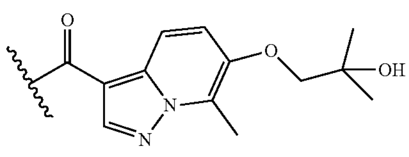 [SMILES: *C(=O)c1cnn2c(C)c(OCC(C)(C)O)ccc12] | N-((aR)-6-((3-carbamoylpyridin-2-yl)oxy)spiro[3.3]heptan-2-yl)-6-(2-hydroxy-2-methylpropoxy)-7-methylpyrazolo[1,5-a]pyridine-3-carboxamide | 494.4 | A: 1.294 B: 1.303 | (500 MHz, DMSO-$d_6$) δ ppm .53 (s, 1H), 8.28 (br d, J = 7.6 Hz, 1H), 8.26 (dd, J = 4.7, 1.7 Hz, 1H), 8.16 (dd, J = 7.5, 1.7 Hz, 1H), 8.06 (d, J = 9.5 Hz, 1H), 7.68 (br s, 1H), 7.61 (br s, 1H), 7.50 (d, J = 9.5 Hz, 1H), 7.10 (dd, J = 7.5, 5.0 Hz, 1H), 5.22 (quin, J = 7.1 Hz, 1H), 4.37 (dq, J = 16.1, 8.0 Hz, 1H), 2.70-2.65 (m, 1H), 2.64 (s, 3H), 2.48-2.40 (m, 2H), 2.38-2.31 (m, 1H), 2.26 (br dd, J = 11.0, 7.6 Hz, 1H), 2.23-2.19 (m, 1H), 2.19-2.11 (m, 2H), 1.23 (s, 6H) |
| 322 | 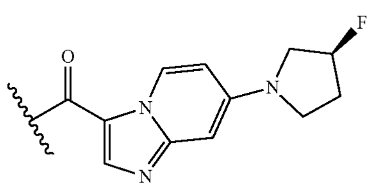 [SMILES: *C(=O)c1cnc2cc(N3CC[C@H](F)C3)ccn12] | N-((aR)-6-((3-carbamoylpyridin-2-yl)oxy)spiro[3.3]heptan-2-yl)-7-((S)-3-fluoropyrrolidin-1-yl)imidazo[1,2-a]pyridine-3-carboxamide | 479.4 | A: 1.274 B: 1.106 | (500 MHz, DMSO-$d_6$) δ ppm 9.16 (br s, 1H), 8.33 (br d, J = 7.3 Hz, 1H), 8.29-8.22 (m, 1H), 8.15 (dd, J = 7.5, 1.7 Hz, 1H), 8.12-7.97 (m, 1H), 7.64 (br d, J = 14.6 Hz, 2H), 7.10 (dd, J = 7.3, 4.9 Hz, 1H), 6.70 (br d, J = 7.6 Hz, 1H), 6.40 (br s, 1H), 5.54-5.36 (m, 1H), 5.21 (quin, J = 7.1 Hz, 1H), 4.34 (dq, J = 15.8, 8.0 Hz, 1H), 2.65 (dt, J = 11.1, 5.7 Hz, 1H), 2.49-2.38 (m, 2H), 2.37-2.22 (m, 3H), 2.20-2.07 (m, 3H) |
| 323 | 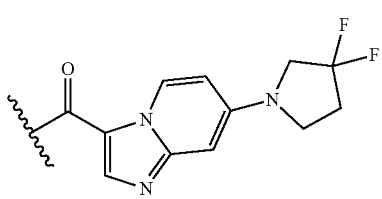 [SMILES: *C(=O)c1cnc2cc(N3CCC(F)(F)C3)ccn12] | N-((aR)-6-((3-carbamoylpyridin-2-yl)oxy)spiro[3.3]heptan-2-yl)-7-(3,3-difluoropyrrolidin-1-yl)imidazo[1,2-a]pyridine-3-carboxamide | 497.1 | A: 1.427 B: 1.173 | (500 MHz, DMSO-$d_6$) δ ppm 9.16 (br d, J = 7.0 Hz, 1H), 8.38 (br d, J = 7.6 Hz, 1H), 8.25 (br d, J = 3.4 Hz, 1H), 8.15 (br d, J = 7.3 Hz, 1H), 8.08 (br s, 1H), 7.64 (br s, 2H), 7.10 (dd, J = 7.2, 5.0 Hz, 1H), 6.71 (br d, J = 6.1 Hz, 1H), 6.46 (br s, 1H), 5.20 (quin, J = 7.1 Hz, 1H), 4.39-4.27 (m, 1H), 3.57 (br t, J = 7.0 Hz, 1H), 2.70-2.60 (m, 1H), 2.60-2.52 (m, 2H), 2.48-2.39 (m, 2H), 2.37-2.27(m, 1H), 2.23 (br dd, J = 10.8, 7.8 Hz, 1H), 2.20-2.08 (m, 3H) |

TABLE 12-continued

| # | Structure | Name | MS | LC | NMR |
|---|---|---|---|---|---|
| 324 | 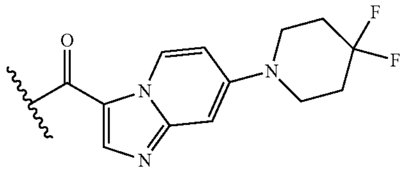 [SMILES: *C(=O)c1cnc2cc(N3CCC(F)(F)CC3)ccn12] | N-((aR)-6-((3-carbamoylpyridin-2-yl)oxy)spiro[3.3]heptan-2-yl)-7-(4,4-difluoropiperidin-1-yl)imidazo[1,2-a]pyridine-3-carboxamide | 511.3 | A: 1.500 B: 1.221 | (500 MHz, DMSO-$d_6$) δ ppm 9.14 (br d, J = 7.6 Hz, 1H), 8.40 (br d, J = 7.3 Hz, 1H), 8.28-8.22 (m, 1H), 8.19-8.13 (m, 1H), 8.11 (br s, 1H), 7.64 (br d, J = 13.1 Hz, 2H), 7.10 (dd, J = 7.3, 4.9 Hz, 1H), 7.03 (br d, J = 6.1 Hz, 1H), 6.86 (br s, 1H), 5.21 (quin, J = 7.0 Hz, 1H), 4.40-4.29 (m, 1H), 3.48 (br s, 1H), 2.65 (dt, J = 11.0, 5.8 Hz, 1H), 2.48-2.40 (m, 2H), 2.38-2.29 (m, 1H), 2.24 (br dd, J = 11.1, 7.8 Hz, 1H), 2.20-2.10 (m, 3H), 2.10-1.98 (m, 4H) |
| 325 | 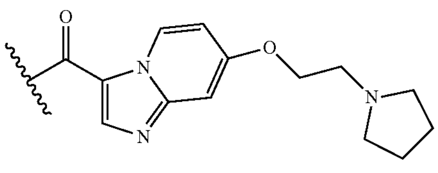 [SMILES: *C(=O)c1cnc2cc(OCCN3CCCC3)ccn12] | N-((aR)-6-((3-carbamoylpyridin-2-yl)oxy)spiro[3.3]heptan-2-yl)-7-(2-(pyrrolidin-1-yl)ethoxy)imidazo[1,2-a]pyridine-3-carboxamide | 505.5 | A: 1.000 B: 0.790 | (500 MHz, DMSO-$d_6$) δ ppm 9.23 (br d, J = 7.0 Hz, 1H), 8.49 (br d, J = 7.3 Hz, 1H), 8.29-8.23 (m, 1H), 8.22 (br s, 1H), 8.15 (dd, J = 7.3, 1.5 Hz, 1H), 7.66 (br s, 1H), 7.62 (br s, 1H), 7.10 (dd, J = 7.3, 4.9 Hz, 1H), 7.04 (br s, 1H), 6.80 (br d, J = 6.1 Hz, 1H), 5.21 (quin, J = 7.0 Hz, 1H), 4.35 (dq, J = 15.9, 7.9 Hz, 1H), 4.16 (br t, J = 5.2 Hz, 2H), 2.83 (br t, J = 5.3 Hz, 2H), 2.65 (dt, J = 11.4, 5.6 Hz, 1H), 2.49-2.41 (m, 2H), 2.38-2.29 (m, 1H), 2.24 (br dd, J = 11.1, 7.5 Hz, 1H), 2.21-2.10 (m, 3H), 1.67 (br s, 4H) |
| 326 | 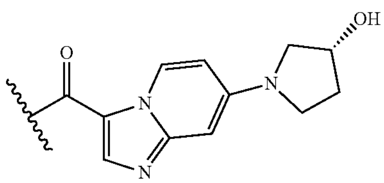 [SMILES: *C(=O)c1cnc2cc(N3CC[C@@H](O)C3)ccn12] | N-((aR)-6-((3-carbamoylpyridin-2-yl)oxy)spiro[3.3]heptan-2-yl)-7-((R)-3-hydroxypyrrolidin-1-yl)imidazo[1,2-a]pyridine-3-carboxamide | 477.5 | A: 1.048 B: 0.963 | (500 MHz, DMSO-$d_6$) δ ppm 9.12 (br s, 1H), 8.31 (br d, J = 7.0 Hz, 1H), 8.25 (br d, J = 4.0 Hz, 1H), 8.15 (br d, J = 7.3 Hz, 1H), 7.64 (br s, 2H), 7.14-7.05 (m, 1H), 6.64 (br d, J = 6.1 Hz, 1H), 6.31 (br s, 1H), 5.25-5.17 (m, 1H), 4.42 (br s, 1H), 4.38-4.29 (m, 1H), 3.70-3.61 (m, 2H), 2.69-2.61 (m, 1H), 2.47-2.39 (m, 2H), 2.35-2.28 (m, 1H), 2.27-2.21 (m, 1H), 2.21-2.10 (m, 3H), 1.92 (br s, 1H) |
| 327 | 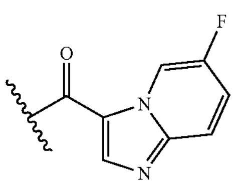 [SMILES: *C(=O)c1cnc2ccc(F)cn12] | N-((aR)-6-((3-carbamoylpyridin-2-yl)oxy)spiro[3.3]heptan-2-yl)-6-fluoroimidazo[1,2-a]pyridine-3-carboxamide | 410.3 | A: 1.302 B: 1.015 | (500 MHz, DMSO-$d_6$) δ ppm 9.43 (br d, J = 2.4 Hz, 1H), 8.71 (br d, J = 7.3 Hz, 1H), 8.36 (s, 1H), 8.28-8.22 (m, 1H), 8.15 (dd, J = 7.6, 1.5 Hz, 1H), 7.75 (dd, J = 9.8, 5.2 Hz, 1H), 7.64 (br d, J = 3.1 Hz, 2H), 7.58-7.49 (m, 1H), 7.10 (dd, J = 7.3, 4.9 Hz, 1H), 5.21 (quin, J = 7.1 Hz, 1H), 4.37 (sxt, J = 8.0 Hz, 1H), 2.72-2.61 (m, 1H), 2.49-2.41 (m, 2H), 2.39-2.30 (m, 1H), 2.25 (br dd, J = 11.4, 7.5 Hz, 1H), 2.22-2.12 (m, 3H) |
| 328 | 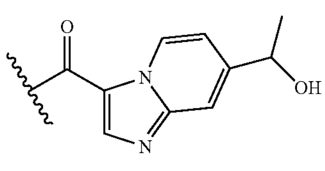 [SMILES: *C(=O)c1cnc2cc(C(C)O)ccn12] | N-((aR)-6-((3-carbamoylpyridin-2-yl)oxy)spiro[3.3]heptan-2-yl)-7-(1-hydroxyethyl)-imidazo[1,2-a]pyridine-3-carboxamide | 436.4 | A: 1.119 B. 0.904 | (500 MHz, DMSO-$d_6$) δ ppm 9.32 (br d, J = 7.0 Hz, 1H), 8.60 (br d, J = 7.6 Hz, 1H), 8.27 (br s, 1H), 8.25 (br d, J = 3.1 Hz, 1H), 8.15 (br d, J = 7.3 Hz, 1H), 7.64 (br s, 2H), 7.56 (br s, 1H), 7.14-6.99 (m, 2H), 5.21 (quin, J = 7.1 Hz, 1H), 4.79 (br s, 1H), 4.42-4.29 (m, 1H), 2.66 (dt, J = 11.2, 5.8 Hz, 1H), 2.48-2.41 (m, 2H), 2.38-2.30 (m, 1H), 2.24 (br dd, J = 11.0, 7.6 Hz, 1H), 2.21-2.10 (m, 3H), 1.35 (d, J = 6.4 Hz, 3H) |

TABLE 12-continued

| | | | | | |
|---|---|---|---|---|---|
| 329 | 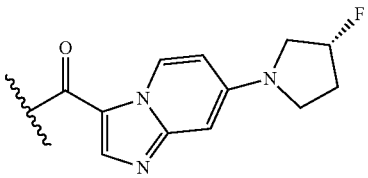 [SMILES: *C(=O)c1cnc2cc(N3CC[C@@H](F)C3)ccn12] | N-((aR)-6-((3-carbamoylpyridin-2-yl)oxy)spiro[3.3]heptan-2-yl)-7-((R)-3-fluoropyrrolidin-1-yl)imidazo[1,2-a]pyridine-3-carboxamide | 479.3 | A: 1.298 B: 1.105 | (500 MHz, DMSO-$d_6$) δ ppm 9.14 (br d, J = 7.3 Hz, 1H), 8.33 (br d, J = 7.6 Hz, 1H), 8.27-8.22 (m, 1H), 8.15 (dd, J = 7.5, 1.4 Hz, 1H), 8.07 (br s, 1H), 7.64 (br d, J = 6.4 Hz, 2H), 7.10 (dd, J = 7.5, 5.0 Hz, 1H), 6.70 (br d, J = 7.0 Hz, 1H), 6.40 (br s, 1H), 5.56-5.35 (m, 1H), 5.20 (quin, J = 7.1 Hz, 1H), 4.34 (dq, J = 16.0, 8.2 Hz, 1H), 3.48-3.35 (m, 1H), 2.65 (dt, J = 11.1, 5.7 Hz, 1H), 2.49-2.39 (m, 2H), 2.37-2.30 (m, 1H), 2.28-2.21 (m, 2H), 2.19-2.08 (m, 3H) |
| 330 | 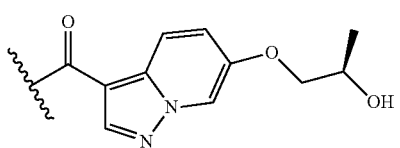 [SMILES: *C(=O)c1cnn2cc(OC[C@@H](C)O)ccc12] | N-((aR)-6-((3-carbamoylpyridin-2-yl)oxy)spiro[3.3]heptan-2-yl)-6-((R)-2-hydroxypropoxy)-pyrazolo[1,5-a]pyridine-3-carboxamide | 466.3 | A: 1.123 B: 1.133 | (500 MHz, DMSO-$d_6$) δ ppm 8.43 (br s, 1H), 8.42 (br s, 1H), 8.29-8.23 (m, 2H), 8.19-8.13 (m, 1H), 8.07 (d, J = 9.8 Hz, 1H), 7.68 (br s, 1H), 7.60 (br s, 1H), 7.25 (dd, J = 9.5, 1.5 Hz, 1H), 7.10 (dd, J = 7.3, 4.9 Hz, 1H), 5.22 (quin, J = 7.1 Hz, 1H), 4.98 (d, J = 4.6 Hz, 1H), 4.37 (sxt, J = 8.1 Hz, 1H), 3.98 (dt, J = 10.8, 5.5 Hz, 1H), 2.71-2.61 (m, 1H), 2.48-2.41 (m, 2H), 2.38-2.31 (m, 1H), 2.26 (br dd, J = 11.1, 7.5 Hz, 1H), 2.23-2.18 (m, 1H), 2.18-2.10 (m, 2H), 1.16 (d, J = 6.4 Hz, 3H) |
| 331 | 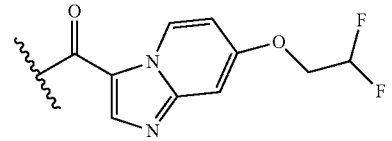 [SMILES: *C(=O)c1cnc2cc(OCC(F)F)ccn12] | N-((aR)-6-((3-carbamoylpyridin-2-yl)oxy)spiro[3.3]heptan-2-yl)-7-(2,2-difluoroethoxy)-imidazo[1,2-a]pyridine-3-carboxamide | 472.4 | A: 1.387 B: 1.097 | (500 MHz, DMSO-$d_6$) δ ppm 9.43 (br d, J = 7.0 Hz, 1H), 8.76 (br d, J = 7.0 Hz, 1H), 8.26 (dd, J = 4.6, 1.8 Hz, 1H), 8.16 (dd, J = 7.6, 1.8 Hz, 1H), 7.69 (br s, 1H), 7.59 (br s, 1H), 7.43-7.29 (m, 1H), 7.15-7.07 (m, 2H), 6.62-6.30 (m, 1H), 5.23 (quin, J = 7.2 Hz, 1H), 4.55 (td, J = 14.6, 2.4 Hz, 2H), 4.37 (sxt, J = 8.0 Hz, 1H), 2.67 (dt, J = 11.2, 5.8 Hz, 1H), 2.43-2.34 (m, 1H), 2.27 (br dd, J = 11.1, 7.5 Hz, 1H), 2.24-2.12 (m, 3H) |
| 332 | 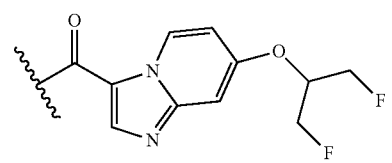 [SMILES: *C(=O)c1cnc2cc(OC(CF)CF)ccn12] | N-((aR)-6-((3-carbamoylpyridin-2-yl)oxy)spiro[3.3]heptan-2-yl)-7-((1,3-difluoropropan-2-yl)oxy)imidazo[1,2-a]pyridine-3-carboxamide | 486.4 | A: 1.350 B: 1.138 | (500 MHz, DMSO-$d_6$) δ ppm 9.29 (br d, J = 7.6 Hz, 1H), 8.49 (br d, J = 7.3 Hz, 1H), 8.26 (br d, J = 3.1 Hz, 1H), 8.21 (br s, 1H), 8.16 (br d, J = 7.0 Hz, 1H), 7.68 (br s, 1H), 7.60 (br s, 1H), 7.27 (br s, 1H), 7.10 (br dd, J = 7.0, 4.9 Hz, 1H), 6.87 (br d, J = 5.5 Hz, 1H), 5.28-5.06 (m, 2H), 4.89-4.80 (m, 1H), 4.80-4.69 (m, 2H), 4.66 (br dd, J = 10.4, 4.9 Hz, 1H), 4.44-4.31 (m, 1H), 3.39 (br s, 1H), 2.71-2.61 (m, 1H), 2.35 (br d, J = 5.2 Hz, 1H), 2.26 (br dd, J = 10.7, 7.6 Hz, 1H), 2.22-2.11 (m, 3H) |
| 333 | 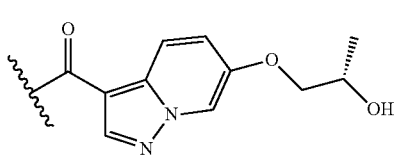 [SMILES: *C(=O)c1cnn2cc(OC[C@H](C)O)ccc12] | N-((aR)-6-((3-carbamoylpyridin-2-yl)oxy)spiro[3.3]heptan-2-yl)-6-((S)-2-hydroxypropoxy)-pyrazolo[1,5-a]pyridine-3-carboxamide | 466.4 | A: 1.184 B: 1.125 | (500 MHz, DMSO-$d_6$) δ ppm 8.42 (s, 1H), 8.41 (s, 1H), 8.30-8.24 (m, 2H), 8.16 (dd, J = 7.5, 1.7 Hz, 1H), 8.06 (d, J = 9.8 Hz, 1H), 7.67 (br s, 1H), 7.61 (br s, 1H), 7.26 (dd, J = 9.8, 1.8 Hz, 1H), 7.10 (dd, J = 7.6, 4.9 Hz, 1H), 5.22 (quin, J = 7.1 Hz, 1H), 4.36 (sxt, J = 8.2 Hz, 1H), 4.02-3.94 (m, 1H), 3.91-3.80 (m, 2H), 2.65 (dt, J = 11.2, 5.8 Hz, 1H), |

TABLE 12-continued

| | | | | | |
|---|---|---|---|---|---|
| | | | | | 2.48-2.39 (m, 2H), 2.36-2.29 (m, 1H), 2.25 (br dd, J = 11.1, 7.5 Hz, 1H), 2.22-2.18 (m, 1H), 2.18-2.10 (m, 2H), 1.15 (d, J = 6.4 Hz, 3H) |
| 334 | 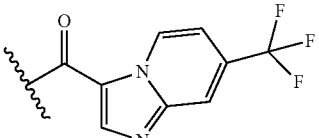 | N-((aR)-6-((3-carbamoylpyridin-2-yl)oxy)spiro[3.3]heptan-2-yl)-7-(trifluoromethyl)-imidazo[1,2-a]pyridine-3-carboxamide | 460.4 | A: 1.521<br>B: 1.411 | (500 MHz, DMSO-d$_6$) δ ppm 9.58 (br d, J = 7.3 Hz, 1H), 8.81 (br d, J = 7.3 Hz, 1H), 8.48 (s, 1H), 8.25 (br d, J = 3.1 Hz, 1H), 8.19-8.12 (m, 2H), 7.66 (br s, 1H), 7.62 (br s, 1H), 7.38 (br d, J = 7.0 Hz, 1H), 7.10 (dd, J = 7.3, 4.9 Hz, 1H), 5.22 (quin, J = 7.0 Hz, 1H), 4.39 (sxt, J = 7.9 Hz, 1H), 2.72-2.60 (m, 1H), 2.41-2.33 (m, 1H), 2.26 (br dd, J = 11.1, 7.5 Hz, 1H), 2.23-2.13 (m, 3H) |
| 335 | 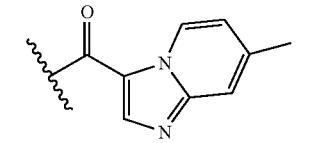 [SMILES: *C(=O)c1cnc2cc(C)ccn12] | N-((aR)-6-((3-carbamoylpyridin-2-yl)oxy)spiro[3.3]heptan-2-yl)-7-methylimidazo[1,2-a]pyridine-3-carboxamide | 406.3 | A: 1.331<br>B: 0.973 | (500 MHz, DMSO-d$_6$) δ ppm 9.27 (d, J = 7.3 Hz, 1H), 8.57 (br d, J = 7.3 Hz, 1H), 8.26 (dd, J = 4.7, 2.0 Hz, 1H), 8.24 (s, 1H), 8.16 (dd, J = 7.3, 1.8 Hz, 1H), 7.65 (br s, 2H), 7.46 (s, 1H), 7.11 (dd, J = 7.3, 4.9 Hz, 1H), 6.96 (d, J = 6.1 Hz, 1H), 5.22 (quin, J = 7.2 Hz, 1H), 4.37 (sxt, J = 8.1 Hz, 1H), 3.17 (d, J = 5.2 Hz, 1H), 2.66 (dt, J = 11.4, 5.8 Hz, 1H), 2.50-2.41 (m, 2H), 2.38 (s, 3H), 2.37-2.30 (m, 1H), 2.25 (dd, J = 11.3, 7.3 Hz, 1H), 2.22-2.12 (m, 2H) |

EXAMPLE 336

Preparation of N-((aR)-6-((3-carbamoylpyridin-2-yl)oxy)spiro[3.3]heptan-2-yl)-7-(4-methylpiperazin-1-yl)imidazo[1,2-a]pyridine-3-carboxamide

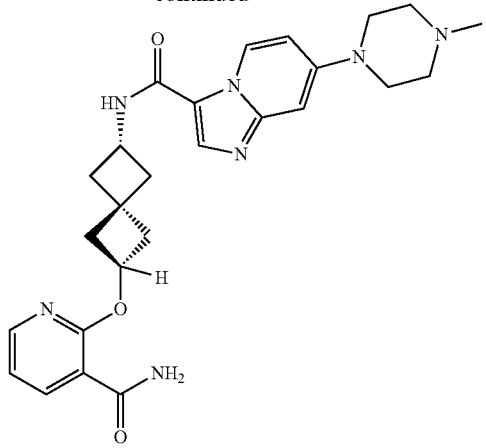

Example 42C (20 mg, 0.081 mmol) was suspended in anhydrous PhMe (1 mL), then trimethylaluminum (2 M in PhMe) (0.121 mL, 0.243 mmol) was added dropwise. After stirring for 5 min at rt (clear solution obtained), methyl 7-(4-methylpiperazin-1-yl)imidazo[1,2-a]pyridine-3-carboxylate (24.4 mg, 0.089 mmol) was added, and the reaction mixture was stirred at 120° C. for 1 h. The reaction mixture was cooled to rt, and carefully quenched with MeOH, then TFA. Solvent was removed under reduced pressure, the residue was diluted with DMF (2 mL), filtered, and purified by reverse phase HPLC to afford Example 336 (8.5 mg, 21% yield). MS (ESI) m/z: 490.1 (M+H)$^+$. $^1$H-NMR (500 MHz, DMSO-d$_6$) δ ppm 9.12 (br d, J=7.4 Hz, 1H), 8.42 (br s, 1H), 8.25 (br d, J=3.3 Hz, 1H), 8.17-8.11 (m, 1H), 8.10 (br s, 1H), 7.68 (br s, 1H), 7.64 (br s, 1H), 7.10 (dd, J=7.2, 5.0 Hz, 1H), 7.00 (br d, J=7.7 Hz, 1H), 6.75 (br s, 1H), 5.26-5.15 (m, 1H), 4.42-4.28 (m, 1H), 3.27 (br s, 3H), 3.16 (br s, 1H), 2.70-2.60 (m, 1H), 2.38-2.30 (m, 1H), 2.27-2.18 (m, 4H), 2.17-2.08 (m, 2H). Analytical HPLC RT=1.513 min (Method A) and 0.906 min (Method B), purity=98%.

The following examples in Table 13 were prepared using a similar procedure to that which was used in the preparation of Example 336. Example 42C was coupled with an ester, included, but not limited to a methyl or an ethyl ester, using trimethylaluminum.

TABLE 13

| Example | R | Name | LCMS (M + H)+ | HPLC Method, RT (min.) | 1H NMR |
|---|---|---|---|---|---|
| 337 | (imidazo[1,2-a]pyridine with 1-methyl-1H-pyrazol-4-yl substituent, acyl) | N-((aR)-6-((3-carbamoylpyridin-2-yl)oxy)spiro[3.3]heptan-2-yl)-7-(1-methyl-1H-pyrazol-4-yl)imidazo[1,2-a]pyridine-3-carboxamide | 472.2 | A: 1.248  B: 1.012 | (500 MHz, DMSO-d$_6$) δ ppm 9.34 (br d, J = 7.2 Hz, 1H), 8.59 (br d, J = 6.9 Hz, 1H), 8.33 (s, 1H), 8.28 (s, 1H), 8.27-8.22 (m, 1H), 8.18-8.12 (m, 1H), 8.07 (s, 1H), 7.85 (s, 1H), 7.70 (br s, 1H), 7.63 (br s, 1H), 7.36 (br d, J = 7.0 Hz, 1H), 7.10 (dd, J = 7.3, 5.0 Hz, 1H), 5.21 (quin, J = 7.0 Hz, 1H), 4.42-4.32 (m, 1H), 3.87 (s, 3H), 2.70-2.61 (m, 1H), 2.49-2.42 (m, 2H), 2.39-2.30 (m, 1H), 2.26 (br dd, J = 10.7, 7.8 Hz, 1H), 2.23-2.13 (m, 3H) |
| 338 | (pyrazolo[1,5-a]pyridine with cyclobutoxy substituent, acyl) | N-((aR)-6-((3-carbamoylpyridin-2-yl)oxy)spiro[3.3]heptan-2-yl)-6-cyclobutoxy-pyrazolo[1,5-a]pyridine-3-carboxamide | 462.3 | A: 1.604  B: 1.597 | (500 MHz, DMSO-d$_6$) δ ppm 8.43 (s, 1H), 8.31 (br d, J = 6.9 Hz, 1H), 8.27 (br d, J = 3.0 Hz, 1H), 8.23 (br s, 1H), 8.16 (br d, J = 7.4 Hz, 1H), 8.07 (d, J = 9.6 Hz, 1H), 7.71 (br s, 1H), 7.63 (br s, 1H), 7.21 (dd, J = 9.6, 1.7 Hz, 1H), 7.11 (dd, J = 7.3, 5.0 Hz, 1H), 5.22 (quin, J = 7.2 Hz, 1H), 4.80-4.70 (m, 1H), 4.42-4.31 (m, 1H), 2.71-2.62 (m, 1H), 2.49-2.40 (m, 4H), 2.37-2.30 (m, 1H), 2.29-2.23 (m, 1H), 2.23-2.18 (m, 1H), 2.18-2.11 (m, 2H), 2.06 (quin, J = 9.7 Hz, 2H), 1.80 (q, J = 10.0 Hz, 1H), 1.72-1.57 (m, 1H) |
| 339 | (pyrazolo[1,5-a]pyridine with (1,1-dioxidotetrahydro-2H-thiopyran-4-yl)oxy substituent, acyl) | N-((aR)-6-((3-carbamoylpyridin-2-yl)oxy)spiro[3.3]heptan-2-yl)-6-((1,1-dioxidotetrahydro-2H-thiopyran-4-yl)oxy)pyrazolo[1,5-a]pyridine-3-carboxamide | 540.5 | A 1.186  B: 1.176 | (500 MHz, DMSO-d$_6$) δ ppm 8.64 (br s, 1H), 8.44 (s, 1H), 8.36 (br d, J = 6.0 Hz, 1H), 8.25 (br d, J = 3.1 Hz, 1H), 8.15 (br d, J = 6.1 Hz, 1H), 8.08 (br d, J = 9.7 Hz, 1H), 7.66 (br d, J = 10.3 Hz, 2H), 7.37 (br d, J = 9.6 Hz, 1H), 7.10 (dd, J = 7.2, 5.0 Hz, 1H), 5.20 (quin, J = 7.0 Hz, 1H), 4.70 (br s, 1H), 4.41-4.28 (m, 1H), 3.32-3.20 (m, 2H), 3.18-3.07 (m, 2H), 2.69-2.60 (m, 1H), 2.48-2.39 (m, 2H), 2.36-2.28 (m, 1H), 2.23 (br d, J = 4.5 Hz, 5H), 2.19-2.09 (m, 3H) |

TABLE 13-continued

| | | | | |
|---|---|---|---|---|
| 340 | [structure] | N-((aR)-6-((3-carbamoylpyridin-2-yl)oxy)spiro[3.3]heptan-2-yl)-7-cyclopropyl-6-(2-(2,2,2-trifluoroethoxy)ethoxy)pyrazolo[1,5-a]pyridine-3-carboxamide | 574.6 | A: 1.757<br>B: 1.764 | (500 MHz, DMSO-$d_6$) δ ppm 8.48 (s, 1H), 8.30 (br d, J = 7.6 Hz, 1H), 8.25 (dd, J = 4.7, 1.7 Hz, 1H), 8.15 (dd, J = 7.5, 1.7 Hz, 1H), 8.01 (d, J = 9.5 Hz, 1H), 7.64 (br d, J = 5.8 Hz, 2H), 7.44 (d, J = 9.8 Hz, 1H), 7.10 (dd, J = 7.6, 4.9 Hz, 1H), 5.21 (quin, J = 7.2 Hz, 1H), 4.35 (sxt, J = 8.1 Hz, 1H), 4.22-4.16 (m, 2H), 4.11 (q, J = 9.5 Hz, 2H), 3.95-3.87 (m, 2H), 2.65 (dt, J = 11.1, 5.7 Hz, 1H), 2.48-2.39 (m, 2H), 2.36-2.28 (m, 1H), 2.24 (br dd, J = 11.3, 7.3 Hz, 1H), 2.21-2.17 (m, 1H), 2.17-2.10 (m, 2H), 1.47-1.37 (m, 2H), 1.07-1.00 (m, 2H) |
| 341 | [structure] | N-((aR)-6-((3-carbamoylpyridin-2-yl)oxy)spiro[3.3]heptan-2-yl)-7-cyclopropyl-6-((1,3-difluoropropan-2-yl)oxy)pyrazolo[1,5-a]pyridine-3-carboxamide | 526.4 | A: 1.612<br>B: 1.619 | (500 MHz, DMSO-$d_6$) δ ppm 8.49 (s, 1H), 8.31 (br d, J = 7.6 Hz, 1H), 8.27-8.23 (m, 1H), 8.15 (dd, J = 7.5, 1.7 Hz, 1H), 8.03 (d, J = 9.5 Hz, 1H), 7.66 (br s, 1H), 7.62 (br s, 1H), 7.45 (d, J = 9.8 Hz, 1H), 7.10 (dd, J = 7.3, 4.9 Hz, 1H), 5.21 (quin, J = 7.1 Hz, 1H), 4.86-4.77 (m, 2H), 4.76-4.68 (m, 2H), 4.67-4.61 (m, 1H), 4.40-4.29 (m, 1H), 2.65 (dt, J = 11.4, 5.8 Hz, 1H), 2.48-2.40 (m, 2H), 2.36-2.30 (m, 1H), 2.24 (br dd, J = 11.3, 7.3 Hz, 1H), 2.22-2.17 (m, 1H), 2.17-2.11 (m, 2H), 1.47-1.40 (m, 2H), 1.08- 1.02 (m, 2H |
| 342 | [structure] | N-((aR)-6-((3-carbamoylpyridin-2-yl)oxy)spiro[3.3]heptan-2-yl)-7-cyclopropyl-6-((tetrahydrofuran-2-yl)methoxy)pyrazolo[1,5-a]pyridine-3-carboxamide | 532.5 | A. 1.609<br>B. 1.615 | (500 MHz, DMSO-$d_6$) δ ppm 8.48 (s, 1H), 8.31-8.22 (m, 2H), 8.16 (dd, J = 7.3, 1.5 Hz, 1H), 8.01 (d, J = 9 8 Hz, 1H), 7.67 (br s, 1H), 7.61 (br s, 1H), 7.45 (d, J = 9.8 Hz, 1H), 7.10 (dd, J = 7.5, 5.0 Hz, 1H), 5.22 (quin, J = 7.2 Hz, 1H), 4.36 (sxt, J = 8.1 Hz, 1H), 4.18-4.10 (m, 1H), 4.06-4.00 (m, 1H), 4.00-3.94 (m, 1H), 3.83-3.74 (m, 1H), 3.73-3.64 (m, 1H), 2.65 (dt, J = 11.0, 5.8 Hz, 1H), 2.59-2.54 (m, 1H), 2.49-2.40 (m, 2H), 2.37-2.29 (m, 1H), 2.25 (br dd, J = 11.1, 7.5 Hz, 1H), 2.22-2.18 (m, 1H), 2.17-2.11 (m, 2H), 2.04-1.95 (m, 1H), 1.92-1.78 (m, 2H), 1.71-1.62 (m, 1H), 1.48-1.40 (m, 2H), 1.04 (br dd, J = 8.5, 2.7 Hz, 2H) |
| 343 | [structure] | N-((aR)-6-((3-carbamoylpyridin-2-yl)oxy)spiro[3.3]heptan-2-yl)-7-cyclopropyl-6-(oxetan-3-yloxy)pyrazolo[1,5-a]pyridine-3-carboxamide | 504.2 | A: 1.585<br>B: 1.575 | (500 MHz, DMSO-$d_6$) δ ppm 8.50 (s, 1H), 8.29 (br d, J = 7.6 Hz, 1H), 8.26 (dd, J = 4.6, 1.8 Hz, 1H), 8.16 (dd, J = 7.3, 1.8 Hz, 1H), 8.00 (d, J = 9.8 Hz, 1H), 7.66 (br s, 1H), 7.61 (br s, 1H), 7.14 (d, J = 9.5 Hz, 1H), 7.10 (dd, J = 7.3, 4.9 Hz, 1H), 5.29 (quin, J = 5.4 Hz, 1H), 5.26-5.16 (m, 1H), 4.88 (t, J = 6.6 Hz, 2H), 4.61 (dd, J = 6.9, 5.0 Hz, 2H), 4.36 (sxt, J = 7.9 Hz, 1H), 2.65 (dt, J = 11.2, 5.8 Hz, 1H), 2.48-2.40 (m, 2H), 2.37-2.29 (m, 1H), 2.25 (br dd, J = 11.1, 7.5 Hz, 1H), 2.19 (br dd, J = 11.9, 7.6 Hz, 1H), 2.17-2.10 (m, 2H), 1.46-1.39 (m, 2H), 1.12-1.06 (m, 2H) |

TABLE 13-continued

| # | Structure | Name | MS | LC | NMR |
|---|---|---|---|---|---|
| 344 | 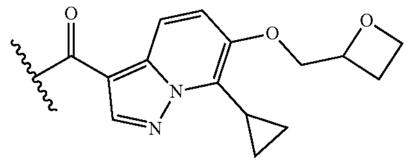 [SMILES: *C(=O)c1cnn2c(C3CC3)c(OCC3CCO3)ccc12] | N-((aR)-6-((3-carbamoylpyridin-2-yl)oxy)spiro[3.3]heptan-2-yl)-7-cyclopropyl-6-(oxetan-2-ylmethoxy)-pyrazolo[1,5-a]pyridine-3-carboxamide | 518.6 | A: 1.435 B: 1.444 | (500 MHz, DMSO-$d_6$) δ ppm 8.50-8.43 (m, 1H), 8.30 (br d, J = 7.0 Hz, 1H), 8.25 (br d, J = 3.4 Hz, 1H), 8.22-8.13 (m, 1H), 8.01 (br d, J = 9.5 Hz, 1H), 7.65 (br s, 1H), 7.63 (br s, 1H), 7.52-7.41 (m, 1H), 7.17-7.06 (m, 1H), 5.26-5.15 (m, 1H), 5.00 (br s, 1H), 4.60-4.51 (m, 1H), 4.52-4.43 (m, 1H), 4.41-4.30 (m, 1H), 4.20 (br dd, J = 11.0, 5.5 Hz, 1H), 4.16-4.08 (m, 1H), 2.73-2.61 (m, 2H), 2.60-2.54 (m, 2H), 2.45 (br d, J = 15.0 Hz, 2H), 2.34 (br d, J = 11.3 Hz, 1H), 2.27-2.22 (m, 1H), 2.21-2.18 (m, 1H), 2 18-2.08 (m, 2H), 1.43 (br d, J = 3.1 Hz, 2H), 1.06 (br dd, J = 8.7, 2.6 Hz, 2H) |
| 345 | 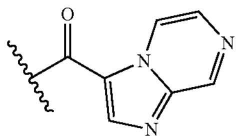 [SMILES: *C(=O)c1cnc2cnccn12] | N-((aR)-6-((3-carbamoyipyridin-2-yl)oxy)spiro[3.3]heptan-2-yl)imidazo[1,2-o]pyrazine-3-carboxamide | 393.3 | A: 1.012 B: 1.044 | (500 MHz, DMSO-$d_6$) δ ppm 9.29 (br d, J = 4.0 Hz, 1H), 9.17 (s, 1H), 8.88 (br d, J = 7.3 Hz, 1H), 8.47 (s, 1H), 8.26 (br d, J = 3.1 Hz, 1H), 8.16 (br d, J = 7.6 Hz, 1H), 8.08 (d, J = 4.6 Hz, 1H), 7.66 (br s, 1H), 7.62 (br s, 1H), 7.10 (dd, J = 7.3, 4.9 Hz, 1H), 5.27-5.17 (m, 1H), 4.44-4.34 (m, 1H), 2.71-2.62 (m, 1H), 2.41-2.32 (m, 1H), 2.26 (br dd, J = 11.0, 7.3 Hz, 1H), 2.24-2.14 (m, 3H) |
| 346 | 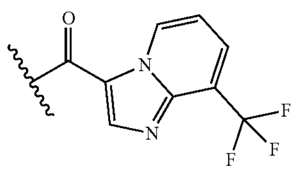 [SMILES: *C(=O)c1cnc2c(C(F)(F)F)cccn12] | N-((aR)-6-((3-carbamoylpyridin-2-yl)oxy)spiro[3.3]heptan-2-yl)-8-(trifluoromethyl)-imidazo[1,2-a]pyridine-3-carboxamide | 460.4 | A: 1.431 B: 1.396 | (500 MHz, DMSO-$d_6$) δ ppm 8.79 (d, J = 7.3 Hz, 1H), 8.42 (s, 1H), 8.26 (dd, J = 4.9, 1.8 Hz, 1H), 8.16 (dd, J = 7.6, 1.8 Hz, 1H), 7.91 (d, J = 7.3 Hz, 1H), 7.67 (br s, 1H), 7.62 (br s, 1H), 7.24 (t, J = 7.2 Hz, 1H), 7.10 (dd, J = 7.3, 4.9 Hz, 1H), 5.22 (quin, J = 7.1 Hz, 1H), 4.39 (sxt, J = 8.2 Hz, 1H), 2.72-2.63 (m, 1H), 2.40-2.34 (m, 1H), 2.26 (br dd, J = 11.4, 7.5 Hz, 1H), 2.24-2.15 (m, 3H) |
| 347 | 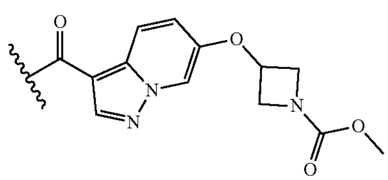 [SMILES: *C(=O)c1cnn2cc(OC3CN(C(=O)OC)C3)ccc12] | methyl 3-((3-(((aR)-6-((3-carbamoylpyridin-2-yl)oxy)spiro[3.3]heptan-2-yl)carbamoyl)-pyrazolo[1,5-a]pyridin-6-yl)oxy)azetidine-1-carboxylate | 521.5 | A: 1.284 B: 1.296 | (500 MHz, DMSO-$d_6$) δ ppm 8.45 (s, 1H), 8.32-8.28 (m, 2H), 8.27-8.23 (m, 1H), 8.16 (dd, J = 7.3, 1.5 Hz, 1H), 8.10 (d, J = 9.5 Hz, 1H), 7.68 (br s, 1H), 7.60 (br s, 1H), 7.26 (dd, J = 9.6, 2.0 Hz, 1H), 7.10 (dd, J = 7.3, 4.9 Hz, 1H), 5.22 (quin, J = 7.2 Hz, 1H), 5.08 (br d, J = 3.4 Hz, 1H), 4.45-4.32 (m, 3H), 3.96-3.87 (m, 2H), 2.65 (br dd, J = 12.2, 7.3 Hz, 1H), 2.48-2.42 (m, 2H), 2.38-2.31 (m, 1H), 2.29-2.19 (m, 2H), 2.18-2.10 (m, 2H) |
| 348 | 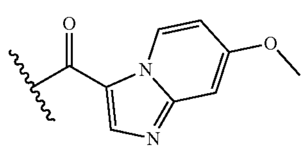 [SMILES: *C(=O)c1cnc2cc(OC)ccn12] | N-((aR)-6-((3-carbamoylpyridin-2-yl)oxy)spiro[3.3]heptan-2-yl)-7-methoxyimidazo[1,2-a]pyridine-3-carboxamide | 422.3 | A: 1.229 B: 1.011 | (500 MHz, DMSO-$d_6$) δ ppm 9.34 (d, J = 7.6 Hz, 1H), 8.71 (br d, J = 7.3 Hz, 1H), 8.36 (br s, 1H), 8.27 (dd, J = 4.9, 1.8 Hz, 1H), 8.17 (dd, J = 7.3, 1.8 Hz, 1H), 7.69 (br s, 1H), 7 61 (br s, 1H), 7.19 (s, 1H), 7.11 (dd, J = 7.3, 4.9 Hz, 1H), 7.01 (dd, J = 7.6, 2.1 Hz, 1H), 5.23 (quin, J = 7.2 Hz, 1H), 4.37 (dq, J = 15.8, 7.8 Hz, 1H), 3.93 (s, 3H), 2.73-2.62 (m, 2H), 2.39-2.32 (m, 1H), 2.27 (br dd, J = 11.3, 7.3 Hz, 1H), 2.24-2.21 (m, 1H), 2.21-2.12 (m, 3H) |

TABLE 13-continued

| | | | | | |
|---|---|---|---|---|---|
| 349 | 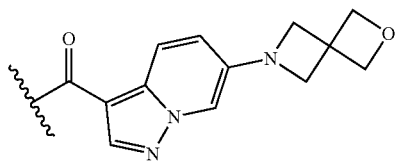 [SMILES: *C(=O)c1cnn2cc(N3CC4(COC4)C3)ccc12] | N-((aR)-6-((3-carbamoylpyridin-2-yl)oxy)spiro[3.3]heptan-2-yl)-6-(2-oxa-6-azaspiro[3.3]heptan-6-yl)pyrazolo[1,5-a]pyridine-3-carboxamide | 489.5 | A: 1.155 B: 1.164 | (500 MHz, DMSO-d$_6$) δ ppm 8.33 (s, 1H), 8.26 (br d, J = 3.4 Hz, 1H), 8.21 (br d, J = 7.6 Hz, 1H), 8.16 (br d, J = 7.6 Hz, 1H), 8.00 (d, J = 9.5 Hz, 1H), 7.82 (s, 1H), 7.66 (br s, 1H), 7.61 (br s, 1H), 7.10 (dd, J = 7.2, 5.0 Hz, 1H), 6.96 (br d, J = 9.5 Hz, 1H), 5.21 (quin, J = 7.2 Hz, 1H), 4.71 (s, 4H), 4.40-4.29 (m, 1H), 3.99 (s, 4H), 2.69-2.61 (m, 1H), 2.48-2.37 (m, 2H), 2.35-2.29 (m, 1H), 2.24 (br dd, J = 11.3, 7.3 Hz, 1H), 2.19 (br dd, J = 11.6, 7.6 Hz, 1H), 2.17-2.09 (m, 2H) |
| 350 | 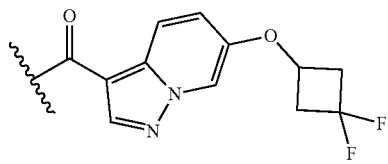 [SMILES: *C(=O)c1cnn2cc(OC3CC(F)(F)C3)ccc12] | N-((aR)-6-((3-carbamoylpyridin-2-yl)oxy)spiro[3.3]heptan-2-yl)-6-(3,3-difluorocyclobutoxy)-pyrazolo[1,5-a]pyridine-3-carboxamide | 498.1 | A: 1.558 B: 1.596 | (500 MHz, DMSO-d$_6$) δ ppm 8.45 (s, 1H), 8.38 (s, 1H), 8.29 (br d, J = 7.6 Hz, 1H), 8.27-8.23 (m, 1H), 8.16 (dd, J = 7.5, 1.7 Hz, 1H), 8.09 (d, J = 9.5 Hz, 1H), 7.68 (br s, 1H), 7.60 (br s, 1H), 7.26 (dd, J = 9.8, 1.8 Hz, 1H), 7.10 (dd, J = 7.3, 4.9 Hz, 1H), 5.22 (quin, J = 7.1 Hz, 1H), 4.83 (br d, J = 4.6 Hz, 1H), 4.42-4.31 (m, 1H), 3.31-3.20 (m, 2H), 2.66 (dt, J = 11.3, 5.6 Hz, 1H), 2.48-2.40 (m, 2H), 2.37-2.31 (m, 1H), 2.26 (br dd, J = 11.3, 7.3 Hz, 1H), 2.22-2.18 (m, 1H), 2.18-2.10 (m, 2H) |
| 351 | 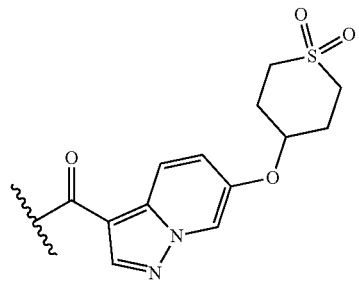 [SMILES: *C(=O)c1cnn2cc(OC3CCS(=O)(=O)CC3)ccc12] | N-((aR)-6-((3-carbamoylpyridin-2-yl)oxy)spiro[3.3]heptan-2-yl)-7-cyclopropyl-6-((1,1-dioxidotetrahydro-2H-thiopyran-4-yl)oxy)pyrazolo[1,5-a]pyridine-3-carboxamide | 580.5 | A: 1.354 B: 1.374 | (500 MHz, DMSO-d$_6$) δ ppm 8.48 (s, 1H), 8.32 (br d, J = 7.3 Hz, 1H), 8.25 (dd, J = 4.9, 1.5 Hz, 1H), 8.15 (dd, J = 7.5, 1.7 Hz, 1H), 8.03 (d, J = 9.5 Hz, 1H), 7.64 (br d, J = 7.0 Hz, 2H), 7.47 (d, J = 9.5 Hz, 1H), 7.10 (dd, J = 7.5, 5.0 Hz, 1H), 5.21 (quin, J = 7.2 Hz, 1H), 4.40-4.30 (m, 1H), 3.29-3.20 (m, 2H), 3.17 (br d, J = 8.2 Hz, 3H), 2.69-2.61 (m, 1H), 2.48-2.40 (m, 2H), 2.39-2.34 (m, 1H), 2.34-2.29 (m, 1H), 2.28-2.17 (m, 6H), 2.17-2.09 (m, 2H), 1.29 (br d, J = 3.7 Hz, 2H), 1.14-1.05 (m, 2H) |
| 352 | 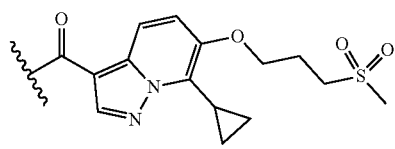 [SMILES: *C(=O)c1cnn2c(C3CC3)c(OCCCS(C)(=O)=O)ccc12] | N-((aR)-6-((3-carbamoylpyridin-2-yl)oxy)spiro[3.3]heptan-2-yl)-7-cyclopropyl-6-(3-(methylsulfonyl)-propoxy)pyrazolo[1,5-a]pyridine-3-carboxamide | 568.5 | A: 1.363 B: 1.330 | (500 MHz, DMSO-d$_6$) δ ppm 8.49 (s, 1H), 8.32-8.23 (m, 2H), 8.16 (br d, J = 7.3 Hz, 1H), 8.03 (d, J = 9.5 Hz, 1H), 7.67 (br s, 1H), 7.61 (br s, 1H), 7.45 (d, J = 9.8 Hz, 1H), 7.10 (dd, J = 7.2, 5.0 Hz, 1H), 5.22 (quin, J = 7.1 Hz, 1H), 4.36 (dq, J = 15.9, 7.9 Hz, 1H), 4.14 (br t, J = 6.3 Hz, 2H), 3.35-3.25 (m, 2H), 3.01 (s, 3H), 2.65 (dt J = 10.9, 5.4 Hz, 1H), 2.48-2.39 (m, 2H), 2.37-2.28 (m, 1H), 2.25 (br dd, J = 11.0, 7.6 Hz, 1H), 2.22-2.18 (m, 1H), 2.18-2.10 (m, 4H), 1.36 (br d, J = 3.7 Hz, 2H), 1.08 (br dd, J = 8.7, 2.3 Hz, 2H) |
| 353 | 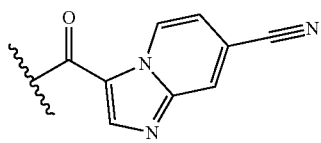 [SMILES: *C(=O)c1cnc2cc(C#N)ccn12] | N-((aR)-6-((3-carbamoylpyridin-2-yl)oxy)spiro[3.3]heptan-2-yl)-7-cyanoimidazo[1,2-a]pyridine-3-carboxamide | 417.2 | A: 1.268 B: 1.222 | (500 MHz, DMSO-d$_6$) δ ppm 9.50 (d, J = 7.3 Hz, 1H), 8.85 (br d, J = 7.3 Hz, 1H), 8.51 (s, 1H), 8.42 (s, 1H), 8.28-8.22 (m, 1H), 8.18-8.11 (m, 1H), 7.66 (br s, 1H), 7.62 (br s, 1H), 7.38 (br d, J = 7.3 Hz, 1H), 7.10 (dd, J = 7.3, 4.9 Hz, 1H), 5.22 (quin, J = 6.9 Hz, 1H), 4.38 (dq, J = 15.6, 8.0 Hz, 1H), 2.71-2.62 (m, 1H), |

TABLE 13-continued

| | | | | | 2.42-2.32 (m, 1H), 2.26 (br dd, J = 11.4, 7.5 Hz, 1H), 2.23-2.13 (m, 3H) |

| 354 | 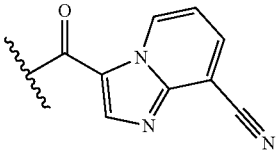 [SMILES: *C(=O)c1cnc2c(C#N)cccn12] | N-((aR)-6-((3-carbamoylpyridin-2-yl)oxy)spiro[3.3]heptan-2-yl)-8-cyanoimidazo[1,2-a]pyridine-3-carboxamide | 417.2 | A: 1.236 B: 1.229 | (500 MHz, DMSO-$d_6$) δ ppm 9.65 (br d, J = 7.0 Hz, 1H), 8.81 (br d, J = 7.3 Hz, 1H), 8.44 (s, 1H), 8.26 (br d, J = 3.4 Hz, 1H), 8.16 (br d, J = 7.3 Hz, 1H), 8.13 (br d, J = 7.0 Hz, 1H), 7.67 (br s, 1H), 7.61 (br s, 1H), 7.25 (t, J = 7.0 Hz, 1H), 7.10 (dd, J = 7.2, 5.0 Hz, 1H), 5.28-5.17 (m, 1H), 4.45-4.33 (m, 1H), 2.71-2.61 (m, 1H), 2.40-2.33 (m, 1H), 2.26 (br dd, J = 10 8, 7.5 Hz, 1H), 2.24-2.14 (m, 3H) |
| 355 | 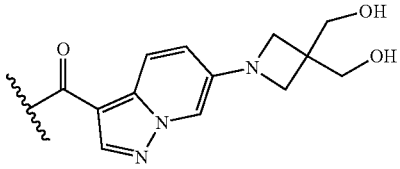 [SMILES: *C(=O)c1cnn2cc(N3CC(CO)(CO)C3)ccc12] | 6-(3,3-bis(hydroxymethyl)-azetidin-1-yl)-N-((aR)-6-((3-carbamoylpyridin-2-yl)oxy)spiro[3.3]heptan-2-yl)pyrazolo[1,5-a]pyridine-3-carboxamide) | 507.7 | A: 1.263 B: 1.268 | (500 MHz, DMSO-$d_6$) δ ppm 8.43 (dd, J = 5.0, 1.7 Hz, 1H), 8.33 (s, 1H), 8.24 (dd, J = 7.5, 1.7 Hz, 1H), 8.17 (br d, J = 7.6 Hz, 1H), 8.01 (d, J = 9.5 Hz, 1H), 7.78 (s, 1H), 7.16 (dd, J = 7.5, 5.0 Hz, 1H), 6.95 (dd, J = 9.5, 1.5 Hz, 1H), 5.20 (quin, J = 7.1 Hz, 1H), 4.36 (dq, J = 16.2, 8.0 Hz, 1H), 3.57 (s, 2H), 3.55 (s, 2H), 2.72-2.63 (m, 1H), 2.47-2.39 (m, 1H), 2.37-2.29 (m, 1H), 2.20 (br dd, J = 11.6, 7.6 Hz, 1H), 2.18-2.10 (m, 3H) |
| 356 | 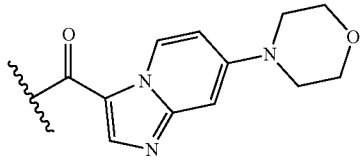 [SMILES: *C(=O)c1cnc2cc(N3CCOCC3)ccn12] | N-((aR)-6-((3-carbamoylpyridin-2-yl)oxy)spiro[3.3]heptan-2-yl)-7-morpholinoimidazo[1,2-a]pyridine-3-carboxamide | 477.4 | A: 1.168 B: 1.037 | (500 MHz, DMSO-$d_6$) δ ppm 9.16 (d, J = 7.9 Hz, 1H), 8.37 (d, J = 7.6 Hz, 1H), 8.26 (dd, J = 4.9, 1.8 Hz, 1H), 8.16 (dd, J = 7.3, 1.8 Hz, 1H), 8.13 (s, 1H), 7.67 (br s, 1H), 7.60 (br s, 1H), 7.10 (dd, J = 7.3, 4.9 Hz, 1H), 7.01 (dd, J = 7.9, 2.1 Hz, 1H), 6.78 (d, J = 1.8 Hz, 1H), 5.22 (quin, J = 7.1 Hz, 1H), 4.36 (sxt, J = 8.1 Hz, 1H), 3.78-3.68 (m, 3H), 3.29-3.20 (m, 3H), 2.66 (dt, J = 11.4, 5.9 Hz, 1H), 2.47-2.40 (m, 1H), 2.38-2.29 (m, 1H), 2.25 (br dd, J = 11.3, 7.3 Hz, 1H), 2.22-2.19 (m, 1H), 2.18-2.11 (m, 2H) |
| 357 | 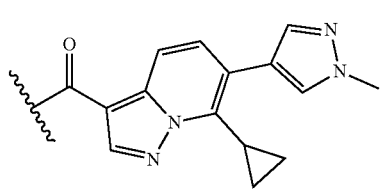 [SMILES: *C(=O)c1cnn2c(C3CC3)c(-c3cnn(C)c3)ccc12] | N-((aR)-6-((3-carbamoylpyridin-2-yl)oxy)spiro[3.3]heptan-2-yl)-7-cyclopropyl-6-(1-methyl-1H-pyrazol-4-yl)-pyrazolo[1,5-a]pyridine-3-carboxamide | 512.5 | A: 1.353 B: 1.322 | (500 MHz, DMSO-$d_6$) δ ppm 8.55 (s, 1H), 8.31 (br d, J = 7.6 Hz, 1H), 8.26 (dd, J = 4.7, 2.0 Hz, 1H), 8.16 (dd, J = 7.5, 1.7 Hz, 1H), 8.10 (d, J = 9.2 Hz, 1H), 8.04 (s, 1H), 7.76 (s, 1H), 7.68 (br s, 1H), 7.61 (br s, 1H), 7.47 (d, J = 9.2 Hz, 1H), 7.10 (dd, J = 7.3, 4.9 Hz, 1H), 5.23 (quin, J = 7.1 Hz, 1H), 4.43-4.34 (m, 1H), 3.90 (s, 3H), 2.70-2.61 (m, 1H), 2.48-2.41 (m, 2H), 2.39-2.30 (m, 2H), 2.26 (br dd, J = 11.3, 7.3 Hz, 1H), 2.23-2.19 (m, 1H), 2.18-2.12 (m, 2H), 1.15-1.09 (m, 2H), 0.66-0.59 (m, 2H) |

EXAMPLE 358

Preparation of N-((aR)-6-((3-carbamoylpyridin-2-yl)oxy)spiro[3.3]heptan-2-yl)-7-((2,2-difluoroethyl)amino)imidazo[1,2-]pyridine-3-carboxamide

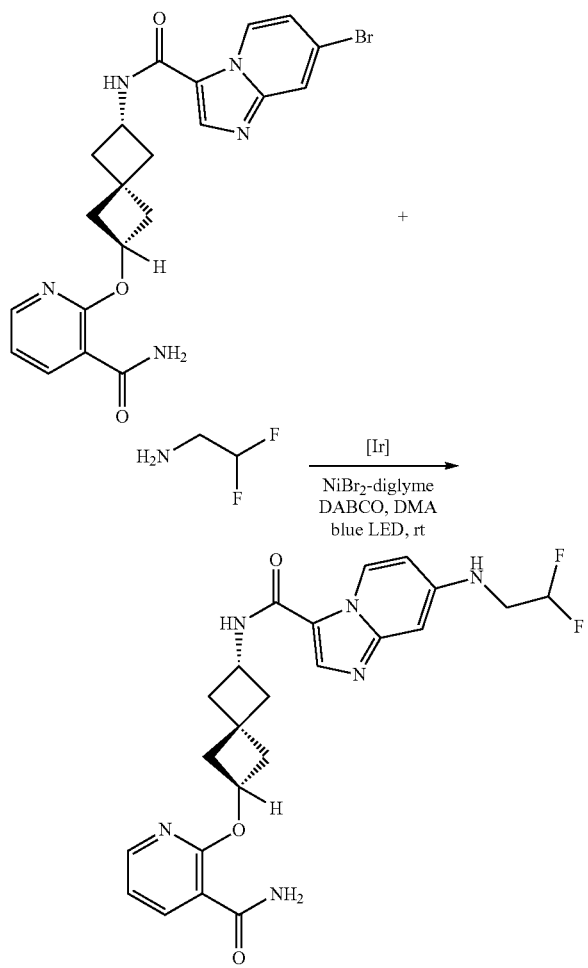

Intermediate 100 (30 mg, 0.064 mmol), (4,4'-di-t-butyl-2,2'-bipyridine)bis[3,5-difluoro-2-[5-trifluoromethyl-2-pyridinyl-kappan)phenyl-kappac]iridium(III) hexafluorophosphate (0.66 mg, 0.638 µmol), nickel(II) bromide ethylene glycol dimethyl ether complex (0.98 mg, 3.19 µmol), and DABCO (12.9 mg, 0.115 mmol) were placed in a vial, then DMA (2 mL) and 2,2-difluoroethanamine (6.5 mg, 0.080 mmol) were added. The mixture was degassed, blanketed under $N_2$ and irradiated with blue LED for 14 h. The reaction mixture was diluted with DMF, filtered and purified by reverse phase HPLC to afford Example 358 (7.0 mg, 22% yield). MS (ESI) m/z: 471.1 (M+H)$^+$. $^1$H-NMR (500 MHz, DMSO-$d_6$) δ ppm 9.16 (br d, J=7.6 Hz, 1H), 8.74 (br d, J=7.0 Hz, 1H), 8.30 (s, 1H), 8.26 (br d, J=3.1 Hz, 1H), 8.16 (br d, J=7.6 Hz, 1H), 7.76 (br s, 1H), 7.69 (br s, 1H), 7.59 (br s, 1H), 7.10 (dd, J=7.2, 5.0 Hz, 1H), 6.95 (br d, J=7.3 Hz, 1H), 6.75 (br s, 1H), 6.38-6.04 (m, 1H), 5.22 (quin, J=7.1 Hz, 1H), 4.35 (dq, J=16.0, 8.0 Hz, 1H), 3.79-3.65 (m, 2H), 2.71-2.61 (m, 1H), 2.42-2.32 (m, 1H), 2.27 (br dd, J=11.4, 7.2 Hz, 1H), 2.23-2.19 (m, 1H), 2.19-2.10 (m, 2H). Analytical HPLC RT=1.192 min (Method A) and 1.037 min (Method B), purity=98%.

EXAMPLE 359

Preparation 7-(3-aminoazetidin-1-yl)-N-((aR)-6-((3-carbamoylpyridin-2-yl)oxy)spiro[3.3]heptan-2-yl)imidazo[1,2-a]pyridine-3-carboxamide

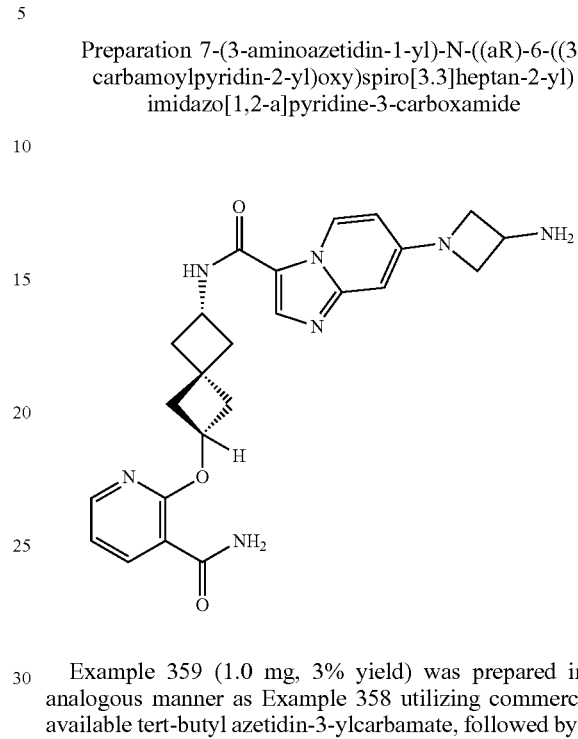

Example 359 (1.0 mg, 3% yield) was prepared in an analogous manner as Example 358 utilizing commercially available tert-butyl azetidin-3-ylcarbamate, followed by Boc deprotection. MS (ESI) m/z: 462.2 (M+H)$^+$. $^1$H-NMR (500 MHz, DMSO-$d_6$) 9.26 (d, J=7.6 Hz, 1H), 8.80 (br d, J=6.4 Hz, 1H), 8.39 (s, 1H), 8.26 (br d, J=3.1 Hz, 2H), 8.20-8.10 (m, 2H), 7.70 (br s, 1H), 7.58 (br s, 2H), 7.25 (s, 1H), 7.15 (s, 1H), 7.10 (br dd, J=7.3, 5.2 Hz, 2H), 7.05 (s, 1H), 6.82 (br d, J=6.1 Hz, 1H), 6.56 (s, 1H), 6.19 (s, 1H), 2.74-2.61 (m, 2H), 2.32-2.21 (m, 3H), 2.20-2.10 (m, 3H). Analytical HPLC RT=0.760 min (Method A) and 0.920 min (Method B), purity=95%.

EXAMPLE 360

Preparation N-((aR)-6-((3-carbamoylpyridin-2-yl)oxy)spiro[3.3]heptan-2-yl)-7-(3,3-difluorocyclobutoxy)imidazo[1,2-a]pyridine-3-carboxamide

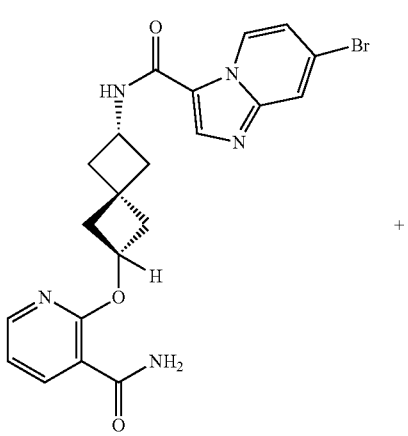

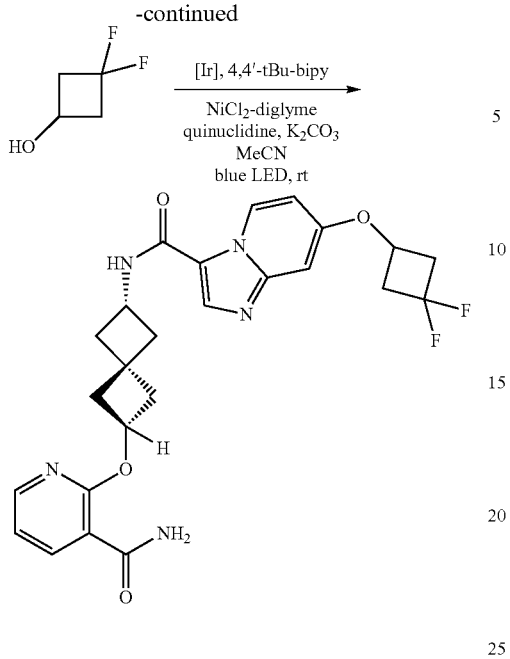

A slurry of Intermediate 100 (40 mg, 0.085 mmol), 3,3-difluorocyclobutanol (11.5 mg, 0.106 mmol), (4,4'-di-t-butyl-2,2'-bipyridine)bis[3,5-difluoro-2-[5-trifluoromethyl-2-pyridinyl -kappaN)phenyl-kappaC]iridium(III) hexafluorophosphate (0.87 mg, 0.85 μmol), nickel(II) bromide ethylene glycol dimethyl ether complex (1.3 mg, 4.3 μmol), 4,4'-di-tert-butyl-2,2'-bipyridine (1.1 mg, 4.3 μmol), potassium carbonate (14.7 mg, 0.106 mmol) and quinuclidine (0.95 mg, 8.50 μmol) in CH$_3$CN (850 μl) was degassed, blanketed under N$_2$ and irradiated with blue LED for 16 h. Additional amounts of 3-difluorocyclobutanol (11.5 mg, 0.106 mmol), (4,4'-di-t-butyl-2,2'-bipyridine)bis[3,5-difluoro-2-[5-trifluoromethyl-2-pyridinyl-kappan)phenyl-kappac]iridium(III) hexafluorophosphate (0.87 mg, 0.850 μmol), nickel(II) bromide ethylene glycol dimethyl ether complex (1.3 mg, 4.25 μmol), 4,4'-di-tert-butyl-2,2'-bipyridine (1.1 mg, 4.25 μmol), potassium carbonate (14.7 mg, 0.106 mmol) and quinuclidine (0.95 mg, 8.50 μmol) were added, the reaction mixture was degassed, blanketed under N$_2$ and irradiated with blue LED for additional 16 h w/ air cooling. The reaction mixture was quenched with TFA, concentrated, suspended in DMF, filtered and purified by reverse phase HPLC to afford Example 360 (4.3 mg, 10% yield). MS (ESI) m/z: 497.9 (M+H)$^+$. $^1$H-NMR (500 MHz, DMSO-d$_6$) δ ppm 9.28 (br d, J=7.6 Hz, 1H), 8.48 (br d, J=7.6 Hz, 1H), 8.31-8.24 (m, 1H), 8.21 (s, 1H), 8.16 (dd, J=7.5, 1.7 Hz, 1H), 7.69 (br s, 1H), 7.59 (br s, 1H), 7.10 (dd, J=7.3, 5.2 Hz, 1H), 6.99 (br s, 1H), 6.82 (br d, J=7.3 Hz, 1H), 5.23 (quin, J=7.2 Hz, 1H), 4.90 (br s, 1H), 4.43-4.31 (m, 1H), 3.28 (br d, J=4.6 Hz, 1H), 2.81-2.70 (m, 2H), 2.70-2.59 (m, 1H), 2.39-2.32 (m, 1H), 2.27 (br dd, J=11.3, 7.3 Hz, 1H), 2.21 (br d, J=4.0 Hz, 1H), 2.20-2.12 (m, 2H). Analytical HPLC RT=1.240 min (Method A) and 1.554 min (Method B), purity=95%.

EXAMPLE 361

Preparation N-((aR)-6-((3-carbamoylpyridin-2-yl)oxy)spiro[3.3]heptan-2-yl)-7-chloroimidazo[1,2-a]pyridine-3-carboxamide

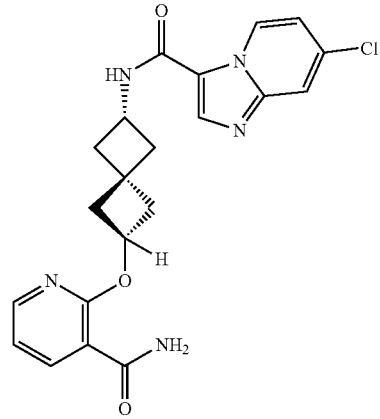

Example 361 (7.6 mg, 28% yield) was obtained as a side-product in a process similar as outlined in Example 360 with 4-methylpiperidin-4-ol, HCl as a reagent. MS (ESI) m/z: 426.3 (M+H)$^+$. $^1$H-NMR (500 MHz, DMSO-d$_6$) δ ppm 9.40 (d, J=7.3 Hz, 1H), 8.68 (br d, J=7.3 Hz, 1H), 8.33 (s, 1H), 8.25 (br d, J=3.1 Hz, 1H), 8.16 (br d, J=7.3 Hz, 1H), 7.85 (s, 1H), 7.66 (br s, 1H), 7.62 (br s, 1H), 7.18 (dd, J=7.3, 1.8 Hz, 1H), 7.10 (dd, J=7.3, 5.2 Hz, 1H), 5.22 (quin, J=7.1 Hz, 1H), 4.37 (dq, J=15.9, 7.8 Hz, 1H), 3.65-3.50 (m, 1H), 2.70-2.61 (m, 1H), 2.49-2.42 (m, 2H), 2.39-2.30 (m, 1H), 2.25 (br dd, J=11.1, 7.5 Hz, 1H), 2.21-2.13 (m, 2H). Analytical HPLC RT=1.441 min (Method A) and 1.236 min (Method B), purity=100%.

EXAMPLE 362

Preparation N-((aR)-6-((3-carbamoylpyridin-2-yl)oxy)spiro[3.3]heptan-2-yl)-7-(1,1-dioxidothiomorpholino)imidazo[1,2-a]pyridine-3-carboxamide

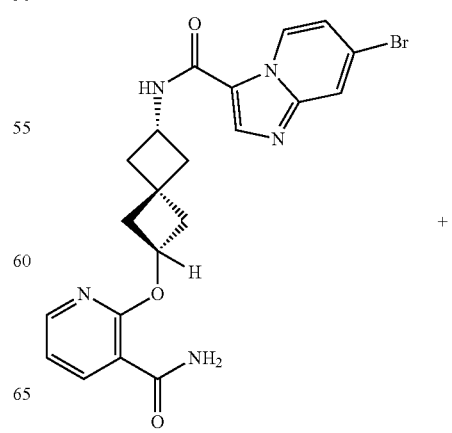

+

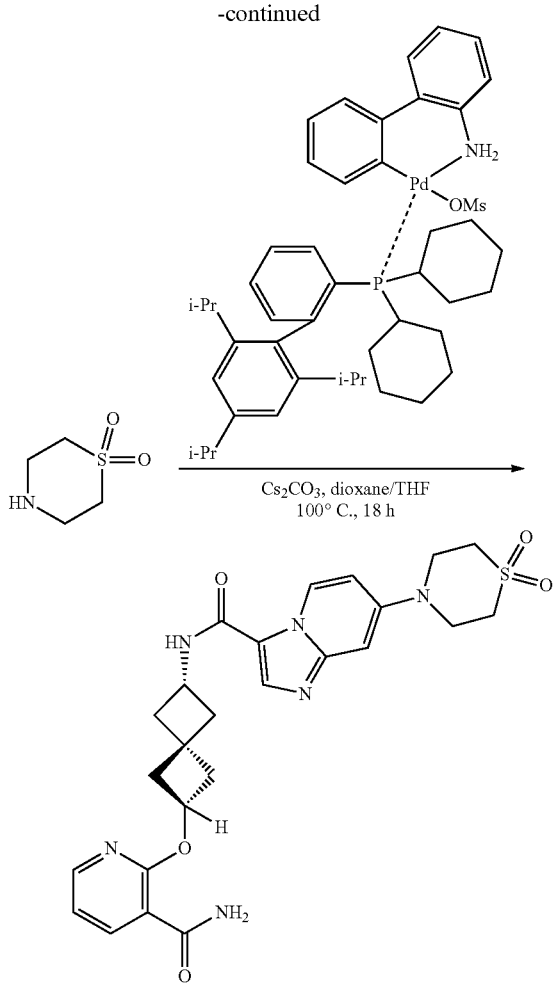

Intermediate 100 (30 mg, 0.064 mmol), thiomorpholine 1,1-dioxide (43.1 mg, 0.319 mmol) and cesium carbonate (62.3 mg, 0.191 mmol) were placed in a pressure vial. Then dioxane (1.0 mL), THF (0.5 mL) and Pd-XPhos G3 (4.1 mg, 4.78 µmol) were added, and the reaction mixture was degassed (3×, vacuum/Ar). The pressure vial was capped, and the reaction mixture was stirred at 100° C. for 18 h. Most of the solvent was removed under reduced pressure, the obtained residue was dissolved in DMF (2 mL), filtered and purified by reverse phase HPLC to afford Example 362 (6.7 mg, 18% yield). MS (ESI) m/z: 525.0 (M+H)+. $^1$H-NMR (500 MHz, DMSO-$d_6$) δ ppm 9.22 (br d, J=6.7 Hz, 1H), 8.51 (br d, J=6.1 Hz, 1H), 8.27 (br d, J=3.1 Hz, 2H), 8.23 (br s, 1H), 8.18-8.13 (m, 1H), 7.70 (br s, 2H), 7.59 (br s, 1H), 7.20 (s, 1H), 7.16 (br d, J=3.1 Hz, 1H), 7.12-7.08 (m, 2H), 7.01 (br d, J=13.7 Hz, 2H), 5.28-5.19 (m, 1H), 4.42-4.33 (m, 1H), 3.96 (br s, 3H), 3.39 (br d, J=5.5 Hz, 1H), 3.18 (br s, 2H), 2.31-2.25 (m, 2H), 2.22-2.14 (m, 3H). Analytical HPLC RT=1.250 min (Method A) and 1.110 min (Method B), purity=89%.

The following examples in Table 14 were prepared using a similar procedure to that which was used in the preparation of Example 235 utilizing Intermediate 101 and the appropriate boronic acids/boronate esters/potassium trifluoroborates. Longer time and higher temperature maybe used to drive the reaction. Microwave conditions (120° C. for 30 min) were also used.

TABLE 14

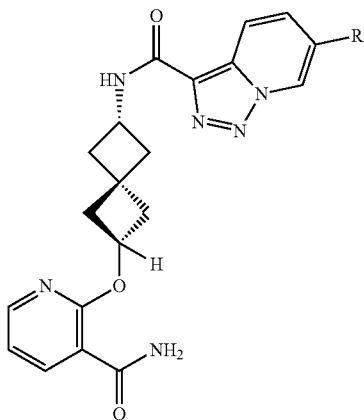

| Example | R | Name | LCMS (M + H)+ | HPLC Method, RT (min.) | $^1$H NMR |
|---|---|---|---|---|---|
| 363 | ![pyrazole-d3] | N-((aR)-6-((3-carbamoylpyridin-2-yl)oxy)spiro[3.3]heptan-2-yl)-6-(1-(2H3)methyl-1H-pyrazol-4-yl)-[1,2,3]triazolo[1,5- | 476.0 | A: 1.276 B: 1.226 | (500 MHz, DMSO-$d_6$) δ ppm 9.42 (s, 1H), 8.81 (br d, J = 7.9 Hz, 1H), 8.31 (s, 1H), 8.25-8.20 (m, 1H), 8.17-8.10 (m, 2H), 8.06 (s, 1H), 7.85 (br d, J = 9.2 Hz, 1H), 7.65 (br s, 1H), 7.56 (br s, 1H), 7.06 (dd, J = 7.3, 4.9 Hz, 1H), 5.18 (quin, J = 7.1 Hz, 1H), 4.39 (sxt, J = 8.1 Hz, 1H), 2.68-2.59 (m, 1H), 2.45-2.41 (m, 1H), 2.40- |

TABLE 14-continued

| # | Structure | Name | MS | HPLC | NMR |
|---|---|---|---|---|---|
| | | a]pyridine-3-carboxamide | | | 2.34 (m, 1H), 2.32-2.25 (m, 3H), 2.22 (br dd, J = 10.8, 7.5 Hz, 1H), 2.16 (br dd, J = 11.4, 7.5 Hz, 1H) |
| 364 | 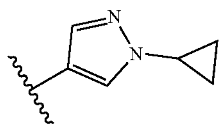 [SMILES: *c1cnn(C2CC2)c1] | N-((aR)-6-((3-carbamoylpyridin-2-yl)oxy)spiro[3.3]heptan-2-yl)-6-(1-cyclopropyl-1H-pyrazol-4-yl)-[1,2,3]triazolo[1,5-a]pyridine-3-carboxamide | 499.1 | A: 1.449 B: 1.439 | (500 MHz, DMSO-$d_6$) δ ppm 9.46 (s, 1H), 8.85 (br d, J = 7.9 Hz, 1H), 8.47 (s, 1H), 8.30-8.22 (m, 1H), 8.20-8.13 (m, 2H), 8.10 (s, 1H), 7.91 (br d, J = 9.2 Hz, 1H), 7.68 (br s, 1H), 7.60 (br s, 1H), 7.10 (dd, J = 7.3, 4.9 Hz, 1H), 5.22 (quin, J = 7.1 Hz, 1H), 4.43 (sxt, J = 8.1 Hz, 1H), 3.83-3.70 (m, 1H), 2.69-2.62 (m, 1H), 2.45-2.39 (m, 1H), 2.36-2.29 (m, 3H), 2.25 (br dd, J = 11.1, 7.5 Hz, 1H), 2.20 (br dd, J = 11.6, 7.6 Hz, 1H), 1.13-1.05 (m, 2H), 1.05-0.97 (m, 2H) |
| 365 | 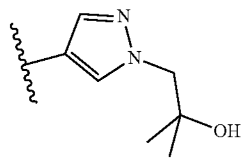 [SMILES: *c1cnn(CC(C)(C)O)c1] | N-((aR)-6-((3-carbamoylpyridin-2-yl)oxy)spiro[3.3]heptan-2-yl)-6-(1-(2-hydroxy-2-methylpropyl)-1H-pyrazol-4-yl)-[1,2,3]triazolo[1,5-a]pyridine-3-carboxamide | 531.1 | A: 1.431 B: 1.413 | (500 MHz, DMSO-$d_6$) δ ppm 9.48 (s, 1H), 8.85 (br d, J = 7.9 Hz, 1H), 8.33 (s, 1H), 8.26 (dd, J = 4.6, 1.8 Hz, 1H), 8.21-8.14 (m, 2H), 8.11 (s, 1H), 7.92 (br d, J = 9.2 Hz, 1H), 7.68 (br s, 1H), 7.60 (br s, 1H), 7.10 (dd, J = 7.3, 4.9 Hz, 1H), 5.22 (quin, J = 7.0 Hz, 1H), 4.43 (sxt, J = 8.2 Hz, 1H), 2.73-2.63 (m, 1H), 2.46 (br d, J = 6.7 Hz, 1H), 2.44-2.38 (m, 1H), 2.36-2.28 (m, 3H), 2.25 (br dd, J = 11.0, 7.6 Hz, 1H), 2.21-2.12 (m, 1H), 1.10 (s, 6H) |
| 366 | 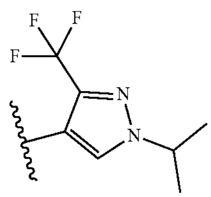 [SMILES: *c1cn(C(C)C)nc1C(F)(F)F] | N-((aR)-6-((3-carbamoylpyridin-2-yl)oxy)spiro[3.3]heptan-2-yl)-6-(1-isopropyl-3-(trifluoromethyl)-1H-pyrazol-4-yl)-[1,2,3]triazolo[1,5-a]pyridine-3-carboxamide | 569.1 | A: 1.967 B: 1.963 | (500 MHz, DMSO-$d_6$) δ ppm 9.20 (s, 1H), 8.92 (br d, J = 7.9 Hz, 1H), 8.46 (s, 1H), 8.30-8.23 (m, 2H), 8.16 (dd, J = 7.5, 1.7 Hz, 1H), 7.71-7.63 (m, 2H), 7.61 (br s, 1H), 7.10 (dd, J = 7.5, 5.0 Hz, 1H), 5.22 (quin, J = 6.9 Hz, 1H), 4.65 (dt, J = 13.2, 6.7 Hz, 1H), 4.44 (sxt, J = 8.1Hz, 1H), 2.71-2.62 (m, 1H), 2.49-2.39 (m, 2H), 2.37-2.29 (m, 3H), 2.29-2.22 (m, 1H), 2.20 (br dd, J = 11.6, 7.6 Hz, 1H), 1.50 (d, J = 6.4 Hz, 6H) |
| 367 | 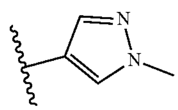 [SMILES: *c1cnn(C)c1] | N-((aR)-6-((3-carbamoyl-pyridin-2-yl)oxy)spiro[3.3]heptan-2-yl)-6-(1-methyl-1H-pyrazol-4-yl)-[1,2,3]triazolo[1,5-a]pyridine-3-carboxamide | 473.1 | A: 1.387 B: 1.383 | (500 MHz, DMSO-$d_6$) δ ppm 9.37 (s, 1H), 8.65 (br d, J = 7.7 Hz, 1H), 8.30 (s, 1H), 8.26 (dd, J = 4.8, 1.9 Hz, 1H), 8.21-8.13 (m, 2H), 8.05 (s, 1H), 7.86 (d, J = 9.2 Hz, 1H), 7.56 (br s, 1H), 7.51 (br s, 1H), 7.09 (dd, J = 7.5, 4.9 Hz, 1H), 5.24 (quin, J = 7.0 Hz, 1H), 4.42 (sxt, J = 8.1 Hz, 1H), 3.89 (s, 3H), 2.67 (dt, J = 11.2, 5.8 Hz, 1H), 2.48-2.41 (m, 1H), 2.39-2.29 (m, 3H), 2.28-2.23 (m, 1H), 2.20 (dd, J = 11.8, 7.3 Hz, 1H) |

EXAMPLE 368

Preparation of 6-bromo-N-((aR)-6-((3-carbamoylpyridin-2-yl)oxy)spiro[3.3]heptan-2-yl)-[1,2,3]triazolo[1,5-a]pyridine-3-carboxamide

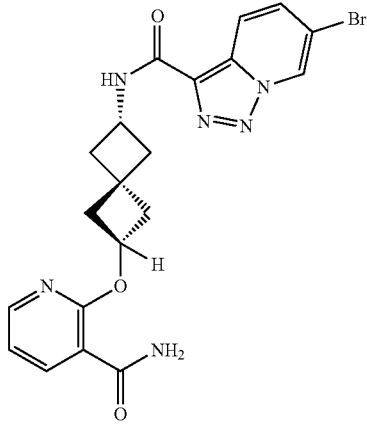

Intermediate 101 (15 mg, 0.032 mmol) was purified by reverse phase HPLC to afford Example 368 (11.2 mg, 75% yield). MS (ESI) m/z: 471.0 (M+H)$^+$. $^1$H-NMR (500 MHz, DMSO-$d_6$) δ ppm 0.59 (s, 1H), 8.92 (br d, J=7.9 Hz, 1H), 8.28-8.22 (m, 1H), 8.18-8.10 (m, 2H), 7.74 (d, J=9.5 Hz, 1H), 7.64 (br d, J=7.6 Hz, 2H), 7.10 (dd, J=7.5, 5.0 Hz, 1H), 5.20 (quin, J=7.0 Hz, 1H), 4.40 (sxt, J=8.1 Hz, 1H), 2.65 (dt, J=11.1, 5.7 Hz, 1H), 2.49-2.44 (m, 1H), 2.44-2.38 (m, 1H), 2.29 (br t, J=9.3 Hz, 3H), 2.26-2.21 (m, 1H), 2.18 (br dd, J=11.7, 7.5 Hz, 1H). Analytical HPLC RT=1.488 min (Method A) and 1.476 min (Method B), purity=100%.

EXAMPLE 369

Preparation of N-((aR)-6-((3-carbamoylpyridin-2-yl)oxy)spiro[3.3]heptan-2-yl)-6-morpholino-[1,2,3]triazolo[1,5-a]pyridine-3-carboxamide

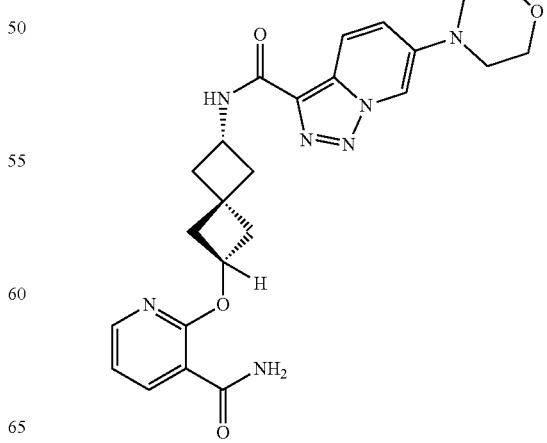

Example 369 (1.8 mg, 5% yield) was prepared in an analogous manner as Example 336 using Intermediate 102. MS (ESI) m/z: 478.2 (M+H)+. $^1$H-NMR (500 MHz, DMSO-$d_6$) δ ppm 7.64 (dd, J=4.7, 1.7 Hz, 1H), 7.54 (dd, J=7.3, 1.8 Hz, 1H), 7.36 (br d, J=9.2 Hz, 1H), 7.24 (br s, 1H), 7.20 (br d, J=8.9 Hz, 1H), 7.07 (br s, 1H), 6.97 (br s, 1H), 6.47 (dd, J=7.3, 4.9 Hz, 1H), 4.63 (quin, J=7.1 Hz. 1H), 4.10 (quin, J=8.3 Hz, 1H), 3.11 (br d, J=4.6 Hz, 4H), 2.16-2.08 (m, 1H), 2.08-1.99 (m, 1H), 1.97-1.87 (m, 1H), 1.84-1.75 (m, 1H), 1.67 (ddd, J=18.8, 11.4, 7.3 Hz, 1H). Analytical HPLC RT=1.128 min (Method A) and 1.153 min (Method B), purity=96%.

EXAMPLE 370

Preparation of N-((aR)-6-((3-carbamoylpyridin-2-yl)oxy)spiro[3.3]heptan-2-yl)-7-(1-methyl-6-oxo-1,6-dihydropyridin-3-yl)imidazo[1,2-a]pyridine-3-carboxamide

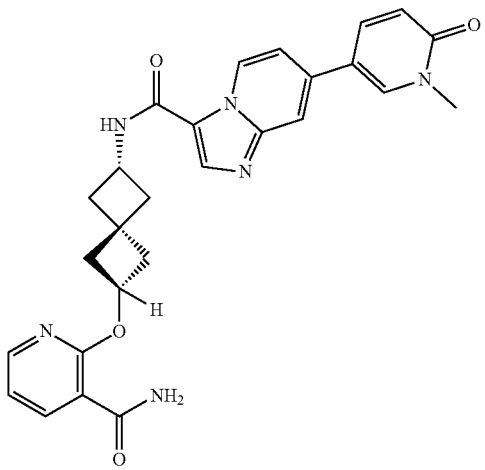

EXAMPLE 370A

Preparation of (3-(((aR)-6-((3-carbamoylpyridin-2-yl)oxy)spiro[3.3]heptan-2-yl)carbamoyl)imidazo[1,2-a]pyridin-7-yl)boronic acid

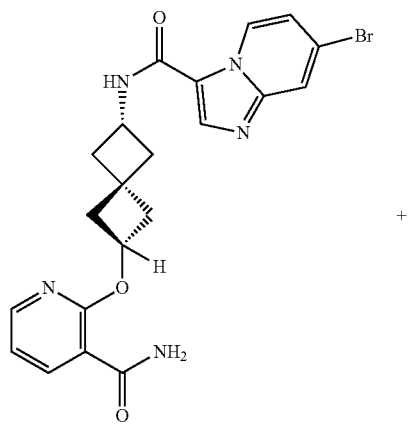

+

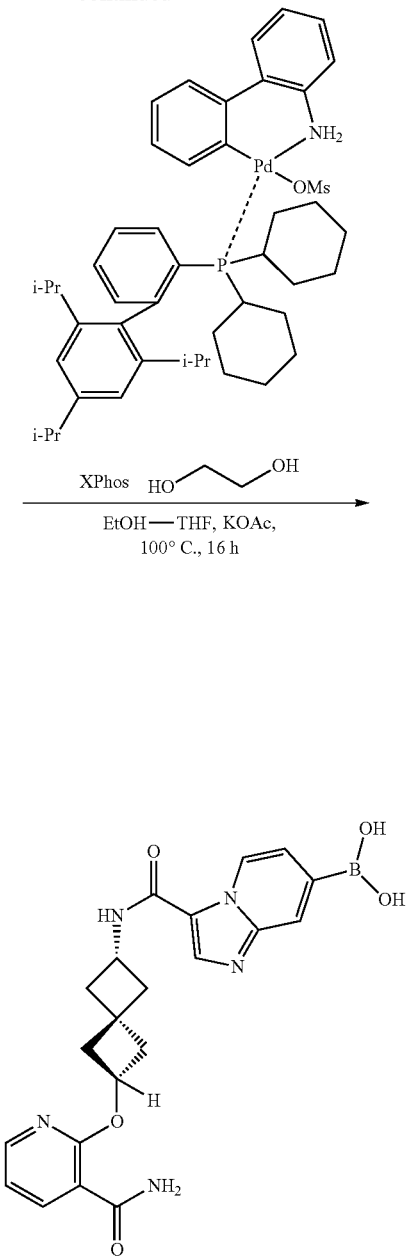

Intermediate 100 (100 mg, 0.213 mmol), hypodiboric acid (57.2 mg, 0.638 mmol), 2-(dicyclohexylphosphino)-2',4',6'-triisopropylbiphenyl (XPhos) (4.1 mg, 8.50 μmol), Pd-XPhos G3 (3.6 mg, 4.25 μmol) and potassium acetate (125 mg, 1.276 mmol) were placed in a pressure vial. Then EtOH (1417 μl), THF (709 μl) and ethane-1,2-diol (71 μl, 1.276 mmol) were added, and the reaction mixture was degassed (3×, vacuum/$N_2$). The pressure vial was capped, and the reaction mixture was stirred at 100° C. for 16 h. Most of the solvent was removed under reduced pressure, and the residue was mixed with water (15 mL), acidified with HCl (aq. 1 M) (1280 μl, 1.28 mmol), and vigorously stirred at rt for 60 min. The solid was collected by filtration, washed with water (3×5 mL), and dried under lyophilizer vacuum to afford Example 370A (30 mg, 28° % yield). MS (ESI) m/z: 436.0 (M+H)+.

EXAMPLE 370

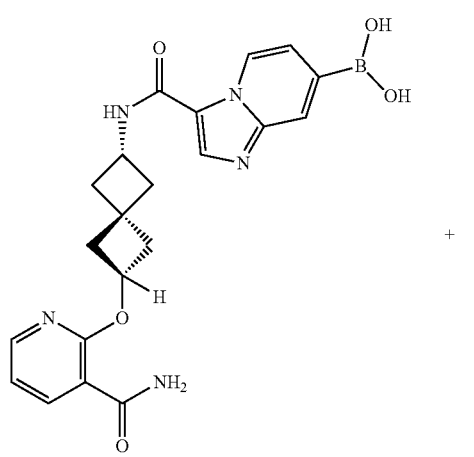

+

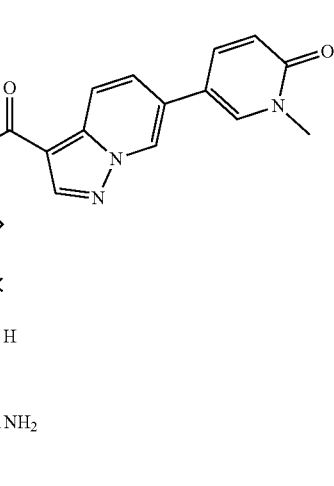

pressure, and the residue was dissolved in DMF (2 mL), filtered and purified by reverse phase HPLC to afford Example 370 (2.2 mg, 8% yield). MS (ESI) m/z: 499.2 (M+H)+. 1H-NMR (500 MHz, DMSO-$d_6$) δ ppm 9.38 (d, J=7.3 Hz, 1H), 8.62 (br d, J=7.3 Hz, 1H), 8.37 (br s, 1H), 8.32 (s, 1H), 8.25 (br d, J=3.1 Hz, 1H), 8.16 (br d, J=7.3 Hz, 1H), 8.02 (br d, J=9.5 Hz, 1H), 7.89 (s, 1H), 7.66 (s, 1H), 7.62 (br s, 1H), 7.40 (br d, J=7.3 Hz, 1H), 7.10 (dd, J=7.2, 5.0 Hz, 1H), 6.53 (d, J=9.5 Hz, 1H), 5.22 (quin, J=7.2 Hz, 1H), 4.45-4.26 (m, 1H), 3.67-3.51 (m, 1H), 2.73-2.60 (m, 1H), 2.48-2.42 (m, 1H), 2.40-2.32 (m, 1H), 2.29-2.12 (m, 4H). Analytical HPLC RT=1.263 min (Method A) and 1.119 min (Method B), purity=97%.

EXAMPLE 371

Preparation of N-((aR)-6-((3-carbamoylpyridin-2-yl)oxy)spiro[3.3]heptan-2-yl)-6-(1-methyl-6-oxo-1,6-dihydropyridin-3-yl)pyrazolo[1,5-a]pyridine-3-carboxamide

EXAMPLE 371A

Preparation of 6-bromo-N-((aR)-6-((3-carbamoylpyridin-2-yl)oxy)spiro[3.3]heptan-2-yl)pyrazolo[1,5-a]pyridine-3-carboxamide

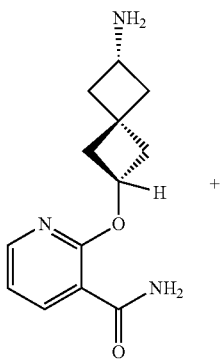

+

Example 370A (25 mg, 0.057 mmol), 5-bromo-1-methylpyridin-2(1H)-one (11.9 mg, 0.063 mmol) and Pd-XPhos G3 (3.7 mg, 4.31 µmol) were placed in a pressure vial. Then THF (1.5 mL) and phosphoric acid, potassium salt (0.5 M aq.) (0.23 mL, 0.115 mmol) were added, and the reaction mixture was degassed (3×, vacuum/Ar). The pressure vial was capped, and the reaction mixture was stirred at 100° C. for 2 h. Most of the solvent was removed under reduced 465
-continued

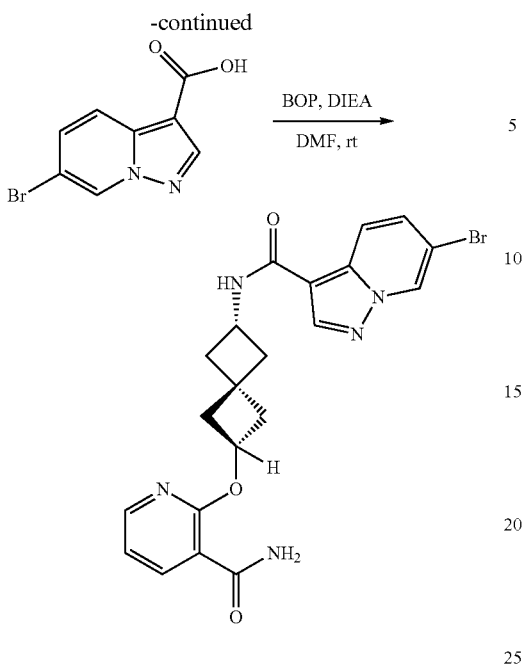

466
-continued

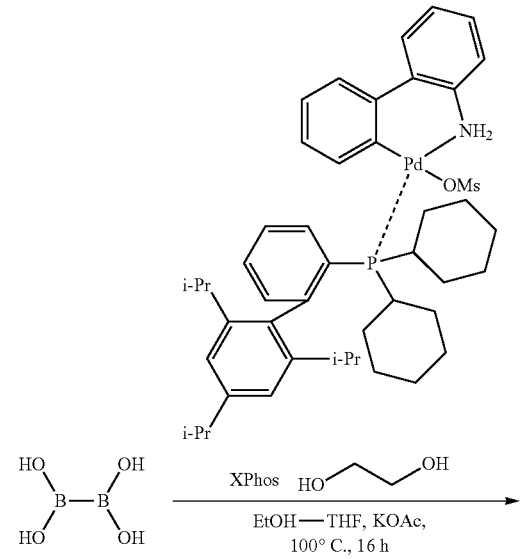

Example 42C (482 mg, 1.950 mmol) and 6-bromopyrazolo[1,5-a]pyridine-3-carboxylic acid (470 mg, 1.950 mmol) were dissolved in anhydrous DMF (5 mL), then DIEA (1.703 mL, 9.75 mmol) was added, followed by BOP (1121 mg, 2.53 mmol). The reaction mixture was stirred at rt for 1 h. The reaction mixture was quenched with MeOH (1.0 mL), and most for the solvent was removed under reduced pressure. To the obtained semi-solid residue, water was added portionwise with sonication (total volume ~25 mL), which resulted in white solid formation. The mixture was stirred at rt for 2 h, filtered using a filter cartridge, washed with water (3×5 mL), and dried in vacuum to afford Example 371A (890 mg, 73% yield) as an off-white solid. MS (ESI) m/z: 470.0 (M+H)$^+$.

EXAMPLE 371B

Preparation of (3-(((aR)-6-((3-carbamoylpyridin-2-yl)oxy)spiro[3.3]heptan-2-yl)carbamoyl)pyrazolo[1,5-a]pyridin-6-yl)boronic acid

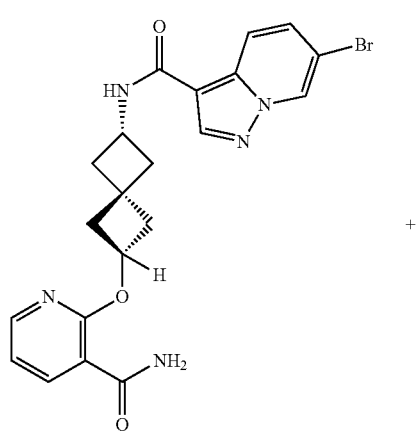

+

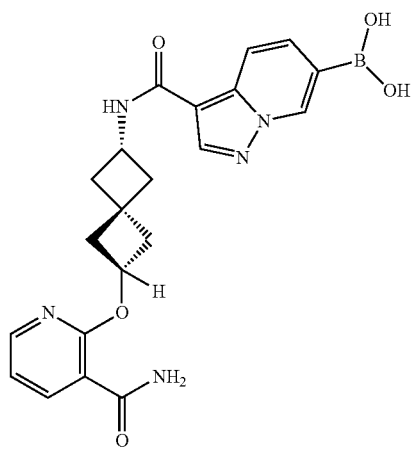

Example 371A (500 mg, 1.063 mmol), hypodiboric acid (286 mg, 3.19 mmol), 2-(dicyclohexylphosphino)-2',4',6'-triisopropylbiphenyl (XPhos) (20.3 mg, 0.043 mmol), Pd-XPhos G3 (18.0 mg, 0.021 mmol) and potassium acetate (626 mg, 6.38 mmol) were placed in a pressure vial. Then EtOH (7087 μl), THF (3544 μl) and ethane-1,2-diol (357 μl, 6.38 mmol) were added, and the reaction mixture was degassed (3×, vacuum/N$_2$). The pressure vial was capped, and the reaction mixture was stirred at 100° C. for 16 h. Most of the solvent was removed under reduced pressure, and the residue was mixed with water (25 mL), acidified with HCl (1 M aq.) (6379 μl, 6.38 mmol), and vigorously stirred at rt for 60 min. The solids were collected by filtration, washed with water (3×5 mL), and dried under lyophilizer vacuum to afford Example 371B (397 mg, 50% yield) as a grey solid. MS (ESI) m/z: 436.25 (M+H)$^+$.

EXAMPLE 371

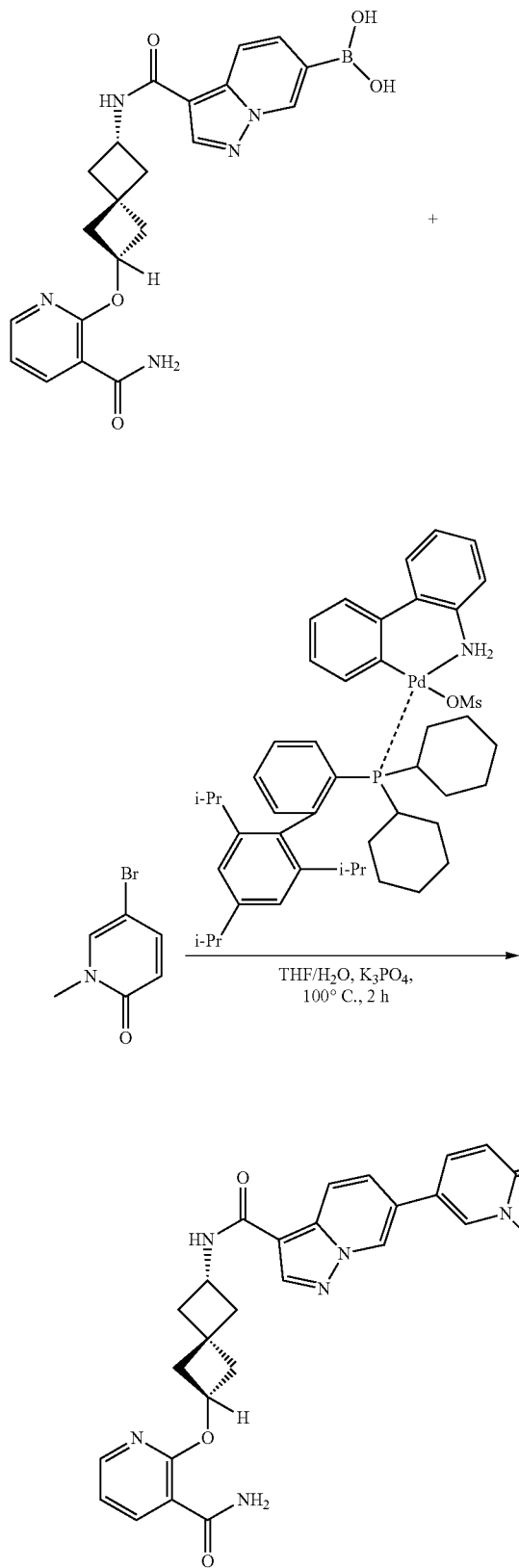

Example 371B (25 mg, 0.057 mmol), 5-bromo-1-methylpyridin-2(1H)-one (11.9 mg, 0.063 mmol) and Pd-XPhos G3 (3.7 mg, 4.31 µmol) were placed in a pressure vial. Then THF (1.5 mL) and phosphoric acid, potassium salt (0.5 M aq.) (0.23 mL, 0.115 mmol) were added, and the reaction mixture was degassed (3×, vacuum/Ar). The pressure vial was capped, and the reaction mixture was stirred at 100° C. for 2 h. Most of the solvent was removed under reduced pressure, and the residue was dissolved in DMF (2 mL), filtered and purified by reverse phase HPLC to afford Example 371 (0.84 mg, 3% yield). MS (ESI) m/z: 499.2 (M+H)$^+$. $^1$H-NMR (500 MHz, DMSO-d$_6$) δ ppm 9.03-8.97 (m, 1H), 8.56 (s, 1H), 8.36 (br d, J=7.3 Hz, 1H), 8.26 (br s, 2H), 8.20 (d, J=9.2 Hz, 1H), 8.16 (dd, J=7.3, 1.8 Hz, 1H), 7.94 (dd, J=9.5, 2.4 Hz, 1H), 7.72 (br d, J=9.5 Hz, 1H), 7.68 (br s, 1H), 7.60 (br s, 1H), 7.10 (dd, J=7.3, 4.9 Hz, 1H), 6.52 (d, J=9.2 Hz, 1H), 5.28-5.19 (m, 1H), 4.43-4.33 (m, 1H), 3.19-3.11 (m, 1H), 2.71-2.62 (m, 1H), 2.39-2.31 (m, 1H), 2.27 (br dd, J=11.1, 7.5 Hz, 1H), 2.24-2.12 (m, 3H), 1.78 (s, 3H). Analytical HPLC RT=1.167 min (Method A) and 1.152 min (Method B), purity=96%.

EXAMPLE 372

Preparation of N-((aR)-6-((3-carbamoylpyridin-2-yl)oxy)spiro[3.3]heptan-2-yl)-1-(difluoromethyl)-6-morpholino-1H-indazole-3-carboxamide

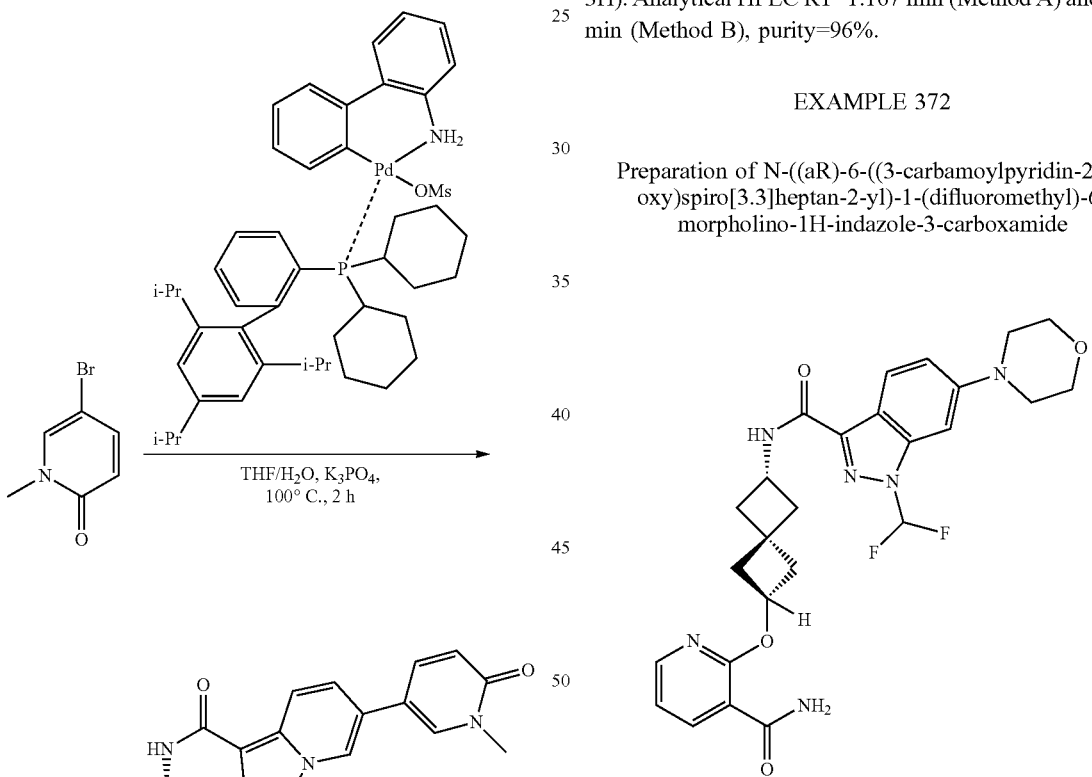

Example 372 (12.1 mg, 32% yield) was prepared in an analogous manner as Example 336 using Intermediate 102. MS (ESI) m/z: 527.0 (M+H)$^+$. $^1$H-NMR (500 MHz, DMSO-d$_6$) δ ppm 8.74 (br d, J=7.9 Hz, 1H), 8.26 (br d, J=3.1 Hz, 1H), 8.19-8.12 (m, 1H), 7.98 (d, J=8.9 Hz, 1H), 7.68 (br s, 1H), 7.60 (br s, 1H), 7.20 (br d, J=8.9 Hz, 1H), 7.15 (s, 1H), 7.10 (dd, J=7.3, 4.9 Hz, 1H), 5.21 (quin, J=7.2 Hz, 1H), 4.46-4.34 (m, 1H), 3.76 (br d, J=4.6 Hz, 4H), 3.25 (br s, 4H), 2.66 (dt, J=11.2, 5.5 Hz, 1H), 2.45 (br dd, J=12.2, 5.5 Hz, 1H), 2.43-2.37 (m, 1H), 2.34-2.22 (m, 4H), 2.20-2.15 (m, 1H). Analytical HPLC RT=1.661 min (Method A) and 1.570 min (Method B), purity=98%.

EXAMPLE 373

Preparation of 6-(benzyloxy)-N-((aR)-6-((3-carbamoylpyridin-2-yl)oxy)spiro[3.3]heptan-2-yl)-7-chloro-[1,2,3]triazolo[1,5-a]pyridine-3-carboxamide

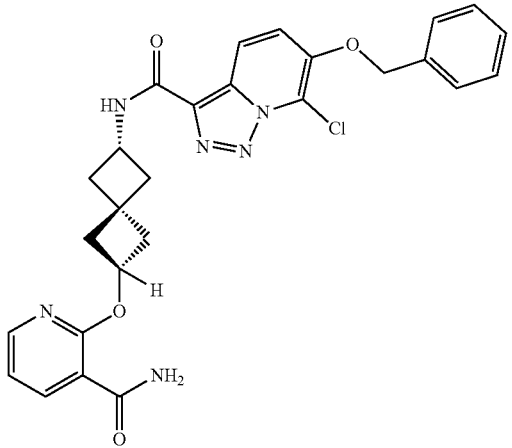

Example 373 (2.8 mg, 5% yield) was prepared in an analogous manner as Example 336 using Intermediate 104. MS (ESI) m/z: 533.1 (M+H)$^+$. $^1$H-NMR (500 MHz, DMSO-d$_6$) δ ppm 8.26 (d, J=5.4 Hz, 1H), 8.16 (dd, J=7.3, 1.8 Hz, 1H), 7.92 (d, J=8.5 Hz, 1H), 7.71-7.58 (m, 3H), 7.48-7.32 (m, 5H), 7.10 (dd, J=7.5, 5.0 Hz, 1H), 5.21 (s, 2H), 5.26-5.18 (m, 1H), 4.80 (quin, J=8.3 Hz, 1H), 2.88-2.67 (m, 1H), 2.65-2.55 (m, 3H), 2.47-2.40 (m, 1H), 2.28 (td, J=12.2, 7.6 Hz, 2H). Analytical HPLC RT=1.364 min (Method A) and 1.928 min (Method B), purity=99%.

EXAMPLE 374

Preparation of 6-(benzyloxy)-N-((aR)-6-((3-carbamoylpyridin-2-yl)oxy)spiro[3.3]heptan-2-yl)-7-cyclopropyl-[1,2,3]triazolo[1,5-a]pyridine-3-carboxamide

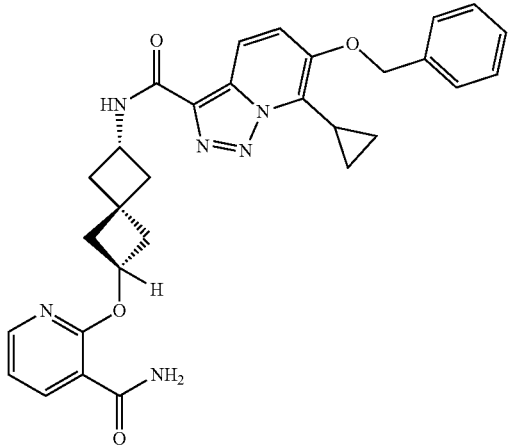

Example 374 (15 mg, 23% yield) was prepared in an analogous manner as Example 336 using Intermediate 105. MS (ESI) m/z: 539.2 (M+H)$^+$. $^1$H-NMR (500 MHz, DMSO-d$_6$) δ ppm 8.27 (dd, J=4.7, 2.0 Hz, 1H), 8.16 (dd, J=7.5, 2.0 Hz, 1H), 7.74-7.65 (m, 2H), 7.61 (br s, 1H), 7.57-7.46 (m, 3H), 7.45-7.32 (m, 3H), 7.10 (dd, J=7.3, 4.9 Hz, 1H), 5.25 (quin, J=6.9 Hz, 1H), 5.18 (s, 2H), 4.82 (br t, J=8.4 Hz, 1H), 2.80-2.69 (m, 1H), 2.68-2.56 (m, 4H), 2.47-2.39 (m, 1H), 2.30 (ddd, J=14.9, 11.7, 7.3 Hz, 3H), 1.06 (br s, 2H), 1.03-0.90 (m, 2H). Analytical HPLC RT=1.823 min (Method A) and 1.865 min (Method B), purity=96%.

EXAMPLE 375

Preparation of N-((aR)-6-((3-carbamoylpyridin-2-yl)oxy)spiro[3.3]heptan-2-yl)-6-(2-hydroxy-2-methylpropoxy)-[1,2,3]triazolo[1,5-a]pyridine-3-carboxamide

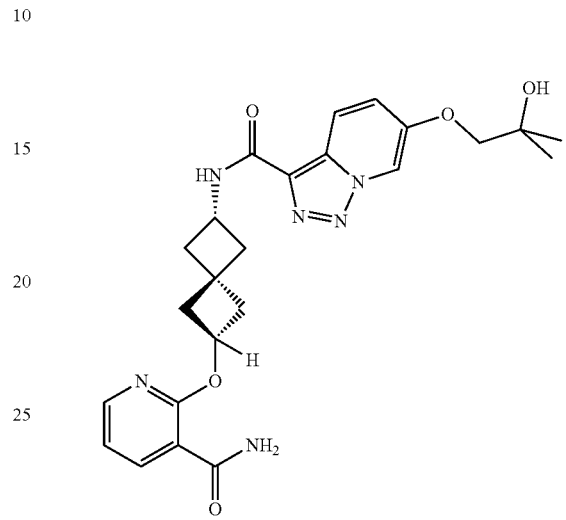

Example 375 (5.3 mg, 14% yield) was prepared in an analogous manner as Example 336 using Intermediate 106. MS (ESI) m/z: 481.2 (M+H)$^+$. $^1$H-NMR (500 MHz, DMSO-d$_6$) δ ppm 8.84 (s, 1H), 8.80 (br d, J=7.9 Hz, 1H), 8.44-8.21 (m, 1H), 8.16 (br d, J=7.3 Hz, 1H), 8.09 (d, J=9.8 Hz, 1H), 7.67 (br s, 1H), 7.61 (br s, 1H), 7.45-7.40 (m, 1H), 7.10 (dd, J=7.5, 5.0 Hz, 1H), 5.21 (br t, J=7.2 Hz, 1H), 4.49-4.34 (m, 1H), 3.87 (s, 2H), 3.54-3.42 (m, 1H), 2.71-2.60 (m, 1H), 2.44-2.38 (m, 1H), 2.33-2.17 (m, 4H), 1.22 (s, 6H). Analytical HPLC RT=1.343 min (Method A) and 1.325 min (Method B), purity=91%.

EXAMPLE 376

Preparation of 6-(benzyloxy)-N-((aR)-6-((3-carbamoylpyridin-2-yl)oxy)spiro[3.3]heptan-2-yl)-5-chloro-3-cyclopropylindolizine-1-carboxamide

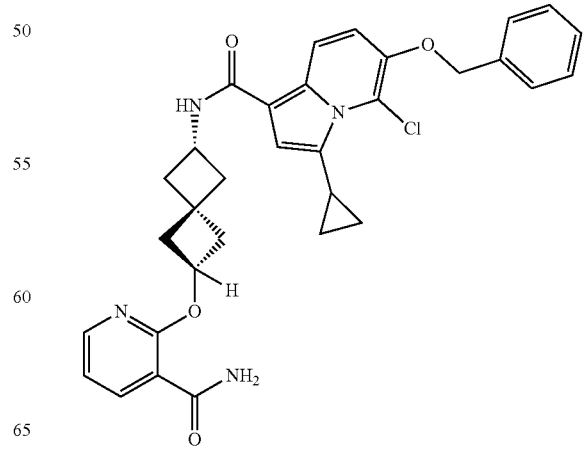

Example 376 (2.8 mg, 7% yield) was prepared in an analogous manner as Example 336 using Intermediate 107. MS (ESI) m/z: 571.1 (M+H)⁺. ¹H-NMR (500 MHz, DMSO-d₆) δ ppm 8.30-8.13 (m, 3H), 7.97 (br d, J=7.6 Hz, 1H), 7.69 (br s, 1H), 7.59 (br s, 1H), 7.47 (br d, J=7.3 Hz, 2H), 7.44-7.30 (m, 3H), 7.22-7.14 (m, 2H), 7.10 (dd, J=7.6, 4.9 Hz, 1H), 5.22 (br t, J=7.2 Hz, 1H), 5.19 (s, 2H), 4.40-4.30 (m, 1H), 2.73-2.56 (m, 2H), 2.47-2.37 (m, 2H), 2.33-2.10 (m, 5H), 1.00-0.94 (m, 2H), 0.78 (br d, J=3.7 Hz, 2H). Analytical HPLC RT=2.262 min (Method A) and 2.273 min (Method B), purity=99%.

EXAMPLE 377

N-[(aR) 2-({6-[1-(4-bromophenyl-5-methyl-1H-pyrazole-4-amido]spiro[3.3]heptan-2-yl}oxy)pyridine-3-carboxamide

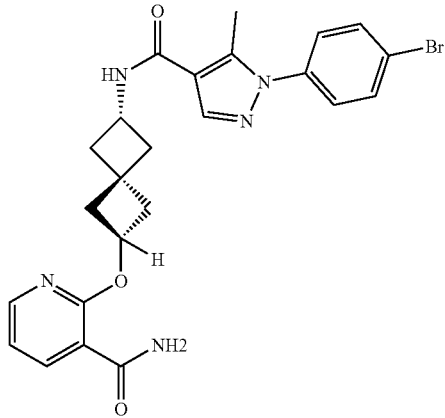

Example 377 was prepared using a similar procedure to that which was used in the preparation of Example 42 by using 1-(4-bromophenyl)-5-methyl-1H-pyrazole-4-carboxylic acid. ¹H NMR (500 MHz, Methanol-d4) δ 8.35 (dd, J=7.6, 2.1 Hz, 1H), 8.29 (dd, J=4.8, 2.1 Hz, 1H), 8.07 (s, 1H), 7.77-7.70 (m, 2H), 7.45-7.39 (m, 2H), 7.11 (dd, J=7.6, 4.8 Hz, 1H), 5.35 (quin, J=7.2 Hz, 1H), 4.49-4.38 (m, 1H), 2.80 (ddd, J=11.6, 6.2, 5.4 Hz, 1H), 2.64-2.55 (m, 2H), 2.53 (s, 3H), 2.50-2.43 (m, 1H), 2.38-2.18 (m, 4H). MS (ESI) m/z: 512.2 (M+H)⁺. Analytical HPLC: RT=9.33 min (Method C); 7.9 min (Method D).

EXAMPLE 378

N-[(aR) 2-[(6-{5-methyl-1-[4-(morpholin-4-yl)phenyl]-1H-pyrazole-4-amido}spiro[3.3]heptan-2-yl)oxy]pyridine-3-carboxamide 1 trifluoroacetic acid salt

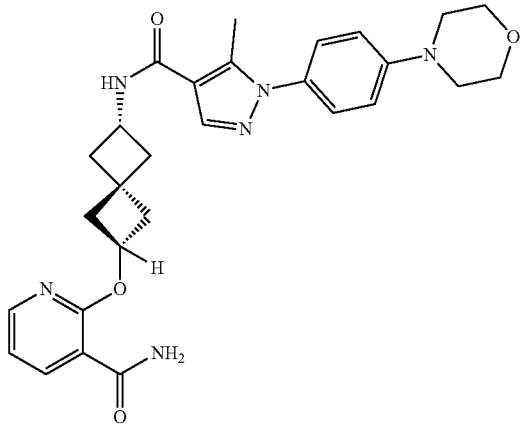

In a 1 dram vial, N-[(aR) 2-((6-(1-(4-bromophenyl)-5-methyl-1H-pyrazole-4-carboxamido)spiro[3.3]heptan-2-yl)oxy)nicotinamide (70 mg, 0.137 mmol), morpholine (21 mg, 0.241 mmol), 1,4-diazabicyclo[2.2.2]octane (27.7 mg, 0.247 mmol) was purged with a stream of N₂. Nickel(II) chloride ethylene glycol dimethyl ether complex (1.5 mg, 6.9 μmol) in 0.5 mL DMA and Ir[DF(CF₃)PPY]₂(DTBBPY)PF₆ (0.490 mL, 1.37 μmol) were added. The reaction was bubbled with N₂, sealed and stirred under blue LED irradiation for 3 hr. The reaction mixture was diluted with MeOH, filtered through a syringe filter and purified by reverse phase prep HPLC to provide N-[(aR) 2-[(6-{5-methyl-1-[4-(morpholin-4-yl)phenyl]-1H-pyrazole-4-amido}spiro[3.3]heptan-2-yl)oxy]pyridine-3-carboxamide, TFA (5.1 mg, 5.8% yield). ¹H NMR (500 MHz, Methanol-d4) δ 8.35 (dd, J=7.57, 2.06 Hz, 1H), 8.29 (dd, J=4.81, 2.06 Hz, 1H), 8.03 (s, 1H), 7.32-7.36 (m, 2H), 7.14-7.18 (m, 2H), 7.09-7.13 (m, 1H), 5.35 (quin, J=7.15 Hz, 1H), 4.40-4.48 (m, 1H), 3.87-3.90 (m, 4H), 3.27-3.30 (m, 4H), 2.80 (dt, J=11.55, 5.78 Hz, 1H), 2.56-2.64 (m, 2H), 2.44-2.50 (m, 4H), 2.34 (dd, J=11.55, 7.15 Hz, 1H), 2.20-2.30 (m, 3H). MS (ESI) m/z: 517.4 (M+H)⁺. Analytical HPLC: RT=7.76 min (Method C); 6.16 min (Method D).

EXAMPLE 379

N-[(aR)-2-{[6-(5-methyl-1-phenyl-1H-pyrazole-4-amido)spiro[3.3]heptan-2-yl]oxy}pyridine-3-carboxamide 1 trifluoroacetic acid salt

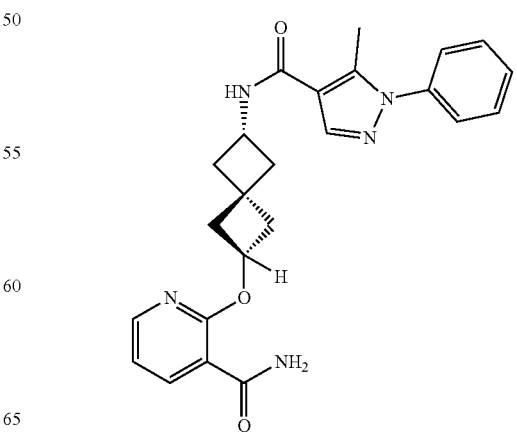

N-[(aR) 2-{[6-(5-methyl-1-phenyl-1H-pyrazole-4-amido)spiro[3.3]heptan-2-yl]oxy}pyridine-3-carboxamide, TFA ws isolated as a side product from the above reaction. $^1$H NMR (500 MHz, Methanol-$d_4$) δ 8.35 (dd, J=7.4, 1.9 Hz, 1H), 8.29 (dd, J=4.8, 2.1 Hz, 1H), 8.06 (s, 1H), 7.61-7.50 (m, 3H), 7.49-7.43 (m, 2H), 7.11 (dd, J=7.6, 4.8 Hz, 1H), 5.35 (quin, J=7.2 Hz, 1H), 4.49-4.39 (m, 1H), 2.83-2.76 (m, 1H), 2.65-2.55 (m, 2H), 2.51 (s, 3H), 2.50-2.43 (m, 1H), 2.34 (dd, J=11.6, 7.4 Hz, 1H), 2.30-2.18 (m, 3H). MS (ESI) m/z: 432.2 (M+H)$^+$. Analytical HPLC: RT=8.22 min (Method C); 6.68 min (Method D).

EXAMPLE 380

N-((aR)-6-((3-carbamoylpyridin-2-yl)oxy)spiro[3.3]heptan-2-yl)-7-methoxy-1-methyl-4,5-dihydro-1H-benzo[g]indazole-3-carboxamide

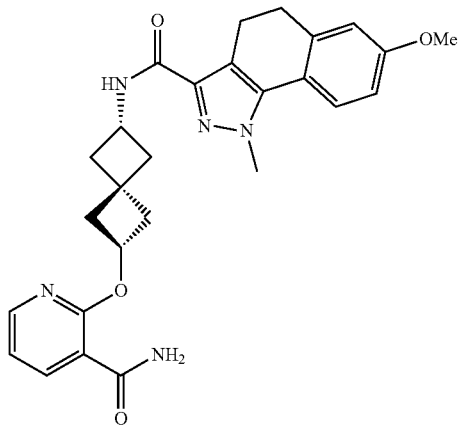

Example 380 was prepared using a similar procedure to that which was used in the preparation of Example 42 by using Intermediate 111. $^1$H NMR (500 MHz, CDCl$_3$) δ ppm 8.50 (dd, J=7.57, 2.06 Hz, 1H) 8.29 (dd, J=4.81, 2.06 Hz, 1H) 7.98 (br s, 1H) 7.48 (d, J=8.53 Hz, 1H) 7.06 (dd, J=7.57, 4.81 Hz, 2H) 6.90 (d, J=2.75 Hz, 1H) 6.80-6.87 (m, 1H) 6.69 (br s, 1H) 5.36 (quin, J=7.15 Hz, 1H) 4.49-4.58 (m, 1H) 4.13 (s, 3H) 3.85 (s, 3H) 3.02-3.08 (m, 2H) 2.85-2.92 (m, 2H) 2.80 (dt, J=11.62, 5.88 Hz, 1H) 2.57-2.69 (m, 2H) 2.48-2.57 (m, 1H) 2.20-2.31 (m, 2H) 2.16 (dd, J=11.28, 8.80 Hz, 2H). MS (ESI) m/z: 488.2 (M+H)$^+$. Analytical HPLC: RT=9.62 min (Method C); 9.59 min (Method D).

EXAMPLE 381

N-((aR)-6-((3-carbamoylpyridin-2-yl)oxy)spiro[3.3]heptan-2-yl)-7-methoxy-2-methyl-4,5-dihydro-2H-benzo[g]indazole-3-carboxamide

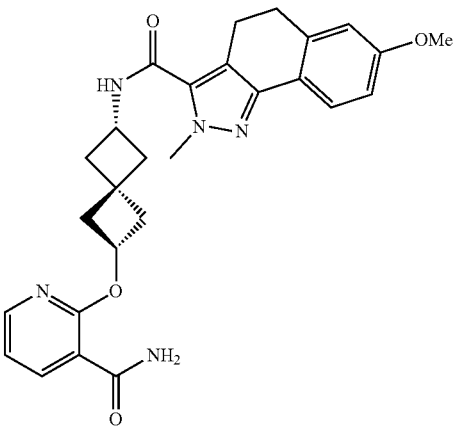

Example 381 was prepared using a similar procedure to that which was used in the preparation of Example 42 by intermediate 110. $^1$H NMR (500 MHz, DMSO-$d_6$) δ=8.36 (br d, J=7.6 Hz, 1H), 8.27 (br d, J=3.1 Hz, 1H), 8.17 (dd, J=1.7, 7.5 Hz, 1H), 7.69 (br s, 1H), 7.64-7.55 (m, 2H), 7.11 (dd, J=4.9, 7.3 Hz, 1H), 6.87 (s, 1H), 6.86-6.80 (m, 1H), 5.23 (quin, J=7.1 Hz, 1H), 4.39-4.29 (m, 1H), 3.90 (s, 3H), 3.77 (s, 3H), 2.89-2.83 (m, 2H), 2.81-2.75 (m, 2H), 2.67 (m, 1H), 2.50-2.43 (m, 2H), 2.40-2.33 (m, 1H), 2.30-2.14 (m, 4H). MS (ESI) m/z: 488.0 (M+H)$^+$. Analytical HPLC: RT=1.63 min (Method A); 1.52 min (Method B).

The following examples in Table 15 were prepared using a similar procedure to that which was used in the preparation of Example 42. Example 42c was coupled with a carboxylic acid. Various bases could be used other than the one described in Example 42, such as TEA, DBU, or DABCO. Various coupling reagents could be used other than the one described in Example 42, such as EDCI, BOP, or T3P.

TABLE 15

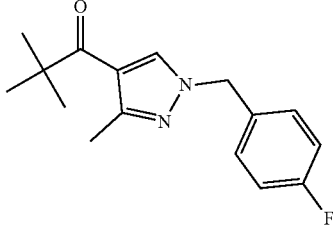 [SMILES: Cc1nn(Cc2ccc(F)cc2)cc1C(=O)C(C)(C)C]

| Example | R | Name | LCMS (M + H)+ | HPLC Method, RT (min.) | 1H NMR |
|---|---|---|---|---|---|
| 382 | 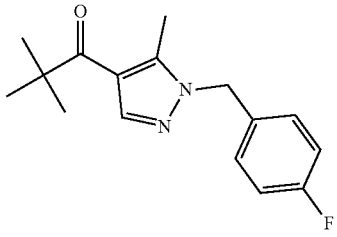 | N-[(aR) 2-[(6-{1-[(4-fluorophenyl)methyl]-3-methyl-1H-pyrazole-4-amido}spiro[3.3]heptan-2-yl)oxy]pyridine-3-carboxamide 1 trifluoroacetic acid salt | 464.1 | C: 6.77 D: 8.16 | 1H NMR (400 MHz, CDCl3) δ 8.51 (dd, J = 7.6, 2.1 Hz, 1H), 8.32 (dd, J = 4.8, 2.0 Hz, 1H), 8.06 (br s, 1H), 7.71 (s, 1H), 7.28-7.18 (m, 2H), 7.13-7.02 (m, 3H), 5.85 (br d, J = 6.2 Hz, 1H), 5.37 (quin, J = 7.2 Hz, 1H), 5.23 (s, 2H), 4.56-4.42 (m, 1H), 2.80 (dt, J = 11.6, 6.0 Hz, 1H), 2.70-2.56 (m, 2H), 2.55-2.45 (m, 4H), 2.33-2.19 (m, 2H), 2.13-2.00 (m, 2H). |
| 383 | 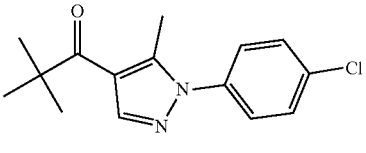 | N-[(aR) 2-[(6-{1-[(4-fluorophenyl)methyl]-5-methyl-1H-pyrazole-4-amido}spiro[3.3]heptan-2-yl)oxy]pyridine-3-carboxamide 1 trifluoroacetic acid salt | 464.2 | C: 6.98 D: 8.38 | 1H NMR (400 MHz, CDCl3) δ 8.42 (dd, J = 7.6, 2.1 Hz, 1H), 8.22 (dd, J = 4.8, 2.0 Hz, 1H), 7.95 (br s, 1H), 7.62 (s, 1H), 7.06-6.91 (m, 5H), 6.87 (br s, 1H), 5.83 (br d, J = 7.3 Hz, 1H), 5.28 (quin, J = 7.2 Hz, 1H), 5.20 (s, 2H), 4.42 (dq, J = 15.8, 8.0 Hz, 1H), 2.71 (dt, J = 11.6, 6.0 Hz, 1H), 2.61-2.49 (m, 2H), 2.48-2.39 (m, 4H), 2.24-2.10 (m, 2H), 2.01 (dd, J = 10.8, 9.2 Hz, 2H). |
| 384 | 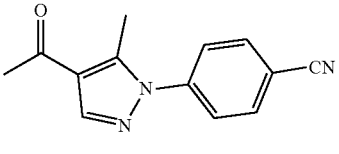 | N-[(aR) 2-({6-[1-(4-chlorophenyl)-5-methyl-1H-pyrazole-4-amido]spiro[3.3]heptan-2-yl}oxy)pyridine-3-carboxamid 1 trifluoroacetic acid salt | 466.1 | C: 5.03 D: 6.90 | 1H NMR (500 MHz, CDCl3) δ 8.49 (dd, J = 7.7, 2.2 Hz, 1H), 8.31 (dd, J = 5.0, 1.9 Hz, 1H), 8.10 (br. s., 1H), 7.84 (s, 1H), 7.54-7.46 (m, 2H), 7.40-7.33 (m, 2H), 7.33-7.28 (br. s, 1H), 7.11-7.04 (m, 1H), 6.04 (d, J = 6.9 Hz, 1H), 5.37 (quin, J = 7.2 Hz, 1H), 4.53 (sxt, J = 7.9 Hz, 1H), 2.81 (dt, J = 11.7, 6.0 Hz, 1H), 2.71-2.59 (m, 2H), 2.59-2.50 (m, 4H), 2.33-2.21 (m, 2H), 2.17-2.07 (m, 2H). |
| 385 | 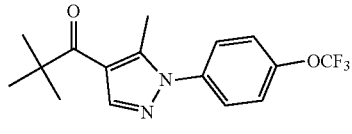 | N-[(aR) 2-({6-{1-(4-cyanophenyl)-5-methyl-1H-pyrazole-4-amido]spiro[3.3]heptan-2-yl}oxy)pyridine-3-carboxamide1 trifluoroacetic acid salt | 457.2 | C: 8.29 D: 6.64 | 1H NMR (400 MHz, CDCl3) δ 8.51 (dd, J = 7.6, 2.1 Hz, 1H), 8.32 (dd, J = 4.8, 2.0 Hz, 1H), 8.07 (br s, 1H), 7.91-7.81 (m, 3H), 7.66-7.59 (m, 2H), 7.10 (dd, J = 7.7, 4.8 Hz, 2H), 6.09 (br d, J = 7.3 Hz, 1H), 5.39 (quin, J = 7.2 Hz, 1H), 4.55 (sxt, J = 8.0 Hz, 1H), 2.83 (dt, J = 11.8, 6.0 Hz, 1H), 2.74-2.52 (m, 6H), 2.29 (ddd, J = 19.4, 11.9, 7.4 Hz, 2H), 2.15 (dd, J = 10.9, 9.4 Hz, 2H). |
| 386 | | N-[(aR) 2-[(6-{5-methyl-1-[4-(trifluoro-methoxy)phenyl]-1H-pyrazole-4-amido}spiro[3.3]heptan-2-yl)oxy]pyridine-3-carboxamide 1 trifluoroacetic acid salt | 516.4 | A: 1.75 B: 1.69 | 1H NMR (500 MHz, DMSO-d6) δ 8.35 (br d, J = 7.3 Hz, 1H), 8.24 (br d, J = 3.1 Hz, 1H), 8.15 (br d, J = 6.4 Hz, 1H), 8.06 (s, 1H), 7.73 (br s, 1H), 7.62-7.55 (m, 3H), 7.51 (br d, J = 8.2 Hz, 2H), 7.11 (dd, J = 7.2, 5.0 Hz, 1H), 5.18 (quin, J = 6.9 Hz, 1H), 4.32-4.22 (m, 1H), 2.67-2.59 (m, |

TABLE 15-continued

| | | | | | |
|---|---|---|---|---|---|
| | | | | | 1H), 2.48-2.38 (m, 5H), 2.35-2.26 (m, 1H), 2.25-2.07 (m, 4H). |
| 387 | | N-[(aR) 2-({6-[1-(4-methanesulfonylphenyl)-5-methyl-1H-pyrazole-4-amido]spiro[3.3]heptan-2-yl}oxy)pyridine-3-carboxamide 1 trifluoroacetic acid salt | 510.4 | A: 1.22<br>B: 1.11 | ¹H NMR (500 MHz, DMSO-d₆) δ 8.30-8.22 (m, 2H), 8.21-8.13 (m, 2H), 8.08 (br d, J = 8.5 Hz, 2H), 7.83 (br d, J = 8.5 Hz, 2H), 7.69 (br s, 1H), 7.60 (br s, 1H), 7.10 (dd, J = 7.3, 4.9 Hz, 1H), 5.23 (quin, J = 7.1 Hz, 1H), 4.33 (sxt, J = 8.1 Hz, 1H), 2.65 (dt, J = 10.9, 5.7 Hz, 1H), 2.58 (s, 3H), 2.48-2.41 (m, 2H), 2.37-2.30 (m, 1H), 2.29-2.11 (m, 4H). |
| 388 | | N-[(aR) 2-({6-[1-(4-cyano-2-fluorophenyl)-5-methyl-1H-pyrazole-4-amido]spiro[3.3]heptan-2-yl}oxy)pyridine-3-carboxamide 1 trifluoroacetic acid salt | 475.1 | A: 1.41<br>B: 1.38 | ¹H NMR (500 MHz, DMSO-d₆) δ 8.33-8.24 (m, 2H), 8.22-8.13 (m, 3H), 7.91 (br d, J = 8.2 Hz, 1H), 7.79 (t, J = 7.9 Hz, 1H), 7.71-7.58 (m, 2H), 7.11 (dd, J = 7.2, 5.0 Hz, 1H), 5.22 (quin, J = 7.1 Hz, 1H), 4.37-4.28 (m, 1H), 2.66 (dt, J = 11.1, 5.7 Hz, 1H), 2.48-2.40 (m, 2H), 2.37 (s, 3H), 2.35-2.29 (m, 1H), 2.28-2.10 (m, 4H). |
| 389 | | N-[(aR) 2-({6-(1-phenyl-1H-1,2,3-triazole)-4-carboxamido]spiro[3.3]heptan-2-yl}oxy)nicotinamide | 418.9 | A: 1.45<br>B: 1.45 | ¹H NMR (500 MHz, DMSO-d₆) δ 9.20 (s, 1H), 8.83 (br d, J = 1.6 Hz, 1H), 8.26 (br d, J = 3.1 Hz, 1H), 8.16 (br d, J = 7.3 Hz, 1H), 7.94 (br d, J = 7.9 Hz, 2H), 7.68 (br s, 1H), 7.63-7.58 (m, 3H), 7.58-7.48 (m, 1H), 7.10 (dd, J = 7.3, 4.9 Hz, 1H), 5.22 (quin, J = 7.1 Hz, 1H), 4.39 (sxt, J = 8.2 Hz, 1H), 2.66 (dt, J = 11.2, 5.8 Hz, 1H), 2.47-2.39 (m, 2H), 2.36-2.16 (m, 5H). |
| 390 | | N-[(aR) 2-({6-(2-phenyl-1H-imidazole)-4-carboxamido]spiro[3.3]heptan-2-yl}oxy)nicotinamide | 417.9 | A: 1.35<br>B: 0.98 | ¹H NMR (500 MHz, DMSO-d₆) δ 8.42 (br s, 1H), 8.28-8.23 (m, 1H), 8.18-8.12 (m, 1H), 7.99 (br d, J = 6.3 Hz, 2H), 7.83 (s, 1H), 7.66 (br d, J = 13.5 Hz, 2H), 7.56-7.42 (m, 3H), 7.13-7.08 (m, 1H), 5.20 (quin, J = 7.2 Hz, 1H), 4.40-4.28 (m, 1H), 2.69-2.61 (m, 1H), 2.49-2.39 (m, 2H), 2.37-2.29 (m, 1H), 2.27-2.12 (m, 4H). |
| 391 | | N-[(aR) 2-({6-(1-(4-cyano-3-fluorophenyl)-5-methyl-1H-pyrazole-4-carboxamido]spiro[3.3]heptan-2-yl}oxy)nicotinamide | 475.2 | A: 1.47<br>B: 1.46 | ¹H NMR (500 MHz, DMSO-d₆) δ 8.31 (br d, J = 7.3 Hz, 1H), 8.28-8.23 (m, 1H), 8.20-8.18 (m, 1H), 8.17-8.13 (m, 1H), 8.08 (t, J = 7.8 Hz, 1H), 7.80 (br d, J = 10.4 Hz, 1H), 7.71-7.56 (m, 3H), 7.10 (dd, J = 7.3, 4.9 Hz, 1H), 5.21 (quin, J = 7.0 Hz, 1H), 4.36-4.27 (m, 1H), 2.68-2.62 (m, 1H), 2.59 (s, 3H), 2.48-2.39 (m, 2H), 2.37-2.29 (m, 1H), 2.27-2.10 (m, 3H). |
| 392 | | N-[(aR) 2-({6-(2,5-dimethyl-1-phenyl-1H-imidazole-4-carboxamido)spiro[3.3]heptan-2-yl}oxy)nicotinamide | 446.2 | C: 7.35<br>D: 7.33 | ¹H NMR (500 MHz, CDCl₃) δ 8.55 (br d, J = 6.9 Hz, 1H), 8.50 (dd, J = 7.6, 2.1 Hz, 1H), 8.34 (dd, J = 4.8, 2.1 Hz, 1H), 8.21 (br s, 1H), 7.72-7.67 (m, 3H), 7.61-7.53 (m, 1H), 7.31-7.26 (m, 2H), 7.09 (dd, J = 7.7, 5.0 Hz, 1H), 5.37 (quin, J = 7.2 Hz, 1H), 4.49 (sxt, J = 7.8 Hz, 1H), 2.83-2.76 (m, 1H), 2.70-2.58 (m, 2H), 2.54 (s, 3H), 2.53-2.47 (m, 1H), 2.41 (s, 3H), 2.30-2.24 (m, 4H). |
| 393 | | N-[(aR) 2-((6-(1-(3-chloro-2-fluorophenyl)-1H-pyrazole-4-carboxamido)spiro[3.3]heptan-2-yl)oxy)nicotinamide | 470.1 | A: 1.60<br>B: 1.59 | ¹H NMR (500 MHz, DMSO-d₆) δ 8.71 (d, J = 1.8 Hz, 1H), 8.43 (br d, J = 7.3 Hz, 1H), 8.29-8.25 (m, 1H), 8.21-8.12 (m, 2H), 7.82 (br t, J = 7.2 Hz, 1H), 7.72-7.63 (m, 2H), 7.60 (br s, 1H), 7.41 (t, J = 8.1 Hz, 1H), 7.11 (dd, J = 7.3, 4.9 Hz, 1H), 5.24 (quin, J = 7.2 Hz, 1H), 4.39-4.26 (m, 1H), 2.71-2.60 (m, 1H), 2.49-2.43 (m, 2H), 2.40-2.32 (m, 1H), 2.31-2.19 (m, 2H), 2.18-2.10 (m, 2H). |

TABLE 15-continued

| 394 | [structure] | N-[(aR) 2-((6-(1-(3-chlorophenyl)-1H-pyrazole-4-carboxamido)spiro[3.3]heptan-2-yl)oxy)nicotinamide | 452.0 | A: 1.70 B: 1.70 | $^1$H NMR (500 MHz, DMSO-$d_6$) δ 8.98 (s, 1H), 8.35 (br d, J = 7.6 Hz, 1H), 8.31-8.24 (m, 1H), 8.20-8.12 (m, 2H), 7.96 (s, 1H), 7.85 (br d, J = 8.2 Hz, 1H), 7.70 (br s, 1H), 7.60 (br s, 1H), 7.56 (t, J = 8.1 Hz, 1H), 7.43 (br d, J = 7.6 Hz, 1H), 7.11 (dd, J = 7.3, 4.9 Hz, 1H), 5.24 (quin, J = 7.1 Hz, 1H), 4.38-4.29 (m, 1H), 2.71-2.60 (m, 1H), 2.50-2.44 (m, 2H), 2.40-2.31 (m, 1H), 2.31-2.19 (m, 2H), 2.19-2.09 (m, 2H). |
|---|---|---|---|---|---|
| 395 | [structure] | N-[(aR) 2-((6-(1-(3-methoxyphenyl)-1H-pyrazole-4-carboxamido)spiro[3.3]heptan-2-yl)oxy)nicotinamide | 448.1 | A: 1.46 B: 1.46 | $^1$H NMR (500 MHz, DMSO-$d_6$) δ 8.91 (s, 1H), 8.39-8.24 (m, 2H), 8.17 (dd, J = 7.3, 1.5 Hz, 1H), 8.13 (s, 1H), 7.70 (br s, 1H), 7.60 (br s, 1H), 7.44-7.38 (m, 3H), 7.11 (dd, J = 7.3, 4.9 Hz, 1H), 6.96-6.90 (m, 1H), 5.24 (quin, J = 7.0 Hz, 1H), 4.38-4.31 (m, 1H), 3.84 (s, 3H), 2.67 (dt, J = 11.3, 5.6 Hz, 1H), 2.49-2.43 (m, 2H), 2.39-2.32 (m, 1H), 2.31-2.19 (m, 2H), 2.18-2.09 (m, 2H). |
| 396 | [structure] | N-[(aR) 2-((6-(1-methyl-5-phenyl-1H-pyrazole-3-carboxamido)spiro[3.3]heptan-2-yl)oxy)nicotinamide | 432.0 | A: 1.55 B: 1.53 | $^1$H NMR (500 MHz, DMSO-$d_6$) δ 8.34-8.25 (m, 2H), 8.20-8.12 (m, 1H), 7.74-7.41 (m, 7H), 7.11 (dd, J = 7.5, 5.0 Hz, 1H), 6.76 (s, 1H), 5.25-5.16 (m, 1H), 4.40-4.27 (m, 1H), 3.90 (s, 3H), 2.72-2.60 (m, 1H), 2.49-2.44 (m, 1H), 2.44-2.37 (m, 1H), 2.33-2.10 (m, 5H). |
| 397 | [structure] | N-[(aR) 2-((6-(1-(2-chlorophenyl)-1H-pyrazole-4-carboxamido)spiro[3.3]heptan-2-yl)oxy)nicotinamide | 451.9 | A: 1.55 B: 1.41 | $^1$H NMR (500 MHz, DMSO-$d_6$) δ 8.54 (s, 1H), 8.37 (br d, J = 7.6 Hz, 1H), 8.30-8.23 (m, 1H), 8.17 (dd, J = 7.5, 1.7 Hz, 1H), 8.13 (s, 1H), 7.75-7.66 (m, 2H), 7.65-7.57 (m, 2H), 7.56-7.49 (m, 2H), 7.11 (dd, J = 7.3, 4.9 Hz, 1H), 5.23 (quin, J = 7.1 Hz, 1H), 4.38-4.28 (m, 1H), 2.67 (dt, J = 11.1, 5.7 Hz, 1H), 2.49-2.42 (m, 2H), 2.39-2.30 (m, 1H), 2.30-2.19 (m, 2H), 2.18-2.08 (m, 2H). |
| 398 | [structure] | N-[(aR) 2-((6-(1-(2-methoxyphenyl)-1H-pyrazole-4-carboxamido)spiro[3.3]heptan-2-yl)oxy)nicotinamide | 448.0 | A: 1.39 B: 1.38 | $^1$H NMR (500 MHz, DMSO-$d_6$) δ 8.56 (s, 1H), 8.30-8.15 (m, 3H), 8.06 (s, 1H), 7.66-7.60 (m, 1H), 7.55 (br s, 2H), 7.44-7.36 (m, 1H), 7.27 (d, J = 8.2 Hz, 1H), 7.13-7.03 (m, 2H), 5.26 (quin, J = 7.0 Hz, 1H), 4.34 (sxt, J = 8.0 Hz, 1H), 3.90 (s, 3H), 2.72-2.63 (m, 1H), 2.52-2.48 (m, 2H), 2.40-2.33 (m, 1H), 2.30-2.12 (m, 4H). |
| 399 | [structure] | N-[(aR) 2-((6-(1-(3-cyanophenyl)-5-methyl-1H-pyrazole-4-carboxamido)spiro[3.3]heptan-2-yl)oxy)nicotinamide | 457.1 | A: 1.41 B: 1.36 | $^1$H NMR (500 MHz, DMSO-$d_6$) δ = 8.29-8.23 (m, 2H), 8.20-8.14 (m, 2H), 8.08 (s, 1H), 7.98-7.93 (m, 1H), 7.90 (br d, J = 8.2 Hz, 1H), 7.77 (br t, J = 7.9 Hz, 1H), 7.70 (br s, 1H), 7.60 (br s, 1H), 7.11 (dd, J = 4.9, 7.6 Hz, 1H), 5.24 (quin, J = 7.2 Hz, 1H), 4.38-4.30 (m, 1H), 2.66 (br dd, J = 5.8, 10.7 Hz, 1H), 2.55 (s, 3H), 2.47-2.41 (m, 2H), 2.38-2.31 (m, 1H), 2.29-2.12 (m, 4H) |
| 400 | [structure] | N-[(aR) 2-((6-(1-(6-methoxypyridin-3-yl)-5-methyl-1H-pyrazole-4-carboxamido)spiro[3.3]heptan-2-yl)oxy)nicotinamide | 457.1 | A: 1.46 B: 1.45 | $^1$H NMR (500 MHz, DMSO-$d_6$) δ = 8.33 (d, J = 2.4 Hz, 1H), 8.28 (dd, J = 1.8, 4.9 Hz, 1H), 8.22-8.15 (m, 2H), 8.13 (s, 1H), 7.87 (dd, J = 2.4, 8.9 Hz, 1H), 7.72-7.67 (m, 1H), 7.63-7.57 (m, 1H), 7.11 (dd, J = 4.9, 7.3 Hz, 1H), 7.00 (d, J = 8.5 Hz, 1H), 5.28-5.20 (m, 1H), 4.38-4.30 (m, 1H), 3.93 (s, 3H), 2.71-2.63 (m, 1H), 2.46 (s, 3H), 2.40-2.43 (m, 1H), 2.38-2.11 (m, 6H) |

EXAMPLE 401

Preparation of N-((aR)-6-((3-carbamoylpyridin-2-yl)oxy)spiro[3.3]heptan-2-yl)-1-(2-cyanopropan-2-yl)-6-fluoro-1H-indazole-3-carboxamide, TFA

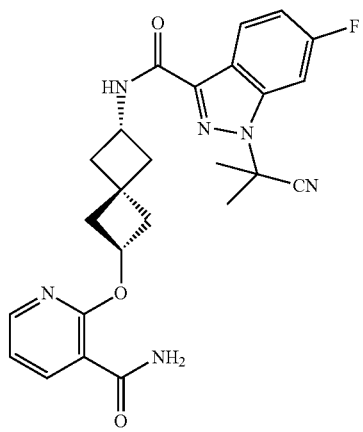

Example 42C (15 mg, 0.061 mmol) and 1-(2-cyanopropan-2-yl)-6-fluoro-1H-indazole-3-carboxylic acid (15.0 mg, 0.061 mmol), prepared in a similar fashion as with Intermediate 113, were dissolved in anhydrous DMF (1.0 mL). To this mixture was then added DIEA (0.053 mL, 0.303 mmol), followed by BOP (29.5 mg, 0.067 mmol). The reaction mixture was stirred at rt for 1 h, quenched with MeOH (0.1 mL), diluted with DMF (2 mL total volume), filtered, and purified by reverse phase HPLC to afford Example 401 (12 mg, 34%). MS(ESI) m/z: 477.2 (M+H)$^+$. $^1$H NMR (400 MHz, DMSO-d$_6$) δ 8.58 (d, J=6.1 Hz, 1H), 8.30-8.21 (m, 2H), 8.16 (dd, J=7.5, 1.7 Hz, 1H), 7.79 (d, J=9.5 Hz; 1H), 7.73-7.53 (m, 2H), 7.32-7.24 (m, 1H), 7.10 (dd, J=7.3, 4.9 Hz, 1H), 5.23 (quin, J=7.1 Hz, 1H), 4.43 (sxt, J=8.2 Hz, 1H), 2.73-2.63 (m, 1H), 2.48-2.40 (m, 2H), 2.37-2.19 (m 5H), 2.15 (s, 6H).

EXAMPLE 402

Preparation of 1-(1-amino-2-methyl-1-oxopropan-2-yl)-N-((aR)-6-((3-carbamoylpyridin-2-yl)oxy)spiro[33]heptan-2-yl)-6-fluoro-1H-indazole-3-carboxamide, TFA

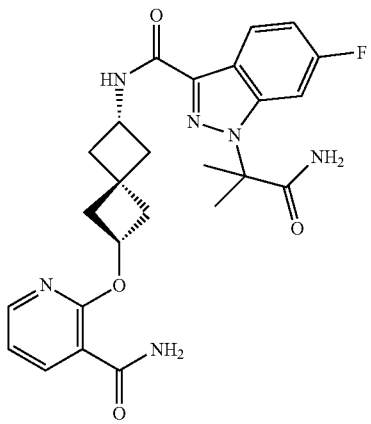

Example 42C (15 mg, 0.061 mmol) and 1-(1-amino-2-methyl-1-oxopropan-2-yl)-6-fluoro-1H-indazole-3-carboxylic acid (16.09 mg, 0.061 mmol), prepared in the same way as Intermediate 112D, were dissolved in anhydrous DMF (1.0 mL). To this mixture was then added DIEA (0.053 mL, 0.303 mmol), followed by BOP (29.5 mg, 0.067 mmol). The reaction mixture was stirred at rt for 1 h, quenched with MeOH (0.1 mL), diluted with DMF (2 mL total volume), filtered, and purified by reverse phase HPLC to afford Example 402 (18 mg, 48%). MS(ESI) m/z: 495.0 (M+H)$^+$. $^1$H NMR (400 MHz, DMSO-d$_6$) δ 8.49 (d, J=7.2 Hz, 1H), 8.26 (d, J=4.6 Hz, 1H), 8.21-8.13 (m, 2H), 7.73-7.60 (m, 2H), 7.44 (d, J=14.1 Hz, 2H), 7.21-7.06 (m, 3H), 5.26-5.17 (m, 1H), 4.50-4.38 (m, 1H), 2.74-2.62 (m, 1H), 2.48-2.40 (m, 1H), 2.36-2.15 (m, 4H), 1.92 (br. s., 2H), 1.80 (s, 6H).

EXAMPLE 403

Preparation of 6-bromo-N-((aR)-6-((3-carbamoylpyridin-2-yl)oxy)spiro[3.3]heptan-2-yl)-1-(2-cyanopropan-2-yl)-1H-indazole-3-carboxamide, TFA

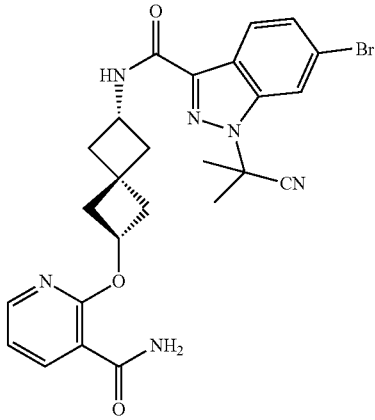

Example 42C (15 mg, 0.061 mmol) and Intermediate 113 (18.76 mg, 0.061 mmol) were dissolved in anhydrous DMF (1.0 mL). To this mixture was then added DIEA (0.053 mL, 0.303 mmol), followed by BOP (29.5 mg, 0.067 mmol). The reaction mixture was stirred at rt for 1 h, quenched with MeOH (0.1 mL), diluted with DMF (2 mL total volume), filtered, and purified by reverse phase HPLC to afford Example 403 (2.8 mg, 7%). MS(ESI) m/z: 537.2 (M+H)$^+$. $^1$H NMR (400 MHz, DMSO-d$_6$) δ 8.69 (br. s., 1H), 8.25 (d, J=4.7 Hz, 1H), 8.19-8.11 (m, 3H), 7.66 (d, J=17.1 Hz, 2H), 7.53 (d, J=8.8 Hz, 1H), 7.10 (dd, J=7.4, 4.9 Hz, 1H), 5.21 (t, J=6.9 Hz, 1H), 4.48-4.35 (m, 1H), 2.72-2.61 (m, 1H), 2.54 (s, 1H), 2.48-2.39 (m, 2H), 2.38-2.15 (m, 4H), 2.13 (s, 6H).

EXAMPLE 404

Preparation of N-((aR)-6-((3-carbamoylpyridin-2-yl)oxy)spiro[3.3]heptan-2-yl)-1-((3,3-difluoro-1-hydroxycyclobutyl)methyl)-6-(1-methyl-1H-pyrazol-4-yl)-1H-indazole-3-carboxamide, TFA

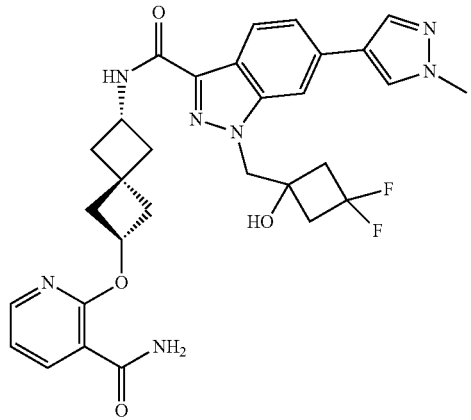

EXAMPLE 404A

Preparation of ethyl 6-bromo-1-((3,3-difluoro-1-hydroxycyclobutyl)methyl)-1H-indazole-3-carboxylate To a microwave vial was added ethyl 6-bromo-1H-indazole-3-carboxylate (100 mg, 0.372 mmol), 5,5-difluoro-1-oxaspiro[2.3]hexane (44.6 mg, 0.372 mmol), $K_2CO_3$ (205 mg, 1.486 mmol) followed by $CH_3CN$ (3 mL) and $H_2O$ (0.2 mL). The reaction mixture was stirred under microwave irradiation at 120° C. for 30 min. The reaction mixture was then concentrated and purified using flash column chromatography to afford Example 404A (13 mg, 8%). MS(ESI) m/z: 390.9 (M+H. Bromine isotope peak).

EXAMPLE 404B

Preparation of 6-bromo-1-((3,3-difluoro-1-hydroxycyclobutyl)methyl)-H-indazole-3-carboxylic acid, HCl To a solution of Example 404A (13 mg, 0.033 mmol) in THF (1 mL) was added LiOH (0.017 mL, 0.033 mmol) and stirred at rt for o.n. The reaction mixture was then acidified with 1N HCl, extracted with EtOAc (10 mL) to afford Example 404B (13 mg, 93%). MS(ESI) m/z: 362.9 (M+H, Bromine isotope peak).

EXAMPLE 404C

Preparation of 6-bromo-N-((aR)-6-((3-carbamoylpyridin-2-yl)oxy)spiro[3.3]heptan-2-yl)-1-((3,3-difluoro-1-hydroxycyclobutyl)methyl)-1H-indazole-3-carboxamide Example 42C (10 mg, 0.040 mmol) and Example 404B (14.6 mg, 0.040 mmol) were dissolved in anhydrous DMF (1.0 mL), then DIEA (0.035 mL, 0.202 mmol) was added, followed by BOP (19.7 mg, 0.044 mmol). The reaction mixture was stirred at rt for 1 h. The reaction mixture was then quenched with MeOH (1 mL), concentrated and purified using flash column chromatography to afford Example 404C (25 mg, 94%). MS(ESI) m/z: 592.0 (M+H, Bromine isotope peak).

EXAMPLE 404

To a degassed solution of Example 404C (25 mg, 0.042 mmol), I-methyl-4-(4,4,5,5-tetramethyl-1,3,2-dioxaborolan-2-yl)-1H-pyrazole (8.8 mg, 0.042 mmol), Phosphoric acid, potassium salt (3 M aq.) (0.071 mL, 0.212 mmol) in DMF (1 mL) was added 2nd Generation XPhos precatalyst (2 mg, 2.54 μmol) and degassed further. The reaction mixture was then heated at 70° C. for 1 h and then quenched with MeOH (0.2 mL), filtered and purified by reverse phase HPLC to afford Example 404 (5.7 mg, 19%). MS(ESI) m/z: 592.1 (M+H)$^+$. $^1$H NMR (400 MHz, DMSO-$d_6$) δ 8.45 (d, J=7.9 Hz, 1H), 8.27 (d, J=2.7 Hz, 1H), 8.21-8.13 (m, 2H), 8.06 (d, J=8.5 Hz, 1H), 7.96-7.86 (m, 2H), 7.72-7.58 (m, 2H), 7.46 (d, J=8.5 Hz, 1H), 7.10 (dd, J=7.3, 4.9 Hz, 1H), 5.86 (s, 1H), 5.23 (t, J=7.0 Hz, 1H), 4.58 (s, 2H), 4.49-4.39 (m, 1H), 3.56-3.40 (m, 1H), 3.14 (d, J=7.3 Hz, 2H), 2.72-2.56 (m, 4H), 2.44 (br. s., 1H), 2.35-2.17 (m, 6H).

EXAMPLE 405

Preparation of N-((aR)-6-((3-carbamoylpyridin-2-yl)oxy)spiro[3.3]heptan-2-yl)-1-((1-hydroxycyclobutyl)methyl)-6-(1-methyl-1H-pyrazol-4-yl)-1H-indazole-3-carboxamide, TFA

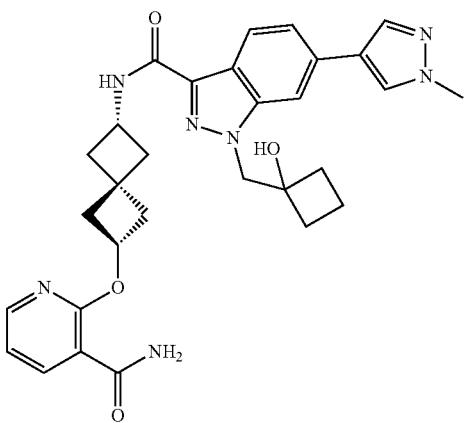

Example 405 is prepared in the same way as Example 404 by replacing 5,5-difluoro-1-oxaspiro[2.3]hexane in step Example 404A with 1-oxaspiro[2,3]hexane to afford Example 405 (12 mg, 24%). MS(ESI) m/z: 556.3 (M+H)$^+$. $^1$H NMR (400 MHz, DMSO-$d_6$) S 8.42 (d, J=7.9 Hz, 1H), 8.27 (d, J=3.1 Hz, 1H), 8.20 (s, 1H), 8.17 (d, J=7.6 Hz, 1H), 8.06 (d, J=8.5 Hz, 1H), 7.93 (d, J=9.5 Hz, 2H), 7.73-7.57 (m, 2H), 7.45 (d, J=8.5 Hz, 1H), 7.10 (dd, J=7.3, 4.9 Hz, 1H), 5.28-5.19 (m, 1H), 4.51 (s, 2H), 4.48-4.40 (m, 1H), 2.71-2.63 (m, 1H), 2.46-2.39 (m, 2H), 2.36-2.17 (m, 7H), 2.01-1.89 (m, 2H), 1.75-1.52 (m, 2H), 1.22 (s, 1H).

EXAMPLE 406

Preparation of N-((aR)-6-((3-carbamoylpyridin-2-yl)oxy)spiro[3.3]heptan-2-yl)-1-(2-cyanopropan-2-yl)-6-(1-methyl-H-pyrazol-4-yl)-1H-indazole-3-carboxamide, TFA

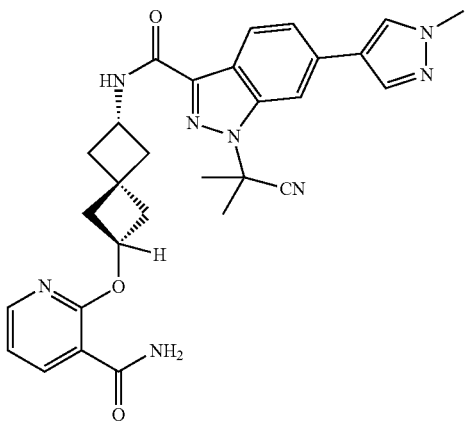

Example 406 is prepared in the same way as Example 404 by replacing Example 404C with Example 403 to afford Example 406 (8.5 mg, 27%). MS(ESI) m/z: 539.5 (M+H)+.
$^1$H NMR (400 MHz, DMSO-d$_6$) δ 8.59 (br. s., 1H), 8.31 (br. s., 1H), 8.25 (d, J=4.6 Hz, 1H), 8.15 (d, J=8.1 Hz, 2H), 8.02 (s, 1H), 7.94 (s, 1H), 7.67 (d, J=13.7 Hz, 2H), 7.59 (d, J=8.4 Hz, 1H), 7.10 (dd, J=7.4, 4.9 Hz, 1H), 5.21 (t, J=6.9 Hz, 1H), 4.47-4.36 (m, 1H), 3.89 (s, 3H), 2.71-2.61 (m, 1H), 2.48-2.39 (m, 2H), 2.37-2.19 (m, 5H), 2.16 (s, 6H).

EXAMPLE 407

Preparation of N-((aR)-6-((3-carbamoylpyridin-2-yl)oxy)spiro[3.3]heptan-2-yl)-1-(2-cyanopropan-2-yl)-6-(1-(difluoromethyl)-1H-pyrazol-4-yl)-1H-indazole-3-carboxamide, TFA

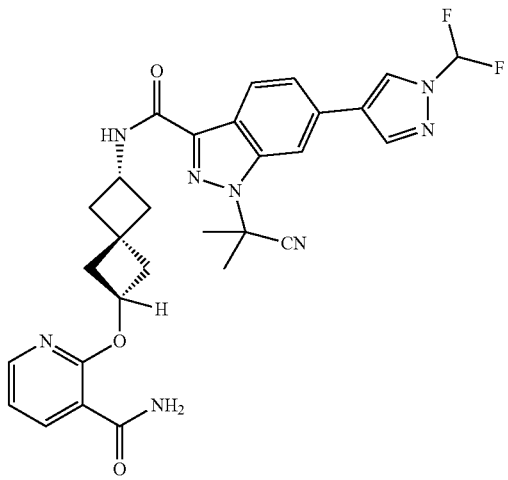

Example 407 is prepared in the same way as Example 404 by replacing Example 404C with Example 403 and 1-methyl-4-(4,4,5,5-tetramethyl-1,3,2-dioxaborolan-2-yl)-1H-pyrazole with 1-(difluoromethyl)-4-(4,4,5,5-tetramethyl-1,3,2-dioxaborolan-2-yl)-1H-pyrazole to afford Example 407 (16 mg, 510/). MS(ESI) m/z: 575.3 (M+H)+.
$^1$H NMR (500 MHz, DMSO-d$_6$) δ 8.94 (s, 1H), 8.57 (d, J=7.9 Hz, 1H), 8.44 (s, 1H), 8.28-8.19 (m, 2H), 8.18-8.10 (m, 2H), 7.97-7.80 (m, 1H), 7.74-7.59 (m, 3H), 7.10 (dd, J=7.3, 4.9 Hz, 1H), 5.22 (quin, J=7.1 Hz, 1H), 4.49-4.34 (m, 1H), 2.71-2.64 (m, 2H), 2.48-2.22 (m, 6H), 2.19 (s, 6H).

EXAMPLE 408

Preparation of 1-(1-amino-2-methyl-1-oxopropan-2-yl)-N-((aR)-6-((3-carbamoylpyridin-2-yl)oxy)spiro[3.3]heptan-2-yl)-6-(1-methyl-1H-pyrazol-4-yl)-1H-indazole-3-carboxamide, TFA

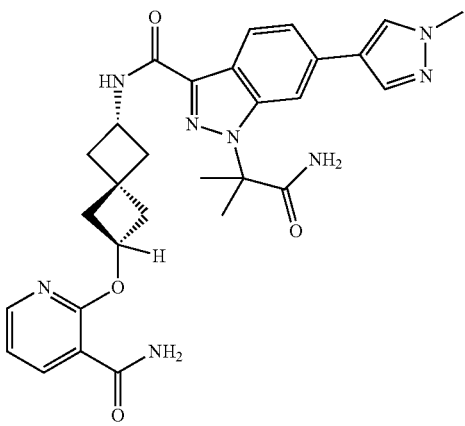

Example 408 is prepared in the same way as Example 404 by replacing Example 404C with Intermediate 112 to afford Example 408 (4.4 mg, 23%). MS(ESI) m/z: 557.2 (M+H).
$^1$H NMR (500 MHz, DMSO-d$_6$) δ 8.41 (br. s., 1H), 8.26 (d, J=4.5 Hz, 1H), 8.20-8.07 (m, 2H), 7.84 (s, 1H), 7.74-7.60 (m, 2H), 7.51-7.34 (m, 4H), 7.10 (dd, J=7.3, 5.0 Hz, 1H). 5.27-5.17 (m, 1H), 4.44 (d, J=7.2 Hz, 1H), 3.87 (s, 3H), 2.67 (d, J=4.8 Hz, 1H), 2.45 (d, J=12.5 Hz, 2H), 2.37-2.14 (m, 4H), 1.91 (br. s., 2H), 1.83 (br. s., 6H).

EXAMPLE 409

Preparation of 1-(1-amino-2-methyl-1-oxopropan-2-yl)-N-((aR)-6-((3-carbamoylpyridin-2-yl)oxy)spiro[3.3]heptan-2-yl)-6-(1-(difluoromethyl)-1H-pyrazol-4-yl)-1H-indazole-3-carboxamide, TFA

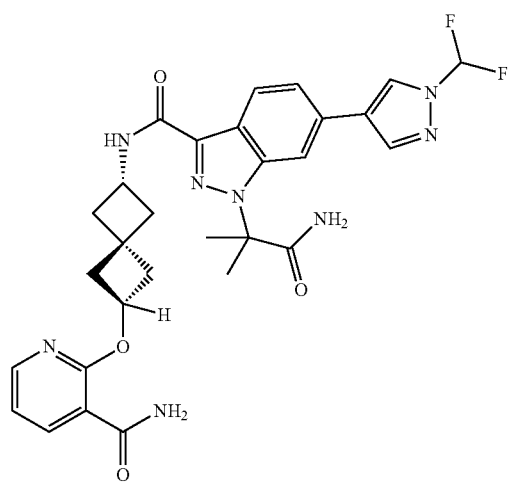

Example 409 is prepared in the same way as Example 404 by replacing Example 404C with Intermediate 112 and 1-methyl-4-(4,4,5,5-tetramethyl-1,3,2-dioxaborolan-2-yl)-1H-pyrazole with 1-(difluoromethyl)-4-(4,4,5,5-tetramethyl-1,3,2-dioxaborolan-2-yl)-1H-pyrazole to afford Example 409 (12 mg, 39%). MS(ESI) m/z: 590.2 (M+H). $^1$H NMR (500 MHz, DMSO-d$_6$) δ 8.75 (s, 1H), 8.41 (d, J=7.9 Hz, 1H), 8.26 (s, 2H), 8.17 (t, J=8.4 Hz, 2H), 7.96-7.55 (m, 6H), 7.37 (d, J=7.3 Hz, 2H), 7.10 (dd, J=7.5, 5.0 Hz, 1H), 5.23 (quin, J=7.1 Hz, 1H), 4.51-4.39 (m, 1H), 2.71-2.64 (m, 1H), 2.48-2.40 (m, 1H), 2.37-2.16 (m, 5H), 1.87 (s, 6H).

EXAMPLE 410

Preparation of 1-(1-amino-2-methyl-1-oxopropan-2-yl)-N-((aR)-6-((3-carbamoylpyridin-2-yl)oxy)spiro[3.3]heptan-2-yl)-6-(3,3,3-trifluoropropoxy)-1H-indazole-3-carboxamide, TFA

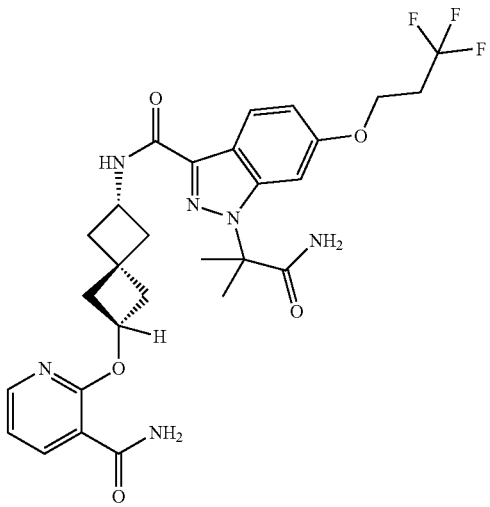

To a degassed solution of Intermediate 112 (25 mg, 0.045 mmol), 3,3,3-trifluoropropan-1-ol (20.5 mg, 0.180 mmol), Cs$_2$CO$_3$ (22.0 mg, 0.068 mmol) in DMF (2 mL) was added ROCKPHOS PD G3 (2.3 mg, 2.70 μmol) and degassed again for 5 mins. The reaction mixture was then heated to 70° C. for 1 h. The reaction mixture was then brought to rt, quenched with MeOH (1 mL), concentrated and purified using reverse phase HPLC to afford Example 410 (3.3 mg, 9%). MS(ESI) m/z: 589.5 (M+H)$^+$. $^1$H NMR (500 MHz, DMSO-d$_6$) δ 8.32 (d, J=8.2 Hz, 1H), 8.27 (dd, J=4.6, 1.8 Hz, 1H), 8.16 (dd, J=7.5, 1.7 Hz, 1H), 8.05 (d, J=8.8 Hz, 1H), 7.71-7.58 (m, 2H), 7.37 (d, J=11.0 Hz, 2H), 7.10 (dd, J=7.3, 4.9 Hz, 1H), 6.93 (dd, J=9.0, 1.7 Hz, 1H), 6.76 (s, 1H), 5.23 (quin, J=7.2 Hz, 1H), 4.51-4.38 (m, 1H), 4.21 (t, J=5.8 Hz, 2H), 2.91-2.77 (m, 2H), 2.74-2.62 (m, 2H), 2.39-2.15 (m, 6H), 1.79 (s, 6H).

EXAMPLE 411

Preparation of N-((aR)-6-((3-carbamoylpyridin-2-yl)oxy)spiro[3.3]heptan-2-yl)-1-(2-cyanopropan-2-yl)-6-(3,3,3-trifluoropropoxy)-1H-indazole-3-carboxamide, TFA

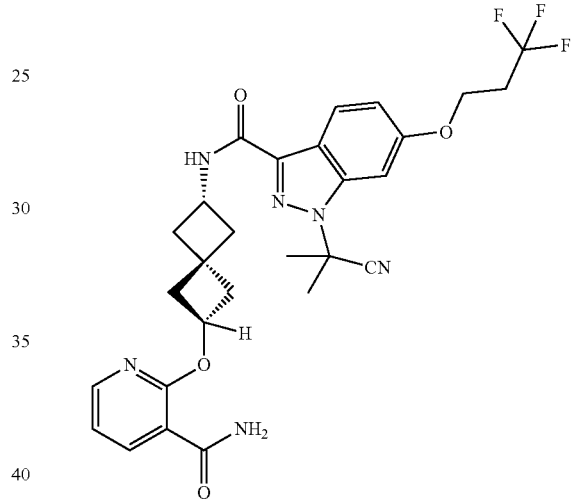

Example 411 is prepared in the same way as Example 410 by replacing Intermediate 112 with Example 403 to afford Example 411 (4.1 mg, 13%). MS(ESI) m/z: 570.9 (M+H). $^1$H NMR (500 MHz, DMSO-d$_6$) δ 8.47 (d, J=8.2 Hz, 1H), 8.30-8.24 (m, 1H), 8.16 (dd, J=7.5, 1.7 Hz, 1H), 8.09 (d, J=8.8 Hz, 1H), 7.72-7.56 (m, 2H), 7.27 (s, 1H), 7.10 (dd, J=7.5, 5.0 Hz, 1H), 7.02 (d, J=8.9 Hz, 1H), 5.23 (quin, J=7.2 Hz, 1H), 4.48-4.34 (m, 3H), 3.89 (s, 1H), 2.96-2.78 (m, 2H), 2.72-2.61 (m, 1H), 2.47-2.39 (m, 1H), 2.37-2.16 (m, 5H), 2.14 (s, 6H).

The following examples in Table 16 were prepared using a similar procedure to that which was used in the preparation of Example 42. Example 42C was coupled with an appropriate carboxylic acid. Various bases could be used other than the one described in Example 42, such as TEA, DBU, or DABCO. Various coupling reagents could be used other than the one described in Example 42, such as EDCI, HATU, or T3P.

TABLE 16

| Example | R | Name | LCMS (M + H)+ | HPLC Method, RT (min.) | 1H NMR |
|---|---|---|---|---|---|
| 412 | (indazole with carboxamide and hydroxymethylpropoxy substituent) | 1-(1-amino-2-methyl-1-oxopropan-2-yl)-N-((aR)-6-((3-carbamoylpyridin-2-yl)oxy)spiro[3.3]heptan-2-yl)-6-(2-hydroxy-2-methyl-propoxy)-1H-indazole-3-carboxamide, TFA | 565.5 | A: 1.357 B: 1.344 | 1H NMR (500 MHz, DMSO-d$_6$) δ 8.40 (br. s., 1H), 8.25 (d, J = 3.1 Hz, 1H), 8.15 (d, J = 7.5 Hz, 1H), 8.00 (d, J = 8.8 Hz, 1H), 7.66 (br. s., 2H), 7.38 (br. s., 2H), 7.31-7.06 (m, 3H), 6.92 (d, J = 8.9 Hz, 1H), 6.69 (s, 1H), 5.20 (t, J = 7.0 Hz, 1H), 4.46-4.34 (m, 1H), 3.15 (s, 1H), 2.73-2.61 (m, 1H), 2.42 (d, J = 11.4 Hz, 1H), 2.35-2.12 (m, 5H), 1.76 (s, 5H), 1.45 (s, 1H), 1.24-1.18 (m, 7H) |
| 413 | (pyrazolo[1,5-a]pyridine with 3,3-difluoro-1-hydroxycyclobutylmethoxy) | N-((aR)-6-((3-carbamoyl-pyridin-2-yl)oxy)spiro[3.3]heptan-2-yl)-6-((3,3-difluoro-1-hydroxycyclobutyl)methoxy)pyrazolo[1,5-a]pyridine-3-carboxamide, TFA | 528.2 | A: 1.354 B: 1.456 | 1H NMR (500 MHz, DMSO-d$_6$) δ 8.47 (s, 1H), 8.43 (s, 1H), 8.30 (d, J = 7.3 Hz, 1H), 8.27-8.23 (m, 1H), 8.16 (dd, J = 7.3, 1.8 Hz, 1H), 8.08 (d, J = 9.8 Hz, 1H), 7.70-7.58 (m, 2H), 7.27 (dd, J = 9.6, 1.7 Hz, 1H), 7.10 (dd, J = 7.5, 5.0 Hz, 1H), 5.22 (t, J = 7.0 Hz, 1H), 4.44-4.30 (m, 1H), 4.02 (s, 2H), 2.93-2.78 (m, 3H), 2.72 (s, 2H), 2.68-2.56 (m, 3H), 2.47-2.39 (m, 1H), 2.38-2.10 (m, 4H) |
| 414 | (pyrazolo[1,5-a]pyridine with 1-hydroxycyclobutylmethoxy) | N-((aR)-6-((3-carbamoyl-pyridin-2-yl)oxy)spiro[3.3]heptan-2-yl)-6-((1-hydroxy-cyclobutyl)methoxy)pyrazolo[1,5-a]pyridine-3-carboxamide, TFA | 492.1 | A: 1.280 B: 1.276 | 1H NMR (500 MHz, DMSO-d$_6$) δ 8.45 (d, J = 14.6 Hz, 2H), 8.26 (d, J = 6.4 Hz, 2H), 8.16 (d, J = 7.3 Hz, 1H), 8.07 (d, J = 9.5 Hz, 1H), 7.68 (br. s., 1H), 7.60 (br. s., 1H), 7.27 (d, J = 9.5 Hz, 1H), 7.10 (dd, J = 7.2, 5.0 Hz, 1H), 5.23 (quin, J = 7.2 Hz, 1H), 4.43-4.33 (m, 1H), 3.98 (s, 2H), 2.65 (dd, J = 11.1, 6.6 Hz, 1H), 2.47-2.41 (m, 1H), 2.38-2.31 (m, 2H), 2.30-2.08 (m, 7H), 2.07-1.96 (m, 2H), 1.73-1.52 (m, 2H) |

The following examples in Table 17 were prepared using a similar procedure as shown in Example 170. Example 42C was coupled with an appropriate ester using trimethylaluminum.

TABLE 17

| Example | R | Name | LCMS (M + H)+ | HPLC Method, RT (min.) | 1H NMR |
|---|---|---|---|---|---|
| 415 | | N-((aR)-6-((3-carbamoyl-pyridin-2-yl)oxy)spiro[3.3]heptan-2-yl)-7-cyclopropyl-6-((3,3-difluoro-1-hydroxy-cyclobutyl)methoxy)pyrazolo[1,5-a]pyridine-3-carboxamide, TFA | 568.2 | A: 1.556 B: 1.555 | 1H NMR (500 MHz, DMSO-d6) δ 8.50 (s, 1H), 8.31-8.23 (m, 2H), 8.16 (dd, J = 7.4, 1.8 Hz, 1H), 8.03 (d, J = 9.6 Hz, 1H), 7.74-7.58 (m, 2H), 7.48 (d, J = 9.8 Hz, 1H), 7.10 (dd, J = 7.4, 4.9 Hz, 1H), 5.91 (s, 1H), 5.22 (quin, J = 7.2 Hz, 1H), 4.37 (sxt, J = 8.1 Hz, 1H), 4.03 (s, 2H), 3.61-3.41 (m, 2H), 2.95-2.81 (m, 2H), 2.71-2.56 (m, 3H), 2.48-2.39 (m, 1H), 2.37-2.10 (m, 5H), 1.49-1.40 (m, 2H), 1.08-1.02 (m, 2H) |
| 416 | | 6-(benzyloxy)-N-((aR)-6-((3-carbamoylpyridin-2-yl)oxy)spiro[3.3]heptan-2-yl)-3-((dimethylamino)methyl)imidazo[1,5-a]pyridine-1-carboxamide, TFA | 555.3 | A: 1.880 B: 1.466 | 1H NMR (500 MHz, DMSO-d6) δ 8.26 (d, J = 3.1 Hz, 1H), 8.16 (d, J = 7.3 Hz, 1H), 8.06 (d, J = 8.5 Hz, 1H), 8.03-7.97 (m, 2H), 7.71-7.57 (m, 2H), 7.50 (d, J = 7.3 Hz, 2H), 7.45-7.32 (m, 3H), 7.13-7.07 (m, 1H), 7.01 (d, J = 11.3 Hz, 1H), 5.27-5.17 (m, 1H), 5.13 (s, 2H), 4.44-4.30 (m, 1H), 3.81 (s, 2H), 3.45 (br. s., 1H), 2.69-2.61 (m, 1H), 2.48-2.34 (m, 2H), 2.33-2.18 (m, 4H), 2.15 (s, 6H) |

The following examples in Table 18 were prepared using a similar procedure as shown in Example 404. Intermediate 115 was coupled with a boronic acid or ester as with Example 404.

TABLE 18

| Example | R | Name | LCMS (M + H)+ | HPLC Method, RT (min.) | ¹H NMR |
|---|---|---|---|---|---|
| 417 | 4-(cyclopropylsulfonyl)phenyl | N-((aR)-6-((3-carbamoylpyridin-2-yl)oxy)spiro[3.3]heptan-2-yl)-2-(4-(cyclopropylsulfonyl)phenyl)thiazole-5-carboxamide, TFA | 539.0 | A: 1.421 B: 1.427 | ¹H NMR (500 MHz, DMSO-d₆) δ 9.02 (d, J = 7.3 Hz, 1H), 8.49 (s, 1H), 8.28-8.19 (m, 3H), 8.15 (d, J = 7.3 Hz, 1H), 8.01 (d, J = 8.2 Hz, 2H), 7.66 (d, J = 6.3 Hz, 2H), 7.10 (dd, J = 7.3, 5.0 Hz, 1H), 5.20 (t, J = 7.0 Hz, 1H), 4.36-4.24 (m, 1H), 4.01 (br. s., 2H), 2.87 (br. s., 1H), 2.65 (dd, J = 11.4, 5.5 Hz, 1H), 2.43-2.12 (m, 5H), 1.14 (br. s., 2H), 1.07 (d, J = 5.4 Hz, 2H) |
| 418 | 4-cyanophenyl | N-((aR)-6-((3-carbamoylpyridin-2-yl)oxy)spiro[3.3]heptan-2-yl)-2-(4-cyanophenyl)thiazole-5-carboxamide, TFA | 460.0 | A: 1.568 B: 1.550 | ¹H NMR (500 MHz, DMSO-d₆) δ 9.00 (d, J = 7.3 Hz, 1H), 8.47 (s, 1H), 8.24 (d, J = 3.4 Hz, 1H), 8.18-8.08 (m, 3H), 7.94 (d, J = 8.2 Hz, 2H), 7.64 (d, J = 17.4 Hz, 2H), 7.09 (dd, J = 7.3, 5.2 Hz, 1H), 5.19 (quin, J = 7.1 Hz, 1H), 4.35-4.24 (m, 1H), 2.69-2.60 (m, 1H), 2.48-2.29 (m, 3H), 2.27-2.11 (m, 4H) |
| 419 | 3-fluoro-4-(methylcarbamoyl)phenyl | N-((aR)-6-((3-carbamoylpyridin-2-yl)oxy)spiro[3.3]heptan-2-yl)-2-(3-fluoro-4-(methylcarbamoyl)phenyl)thiazole-5-carboxamide, TFA | 510.4 | A: 1.304 B: 1.394 | ¹H NMR (500 MHz, DMSO-d₆) δ 8.99 (d, J = 6.7 Hz, 1H), 8.44 (s, 1H), 8.39 (br. s., 1H), 8.23 (br. s., 1H), 8.15 (d, J = 7.3 Hz, 1H), 7.88-7.79 (m, 2H), 7.73 (t, J = 7.6 Hz, 1H), 7.68-7.59 (m, 2H), 7.10 (d, J = 5.5 Hz, 1H), 5.19 (t, J = 6.9 Hz, 1H), 4.29 (d, J = 7.6 Hz, 1H), 3.96-3.64 (m, 2H), 2.78 (d, J = 3.7 Hz, 3H), 2.64 (br. s., 1H), 2.34 (br. s., 1H), 2.26-2.10 (m, 4H) |
| 420 | 3-cyanophenyl | N-((aR)-6-((3-carbamoylpyridin-2-yl)oxy)spiro[3.3]heptan-2-yl)-2-(3-cyanophenyl)thiazole-5-carboxamide, TFA | 460.3 | A: 1.561 B: 1.634 | ¹H NMR (500 MHz, DMSO-d₆) δ 8.94 (d, J = 7.3 Hz, 1H), 8.48 (s, 1H), 8.39 (s, 1H), 8.32-8.23 (m, 2H), 8.16 (d, J = 7.6 Hz, 1H), 7.97 (d, J = 7.6 Hz, 1H), 7.73 (t, J = 7.9 Hz, 1H), 7.69-7.56 (m, 2H), 7.10 (dd, J = 7.3, 5.2 Hz, 1H), 5.22 (quin, J = 7.2 Hz, 1H), 4.37-4.26 (m, 1H), 3.88 (s, 1H), 2.70-2.61 (m, 1H), 2.48-2.42 (m, 1H), 2.36 (t, J = 11.7 Hz, 1H), 2.30-2.13 (m, 4H) |

EXAMPLE 421

Preparation of 3-bromo-N-((aR)-6-((3-carbamoylpyridin-2-yl)oxy)spiro[3.3]heptan-2-yl)imidazo[1,5-a]pyridine-1-carboxamide

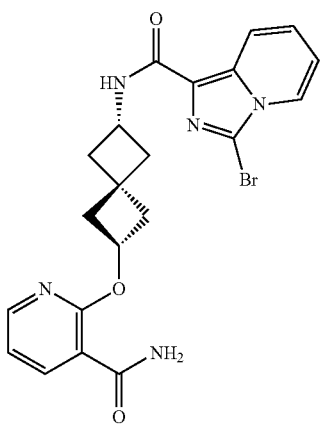

Example 421 (16.5 mg, 57%) was prepared in a analogous manner as Example 15 replacing Intermediate 4 with commercially available 3-bromoimidazo[1,5-a]pyridine-1-carboxylic acid and coupling with Example 42C. MS (ESI) m/z: 470.0 (M+H)+. $^1$H NMR (500 MHz, DMSO-$d_6$) δ 8.40-8.31 (m, 1H), 8.29-8.24 (m, 1H), 8.22 (d, J=7.1 Hz, 1H), 8.15 (s, 1H), 8.13-8.07 (m, 1H), 7.72-7.61 (m, 2H), 7.26-7.17 (m, 1H), 7.14-7.07 (m, 1H), 7.01 (s, 1H), 5.24-5.15 (m, 1H), 4.44-4.32 (m, 1H), 2.68-2.61 (m, 1H), 2.49-2.43 (m, 1H), 2.43-2.35 (m, 1H), 2.25 (d, J=9.1 Hz, 4H), 2.20-2.13 (m, 1H). Analytical HPLC RT=1.840 min (Method A) and 1.661 min (Method B), purity=99%.

EXAMPLE 422

Preparation of 2-(((aR)-6-(3-(4-methylpiperazin-1-yl)-5-(trifluoromethyl)benzamido)spiro[3.3]heptan-2-yl)oxy)nicotinamide

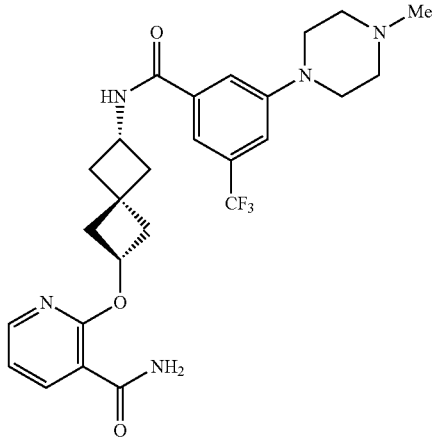

Example 422 (13.8 mg, 44%) was prepared in a analogous manner as Example 15 replacing Intermediate 4 with commercially available 3-(4-methylpiperazin-1-yl)-5-(trifluoromethyl)benzoic acid and coupling with Example 42C. MS (ESI) m/z: 518.3 (M+H)+. $^1$H NMR (500 MHz, DMSO-$d_6$) δ 8.79 (d, J=6.2 Hz, 1H), 8.29-8.23 (m, 1H), 8.16 (dd, J=7.4, 1.7 Hz, 1H), 7.50 (s, 1H), 7.29 (s, 1H), 7.11 (dd, J=7.4, 4.9 Hz, 1H), 5.21 (t, J=7.1 Hz, 1H), 4.34 (d, J=7.9 Hz, 1H), 3.26 (br. s., 4H), 2.65 (d, J=5.4 Hz, 1H), 2.46 (br. s., 5H), 2.33 (d, J=4.7 Hz, 1H), 2.29-2.13 (m, 7H). Analytical HPLC RT=1.832 min (Method A) and 1.241 min (Method B), purity=100%.

EXAMPLE 423

Preparation of 2-(((aR)-6-(3-(tert-butyl)benzamido)spiro[3.3]heptan-2-yl)oxy)nicotinamide

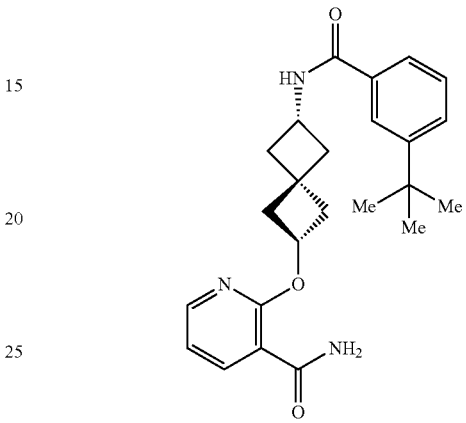

Example 423 (13.3 mg, 54%) was prepared in a analogous manner as Example 15 replacing Intermediate 4 with commercially available 3-(tert-butyl)benzoic acid and coupling with Example 42C. MS (ESI) m/z: 408.3 (M+H)+. $^1$H NMR (500 MHz, DMSO-$d_6$) δ 8.62 (br. s., 1H), 8.26 (dd, J=4.8, 1.9 Hz, 1H), 8.16 (d, J=7.4 Hz, 1H), 7.62 (d, J=7.7 Hz, 1H), 7.54 (d, J=7.8 Hz, 1H), 7.40-7.33 (m, 1H), 7.11 (dd, J=7.3, 5.0 Hz 1H), 5.21 (s, 1H), 4.41-4.29 (m, 1H), 2.69-2.62 (m, 1H), 2.48 (br. s., 2H), 2.37-2.29 (m, 1H), 2.29-2.14 (m, 4H), 1.29 (s, 9H). Analytical HPLC RT=1.813 min (Method A) and 1.789 min (Method B), purity=100%.

EXAMPLE 424

Preparation of 6-bromo-N-((aR)-6-((3-carbamoylpyridin-2-yl)oxy)spiro[3.3]heptan-2-yl)-2-methyl-2H-indazole-4-carboxamide

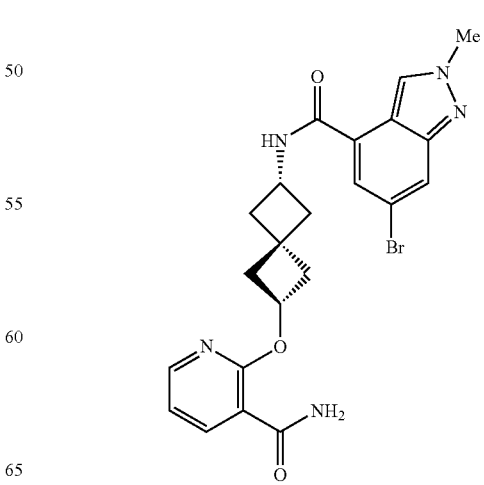

Example 424 (12 mg, 20%) was prepared in a analogous manner as Example 15 replacing Intermediate 4 with Intermediate 117 and coupling with Example 42C. MS (ESI) m/z: 484.0 (M+H)⁺. ¹H NMR (400 MHz, CD₃OD) δ 8.55-8.50 (m, 1H), 8.38-8.34 (m, 1H), 8.33-8.29 (m, 1H), 8.00-7.96 (m, 1H), 7.70 (d, J=1.3 Hz, 1H), 7.16-7.09 (m, 1H), 5.42-5.32 (m, 1H), 4.57-4.46 (m, 1H), 4.26 (s, 3H), 2.87-2.78 (m, 1H), 2.69-2.59 (m, 2H), 2.56-2.46 (m, 1H), 2.40-2.34 (m, 1H), 2.34-2.26 (m, 3H). Analytical HPLC RT=10.40 min (Method C) and 12.40 min (Method D), purity=99%.

EXAMPLE 425

Preparation of 6-bromo-N-((aR)-6-((3-carbamoylpyridin-2-yl)oxy)spiro[3.3]heptan-2-yl)-1-methyl-1H-indazole-4-carboxamide

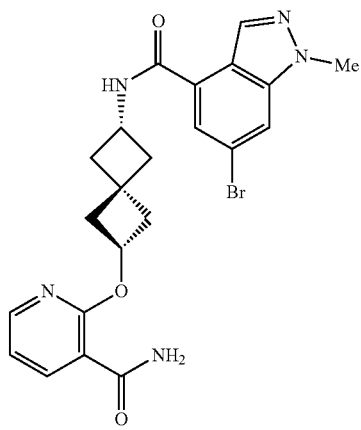

Example 425 (14 mg, 22%) was prepared in a analogous manner as Example 15 replacing Intermediate 4 with Intermediate 117 and coupling with Example 42C. MS (ESI) m/z: 484.0 (M+H)⁺. ¹H NMR (500 MHz, CD₃OD) δ 8.39-8.34 (m, 1H), 8.33-8.29 (m, 2H), 8.05-8.00 (m, 1H), 7.74-7.70 (m, 1H), 7.16-7.09 (m, 1H), 5.43-5.32 (m, 1H), 4.58-4.47 (m, 1H), 4.10 (s, 3H), 2.88-2.79 (m, 1H), 2.69-2.60 (m, 2H), 2.57-2.48 (m, 1H), 2.41-2.34 (m, 1H), 2.34-2.26 (m, 3H). Analytical HPLC RT=10.65 min (Method C) and 12.83 min (Method D), purity=97%.

EXAMPLE 426

Preparation of N-((aR)-6-((3-carbamoylpyridin-2-yl)oxy)spiro[3.3]heptan-2-yl)-2-oxo-6-(trifluoromethyl)-1,4-dihydro-2H-benzo[d][1,3]oxazine-8-carboxamide

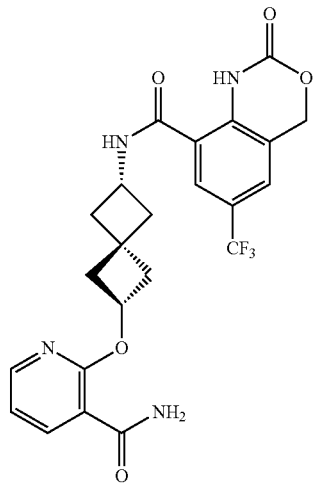

Example 426 (13.8 mg, 46%) was prepared in a analogous manner as Example 15 replacing Intermediate 4 with 2-oxo-6-(trifluoromethyl)-1,4-dihydro-2H-benzo[d][1,3]oxazine-8-carboxylic acid and coupling with Example 42C. MS (ESI) m/z: 491.1 (M+H)⁺. ¹H NMR (500 MHz, DMSO-d₆) δ 10.84 (br. s., 1H), 9.18 (d, J=6.6 Hz, 1H), 8.27 (d, J=3.6 Hz, 1H), 8.22 (br. s., 1H), 8.19-8.14 (m, 1H), 7.82 (br. s., 1H), 7.76-7.69 (m, 1H), 7.63 (br. s., 1H), 7.11 (dd, J=7.4, 4.9 Hz, 1H), 5.43 (s, 2H), 5.22 (s, 1H), 4.45-4.29 (m, 1H), 2.73-2.62 (m, 1H), 2.42-2.33 (m, 1H), 2.32-2.17 (m, 4H). Analytical HPLC RT=1.680 min (Method A) and 1.677 min (Method B), purity=100%.

EXAMPLE 427

Preparation of 2-(((aR)-6-(3-bromo-5-(trifluoromethyl)benzamido)spiro[3.3]heptan-2-yl)oxy)nicotinamide

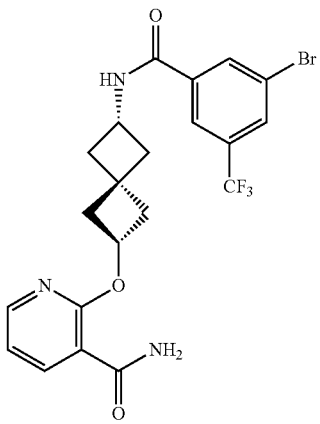

Example 427 (11 mg, 7%) was prepared in a analogous manner as Example 15 replacing Intermediate 4 with commercially available 3-bromo-5-(trifluoromethyl)benzoic acid and coupling with Example 42C. MS (ESI) m/z: 498.1 (M+H)+. 1H NMR (500 MHz, DMSO-d6) δ 8.97 (d, J=6.6 Hz, 1H), 8.33 (s, 1H), 8.27 (d, J=4.8 Hz, 1H), 8.17 (d, J=7.7 Hz, 3H), 7.72 (br. s., 1H), 7.62 (br. s., 1H), 7.11 (dd, J=7.4, 4.9 Hz, 1H), 5.22 (t, J=7.2 Hz, 1H), 4.42-4.30 (m, 1H), 2.66 (dd, J=11.3, 5.8 Hz, 1H), 2.48-2.43 (m, 1H), 2.40-2.32 (m, 1H), 2.30-2.15 (m, 4H). Analytical HPLC RT=1.958 min (Method A) and 1.911 min (Method B), purity=94%.

EXAMPLE 428

Preparation of 2-(((aR)-6-(3-(1-methyl-1H-pyrazol-4-yl)-5-(trifluoromethyl)benzamido)spiro[3.3]heptan-2-yl)oxy)nicotinamide

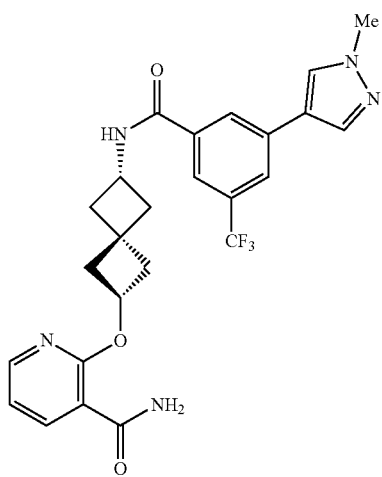

Example 427 (0.075 g, 0.15 mmol), 1-methyl-4-(4,4,5,5-tetramethyl-1,3,2-dioxaborolan-2-yl)-1H-pyrazole (0.031 g, 0.15 mmol), and 3M aqueous K3PO4 (0.125 mL, 0.376 mmol) were all added to a vial containing DMF (2 mL). The mixture was degassed thoroughly by 3 cycles of evacuation and nitrogen back-fill. 2nd generation XPhos precatalyst (7 mg, 9.03 µmol) was added followed by one more evacuation/nitrogen back-fill cycle. The reaction was heated to 70° C. for 1 h. The crude mixture was directly purified by prep HPLC to afford Example 428 (11 mg, 14%) as a grey solid. MS (ESI) m/z: 499.9 (M+H)+. 1H NMR (500 MHz, DMSO-d6) δ 8.89 (d, J=6.6 Hz, 1H), 8.34 (s, 1H), 8.27 (br. s., 2H), 8.16 (dd, J=7.5, 1.8 Hz, 1H), 8.05 (d, J=3.3 Hz, 2H), 7.94 (s, 1H), 7.76-7.59 (m, 2H), 7.11 (dd, J=7.4, 4.9 Hz, 1H), 5.22 (t, J=7.1 Hz, 1H), 4.38 (d, J=8.0 Hz, 1H), 2.67 (d, J=5.5 Hz, 1H), 2.37 (br. s., 1H), 2.31-2.14 (m, 4H).

Analytical HPLC RT=1.703 min (Method A) and 1.694 min (Method B), purity=96%.

EXAMPLE 429

Preparation of 6-bromo-N-((aR)-6-((3-carbamoylpyridin-2-yl)oxy)spiro[3.3]heptan-2-yl)-3-(trifluoromethyl)imidazo[1,5-a]pyridine-1-carboxamide

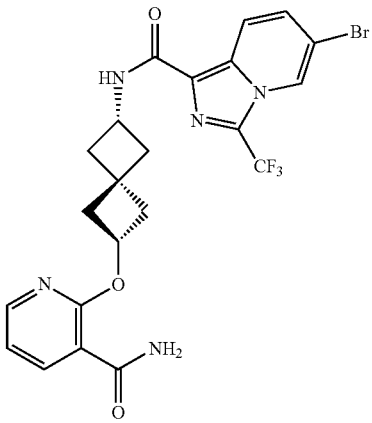

Example 429 (28.6 mg, 80%) was prepared in a analogous manner as Example 15 replacing Intermediate 4 with Intermediate 118 and coupling with Example 42C. MS (ESI) m/z: 538.0 (M+H)+. 1H NMR (500 MHz, DMSO-d6) δ 8.71 (s, 1H), 8.53 (d, J=5.7 Hz, 1H), 8.25 (d, J=3.2 Hz, 1H), 8.21 (d, J=9.7 Hz, 1H), 8.19-8.12 (m, 1H), 7.67 (br. s., 2H), 7.49 (d, J=9.7 Hz, 1H), 7.11 (dd, J=7.4, 4.9 Hz, 1H), 5.19 (s, 1H), 4.38 (s, 1H), 2.65 (br. s., 1H), 2.46 (br. s., 1H), 2.40 (br. s., 1H), 2.17 (br. s., 1H). Analytical HPLC RT=1.894 min (Method A) and 1.924 min (Method B), purity=98%.

EXAMPLE 430

Preparation of N-((aR)-6-((3-carbamoylpyridin-2-yl)oxy)spiro[3.3]heptan-2-yl)-3-(trifluoromethyl)imidazo[1,5-a]pyridine-1-carboxamide

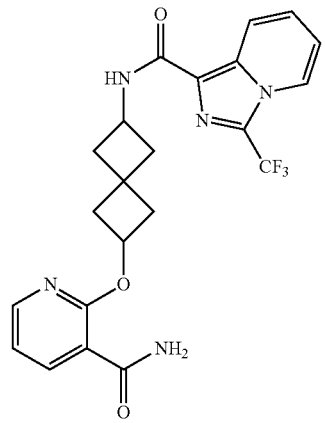 [SMILES: NC(=O)c1cccnc1OC1CC2(CC(NC(=O)c3nc(C(F)(F)F)n4ccccc34)C2)C1]

Example 430 (28.6 mg, 80%) was prepared in a analogous manner as Example 27 replacing Intermediate 24 with Intermediate 120 and coupling with Example 42C. MS (ESI) m/z: 460.2 (M+H)+. 1H NMR (500 MHz, DMSO-d6) δ 8.56-8.50 (m, 1H), 8.50-8.43 (m, 1H), 8.26 (d, J=4.2 Hz, 2H), 8.16 (d, J=7.5 Hz, 1H), 7.75-7.61 (m, 2H), 7.44-7.35 (m, 1H), 7.17 (s, 1H), 7.11 (d, J=2.4 Hz, 1H), 5.27-5.15 (m, 1H), 4.47-4.35 (m, 1H), 2.71-2.60 (m, 1H), 2.49-2.44 (m, 1H), 2.44-2.36 (m, 1H), 2.27-2.22 (m, 1H), 2.21-2.14 (m, 1H). Analytical HPLC RT=1.701 min (Method A) and 1.667 min (Method B), purity=100%.

EXAMPLE 431

Preparation of 6-(benzyloxy)-N-((aR)-6-((3-carbamoylpyridin-2-yl)oxy)spiro[3.3]heptan-2-yl)-3-(trifluoromethyl)imidazo[1,5-a]pyridine-1-carboxamide

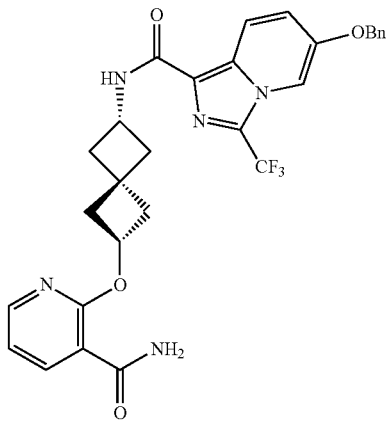

Example 431 (720 mg, 77%) was prepared in a analogous manner as Example 15 replacing Intermediate 4 with Intermediate 119 and coupling with Example 42C. MS (ESI) m/z: 566.5 (M+H)$^+$. $^1$H NMR (500 MHz, DMSO-d$_6$) δ 8.46 (d, J=7.2 Hz, 1H), 8.30-8.26 (m, 1H), 8.23 (d, J=9.9 Hz, 1H), 8.17 (dd, J=7.4, 1.5 Hz, 1H), 7.97 (s, 1H), 7.72 (br. s., 1H), 7.62 (br. s., 1H), 7.51 (d, J=7.2 Hz, 2H), 7.43 (t, J=7.4 Hz, 2H), 7.40-7.34 (m, 1H), 7.28 (d, J=9.9 Hz, 1H), 7.11 (dd, J=7.3, 5.0 Hz, 1H), 5.27-5.16 (m, 3H), 4.47-4.36 (m, 1H), 2.70-2.60 (m, 1H), 2.49-2.44 (m, 1H), 2.43-2.36 (m, 1H), 2.36-2.14 (m, 5H). Analytical HPLC RT=2.149 min (Method A) and 2.154 min (Method B), purity=98%.

EXAMPLE 432

Preparation of 1-(((aR)-6-((3-carbamoylpyridin-2-yl)oxy)spiro[3.3]heptan-2-yl)carbamoyl)-3-(trifluoromethyl)imidazo[1,5-a]pyridin-6-yl trifluoromethanesulfonate

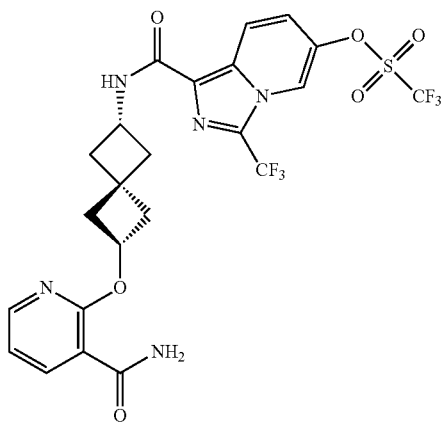

EXAMPLE 432A

Preparation of N-((aR)-6-((3-carbamoylpyridin-2-yl)oxy)spiro[3.3.1]heptan-2-yl)-6-hydroxy-3-(trifluoromethyl)imidazo[1,5-a]pyridine-1-carboxamide

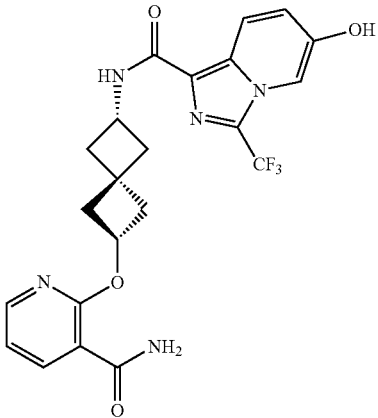

Dissolved Example 431 (0.5 g, 0.884 mmol) in EtOH (25 mL). Flushed reactor with nitrogen and added Pd—C (0.094 g, 0.088 mmol). Stirred under 55 psi of hydrogen for 8 hours. Filtered through Celite and concentrated. Isolated 432A (0.38 g, 0.799 mmol, 90% yield) as a white solid. MS (ESI) m/z: 476.1 (M+H)$^+$.

EXAMPLE 432

Preparation of 1-(((aR)-6-((3-carbamoylpyridin-2-yl)oxy)spiro[3.3]heptan-2-yl)carbamoyl)-3-(trifluoromethyl)imidazo[1,5-a]pyridin-6-yl trifluoromethanesulfonate

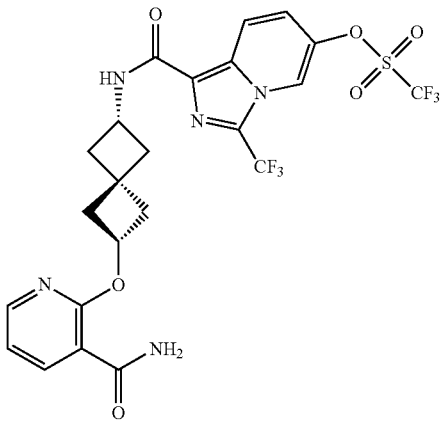

Dissolved Example 432A (0.10 g, 0.21 mmol) and Et$_3$N (0.029 mL, 0.21 mmol) in CH$_2$Cl$_2$ (10 mL) and added 1,1,1-trifluoro-N-phenyl-N-((trifluoromethyl)sulfonyl)methanesulfonamide (0.075 g, 0.21 mmol). After stirring at rt overnight, the reaction was concentrated and the residue was purified by prep HPLC to yield Example 432 (90 mg, 70%) as a white solid. MS (ESI) m/z: 608.0 (M+H)$^+$. $^1$H NMR (500 MHz, DMSO-d$_6$) δ 9.16 (s, 1H), 8.61 (d, J=7.9

Hz, 1H), 8.42 (d, J=10.1 Hz, 1H), 8.27 (dd, J=4.9, 1.8 Hz, 1H), 8.17 (dd, J=7.6, 1.8 Hz, 1H), 7.68 (br. s., 1H), 7.61 (br. s., 1H), 7.54 (d, J=11.3 Hz, 1H), 7.11 (dd, J=7.6, 4.9 Hz, 1H), 5.22 (t, J=7.2 Hz, 1H), 4.42 (d, J=8.2 Hz, 1H), 2.70-2.60 (m, 1H), 2.50-2.45 (m, 1H), 2.45-2.38 (m, 1H), 2.37-2.29 (m, 3H), 2.25 (dd, J=11.3, 7.6 Hz, 1H), 2.19 (dd, J=11.7, 7.5 Hz, 1H). Analytical HPLC RT=2.048 min (Method A) and 2.026 min (Method B), purity=100%.

EXAMPLE 433

Preparation of N-((aR)-6-((3-carbamoylpyridin-2-yl)oxy)spiro[3.3]heptan-2-yl)-6-(1-methyl-1H-pyrazol-4-yl)-3-(trifluoromethyl)imidazo[1,5-a]pyridine-1-carboxamide

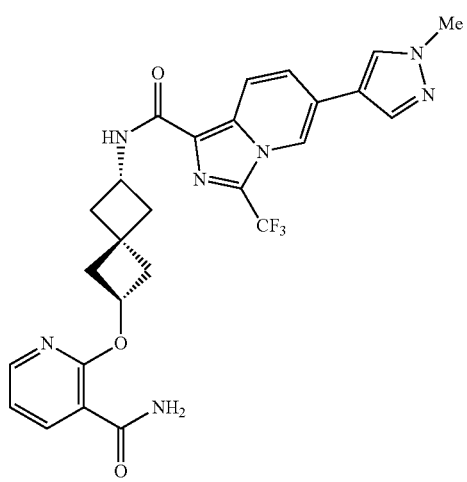

Example 433 (17 mg, 47%) was prepared in a analogous manner as Example 428 replacing Example 427 with Example 432. MS (ESI) m/z: 540.4 (M+H)$^+$. $^1$H NMR (500 MHz, DMSO-d$_6$) δ 8.52 (s, 1H), 8.42 (d, J=8.2 Hz, 1H), 8.37 (s, 1H), 8.32-8.24 (m, 2H), 8.17 (d, J=7.3 Hz, 1H), 8.06 (s, 1H), 7.71-7.57 (m, 3H), 7.14-7.07 (m, 1H), 5.22 (quin, J=7.1 Hz, 1H), 4.47-4.37 (m, 1H), 2.66 (dt, J=11.3, 5.6 Hz, 1H), 2.49-2.45 (m, 1H), 2.44-2.37 (m, 1H), 2.35-2.28 (m, 3H), 2.25 (dd, J=10.8, 7.5 Hz, 1H), 2.19 (dd. J=11.4, 7.5 Hz, 1H). Analytical HPLC RT=1.614 min (Method A) and 1.619 min (Method B), purity=98%.

EXAMPLE 434

Preparation of N-((aR)-6-((3-carbamoylpyridin-2-yl)oxy)spiro[3.3]heptan-2-yl)-6-(2-hydroxy-2-methylpropoxy)-3-(trifluoromethyl)imidazo[1,5-a]pyridine-1-carboxamide

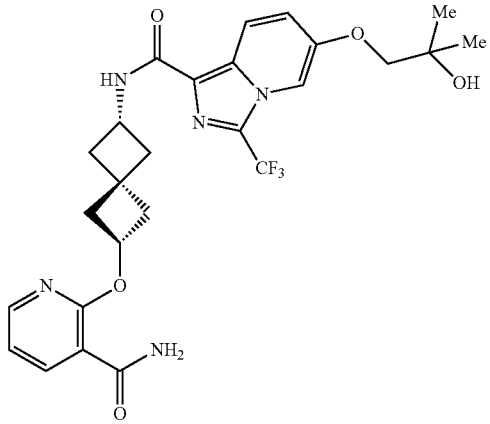

Dissolved Example 432A (0.05 g, 0.105 mmol) in DMF (2 mL) and added 2,2-dimethyloxirane (8 mg, 0.105 mmol) and Cs$_2$CO$_3$ (0.034 g, 0.105 mmol). The mixture was heated to 70° C. for 2 hours then cooled to rt. The crude was purified by prep HPLC to yield Example 434 (1.6 mg, 3%). MS (ESI) m/z: 548.4 (M+H)$^+$. $^1$H NMR (500 MHz, DMSO-d$_6$) δ 8.40 (d, J=8.2 Hz, 1H), 8.26 (br. s., 2H), 8.22 (d, J=10.1 Hz, 1H), 8.16 (d, J=7.3 Hz, 2H), 7.88 (s, 1H), 7.73-7.56 (m, 4H), 7.24 (d, J=9.5 Hz, 1H), 7.10 (br. s., 2H), 5.27-5.15 (m, 2H), 4.45-4.37 (m, 1H), 4.37-4.26 (m, 1H), 4.10 (br. s., 1H), 3.17 (br. s., 1H), 3.01 (br. s., 1H), 2.95-2.90 (m, 1H), 2.64 (br. s., 2H), 2.34-2.12 (m, 9H), 1.16 (t, J=7.2 Hz, 2H), 1.00 (d, J=6.1 Hz, 2H). Analytical HPLC RT=1.63 min (Method A) and 1.64 min (Method B), purity=97%.

EXAMPLE 435

Preparation of 6-(benzyloxy)-N-((aR)-6-((3-carbamoylpyridin-2-yl)oxy)spiro[3.3]heptan-2-yl)-3-(difluoromethyl)imidazo[1,5-a]pyridine-1-carboxamide

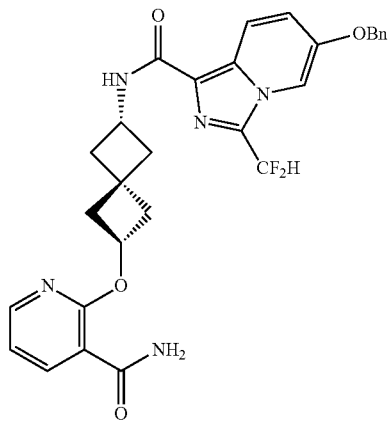

Example 435 (8.1 mg, 6%) was prepared in a analogous manner as Example 15 replacing Intermediate 4 with Intermediate 122 and coupling with Example 42C. MS (ESI) m/z: 548.5 (M+H)$^+$. $^1$H NMR (500 MHz, DMSO-d$_6$) δ 8.33 (d, J=8.2 Hz, 1H), 8.27 (d, J=3.1 Hz, 1H), 8.21-8.10 (m, 3H), 7.67 (br. s., 1H), 7.62 (d, J=6.1 Hz, 1H), 7.54-7.47 (m, 2H), 7.42 (t, J=7.3 Hz, 2H), 7.40-7.34 (m, 1H), 7.18 (d, J=10.1 Hz, 1H), 7.11 (dd, J=7.3, 4.9 Hz, 1H), 5.25-5.19 (m, 1H), 5.19-5.12 (m, 2H), 4.45-4.34 (m, 1H), 2.71-2.60 (m, 1H), 2.51-2.45 (m, 3H), 2.39 (d, =11.3 Hz, 1H), 2.34-2.22 (m, 4H), 2.18 (dd, J=11.6, 7.3 Hz, 1H). Analytical HPLC RT=2.06 min (Method A) and 1.98 min (Method B), purity=100%.

EXAMPLE 436

Preparation of N-((aR)-6-((3-carbamoylpyridin-2-yl)oxy)spiro[3.3]heptan-2-yl)-3-(difluoromethyl)-6-(2-methylthiazol-5-yl)imidazo[1,5-a]pyridine-1-carboxamide

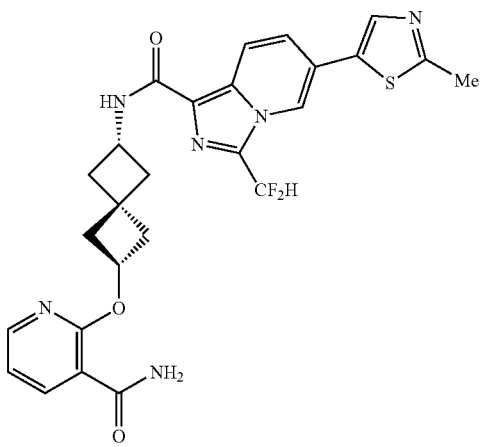

EXAMPLE 436A

Preparation of 6-bromo-N-((aR)-6-((3-carbamoylpyridin-2-yl)oxy)spiro[3.3]heptan-2-yl)-3-(difluoromethyl)imidazo[1,5-a]pyridine-1-carboxamide

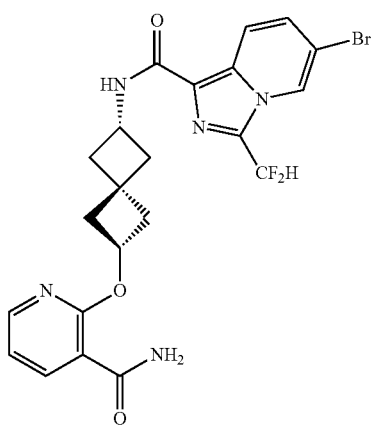

Example 436A (375 mg, 90%) was prepared in a analogous manner as Example 15 replacing Intermediate 4 with Intermediate 121 and coupling with Example 42C. MS (ESI) m/z: 522.0 (M+H)$^+$.

EXAMPLE 436

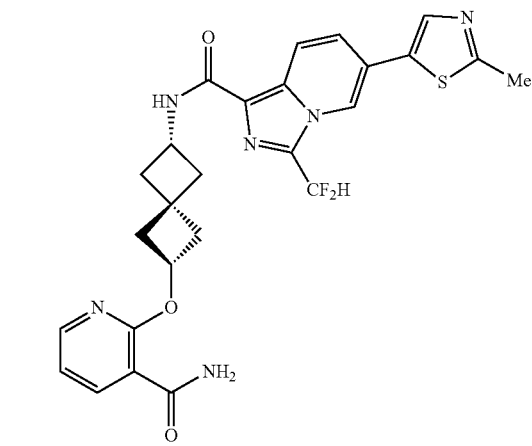

Example 436 (8.4 mg, 23%) was prepared in a analogous manner as Example 428 replacing Example 427 with Example 436A and 1-methyl-4-(4,4,5,5-tetramethyl-1,3,2-dioxaborolan-2-yl)-1H-pyrazole with 2-methyl-5-(4,4,5,5-tetramethyl-1,3,2-dioxaborolan-2-yl)thiazole. MS (ESI) m/z: 539.4 (M+H)$^+$. $^1$H NMR (500 MHz, DMSO-d$_6$) δ 8.71 (s, 1H), 8.42 (d, J=8.2 Hz, 1H), 8.30-8.24 (m, 2H), 8.22-8.15 (m, 2H), 7.70 (br. s, 1H), 7.66 (t, J=52 Hz, 1H), 7.61 (d, J=9.8 Hz, 2H), 7.11 (dd, J=7.5, 5.0 Hz, 1H), 5.23 (t, J=7.2 Hz, 1H), 4.49-4.37 (m, 1H), 2.67 (dt, J=11.3, 6.0 Hz, 1H), 2.44-2.38 (m, 1H), 2.37-2.16 (m, 5H). Analytical HPLC RT=1.67 min (Method A) and 1.72 min (Method B), purity=100%.

EXAMPLE 437

Preparation of N-((aR)-6-((3-carbamoylpyridin-2-yl)oxy)spiro[3.3]heptan-2-yl)-3-(difluoromethyl-6-(1-methyl-H-imidazol-5-yl)imidazo[1,5-a]pyridine-1-carboxamide

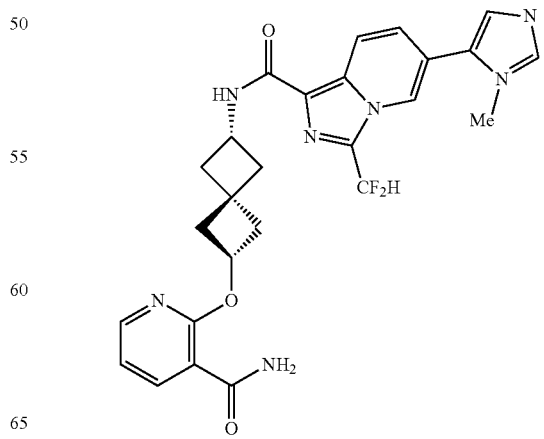

Example 437 (8 mg, 23%) was prepared in a analogous manner as Example 428 replacing Example 427 with Example 436A and 1-methyl-4-(4,4,5,5-tetramethyl-1,3,2-dioxaborolan-2-yl)-1H-pyrazole with 1-methyl-1H-imidazol-5-yl)boronic acid. MS (ESI) m/z: 522.3 (M+H)+. 1H NMR (500 MHz, DMSO-d6) δ 8.58 (s, 1H), 8.41 (d, J=8.2 Hz, 1H), 8.30-8.24 (m, 2H), 8.17 (dd, J=7.3, 1.8 Hz, 1H), 7.81 (s, 1H), 7.68 (br. s., 1H), 7.61 (t, J=52 Hz, 1H), 7.47 (d, J=9.8 Hz, 1H), 7.24 (s, 1H), 7.11 (dd, J=7.3, 4.9 Hz, 1H), 5.23 (t, J=7.0 Hz, 1H), 4.49-4.38 (m, 1H), 3.74 (s, 2H), 2.66 (dd, J=11.0, 5.8 Hz, 1H), 2.49-2.46 (m, 1H), 2.45-2.38 (m, 1H), 2.35-2.16 (m, 5H), 1.91 (s, 2H). Analytical HPLC RT=1.35 min (Method A) and 1.11 min (Method B), purity=100%.

EXAMPLE 438

N-((aR)-6-((3-carbamoylpyridin-2-yl)oxy)spiro[3.3]heptan-2-yl)-3-(difluoromethyl)-6-(1-methyl-3-(trifluoromethyl)-1H-pyrazol-4-yl)imidazo[1,5-a]pyridine-1-carboxamide

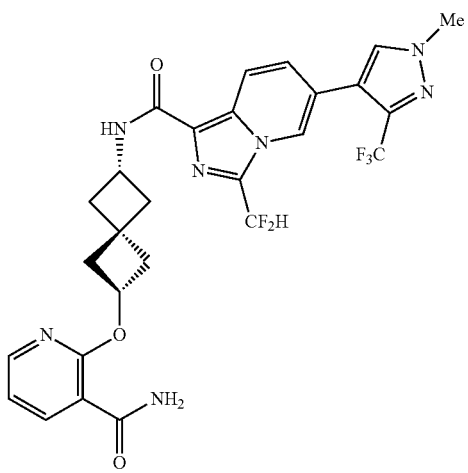

Example 438 (6.2 mg, 16%) was prepared in a analogous manner as Example 428 replacing Example 427 with Example 436A and 1-methyl-4-(4,4,5,5-tetramethyl-1,3,2-dioxaborolan-2-yl)-1H-pyrazole with 1-methyl-4-(4,4,5,5-tetramethyl-1,3,2-dioxaborolan-2-yl)-3-(trifluoromethyl)-1H-pyrazole. MS (ESI) m/z: 590.5 (M+H)+. 1H NMR (500 MHz, DMSO-d6) δ 8.51 (s, 1H), 8.42 (d, J=8.2 Hz, 1H), 8.33 (s, 1H), 8.31-8.24 (m, 2H), 8.17 (dd, J=7.6, 1.8 Hz, 1H), 7.68 (br. s., 1H), 7.61 (br. s., 1H), 7.54 (t, J=52 Hz 1H), 7.34 (d, J=9.5 Hz, 1H), 7.11 (dd, J=7.3, 4.9 Hz, 1H), 5.22 (t, J=7.2 Hz, 1H), 4.48-4.37 (m, 1H), 3.99 (s, 3H), 2.66 (dt, J=11.2, 5.8 Hz, 1H), 2.49-2.45 (m, 1H), 2.45-2.38 (m, 1H), 2.35-2.14 (m, 5H). Analytical HPLC RT=1.82 min (Method A) and 1.89 min (Method B), purity=99%.

EXAMPLE 439

Preparation of N-((aR)-6-((3-carbamoylpyridin-2-yl)oxy)spiro[3.3]heptan-2-yl)-3-(difluoromethyl)-6-(1-methyl-1H-pyrazol-4-yl)imidazo[1,5-a]pyridine-1-carboxamide

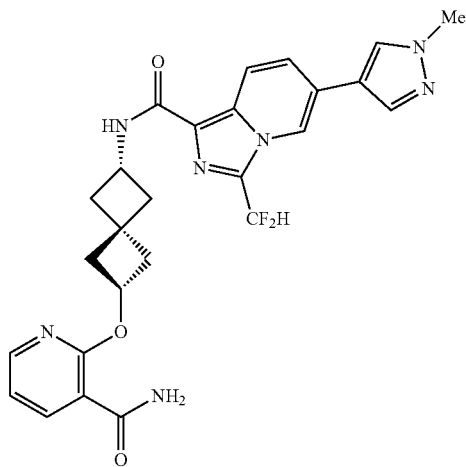

Example 439 (12.4 mg, 35%) was prepared in a analogous manner as Example 428 replacing Example 427 with Example 436A. MS (ESI) m/z: 522.4 (M+H)+. 1H NMR (500 MHz, DMSO-d6) δ 8.66 (s, 1H), 8.35 (d, J=8.2 Hz, 1H), 8.30-8.24 (m, 2H), 8.21 (d, J=9.2 Hz, 1H), 8.16 (dd, J=7.3, 1.8 Hz, 1H), 8.00 (s, 1H), 7.64 (d, J=9.5 Hz, 2H), 7.57 (d, J=9.5 Hz, 1H), 7.55 (t, J=52 Hz, 1H), 7.11 (dd, J=7.3, 4.9 Hz, 1H), 5.21 (t, J=7.2 Hz, 1H), 4.46-4.35 (m, 1H), 3.88 (s, 3H), 2.71-2.61 (m, 1H), 2.49-2.38 (m, 2H), 2.35-2.14 (m, 5H). Analytical HPLC RT=1.50 min (Method A) and 1.50 min (Method B), purity=100%.

EXAMPLE 440

Preparation of N-((aR)-6-((3-carbamoylpyridin-2-yl)oxy)spiro[3.3]heptan-2-yl)-3-(difluoromethyl)-6-morpholinoimidazo[1,5-a]pyridine-1-carboxamide

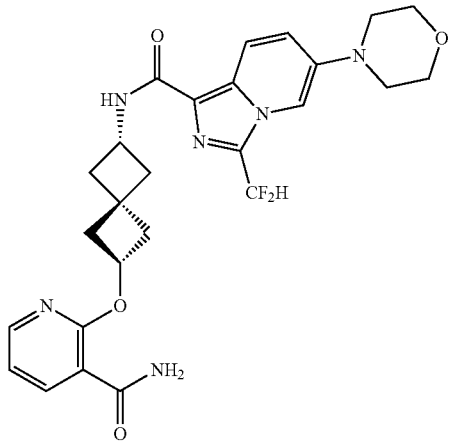

509

A slurry of Example 436A (0.04 g, 0.077 mmol), morpholine (6.70 mg, 0.077 mmol), (4,4'-di-t-butyl-2,2'-bipyridine)bis[3,5-difluoro-2-[5-trifluoromethyl-2-pyridinyl-kappaN)phenyl-kappaC]Ir(III) PF$_6$ (0.792 mg, 0.769 µmol), NiCl$_2$ glyme complex (0.845 mg, 3.84 µmol) and DABCO (0.016 g, 0.138 mmol) in DMA (0.769 mL) was degassed, blanketed under N$_2$ and irradiated with blue LED for 18 hours. The reaction was directly purified by prep HPLC to afford Example 440 (17.7 mg, 42%). MS (ESI) m/z: 527.2 (M+H)$^+$. $^1$H NMR (500 MHz, DMSO-d$_6$) δ 8.29 (d, J=7.9 Hz, 1H), 8.22 (d, J=4.6 Hz, 1H), 8.15 (d, J=7.6 Hz, 1H), 8.04 (d, J=9.8 Hz, 1H), 7.74 (br. s., 1H), 7.62 (s, 1H), 7.56 (br. s., 1H), 7.38 (t, J=52 Hz, 1H), 7.31 (d, J=10.1 Hz, 1H), 7.10 (dd, J=7.3, 4.9 Hz, 1H), 5.16 (s, 1H), 4.38-4.27 (m, 1H), 4.11-4.05 (m, 2H), 3.73 (br. s., 3H), 3.06 (br. s., 4H), 2.68-2.60 (m, 1H), 2.49-2.37 (m, 3H), 2.36-2.26 (m, 1H), 2.23-2.09 (m, 4H). Analytical HPLC RT=1.56 min (Method A) and 1.54 min (Method B), purity=95%.

EXAMPLE 441

Preparation of N-((aR)-6-((3-carbamoylpyridin-2-yl)oxy)spiro[3.3]heptan-2-yl)-3-(difluoromethyl)-6-(3-hydroxy-3-methylbutoxy)imidazo[1,5-a]pyridine-1-carboxamide

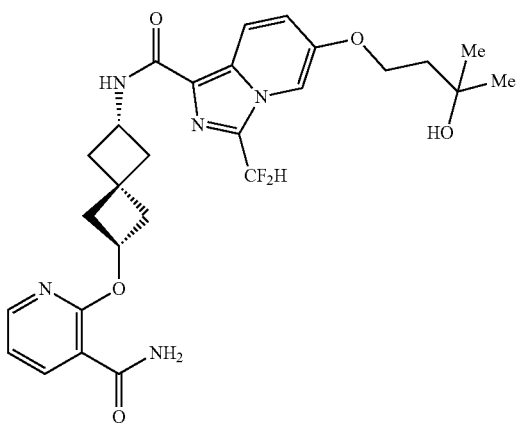

A slurry of Example 436A (0.04 g, 0.077 mmol), 3-methylbutane-1,3-diol (8.01 mg, 0.077 mmol), (4,4'-di-tert-butyl-2,2'-bipyridine)bis[3,5-difluoro-2-[5-trifluoromethyl-2-pyridinyl-kappaN)phenyl-kappaC]Ir(III) PF$_6$ (0.792 mg, 0.769 µmol), NiCl$_2$ glyme complex (0.845 mg, 3.84 µmol), 4,4'-di-tert-butyl-2,2'-bipyridine (1.032 mg, 3.84 µmol) and quinuclidine (0.855 mg, 7.69 µmol) in CH$_3$CN (0.769 mL) was degassed, blanketed under N$_2$ and irradiated with blue LED. The reaction was directly purified by prep HPLC to afford Example 441 (7.7 mg, 18%). MS (ESI) m/z: 544.1 (M+H)$^+$. $^1$H NMR (500 MHz, DMSO-d$_6$) δ 8.32 (d, J=7.9 Hz, 1H), 8.22 (d, J=3.4 Hz, 1H), 8.15 (d, J=7.3 Hz, 1H), 8.06 (d, J=9.8 Hz, 1H), 7.90 (s, 1H), 7.74 (br. s., 1H), 7.56 (br. s., 1H), 7.40 (t, J=52 Hz, 1H), 7.10 (dd, J=7.3, 4.9 Hz, 1H), 7.06 (d, J=10.4 Hz, 1H), 5.15 (s, 1H), 4.38-4.27 (m, 1H), 4.14-4.05 (m, 3H), 2.69-2.59 (m, 1H), 2.49-2.38 (m, 2H), 2.36-2.25 (m, 1H), 2.23-2.09 (m, 3H), 1.87 (t, J=6.9 Hz, 2H). Analytical HPLC RT=1.58 min (Method A) and 1.56 min (Method B), purity=99%.

EXAMPLE 442

Preparation of N-((aR)-6-((3-carbamoylpyridin-2-yl)oxy)spiro[3.3]heptan-2-yl)-3-(difluoromethyl)-6-((2-hydroxy-2-methylpropyl)amino)imidazo[1,5-a]pyridine-1-carboxamide

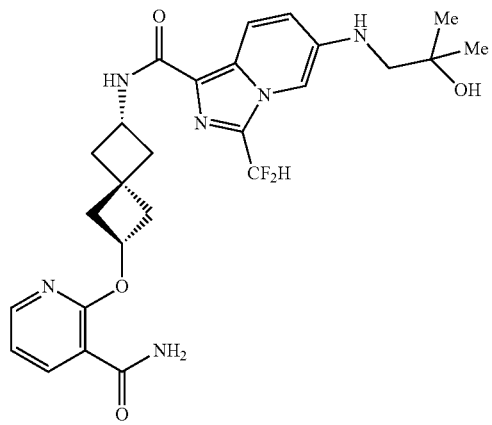

Example 442 (4.4 mg, 14%) was prepared in a analogous manner as Example 440 replacing morpholine with 1-amino-2-methylpropan-2-ol. MS (ESI) m/z: 529.3 (M+H)$^+$. $^1$H NMR (500 MHz, DMSO-d$_6$) δ 8.27 (d, J=3.4 Hz, 1H), 8.17 (d, J=7.3 Hz, 1H), 8.14-8.05 (m, 1H), 7.95 (s, 1H), 7.72-7.56 (m, 2H), 7.17 (t, J=52 Hz, 1H), 7.10 (dd, J=7.3, 4.9 Hz, 1H), 5.26-5.17 (m, 1H), 4.39-4.29 (m, 1H), 2.91-2.88 (m, 1H), 2.79 (s, 1H), 2.73 (s, 1H), 2.49-2.42 (m, 1H), 2.37 (br. s., 1H), 2.30-2.13 (m, 5H), 1.95-1.90 (m, 2H). Analytical HPLC RT=1.32 min (Method A) and 1.32 min (Method B), purity=96%.

EXAMPLE 443

Preparation of 6-((1-amino-2-methylpropan-2-yl)oxy)-N-((aR)-6-((3-carbamoylpyridin-2-yl)oxy)spiro[3.3]heptan-2-yl)-3-(difluoromethyl)imidazo[1,5-a]pyridine-1-carboxamide

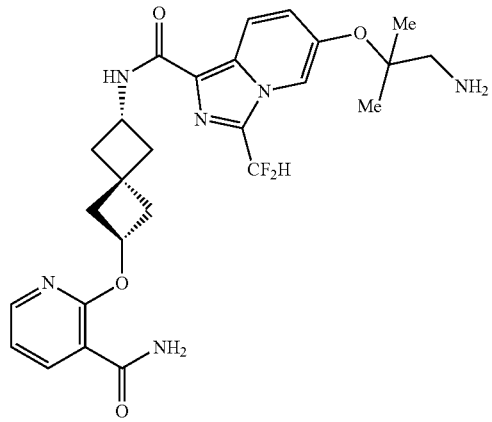

Example 443 (1.8 mg, 6%) was prepared in a analogous manner as Example 440 replacing morpholine with 1-amino-2-methylpropan-2-ol. MS (ESI) m/z: 529.4 (M+H)⁺. ¹H NMR (500 MHz, DMSO-d₆) δ 8.26 (d, J=4.6 Hz, 1H), 8.20-8.13 (m, 1H), 8.08 (d, J=8.2 Hz, 1H), 7.72-7.54 (m, 2H), 7.16 (t, J=52 Hz, 1H), 7.15-7.08 (m, 1H), 5.25-5.16 (m, 2H), 4.38-4.26 (m, 1H), 2.79 (s, 2H), 2.63 (dd, J=11.3, 5.8 Hz, 1H), 2.48-2.33 (m, 2H), 2.31-2.10 (m, 5H), 1.93 (s, 2H). Analytical HPLC RT=1.23 min (Method A) and 1.20 min (Method B), purity=100%.

EXAMPLE 444

Preparation of N-((aR)-6-((3-carbamoylpyridin-2-yl)oxy)spiro[3.3]heptan-2-yl)-3-(difluoromethyl)-6-((2S,6R)-2,6-dimethylmorpholino)imidazo[1,5-a]pyridine-1-carboxamide

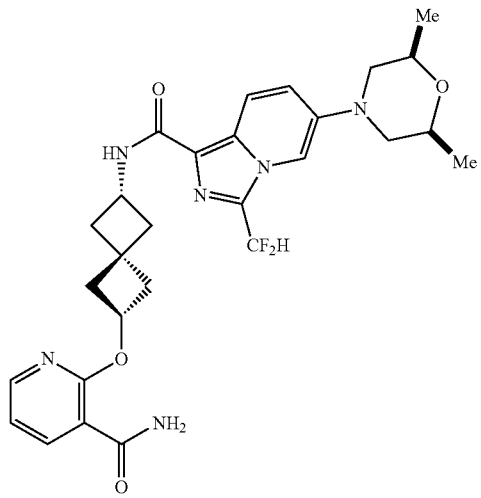

Example 444 (11 mg, 20%) was prepared in a analogous manner as Example 440 replacing morpholine with cis-2,6-dimethylmorpholine. MS (ESI) m/z: 555.2 (M+H)⁺. ¹H NMR (500 MHz, DMSO-d₆) δ 8.27 (d, J=7.0 Hz, 2H), 8.17 (d, J=7.3 Hz, 1H), 8.08 (d, J=10.1 Hz, 1H), 7.71-7.65 (m, 2H), 7.61 (br. s., 1H), 7.53 (t, J=52 Hz, 1H), 7.39 (d, J=10.1 Hz, 1H), 7.11 (dd, J=7.3, 4.9 Hz, 1H), 5.21 (t, J=7.0 Hz, 1H), 4.39 (d, J=8.2 Hz, 1H), 3.73 (br. s., 1H), 2.65 (d, J=4.6 Hz, 1H), 2.51 (br. s., 4H), 2.49-2.44 (m, 1H), 2.40 (br. s., 1H), 2.33-2.22 (m, 6H), 2.18 (dd, J=11.4, 7.5 Hz, 1H), 1.17 (d, J=6.4 Hz, 6H). Analytical HPLC RT=1.82 min (Method A) and 1.80 min (Method B), purity=95%.

EXAMPLE 445

Preparation of N-((aR)-6-((3-carbamoylpyridin-2-yl)oxy)spiro[3.3]heptan-2-yl)-3-(difluoromethyl)-6-(1,3-dimethyl-1H-pyrazol-4-yl)imidazo[1,5-a]pyridine-1-carboxamide

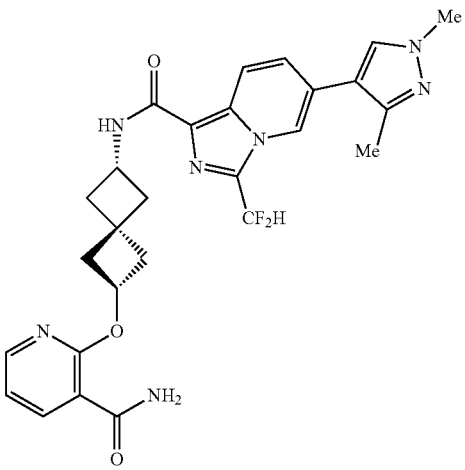

Example 445 (16.8 mg, 63%) was prepared in a analogous manner as Example 428 replacing Example 427 with Example 436A and 1-methyl-4-(4,4,5,5-tetramethyl-1,3,2-dioxaborolan-2-yl)-1H-pyrazole with 1,3-dimethyl-4-(4,4,5,5-tetramethyl-1,3,2-dioxaborolan-2-yl)-1H-pyrazole. MS (ESI) m/z: 536.6 (M+H)⁺. ¹H NMR (500 MHz, DMSO-d₆) δ 8.40 (s, 1H), 8.36 (d, J=8.2 Hz, 1H), 8.27 (d, J=3.4 Hz, 1H), 8.23 (d, J=9.5 Hz, 1H), 8.17 (d, J=7.3 Hz, 1H), 8.06 (s, 1H), 7.67 (d, J=7.6 Hz, 1H), 7.62 (br. s., 1H), 7.56 (t, J=52 Hz, 1H), 7.44 (d, J=8.9 Hz, 1H), 7.15-7.07 (m, 1H), 5.27-5.16 (m, 1H), 4.49-4.36 (m, 1H), 3.81 (s, 3H), 2.70-2.61 (m, 1H), 2.55 (s, 1H), 2.47 (d, J=6.1 Hz, 1H), 2.45-2.38 (m, 1H), 2.33 (s, 3H), 2.31-2.15 (m, 4H). Analytical HPLC RT=1.56 min (Method A) and 1.59 min (Method B), purity=97%.

EXAMPLE 446

Preparation of 2-(((aR)-6-(3-(2-methylthiazol-5-yl)-5-(trifluoromethyl)benzamido)spiro[3.3]heptan-2-yl)oxy)nicotinamide

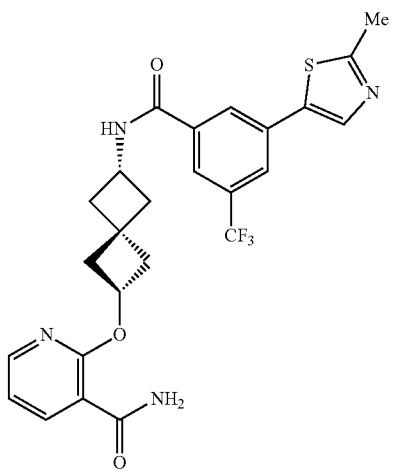

Example 446 (7.7 mg, 37%) was prepared in a analogous manner as Example 428 replacing 1-methyl-4-(4,4,5,5-tetramethyl-1,3,2-dioxaborolan-2-yl)-1H-pyrazole with 2-methyl-5-(4,4,5,5-tetramethyl-1,3,2-dioxaborolan-2-yl)thiazole. MS (ESI) m/z: 517.1 (M+H)+. $^1$H NMR (500 MHz, DMSO-$d_6$) δ 8.96 (d, J=7.0 Hz; 1H), 8.28 (d, J=7.0 Hz, 3H), 8.17 (d, J=7.3 Hz, 1H), 8.12 (s, 2H), 7.69 (br. s., 1H), 7.61 (br. s., 1H), 7.11 (dd, J=7.3, 4.9 Hz, 1H), 5.30-5.17 (m, 1H), 4.46-4.32 (m, 1H), 2.76-2.62 (m, 4H), 2.43-2.33 (m, 1H), 2.32-2.17 (m, 4H). Analytical HPLC RT=1.81 min (Method A) and 1.78 min (Method B), purity=100%.

EXAMPLE 447

Preparation of 2-(((aR)-6-(3-(1-methyl-3-(trifluoromethyl)-1H-pyrazol-4-yl)-5-(trifluoromethyl)benzamido)spiro[3.3]heptan-2-yl)oxy)nicotinamide

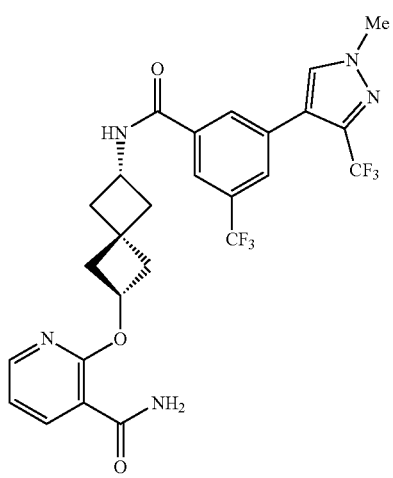

Example 447 (20.2 mg, 89%) was prepared in a analogous manner as Example 428 replacing 1-methyl-4-(4,4,5,5-tetramethyl-1,3,2-dioxaborolan-2-yl)-1H-pyrazole with 1-methyl-4-(4,4,5,5-tetramethyl-1,3,2-dioxaborolan-2-yl)-3-(trifluoromethyl)-1H-pyrazole. MS (ESI) m/z: 568.2 (M+H)+. $^1$H NMR (500 MHz, DMSO-$d_6$) δ 8.92 (d, J=7.0 Hz, 1H), 8.34 (s, 1H), 8.27 (d, J=3.1 Hz, 1H), 8.18 (d, J=5.8 Hz, 3H), 7.84 (s, 1H), 7.68 (br. s., 1H), 7.61 (br. s., 1H), 7.11 (dd, J=7.3, 4.9 Hz, 1H), 5.23 (t, J=7.0 Hz, 1H), 4.43-4.32 (m, 1H), 3.99 (s, 3H), 3.46 (d, J=4.3 Hz, 1H), 2.72-2.62 (m, 1H), 2.37 (br. s., 1H), 2.31-2.14 (m, 4H). Analytical HPLC RT=1.93 min (Method A) and 1.98 min (Method B), purity=100%.

EXAMPLE 448

Preparation of 2-((aR)-6-(3-(1,3-dimethyl-1H-pyrazol-4-yl)-5-(trifluoromethyl)benzamido)spiro[3.3]heptan-2-yl)oxy)nicotinamide

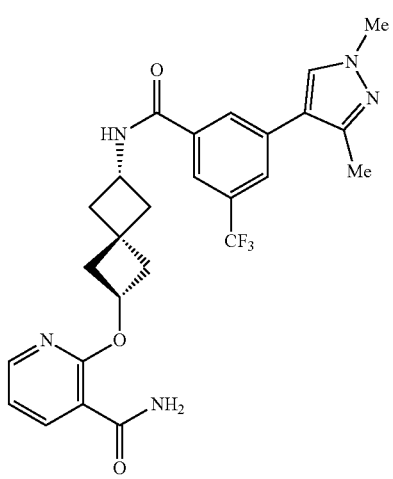

Example 448 (18.1 mg, 82%) was prepared in a analogous manner as Example 428 replacing 1-methyl-4-(4,4,5,5-tetramethyl-1,3,2-dioxaborolan-2-yl)-1H-pyrazole with 1,3-dimethyl-4-(4,4,5,5-tetramethyl-1,3,2-dioxaborolan-2-yl)-1H-pyrazole. MS (ESI) m/z: 514.2 (M+H)+. $^1$H NMR (500 MHz, DMSO-$d_6$) δ 8.27 (d, J=3.1 Hz, 1H), 8.19-8.13 (m, 2H), 8.11 (s, 1H), 8.01 (s, 1H), 7.84 (s, 1H), 7.69 (br. s., 1H), 7.61 (br. s., 1H), 7.11 (dd, J=7.5, 5.0 Hz, 1H), 5.23 (t, J=7.2 Hz, 1H), 4.44-4.33 (m, 1H), 3.81 (s, 3H), 2.71-2.63 (m, 1H), 2.40-2.35 (m, 1H), 2.33 (s, 3H), 2.31-2.16 (m, 4H). Analytical HPLC RT=1.66 min (Method A) and 1.74 min (Method B), purity=100%.

EXAMPLE 449

Preparation of 2-(((aR)-6-(3-(1-methyl-1H-imidazol-5-yl)-5-(trifluoromethyl)benzamido)spiro[3.3]heptan-2-yl)oxy)nicotinamide

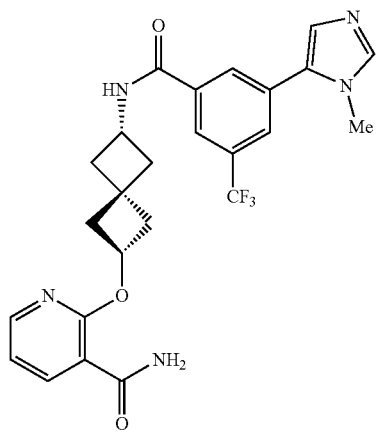

Example 449 (24 mg, 79%) was prepared in a analogous manner as Example 428 replacing 1-methyl-4-(4,4,5,5-tetramethyl-1,3,2-dioxaborolan-2-yl)-1H-pyrazole with (1-methyl-1H-imidazol-5-yl)boronic acid. MS (ESI) m/z: 500.4 (M+H)⁺. ¹H NMR (500 MHz, DMSO-$d_6$) δ 8.96 (d, J=7.0 Hz, 1H), 8.89 (br. s., 1H), 8.31 (d, J=7.9 Hz, 2H), 8.27 (d, J=3.1 Hz, 1H), 8.17 (d, J=7.6 Hz, 1H), 8.13 (s, 1H), 7.85 (s, 1H), 7.70 (br. s., 1H), 7.60 (br. s., 1H), 7.11 (dd, J=7.3, 4.9 Hz, 1H), 5.24 (t, J=7.0 Hz, 1H), 4.40 (d, J=7.6 Hz, 1H), 3.84 (s, 3H), 2.68 (br. s., 1H), 2.38 (d, J=6.4 Hz, 1H), 2.28 (dd, J=11.4, 7.5 Hz, 1H), 2.26-2.17 (m, 3H). Analytical HPLC RT=1.49 min (Method A) and 1.20 min (Method B), purity=99%.

EXAMPLE 450

Preparation of 2-(((aR)-6-(3-(4-hydroxy-4-methylpiperidin-1-yl)-5-(trifluoromethyl)benzamido)spiro[3.3]heptan-2-yl)oxy)nicotinamide

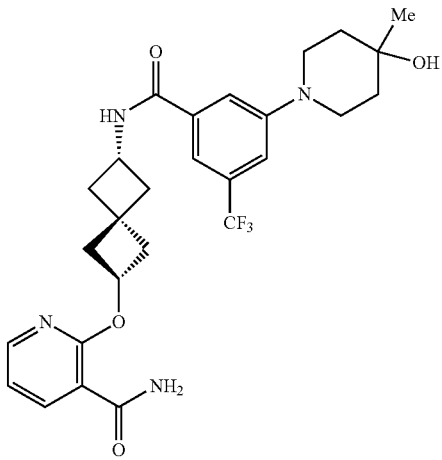

Example 450 (1.4 mg, 4%) was prepared in a analogous manner as Example 440 replacing Example 436 with Example 427 and replacing morpholine with 4-methylpiperidin-4-ol. MS (ESI) m/z: 533.2 (M+H)⁺. ¹H NMR (500 MHz, DMSO-$d_6$) δ 8.74 (d, J=7.3 Hz, 1H), 8.31-8.23 (m, 1H), 8.17 (dd, J=7.5, 1.7 Hz, 1H), 7.71 (br. s., 1H), 7.60 (br. s., 2H), 7.47 (s, 1H), 7.27 (s, 1H), 7.11 (dd, J=7.3, 4.9 Hz, 1H), 5.31-5.16 (m, 1H), 4.43-4.31 (m, 1H), 3.48 (d, J=12.5 Hz, 1H), 3.30-3.18 (m, 2H), 2.67 (dt, J=11.3, 6.0 Hz, 1H), 2.50-2.43 (m, 2H), 2.41-2.31 (m, 1H), 2.31-2.16 (m, 4H), 1.69 (s, 2H), 1.63-1.50 (m, 4H), 1.17 (s, 3H). Analytical HPLC RT=1.65 min (Method A) and 1.53 min (Method B), purity=100%.

EXAMPLE 451

Preparation of N-((aR)-6-((3-carbamoylpyridin-2-yl)oxy)spiro[3.3]heptan-2-yl)-3-(difluoromethyl)-6-(2-(2-hydroxyethyl)morpholino)imidazo[1,5-a]pyridine-1-carboxamide

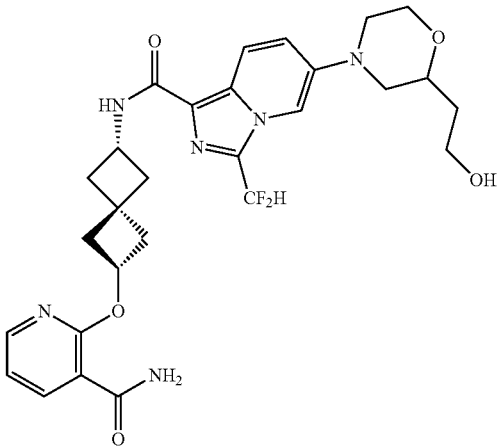

Example 451 (16.7 mg, 27%) was prepared in a analogous manner as Example 440 replacing morpholine with 2-(morpholin-2-yl)ethanol. MS (ESI) m/z: 571.4 (M+H)⁺. ¹H NMR (500 MHz, DMSO-$d_6$) δ 8.31-8.23 (m, 2H), 8.16 (dd, J=7.6, 1.8 Hz, 1H), 8.08 (d, J 10.1 Hz, 1H), 7.66 (d, J=19.5 Hz, 2H), 7.50 (t, J=52 Hz, 1H), 7.39 (br. s., 1H), 7.11 (dd, J=7.3, 4.9 Hz, 1H), 5.20 (s, 1H), 4.42-4.31 (m, 1H), 3.98-3.90 (m, 1H), 3.73-3.61 (m, 1H), 3.58-3.51 (m, 1H), 3.51-3.34 (m, 1H), 2.74-2.59 (m, 2H), 2.48-2.36 (m, 3H), 2.34-2.13 (m, 5H), 1.64 (d, J=6.4 Hz, 2H), 1.21 (s, 1H). Analytical HPLC RT=1.40 min (Method A) and 1.31 min (Method B), purity=90%.

EXAMPLE 452

Preparation of 2-(((aR)-6-(3-(2-oxa-5-azabicyclo[2.2.1]heptan-5-yl)-5-(trifluoromethyl)benzamido)spiro[331]heptan-2-yl)oxy)nicotinamide

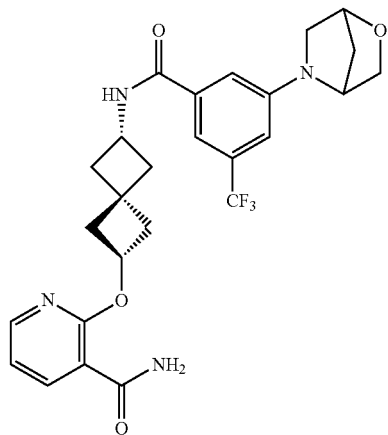

Example 452 (3.5 mg, 11%) was prepared in a analogous manner as Example 440 by replacing Example 436A with Example 427 and by replacing morpholine with 2-oxa-5-azabicyclo[2.2.1]heptane. MS (ESI) m/z: 517.5 (M+H)+. 1H NMR (500 MHz, DMSO-$d_6$) δ 8.73 (d, J=7.3 Hz, 1H), 8.26 (d, J=3.1 Hz, 1H), 8.16 (d, J=7.3 Hz, 1H), 7.65 (br. s., 2H), 7.35 (s, 1H), 7.23 (br. s., 1H), 7.11 (dd, J=7.3, 4.9 Hz, 1H), 6.95 (br. s., 1H), 5.21 (t, J=7.2 Hz, 1H), 4.73-4.61 (m, 2H), 4.40-4.27 (m, 1H), 3.72 (d, J=5.8 Hz, 3H), 3.12-3.02 (m, 1H), 2.71-2.61 (m, 1H), 2.46 (dd, J=12.1, 6.6 Hz, 2H), 2.40-2.29 (m, 1H), 2.29-2.13 (m, 4H), 1.96-1.83 (m, 2H), 1.16 (q, J=7.1 Hz, 1H). Analytical HPLC RT=1.69 min (Method A) and 1.77 min (Method B), purity=96%.

EXAMPLE 453

Preparation of N-((aR)-6-((3-carbamoylpyridin-2-yl)oxy)spiro[3.3]heptan-2-yl)-3-(difluoromethyl)-6-((N-methylacetamido)methyl)imidazo[1,5-a]pyridine-1-carboxamide

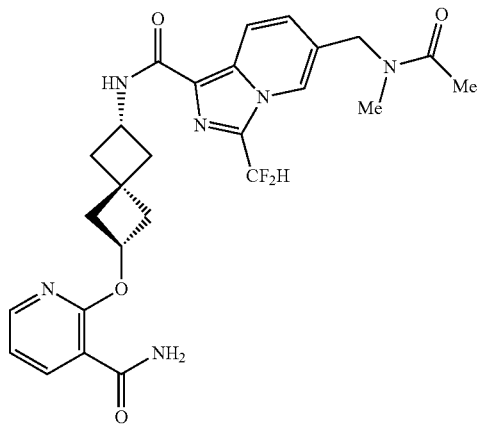

Example 453 (2.9 mg, 7%) was isolated as a side-product in the reaction coupling Example 436A with 2-oxa-5-azabicyclo[2.2.1]heptane. MS (ESI) m/z: 527.2 (M+H)+. 1H NMR (500 MHz, DMSO-$d_6$) δ 8.43 (s, 1H), 8.35 (d, J=8.2 Hz, 1H), 8.27 (d, J=3.1 Hz, 1H), 8.21-8.14 (m, 2H), 7.68 (br. s., 1H), 7.62 (br. s., 1H), 7.51 (t, J=52 Hz, 1H), 7.16 (d, J=9.5 Hz, 1H), 7.11 (dd, J=7.3, 4.9 Hz, 1H), 5.22 (s, 1H), 4.53 (s, 1H), 4.46-4.34 (m, 1H), 3.56-3.43 (m, 1H), 3.00-2.88 (m, 3H), 2.71-2.61 (m, 1H), 2.41 (br. s., 1H), 2.34-2.15 (m, 5H), 2.14-2.04 (m, 3H). Analytical HPLC RT=1.31 min (Method A), purity=96%.

EXAMPLE 454

Preparation of 2-(((aR)-6-(3-(1,5-dimethyl-1H-pyrazol-4-yl)-5-(trifluoromethyl)benzamido)spiro[3.3]heptan-2-yl)oxy)nicotinamide

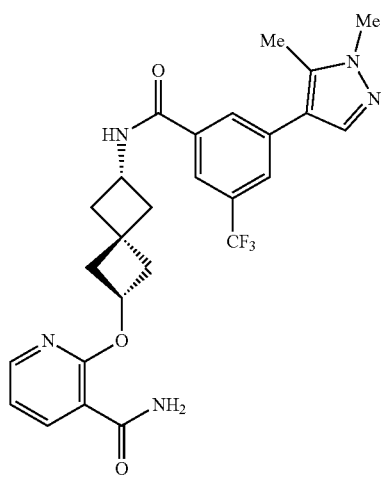

Example 454 (8.2 mg, 23%) was prepared in a analogous manner as Example 428 replacing 1-methyl-4-(4,4,5,5-tetramethyl-1,3,2-dioxaborolan-2-v yl)-1H-pyrazole with 1,5-dimethyl-4-(4,4,5,5-tetramethyl-1,3,2-dioxaborolan-2-yl)-1H-pyrazole. MS (ESI) m z: 514.1 (M+H)+. 1H NMR (500 MHz, DMSO-$d_6$) δ 8.94 (d, J=7.3 Hz, 1H), 8.24 (d, J=3.1 Hz, 1H), 8.16 (d, J=7.3 Hz, 1H), 8.07 (s, 1H), 7.99 (s, 1H), 7.79 (s, 1H), 7.72 (s, 2H), 7.60 (br. s., 1H), 7.11 (dd, J=7.5, 5.0 Hz, 1H), 5.19 (t, J=7.2 Hz, 1H), 4.34 (d, J=7.6 Hz, 1H), 4.02-3.91 (s, 3H), 3.77 (s, 2H), 3.16 (d, J=4.6 Hz, 1H), 2.65 (d, J=4.9 Hz, 1H), 2.49-2.42 (m, 2H), 2.36 (s, 4H), 2.28-2.13 (m, 4H). Analytical HPLC RT=1.66 min (Method A) and 1.65 min (Method B), purity=100%.

EXAMPLE 455

Preparation of N-((aR)-6-((3-carbamoylpyridin-2-yl)oxy)spiro[3.3]heptan-2-yl)-3-(difluoromethyl)-6-((S)-3-(hydroxymethyl)piperazin-1-yl)imidazo[1,5-a]pyridine-1-carboxamide

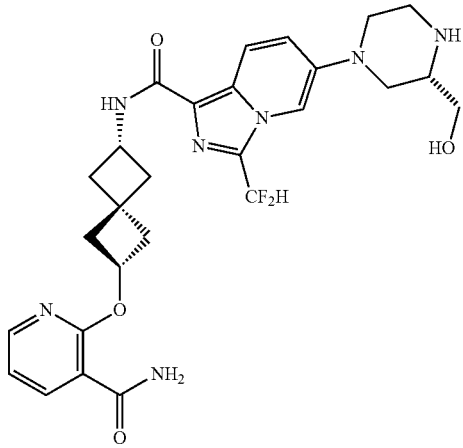

Example 455 (1.5 mg, 2.5%) was prepared in a analogous manner as Example 440 by replacing morpholine with (S)-tert-butyl 2-(hydroxymethyl)piperazine-1-carboxylate followed by TFA deprotection of the Boc group. MS (ESI) m/z: 556.2 (M+H)+. 1H NMR (500 MHz, DMSO-d6) δ 8.32 (d, J=8.2 Hz, 1H), 8.27 (d, J=3.1 Hz, 1H), 8.20-8.11 (m, 2H), 8.06 (s, 1H), 7.69 (br. s., 1H), 7.60 (br. s., 1H), 7.56 (t, J=52 Hz, 1H), 7.16-7.07 (m, 2H), 5.22 (s, 1H), 4.46-4.33 (m, 1H), 3.97-3.84 (m, 2H), 3.02-2.88 (m, 2H), 2.87-2.74 (m, 2H), 2.65 (d, J=7.6 Hz, 2H), 2.40 (d, J=9.8 Hz, 2H), 2.34-2.14 (m, 5H), 1.89 (s, 4H). Analytical HPLC RT=1.02 min (Method A) and 0.92 min (Method B), purity=85%.

EXAMPLE 456

Preparation of 2-(((aR)-6-(3-(8-oxa-3-azabicyclo[3.2.1]octan-3-yl)-5-(trifluoromethyl)benzamido)spiro[3.3]heptan-2-yl)oxy)nicotinamide

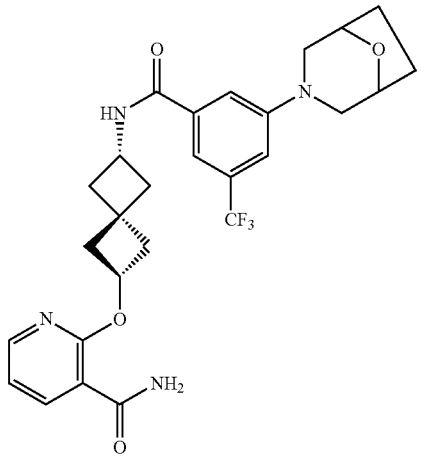

Example 456 (5 mg, 9%) was prepared in a analogous manner as Example 440 by replacing Example 436A with Example 427 and by replacing morpholine with 8-oxa-3-azabicyclo[3.2.1]octane. MS (ESI) m/z: 531.1 (M+H)+. 1H NMR (500 MHz, DMSO-d6) δ 8.71 (d, J=7.3 Hz, 1H), 8.27 (d, J=2.7 Hz, 1H), 8.17 (d, J=7.6 Hz, 1H), 7.70 (br. s., 1H), 7.60 (br. s., 1H), 7.50 (br. s., 2H), 7.20 (s, 1H), 7.11 (dd, J=7.3, 4.9 Hz, 1H), 5.24 (t, J=7.2 Hz, 1H), 4.47 (br. s., 2H), 4.42-4.31 (m, 1H), 3.54 (d, J=11.6 Hz, 1H), 2.91 (d, J=10.1 Hz, 2H), 2.71-2.62 (m 1H), 2.35 (br. s., 1H), 2.31-2.15 (m, 4H), 1.86 (d, J=18.3 Hz, 5H), 1.24 (s, 3H). Analytical HPLC RT=1.79 min (Method A) and 1.79 min (Method B), purity=100%.

EXAMPLE 457

Preparation of 6-bromo-N-((aR)-6-((3-carbamoylpyridin-2-yl)oxy)spiro[3.3]heptan-2-yl)-3-methylimidazo[1,5-a]pyridine-1-carboxamide

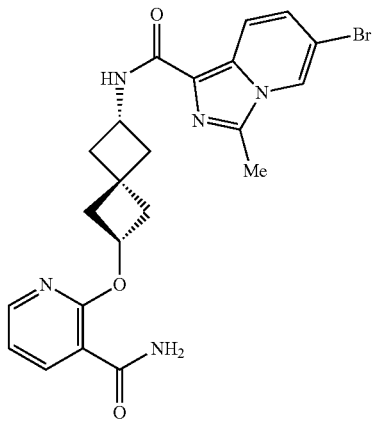

Example 457 (198 mg, 75%) was prepared in a analogous manner as Example 15 replacing Intermediate 4 with Intermediate 123 and coupling with Example 42C. MS (ESI) m/z: 484.2 (M+H)+. 1H NMR (500 MHz, DMSO-d6) δ 8.55 (s, 1H), 8.27 (d, J=3.1 Hz, 1H), 8.16 (d, J=7.6 Hz, 2H), 7.98 (d, J=9.5 Hz, 1H), 7.71-7.55 (m, 2H), 7.18-7.06 (m, 2H), 5.21 (t, J=7.2 Hz, 1H), 4.44-4.32 (m, 1H), 2.70-2.58 (m, 4H), 2.49-2.44 (m, 1H), 2.44-2.35 (m, 1H), 2.34-2.14 (m, 6H). Analytical HPLC RT=1.58 min (Method A) and 1.59 min (Method B), purity=99%.

EXAMPLE 458

Preparation of N-((aR)-6-(3-carbamoylpyridin-2-yl)oxy)spiro[3.3]heptan-2-yl)-6-(1,5-dimethyl-1H-pyrazol-4-yl)-3-methylimidazo[1,5-a]pyridine-1-carboxamide

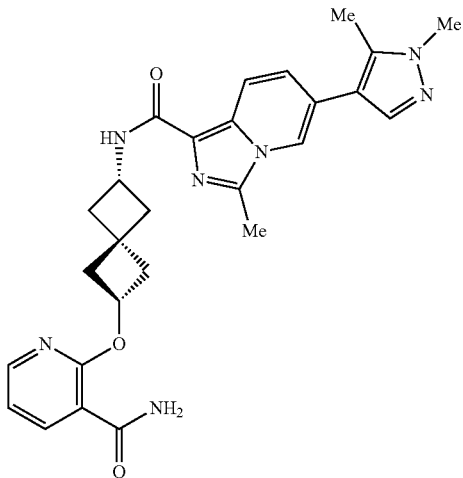

Example 458 (14.8 mg, 47%) was prepared in a analogous manner as Example 428 replacing Example 427 with Example 457 and by replacing 1-methyl-4-(4,4,5,5-tetramethyl-1,3,2-dioxaborolan-2-yl)-1H-pyrazole with 1,5-dimethyl-4-(4,4,5,5-tetramethyl-1,3,2-dioxaborolan-2-yl)-1H-pyrazole. MS (ESI) m/z: 500.2 (M+H)+. 1H NMR (500 MHz, DMSO-d6) δ 8.31-8.23 (m, 1H), 8.17 (dd, J=7.3, 1.8 Hz, 1H), 8.06 (d, J=9.2 Hz, 3H), 7.72-7.56 (m, 3H), 7.18 (d, J=9.8 Hz, 1H), 7.11 (dd, J=7.3, 4.9 Hz, 1H), 5.22 (quin, J=7.1 Hz, 1H), 4.46-4.32 (m, 1H), 3.80 (s, 3H), 2.70-2.62 (m, 4H), 2.41 (s, 4H), 2.35-2.14 (m, 5H). Analytical HPLC RT=1.35 min (Method A) and 1.22 min (Method B), purity=99%.

EXAMPLE 459

Preparation of N-((aR)-6-((3-carbamoylpyridin-2-yl)oxy)spiro[3.3]heptan-2-yl)-6-(1,3-dimethyl-1H-pyrazol-4-yl)-3-methylimidazo[15-a]pyridine-1-carboxamide

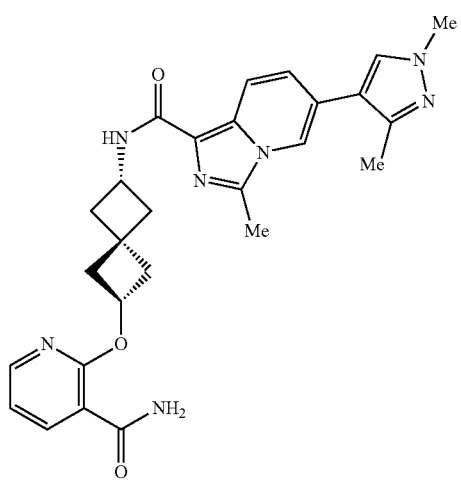

Example 459 (23.3 mg, 75%) was prepared in a analogous manner as Example 428 replacing Example 427 with Example 457 and by replacing 1-methyl-4-(4,4,5,5-tetramethyl-1,3,2-dioxaborolan-2-yl)-1H-pyrazole with 1,3-dimethyl-4-(4,4,5,5-tetramethyl-1,3,2-dioxaborolan-2-yl)-1H-pyrazole. MS (ESI) m/z: 500.1 (M+H)+. 1H NMR (500 MHz, DMSO-d6) δ 8.30-8.23 (m, 1H), 8.17 (dd, J=7.5, 1.9 Hz, 1H), 8.13-8.02 (m, 3H), 7.99 (s, 1H), 7.76-7.61 (m, 2H), 7.21 (d, J=9.3 Hz, 1H), 7.11 (dd, J=7.5, 4.9 Hz, 1H), 5.21 (t, J=7.1 Hz, 1H), 4.39 (d, J=8.2 Hz, 1H), 3.83-3.74 (m, 3H), 2.69-2.61 (m, 4H), 2.49-2.38 (m, 2H), 2.34 (s, 3H), 2.32-2.13 (m, 5H). Analytical HPLC RT=1.48 min (Method A) and 1.41 min (Method B), purity=100%.

EXAMPLE 460

Preparation of N-((aR)-6-((3-carbamoylpyridin-2-yl)oxy)spiro[3.3]heptan-2-yl)-3-methyl-6-(l-methyl-1H-pyrazol-4-yl)imidazo[1,5-a]pyridine-1-carboxamide

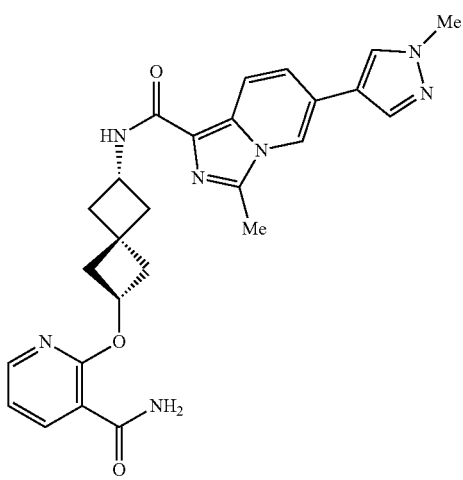

Example 460 (28.8 mg, 93%) was prepared in a analogous manner as Example 428 replacing Example 427 with Example 457. MS (ESI) m/z: 486.2 (M+H)+. 1H NMR (500 MHz, DMSO-d6) δ 8.39 (s, 1H), 8.29-8.24 (m, 1H), 8.21 (s, 1H), 8.17 (dd, J=7.3, 1.8 Hz, 1H), 8.07-8.01 (m, 2H), 7.99 (s, 1H), 7.65 (d, J=12.2 Hz, 2H), 7.33 (d, J=9.5 Hz, 1H), 7.11 (dd, J=7.3, 4.9 Hz, 1H), 5.21 (t, J=7.0 Hz, 1H), 4.44-4.33 (m, 1H), 3.88 (s, 3H), 2.65 (s, 4H), 2.49-2.37 (m, 3H), 2.35-2.13 (m, 6H). Analytical HPLC RT=1.30 min (Method A) and 1.22 min (Method B), purity=97%.

EXAMPLE 461

2-Amino-N-((aR)-6-((3-carbamoylpyridin-2-yl)oxy)spiro[3.3]heptan-2-yl)quinazoline-4-carboxamide, 2 TFA

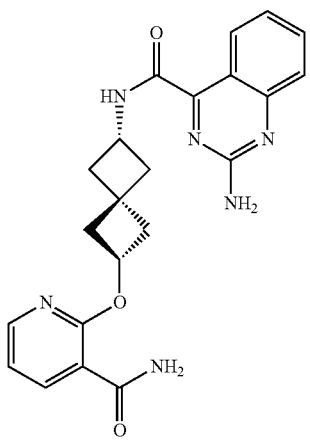

To Example 42C (0.009 g, 0.036 mmol) and 2-aminoquinazoline-4-carboxylic acid (6.9 mg, 0.036 mmol) in DMF (0.5 mL), was added DIEA (0.032 mL, 0.182 mmol), followed by BOP (0.018 g, 0.040 mmol). The mixture was stirred at rt overnight, then was purified by preparative HPLC to afford Example 461 (0.7 mg, 3% yield). MS (ESI) m/z: 419.1 (M+H)+. $^1$H NMR (500 MHz, DMSO-$d_6$) δ 9.03 (d, J=7.6 Hz, 1H), 8.31-8.22 (m, 1H), 8.17 (d, J=5.8 Hz, 1H), 8.02 (d, J=8.2 Hz, 1H), 7.82-7.67 (m, 2H), 7.61 (br. s., 1H), 7.47 (d, J=8.5 Hz, 1H), 7.23 (t, J=7.5 Hz, 1H), 7.11 (dd, J=7.3, 5.0 Hz, 1H), 7.01 (s, 2H), 5.24 (s, 1H), 4.51-4.35 (m, 1H), 2.72-2.65 (m, 1H), 2.43-2.36 (m, 1H), 2.28 (dd, J=11.3, 7.4 Hz, 1H), 2.25-2.12 (m, 2H), 1.86-1.76 (m, 3H). Analytical HPLC RT=1.27 min (Method A) and 1.05 min (Method B), purity=94%.

EXAMPLE 462

Preparation of N-((aR)-6-((3-carbamoylpyridin-2-yl)oxy)spiro[3.3]heptan-2-yl)-7-cyclopropyl-6-((1-hydroxycyclobutyl)methoxy)pyrazolo[1,5-a]pyridine-3-carboxamide, TFA

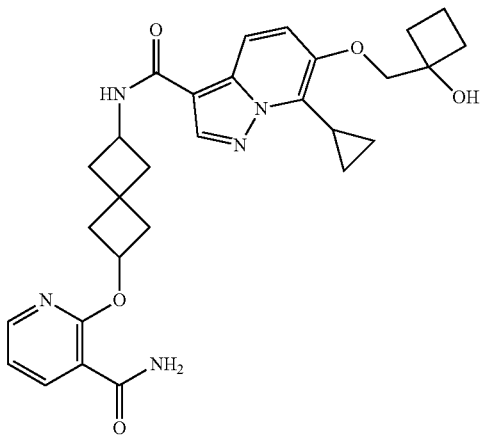 [SMILES: NC(=O)c1cccnc1OC1CC2(CC(NC(=O)c3cnn4c(C5CC5)c(OCC5(O)CCC5)ccc34)C2)C1]

Intermediate 42C (25 mg, 0.101 mmol) was suspended in anhydrous PhMe (2 mL), then Me$_3$Al (2 M in PhMe) (0.152 mL, 0.303 mmol) was added dropwise. After stirring for 5 min at rt, Intermediate 127 (32 mg, 0.101 mmol) was added, and the reaction mixture was stirred at 120° C. for 30 min under microwave irradiation. The reaction mixture was cooled to rt, and carefully quenched with TFA. Solvent was removed under reduced pressure, the residue was diluted with DMF (2 mL), filtered, and purified by reverse phase HPLC to afford Example 462 (7.4 mg, 13%). MS (ESI) m/z: 532.3 (M+H)+. $^1$H NMR (500 MHz, DMSO-$d_6$) δ ppm 8.49 (s, 1H), 8.31-8.24 (m, 2H), 8.16 (dd, J=7.5, 1.8 Hz, 1H), 8.01 (d, J=9.6 Hz, 1H), 7.73-7.58 (m, 2H), 7.49 (d, J=9.7 Hz, 1H), 7.10 (dd, J=7.5, 4.9 Hz, 1H), 5.22 (quin, J=7.2 Hz, 1H), 4.43-4.30 (m, 1H), 3.97 (s, 2H), 2.71-2.57 (m, 2H), 2.48-2.39 (m, 2H), 2.38-1.95 (m, 10H), 1.75-1.47 (m, 4H), 1.06-0.98 (m, 2H). Analytical HPLC RT=1.562 min (Method A) and 1.550 (Method B) min, purity=96%.

EXAMPLE 463

Preparation of 7-(benzyloxy)-N-((aR)-6-((3-carbamoylpyridin-2-yl)oxy)spiro[3.3]heptan-2-yl)imidazo[1,2-a]pyridine-2-carboxamide, TFA salt

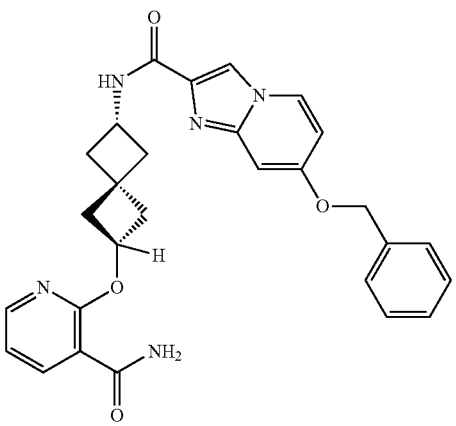

EXAMPLE 463A

Preparation of ethyl 7-(benzyloxy)imidazo[1,2-a]pyridine-2-carboxylate

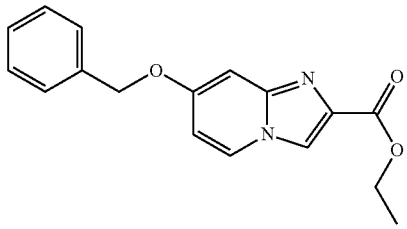 [SMILES: CCOC(=O)c1cn2ccc(OCc3ccccc3)cc2n1]

In a vial, combined 5-(benzyloxy)pyridin-2-amine (0.72 g, 3.60 mmol) and ethyl 3-bromo-2-oxopropanoate (0.451 mL, 3.60 mmol) in EtOH (10 mL), and the reaction mixture was heated to 80° C. After 24 h. the reaction was cooled to rt and solid was filtered off and dried on vacuum to afford Example 463A (0.70 g, 66% yield, as a tan solid. LCMS (ESI) m/z: 296.9 [M+H]+. $^1$H NMR (400 MHz, CDCl$_3$) δ 8.63 (d, J=9.9 Hz, 1H), 8.33 (s, 1H), 8.21 (d, J=1.8 Hz, 1H), 7.68 (dd, J=9.9, 2.4 Hz, 1H), 7.55-7.37 (m, 5H), 5.24 (s, 2H), 4.51 (q, J=7.0 Hz, 2H), 1.51 (t, J=7.2 Hz, 3H).

EXAMPLE 463B

Preparation of 7-(benzyloxy)imidazo[1,2-a]pyridine-2-carboxylic acid

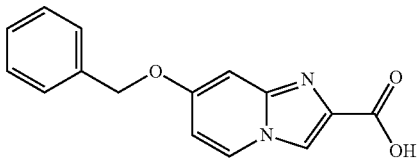 [SMILES: O=C(O)c1cn2ccc(OCc3ccccc3)cc2n1]

Example 463A (0.23 g, 0.77 mmol) was placed in THF (2 mL) and MeOH (1 mL) and 1M aq. LiOH (1.55 mL, 1.55 mmol). The reaction was heated in microwave for 20 min at 120° C. The solvents were concentrated, then 1N HCl was added, and the resultant solid was collected to give Example 463B (0.165 g, 79% yield) as a white solid. LCMS(ESI) m/z: 269.0 [M+H]+. $^1$H NMR (400 MHz, DMSO-d$_6$) δ 8.44 (s, 2H), 7.60 (d, J=9.9 Hz, 1H), 7.55-7.48 (m, 2H), 7.47-7.35 (m, 3H), 7.34-7.26 (m, 1H), 5.12 (s, 2H).

EXAMPLE 463

To Example 463B (48.1 mg, 0.179 mmol) and Example 42C (89 mg, 0.35 mmol was added DMF (0.25 mL) followed by BOP (79 mg, 0.18 mmol) and DIEA (0.09 mL, 0.53 mmol). After 2 h, the reaction was diluted with DMF, filtered and purified by reverse phase HPLC to afford Example 463 (8.3 mg, 7% yield). LCMS(ESI) m/z: 498.2 [M+H]$^+$. $^1$H NMR (500 MHz, DMSO-d$_6$) δ 8.43 (br d, J=8.2 Hz, 1H), 8.40 (br s, 1H), 8.31-8.26 (m, 1H), 8.25 (s, 1H), 8.17 (dd, J=7.3, 1.5 Hz, 1H), 7.69 (br s, 1H), 7.61 (br s, 1H), 7.56-7.48 (m, 3H), 7.43 (br t. J=7.3 Hz, 2H), 7.38 (br d, J=7.3 Hz, 1H), 7.21 (dd, J=9.8, 1.8 Hz, 1H), 7.11 (dd, J=7.3, 4.9 Hz, 1H), 5.22 (quin, J=7.2 Hz, 1H), 5.08 (s, 2H), 4.44-4.29 (m, 1H), 2.66 (dt, J=10.8, 5.6 Hz, 1H), 2.49-2.43 (m, 1H), 2.44-2.36 (m, 1H), 2.35-2.14 (m, 5H). Analytical HPLC 1.77 min (Method A) and 1.46 min. (Method B), purity 94%.

EXAMPLE 464

Preparation of N-((aR)-6-((3-carbamoylpyridin-2-yl)oxy)spiro[3.3]heptan-2-yl)-6-methoxyimidazo[1,2-a]pyridine-2-carboxamide, TFA salt

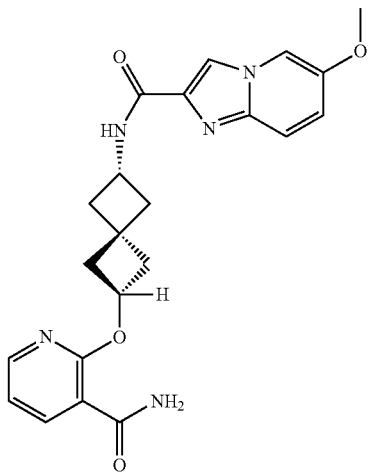

Example 464 was synthesized in a similar manner as Example 463, starting with 5-methoxypyridin-2-amine instead of 5-(benzyloxy)pyridin-2-amine to afford (12.3 mg, 29% yield) of the title compound. LCMS(ESI) m/z: 422.1 [M+H]$^+$, $^1$H NMR (500 MHz, DMSO-d$_6$) δ 8.41 (br d, J=7.9 Hz, 1H), 8.26 (br d J=1.2 Hz, 2H), 8.24 (s, 1H), 8.19-8.14 (m, 1H), 7.67 (br s, 1H), 7.62 (br s, 1H), 7.50 (d, J=9.8 Hz, 1H), 7.17-7.05 (m, 2H), 5.21 (quin, J=6.9 Hz, 1H), 4.43-4.26 (m, 1H), 3.75 (s, 3H), 2.65 (dt, J=11.1, 5.7 Hz, 1H), 2.47-2.37 (m, 2H), 2.33-2.10 (m, 5H). Analytical HPLC 1.40 min (Method A) and 1.14 min. (Method B), purity 98%.

---

What is claimed is:

1. A compound of Formula (I):

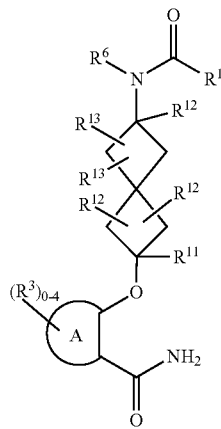

or a stereoisomer, a tautomer, or a pharmaceutically-acceptable salt thereof, wherein:

Ring A is selected from phenyl or 6-membered heteroaryl comprising carbon atoms and 1-3 nitrogen atoms;

$R^1$ is selected from $C_{1-4}$ alkyl, $NR^5R^5$, $OR^5$, —$(CR^4R^4)_n$— $C_{3-10}$ carbocycle and —$(CR^4R^4)_n$-4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$ is independently selected from H and $C_{1-5}$ alkyl optionally substituted with halogen, $C_{1-4}$ alkoxy, —OH, CN, —$CO_2H$, —$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$;

$R^3$, at each occurrence, is independently selected from halogen, $C_{1-6}$ alkyl, $C_{2-6}$ alkenyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl)$_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, a carbocycle, and a heterocycle, wherein said alkyl, alkenyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered heterocycle substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —$NHCO(C_{1-4}$ alkyl), —$NHCOCF_3$, —$NHCO_2(C_{1-4}$ alkyl), —$NHCO_2(CH_2)_2$ $O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, —$(CH_2)_n$—C(O)$C_{1-4}$alkyl, —$(CH_2)_n$—C(O)carbocycle, —$(CH_2)_n$—C(O)heterocycle, —$(CH_2)_n$—C(O)$NR^aR^a$, —$(CH_2)_n$—$NR^aC(O)$ $C_{1-4}$alkyl, —$(CH_2)_n$—C(O)OC$_{1-4}$alkyl, —$(CH_2)_n$—C(O)$C_{1-4}$alkyl, —$(CH_2)_n$—C(O)O-carbocycle, —$(CH_2)_n$—C(O)O-heterocycle, —$(CH_2)_n$—$SO_2$alkyl, —$(CH_2)_n$ $SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, $CO_2(C_{1-4}$ alkyl), —$(CHR^{10})_n NR^aR^a$, $S(O)_p(C_{1-4}$ alkyl), —$(CHR^{10})_n CONR^aR^a$, —$(CHR^{10})_n NR^aCO(C_{1-4}$ alkyl), —$(CHR^{10})_n OCONR^a(CH_2)_n CO_2R^a$, $S(O)_p C_{1-4}$ alkyl, $S(O)_p NR^aR^a$, —$O(CHR^{10})_n$carbocycle, —$O(CHR^{10})_n$heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^{11}$ is independently selected from H and $C_{1-3}$ alkyl optionally substituted with halogen, $C_{1-4}$ alkoxy, —OH, CN, —$CO_2H$, —$CO_2(C_{1-4}$ alkyl), —$CO(C_{1-4}$ alkyl), —$CONH_2$, —$CONH(C_{1-4}$ alkyl), and —$CON(C_{1-4}$ alkyl)$_2$;

$R^{12}$ and $R^{13}$ are independently selected from H, OH, —$OC_{1-3}$ alkyl substituted with 0-4 $R^d$, $C_{1-3}$ alkyl with substituted with 0-4 $R^d$;

$R^a$, at each occurrence, is independently selected from H, $C_{1-4}$ alkyl, —$(CH_2)_n OH$, $CO(C_{1-4}$ alkyl), $COCF_3$, $CO_2$ $(C_{1-4}$ alkyl), —$CONH_2$, —CONH—$C_{1-4}$ alkylene-$CO_2$ $(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)C_{1-4}$ alkyl, $NH_2$, $NO_2$, $N(C_{1-4}$ alkyl$)_2$, $CO(C_{1-4}$ alkyl), $CO(C_{1-4}$ haloalkyl), $CO_2H$, $CO_2(C_{1-4}$ alkyl), $CONH_2$, —$CONH(C_{1-4}$ alkyl), —$CON(C_{1-4}$ alkyl$)_2$, —CONH—$C_{1-4}$ alkylene-O($C_{1-4}$ alkyl), —CONH—$C_{1-4}$ alkylene-NH($C_{1-4}$ alkyl), —CONH—$C_{1-4}$ alkylene-N($C_{1-4}$ alkyl$)_2$, —$C_{1-4}$ alkylene-O—P(O)(OH)$_2$, —$NHCO_2(C_{1-4}$ alkyl), —$R^c$, $COR^c$, $CO_2R^c$, and $CONHR^c$, wherein said alkyl and alkoxy are substituted with $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl);

n, at each occurrence, is independently selected from 0, 1, 2, 3, and 4; and p, at each occurrence, is independently selected from 0, 1, and 2.

2. The compound of claim 1, having Formula (II):

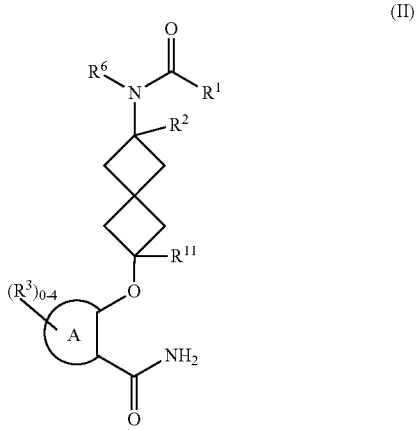

(II)

or a stereoisomer, a tautomer, or a pharmaceutically-acceptable salt thereof, wherein Ring A is selected from phenyl or 6-membered heteroaryl comprising carbon atoms and 1-2 nitrogen atoms;

$R^1$ is selected from $NR^5R^5$, $OR^5$, —$(CR^4R^4)_nC_{3-10}$ carbocycle and —$(CR^4R^4)_n$-4- to 15-membered heterocycle comprising carbon atoms and 1-4 heteroatoms selected from N, $NR^8$, O, and $S(O)_p$; wherein said carbocycle, and heterocycle are substituted with 1-4 $R^7$;

$R^2$ is independently selected from H and $C_{1-5}$ alkyl optionally substituted with halogen, $C_{1-4}$ alkoxy, —OH, and CN, $R^3$, at each occurrence, is independently selected from halogen, $C_{1-6}$ alkyl, $C_{2-6}$ alkenyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl$)_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, a carbocycle, and a heterocycle, wherein said alkyl, alkenyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl$)_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered heterocycle substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, —$(CH_2)_n$—C(O)$C_{1-4}$alkyl, —$(CH_2)_n$—C(O)carbocycle, —$(CH_2)_n$—C(O)heterocycle, —$(CH_2)_n$—C(O)$NR^aR^a$, —$(CH_2)_n$—$NR^aC(O)C_{1-4}$alkyl, —$(CH_2)_n$—C(O)O$C_{1-4}$alkyl, —$(CH_2)_n$—C(O)$C_{1-4}$alkyl, —$(CH_2)_n$—C(O)O-carbocycle, —$(CH_2)_n$—C(O)O-heterocycle, —$(CH_2)_n$—$SO_2$alkyl, —$(CH_2)_n$ $SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, alkenyl, alkynyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, CO($C_{1-4}$ alkyl), $CO_2H$, $CO_2(C_{1-4}$ alkyl), —(CHR$^{10}$)$_n$NR$^a$R$^a$, S(O)$_p$($C_{1-4}$ alkyl), —(CHR$^{10}$)$_n$CONR$^a$R$^a$, —(CHR$^{10}$)$_n$NR$^a$CO($C_{1-4}$ alkyl), —(CHR$^{10}$)$_n$OCONR$^a$(CH$_2$)$_n$CO$_2$R$^a$, S(O)$_p$$C_{1-4}$ alkyl, S(O)$_p$NR$^a$R$^a$, —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and $C_{1-4}$ alkyl;

R$^{11}$ is independently selected from H and $C_{1-3}$ alkyl optionally substituted with halogen, $C_{1-4}$ alkoxy, —OH, and CN;

R$^a$, at each occurrence, is independently selected from H, $C_{1-4}$ alkyl, —(CH$_2$)$_n$OH, CO($C_{1-4}$ alkyl), COCF$_3$, CO$_2$($C_{1-4}$ alkyl), —CONH$_2$, —CONH—$C_{1-4}$ alkylene-CO$_2$($C_{1-4}$ alkyl), $C_{1-4}$ alkylene-CO$_2$($C_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, OH, halogen, $C_{1-4}$ alkyl, $C_{1-4}$ alkoxy, OCF$_3$, OC(O)$C_{1-4}$ alkyl, NH$_2$, NO$_2$, N($C_{1-4}$ alkyl)$_2$, CO($C_{1-4}$ alkyl), CO($C_{1-4}$ haloalkyl), CO$_2$H, CO$_2$($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —NHCO$_2$($C_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—$C_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N($C_{1-4}$ alkyl), O, and S(O)$_p$; wherein each ring moiety is substituted with 0-2 R$^d$;

R$^d$, at each occurrence, is independently selected from =O, halogen, —OH, $C_{1-4}$ alkyl, NH$_2$, NH($C_{1-4}$ alkyl), N($C_{1-4}$ alkyl)$_2$, $C_{1-4}$ alkoxy, and —NHCO($C_{1-4}$ alkyl);

n, at each occurrence, is independently selected from 0, 1, 2, 3, and 4; and p, at each occurrence, is independently selected from 0, 1, and 2.

3. The compound of claim 2, having Formula (III):

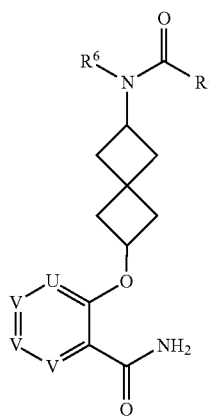

(III)

or a stereoisomer, a tautomer, or a pharmaceutically-acceptable salt thereof, wherein:

U and V are independently selected from CH, CR$^3$, and N; provided when U or V is N, the one U and three V variables represent no more than 2 nitrogen atoms;

R$^1$ is selected from NR$^5$R$^5$, OR$^5$, —(CR$^4$R$^4$)$_n$$C_{3-10}$ carbocycle and —(CR$^4$R$^4$)$_n$-4- to 15-membered heterocycle comprising carbon atoms and 1-4 heteroatoms selected from N, NR$^8$, O, and S(O)$_p$; wherein said carbocycle, and heterocycle are substituted with 1-4 R$^7$;

R$^3$, at each occurrence, is independently selected from halogen, $C_{1-6}$ alkyl, $C_{2-6}$ alkenyl, $C_{1-4}$ alkoxy, $C_{1-4}$ alkylthio, $C_{1-4}$ haloalkyl, —CH$_2$OH, —OCH$_2$F, —OCHF$_2$, —OCF$_3$, CN, —NH$_2$, —NH($C_{1-4}$ alkyl), —N($C_{1-4}$ alkyl)$_2$, —CO$_2$H, —CH$_2$CO$_2$H, —CO$_2$($C_{1-4}$ alkyl), —CO($C_{1-4}$ alkyl), —CH$_2$NH$_2$, —CONH$_2$, —CONH($C_{1-4}$ alkyl), —CON($C_{1-4}$ alkyl)$_2$, —OCH$_2$CO$_2$H, —NHCO($C_{1-4}$ alkyl), —NHCO$_2$($C_{1-4}$ alkyl), —NHSO$_2$($C_{1-4}$ alkyl), —SO$_2$NH$_2$, —C(=NH)NH$_2$, a carbocycle, and a heterocycle, wherein said alkyl, alkenyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, $C_{1-4}$ haloalkyl, OCH$_2$F, OCHF$_2$, OCF$_3$, —NH($C_{1-4}$ alkyl), —N($C_{1-4}$ alkyl)$_2$, $C_{1-4}$ alkoxy, CH$_2$OH, CH$_2$O($C_{1-4}$ alkyl), CH$_2$CO$_2$H, CH$_2$CO$_2$($C_{1-4}$ alkyl), $C_{1-4}$ alkyl, a carbocycle, and a heterocycle, wherein said alkyl, alkoxy, haloalkyl, carbocycle, and heterocycle are substituted with 0-4 R$^9$;

R$^5$, at each occurrence, is independently selected from H, $C_{1-4}$ alkyl, —(CR$^6$R$^6$)$_n$—$C_{3-10}$ carbocycle and —(CR$^6$R$^6$)$_n$-4- to 10-membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form a 4- to 15-membered heterocycle substituted with 1-4 R$^7$;

R$^6$, at each occurrence, is independently selected from H, $C_{1-4}$ alkyl, CH$_2$NH$_2$, $C_{1-4}$ haloalkyl, $C_{1-4}$ alkoxy, CH$_2$OH, CH$_2$O($C_{1-4}$ alkyl), CH$_2$CO$_2$H, CH$_2$CO$_2$($C_{1-4}$ alkyl), a carbocycle, and a heterocycle, wherein said alkyl, alkoxy, haloalkyl, carbocycle, and heterocycle are substituted with 0-4 R$^9$;

R$^7$, at each occurrence, is independently selected from H, =O, NO$_2$, halogen, $C_{1-4}$ alkyl, $C_{2-4}$ alkenyl, $C_{1-4}$ alkoxy, CN, OH, CF$_3$, —(CH$_2$)$_n$—CO$_2$H, —(CH$_2$)$_n$—CO$_2$($C_{1-4}$ alkyl), —(CH$_2$)$_n$—NR$^8$R$^8$, —NHCOH, —NHCO($C_{1-4}$ alkyl), —NHCOCF$_3$, —NHCO$_2$($C_{1-4}$ alkyl), —NHCO$_2$(CH$_2$)$_2$O($C_{1-4}$ alkyl), —NHCO$_2$(CH$_2$)$_3$O($C_{1-4}$ alkyl), —NHCO$_2$(CH$_2$)$_2$OH, —NHCO$_2$(CH$_2$)$_2$NH$_2$, —NHCO$_2$(CH$_2$)$_2$N($C_{1-4}$ alkyl)$_2$, —NHCO$_2$CH$_2$CO$_2$H, —CH$_2$NHCO$_2$($C_{1-4}$ alkyl), —NHC(O)NR$^8$R$^8$, —NHSO$_2$($C_{1-4}$ alkyl), —S(O)$_p$($C_{1-4}$ alkyl), —SO$_2$NH$_2$, —SO$_2$NH($C_{1-4}$ alkyl), —SO$_2$N($C_{1-4}$ alkyl)$_2$, —SO$_2$NH(CH$_2$)$_2$OH, —SO$_2$NH(CH$_2$)$_2$O($C_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkoxy, carbocycle, and heterocycle are substituted with 0-4 R$^9$;

R$^8$, at each occurrence, is independently selected from H, $C_{1-4}$ alkyl, $C_{2-4}$ alkenyl, $C_{2-4}$ alkynyl, —(CH$_2$)$_n$—C(O)

$C_{1-4}$alkyl, —$(CH_2)_n$—C(O)carbocycle, —$(CH_2)_n$—C(O)heterocycle, —$(CH_2)_n$—C(O)NR$^a$R$^a$, —$(CH_2)_n$—NR$^a$C(O)$C_{1-4}$alkyl, —$(CH_2)_n$—C(O)O$C_{1-4}$alkyl, —$(CH_2)_n$—C(O)$C_{1-4}$alkyl, —$(CH_2)_n$—C(O)O-carbocycle, —$(CH_2)_n$—C(O)O-heterocycle, —$(CH_2)_n$—SO$_2$alkyl, —$(CH_2)_n$ SO$_2$carbocycle, —$(CH_2)_n$—SO$_2$heterocycle, —$(CH_2)_n$—SO$_2$NR$^a$R$^a$, —$(CH_2)_n$-carbocycle, and —$(CH_2)_n$-heterocycle, wherein said alkyl, alkenyl, alkynyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, =O, CN, NO$_2$, $C_{1-4}$ alkyl, $C_{1-4}$ alkoxy, CO($C_{1-4}$ alkyl), CO$_2$H, CO$_2$($C_{1-4}$ alkyl), —(CHR$^{10}$)$_n$NR$^a$R$^a$, S(O)$_p$($C_{1-4}$ alkyl), —(CHR$^{10}$)$_n$CONR$^a$R$^a$, —(CHR$^{10}$)$_n$NR$^a$CO($C_{1-4}$ alkyl), —(CHR$^{10}$)$_n$OCONR$^a$(CH$_2$)$_n$CO$_2$R$^a$, S(O)$_p$$C_{1-4}$ alkyl, S(O)$_p$NR$^a$R$^a$, —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and $C_{1-4}$ alkyl;

R$^a$, at each occurrence, is independently selected from H, $C_{1-4}$ alkyl, —(CH$_2$)$_n$OH, CO($C_{1-4}$ alkyl), COCF$_3$, CO$_2$($C_{1-4}$ alkyl), —CONH$_2$, —CONH—$C_{1-4}$ alkylene-CO$_2$($C_{1-4}$ alkyl), $C_{1-4}$ alkylene-CO$_2$($C_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, OH, halogen, $C_{1-4}$ alkyl, $C_{1-4}$ alkoxy, OCF$_3$, OC(O)O$C_{1-4}$ alkyl, NH$_2$, NO$_2$, N($C_{1-4}$ alkyl)$_2$, CO($C_{1-4}$ alkyl), CO($C_{1-4}$ haloalkyl), CO$_2$H, CO$_2$($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —NHCO$_2$($C_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and S(O)$_p$; wherein each ring moiety is substituted with 0-2 R$^d$;

R$^d$, at each occurrence, is independently selected from =O, halogen, —OH, $C_{1-4}$ alkyl, NH$_2$, NH($C_{1-4}$ alkyl), N($C_{1-4}$ alkyl)$_2$, $C_{1-4}$ alkoxy, and —NHCO($C_{1-4}$ alkyl), and a heterocycle containing carbon atoms and 1-4 heteroatoms selected from the group consisting of: N, NH, N($C_{1-4}$ alkyl), O, and S(O)$_p$;

n, at each occurrence, is independently selected from 0, 1, 2, 3, and 4; and p, at each occurrence, is independently selected from 0, 1, and 2.

4. The compound of claim 3, having Formula (IV):

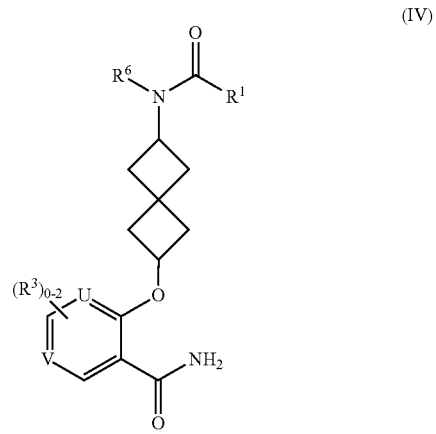

(IV)

or a stereoisomer, a tautomer, or a pharmaceutically-acceptable salt thereof, wherein:
U and V are independently selected from CH, CR$^3$, and N; provided at least one of U and V is N;
R$^1$ is selected from —$(CH_2)_n$—$C_{3-10}$ carbocycle, and —$(CH_2)_n$-5- to 14-membered heterocycle, wherein said carbocycle and heterocycle are substituted with 1-4 R$^7$;
R$^3$, at each occurrence, is independently selected from halogen, $C_{1-6}$ alkyl, and $C_{1-4}$ alkoxy;
R$^6$, at each occurrence, is independently selected from H and $C_{1-4}$ alkyl;
R$^7$, at each occurrence, is independently selected from H, =O, NO$_2$, halogen, $C_{1-4}$ alkyl, $C_{1-4}$ alkoxy, CN, OH, CF$_3$, —(CH$_2$)$_n$—CO$_2$H, —(CH$_2$)$_n$—CO$_2$($C_{1-4}$ alkyl), —(CH$_2$)$_n$—NR$^8$R$^8$, —NHCOH, —NHCO($C_{1-4}$ alkyl), —NHCOCF$_3$, —NHCO$_2$($C_{1-4}$ alkyl), —NHCO$_2$(CH$_2$)$_2$O($C_{1-4}$ alkyl), —NHCO$_2$(CH$_2$)$_3$O($C_{1-4}$ alkyl), —NHCO$_2$(CH$_2$)$_2$OH, —NHCO$_2$(CH$_2$)$_2$NH$_2$, —NHCO$_2$(CH$_2$)$_2$N($C_{1-4}$ alkyl)$_2$, —NHCO$_2$CH$_2$CO$_2$H, —CH$_2$NHCO$_2$($C_{1-4}$ alkyl), —NHC(O)NR$^8$R$^8$, —NHSO$_2$($C_{1-4}$ alkyl), —S(O)$_2$($C_{1-4}$ alkyl), —SO$_2$NH$_2$, —SO$_2$NH($C_{1-4}$ alkyl), —SO$_2$N($C_{1-4}$ alkyl)$_2$, —SO$_2$NH(CH$_2$)$_2$OH, —SO$_2$NH(CH$_2$)$_2$O($C_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

R$^8$, at each occurrence, is independently selected from H, $C_{1-4}$ alkyl, $C_{2-4}$ alkenyl, C(O)$C_{1-4}$alkyl, C(O)carbocycle, C(O)heterocycle, —(CH$_2$)$_n$—C(O)NR$^a$R$^a$, —(CH$_2$)$_n$—NR$^a$C(O)$C_{1-4}$alkyl, C(O)OC$_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, alkenyl, carbocycle, and heterocycle are substituted with 0-4 R$^9$;

alternatively, R$^8$ and R$^8$ are taken together with the nitrogen atom to which they are attached to form a 4- to 10-membrane heterocycle substituted with 0-4 R$^9$;

R$^9$, at each occurrence, is independently selected from halogen, OH, CN, NO$_2$, CHF$_2$, CF$_3$, $C_{1-4}$ alkyl, $C_{1-4}$ alkoxy, CH$_2$OH, CO($C_{1-4}$ alkyl), CO$_2$H, CO$_2$($C_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO($C_{1-4}$ alkyl), —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, OC(O)C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

5. The compound of claim 4, having Formula (IVb):

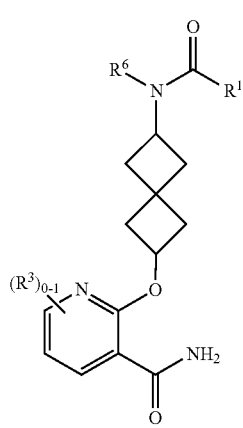

(IVb)

or a stereoisomer, a tautomer, or a pharmaceutically-acceptable salt thereof, wherein:

R$^1$ is selected from

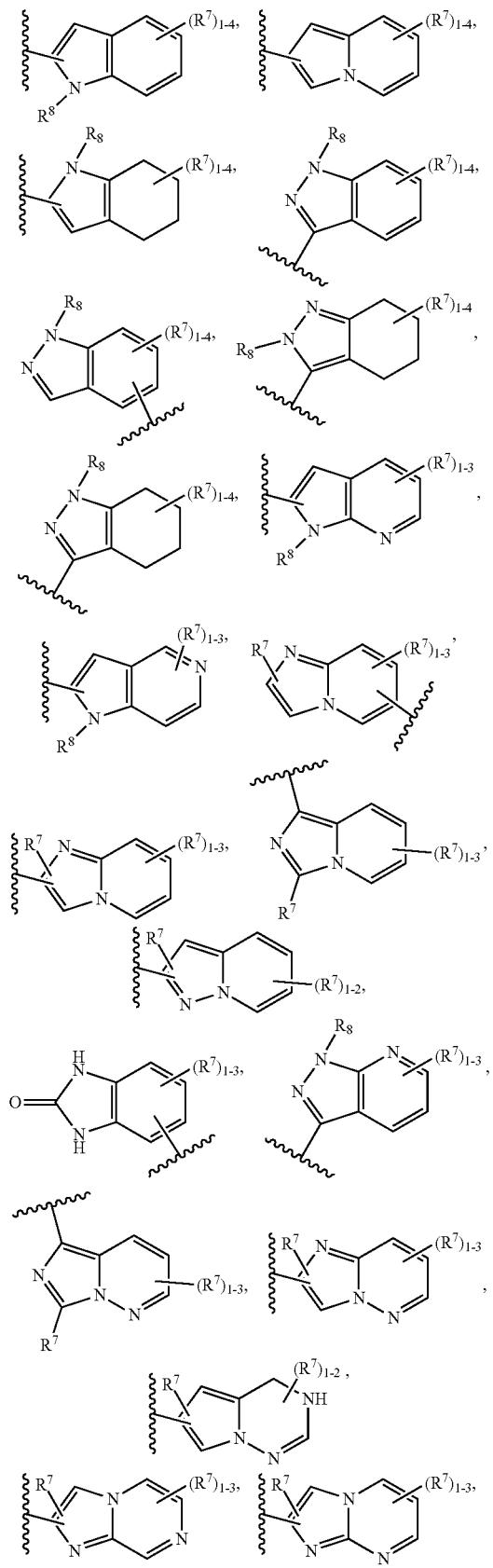

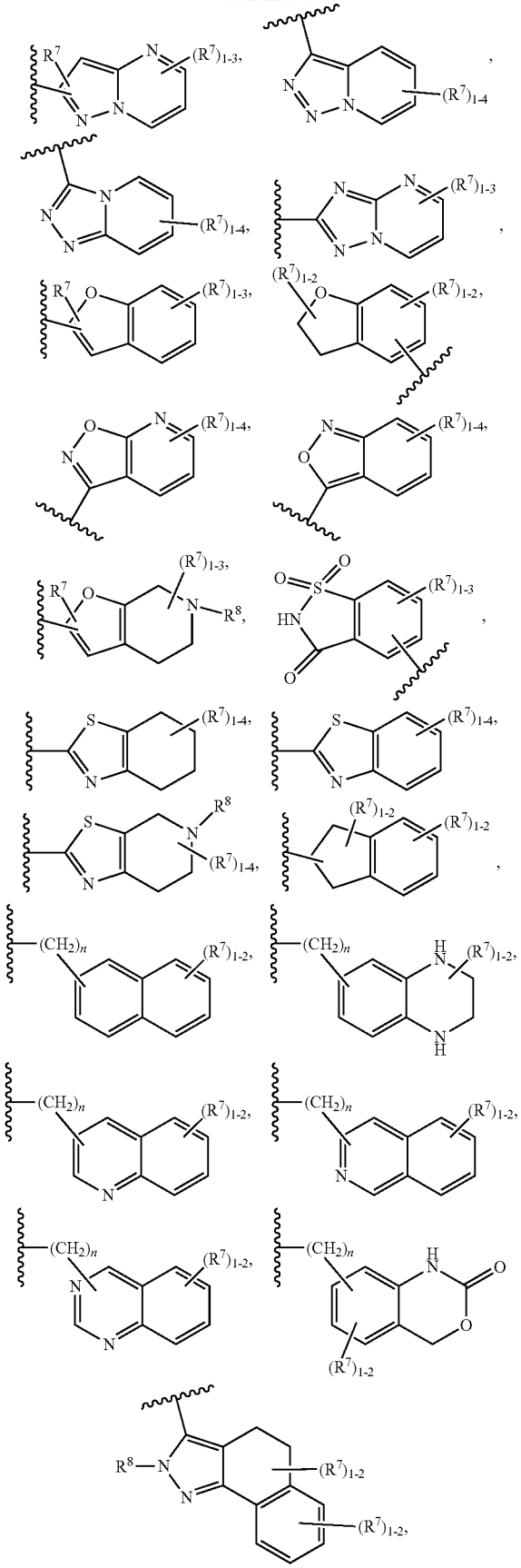
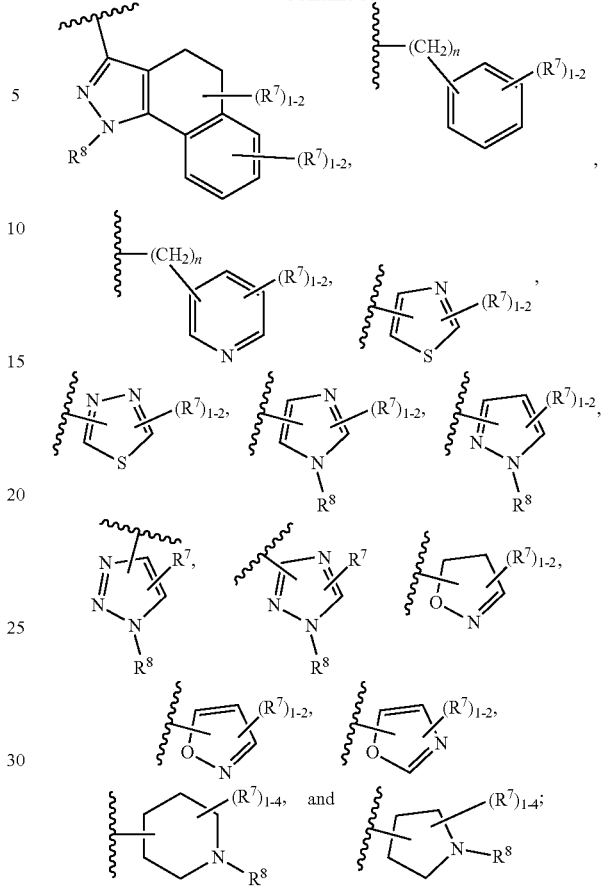

$R^3$ is $C_{1-4}$ alkoxy;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$SO_2N(C_{1-4}$ alkyl)$_2$-carbocycle, —$SO_2N(C_{1-4}$ alkyl)-heterocycle comprising carbon atoms and 1-4 heteroatoms selected from N, $NR^8$, O, and $S(O)_p$, $(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkoxy, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, —$(CH_2)_n$—$C(O)NR^aR^a$, $C(O)OC_{1-4}$alkyl, $C(O)O$-carbocycle, $C(O)O$-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$(CH_2)_nNHCO(C_{1-4}$ alkyl), —$S(O)_2(C_{1-4}$ alkyl), —$S(O)_2(C_{1-4}$ alkyl), —$O(CH_2)_n$heterocycle, —$O(CH_2)_{2-4}NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^a$, at each occurrence, is independently selected from H and $C_{1-4}$ alkyl; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$; and $R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$alkyl), —$CONH$—$C_{1-4}$ alkylene-$N(C_{1-4}$alkyl)$_2$, and —$NHCO_2(C_{1-4}$ alkyl).

6. The compound of claim 4 or a stereoisomer, a tautomer, or a pharmaceutically-acceptable salt thereof, wherein:

$R^1$ is selected from

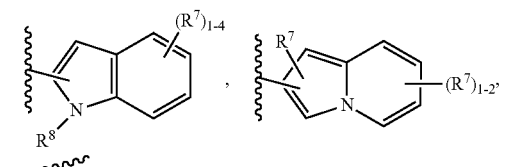

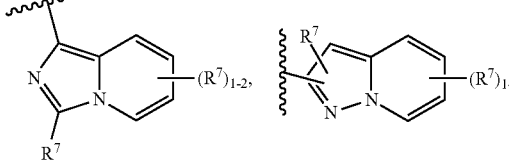

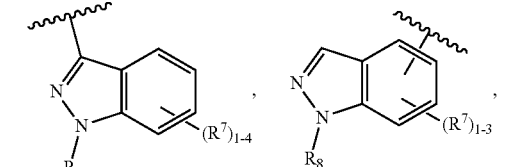

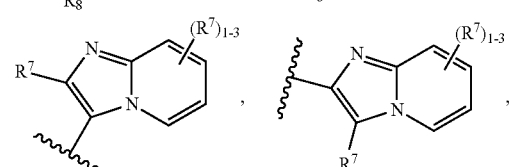

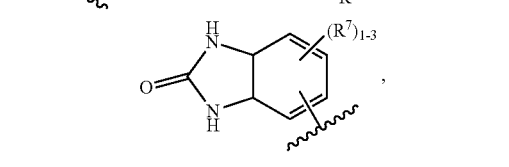

-continued

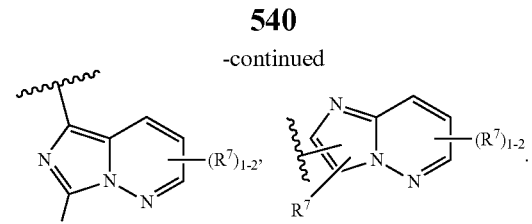

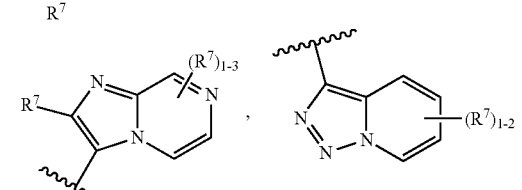

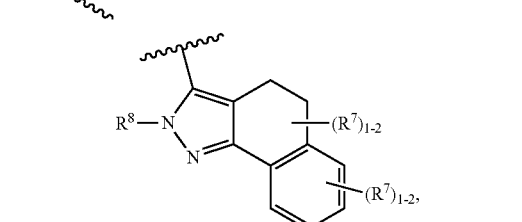

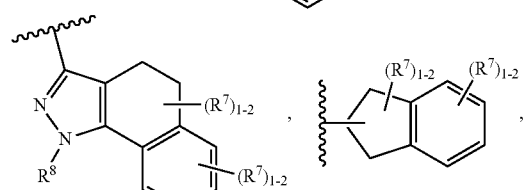

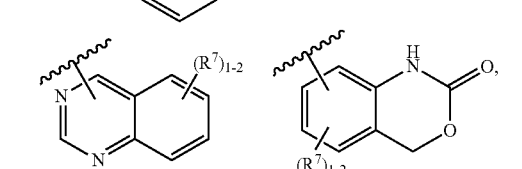

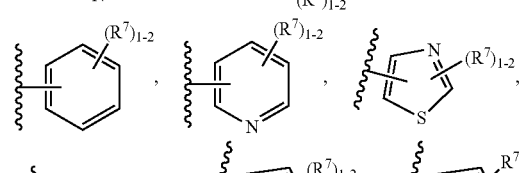

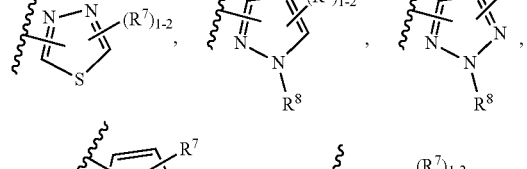

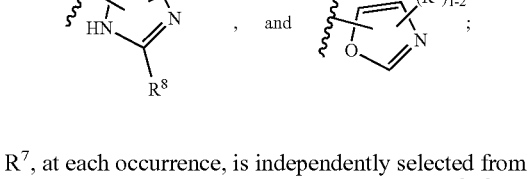

$R^7$, at each occurrence, is independently selected from H, halogen, $C_{1-4}$ alkyl, $C_{1-4}$ alkoxy, —$NR^8R^8$, $C_{3-6}$ cycloalkyl, phenyl, and —$(CH_2)_n$-heterocycle comprising carbon atoms and 1-4 heteroatoms selected from N, $NR^8$, O, and $S(O)_p$, wherein said alkyl, alkoxy, cycloalkyl phenyl, and heterocycle are substituted with 0-4 $R^9$;

$R^8$, at each occurrence, is independently selected from H, $C_{1-4}$ alkyl, —$(CH_2)_n$—$C_{3-6}$cycloalkyl, —$(CH_2)_n$-phenyl, and —$(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

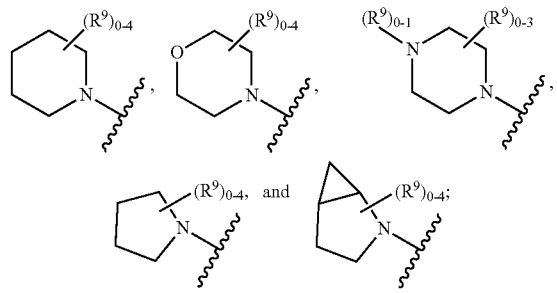

$R^9$, at each occurrence, is independently selected from F, Cl, OH, =O, CN, $C_{1-4}$ alkyl, $C_{1-4}$ alkoxy, —$(CH_2)_nNR^aR^a$, —$(CH_2)_nCONR^aR^a$, $C_{3-6}$cycloalkyl, and a 4- to 10-membered heterocycle, wherein said alkyl, alkoxy, cycloalkyl, and heterocycle are substituted with 0-4 $R^b$;

$R^a$, at each occurrence, is independently selected from H, $C_{1-4}$ alkyl, —$(CH_2)_nOH$, CO($C_{1-4}$ alkyl), COCF$_3$, CO$_2$($C_{1-4}$ alkyl), —CONH$_2$, —CONH—$C_{1-4}$ alkylene-CO$_2$($C_{1-4}$ alkyl), and $C_{1-4}$ alkylene-CO$_2$($C_{1-4}$ alkyl); and $R^b$, at each occurrence, is independently selected from halogen, $C_{1-4}$ alkyl, $C_{1-4}$ alkoxy, OCF$_3$, NH$_2$, NO$_2$, N($C_{1-4}$ alkyl)$_2$, CO($C_{1-4}$ alkyl), CO($C_{1-4}$ haloalkyl), CO$_2$($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, and —NHCO$_2$($C_{1-4}$ alkyl).

7. The compound of claim 6 or a stereoisomer, a tautomer, or a pharmaceutically-acceptable salt thereof, wherein:
$R^1$ is selected from

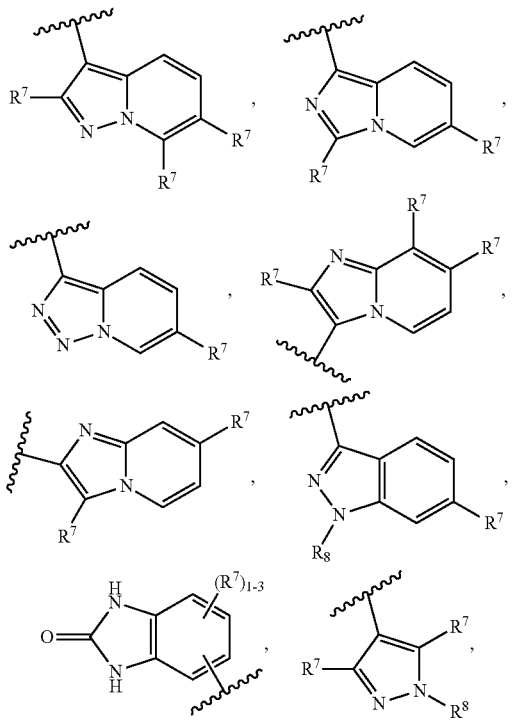

-continued

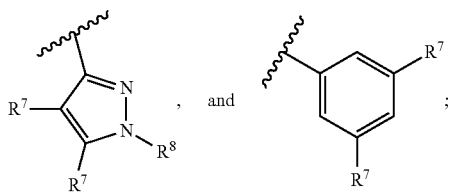

$R^7$, at each occurrence, is independently selected from H, halogen, CN, $C_{1-4}$ alkyl, $C_{1-4}$ alkoxy, —NR$^8$R$^8$, $C_{3-6}$ cycloalkyl, phenyl, and heterocycle comprising carbon atoms and 1-4 heteroatoms selected from N, NR$^8$, O, and S(O)$_p$, wherein said alkyl, alkoxy, cycloalkyl, phenyl, and heterocycle are substituted with 0-4 $R^9$;

$R^8$, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

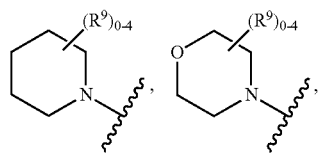

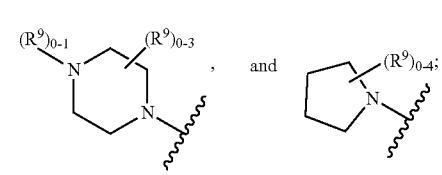

$R^9$, at each occurrence, is independently selected from F, Cl, OH, CN, $C_{1-4}$ alkyl, $C_{1-4}$ alkoxy, —$(CH_2)_nNR^aR^a$, $C_{3-6}$ cycloalkyl, and a 4- to 10-membered heterocycle, wherein said alkyl, alkoxy, cycloalkyl, and heterocycle are substituted with 0-4 $R^b$;

$R^a$, at each occurrence, is independently selected from H, $C_{1-4}$ alkyl, —$(CH_2)_nOH$, CO($C_{1-4}$ alkyl), COCF$_3$, CO$_2$($C_{1-4}$ alkyl), —CONH$_2$, —CONH—$C_{1-4}$ alkylene-CO$_2$($C_{1-4}$ alkyl), and $C_{1-4}$ alkylene-CO$_2$($C_{1-4}$ alkyl); and $R^b$, at each occurrence, is independently selected from halogen, $C_{1-4}$ alkyl, $C_{1-4}$ alkoxy, OCF$_3$, NH$_2$, NO$_2$, N($C_{1-4}$ alkyl)$_2$, CO($C_{1-4}$ alkyl), CO($C_{1-4}$ haloalkyl), C$_2$($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, and —NHCO$_2$($C_{1-4}$ alkyl).

8. The compound of claim 3, having Formula (IVc), Formula (IVd) or Formula (IVe):

(IVc)
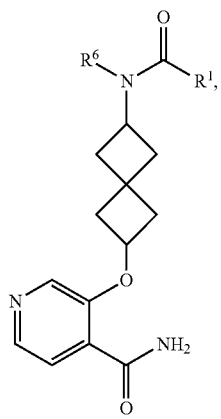
(IVd)
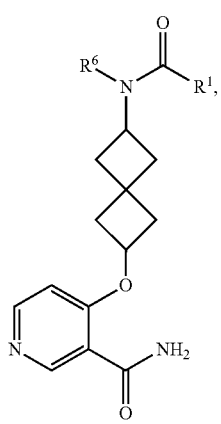
(IVe)
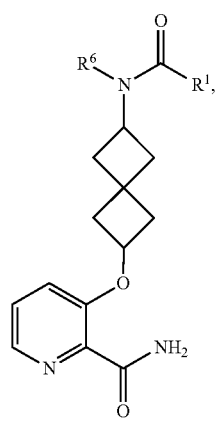
or a stereoisomer, a tautomer, or a pharmaceutically-acceptable salt thereof.
9. The compound of claim 3, having Formula (IVf), Formula (IVg), or Formula (IVh):
(IVf)
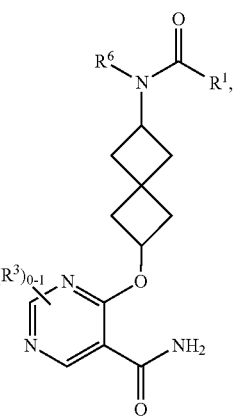
(IVg)
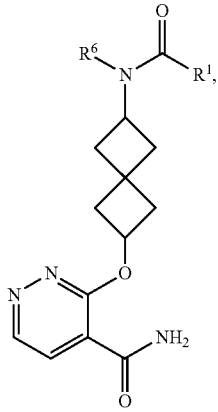
(IVh)
or a stereoisomer, a tautomer, or a pharmaceutically-acceptable salt thereof.

10. The compound of claim 3, having Formula (IVi):

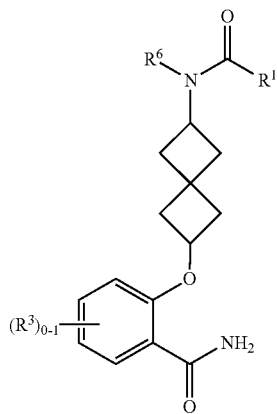

or a stereoisomer, a tautomer, or a pharmaceutically-acceptable salt thereof, wherein:

$R^1$ is independently selected from

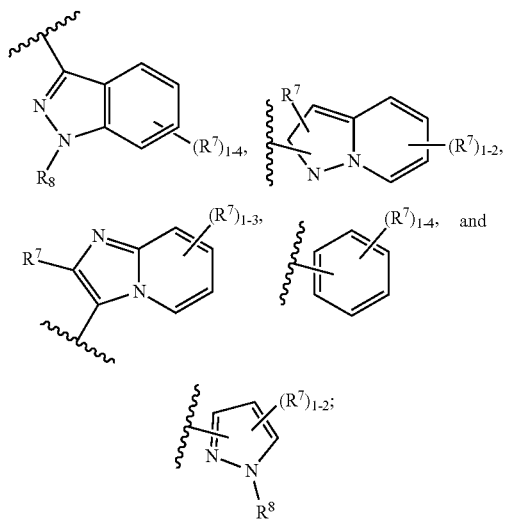

$R^3$, at each occurrence, is independently selected from halogen, $C_{1-6}$ alkyl, $C_{2-6}$ alkenyl, $C_{1-4}$ alkoxy,

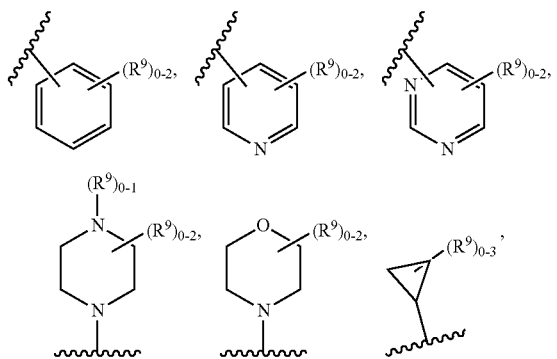

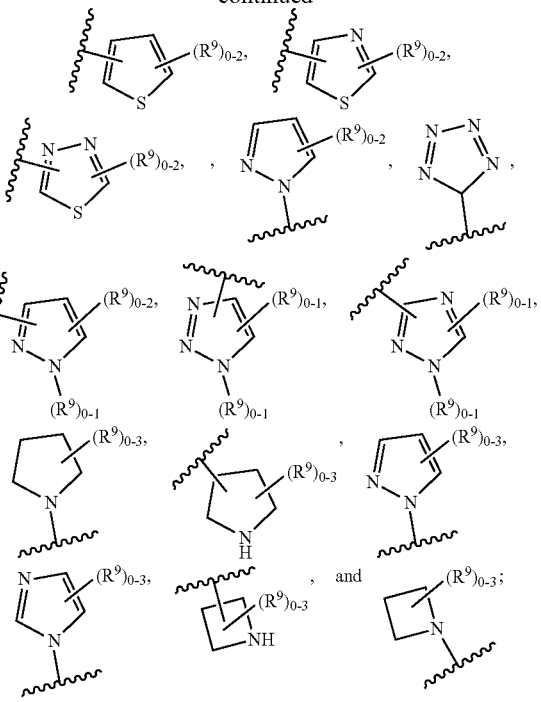

wherein said alkyl, alkenyl, and alkoxy are substituted with 0-4 $R^9$;

$R^7$, at each occurrence, is independently selected from H, $C_{1-4}$ alkyl, $C_{1-4}$ alkoxy, —$NR^8R^8$, —$S(O)_2(C_{1-4}$ alkyl), —O-heterocycle, $C_{3-6}$ cycloalkyl, phenyl, and heterocycle comprising carbon atoms and 1-4 heteroatoms selected from N, $NR^8$, O, and $S(O)_p$, wherein said alkyl, alkoxy, cycloalkyl phenyl, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, —$(CH_2)_n$—$C(O)NR^aR^a$, $C(O)OC_{1-4}$alkyl, $C(O)O$-carbocycle, $C(O)O$-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, $CO_2(C_{1-4}$ alkyl), —$(CHR^{10})_n NR^aR^a$, $S(O)_p(C_{1-4}$ alkyl), —$(CHR^{10})_n CONR^aR^a$, —$(CHR^{10})_n NR^aCO(C_{1-4}$ alkyl), —$(CHR^{10})_n OCONR^a(CH_2)_n CO_2R^a$, $S(O)_p C_{1-4}$ alkyl, $S(O)_p NR^aR^a$, —$O(CHR^{10})_n$carbocycle, —$O(CHR^{10})_n$heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^a$, at each occurrence, is independently selected from H and $C_{1-4}$ alkyl; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$; and $R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2H$, $CO_2(C_{1-4}$ alkyl), $CONH_2$, —CONH$(C_{1-4}$ alkyl), —CON$(C_{1-4}$ alkyl$)_2$, —CONH—$C_{1-4}$ alkylene-O$(C_{1-4}$ alkyl), —CONH—$C_{1-4}$ alkylene-N$(C_{1-4}$ alkyl$)_2$, and —NHCO$_2(C_{1-4}$ alkyl).

11. The compound of claim 10, having Formula (IVj):

(IVj)

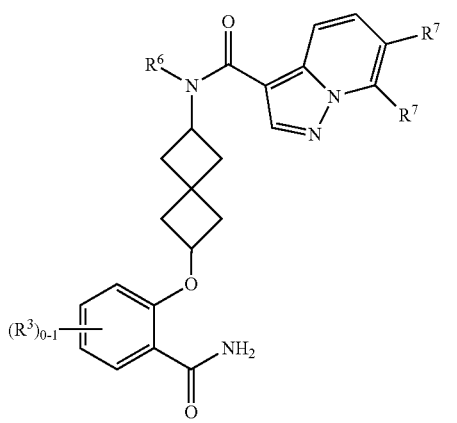

or a stereoisomer, a tautomer, or a pharmaceutically-acceptable salt thereof, wherein:

$R^3$, at each occurrence, is independently selected from F, Cl, Br, $C_{1-6}$ alkyl, $C_{2-6}$ alkenyl, $C_{1-4}$ alkoxy,

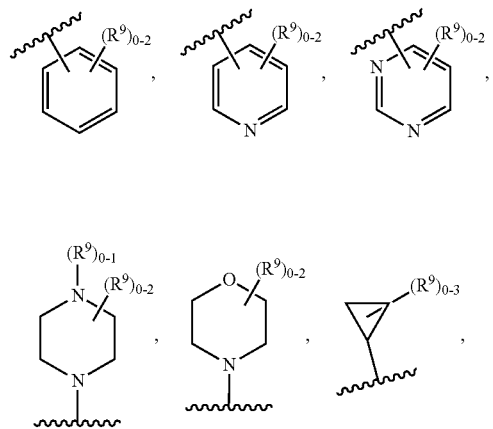

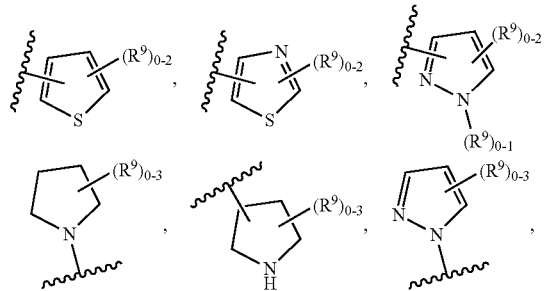

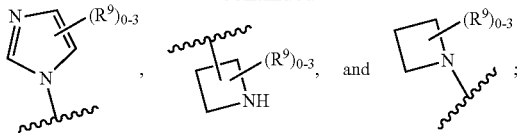

wherein said alkyl, alkenyl, and alkoxy are substituted with 0-4 $R^9$;

$R^7$, at each occurrence, is independently selected from H, $C_{1-4}$ alkyl substituted with 0-4 $R^9$, $C_{1-4}$ alkoxy substituted with 0-4 $R^9$, $NR^8R^8$, $C_{3-6}$ cycloalkyl, —O-heterocycle, and wherein said alkyl, alkoxy, $C_{3-6}$ cycloalkyl, heterocycle are substituted with 0-4 $R^9$ and wherein the heterocycle comprising carbon atoms and 1-4 heteroatoms selected from N, $NR^8$, O, and $S(O)_p$;

$R^8$, at each occurrence, is independently selected from H, $C_{1-4}$ alkyl, $C(O)OC_{1-4}$alkyl and phenyl;

alternatively, $R^8$ and $R^8$ are taken together with the nitrogen atom to which they are attached to form a 4- to 10-membered heterocycle selected from

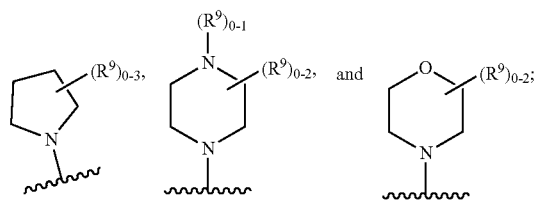

$R^9$, at each occurrence, is independently selected from halogen, OH, =O, CN, $NO_2$, $CHF_2$, $CF_3$, $C_{1-4}$ alkyl, $C_{2-4}$ alkenyl, $C_{1-4}$ alkoxy, $CH_2OH$, $CO_2H$, $CO_2(C_{1-4}$ alkyl), $CH_2OC(O)NH(CH_2)_{1-2}C(O)OH$, $CH_2OC(O)NH(CH_2)_{1-2}C(O)OC_{1-4}$ alkyl; $CONH_2$, —$(CH_2)_n NR^aR^a$, —$(CH_2)_n CONR^aR^a$, —$(CH_2)_n NHCO(C_{1-4}$ alkyl), —$S(O)_2(C_{1-4}$ alkyl), —$O(CH_2)_n$heterocycle, —$O(CH_2)_{2-4}NR^aR^a$, and —$(CR^{10}R^{10})_n$-4- to 10-membered heterocycle, wherein said alkyl, alkenyl, alkoxy, carbocycle, and heterocycle are substituted with 0-4 $R^b$;

$R^{10}$, at each occurrence, is independently selected from H and $C_{1-4}$ alkyl;

$R^a$, at each occurrence, is independently selected from H and $C_{1-4}$ alkyl; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$; and $R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2H$, $CO_2(C_{1-4}$ alkyl), $CONH_2$, —CONH$(C_{1-4}$ alkyl), —CON$(C_{1-4}$ alkyl$)_2$, —CONH—$C_{1-4}$ alkylene-O$(C_{1-4}$ alkyl), —CONH—$C_{1-4}$ alkylene-N$(C_{1-4}$ alkyl$)_2$, and —NHCO$_2(C_{1-4}$ alkyl).

12. The compound of claim 1, having Formula (V):

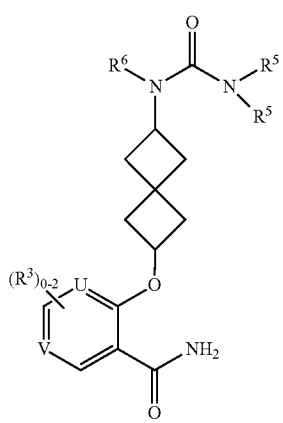

(V)

or a stereoisomer, a tautomer, or a pharmaceutically-acceptable salt thereof, wherein:

U and V are independently selected from CH, $CR^3$, and N;

$R^5$, at each occurrence, is independently selected from H, $C_{1-4}$ alkyl, $-(CR^6R^6)_n-C_{3-10}$ carbocycle, and $-(CR^6R^6)_n$-4 to 10-membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form a 4- to 10-membered heterocycle substituted with 1-4 $R^7$;

$R^7$, at each occurrence, is independently selected from H, =O, $NO_2$, halogen, $C_{1-4}$ alkyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n-NR^8R^8$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl)$_2$, $-NHCO_2CH_2CO_2H$, $-CH_2NHCO_2(C_{1-4}$ alkyl), $-NHC(O)NR^8R^8$, $-NHSO_2(C_{1-4}$ alkyl), $-S(O)_p(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-(CH_2)_n-CONR^8R^8$, $-O(CH_2)_n$-carbocycle, $-O(CH_2)_n$-heterocycle, $-NHCO$-carbocycle, $-NHCO$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, $-(CH_2)_nC(O)NR^aR^a$, $C(O)OC_{1-4}$alkyl, $C(O)$O-carbocycle, $C(O)$O-heterocycle, $SO_2$alkyl, $SO_2$carbocycle, $SO_2$heterocycle, $SO_2NR^aR^a$, $-(CH_2)_n$-carbocycle, and $-(CH_2)_n$-heterocycle, wherein said alkyl, carbocycle, and heterocycle are substituted with 0-4 $R^9$;

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), $-(CHR^{10})_nNR^aR^a$, $-(CHR^{10})_nCONR^aR^a$, $-(CHR^{10})_nNR^aCO(C_{1-4}$ alkyl), $-O(CHR^{10})_n$-carbocycle, $-O(CHR^{10})_n$heterocycle, $-O(CHR^{10})_nNR^aR^a$, and $-(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^a$, at each occurrence, is independently selected from H, $C_{1-4}$ alkyl, $-(CH_2)_nOH$, $CO(C_{1-4}$ alkyl), $COCF_3$, $CO_2(C_{1-4}$ alkyl), $-CONH_2$, $-CONH-C_{1-4}$ alkylene-$CO_2(C_{1-4}$ alkyl), $C_{1-4}$ alkylene-$CO_2(C_{1-4}$ alkyl), $R^c$, $CO_2^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, $-CONH(C_{1-4}$ alkyl), $-CON(C_{1-4}$ alkyl)$_2$, $-CONH-C_{1-4}$ alkylene-$O(C_{1-4}$ alkyl), $-CONH-C_{1-4}$ alkylene-$N(C_{1-4}$ alkyl)$_2$, $-NHCO_2(C_{1-4}$ alkyl), $-R^c$, $COR^c$, $CO_2R^c$, and $CONHR^c$;

$R^c$, at each occurrence, is independently selected from $-(CH_2)_n-C_{3-6}$ cycloalkyl, $-(CH_2)_n$-phenyl, and $-(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, $-OH$, $C_{1-4}$ alkyl, $NH_2$, $NH(C_{1-4}$ alkyl), $N(C_{1-4}$ alkyl)$_2$, $C_{1-4}$ alkoxy, and $-NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4; and p, at each occurrence, is independently selected from 0, 1, and 2.

13. The compound of claim 12 or a stereoisomer, a tautomer, or a pharmaceutically-acceptable salt thereof, wherein:

$R^5$ is selected from H, $C_{1-4}$ alkyl substituted with 1-4 $R^7$,

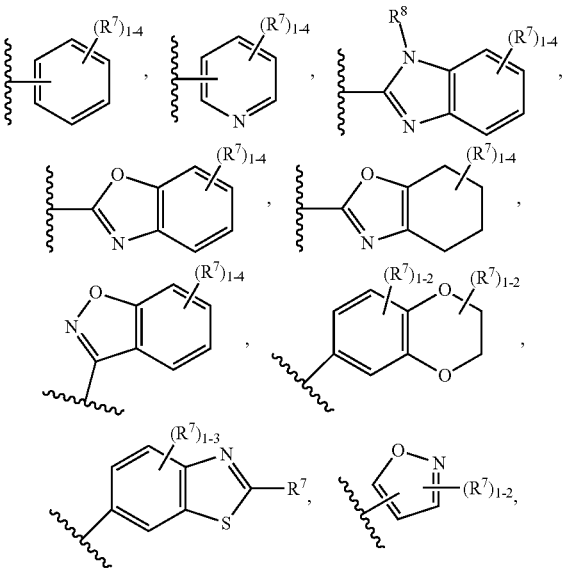

551

-continued

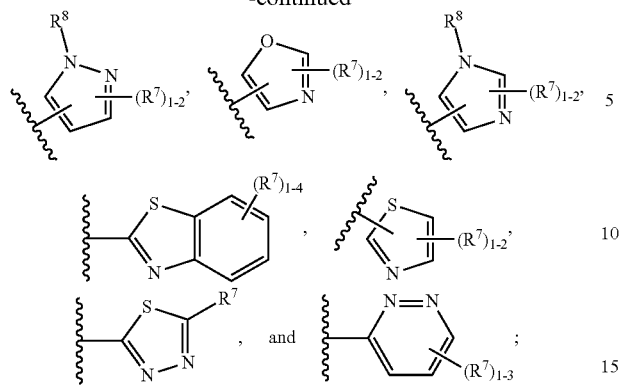

alternatively, $R^5$ and $R^5$ are taken together with the nitrogen atom to which they are attached to form a heterocycle selected from

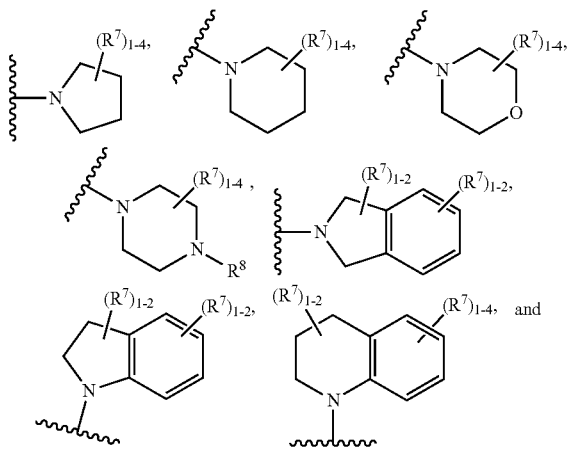

552

-continued

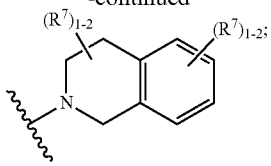

$R^7$, at each occurrence, is independently selected from H, halogen, $C_{1-4}$ alkyl, $C_{1-4}$ alkoxy, CN, OH, $CF_3$, $-NR^8R^8$, $SO_2C_{1-4}$alkyl, $-(CH_2)_n$-carbocycle, and $-(CH_2)_n$-heterocycle, wherein said alkyl, alkoxy, carbocycle, and heterocycle are substituted with 0-4 $R^9$, $R^8$, at each occurrence, is independently selected from H and $C_{1-4}$ alkyl; and $R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, $-NH_2$, and a 4- to 10-membered heterocycle.

14. A pharmaceutical composition comprising one or more compounds of claim 1 and a pharmaceutically acceptable carrier or diluent.

15. A method for prophylaxis and/or treatment of disorders associated with aberrant Rho kinase activity, comprising administering to a patient in need thereof a therapeutically effective amount of the pharmaceutical composition of claim 14.

16. The method of claim 15, wherein said disorder is selected from the group consisting of a cardiovascular disorder, a smooth muscle related disorder, a fibrotic disease, an inflammatory disease, neuropathic disorders, oncologic disorders, and an autoimmune disorder.

17. The method of claim 16, wherein said cardiovascular disorder is selected from the group consisting of angina, atherosclerosis, stroke, cerebrovascular disease, heart failure, coronary artery disease, myocardial infarction, peripheral vascular disease, stenosis, vasospasm, hypertension and pulmonary hypertension.

* * * * *